United States Patent
Fretz et al.

(10) Patent No.: US 12,011,444 B2
(45) Date of Patent: Jun. 18, 2024

(54) N-SUBSTITUTED INDOLE DERIVATIVES AS PGE2 RECEPTOR MODULATORS

(71) Applicant: Idorsia Pharmaceuticals Ltd, Allschwil (CH)

(72) Inventors: Heinz Fretz, Gunten (CH); Isabelle Lyothier, Allschwil (CH); Julien Pothier, Allschwil (CH); Sylvia Richard-Bildstein, Allschwil (CH); Thierry Sifferlen, Allschwil (CH); Lorenza Wyder Peters, Munich (DE); Davide Pozzi, Allschwil (CH); Olivier Corminboeuf, Allschwil (CH)

(73) Assignee: IDORSIA PHARMACEUTICALS LTD, Allschwil (CH)

( * ) Notice: Subject to any disclaimer, the term of this patent is extended or adjusted under 35 U.S.C. 154(b) by 86 days.

(21) Appl. No.: 17/549,828

(22) Filed: Dec. 13, 2021

(65) Prior Publication Data
US 2022/0175775 A1 Jun. 9, 2022

Related U.S. Application Data

(62) Division of application No. 15/777,597, filed as application No. PCT/EP2016/078028 on Nov. 17, 2016, now Pat. No. 11,241,431.

(30) Foreign Application Priority Data

Nov. 20, 2015 (WO) ................ PCT/EP2015/077269

(51) Int. Cl.
| | |
|---|---|
| *A61K 31/506* | (2006.01) |
| *A61K 45/06* | (2006.01) |
| *A61P 35/00* | (2006.01) |
| *C07D 403/12* | (2006.01) |
| *C07D 403/14* | (2006.01) |
| *C07D 413/14* | (2006.01) |
| *C07D 417/14* | (2006.01) |

(52) U.S. Cl.
CPC ............ *A61K 31/506* (2013.01); *A61K 45/06* (2013.01); *A61P 35/00* (2018.01); *C07D 403/12* (2013.01); *C07D 403/14* (2013.01); *C07D 413/14* (2013.01); *C07D 417/14* (2013.01)

(58) Field of Classification Search
CPC .... A61K 31/506; A61K 45/06; C07D 403/12; C07D 403/14; C07D 405/14; C07D 409/14; C07D 413/14; C07D 417/14; A61P 35/00
See application file for complete search history.

(56) References Cited

U.S. PATENT DOCUMENTS

| | | |
|---|---|---|
| 5,948,786 A | 9/1999 | Fujiwara et al. |
| 9,518,044 B2 | 12/2016 | Jiang et al. |
| 11,241,431 B2 | 2/2022 | Fretz et al. |
| 11,325,899 B2 | 5/2022 | Boss et al. |
| 11,446,298 B2 | 9/2022 | Boss et al. |
| 11,712,438 B2 | 8/2023 | Boss et al. |
| 2008/0280891 A1 | 11/2008 | Kelly et al. |
| 2010/0216803 A1 | 8/2010 | Zenkoh et al. |
| 2011/0028463 A1 | 2/2011 | Nozawa et al. |
| 2011/0144153 A1 | 6/2011 | Nozawa et al. |
| 2013/0197199 A1 | 8/2013 | Takayama et al. |
| 2013/0225528 A1 | 8/2013 | Wang et al. |
| 2016/0130232 A1 | 5/2016 | Ikegami et al. |
| 2016/0214977 A1 | 7/2016 | Peters et al. |

(Continued)

FOREIGN PATENT DOCUMENTS

| | | |
|---|---|---|
| EP | 1661896 A1 | 5/2006 |
| EP | 2014657 A1 | 1/2009 |

(Continued)

OTHER PUBLICATIONS

Lamptey et al. Int J Mol Sci. Feb. 2022;23(3): 1851, Feb. 6, 2022 (Year: 2022).*
Dawson, Nature, Neuroscience, Oct. 21, 2018 (Year: 2018).*
Abramov, Medicinal Research Reviews, 2603-5, 2021 (Year: 2021).*
Yankner, Annu Rev Pathol Mech. Dis, 2008 (Year: 2008).*
Univ of Pittsburgh, Dept. of Neurology, Neurodegenerative diseases (Year: 2023).*
Johns Hopkins Medicine, 2023 (Year: 2023).*
Makabe et al. Molecular Human Reproduction, 2020 (Year: 2020).*

(Continued)

*Primary Examiner* — Umamaheswari Ramachandran
(74) *Attorney, Agent, or Firm* — Hoxie & Associates LLC

(57) ABSTRACT

The present invention relates to derivatives of formula (I)

Formula (I)

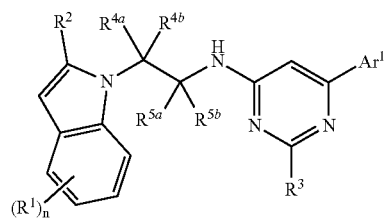

wherein $(R^1)_n$, $R^2$, $R^3$, $R^{4a}$, $R^{4b}$, $R^{5a}$, $R^{5b}$ and $Ar^1$ are as described in the description, to their preparation, to pharmaceutically acceptable salts thereof, and to their use as pharmaceuticals, to pharmaceutical compositions containing one or more compounds of formula (I), and especially to their use as modulators of the prostaglandin 2 receptors EP2 and/or EP4.

23 Claims, No Drawings

(56) References Cited

U.S. PATENT DOCUMENTS

| | | |
|---|---|---|
| 2016/0318905 A1 | 11/2016 | Peters et al. |
| 2018/0002308 A1 | 1/2018 | Asada et al. |
| 2018/0030030 A1 | 2/2018 | Okuda et al. |
| 2023/0165859 A1 | 6/2023 | Fretz et al. |

FOREIGN PATENT DOCUMENTS

| | | |
|---|---|---|
| EP | 2711364 A1 | 3/2014 |
| WO | WO 2001/072302 A1 | 10/2001 |
| WO | WO 2002/032422 A2 | 4/2002 |
| WO | WO 2002/032900 A2 | 4/2002 |
| WO | WO 2002/050032 A1 | 6/2002 |
| WO | WO 2002/050033 A1 | 6/2002 |
| WO | WO 2002/064564 A1 | 8/2002 |
| WO | WO 2003/086390 A1 | 10/2003 |
| WO | WO 2003/087061 A1 | 10/2003 |
| WO | WO 2003/099857 A1 | 12/2003 |
| WO | WO 2004/067524 A1 | 8/2004 |
| WO | WO 2005/019218 A1 | 3/2005 |
| WO | WO 2005/021508 A1 | 3/2005 |
| WO | WO 2005/026129 A1 | 3/2005 |
| WO | WO 2005/037812 A1 | 4/2005 |
| WO | WO 2005/080367 A1 | 9/2005 |
| WO | WO 2005/105732 A1 | 11/2005 |
| WO | WO 2005/105733 A1 | 11/2005 |
| WO | WO 2006/044732 A2 | 4/2006 |
| WO | WO 2006/122403 A1 | 11/2006 |
| WO | WO 2006/128129 A2 | 11/2006 |
| WO | WO 2007/121280 A1 | 10/2007 |
| WO | WO 2007/121578 A1 | 11/2007 |
| WO | WO 2007/143825 A1 | 12/2007 |
| WO | 2008/008059 A1 | 1/2008 |
| WO | WO 2008/006583 A1 | 1/2008 |
| WO | WO 2008/017164 A1 | 2/2008 |
| WO | 2008/039882 A1 | 4/2008 |
| WO | 2008/104055 A1 | 9/2008 |
| WO | 2008/116304 A1 | 10/2008 |
| WO | WO 2008/123207 A1 | 10/2008 |
| WO | 2008/152093 A2 | 12/2008 |
| WO | 2009/005076 A1 | 1/2009 |
| WO | 2009/047359 A1 | 4/2009 |
| WO | 2009/105220 A1 | 8/2009 |
| WO | 2009/139373 A1 | 11/2009 |
| WO | WO 2010/019796 A1 | 2/2010 |
| WO | WO 2010/032123 A1 | 3/2010 |
| WO | WO 2010/034110 A1 | 4/2010 |
| WO | WO 2011/022348 A1 | 2/2011 |
| WO | WO 2011/063181 A1 | 5/2011 |
| WO | WO 2011/144742 A1 | 11/2011 |
| WO | WO 2012/039972 A1 | 3/2012 |
| WO | WO 2012/043634 A1 | 4/2012 |
| WO | WO 2012/066065 A1 | 5/2012 |
| WO | WO 2012/066070 A1 | 5/2012 |
| WO | WO 2012/076063 A1 | 6/2012 |
| WO | WO 2012/103071 A2 | 8/2012 |
| WO | WO 2012/127032 A1 | 9/2012 |
| WO | WO 2012/149528 A1 | 11/2012 |
| WO | WO 2012/177618 A1 | 12/2012 |
| WO | WO 2013/004290 A1 | 1/2013 |
| WO | WO 2013/020945 A1 | 2/2013 |
| WO | WO 2013/090552 A1 | 6/2013 |
| WO | WO 2013/163190 A1 | 10/2013 |
| WO | WO 2014/004229 A1 | 1/2014 |
| WO | WO 2014/004230 A1 | 1/2014 |
| WO | WO 2014/084778 A1 | 6/2014 |
| WO | WO 2014/086739 A1 | 6/2014 |
| WO | WO 2014/122267 A1 | 8/2014 |
| WO | WO 2014/126746 A1 | 8/2014 |
| WO | WO 2014/186218 A1 | 11/2014 |
| WO | WO 2014/200075 A1 | 12/2014 |
| WO | WO 2015/033299 A1 | 3/2015 |
| WO | WO 2015/034820 A1 | 3/2015 |
| WO | WO 2015/044900 A1 | 4/2015 |
| WO | WO 2015/058031 A1 | 4/2015 |
| WO | WO 2015/058067 A1 | 4/2015 |
| WO | WO 2015/091475 A1 | 6/2015 |
| WO | WO 2015/094902 A1 | 6/2015 |
| WO | WO 2015/094912 A1 | 6/2015 |
| WO | WO 2015/147020 A1 | 10/2015 |
| WO | WO 2015/167825 A1 | 11/2015 |
| WO | WO 2015/179615 A1 | 11/2015 |
| WO | WO 2015/187089 A1 | 12/2015 |
| WO | WO 2016/021742 A1 | 2/2016 |
| WO | WO 2016/111347 A1 | 7/2016 |
| WO | WO 2017/014323 A1 | 1/2017 |
| WO | WO 2017/066633 A1 | 4/2017 |
| WO | WO 2018/013840 A1 | 1/2018 |
| WO | WO 2018/210987 A1 | 11/2018 |
| WO | WO 2018/210988 A1 | 11/2018 |
| WO | WO 2018/210992 A1 | 11/2018 |
| WO | WO 2018/210994 A1 | 11/2018 |
| WO | WO 2018/210995 A1 | 11/2018 |

OTHER PUBLICATIONS

Pneumonia, NHLBI, NIH (Year: 2022).*
U.S. Appl. No. 16/614,209, filed Nov. 15, 2019, Boss et al.
U.S. Appl. No. 16/614,211, filed Nov. 15, 2019, , Boss et al.
U.S. Appl. No. 16/614,268, filed Nov. 15, 2019, Fretz et al.
U.S. Appl. No. 16/614,594, filed Nov. 18, 2019, Boss et al.
U.S. Appl. No. 16/614,605, filed Nov. 18, 2019, Boss et al.
Ahmadi, et al., "Prevention of Both Direct and Cross-Priming of Antitumor CD8+ T-Cell Responses Following Overproduction of Prostaglandin E2 by Tumor Cells In vivo," Cancer Res, vol. 68, No. 18, p. 7520-7529, (2008).
Alaa, et al., "Prostaglandin $E^2$ receptor 2 overexpression in squamous cell carcinoma of lung correlates with $p16^{INK4A}$ methylation and an unfavorable prognosis," International Journal of Oncology, vol. 34, No. 3, p. 805-812, (2009).
Al-Wadei, et al., "Celecoxib and GABA Cooperatively Prevent the Progression of Pancreatic Cancer in Vitro and in Xenograft Models of Stress-Free and Stress-Exposed Mice," PLOS One, vol. 7, No. 8, e43376, p. 1-11, (2012).
American Chemical Society (ACS), "1448123-30-5 and 1448075-88-4," SciFinder, p. 1, (2018).
Attur, et al., "Prostaglandin E2 Exert Catabolic Effects in Osteoarthritis Cartilage: Evidence for Signaling via the EP4 Receptor," The Journal of Immunology, vol. 181, No. 7, p. 5082-5088, (2008).
Babaev, et al., "Macrophage EP4 Deficiency Increases Apoptosis and Suppresses Early Atherosclerosis," Cell Metabolism, vol. 8, p. 492-501, (2008).
Babaev, et al., "Macrophage EP4 Deficiency Increases Apoptosis and Suppresses Early Atherosclerosis," Cell Metabolism, vol. 8, No. 6, p. 492-501, supplemental data, (2008).
Badawi, et al., "Expression of Cycooxygenase-2 and Peroxisome Proliferator-Activated Receptor-γand Levels of Prostaglandin E2 and -Deoxy-$\Delta^{12}$,14-Prostaglandin $J_2$ In Human Breast Cancer and Metastasis," Int. J. Cancer, vol. 103, No. 1, p. 84-90, (2003).
Banu, et al., "Selective Inhibition of Prostaglandin E2 Receptors EP2 and EP4 Induces Apoptosis of Human Endometriotic Cells through Suppression of ERK1/2, $NF_KB$, and β-Cantenin Pathways and Activation of Intrinsic Apoptic Mechanisms," Mol Endocrinol, vol. 23, No. 8, p. 1291-1305, (2009).
Bao, et al., "The regulation of CD4+ T cell immune responses toward TH2 cell development of prostaglandin E2," International Immunopharmacology, vol. 11, p. 1599-1605, (2011).
Bonavita et al., "Antagonistic Inflammatory Phenotypes Dictate Tumor Fate and Response to Immune Checkpoint Blockade," Immunity (2020), 53, 1215-1229.
Boyd et al., "A novel series of potent and selective $EP^4$ receptor ligands: Facile modulation of agonism and antagonism," Bioorganic and Medicinal Chemistry Letters, vol. 21, p. 484-487, (2011).
Brotons, et al., "A Systematic Review of Aspirin in Primary Prevention: Is It Time for a New Approach?," Am J Cardiovasc Drugs, vol. 15, p. 113-133, (2015).
Bryk, et al., "Identification of new inhibitors of protein kinase R guided by statistical modeling," Bioorganic & Medical Chemistry Letters, vol. 21, No. 13, p. 4108-4114, (2011).

(56) References Cited

OTHER PUBLICATIONS

Bryk, et al., "Identification of new inhibitors of protein kinase R guided by statistical modeling," Bioorganic & Medical Chemistry Letters, vol. 21, No. 13, p. 4108-4114—supplemental data, (2011).
Caiazzo, et al., "Adenosine signaling mediates the anti-inflammatory effects of the COX-2 inhibitor nimesulide," Biochemical Pharmacology, vol. 112, p. 72-81, (2016).
Chen et al., "Prostaglandin E2 and the protein kinase A pathway mediate arachidonic acid induction of c-fos in human prostate cancer cells," British Journal of Cancer, 2000, vol. 82(12): 2000-2006.
Chen, et al., "A novel antagonist of the prostaglandin $E_2$ $EP_4$ receptor inhibits Th1 differentiation and Th17 expansion and is orally active in arthritis models," British Journal of Pharmacology, vol. 160, No. 2, p. 292-310, (2010).
Chow, et al., "Celecoxib anti-aromatase neoadjuvant (CAAN) trial for locally advanced breast cancer," Journal of Steroid Biochemistry and Molecular Biology, vol. 111, p. 13-17, (2008).
Chuang, et al., "Inhibition of CD36-Dependent Phagocytosis by Prostaglandin $E_2$ Contributes to the Development of Endometriosis," The American Journal of Pathology, vol. 176, No. 2, p. 850-60, (2010).
Cimino, et al., "Therapeutic targets in prostaglandin $E_2$ signaling for neurologic disease," Curr Med Chem, vol. 15, No. 19, p. 1863-1869, (2008).
Cipollone, et al., "Association Between Prostaglandin E Receptor Subtype EP4 Overexpression and Unstable Phenotype in Atherosclerotic Plaques in Human," Arterioscler Thromb Vasc Biol., vol. 25, p. 1925-1931, (2005).
Clark, et al., "MF498 [N-{[4-(5,9-Diethoxy-6-oxo-6,8-dihydro-7H-pyrrolo[3,4-g]quinoin-7-y1)-3-methylbenzyl]sufonyl}-2-(2-methoxyphenyl)acetamide], a Selective E Prostanoid Receptor 4 Antagonist, Relieves Joint Inflammation and Pain in Rodent Models of Rheumatoid and Osteoarthritis," The Journal of Pharmacology and Experimental Therapeutics, vol. 325, No. 2, p. 425-434, (2008).
Colucci, et al., "Discovery of 4-{1-[{{1-[4-(trifluoromethyl)benzyl]-1H-indol-7-yl} carbonyl)amino]cyclopropyl} benzoic acid (MF-766), a highly potent and selective $EP_4$ antagonist for treating inflammatory pain," Bioorganic & Medicinal Chemistry Letters, vol. 20, p. 3760-3763, (2010).
Davis, et al., "COX-2 Inhibitors as Radiosensitizing Agents for Cancer Therapy," Am J Clin Oncol, vol. 26, No. 4-Suppl 2, p. S58-S61, (2003).
Delong, et al., "Use of Cyclooxygenase-2 Inhibition to Enhance the Efficacy of Immunotherapy," Cancer Research, vol. 63, p. 7845-7852, (2003).
Demeure, et al., "Prostaglandin $E_2$ primes naive T cells for the production of anti-inflammatory cytokines," Eur J. Immunol., vol. 27, p. 3526-3531, (1997).
Drew, et al., "Aspirin and colorectal cancer: the promise of precision chemoprevention," Nature Reviews: Cancer, vol. 16, p. 173-186, (2016).
Eberstål, et al., "Inhibition of cyclooxygenase-2 enhances immunotherapy against experimental brain tumors," Cancer Immunology, vol. 61, No. 8, p. 1191-1199, (2012).
Eberstål, et al., "Intratumoral COX-2 inhibition enhances GM-CSF immunotherapy against established mouse GL261 brain tumors," International Journal of Cancer, vol. 134,p. 2748-2753, (2014).
Elberg, et al., "EP2 receptor mediates $PGE_2$-induced cytogenesis of human renal epithelial cells," Am J Physiol Renal Physiol, vol. 293, p. F1622-F1632, (2007).
Esaki, et al., "Dual roles of $PGE_2$-EP4 signaling in mouse experimental autoimmune encephalomyelitis," PNAS, vol. 107, No. 27, p. 12233-12238, (2010).
Falandry, et al., "Celecoxib and exemestane versus placebo and exemestane in postmenopausal metastatic breast cancer patients: a double-blind phase III GINECO study," Breast Cancer Res Treat, vol. 116, p. 501-508, (2009).

Fischer, et al., "Coxibs and Other Nonsteroidal Anti-Inflammatory Drugs in Animal Models of Cancer Chemoprevention," Cancer Prevention Research, vol. 4, No. 11, p. 1728-1735, (2011).
Fu, et al., "Anti-cancer effects of COX-2 inhibitors and their correlation with angiogenesis and invasion in gastric cancer," World J Gastroenterol, vol. 10, No. 13, p. 1971-1974, (2004).
Fulton, et al., "Targeting Prostaglandin E EP Receptors to Inhibit Metastasis," Cancer Res, vol. 66, No. 20, pp. 9794-9797, (2006).
Funahashi, et al., "Delayed Progression of Pancreatic Intraepithelial Neoplasia in a Conditional $Kras^{G12D}$ Mouse Model by a Selective Cyclooxygenase-2 Inhibitor," Cancer Res, vol. 67, No. 15, p. 7068-7071, (2007).
Gallo, et al., "Prognostic Significance of Cyclooxygenase-2 Pathway and Angiogenesis in Head and Neck Squamous Cell Carcinoma," Human Pathology, vol. 33, No. 7, pp. 708-714, (2002).
Ganesh, "Evaluation of WO 2012/177618 A1 and US-2014/0179750 A1: novel small molecule antagonists of prostaglandin-E2 receptor EP2," Expert Opinion on Therapeutic Patents, 2015, vol. 25(7): 837-44.
Garcia-Roddriguez, et al., "Coxibs: Pharmacology, Toxicity and Efficacy in Cancer Clinical Trials," Recent Results in Cancer Research, vol. 191, p. 67-93, (2013).
Generali, et al., "COX-2 expression is predictive for early relapse and aromatase inhibitor resistance in patients with ductal carcinoma in situ of the breast, and is a target for treatment," British Journal of Cancer, vol. 111, p. 46-54, (2014).
Ghosh, et al., "COX-2 as a target for cancer chemotherapy," Pharmacological Reports, vol. 62, p. 233-244, (2010).
Goodwin et al., "Beyond DNA repair: DNA-PK function in cancer," Cancer Discov., 2014, vol. 4(10): 1126-1139.
Greene, et al., "Protective Groups in Organic Synthesis," Wiley-Interscience, 52 pages, (1999).
Greenhough, et al., "The COX-2/$PGE_2$ pathway: key roles in the hallmarks of cancer and adaptation to the tumour microenvironment," Carcinogenesis, vol. 30, No. 3, p. 377-386, (2009).
Hahn, et al., "Short-term dietary administration of celecoxib enhances the efficacy of tumor lysate-pulsed dendritic cell vaccines in treating murine breast cancer," Int. J. Cancer, vol. 118, No. 9, p. 2220-2231, (2006).
Harris, et al., "Prostaglandins as modulators of immunity," Trends in Immunology, vol. 23, No. 3, p. 144-150, (2002).
Heinrich-Stahl, et al., "Handbook of Pharmaceutical Salts: Properties, Selection, and Use," Wiley-VCH, p. 329-350, (2008).
Higgins, et al., "Enhancing immune responses to tumor-associated antigens," Cancer Biology & Therapy, vol. 8, No. 15, p. 1440-1449, (2009).
Hizaki, et al., "Abortive expansion of the cumulus and impaired fertility in mice lacking the prostaglandin E receptor subtype $EP_2$," Proc. Natl. Acad. Sci. USA, vol. 96, p. 10501-10506, (1999).
Honda, et al., "Prostacyclin-IP signaling and prostaglandin $E_2$-EP2/EP4 signaling both mediate joint inflammation in mouse collagen-induced arthritis," The Journal of Experimental Medicine, vol. 203, No. 2, p. 325-335, (2006).
Hong et al., "First-in-human phase I study of immunomodulatory E7046, an antagonist of PGE2-receptor E-type 4 (EP4), in patients with advance cancers," J. Immunother. Cancer (2020), 8.
Hoshino, et al., "Improvement of cognitive function in Alzheimer's disease model mice by genetic and pharmacological inhibition of the $EP_4$ receptor," Journal of Neurochemistry, vol. 120, p. 795-805, (2012).
Hoskin, et al., "Inhibition of T cell and natural killer cell function by adenosine and its contribution to immune evasion by tumor cells (Review)," International Journal of Oncology, vol. 32, p. 527-535, (2008).
Jain, et al., "Prostaglandin $E_2$ Regulates Tumor Angiogenesis in Prostate Cancer," Cancer Res, vol. 68, No. 19, p. 7750-7759, (2008).
Jin, et al., "Prostaglandin $E_2$ receptor subtype 2 (EP2) regulates microglial activation and associated neurotoxicity induced by aggregated α-synuclein," Journal of Neuroinflammation, vol. 4, No. 2, p. 1-10, (2007).
Kalinski, et al., "Regulation of Immune Responses by Prostaglandin $E_2$," The Journal of Immunology, vol. 188, p. 21-28, (2012).

(56) References Cited

OTHER PUBLICATIONS

Keene, et al., "Suppressed Accumulation of Cerebral Amyloid β Peptides in Aged Transgenic Alzheimer's Disease Mice by Transplantation with Wild-Type or Prostaglandin $E_2$ Receptor Subtype 2-Null Bone Marrow," The American Journal of Pathology, vol. 177, No. 1, p. 346-354, (2010).

Kennedy, et al., "Salt-sensitive hypertension and reduced fertility in mice lacking the prostaglandin $EP_2$ receptor," Nature Medicine, vol. 5, No. 2, p. 217-220, (1999).

Kim, et al., "IFN-γ Inhibits the Suppressive Effects of $PGE_2$ on the Production of Tumor Necrosis Factor-α by Mouse Macrophages," Immunology Investigations: A Journal of Molecular and Cellular Immunology, vol. 29, No. 3, p. 257-269, (2000).

Kofler, et al., "Decreased RORC-dependent silencing of prostaglandin receptor EP2 induces autoimmune Th17 cells," The Journal of Clinical Investigation, vol. 124, No. 6, p. 2513-2522, (2014).

Kojima, et al., "Prostaglandin E2 activates RAP1 via EP2/EP4 receptors and cAMP-signaling in rheumatoid synovial fibroblasts: Involvement of EPAC1 and PKA: The regulation of Rap1 by $PGE_2$ in RSF," Prostaglandins Other Lipid Mediat, vol. 89. No. 1-2, p. 26-33, (2009).

Kundu, et al., "Antagonism of the prostaglandin E receptor EP4 inhibits metastasis and enhances NK function," Breast Cancer Res Treat, vol. 117, No. 2, p. 235-242, (2009).

Kuo, et al., "Prognostic Role of PGE2 Receptor EP2 in Esophageal Squamous Cell Carcinoma," Ann Surg Oncol, vol. 16, p. 352-360, (2009).

Lee, et al., "Selective blockade of prostaglandin E2 receptors EP2 and EP4 signaling inhibits proliferation of human endometriotic epithelial cells and stromal cells through distinct cell cycle arrest," Fertility and Sterility, vol. 93, No. 8, p. 2498-2506, (2010).

Lee, et al., "Selective Inhibition of Prostaglandin E2 Receptors EP2 and EP4 Inhibits Adhesion of Human Endometriotic Epithelial and Stromal Cells Through Suppression of Integrin-Mediated Mechanisms," Biology of Reproduction, vol. 88, No. 3, Article: 77, p. 1-11, (2013).

Li, et al., Hydrogel dual delivered celecoxib and anti-PD-1 synergistically improve antitumor immunity, Oncoimmunology, vol. 5, No. 2, p. e1074374-1-e1074374-12, (12 pages), (2016).

Liang, et al., "The $PGE_2$ EP2 receptor accelerates disease progression and inflammation in a model of amyotrophic lateral sclerosis," Ann Neurol, vol. 64, No. 3, p. 304-314, (2008).

Liang, et al., "Function of COX-2 and Prostaglandins in Neurological Disease," J Mol Neurosci, vol. 33, p. 94-99, (2007).

Liang, et al., "Deletion of the Prostaglandin $E_2$ EP2 Receptor Reduces Oxidative Damage and Amyloid Burden in a Model of Alzheimer's Disease," The Journal of Neuroscience, vol. 25, No. 44, p. 10180-10187, (2005).

Lustberg, et al., "Phase II Trial of Neoadjuvant Exemestane in Combination With Celecoxib in Postmenopausal Women Who Have Breast Cancer," Clin. Breast Cancer, vol. 11, No. 4, p. 221-227, (2011).

Ma, et al., "A prostaglandin E (PGE) receptor EP4 antagonist protects natural killer cells from $PGE_2$-mediated immunosuppression and inhibits breast cancer metastasis," Oncoimmunology, vol. 2, No. 1, pp. e22647-1-e22647-8, (8 pages), (2013).

Maag, et al., "Prodrugs: Challenges and Rewards," Springer, ISBN: 978-0-387-49785-3, (2007).

Mandapathil, et al., "Generation and Accumulation of Immunosuppressive Adenosine by Human $CD4^+$ $CD25^{high}FOXP3^+$ Regulatory T Cells," The Journal of Biological Chemistry, vol. 285, No. 10, p. 7176-7186, (2010).

Mandapathil, et al., "Adenosine and Prostaglandin $E_2$ Cooperate in the Suppression of Immune Responses Mediated by Adaptive Regulatory T Cells," The Journal of Biological Chemistry, vol. 285, No. 36, p. 27571-27580, (2010).

Markosyan, et al., "Mammary Carcinoma Cell Derived Cyclooxygenase 2 Suppresses Tumor Immune Surveillance by Enhancing Intratumoral Immune Checkpoint Activity," Breast Cancer Research, vol. 15, No. 5, Article: R75, p. 1-13, (2013).

Marugan et al., "Evaluation of Quinazoline Analogues as Glucocerebrosidase Inhibitors with Chaperone Activity," J Med Chem., 2011, vol. 54(4): 1033-1058.

Matsumoto, et al., "Diversification of Cyclooxygenase-2-Derived Prostaglandins in Ovulation and Implantation[1]," Biology of Reproduction, vol. 64, p. 1557-1565, (2001).

Maubach, et al., "BGC20-1531, a novel, potent and selective prostanoid $EP_4$ receptor antagonist: a putative new treatment for migraine headache," British Journal of Pharmacology, vol. 156, p. 316-327, (2009).

Medeiros, et al., "Efferocytosis impairs pulmonary macrophage and lung antibacterial function via $PGE_2$/ EP2 signaling," J. Exp. Med, vol. 206, No. 1, p. 61-68, (2009).

Mitsuhashi, et al., "Regulation of interleukin-12 gene expression and its anti-tumor activities by prostaglandin $E_2$ derived from mammary carcinomas," J Leukoc Biol, vol. 76, No. 2, p. 322-332 (1-18), (2004).

Miyata, et al., "Tumor-associated Stromal Cells Expressing E-prostanoid 2 or 3 Receptors in Prostate Cancer: Correlation With Tumor Aggressiveness and Outcome by Angiogenesis and Lymphangiogenesis," Urology, vol. 81, p. 136-142, (2013).

Miyaura, et al., "Impaired Bone Resorption to Prostaglandin $E_2$ in Prostaglandin E Receptor EP4-knockout Mice," The Journal of Biological Chemistry, vol. 275, No. 26, p. 19819-19823, (2000).

Montine, et al., "Neuronal oxidative damage from activated innate immunity is $EP_2$ receptor-dependent," Journal of Neurochemistry, vol. 83, p. 463-470, (2002).

Motz, et al., "Tumor endothelium FasL establishes a selective immune barrier promoting tolerance in tumors," Nature Medicine, vol. 20, No. 6, p. 607-615, (2014).

Mu, et al., "Understanding DP receptor antagonism using a CoMSIA approach," Bioorganic & Medical Chemistry Letters, vol. 21, p. 66-75, (2011).

Murase, et al., "Effect of prostanoid $EP_4$ receptor antagonist, CJ-042,794, in rat models of pain and inflammation," European Journal of Pharmacology, vol. 580, p. 116-121, (2008).

Nakanishi, et al., "Multifaceted roles of $PGE_2$ in inflammation and cancer[1]," Semin Immunopathol, vol. 35, No. 2, p. 125-137, (2013).

Nakanishi, et al., "COX-2 inhibition alters the phenotype of tumor-associated macrophages from M2 to M1 in $Apc^{Min/+}$ mouse polyps," Carcinogenesis, vol. 32, No. 9, p. 1333-1339, (2011).

Nakao, et al., "CJ-023,423, a Novel, Potent and Selective Prostaglandin $EP_4$ Receptor Antagonist with Antihyperalgesic Properties," The Journal of Pharmacology and Experimental Therapeutics, vol. 322, No. 2, p. 686-694, (2007).

Neidle, S., Ed., Cancer Drug Design and Discovery, Chapter 18 by H. Pearce et al. entitled "Failure Modes in Anticancer Drug Discovery and Development," pp. 424-435, Elsevier Inc., copyright 2008.

Obermajer, et al., "Positive feedback between $PGE_2$ and COX2 redirects the differentiation of human dendritic cells toward stable myeloid-derived suppressor cells," Blood, vol. 118, No. 20, p. 5498-5505, (2011).

Obermajer, et al., "Key role of the positive feedback between $PGE_2$ and COX2 in the biology of myeloid-derived suppressor cells," Oncoimmunology, vol. 1, No. 5, p. 762-764, (2012).

Oshima, et al., "Prostaglandin $E_2$ signaling and bacterial infection recruit tumor—promoting macrophages to mouse gastric tumors," Gastroenterology, vol. 140, No. 2, p. 596-600, (2011).

Peluffo, et al., "A Prostaglandin E2 receptor antagonist prevents pregnancies during a preclinical contraceptive trial with female macaques," Human Reproduction, vol. 29, No. 7, p. 1400-1412, (2014).

"Pittsburgh Institute for Neurodegenerative Diseases," www.neurology.upmc.edu/pind/, 2 pages, dated 2012.

Pockaj, et al., "Reduced T-Cell and Dendritic Cell Function is Related to Cyclooxygenase-2 Overexpression and Prostaglandin $E_2$ Secretion in Patients With Breast Cancer," Annals of Surgical Oncology, vol. 11, No. 3, p. 328-339, (2004).

Pooler, et al., "Prostaglandin $E_2$ regulates amyloid precursor protein expression via the EP2 receptor in cultured rat microglia," Neuroscience Letters, vol. 362, p. 127-130, (2004).

(56) References Cited

OTHER PUBLICATIONS

Pozzi, et al., "Colon Carcinoma Cell Growth is Associated with Prostaglandin E$_2$/EP4 Receptor-evoked ERK Activation," The Journal of Biological Chemistry, vol. 279, No. 28, p. 29797-29804, (2004).
Qui et al., "Small-molecule inhibition of prostaglandin E receptor 2 impairs cyclooxygenase-associated malignant glioma growth," Br J Pharmacol. (2019), 176, 1680-1699.
Rautio, et al., "Prodrugs and Targeted Delivery Towards Better ADME Properties," Wiley, vol. 47, (2010).
Reinold, et al., "Spinal Inflammatory hyperalgesia is mediated by prostaglandin E receptors of the EP2 subtype," J. Clin. Invest, vol. 115, No. 3, p. 673-679, (2005).
Remington, "Part 5—Pharmaceutics Manufacturing," The Science and Practice of Pharmacy, 21st Edition, Lippincott Williams & Wilkins, 5 pages (2005).
Sahin, et al., "Impact of non-steroidal anti-inflammatory drugs on gastrointestinal cancers: Current state-of-the science," Cancer Letters, vol. 345, p. 249-257, (2014).
Santulli, et al., "Hormonal Therapy Deregulates Prostaglandin-Endoperoxidase Synthase 2 (*PTGS2*) Expression in Endometriotic Tissues," J Clin Endocrinol Metab, vol. 99, No. 3, p. 881-890, (2014).
Schiffman, et al., "PGE$_2$/EP4 signaling in peripheral immune cells promotes development of experimental autoimmune encephalomyelitis," Biochemical Pharmacology, vol. 87, p. 625-635, (2014).
Sharma, et al., "Tumor Cyclooxygenase-2/ Prostaglandin E$_2$—Dependent Promotion of FOXP3 Expression and CD4$^+$CD25$^+$T Regulatory Cell Activities in Lung Cancer," Cancer Res, vol. 65, No. 12, p. 5211-5220, (2005).
Shie, et al., "Microglial EP2 is Critical to Neurotoxicity From Activated Cerebral Innate Immunity," GLIA, vol. 52, p. 70-77, (2005).
Shirakami et al., "Inhibitory effects of a selective prostaglandin E2 receptor antagonist RQ-15986 on inflammation-related colon tumorigenesis in APC-mutant rats," Plos One (2021), 16 (5).
Sinha, et al., "Prostaglandin E2 Promotes Tumor Progression by Inducing Myeloid—Derived Suppressor Cells," Cancer Res, vol. 67, No. 9, p. 4507-4513, (2007).
Specht, et al., "Prostaglandins, But Not Tumor-Derived IL10, Shut Down Concomitant Tumor-Specific CTL Reponses During Murine Plasmacytoma Progression," Int J. Cancer, vol. 91, p. 705-712, (2001).
Stolina, et al., "Specific Inhibition of Cyclooxygenase 2 Restores Antitumor Reactivity by Altering the Balance of IL-10 and IL-12 Synthesis," The Journal of Immunology, vol. 164, p. 361-370, (2000).
Suzawa, et al., "The Role of Prostaglandin E Receptor Subtypes (EP1, EP2, EP3, and EP4) in Bone Resorption: An Analysis Using Specific Agonists for the Respective EPs," Endocrinology, vol. 141, No. 4, p. 1554-1559, (2000).
Takadera, et al., "Prostaglandin E2 deteriorates N-methyl-D-aspartate receptor—mediated cytotoxicity possibly by activating EP2 receptors in cultured cortical neurons," Life Sciences, vol. 78, p. 1878-1883, (2006).
Take et al., "Prostaglandin E Receptor 4 Antagonist in Cancer Immunotherapy: Mechanisms of Action," Front. Immunol. (2020), 11:324.
Terada, et al., "Identification of EP4 as a Potential Target for the Treatment of Castration-Resistant Prostate Cancer Using a Novel Xenograft Model," Cancer Res, vol. 70, No. 4, p. 1606-1615, (2010).
Tilley, et al., "Reproductive failure and reduced blood pressure in mice lacking the EP2 prostaglandin E2 receptor," The Journal of Clinical Investigation, vol. 103, No. 11, p. 1539-1545, (1999).
Tomita, et al., "Effects of Selective Prostaglandin EP4 Receptor Antagonist on Osteoclast Formation and Bone Resorption In Vitro," Bone, vol. 30, No. 1, p. 159-163, (2002).
Toomey, et al., "Therapeutic vaccination with dendritic cells pulsed with tumor—derived Hsp70 and COX-2 inhibitor induces protective immunity against B16 melanoma," Vaccine, vol. 26, p. 3540-3549, (2008).
Veltman, et al., "COX-2 inhibition improves immunotherapy and is associated with decreased Nos. of myeloid-derived suppressor cells in mesothelioma. Celecoxib influences MDSC function," BMC Cancer, vol. 10, Article: 464, p. 1-13, (2010).
Volenec, et al., "Mouse Colostomy Model for Studies on Large Bowel Cancer," Journal of Surgical Oncology, vol. 13, p. 39-44, (1980).
Wang, et al., "Recent advances in basic science Prostaglandins and Cancer," Gut, vol. 55, p. 115-122, (2006).
Wang, et al., "Prostaglandin E2 Induces Vascular Endothelial Growth Factor Secretion in Prostate Cancer Cells Through EP2 Receptor-Mediated cAMP Pathway," Molecular Carcinogenesis, vol. 46, p. 912-923, (2007).
Wang, et al., "Chemoprevention of Cancers in Gastrointestinal Tract with Cyclooxygenase 2 Inhibitors," Current Pharmaceutical Design, vol. 19, p. 115-125, (2013).
Wang et al., "Combination of EP4 antagonist MF-766 and anti-PD-1 promotes anti-tumor efficacy by modulating both lymphocytes and myeloid cells," Oncoimmunology (2021), 10 (1).
Wouters, et al., "Pharmaceutical Salts and Co-crystals," (RSC Drug Discovery Series No. 16, ISSN: 2041-3203, Publisher: The Royal Society of Chemistry), (2012).
Xin, et al., "Targeting COX-2 and EP4 to control tumor growth, angiogenesis, lymphangiogenesis and metastasis to the lungs and lymph nodes in a breast cancer model," Laboratory Investigation, vol. 92, p. 1115-1128, (2012).
Xu, et al., "An EP4 Antagonist ONO-AE3-208 Suppresses Cell Invasion, Migration, and Metastasis of Prostate Cancer," Cell Biochem Biophys, vol. 70, p. 521-527, (2014).
Xu, et al., "Molecular docking and synthesis of novel quinazoline analogues as inhibitors of transcription factors NF-κB activation and their anti-cancer activities," Bioorganic & Medicinal Chemistry, vol. 21, p. 540-546, (2013).
Yamaguchi, et al., "Gefitinib and celecoxib in advanced metastatic gastrointestinal tumors: a pilot feasibility study," J Gastrointest Oncol, vol. 5, No. 1, p. 57-66, (2014).
Yang, et al., "Host and Direct Antitumor Effects and Profound Reduction in Tumor Metastasis with Selective EP4 Receptor Antagonism," Cancer Res, vol. 66, No. 19, p. 9665-9672, (2006).
Zelenay, et al., "Cyclooxygenase-Dependent Tumor Growth through Evasion of Immunity," Cell, vol. 162, p. 1257-1270, (2015).
Zhang, et al., "Enhancement of Antitumor Activity by Combination of Tumor Lysate-Pulsed Dendritic Cells and Celecoxib in a Rat Glioma Model," Oncology Research, vol. 20, No. 10, p. 447-455, (2013).
Zhang, et al., "Tumor Growth Inhibition by Simultaneously Blocking Epidermal Growth Factor Receptor and Cyclooxygenase-2 in a Xenograft Model," Clin Cancer Res, vol. 11, No. 17, p. 6261-6269, (2005).
Zhang, et al., "PGE2 promotes angiogenesis through EP4 and PKA Cγ pathway," Blood, vol. 118, No. 19, p. 5355-5364, (2011).
U.S. Appl. No. 18/058,873, filed Nov. 27, 2022, Fretz et al.

\* cited by examiner

N-SUBSTITUTED INDOLE DERIVATIVES AS PGE2 RECEPTOR MODULATORS

CROSS REFERENCE TO RELATED APPLICATIONS

This application is a divisional of U.S. patent application Ser. No. 15/777,597, filed on May 18, 2018, which is a United States Application under 35 U.S.C. 371 of PCT Application No. PCT/EP2016/078028, filed on Nov. 17, 2016, which claims the benefit of PCT Application No. PCT/EP2015/077269, filed on Nov. 20, 2015, the contents of each of which are incorporated herein by reference.

The present invention relates to novel N-substituted indole derivatives of formula (I) and their use as pharmaceuticals. The invention also concerns related aspects including processes for the preparation of the compounds, pharmaceutical compositions containing one or more compounds of formula (I), and their use as modulators of the PGE2 receptors EP2 (alias PTGER2, alias PGE2 Receptor EP2 Subtype) and/or EP4 (alias PTGER4, alias EP4R, alias PGE2 Receptor EP4 Subtype). The compounds of formula (I) may especially be used as single agents or in combination with one or more therapeutic agents and/or chemotherapy and/or radiotherapy and/or immunotherapy in the prevention/prophylaxis or treatment of cancers; in particular the prevention/prophylaxis or treatment of melanoma; lung cancer; bladder cancer; renal carcinomas; gastro-intestinal cancers; endometrial cancer; ovarian cancer; cervical cancer; and neuroblastoma.

Prostaglandin E2 (PGE2) is a bioactive lipid that can elicit a wide range of biological effects associated with inflammation and cancer. PGE2 belongs to the prostanoid family of lipids. Cyclooxygenase (COX) is the rate-limiting enzyme in the synthesis of biological mediators termed prostanoids, consisting of prostaglandin PGD2, PGE2, PGF2a, prostacyclin PGI2, and thromboxane TXA2. Prostanoids function via activation of seven transmembrane G-protein-coupled receptors (GPCRs), in particular EP1, EP2, EP3, and EP4 are receptors for PGE2. Activation of both EP2 and EP4 by PGE2 stimulates adenylate cyclase, resulting in elevation of cytoplasmic cAMP levels to initiate multiple downstream events via its prototypical effector Protein kinase A. In addition, PGE2 is also able to signal via PI3K/AKT and Ras-MAPK/ERK signalling.

Cancers figure among the leading causes of death worldwide. Tumors are comprised of abnormally proliferating malignant cancer cells but also of a functionally supportive microenvironment. This tumor microenvironment is comprised of a complex array of cells, extracellular matrix components, and signaling molecules and is established by the altered communication between stromal and tumor cells. As tumors expand in size, they elicit the production of diverse factors that can help the tumor to grow such as angiogenic factors (promoting ingrowth of blood vessels) or that can help to evade the attack of the host immune response. PGE2 is such an immuno-modulatory factor produced in tumors.

It is well established that COX2, mainly via PGE2, promotes overall growth of tumors and is upregulated and correlates with clinical outcome in a high percentage of common cancers, especially colorectal, gastric, esophageal, pancreatic, breast and ovarian cancer. High COX-2 and PGE2 expression levels are associated with neoplastic transformation, cell growth, angiogenesis, invasiveness, metastasis and immune evasion.

The finding that COX2 is over-expressed and plays an important role in carcinogenesis in gastrointestinal (GI) cancers including among others esophagus, gastric and colorectal cancers has led to the fact that COX-inhibitors (Coxibs), including Celecoxib, and other nonsteroidal anti-inflammatory drugs (NSAID), including aspirin, are among the most studied cancer chemopreventive agents in development today (for review see for example Wang R et al, Curr Pharm Des. 2013; 19(1):115-25; Garcia Rodriguez L A et al, Recent Results Cancer Res. 2013; 191:67-93, Sahin I H et al, Cancer Lett. 2014 Apr. 10; 345(2):249-57; Drew D A et al, Nat Rev Cancer 2016, 16:173; Brotons C et al, Am J Cardiovasc Drugs. 2015 April; 15(2):113) In addition to COX2 and PGE2, also EP receptors, especially EP2 and EP4, are aberrantly over-expressed in multiple types of cancers, especially in gastro-intestinal (GI) cancers and pancreatic cancer. Furthermore, the overexpression of PGE2 and/or EP2 and/or EP4 correlates with diseases progression in some cancer types such as oesophageal squamous cell carcinoma (Kuo K T et al, Ann Surg Onc 2009; 16(2), 352-60); squamous cell carcinoma of the lung (Alaa M et al, Int J Oncol 2009, 34(3); 805-12); prostate cancer (Miyata Y et al, Urology 2013, 81(1):136-42); Badawi A F and Badr M Z Int J Cancer. 2003, 103(1):84-90); head and neck squamous cell carcinoma (Gallo 0 et al, Hum Pathol. 2002, 33(7):708-14).

In accordance to studies performed with Coxibs, in mice, knockout of either COX1, COX2, microsomal prostaglandin E synthase 1 (mPTGES1), EP2 or EP4 resulted in reduced tumor incidence and progression in different tumor models. Conversely, overexpression of COX2 or mPTGES1 in transgenic mice resulted in increased tumor incidence and tumor burden (for review see Nakanishi M. and Rosenberg D. W., Seminars in Immunopathology 2013, 35: 123-137; Fischer S M et al Cancer Prev Res (Phila) 2011 November; 4(11): 1728-35; Fulton A M et al Cancer Res 2006; 66(20); 9794-97).

Several pharmacological studies to inhibit tumor growth and progression using EP receptor antagonists or COX2 inhibitors in different tumor models have been conducted in mice. Among others, EP antagonists and/or COX2 inhibitors reduced tumor growth and metastasis in experimental models of colorectal cancer (e.g Yang L et al Cancer Res 2006, 66(19), 9665-9672; Pozzi A. et al JBC 279(28); 29797-29804), lung carcinomas (Sharma S et al Cancer Res 2005 65(12), 5211-5220), gastro-intestinal cancer (Oshima H et al Gastroenterology 2011, 140(2); 596-607; Fu S L et al world J Gastroenterol 2004, 10(13); 1971-1974), breast cancer (Kundu N et al, Breast Cancer Res Treat 117, 2009; 235-242; Ma X et al, OncoImmunology 2013; Xin X et al Lab Investigation 2012, 1-14; Markosyan N et al; Breast Cancer Res 2013, 15:R75), prostate cancer (Xu S et al, Cell Biochem Biophys 2014, Terada et al Cancer Res 70(4) 2010; 1606-1615), pancreatic cancer (Al-Wadei H A et al, PLOS One 2012, 7(8):e43376; Funahashi H et al, Cancer Res 2007, 67(15):7068-71). COX2 inhibitors were approved for the treatment of familial adenomatous polyposis (FAP) which is an inherited pre-disposition syndrome for colorectal cancer, but later retracted due to cardiovascular side effects.

Mechanistically, PGE2 signalling is mainly involved in the crosstalk between tumor and stromal cells, thereby creating a microenvironment which is favourable for the tumor to grow. In particular, PGE2 signalling via EP2 and EP4 can for example (i) suppress the cytotoxicity and cytokine production of natural killer cells, (ii) skew the polarization of tumor-associated macrophages towards tumor-promoting M2 macrophages (see for example Nakanishi Y et al Carcinogenesis 2011, 32:1333-39), (iii) regulate the activation, expansion and effector function of both Tregs (regulatory T cells) and MDSC (myeloid derived suppressor cells), which are potent immunosuppressive cells that accumulate in tumors both in patients and in experimental animal models (see for example Sharma S et al, Cancer Res 2005, 5(12):5211-20; Sinha P et al Cancer Res 2007, 67(9), 4507-4513; Obermajer N et al, Blood 2011, 118(20):5498-5505); (iv) down-regulate IFN-γ, TNF-α IL-12 and IL-2 expression in immune cells such as natural killer cells, T-cells, dendritic cells and macrophages, impairing the ability of these immune cells to induce tumor cell apoptosis and restrain tumorigenesis (see for example Bao Y S et al, Int Immunopharmacol. 2011; 11(10):1599-605; Kim J G and Hahn Y S, Immunol Invest. 2000; 29(3):257-69; Demeuere C E et al, Eur J Immunol. 1997; 27(12):3526-31; Mitsuhashi M et al, J Leukoc Biol. 2004; 76(2):322-32; Pockaj B A et al, Ann Surg Oncol. 2004; 11(3):328-39; (v) suppress activation, IL-2 responsivness, expansion and cytotoxicity of T-cells thereby contributing to local immunsuppresion (see for example Specht C et al, Int J Cancer 200191:705-712); (vi) inhibit maturation of dendritic cells, their ability to present antigens and to produce IL-12, resulting in abortive activation of cytotoxic T-cells (see for example Ahmadi M et al, Cancer Res 2008, 68(18):7250-9; Stolina M et al, J Immunol 2000, 164:361-70); (vii) regulate tumor angiogenesis (formation of new blood vessels for nutrient and oxygen supply) by enhancing endothelial cell motility and survival as well as by increasing the expression of VEGF (vascular endothelial growth factor) (see for example Zhang Y and Daaka Y, Blood 2011; 118(19):5355-64; Jain S et al, Cancer Res. 2008; 68(19):7750-9; Wang and Klein, Molecular Carcinogenesis 2007, 46:912-923; (viii) enhance tumor cell survival (via PI3K/AKT and MAPK signalling). For review see for example Kalinski P, J Immunol 2012, 188(1), 21-28; Obermajer N et al, Oncoimmunology 1(5), 762-4; Greenhough A et al, carcinogenesis 2009, 30(3), 377-86; Wang D and Dubois R N, Gut 2006, 55, 115-122; Harris S G e al Trends Immunol 2002, 22, 144-150).

Coxibs have been shown to render tumor cells more sensitive to radiation and chemotherapy and several clinical trials have been performed or are ongoing combining Coxibs with radio- and/or chemotherapy (for review see e.g Ghosh N et al, Pharmacol Rep. 2010 March-April; 62(2):233-44; Davis T W et al, Am J Clin Oncol. 2003, 26(4):S58-61; see also Higgins J P et al, Cancer Biol Ther 2009, 8:1440-49).

Furthermore, there is some evidence of additive effects and/or synergy between Coxibs and epidermal growth factor receptor (EGFR) inhibitors (see for example Zhang X et al, Clin Cancer Res. 2005, 11(17):6261-9; Yamaguchi N H et al, J Gastrointest Oncol. 2014, 5(1):57-66); and with aromatase inhibitors (see for example Generali D et al, Br J Cancer. 2014; 111(1):46-54; Lustberg M B et all, Clin Breast Cancer. 2011 August; 11(4):221-7; Falandry C et al, Breast Cancer Res Treat. 2009 August; 116(3):501-8); Chow L W et al, J Steroid Biochem Mol Biol. 2008, 111(1-2):13-7).

Moreover, additive/synergistic effects have been seen in different mouse tumor models when Aspirin (a COX1/2 inhibitor) was combined with and anti-VEGF antibody (Motz G T et al; Nat Med 2014 20(6):607) and this combination is currently under investigation in clinical trials (NCT02659384).

Recently, it has been shown that, if combined, different immunotherapeutic approaches can have enhanced anti-tumor efficacy. Due to the immune-modulatory properties of PGE2, Coxibs have thus also been used in combination with different immunotherapeutic approaches. In particular, additive or even synergistic effects could be observed when Coxibs were combined with dendritic cell vaccination in a rat glioma model and in a mouse mesothelioma or melanoma model (Zhang H et al, Oncol Res. 2013; 20(10):447-55; Veltman J D et al, BMC Cancer. 2010; 10:464; Toomey D et all, Vaccine. 2008 Jun. 25; 26(27-28):3540-9); with granulocyte-macrophage colony-stimulating factor (GM-CSF) in mouse brain tumors (Eberstál S et al, Int J Cancer. 2014 Jun. 1; 134(11):2748-53); with interferon gamma (IFN-γ) in brain tumors (Eberstál S et al, Cancer Immunol Immunother. 2012, 61(8):1191-9); with dendritic cell vaccination or with GM-CSF in a mouse breast cancer model (Hahn T et al, Int J Cancer. 2006,118(9):2220-31); and with adenoviral interferon beta (IFN-β) therapy in a mouse mesothelioma model (DeLong P et al, Cancer Res. 2003 Nov. 15; 63(22):7845-52). Along these lines, additive or even synergistic effects of Coxibs and/or EP2 and/or EP4 antagonists can also be envisaged with agents acting on cytotoxic T-lymphocyte-associated protein 4 (CTLA-4) such as anti-CTLA-4 antibodies; anti-TIM-3 antibodies, anti-Lag-3 antibodies; anti-TIGIT antibodies; or, in particular, with agents acting on programmed cell death protein 1 (PD1), such as anti-PD1 or anti-PDL1 (programmed cell death ligand 1) antibodies (Yongkui Li et al Oncoimmunology 2016, 5(2):e1074374; Zelenay S et al, Cell 2015, 162; 1-14; WO2013/090552, which indicates a synergistic effect of dual EP2 and EP4 blockade in combination with agents acting on PD1).

Adenosine is another endogenous factor with anti-inflammatory properties that is generated through the activity of ectonucleotidases, CD39 and CD73, expressed on various cell types, including regulatory T cells (Treg) (Mandapathil M et al, J Biol Chem. 2010; 285(10):7176-86). Immune cells also respond to Adenosine, because they bear receptors for ADO, which are mainly of the A2a/A2b type (Hoskin D W, et al, Int J Oncol 2008, 32:527-535). Signaling via Adenosine receptors and EP2/EP4 receptors converges on the cytoplasmic adenylyl cyclase, leading to up-regulation of cAMP. It was shown that Adenosine and PGE2 cooperate in the suppression of immune responses mediated by regulatory T cells (Mandapathil M et al, J Biol Chem. 2010; 285(36):27571-80; Caiazzo E et al, Biochem Pharmacol. 2016; 112:72-81).

Thus, the present EP2 and/or EP4 antagonists may be useful, alone, or in combination with one or more therapeutic agents and/or chemotherapy and/or radiotherapy and/or immunotherapy; in particular in combination with chemotherapy, radiotherapy, EGFR inhibitors, aromatase inhibitors, anti-angiogenic drugs, adenosine inhibitors, immunotherapy such as especially PD1 and/or PDL1 blockade, or other targeted therapies; for the prevention/prophylaxis or treatment of cancers, notably for the prevention/prophylaxis or treatment of skin cancer including melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastro-intestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; and virally induced tumors.

In addition, selective or dual EP2 and/or EP4 antagonists may be useful in several other diseases or disorders responding for example to treatment with COX2 inhibitors, with the advantage that EP2 and/or EP4 antagonists should not possess the potential cardiovascular side effects seen with COX2 inhibitors, which are mainly due to interference with PGI2 and TXA2 synthesis (see for example Boyd M J et al, bioorganic and medicinal chemistry letters 21, 484, 2011). For example, blockade of prostaglandin production by COX inhibitors is the treatment of choice for pain, including especially inflammatory pain and painful menstruation. Thus EP2 and/or EP4 and/or dual EP2/EP4 antagonists may be useful for the treatment of pain, especially inflammatory pain. Evidence from EP2 knockout mice suggest that EP2 antagonists can be used for the treatment of inflammatory hyperalgesia (Reinold H et al, J Clin Invest 2005, 115(3): 673-9). In addition, EP4 antagonists have beneficial effect in vivo in inflammatory pain models (eg Murase A, Eur J Pharmacol 2008; Clark P, J Pharmacol Exp Ther. 2008; Maubach K A Br J Pharmacol. 2009; Colucci J Bioorg Med Chem Lett. 2010, Boyd M J et al, Bioorg Med Chem Lett 2011, Chn Q et al Br J Phramacol 2010, Nakao K et al, J Pharmacol Exp Ther. 2007 August; 322(2):686-94). Administration of an EP2 in combination with an EP4 antagonist showed significant, but partial inhibition of joint inflammation in mouse collagen-induced arthritis model (Honda T et al J Exp Med 2006, 203(2):325-35).

EP2 and/or dual EP2/EP4 antagonists may be of use to decrease female fertility, i.e. they have been shown to prevent pregnancy if used as contraceptive in macaques (Peluffo M C et al Hum Reprod 2014). EP2 knockout mice have decreased fertility, smaller litter sizes and reduced cumulus expansion (Matsumoto et al, Biology of reproduction 2001, 64; 1557-65; Hitzaki et al, PNAS 1999, 96(18), 10501-10506; Tilley S L J Clin Inves 1999, 103(11):1539-45; Kennedy C R et al, Nat Med 1999 5(2):217-20).

There is also rationale that EP2 and/or EP4 antagonists may be of use to prevent or treat endometriosis: for example EP2, EP3 and EP4 and COX2 are overexpressed in endometriosis cell lines and tissues (e.g. Santulli P et al J Clin Endocrinol Metab 2014, 99(3):881-90); antagonist treatment was shown to inhibit the adhesion of endometrial cells in vitro (Lee J et al Biol Reprod 2013, 88(3):77; Lee J et al Fertil Steril 201, 93(8):2498-506); COX2 inhibitors have been shown to reduce endometric lesions in mice via EP2 (Chuang P C et al, Am J Pathol 2010, 176(2):850-60); and antagonist treatment has been shown to induce apoptosis of endometric cells in vitro (Banu S K et al, MOI endocrinol 2009, 23(8) 1291-305).

Dual EP2/EP4 antagonists, or the combination of a selective EP2 antagonists with a selective EP4 antagonist, may be of potential use for autoimmune disorders; e.g. they have been shown to be effective in mouse model for multiple sclerosis (MS) (Esaki Y et al PNAS 2010, 107(27):12233-8; Schiffmann S et al, Biochem Pharmacol. 2014, 87(4): 625-35; see also Kofler D M et al J Clin Invest 2014, 124(6): 2513-22). Activation of EP2/EP4 signalling in cells in vitro (Kojima F et al Prostaglandins Other Lipid Mediat 2009, 89:26-33) linked dual or selective EP2 and/or EP4 antagonists to the treatment of rheumatoid arthritis. Also, elevated levels of PGE(2) have been reported in synovial fluid and cartilage from patients with osteoarthritis (OA) and it has been shown that PGE2 stimulates matrix degradation in osteoarthritis chondrocytes via the EP4 receptor (Attur M et al, J Immunol. 2008; 181(7):5082-8).

EP4 overexpression is associated with enhanced inflammatory reaction in atherosclerotic plaques of patients (Cipollone F et al, Artherioscler Thromb Vasc Biol 2005, 25(9); 1925-31), thus the use of EP4 and/or dual EP2/EP4 antagonists may be indicated for plaque stabilization and prevention/prophylaxis of acute ischemic syndromes. In addition, EP4 deficiency suppresses early atherosclerosis, by compromising macrophage survival (Babaev V R et al, Cell Metab. 2008 December; 8(6):492-501) EP2 and/or dual EP2/EP4 antagonists may also be useful in the treatment of pneumonia: intrapulmonary administration of apoptotic cells demonstrated that PGE(2) via EP2 accounts for subsequent impairment of lung recruitment of leukocytes and clearance of Streptococcus pneumoniae, as well as enhanced generation of IL-10 in vivo (Medeiros A1 et al J Exp Med 2009 206(1):61-8).

EP2 and/or dual EP2/EP4 antagonists may in addition be useful for the treatment of neurodegenerative diseases (for review see Cimino P J et al, Curr Med Chem. 2008; 15(19):1863-9). EP2 receptor accelerates progression of inflammation in a mouse model of amyotrophic lateral sclerosis (ALS) (Liang X et al, Ann Neurol 2008, 64(3): 304-14); COX2 inhibitors have been shown to be neuroprotective in rodent models of stroke, Parkinson disease and ALS (for review see Liang X et al J Mol Neurosci 2007, 33(1):94-9), decreased neurotoxicity was observed in EP2 knockout mice treated with parkinsonian toxican (Jin J et al, J Neuroinflammation 2007, 4:2), PGE2 via EP2 aggravates neurodegeneration in cultured rat cells (Takadera T et al, Life Sci 2006, 78(16): 1878-83); Reduced amyloid burden was observed in Alzheimer's disease mouse model if crossed with EP2 knockout mice (Liang X et al J Neurosci 2005, 25(44):10180-7; Keene C D et al, Am J Pathol. 2010, 177(1):346-54). EP2 null mice are protected from CD14-dependent/innate immunity mediated neuronal damage in neurodegenerative disease (Shie F S et al Glia 2005, 52(1): 70-7); PGE2 via EP2 increases amyloid precursor protein (APP) expression in cultured rat microglial cells (Pooler A M et al Neurosci. Lett. 2004, 362(2):127-30). EP2 antagonist limits oxidative damage from activation of innate immunity (intracranial injection of LPS) in the brain and could be used for Alzheimer or HIV associated dementia (Montine T J et al, J Neurochem 2002, 83(2):463-70). In an Alzheimer's disease mouse model cognitive function could be improved by genetic and pharmacological inhibition of EP4 (Hoshino T et al, J Neurochem 2012, 120(5):795-805).

EP2 and/or dual EP2/EP4 antagonists may also be useful to treat autosomal dominant polycystic kidney disease (ADPKD): PGE2 via EP2 induces cystogenesis of human renal epithelial cells; and EP2 was found to be overexpressed in patient samples (Elberg G et al, Am J Physiol Renal Physiol 2007, 293(5):F1622-32).

EP4 and/or dual EP2/EP4 antagonists may also be useful to treat osteoporosis: PGE2 stimulates bone resorption mainly via EP4 and partially via EP2 (Suzawa T et all, Endocrinology. 2000 April; 141(4):1554-9), EP4 knockout mice show impaired bone resorption (Miyaura C et al, J Biol Chem 2000, 275(26): 19819-23) and an EP4 antagonists showed partial inhibition of PGE(2)-stimulated osteoclastogenesis and osteoclastic bone resorption (Tomita M et al, Bone. 2002 January; 30(1):159-63).

WO2008/152093 discloses selective EP2 receptor modulators which comprise an indole ring linked to the rest of the molecule in position 3, and a pyrimidine moiety which however is not substituted with a directly linked aromatic substituent. WO2006/044732 discloses pyrimidine compounds which are modulators of PGD2 claimed to be useful e.g. in the treatment of allergic diseases; however for example the exemplified compound CAS 1001913-77-4 has been tested to be inactive on both the EP2 and the EP4 receptor in the in vitro assay set out in the experimental part below. WO2008/006583 discloses pyrimidin derivatives which are ALK-5 inhibitors. WO2006/044732 and WO2008/039882 disclose certain pyrimidine derivatives as protaglandin D2 receptor antagonists. Pyrimidin-2-yl derivatives are disclosed in WO2013/020945, WO2012/127032, WO2011/144742, Bioorg. Med. Chem 2011, 21(13) 4108-4114 and Bioorg. Med. Chem 2011, 21(1) 66-75. Certain indole-1-acetamide compounds are known as library compounds, e.g. CAS 1448123-30-5 and CAS 1448075-88-4. Further compounds which are claimed to be active as anti-cancer agents are disclosed in WO2006/128129, WO2008/008059 and Bioorg. Med. Chem 2013, 21(2), 540-546.

The present invention provides novel N-substituted indole derivatives of formula (I) which are modulators of the prostaglandin 2 receptors EP2 and/or EP4. Certain compounds of the present invention are dual antagonists of both the EP2 and the EP4 receptor. The present compounds may, thus, be useful for the prevention/prophylaxis or treatment of diseases which respond to the blockage of the EP2 receptors and/or the EP4 receptors such as especially cancers; as well as pain including especially inflammatory pain and painful menstruation; endometriosis; acute ischemic syndromes in atherosclerotic patients; pneumonia; neurodegenerative diseases including amyotrophic lateral sclerosis, stroke; Parkinson disease, Alzheimer's disease and HIV associated dementia; autosomal dominant polycystic kidney disease; and to control female fertility.

1) A first aspect of the invention relates to compounds of the formula (I)

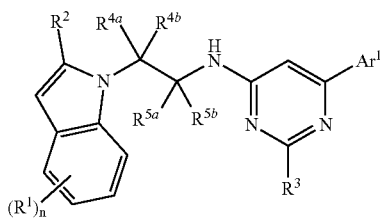

Formula (I)

wherein $(R^1)_n$ represents (in addition to $R^2$) one, two or three optional substituents on the indole ring (i.e. n represents the integer 0, 1, 2, or 3), wherein said substituents are independently selected from $(C_{1-3})$alkyl (especially methyl), $(C_{1-3})$alkoxy (especially methoxy), halogen (especially fluoro, chloro, or bromo), $(C_{1-3})$fluoroalkyl (especially trifluoromethyl), $(C_{1-3})$fluoroalkoxy (especially trifluoromethoxy), or cyano; or two $R^1$ together form a group —O—$CH_2$—O—, and the remaining $R^1$, if present, represents halogen (especially fluoro or chloro);

$R^2$ represents $(C_{1-4})$alkyl (especially methyl), halogen (especially chloro), or cyano;

$R^3$ represents hydrogen, methyl or trifluoromethyl (especially hydrogen);

$R^{4a}$ and $R^{4b}$ independently represent hydrogen, methyl, or $R^{4a}$ and $R^{4b}$ together with the carbon atom to which they are attached represent a cycloprop-1,1-diyl group;

$R^{5a}$ and $R^{5b}$ independently represent hydrogen, methyl, or $R^{5a}$ and $R^{5b}$ together with the carbon atom to which they are attached represent a cycloprop-1,1-diyl group;

$Ar^1$ represents phenyl, or 5- or 6-membered heteroaryl (notably 5-membered heteroaryl, especially thiophenyl or thiazolyl); wherein said phenyl or 5- or 6-membered heteroaryl independently is mono-, di- or tri-substituted, wherein the substituents are independently selected from $(C_{1-6})$alkyl (especially methyl, ethyl, n-propyl, isopropyl, n-butyl, isobutyl, 1-methyl-propan-1-yl, tert.-butyl, 3-methyl-butyl);

$(C_{1-4})$alkoxy (especially methoxy, ethoxy, n-propoxy, isopropoxy, n-butoxy, isobutoxy);

$(C_{1-3})$fluoroalkyl, wherein said $(C_{1-3})$fluoroalkyl is optionally substituted with hydroxy (especially trifluoromethyl, 2,2,2-trifluoro-1-hydroxy-ethyl);

$(C_{1-3})$fluoroalkoxy (especially difluoromethoxy, trifluoromethoxy, 2,2,2-trifluoroethoxy);

halogen (especially fluoro, chloro, bromo);

cyano;

$(C_{3-6})$cycloalkyl, wherein said $(C_{3-6})$cycloalkyl is unsubstituted or mono-substituted with amino (especially cyclopropyl, 1-amino-cyclopropyl);

$(C_{4-6})$cycloalkyl containing a ring oxygen atom, wherein said $(C_{4-6})$cycloalkyl containing a ring oxygen atom is unsubstituted or mono-substituted with fluoro, hydroxy, or methoxy (especially 3-fluoro-oxetan-3-yl, 3-hydroxy-oxetan-3-yl, 3-methoxy-oxetan-3-yl);

$(C_{3-6})$cycloalkyl-oxy (especially cyclobutyl-oxy, cyclopentyl-oxy);

hydroxy;

nitro;

—B(OH)$_2$;

2,2,2-trifluoro-1,1-dihydroxy-ethyl;

—$X^1$—CO—$R^{O1}$, wherein $X^1$ represents a direct bond, $(C_{1-3})$alkylene (especially —$CH_2$—, —$CH_2$—$CH_2$—), —O—$(C_{1-3})$alkylene-* (especially —O—$CH_2$—*, —O—$CH(CH_3)$—*, —O—$CH_2$—$CH_2$—*), —NH—$(C_{1-3})$alkylene-* (especially —NH—$CH_2$—*, —NH—$CH(CH_3)$—*), —S—$CH_2$—*, —$CF_2$—, —CH=CH—, —CH=CH—, —NH—CO—*, —CO—, or $(C_{3-5})$cycloalkylene; wherein the asterisks indicate the bond that is linked to the —CO—$R^{O1}$ group; and $R^{O1}$ represents

—OH;

—O—$(C_{1-4})$alkyl (especially ethoxy, methoxy);

—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —$NH_2$;

—O-phenyl;

—O—CH$_2$—CO—R$^{O4}$, wherein R$^{O4}$ represents hydroxy, or (C$_{1-4}$)alkoxy, or —N[(C$_{1-4}$)alkyl]$_2$;

—O—CH$_2$—O—CO—R$^{O5}$, wherein R$^{O5}$ represents (C$_{1-4}$)alkyl or (C$_{1-4}$)alkoxy; or —O—CH$_2$—CH$_2$—N[(C$_{1-4}$)alkyl]$_2$ (especially —O—CH$_2$—CH$_2$—N(CH$_3$)$_2$);

(5-methyl-2-oxo-[1,3]dioxol-4-yl)-methyloxy-;

[wherein in particular such group —X$^1$—CO—R$^{O1}$ represents —COOH, —CO—O—C$_2$H$_5$, —O—CH$_2$—COOH, —NH—CH$_2$—COOH, —CO—NH—SO$_2$—CH$_3$, —CO—NH—SO$_2$—C(CH$_3$)$_2$, —CO—NH—SO$_2$-cyclopropyl, —CO—NH—SO$_2$-phenyl, —COO—CH$_3$, —CO—NH—SO$_2$-ethyl, —CO—NH—SO$_2$—NH$_2$, —COO—CH$_2$—COOH, —COO—CH$_2$—CH$_2$—N(CH$_3$)$_2$, —COO—CH$_2$—CO—N(CH$_3$)$_2$, —CO—O—CH$_2$—O—CO—O-ethyl, —COO—CH$_2$—O—CO-propyl, (5-methyl-2-oxo-[1,3]dioxol-4-yl)-methyl-O—CO—, —CH$_2$—COOH, —CH$_2$—CO—O-ethyl, —CH$_2$—CH$_2$—COOH, —CF$_2$—COOH, —CH=CH—COOH, —CH=CH—CO—O-ethyl, —NH—CO—COOH, —CO—COOH, —O—CH$_2$—CH$_2$—COOH, —O—CH(CH$_3$)—COOH, —NH—CH(CH$_3$)—COOH, —NH—CH$_2$—COO—CH$_3$, —COO-phenyl, 1-carboxy-cyclopropan-1-yl, 1-carboxy-cyclopentan-1-yl];

—CO—CH$_2$—CN;

—CO—CH$_2$—OH;

—CO—H;

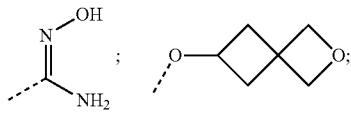

2-hydroxy-3,4-dioxo-cyclobut-1-enyl;

hydroxy-(C$_{1-4}$)alkyl (especially hydroxymethyl, 1-hydroxy-ethyl);

dihydroxy-(C$_{2-4}$)alkyl (especially 1,2-dihydroxy-ethyl);

hydroxy-(C$_{2-4}$)alkoxy (especially 2-hydroxy-ethoxy);

(C$_{1-4}$)alkoxy-(C$_{2-4}$)alkoxy (especially 2-methoxy-ethoxy);

—(CH$_2$)$_m$—NR$^{N1}$R$^{N2}$, wherein m represents the integer 0 or 1; and wherein R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl, or —SO$_2$—(C$_{1-4}$)alkyl (wherein preferably at least one of R$^{N1}$ and R$^{N2}$ represents hydrogen);

or R$^{N1}$ independently represents hydrogen or (C$_{1-4}$)alkyl, and R$^{N2}$ independently represents —CO—H, —CO—(C$_{1-3}$)alkyl, —CO—(C$_{1-3}$)alkylene-OH, or —CO—O—(C$_{1-3}$)alkyl;

or R$^{N1}$ and R$^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;

(especially such group —(CH$_2$)$_m$—NR$^{N1}$R$^{N2}$ represents amino, methylamino, ethylamino, propylamino, amino-methyl, methylamino-methyl, isobutylamino-methyl, cyclopropylamino-methyl, cyclobutylamino-methyl, (2-methoxy-ethyl)amino-methyl, —NH—SO$_2$-methyl, —NH—SO$_2$-ethyl, or (2,2,2-trifluoro-ethyl)-amino; or —CH$_2$—NH—SO$_2$—CH$_3$; or —NH—CO—H, —N(C$_2$H$_5$)—CO—H, —NH—CO—C$_2$H$_5$, —NH—CO—CH$_2$—CH$_2$—OH, —NH—COO—CH$_3$, —N(CH$_3$)—COO—CH$_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl);

—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, hydroxy-(C$_{2-4}$)alkoxy, benzyloxy, or hydroxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—C$_2$H$_4$—OCH$_3$, —CO—NH—O—C$_2$H$_4$—OH, —CO—NH—C$_2$H$_4$—N(CH$_3$)$_2$, —CO—NH—O-benzyl, or —CO—N(CH$_3$)$_2$, —CO—NH-isopropyl, or —CO—NH—OH);

—NH—CO—NR$^{N5}$R$^{N6}$ wherein R$^{N5}$ and R$^{N6}$ independently represent hydrogen or (C$_{1-4}$)alkyl (wherein preferably at least one of R$^{N5}$ and R$^{N6}$ represents hydrogen; and wherein particular examples of such group —NH—CO—NR$^{N5}$R$^{N6}$ are —NH—CO—NH$_2$, and —NH—CO—NH—C$_2$H$_5$);

—SO$_2$—R$^{S1}$ wherein R$^{S1}$ represents hydroxy, (C$_{1-4}$)alkyl (especially methyl), or —NR$^{N7}$R$^{N8}$ wherein R$^{N7}$ and R$^{N8}$ independently represent hydrogen or (C$_{1-3}$)alkyl (wherein preferably at least one of R$^{N7}$ and R$^{N8}$ represents hydrogen; and wherein particular examples of such group —SO$_2$—R$^{S1}$ are —SO$_2$—CH$_3$, —SO$_2$—NH$_2$, —SO$_2$—OH, —SO$_2$—NH—CH$_3$);

—S—R$^{S2}$ wherein R$^{S2}$ represents (C$_{1-4}$)alkyl (especially methyl, ethyl, n-propyl, isopropyl, isobutyl), (C$_{3-6}$)cycloalkyl (especially cyclobutyl), or 2-fluoro-vinyl;

5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);

phenyl-oxy, wherein the phenyl is optionally mono-substituted with halogen (especially 4-fluorophenoxy);

benzooxazol-2-yl; or

—(CH$_2$)$_p$-HET, wherein p represents the integer 0 or 1; and wherein HET represents a 5- or 6-membered heteroaryl, wherein said 5- or 6-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, fluoro, 2-amino-2-oxo-ethyl, 2-carboxy-ethyl, (C$_{3-5}$)cycloalkyl (especially cyclopropyl), or —NR$^{N9}$R$^{N10}$ wherein R$^{N9}$ and R$^{N10}$ independently represent hydrogen or (C$_{1-3}$)alkyl (especially methyl); (especially such group —(CH$_2$)$_p$-HET is 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, pyrazol-1-yl-methyl, 1H-imidazol-4-yl, 3H-[1,2,3]triazol-4-yl, 5-methyl-1H-imidazol-4-yl, 1,2-dimethyl-1H-imidazol-4-yl, 1,5-dimethyl-1H-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, or pyridin-2-yl);

or Ar$^1$ represents 8- to 10-membered bicyclic heteroaryl (especially indazolyl, benzoimidazolyl, indolyl, benzotriazolyl, benzooxazolyl, quinoxalinyl, isoquinolinyl, quinolinyl, pyrrolopyridinyl, or imidazopyridinyl); wherein said 8- to 10-membered bicyclic heteroaryl independently is unsubstituted, mono-, di- or tri-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); (C$_{1-3}$)fluoroalkoxy (especially trifluoromethoxy); halogen; cyano; hydroxy, or —(C$_{0-3}$)alkylene-COOR$^{O2}$ wherein R$^{O2}$ represents hydrogen or (C$_{1-4}$)alkyl (especially methyl); (especially such 8- to 10-membered bicyclic heteroaryl is 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, quinolin-5-yl, 1H-indol-2-yl, 1H-indol-3-yl, 1H-indol-4-yl, 1H-indazol-5-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 3-methoxy-1H-indazol-6-yl, 6-methoxy-1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl; preferably such 8- to 10-membered bicyclic heteroaryl is 1H-benzoimidazol-5-yl, 1H-indol-6-yl, 1H-indol-5-yl, 1H-indol-2-yl, 1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl);

or Ar$^1$ represents 8- to 10-membered partially aromatic fused bicyclic heterocyclyl comprising one to four heteroatoms independently selected from nitrogen, oxygen and sulfur (especially 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 2,3-dihydro-benzooxazolyl, 1,2,3,4-tetrahydro-quinazolinyl, 1,2,3,4-tetrahydro-isoquinolinyl, or 1,2,3,4-tetrahydro-phthalazinyl); wherein said 8- to 10-membered heterocyclyl is linked to the rest of the molecule at the aromatic ring moiety; wherein said 8- to 10-membered heterocyclyl independently is unsubstituted, mono-, or di-substituted, wherein the substituents are independently selected from oxo. (C$_{1-6}$)alkyl (especially methyl, ethyl, propyl, butyl, isobutyl), and —(C$_{0-3}$)alkylene-COOR$^{O3}$ wherein R$^{O3}$ represents hydrogen or (C$_{1-3}$)alkyl; (especially such 8- to 10-membered partially aromatic fused bicyclic heterocyclyl is 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, 2-isobutyl-1-oxo-2,3-dihydro-isoindol-5-yl, 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-methyl-3-oxo-2,3-dihydro-1H-indazol-6-yl, 1-(carboxymethyl)-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, 1-oxo-1,2,3,4-tetrahydro-isoquinolin-6-yl, or 1,4-dioxo-1,2,3,4-tetrahydro-phthalazin-6-yl; preferably such group (Ar-III) is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, or 1-oxo-1,2,3,4-tetrahydro-isoquinolin-6-yl).

The compounds of formula (I) may contain one or more stereogenic or asymmetric centers, such as one or more asymmetric carbon atoms, which are allowed to be present in (R)- as well as (S)-configuration. The compounds of formula (I) may further encompass compounds with one or more double bonds which are allowed to be present in Z- as well as E-configuration and/or compounds with substituents at a ring system which are allowed to be present, relative to each other, in cis- as well as trans-configuration. The compounds of formula (I) may thus be present as mixtures of stereoisomers or preferably as pure stereoisomers. Mixtures of stereoisomers may be separated in a manner known to a person skilled in the art.

In case a particular compound (or generic structure) is designated as (R)- or (S)-enantiomer, such designation is to be understood as referring to the respective compound (or generic structure) in enriched, especially essentially pure, enantiomeric form. Likewise, in case a specific asymmetric center in a compound is designated as being in (R)- or (S)-configuration or as being in a certain relative configuration, such designation is to be understood as referring to the compound that is in enriched, especially essentially pure, form with regard to the respective configuration of said asymmetric center. In analogy, cis- or trans-designations are to be understood as referring to the respective stereoisomer of the respective relative configuration in enriched, especially essentially pure, form. Likewise, in case a particular compound (or generic structure) is designated as Z- or E-stereoisomer (or in case a specific double bond in a compound is designated as being in Z- or E-configuration), such designation is to be understood as referring to the respective compound (or generic structure) in enriched, especially essentially pure, stereoisomeric form (or to the compound that is in enriched, especially essentially pure, form with regard to the respective configuration of the double bond).

The term "enriched", when used in the context of stereoisomers, is to be understood in the context of the present invention to mean that the respective stereoisomer is present in a ratio of at least 70:30, especially of at least 90:10 (i.e., in a purity of at least 70% by weight, especially of at least 90% by weight), with regard to the respective other stereoisomer/the entirety of the respective other stereoisomers.

The term "essentially pure", when used in the context of stereoisomers, is to be understood in the context of the present invention to mean that the respective stereoisomer is present in a purity of at least 95% by weight, especially of at least 99% by weight, with regard to the respective other stereoisomer/the entirety of the respective other stereoisomers.

The present invention also includes isotopically labelled, especially $^2$H (deuterium) labelled compounds of formula (I) according to embodiments 1) to 31), which compounds are identical to the compounds of formula (I) except that one or more atoms have each been replaced by an atom having the same atomic number but an atomic mass different from the atomic mass usually found in nature. Isotopically labelled, especially $^2$H (deuterium) labelled compounds of formula (I) and salts thereof are within the scope of the present invention. Substitution of hydrogen with the heavier isotope $^2$H (deuterium) may lead to greater metabolic stability, resulting e.g. in increased in-vivo half-life or reduced dosage requirements, or may lead to reduced inhibition of cytochrome P450 enzymes, resulting e.g. in an improved safety profile. In one embodiment of the invention, the compounds of formula (I) are not isotopically labelled, or they are labelled only with one or more deuterium atoms. In a sub-embodiment, the compounds of formula (I) are not isotopically labelled at all. Isotopically labelled compounds of formula (I) may be prepared in analogy to the methods described hereinafter, but using the appropriate isotopic variation of suitable reagents or starting materials.

In this patent application, a bond drawn as a dotted line shows the point of attachment of the radical drawn. For example, the radical drawn below

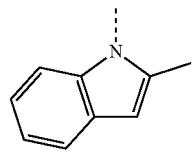

is the 2-methyl-1H-indol-1-yl group.

In some instances, the compounds of formula (I) may contain tautomeric forms. Such tautomeric forms are encompassed in the scope of the present invention. In case tautomeric forms exist of a certain residue, and only one form of such residue is disclosed or defined, the other tautomeric form(s) are understood to be encompassed in such disclosed residue. For example the group 2-oxo-2,3-dihydro-1H-benzo[d]imidazol-5-yl is to be understood as also encompassing its tautomeric forms 2-hydroxy-1H-benzo[d]imidazol-5-yl and 2-hydroxy-3H-benzo[d]imidazol-5-yl. Similarly, 5-oxo-4,5-dihydro-[1,2,4]oxadiazol-3-yl (alternatively named 5-oxo-4H-[1,2,4]oxadiazol-3-yl) encompasses its tautomeric form 5-hydroxy-[1,2,4]oxadiazol-3-yl, and 3-oxo-2,3-dihydro-[1,2,4]oxadiazol-5-yl (alternatively named 3-oxo-2H-[1,2,4]oxadiazol-5-yl) encompasses its tautomeric form 3-hydroxy-[1,2,4]oxadiazol-5-yl.

Where the plural form is used for compounds, salts, pharmaceutical compositions, diseases and the like, this is intended to mean also a single compound, salt, or the like.

Any reference to compounds of formula (I) according to embodiments 1) to 31) is to be understood as referring also to the salts (and especially the pharmaceutically acceptable salts) of such compounds, as appropriate and expedient.

The term "pharmaceutically acceptable salts" refers to salts that retain the desired biological activity of the subject compound and exhibit minimal undesired toxicological effects. Such salts include inorganic or organic acid and/or base addition salts depending on the presence of basic and/or acidic groups in the subject compound. For reference see for example "Handbook of Pharmaceutical Salts. Properties, Selection and Use.", P. Heinrich Stahl, Camille G. Wermuth (Eds.), Wiley-VCH, 2008; and "Pharmaceutical Salts and Co-crystals", Johan Wouters and Luc Quéré (Eds.), RSC Publishing, 2012.

Definitions provided herein are intended to apply uniformly to the compounds of formula (I), as defined in any one of embodiments 1) to 26), and, mutatis mutandis, throughout the description and the claims unless an otherwise expressly set out definition provides a broader or narrower definition. It is well understood that a definition or preferred definition of a term defines and may replace the respective term independently of (and in combination with) any definition or preferred definition of any or all other terms as defined herein. Whenever the group Ar$^1$ or substituents thereof are further defined, such definitions are intended to apply mutatis mutandis also to the groups (Ar-I), (Ar-II), (Ar-IV), (Ar-V), and (Ar-VI) and their respective substituents.

Whenever a substituent is denoted as optional, it is understood that such substituent may be absent, in which case all positions having a free valency (to which such optional substituent could have been attached to; such as for example in an aromatic ring the ring carbon atoms and/or the ring nitrogen atoms having a free valency) are substituted with hydrogen where appropriate.

The term "halogen" means fluorine, chlorine, bromine, or iodine; especially fluorine, chlorine, or bromine; preferably fluorine or chlorine.

The term "alkyl", used alone or in combination, refers to a saturated straight or branched chain hydrocarbon group containing one to six carbon atoms. The term "$(C_{x-y})$alkyl" (x and y each being an integer), refers to an alkyl group as defined before, containing x to y carbon atoms. For example a $(C_{1-6})$alkyl group contains from one to six carbon atoms. Examples of alkyl groups are methyl, ethyl, propyl, isopropyl, butyl, isobutyl, tert.-butyl, 3-methyl-butyl, 2,2-dimethyl-propyl and 3,3-dimethyl-butyl. For avoidance of any doubt, in case a group is referred to as e.g. propyl or butyl, it is meant to be n-propyl, respectively n-butyl. Preferred are methyl and ethyl. Most preferred is methyl. Preferred for substituents of $Ar^1$ being phenyl or 5- or 6-membered heteroaryl are methyl, ethyl, propyl, isobutyl, 1-methyl-propan-1-yl, tert.-butyl, 3-methyl-butyl.

The term "—$(C_{x-y})$alkylene-", used alone or in combination, refers to bivalently bound alkyl group as defined before containing x to y carbon atoms. Preferably, the points of attachment of a —$(C_{1-y})$alkylene group are in 1,1-diyl, in 1,2-diyl, or in 1,3-diyl arrangement. In case a $(C_{0-y})$alkylene group is used in combination with another substituent, the term means that either said substituent is linked through a $(C_{x-y})$alkylene group to the rest of the molecule, or it is directly attached to the rest of the molecule (i.e. a $(C_0)$ alkylene group represents a direct bond linking said substituent to the rest of the molecule). The alkylene group —$C_2H_4$— refers to —$CH_2$—$CH_2$— if not explicitly indicated otherwise. For the linker $X^1$, examples of $(C_{1-3})$ alkylene groups are —$CH_2$—, —$CH(CH_3)$—, —C$(CH_3)_2$—, and —$CH_2$—$CH_2$—, especially —$CH_2$— and —$CH_2$—$CH_2$—. Examples of $(C_{0-3})$alkylene groups as used in the substituents —$(C_{0-3})$alkylene-COOR$^{O2}$ and $(C_{0-3})$alkylene-COOR$^{O3}$, respectively, are $(C_0)$alkylene, and methylene, respectively.

The term "alkoxy", used alone or in combination, refers to an alkyl-O— group wherein the alkyl group is as defined before. The term "$(C_{x-y})$alkoxy" (x and y each being an integer) refers to an alkoxy group as defined before containing x to y carbon atoms. For example a $(C_{1-4})$alkoxy group means a group of the formula $(C_{1-4})$alkyl-O— in which the term "$(C_{1-4})$alkyl" has the previously given significance. Examples of alkoxy groups are methoxy, ethoxy, n-propoxy, isopropoxy, n-butoxy, isobutoxy, sec.-butoxy and tert.-butoxy. Preferred are ethoxy and especially methoxy. Preferred for substituents of $Ar^1$ being phenyl or 5- or 6-membered heteroaryl are methoxy, ethoxy, propoxy, butoxy, isobutoxy.

The term "fluoroalkyl", used alone or in combination, refers to an alkyl group as defined before containing one to three carbon atoms in which one or more (and possibly all) hydrogen atoms have been replaced with fluorine. The term "$(C_{x-y})$fluoroalkyl" (x and y each being an integer) refers to a fluoroalkyl group as defined before containing x to y carbon atoms. For example a $(C_{1-3})$fluoroalkyl group contains from one to three carbon atoms in which one to seven hydrogen atoms have been replaced with fluorine. Representative examples of fluoroalkyl groups include trifluoromethyl, 2-fluoroethyl, 2,2-difluoroethyl and 2,2,2-trifluoroethyl. Preferred are $(C_1)$fluoroalkyl groups such as trifluoromethyl. An example of "$(C_{1-3})$fluoroalkyl, wherein said $(C_{1-3})$fluoroalkyl is optionally substituted with hydroxy" is 2,2,2-trifluoro-1-hydroxy-ethyl.

The term "fluoroalkoxy", used alone or in combination, refers to an alkoxy group as defined before containing one to three carbon atoms in which one or more (and possibly all) hydrogen atoms have been replaced with fluorine. The term "$(C_{x-y})$fluoroalkoxy" (x and y each being an integer) refers to a fluoroalkoxy group as defined before containing x to y carbon atoms. For example a $(C_{1-3})$fluoroalkoxy group contains from one to three carbon atoms in which one to seven hydrogen atoms have been replaced with fluorine. Representative examples of fluoroalkoxy groups include trifluoromethoxy, difluoromethoxy, 2-fluoroethoxy, 2,2-difluoroethoxy and 2,2,2-trifluoroethoxy. Preferred are $(C_1)$ fluoroalkoxy groups such as trifluoromethoxy and difluoromethoxy, as well as 2,2,2-trifluoroethoxy.

The term "cycloalkyl", used alone or in combination, refers to a saturated monocyclic hydrocarbon ring containing three to six carbon atoms. The term "$(C_{x-y})$cycloalkyl" (x and y each being an integer), refers to a cycloalkyl group as defined before containing x to y carbon atoms. For example a $(C_{3-6})$cycloalkyl group contains from three to six carbon atoms. Examples of cycloalkyl groups are cyclopropyl, cyclobutyl, cyclopentyl, cyclohexyl, and cycloheptyl. Preferred are cyclopropyl, cyclobutyl, and cyclopentyl; especially cyclopropyl. Examples of $(C_{3-6})$cycloalkyl groups wherein said $(C_{3-6})$cycloalkyl is optionally mono-substituted with amino are cyclopropyl, 1-amino-cyclopropyl. Examples of $(C_{3-6})$cycloalkyl groups wherein said $(C_{3-6})$ cycloalkyl is mono-substituted with —COOH are 1-carboxy-cyclopropyl, 1-carboxy-cyclopentyl.

The term "—$(C_{x-y})$cycloalkylene-", used alone or in combination, refers to bivalently bound cycloalkyl group as defined before containing x to y carbon atoms. Preferably, the points of attachment of any bivalently bound cycloalkyl group are in 1,1-diyl, or in 1,2-diyl arrangement. Examples are cyclopropan-1,1-diyl, cyclopropan-1,2-diyl, and cyclopentan-1,1-diyl; preferred is cyclopropan-1,1-diyl.

Examples of $(C_{3-6})$cycloalkyl-oxy are cyclobutyl-oxy, and cyclopentyl-oxy.

Alkylated amino groups —N[$(C_{1-4})$alkyl]$_2$ as used in groups —$X^1$—CO—$R^{O1}$, wherein $R^{O1}$ represents —O—$CH_2$—CO—$R^{O4}$, wherein $R^{O4}$ represents —N[$(C_{1-4})$alkyl]$_2$; or wherein $R^{O1}$ represents —O—$CH_2$—$CH_2$—N[$(C_{1-4})$alkyl]$_2$ are such that the two respective $(C_{1-4})$alkyl groups are independently selected. A preferred example of such amino group —N[$(C_{1-4})$alkyl]$_2$ is —N(CH$_3$)$_2$.

The term "heterocycle", used alone or in combination, and if not explicitly defined in a broader or more narrow way, refers to a saturated monocyclic hydrocarbon ring containing one or two (especially one) ring heteroatoms independently selected from nitrogen, sulfur, and oxygen (especially one nitrogen atom, two nitrogen atoms, one nitrogen atom and one oxygen atom, or one nitrogen atom and one sulfur atom). The term "$(C_{x-y})$heterocycle" refers to such a heterocycle containing x to y ring atoms. Heterocycles are unsubstituted or substituted as explicitly defined.

The term "8- to 10-membered partially aromatic fused bicyclic heterocyclyl" refers to 5- or 6-membered aromatic ring which is fused to a 5- or 6-membered non-aromatic ring (especially a $(C_{5-6})$heterocycle as defined before), wherein said fused ring system comprises in total one to a maximum of four heteroatoms independently selected from nitrogen, oxygen and sulfur. Such 8- to 10-membered partially aromatic fused bicyclic heterocyclyl is linked to the rest of the molecule at the aromatic ring moiety. A preferred sub-group of such "8- to 10-membered partially aromatic fused bicyclic heterocyclyl" are phenyl groups which are fused to a $(C_{5-6})$heterocycle as defined before. Examples are 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, and 2,3-dihydro-isoindolyl; and, in addition to the before listed: 2,3-dihydro-benzooxazol-6-yl, 2,3-dihydro-benzooxazol-5-yl, 1,2,3,4-tetrahydro-quinazolin-6-yl, 1,2,3,4-tetrahydro-quinazolin-7-yl, 1,2,3,4-tetrahydro-isoquinolin-6-yl, 1,2,3,4-tetrahydro-phthalazin-6-yl. The above groups are unsubstituted, mono-, or di-substituted, wherein the substituents are independently selected from oxo, $(C_{1-6})$alkyl, and —$(C_{0-3})$alkylene-COOR$^{O3}$ wherein R$^{O3}$ represents hydrogen or $(C_{1-3})$alkyl (especially methyl); especially substituents are independently selected from oxo, methyl, ethyl, propyl, butyl, isobutyl, wherein the substituents are preferably attached to the fused 5- or 6-membered non-aromatic ring. Oxo substituents are preferably attached to a ring carbon atom which is in alpha position to a ring nitrogen atom. Preferred examples of such 8- to 10-membered partially aromatic fused bicyclic heterocyclyl groups are 2,3-dihydro-benzofuranyl, 2,3-dihydro-1H-indolyl, 2,3-dihydro-benzo[1,4]dioxinyl; as well as the oxosubstituted heterocyclyl groups 3-oxo-2,3-dihydro-1H-indazolyl, 2-oxo-2,3-dihydro-1H-benzo[d]imidazolyl, 3-oxo-2,3-dihydrobenzo[d]isoxazolyl, 2-oxo-1,3-dihydro-indolyl, 1-oxo-2,3-dihydro-isoindolyl, 2-oxo-2,3-dihydro-benzooxazolyl, 2-oxo-1,2,3,4-tetrahydro-quinazolinyl, 1-oxo-1,2,3,4-tetrahydro-isoquinolinyl, 1,4-dioxo-1,2,3,4-tetrahydro-phthalazinyl; wherein the above groups optionally carry one (further) substituent independently selected from $(C_{1-6})$alkyl, and —$(C_{0-3})$alkylene-COOR$^{O3}$ wherein R$^{O3}$ represents hydrogen or $(C_{1-3})$alkyl (especially methyl). Particular examples are 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, 2-isobutyl-1-oxo-2,3-dihydro-isoindol-5-yl; and, in addition to the before listed: 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-methyl-3-oxo-2,3-dihydro-1H-indazol-6-yl, 1-(carboxymethyl)-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, 1-oxo-1,2,3,4-tetrahydro-isoquinolin-6-yl, 1,4-dioxo-1,2,3,4-tetrahydro-phthalazin-6-yl; preferred are 2,3-dihydro-1H-indol-5-yl, 3-oxo-2,3-dihydro-1H-indazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, and 1-oxo-2-propyl-2,3-dihydro-isoindol-5-yl; and especially 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, and 1-oxo-1,2,3,4-tetrahydro-isoquinolin-6-yl.

For avoidance of doubt, certain groups having tautomeric forms which are considered predominantly non-aromatic, such as for example 2-oxo-2,3-dihydro-1H-benzo[d]imidazolyl groups, are defined herein as 8- to 10-membered partially aromatic fused bicyclic heterocyclyl groups, even though their corresponding tautomeric form (2-hydroxy-1H-benzo[d]imidazolyl) could also be considered as a 8- to 10-membered bicyclic heteroaryl group.

The term "aryl", used alone or in combination, means phenyl or naphthyl, especially phenyl. The above-mentioned aryl groups are unsubstituted or substituted as explicitly defined.

Examples of the substituent $Ar^1$ representing phenyl are especially those which are at least mono-substituted in para position with respect to the point of attachment of the rest of the molecule. In addition, such group $Ar^1$ representing phenyl may carry one or two further substituents, especially in one or both meta positions with respect to the point of attachment of the rest of the molecule. The respective substituents of such phenyl groups are as explicitly defined.

The term "heteroaryl", used alone or in combination, means a 5- to 10-membered monocyclic or bicyclic aromatic ring containing one to a maximum of four heteroatoms, each independently selected from oxygen, nitrogen and sulfur. Examples of such heteroaryl groups are 5-membered heteroaryl groups such as furanyl, oxazolyl, isoxazolyl, oxadiazolyl, thiophenyl, thiazolyl, isothiazolyl, thiadiazolyl, pyrrolyl, imidazolyl, pyrazolyl, triazolyl, tetrazolyl; 6-membered heteroaryl groups such as pyridinyl, pyrimidinyl, pyridazinyl, pyrazinyl; and 8- to 10-membered bicyclic heteroaryl groups such as indolyl, isoindolyl, benzofuranyl, isobenzofuranyl, benzothiophenyl, indazolyl, benzimidazolyl, benzoxazolyl, benzisoxazolyl, benzothiazolyl, benzoisothiazolyl, benzotriazolyl, benzoxadiazolyl, benzothiadiazolyl, thienopyridinyl, quinolinyl, isoquinolinyl, naphthyridinyl, cinnolinyl, quinazolinyl, quinoxalinyl, phthalazinyl, pyrrolopyridinyl, pyrazolopyridinyl, pyrazolopyrimidinyl, pyrrolopyrazinyl, imidazopyridinyl, imidazopyridazinyl, and imidazothiazolyl. The above-mentioned heteroaryl groups are unsubstituted or substituted as explicitly defined.

For the substituent $Ar^1$ representing a "5- or 6-membered heteroaryl", the term means the above-mentioned 5- or 6-membered groups such as especially pyridinyl, pyrimidinyl, pyrrolyl, pyrazolyl, isoxazolyl, thiazolyl or thiophenyl. Notably, the term refers to 5-membered groups such as especially thiazolyl or thiophenyl; in particular thiophen-2-yl, thiophen-3-yl, thiazol-2-yl, thiazol-4-yl, thiazol-5-yl. Preferred is thiophenyl, especially thiophen-2-yl; or thiazolyl, especially thiazol-2-yl. The above groups are unsubstituted or substituted as explicitly defined.

For the substituent $Ar^1$ representing a "8- to 10-membered bicyclic heteroaryl" the term means the above-mentioned 8- to 10-membered heteroaryl groups. Notably, the term refers to 9- or 10-membered heteroaryl groups, such as especially indazolyl, benzoimidazolyl, indolyl, benzotriazolyl, benzooxazolyl, quinoxalinyl, isoquinolinyl, quinolinyl, and, in addition to the before listed: pyrrolopyridinyl, and imidazopyridinyl. The above groups are unsubstituted or substituted as explicitly defined. Particular examples are 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, and quinolin-6-yl. In addition to the above-listed, further particular examples are 1H-indol-2-yl, 1H-indol-3-yl, 1H-indol-4-yl, 1H-indazol-5-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 3-methoxy-1H-indazol-6-yl, 6-methoxy-1H-indazol-5-yl, 5-carboxy-1H-indol-2-yl, 6-carboxy-1H-indol-2-yl, 5-(methoxycarbonyl)-1H-indol-2-yl, 6-(methoxycarbonyl)-1H-indol-2-yl. Preferred examples are 1H-benzoimidazol-5-yl, 1H-indol-6-yl, 1H-indol-5-yl, 1H-indol-2-yl, 1H-indazol-5-yl, 5-carboxy-1H-indol-2-yl, 6-carboxy-1H-indol-2-yl, 5-(methoxycarbonyl)-1H-indol-2-yl, and 6-(methoxycarbonyl)-1H-indol-2-yl.

For the substituent "—$(CH_2)_p$-HET, wherein p represents the integer 0 or 1, and wherein HET represents a 5- or 6-membered heteroaryl", such 5- or 6-membered heteroaryl is as defined before; notably a nitrogen containing 5- or 6-membered heteroaryl such as especially oxazolyl, isoxazolyl, oxadiazolyl, thiazolyl, isothiazolyl, thiadiazolyl, imidazolyl, pyrazolyl, triazolyl, tetrazolyl, pyridinyl, pyrimidinyl, pyridazinyl, or pyrazinyl. The above groups are unsubstituted or substituted as explicitly defined. The group —$(CH_2)$— is preferably absent, i.e. p represents the integer 0 and the group HET is directly bound to the rest of the molecule. Particular examples of —$(CH_2)$, -HET are the —$(CH_2)_0$-HET groups 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxo-ethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, and 6-methoxy-pyridazin-3-yl; as well as the —$(CH_2)$, -HET group pyrazol-1-yl-methyl. In addition to the above-listed, further particular examples are the —$(CH_2)_0$-HET groups 3H-imidazol-4-yl, 3H-[1,2,3]triazol-4-yl, 5-methyl-1H-imidazol-4-yl, 1,2-dimethyl-1H-imidazol-4-yl, 1,5-dimethyl-1H-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, as well as pyridin-2-yl. For avoidance of doubt, certain groups having tautomeric forms which are predominantly aromatic, such as for example 3-hydroxy-isoxazolyl groups, are defined herein as heteroaryl groups, even though their corresponding tautomeric form 3-oxo-2,3-dihydro-2H-isoxazolyl could also be considered as a non-aromatic group.

The term "cyano" refers to a group —CN.

The term "oxo" refers to a group =O which is preferably attached to a chain or ring carbon or sulfur atom as for example in a carbonyl group —(CO)—, or a sulfonyl group —$(SO_2)$—.

Examples of "—$(CH_2)_m$—$NR^{N1}R^{N2}$" groups as used for substituents of $Ar^1$ being phenyl or 5- or 6-membered heteroaryl are amino, methylamino, ethylamino, propylamino, amino-methyl, methylamino-methyl, isobutylamino-methyl, cyclopropylamino-methyl, cyclobutylamino-methyl, (2-methoxyethyl)amino-methyl, —NH—$SO_2$-methyl, —NH—$SO_2$-ethyl, or (2,2,2-trifluoro-ethyl)-amino; or pyrrolidin-1-yl, 2-oxo-pyrrolidin-1-yl, 1,1-dioxo-isothiazolidin-2-yl, and morpholin-4-yl. Further examples are —$CH_2$—NH—$SO_2$—$CH_3$; —NH—CO—H, —$N(C_2H_5)$—CO—H, —NH—CO—$C_2H_5$, —NH—CO—$CH_2$—$CH_2$—OH, —NH—COO—$CH_3$, —$N(CH_3)$—COO—$CH_3$, azetidin-1-yl, and piperidin-1-yl. Preferred examples of the substituents "—$(CH_2)_m$—$NR^{N1}R^{N2}$ wherein $R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl, or —$SO_2$—$(C_{1-4})$alkyl" as used for substituents of the group $Ar^1$ are those wherein at least one of $R^{N1}$ and $R^{N2}$ represents hydrogen, such as amino, methylamino, ethylamino, propylamino, amino-methyl, methylamino-methyl, isobutylamino-methyl, cyclopropylamino-methyl, cyclobutylamino-methyl, (2-methoxyethyl)amino-methyl, —NH—$SO_2$-methyl, —NH—$SO_2$-ethyl, and (2,2,2-trifluoro-ethyl)-amino. Preferred examples of the substituents "—$(CH_2)_m$—$NR^{N1}R^{N2}$ wherein $R^{N1}$ represents hydrogen or $(C_{1-4})$alkyl, and $R^{N2}$ independently represents —CO—H, —CO—$(C_{1-3})$alkyl, —CO—$(C_{1-3})$alkylene-OH, or —CO—O—$(C_{1-3})$alkyl" as used for substituents of the group $Ar^1$ are those wherein $R^{N1}$ represents hydrogen, methyl, or ethyl; and $R^{N2}$ independently represents —CO—H, —CO—$CH_3$, —CO—$C_2H_5$, —CO—$C_2H_4$—OH, or —COO—$CH_3$. Examples of —$NR^{N1}R^{N2}$ rings in the substituents "—$(CH_2)_m$—$NR^{N1}R^{N2}$, wherein $R^{N1}$ and $R^{N2}$ together with the nitrogen to which they are attached form a 4, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom" as used for substituents of the group $Ar^1$ are pyrrolidin-1-yl, morpholin-4-yl, isothiazolidin-2-yl, azetidin-1-yl, and piperidin-1-yl; wherein said groups are unsubstituted or substituted as explicitly defined. Particular examples of such —$(CH_2)_m$—$NR^{N1}R^{N2}$ groups are pyrrolidin-1-yl, 2-oxo-pyrrolidin-1-yl, 1,1-dioxo-isothiazolidin-2-yl, and morpholin-4-yl; as well as azetidin-1-yl, and piperidin-1-yl.

Examples of a group "—NH—CO—$NR^{N5}R^{N6}$" as used for substituents of the group $Ar^1$ are ureido (—NH—CO—$NH_2$) and 3-ethylureido (—NH—CO—NH—$C_2H_5$).

Examples of a group "—CO—$NR^{N3}R^{N4}$" as used for substituents of the group $Ar^1$ are preferably groups wherein at least one of $R^{N3}$ and $R^{N4}$ represents hydrogen (or less preferred, methyl). Particular examples of such group —CO—$NR^{N3}R^{N4}$ are —CO—$NH_2$, —CO—$NH(CH_3)$, —CO—$N(CH_2)$, —CO—$NH(C_2H_5)$, —CO—NH—O-methyl, —CO—NH—O-ethyl, —CO—NH—O-isopropyl, —CO—NH—$C_2H_4$—OH, —CO—NH—O—$C_2H_4$—OH, —CO—NH—$C_2H_4$—$OCH_3$, —CO—NH—$C_2H_4$—$N(CH_3)_2$, and —CO—NH—O-benzyl. Further examples are —CO—NH-isopropyl and —CO—NH—OH, as well as —CO—$N(CH_3)_2$.

Examples of a group "—$X^1$—CO—$R^{O1}$" as used for substituents of the group $Ar^1$ are especially the following groups:

a) $X^1$ represents a direct bond; and $R^{O1}$ represents —OH; (i.e. —$X^1$—CO—$R^{O1}$ represents —COOH); or b) $X^1$ represents a direct bond; and $R^{O1}$ represents —O—$(C_{1-4})$alkyl (especially ethoxy, or methoxy); (i.e.

—$X^1$—CO—$R^{O1}$ represents —CO—$(C_{1-4})$alkoxy (especially ethoxycarbonyl, methoxycarbonyl)); or c) $X^1$ represents a direct bond; and $R^{O1}$ represents —NH—$SO_2$—$R^{S3}$; wherein $R^{S3}$ represents $(C_{1-4})$alkyl; $(C_{3-6})$cycloalkyl wherein the $(C_{3-6})$cycloalkyl optionally contains a ring oxygen atom; $(C_{3-6})$cycloalkyl-$(C_{1-3})$alkylene wherein the $(C_{3-6})$cycloalkyl optionally contains a ring oxygen atom; $(C_{1-3})$fluoroalkyl; phenyl; or —$NH_2$; (i.e. —$X^1$—CO—$R^{O1}$ represents —CO—NH—$SO_2$—$R^{S3}$ wherein $R^{S3}$ represents the above mentioned groups; notably methyl, ethyl, isopropyl, cyclopropyl, trifluoromethyl, phenyl, amino; especially —$X^1$—CO—$R^{O1}$ represents —CO—NH—$SO_2$—$CH_3$, —CO—NH—$SO_2$—$C(CH_3)_2$, —CO—NH—$SO_2$-cyclopropyl, —CO—NH—$SO_2$-phenyl, —CO—NH—$SO_2$-ethyl, or —CO—NH—$SO_2$—$NH_2$); or d) $X^1$ represents $(C_{1-3})$alkylene (especially —$CH_2$—, —$CH_2$—$CH_2$—), —O—$(C_{1-3})$alkylene-* (especially —O—$CH_2$—*, —O—$CH(CH_3)$—*, —O—$CH_2$—$CH_2$—*), —NH—$(C_{1-3})$alkylene-* (especially —NH—$CH_2$—*, —NH—$CH(CH_3)$—*), —S—$CH_2$—*, —$CF_2$—, —CH=CH—, or —CH=CH— [in a sub-embodiment $X^1$ represents especially —O—$CH_2$—*, —NH—$CH_2$—*, —S—$CH_2$—*, or $(C_{1-3})$alkylene]; wherein the asterisks indicate the bond that is linked to the —CO—$R^{O1}$ group; and $R^{O1}$ represents —OH (i.e. —$X^1$—CO—$R^{O1}$ represents —$X^1$—COOH wherein $X^1$ represents the above mentioned groups; especially —$X^1$—CO—$R^{O1}$ represents —O—$CH_2$—COOH or —NH—$CH_2$—COOH; as well as —$CH_2$—COOH, —$CH_2$—$CH_2$—COOH, —$CF_2$—COOH, —CH=CH—COOH, —CH=CH—COOH, —O—$CH_2$—$CH_2$—COOH, —O—$CH(CH_3)$—COOH, or —NH—$CH(CH_3)$—COOH); or e) —$X^1$ represents —NH—CO—* or —CO—; wherein the asterisk indicates the bond that is linked to the —CO—$R^{O1}$ group; and $R^{O1}$ represents —OH (i.e. —$X^1$—CO—$R^{O1}$ represents —$X^1$—COOH wherein $X^1$ represents the above mentioned groups; especially —$X^1$—CO—$R^{O1}$ represents —NH—CO—COOH, —CO—COOH); or f) $X^1$ represents $(C_{3-5})$cycloalkylene; and $R^{O1}$ represents —OH; (i.e. —$X^1$—CO—$R^{O1}$ represents $(C_{3-6})$cycloalkyl which is mono-substituted with COOH; especially —$X^1$—CO—$R^{O1}$ represents 1-carboxy-cyclopropan-1-yl or 1-carboxy-cyclopentan-1-yl); or g) $X^1$ represents a direct bond; and $R^{O1}$ represents —O—$CH_2$—CO—$R^{O4}$, wherein $R^{O4}$ represents hydroxy, or $(C_{1-4})$alkoxy, or —$N[(C_{1-4})alkyl]_2$; especially —$X^1$—CO—$R^{O1}$ represents —COO—$CH_2$—COOH; or wherein each of the groups a), b), c), d), e), f), and g) forms a particular sub-embodiment.

Compounds of Formula (I) containing a group "—$X^1$—CO—$R^{O1}$" wherein $X^1$ represents —CH=CH— may be in E- or Z-configuration. Preferably, such groups are in E-configuration.

Whenever a group $Ar^1$ is substituted with a substituent comprising a carboxylic acid group —COOH (such as in the substituents —$(C_{0-3})$alkylene-COO$R^{O2}$ wherein $R^{O2}$ represents hydrogen; —$(C_{0-3})$alkylene-COO$R^{O3}$ wherein $R^{O3}$ represents hydrogen; or in the substituents —$X^1$—CO—$R^{O1}$ wherein $R^{O1}$ represents —OH, especially in the —$X^1$—CO—$R^{O1}$ groups a), d), e) and f) above) such carboxylic acid group may be present in form of a prodrug group. Such prodrugs are encompassed in the scope of the present invention. In certain instances, compounds comprising such carboxylic acid prodrug groups may as such exhibit biological activity on the EP2 and/or EP4 receptor, whereas in other instances, such compounds comprising such carboxylic acid prodrug groups require (e.g. enzymatic) cleavage of the prodrug to exhibit biological activity on the EP2 and/or EP4 receptor. Prodrugs of the carboxylic acid functional group are well known in the art (see for example J. Rautio (Ed.) Prodrugs and Targeted Delivery: Towards Better ADME Properties, Volume 47, Wiley 2010, ISBN: 978-3-527-32603-7; H. Maag in Stella, V., Borchardt, R., Hageman, M., Oliyai, R., Maag, H., Tilley, J. (Eds.) Prodrugs: Challenges and Rewards, Springer 2007, ISBN 978-O-387-49785-3).

Particular examples of prodrugs, for example suitable for —$X^1$—COOH groups are:

ester groups —$X^1$—CO—O—$P^1$ wherein $P^1$ is for example $(C_{1-4})$alkyl; $(C_{3-6})$cycloalkyl wherein the $(C_{3-6})$cycloalkyl optionally contains a ring oxygen atom; $(C_{3-6})$cycloalkyl-$(C_{1-3})$alkyl wherein the $(C_{3-6})$cycloalkyl optionally contains a ring oxygen atom; $(C_{1-3})$fluoroalkyl; hydroxy-$(C_{2-4})$alkyl; or $(C_{1-4})$alkoxy-$(C_{2-4})$alkyl (especially $P^1$ is $(C_{1-4})$alkyl, in particular methyl or ethyl);

groups —$X^1$—CO—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom; $(C_{3-6})$cycloalkyl-$(C_{1-3})$alkyl wherein the $(C_{3-6})$cycloalkyl optionally contains a ring oxygen atom; $(C_{1-3})$fluoroalkyl, phenyl, —$NH_2$; (especially $R^{S3}$ is $(C_{1-4})$alkyl, $(C_{3-6})$cycloalkyl, or phenyl; in particular methyl);

groups —$X^1$—CO—$R^{O1}$ wherein $R^{O1}$ represents —O—$CH_2$—CO—$R^{O4}$, wherein $R^{O4}$ represents hydroxy, or $(C_{1-4})$alkoxy, or —$N[(C_{1-4})alkyl]_2$ (especially —COO—$CH_2$—COOH, —COO—$CH_2$—CO—$N(CH_3)_2$);

groups —$X^1$—CO—$R^{O1}$ wherein $R^{O1}$ represents —O—$CH_2$—O—CO—$R^{O5}$, wherein $R^{O5}$ represents $(C_{1-4})$alkyl or $(C_{1-4})$alkoxy (especially —COO—$CH_2$—O—CO—O-ethyl, —COO—$CH_2$—O—CO-propyl);

groups —$X^1$—CO—$R^{O1}$ wherein $R^{O1}$ represents —O—$CH_2$—$CH_2$—$N[(C_{1-4})alkyl]_2$ (especially —COO—$CH_2$—$CH_2$—$N(CH_3)_2$); and groups —$X^1$—CO—$R^{O1}$ wherein $R^{O1}$ represents 5-methyl-2-oxo-[1,3]dioxol-4-yl)-methyloxy-.

Examples of "hydroxy-$(C_{1-4})$alkyl" groups as used for substituents of the group $Ar^1$ are hydroxymethyl and 1-hydroxy-ethyl.

An example of "dihydroxy-$(C_{2-4})$alkyl" groups as used for substituents of the group $Ar^1$ is 1,2-dihydroxyethyl.

An example of "hydroxy-$(C_{2-4})$alkoxy" groups as used for substituents of the group $Ar^1$ is 2-hydroxy-ethoxy.

An example of "$(C_{1-4})$alkoxy-$(C_{2-4})$alkoxy" groups as used for substituents of the group $Ar^1$ is 2-methoxy-ethoxy.

Examples of a group "—$SO_2$—$R^{S1}$" as used for substituents of the group $Ar^1$ are —$SO_2$—$CH_3$, —$SO_2$—$NH_2$, —$SO_2$—OH, —$SO_2$—NH—$CH_3$.

Examples of a group "S—$R^{S2}$" as used for substituents of the group $Ar^1$ are methylsulfanyl, ethylsulfanyl, n-propylsulfanyl, isopropylsulfanyl, isobutylsulfanyl), cyclobutylsulfanyl, and (2-fluoro-vinyl)-sulfanyl.

An example of a "$(C_{1-4})$alkoxy-$(C_{2-4})$alkyl" group is 2-methoxyethyl.

An example of a "hydroxy-$(C_{2-4})$alkoxy" group is 2-hydroxy-ethoxy.

An example of a "hydroxy-($C_{2-4}$)alkyl" group is 2-hydroxy-ethyl.

An example of a "—CO—($C_{1-4}$)alkoxy" group as used for substituents of the group $Ar^1$ is ethoxycarbonyl. Such groups may also be useful as prodrugs of the respective —COOH substituent.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C. Besides, the term "room temperature" as used herein refers to a temperature of about 25° C.

Further embodiments of the invention are presented hereinafter:

2) A second embodiment relates to compounds according to embodiment 1), wherein $R^3$ represents hydrogen.

3) Another embodiment relates to compounds according to embodiment 1), wherein $R^3$ represents methyl or trifluoromethyl.

4) Another embodiment relates to compounds according to any one of embodiments 1) to 3), wherein $R^{4a}$ and $R^{4b}$ both represent hydrogen.

5) Another embodiment relates to compounds according to any one of embodiments 1) to 4), wherein $R^{5a}$ and $R^{5b}$ both represent hydrogen. Particular compounds of formula (I) are compounds wherein $R^{4a}$ and $R^{4b}$ both represent hydrogen; and $R^{5a}$ and $R^{5b}$ both represent hydrogen.

6) Another embodiment relates to compounds according to any one of embodiments 1) to 5), wherein $Ar^1$ represents phenyl, or 5- or 6-membered heteroaryl (notably 5-membered heteroaryl, especially thiophenyl or thiazolyl); wherein said phenyl or 5- or 6-membered heteroaryl independently is mono-, di- or tri-substituted; wherein one of said substituents is selected from ($C_{1-4}$)alkoxy (especially methoxy);

($C_{1-3}$)fluoroalkyl, wherein said ($C_{1-3}$)fluoroalkyl is optionally substituted with hydroxy (especially 2,2,2-trifluoro-1-hydroxy-ethyl);

($C_{3-6}$)cycloalkyl, wherein said ($C_{3-6}$)cycloalkyl is optionally mono-substituted with amino (especially 1-amino-cyclopropyl);

($C_{3-6}$)cycloalkyl, wherein said ($C_{3-6}$)cycloalkyl is optionally mono-substituted with —COOH (especially 1-carboxy-cyclopropyl, 1-carboxy-cyclopentyl); hydroxy;

—$X^1$—CO—$R^{O1}$, wherein $X^1$ represents a direct bond, —O—$CH_2$—*, —NH—$CH_2$—*, —S—$CH_2$—*, or ($C_{1-3}$)alkylene; wherein the asterisks indicate the bond that is linked to the —CO—$R^{O1}$ group; and $R^{O1}$ represents —OH, —O—($C_{1-4}$)alkyl (especially ethoxy), or —NH—$SO_2$—$R^{Sa}$ wherein $R^{S3}$ represents ($C_{1-4}$)alkyl, ($C_{3-6}$)cycloalkyl wherein the ($C_{3-6}$)cycloalkyl optionally contains a ring oxygen atom; ($C_{3-6}$)cycloalkyl-($C_{1-3}$)alkyl wherein the ($C_{3-6}$)cycloalkyl optionally contains a ring oxygen atom; ($C_{1-3}$)fluoroalkyl, phenyl, or —$NH_2$;

[wherein in a sub-embodiment such group —$X^1$—CO—$R^{O1}$ represents especially —COOH, —CO—($C_{1-4}$)alkoxy, —O—$CH_2$—COOH, —NH—$CH_2$—COOH, —CO—NH—$SO_2$—($C_{1-4}$)alkyl, —CO—NH—$SO_2$—($C_{3-6}$)cycloalkyl, or —CO—NH—$SO_2$-phenyl; in particular, such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—C($CH_3$)$_2$, —CO—NH—$SO_2$-cyclopropyl, or —CO—NH—$SO_2$-phenyl];

—CO—$CH_2$—CN;

hydroxy-($C_{1-4}$)alkyl (especially hydroxymethyl);

($CH_2$)$_m$—$NR^{N1}R^{N2}$, wherein m represents the integer 0 or 1 (especially 1); and wherein $R^{N1}$ and $R^{N2}$ independently represent hydrogen, ($C_{1-4}$)alkyl, ($C_{1-4}$)alkoxy-($C_{2-4}$)alkyl, or ($C_{3-6}$)cycloalkyl; or $R^{N1}$ and $R^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —($CH_2$)$_m$—$NR^{N1}R^{N2}$ represents amino, amino-methyl, methylamino-methyl, isobutylamino-methyl, cyclopropylamino-methyl, cyclobutylamino-methyl, (2-methoxyethyl)amino-methyl, 2-oxo-pyrrolidin-1-yl, 1,1-dioxo-isothiazolidin-2-yl, or morpholin-4-yl);

—CO—$NR^{N3}R^{N4}$ wherein $R^{N3}$ and $R^{N4}$ independently represent hydrogen, ($C_{1-4}$)alkyl, hydroxy-($C_{2-4}$)alkyl, ($C_{1-3}$)alkoxy-($C_{2-4}$)alkyl, dimethylamino-($C_{2-4}$)alkyl, ($C_{1-4}$)alkoxy, hydroxy-($C_{2-4}$)alkoxy, or benzyloxy (wherein preferably at least one of $R^{N3}$ and $R^{N4}$ represents hydrogen; and wherein particular examples of such group —CO—$NR^{N3}R^{N4}$ are —CO—$NH_2$, —CO—NH($CH_3$), —CO—NH($C_2H_5$), —CO—NH—O-methyl, —CO—NH—O-ethyl, —CO—NH—O-isopropyl, —CO—NH—$C_2H_4$—OH, —CO—NH—$C_2H_4$—$OCH_3$, —CO—NH—O—$C_2H_4$—OH, —CO—NH—$C_2H_4$—N($CH_3$)$_2$, —CO—NH—O-benzyl);

NH—CO—$NR^{N5}R^{N6}$ wherein $R^{N5}$ and $R^{N6}$ independently represent hydrogen or ($C_{1-4}$)alkyl; (especially such group is —NH—CO—$NH_2$, —NH—CO—NH—$C_2H_5$)

—$SO_2$—$R^{S1}$ wherein $R^{S1}$ represents hydroxy, ($C_{1-4}$)alkyl (especially methyl), or —$NR^{N7}R^{N8}$ wherein $R^{N7}$ and $R^{N8}$ independently represent hydrogen or ($C_{1-3}$)alkyl; (especially such group is —$SO_2$—$CH_3$, —$SO_2$—$NH_2$, —$SO_2$—OH, —$SO_2$—NH—$CH_3$)

5-oxo-4,5-dihydro-[1,2,4]oxadiazol-3-yl, or

—($CH_2$)$_p$-HET, wherein p represents the integer 0 or 1 (especially 0); and wherein HET represents a 5- or 6-membered heteroaryl, wherein said 5- or 6-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, fluoro, 2-amino-2-oxo-ethyl, 2-carboxy-ethyl, or —$NR^{N9}R^{N10}$ wherein $R^{N9}$ and $R^{N10}$ independently represent hydrogen or ($C_{1-3}$)alkyl (especially amino, dimethylamino);

and the remaining one or two of said substituents (if present) is/are independently selected from
- $(C_{1-6})$alkyl (especially methyl, ethyl, propyl, isobutyl, 1-methyl-propan-1-yl, tert.-butyl, 3-methyl-butyl);
- $(C_{1-4})$alkoxy (especially methoxy, ethoxy, propoxy, isopropoxy, butoxy, isobutoxy);
- $(C_{1-3})$fluoroalkyl (especially trifluoromethyl);
- $(C_{1-3})$fluoroalkoxy (especially difluoromethoxy, trifluoromethoxy, 2,2,2-trifluoroethoxy);
- halogen (especially fluoro or chloro);
- $(C_{3-6})$cycloalkyl (especially cyclopropyl);
- $(C_{3-6})$cycloalkyl-oxy (especially cyclobutyl-oxy, cyclopentyl-oxy);
- hydroxy;
- nitro;
- —$(CH_2)_m$—$NR^{N1}R^{N2}$, wherein m represents the integer 0 or 1 (especially 0); and wherein $R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl (especially 2,2,2-trifluoro-ethyl), -or —$SO_2$—$(C_{1-4})$alkyl; or $R^{N1}$ and $R^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom (especially such group —$(CH_2)_m$—$NR^{N1}R^{N2}$ represents amino, methylamino, ethylamino, propylamino, —NH—$SO_2$-methyl, —NH—$SO_2$-ethyl, or (2,2,2-trifluoro-ethyl)-amino; or pyrrolidin-1-yl);
- —S—$R^{S2}$ wherein $R^{S2}$ represents $(C_{1-4})$alkyl (especially methyl, ethyl, n-propyl, isopropyl, isobutyl), $(C_{3-6})$cycloalkyl (especially cyclobutyl), or 2-fluoro-vinyl; or
- phenyl-oxy, wherein the phenyl is optionally mono-substituted with halogen (especially 4-fluorophenoxy);

or $Ar^1$ represents 8- to 10-membered bicyclic heteroaryl (especially indazolyl, benzoimidazolyl, indolyl, benzotriazolyl, benzooxazolyl, quinoxalinyl, isoquinolinyl, quinolinyl; or pyrrolopyridinyl, or imidazopyridinyl); wherein said 8- to 10-membered bicyclic heteroaryl independently is unsubstituted, mono-, di- or tri-substituted, wherein the substituents are independently selected from $(C_{1-4})$alkyl (especially methyl); $(C_{1-4})$alkoxy (especially methoxy); $(C_{1-3})$fluoroalkyl (especially trifluoromethyl); halogen; or —COOH;

or $Ar^1$ represents 8- to 10-membered partially aromatic fused bicyclic heterocyclyl comprising one to four heteroatoms independently selected from nitrogen, oxygen and sulfur (especially 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl; or 2,3-dihydro-benzooxazol-6-yl, or 2,3-dihydro-benzooxazol-5-yl, or 1,2,3,4-tetrahydro-quinazolin-6-yl, or 1,2,3,4-tetrahydro-quinazolin-7-yl, or 1,2,3,4-tetrahydro-isoquinolin-6-yl, or 1,2,3,4-tetrahydro-phthalazin-6-yl); wherein said 8- to 10-membered heterocyclyl is linked to the rest of the molecule at the aromatic ring moiety; wherein said 8- to 10-membered heterocyclyl independently is unsubstituted, mono-, or di-substituted, wherein the substituents are independently selected from oxo and $(C_{1-6})$alkyl (especially methyl, ethyl, propyl, butyl, isobutyl).

7) Another embodiment relates to compounds according to any one of embodiments 1) to 5), wherein $Ar^1$ represents phenyl, or 5- or 6-membered heteroaryl (notably 5-membered heteroaryl, especially thiophenyl or thiazolyl); wherein said phenyl or 5- or 6-membered heteroaryl independently is mono-, di- or tri-substituted; wherein one of said substituents is selected from
- $(C_{1-4})$alkoxy (especially methoxy);
- $(C_{1-3})$fluoroalkyl, wherein said $(C_{1-3})$fluoroalkyl is unsubstituted or mono-substituted with hydroxy (especially 2,2,2-trifluoro-1-hydroxy-ethyl);
- $(C_{3-6})$cycloalkyl, wherein said $(C_{3-6})$cycloalkyl is unsubstituted or mono-substituted with amino (especially 1-amino-cyclopropyl);
- $(C_{4-6})$cycloalkyl containing a ring oxygen atom, wherein said $(C_{4-6})$cycloalkyl containing a ring oxygen atom is unsubstituted or mono-substituted with fluoro, hydroxy, or methoxy (especially 3-fluoro-oxetan-3-yl, 3-hydroxy-oxetan-3-yl, 3-methoxy-oxetan-3-yl);
- hydroxy;
- —$B(OH)_2$;
- 2,2,2-trifluoro-1,1-dihydroxy-ethyl;
- —$X^1$—CO—$R^{O1}$, wherein
  $X^1$ represents a direct bond, $(C_{1-3})$alkylene (especially —$CH_2$—, —$CH_2$—$CH_2$—), —O—$(C_{1-3})$alkylene-* (especially —O—$CH_2$—*, —O—CH($CH_3$)—*, —O—$CH_2$—$CH_2$—*), —NH—$(C_{1-3})$alkylene-* (especially —NH—$CH_2$—*, —NH—CH($CH_3$)—*), —S—$CH_2$—*, —$CF_2$—, —CH=CH—, —CH—CH—, —NH—CO—*, —CO—, or $(C_{3-5})$cycloalkylene; wherein the asterisks indicate the bond that is linked to the —CO—$R^{O1}$ group; and
  $R^{O1}$ represents
  - —OH;
  - —O—$(C_{1-4})$alkyl (especially ethoxy, methoxy);
  - —NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —$NH_2$;
  - —O-phenyl;
  - —O—$CH_2$—CO—$R^{O4}$, wherein $R^{O4}$ represents hydroxy, or $(C_{1-4})$alkoxy, or —$N[(C_{1-4})$alkyl$]_2$;
  - —O—$CH_2$—O—CO—$R^{O4}$, wherein $R^{O5}$ represents $(C_{1-4})$alkyl or $(C_{1-4})$alkoxy; or
  - —O—$CH_2$—$CH_2$—$N[(C_{1-4})$alkyl$]_2$ (especially —O—$CH_2$—$CH_2$—$N(CH_3)_2$);
  - (5-methyl-2-oxo-[1,3]dioxol-4-yl)-methyloxy-;
  - [wherein in particular, such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—C($CH_3$)$_2$, —CO—NH—$SO_2$-cyclopropyl, —CO—NH—$SO_2$-phenyl, —COO—$CH_3$, —CO—NH—$SO_2$-ethyl, —CO—NH—$SO_2$—$NH_2$, —COO—$CH_2$—COOH, —COO—$CH_2$—$CH_2$—$N(CH_3)_2$, —COO—$CH_2$—CO—$N(CH_3)_2$, —COO—$CH_2$—O—CO—O-ethyl, —COO—$CH_2$—O—CO-propyl, (5-methyl-2-oxo-[1,3]dioxol-4-yl)-methyl-O—CO—, —$CH_2$—COOH, —$CH_2$—CO—O-ethyl, —$CH_2$—$CH_2$—COOH, —$CF_2$—COOH, —CH=CH—COOH, —CH—CH—CO—O- ethyl, —NH—CO—COOH, —CO—COOH, —O—CH$_2$—CH$_2$—COOH, —O—CH(CH$_3$)—COOH, —NH—CH(CH$_3$)—COOH, —NH—CH$_2$—COO—CH$_3$, —COO-phenyl, 1-carboxy-cyclopropan-1-yl, 1-carboxy-cyclopentan-1-yl];
—CO—CH$_2$—CN;
—CO—CH$_2$—OH;
—CO—H;

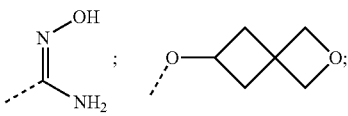

2-hydroxy-3,4-dioxo-cyclobut-1-enyl;
hydroxy-(C$_{1-4}$)alkyl (especially hydroxymethyl, 1-hydroxy-ethyl);
dihydroxy-(C$_{2-4}$)alkyl (especially 1,2-dihydroxyethyl);
hydroxy-(C$_{2-4}$)alkoxy (especially 2-hydroxy-ethoxy);
(C$_{1-4}$)alkoxy-(C$_{2-4}$)alkoxy (especially 2-methoxy-ethoxy);
—(CH$_2$)$_m$—NR$^{N1}$R$^{N2}$, wherein m represents the integer 0 or 1; and wherein
R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl, -or —SO$_2$—(C$_{1-4}$)alkyl (wherein preferably at least one of R$^{N1}$ and R$^{N2}$ represents hydrogen);
or R$^{N1}$ independently represents hydrogen or (C$_{1-4}$)alkyl, and R$^{N2}$ independently represents —CO—H, —CO—(C$_{1-3}$)alkyl, —CO—(C$_{1-3}$)alkylene-OH, or —CO—O—(C$_{1-3}$)alkyl;
or R$^{N1}$ and R$^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;
(especially such group —(CH$_2$)$_m$—NR$^{N1}$R$^{N2}$ represents amino, methylamino, ethylamino, propylamino, amino-methyl, methylamino-methyl, isobutylamino-methyl, cyclopropylamino-methyl, cyclobutylamino-methyl, (2-methoxyethyl)amino-methyl, —NH—SO$_2$-methyl, —NH—SO$_2$-ethyl, or (2,2,2-trifluoro-ethyl)-amino; or —CH$_2$—NH—SO$_2$—CH$_3$; or —NH—CO—H, —N(C$_2$H$_5$)—CO—H, —NH—CO—C$_2$H$_5$, —NH—CO—CH$_2$—CH$_2$—OH, —NH—COO—CH$_3$, —N(CH$_3$)—COO—CH$_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl);
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, hydroxy-(C$_{2-4}$)alkoxy, benzyloxy, or hydroxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—C$_2$H$_4$—OCH$_3$, —CO—NH—O—C$_2$H$_4$—OH, —CO—NH—C$_2$H$_4$—N(CH$_3$)$_2$, —CO—NH—O-benzyl, or —CO—N(CH$_3$)$_2$, —CO—NH-isopropyl, or —CO—NH—OH);
—NH—CO—NR$^{N5}$R$^{N6}$ wherein R$^{N5}$ and R$^{N6}$ independently represent hydrogen or (C$_{1-4}$)alkyl; (especially such group is —NH—CO—NH$_2$, —NH—CO—NH—C$_2$H$_5$)
—SO$_2$—R$^{S1}$ wherein R$^{S1}$ represents hydroxy, (C$_{1-4}$)alkyl (especially methyl), or —NR$^{N7}$R$^{N8}$ wherein R$^{N7}$ and R$^{N8}$ independently represent hydrogen or (C$_{1-3}$)alkyl; (especially such group is —SO$_2$—CH$_3$, —SO$_2$—NH$_2$, —SO$_2$—OH, —SO$_2$—NH—CH$_3$)
5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);
benzooxazol-2-yl; or
—(CH$_2$)$_p$-HET, wherein p represents the integer 0 or 1 (especially 0); and wherein HET represents a 5- or 6-membered heteroaryl, wherein said 5- or 6-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, fluoro, 2-amino-2-oxo-ethyl, 2-carboxy-ethyl, (C$_{3-5}$)cycloalkyl (especially cyclopropyl), or —NR$^{N9}$R$^{N10}$ wherein R$^{N9}$ and R$^{N10}$ independently represent hydrogen or (C$_{1-3}$)alkyl (especially amino, dimethylamino); (especially such group —(CH$_2$)$_p$-HET is 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, pyrazol-1-yl-methyl, 1H-imidazol-4-yl, 3H-[1,2,3]triazol-4-yl, 5-methyl-1H-imidazol-4-yl, 1,2-dimethyl-1H-imidazol-4-yl, 1,5-dimethyl-1H-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, or pyridin-2-yl);
and the remaining one or two of said substituents (if present) is/are independently selected from (C$_{1-6}$)alkyl (especially methyl, ethyl, n-propyl, isopropyl, n-butyl, isobutyl, 1-methyl-propan-1-yl, tert.-butyl, 3-methyl-butyl);

(C$_{1-4}$)alkoxy (especially methoxy, ethoxy, n-propoxy, isopropoxy, n-butoxy, isobutoxy);

(C$_{1-3}$)fluoroalkyl (especially trifluoromethyl);

(C$_{1-3}$)fluoroalkoxy (especially difluoromethoxy, trifluoromethoxy, 2,2,2-trifluoroethoxy);

halogen (especially fluoro or chloro);

(C$_{3-6}$)cycloalkyl (especially cyclopropyl);

(C$_{3-6}$)cycloalkyl-oxy (especially cyclobutyl-oxy, cyclopentyl-oxy);

hydroxy;

nitro;

—(CH$_2$)$_m$—NR$^{N1}$R$^{N2}$, wherein m represents the integer 0 or 1 (especially 0); and wherein R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl (especially 2,2,2-trifluoro-ethyl), -or —SO$_2$—(C$_{1-4}$)alkyl; or R$^{N1}$ and R$^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom (especially such group —(CH$_2$)$_m$—NR$^{N1}$R$^{N2}$ represents amino, methylamino, ethylamino, propylamino, —NH—SO$_2$-methyl, —NH—SO$_2$-ethyl, or (2,2,2-trifluoro-ethyl)-amino; or pyrrolidin-1-yl);

—S—R$^{S2}$ wherein R$^{S2}$ represents (C$_{1-4}$)alkyl (especially methyl, ethyl, n-propyl, isopropyl, isobutyl), (C$_{3-6}$)cycloalkyl (especially cyclobutyl), or 2-fluoro-vinyl; or phenyl-oxy, wherein the phenyl is optionally mono-substituted with halogen (especially 4-fluorophenoxy);

or Ar$^1$ represents 8- to 10-membered bicyclic heteroaryl (especially indazolyl, benzoimidazolyl, indolyl, benzotriazolyl, benzooxazolyl, quinoxalinyl, isoquinolinyl, quinolinyl, pyrrolopyridinyl, or imidazopyridinyl); wherein said 8- to 10-membered bicyclic heteroaryl independently is unsubstituted, mono-, di- or tri-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); halogen; and —(C$_{0-3}$)alkylene-COOR$^{O2}$ wherein R$^{O2}$ represents hydrogen or (C$_{1-4}$)alkyl (especially methyl); (especially such 8- to 10-membered bicyclic heteroaryl 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, quinolin-6-yl, 1H-indol-2-yl, 1H-indol-3-yl, 1H-indol-4-yl, 1H-indazol-5-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 3-methoxy-1H-indazol-6-yl, 6-methoxy-1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl; preferably such 8- to 10-membered bicyclic heteroaryl is 1H-benzoimidazol-5-yl, 1H-indol-6-yl, 1H-indol-5-yl, 1H-indol-2-yl, 1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl);

or Ar$^1$ represents 8- to 10-membered partially aromatic fused bicyclic heterocyclyl comprising one to four heteroatoms independently selected from nitrogen, oxygen and sulfur (especially 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 2,3-dihydro-benzooxazolyl, 1,2,3,4-tetrahydro-quinazolinyl, 1,2,3,4-tetrahydro-isoquinolinyl, or 1,2,3,4-tetrahydro-phthalazinyl); wherein said 8- to 10-membered heterocyclyl is linked to the rest of the molecule at the aromatic ring moiety; wherein said 8- to 10-membered heterocyclyl independently is unsubstituted, mono-, or di-substituted, wherein the substituents are independently selected from oxo, (C$_{1-6}$)alkyl (especially methyl, ethyl, propyl, butyl, isobutyl), and —(C$_{0-3}$)alkylene-COOR$^{O3}$ wherein R$^{O3}$ represents hydrogen or (C$_{1-3}$)alkyl; (especially such 8- to 10-membered partially aromatic fused bicyclic heterocyclyl is 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, 2-isobutyl-1-oxo-2,3-dihydro-isoindol-5-yl, 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-methyl-3-oxo-2,3-dihydro-1H-indazol-6-yl, 1-(carboxymethyl)-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, 1-oxo-1,2,3,4-tetrahydro-isoquinolin-6-yl, or 1,4-dioxo-1,2,3,4-tetrahydro-phthalazin-6-yl; preferably such group (Ar-III) is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, or 1-oxo-1,2,3,4-tetrahydro-isoquinolin-6-yl).

8) Another embodiment relates to compounds according to any one of embodiments 1) to 5), wherein Ar$^1$ represents a phenyl group of the structure (Ar-I):

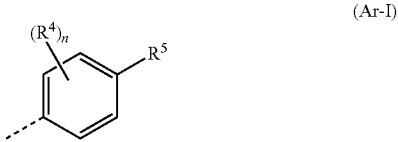

(Ar-I)

wherein
R⁵ represents;
- ($C_4$)alkoxy (especially methoxy);
- ($C_{1-3}$)fluoroalkyl, wherein said ($C_{1-3}$)fluoroalkyl is optionally substituted with hydroxy (especially 2,2,2-trifluoro-1-hydroxy-ethyl);
- ($C_{3-6}$)cycloalkyl, wherein said ($C_{3-6}$)cycloalkyl is optionally mono-substituted with amino (especially 1-amino-cyclopropyl);
- ($C_{3-6}$)cycloalkyl, wherein said ($C_{3-6}$)cycloalkyl is optionally mono-substituted with —COOH (especially 1-carboxy-cyclopropyl, 1-carboxy-cyclopentyl);
- hydroxy;
- —$X^1$—CO—$R^{O1}$, wherein
  $X^1$ represents a direct bond, —O—CH₂—*, —NH—CH₂—*, —S—CH₂—*, or ($C_{1-3}$)alkylene; wherein the asterisks indicate the bond that is linked to the —CO—$R^{O1}$ group; and
  $R^{O1}$ represents —OH, —O—($C_{1-4}$)alkyl (especially ethoxy), or —NH—SO₂—$R^{S3}$ wherein $R^{S3}$ represents ($C_{1-4}$)alkyl, ($C_{3-6}$)cycloalkyl wherein the ($C_{3-6}$)cycloalkyl optionally contains a ring oxygen atom; ($C_{3-6}$)cycloalkyl-($C_{1-3}$)alkyl wherein the ($C_{3-6}$)cycloalkyl optionally contains a ring oxygen atom; ($C_{1-3}$)fluoroalkyl, phenyl, or —NH₂.
  [wherein in a sub-embodiment such group —$X^1$—CO—$R^{O1}$ represents especially —COOH, —CO—($C_{1-4}$)alkoxy, —O—CH₂—COOH, —NH—CH₂—COOH, —CO—NH—SO₂—($C_{1-4}$)alkyl, —CO—NH—SO₂—($C_{3-6}$)cycloalkyl, or —CO—NH—SO₂-phenyl; in particular, such group —$X^1$—CO—$R^{O1}$ represents —COOH, —CO—O—C₂H₅, —O—CH₂—COOH, —NH—CH₂—COOH, —CO—NH—SO₂—CH₃, —CO—NH—SO₂—C(CH₃)₂, —CO—NH—SO₂-cyclopropyl, or —CO—NH—SO₂-phenyl];
- —CO—CH₂—CN;
- hydroxy-($C_{1-4}$)alkyl (especially hydroxymethyl);
- —(CH₂)$_m$—NR$^{N1}$R$^{N2}$, wherein m represents the integer 0 or 1 (especially 1); and wherein R$^{N1}$ and R$^{N2}$ independently represent hydrogen, ($C_{1-4}$)alkyl, ($C_{1-4}$)alkoxy-($C_{2-4}$)alkyl, or ($C_{3-6}$)cycloalkyl; or R$^{N1}$ and R$^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —(CH₂)$_m$—NR$^{N1}$R$^{N2}$ represents amino, amino-methyl, methylamino-methyl, isobutylamino-methyl, cyclopropylamino-methyl, cyclobutylamino-methyl, (2-methoxyethyl)amino-methyl, 2-oxo-pyrrolidin-1-yl, 1,1-dioxo-isothiazolidin-2-yl, or morpholin-4-yl);
- —CO—NR$^{N3}$R$^{N4}$ wherein R$^{N3}$ and R$^{N4}$ independently represent hydrogen, ($C_{1-4}$)alkyl, hydroxy-($C_{2-4}$)alkyl, ($C_{1-3}$)alkoxy-($C_{2-4}$)alkyl, dimethylamino-($C_{2-4}$)alkyl, ($C_{1-4}$)alkoxy, hydroxy-($C_{2-4}$)alkoxy, or benzyloxy; (wherein preferably at least one of R$^{N3}$ and R$^{N4}$ represents hydrogen; and wherein particular examples of such group —CO—NR$^{N3}$R$^{N4}$ are —CO—NH₂, —CO—NH(CH₃), —CO—NH(C₂H₅), —CO—NH—O-methyl, —CO—NH—O-ethyl, —CO—NH—O-isopropyl, —CO—NH—C₂H₄—OH, —CO—NH—O—C₂H₄—OH, —CO—NH—C₂H₄—OCH₃, —CO—NH—C₂H₄—N(CH₃)₂, —CO—NH—O-benzyl)
- —NH—CO—NR$^{N5}$R$^{N6}$ wherein R$^{N5}$ and R$^{N6}$ independently represent hydrogen or ($C_{1-4}$)alkyl (especially such group represents —NH—CO—NH₂, —NH—CO—NH—C₂H₅);
- —SO₂—R$^{S1}$ wherein R$^{S1}$ represents hydroxy, ($C_{1-4}$)alkyl (especially methyl), or —NR$^{N7}$R$^{N8}$ wherein R$^{N7}$ and R$^{N8}$ independently represent hydrogen or ($C_{1-3}$)alkyl (especially such group represents —SO₂—CH₃, —SO₂—NH₂, —SO₂—OH, —SO₂—NH—CH₃);
- 5-oxo-4,5-dihydro-[1,2,4]oxadiazol-3-yl, or
- —(CH₂)$_p$-HET, wherein p represents the integer 0 or 1 (especially 0); and wherein HET represents a 5- or 6-membered heteroaryl, wherein said 5- or 6-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, fluoro, 2-amino-2-oxo-ethyl, 2-carboxy-ethyl, or —NR$^{N9}$R$^{N10}$ wherein R$^{N9}$ and R$^{N10}$ independently represent hydrogen or ($C_{1-3}$) alkyl (especially amino, dimethylamino); (especially such group —(CH₂)$_p$-HET is 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, or pyrazol-1-yl-methyl);

and (R⁴)$_n$ represents one or two optional substituents (i.e. n represents the integer 0, 1, or 2) independently selected from
- ($C_{1-6}$)alkyl (especially methyl, ethyl, propyl, isobutyl, 1-methyl-propan-1-yl, tert.-butyl, 3-methyl-butyl);
- ($C_{1-4}$)alkoxy (especially methoxy, ethoxy, propoxy, isopropoxy, butoxy, isobutoxy);
- ($C_{1-3}$)fluoroalkyl (especially trifluoromethyl);
- ($C_{1-3}$)fluoroalkoxy (especially difluoromethoxy, trifluoromethoxy, 2,2,2-trifluoroethoxy);

halogen (especially fluoro or chloro);
($C_{3-6}$)cycloalkyl (especially cyclopropyl);
($C_{3-6}$)cycloalkyl-oxy (especially cyclobutyl-oxy, cyclopentyl-oxy);
hydroxy;
nitro;
—$(CH_2)_m$—$NR^{N1}R^{N2}$, wherein m represents the integer 0 or 1 (especially 0); and wherein $R^{N1}$ and $R^{N2}$ independently represent hydrogen, ($C_{1-4}$)alkyl, ($C_{1-4}$)alkoxy-($C_{2-4}$)alkyl, ($C_{3-6}$)cycloalkyl, ($C_{2-3}$)fluoroalkyl (especially 2,2,2-trifluoro-ethyl), -or —$SO_2$—($C_{1-4}$)alkyl; or $R^{N1}$ and $R^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —$(CH_2)_m$—$NR^{N1}R^{N2}$ represents amino, methylamino, ethylamino, propylamino, —NH—$SO_2$-methyl, —NH—$SO_2$-ethyl, or (2,2,2-trifluoro-ethyl)-amino; or pyrrolidin-1-yl);
—S—$R^{S2}$ wherein $R^{S2}$ represents ($C_{1-4}$)alkyl (especially methyl, ethyl, n-propyl, isopropyl, isobutyl), ($C_{3-6}$)cycloalkyl (especially cyclobutyl), or 2-fluoro-vinyl; or
phenyl-oxy, wherein the phenyl is optionally mono-substituted with halogen (especially 4-fluorophenoxy);

or $Ar^1$ represents a 5-membered heteroaryl group of the structure (Ar-II):

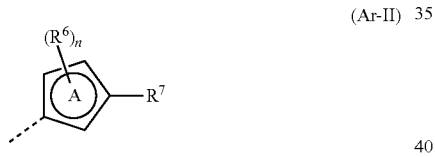

(Ar-II)

wherein in (Ar-II) the ring A represents a 5-membered heteroaryl ring (wherein it is well understood that in (Ar-II) the substituent $R^7$ is attached in meta-position with respect to the point of attachment of the rest of the molecule) (notably a thiophenyl or a thiazolyl ring; especially thiophen-2-yl wherein $R^7$ is attached in position 5, or thiazol-2-yl wherein $R^7$ is attached in position 5);

wherein
$R^7$ represents
($C_{1-4}$)alkoxy (especially methoxy);
($C_{3-6}$)cycloalkyl, wherein said ($C_{3-6}$)cycloalkyl is optionally mono-substituted with amino (especially 1-amino-cyclopropyl);
($C_{3-6}$)cycloalkyl, wherein said ($C_{3-6}$)cycloalkyl is optionally mono-substituted with —COOH (especially 1-carboxy-cyclopropyl, 1-carboxy-cyclopentyl);
hydroxy;
—$X^1$—CO—$R^{O1}$, wherein
$X^1$ represents a direct bond, —O—$CH_2$—*, —NH—$CH_2$—*, —S—$CH_2$—*, or ($C_{1-3}$)alkylene; wherein the asterisks indicate the bond that is linked to the —CO—$R^{O1}$ group; and
$R^{O1}$ represents —OH, —O—($C_{1-4}$)alkyl (especially ethoxy), or —NH—$SO_2$—$R^{S3}$ wherein $R^{S3}$ represents ($C_{1-4}$)alkyl, ($C_{3-6}$)cycloalkyl wherein the ($C_{3-6}$)cycloalkyl optionally contains a ring oxygen atom; ($C_{3-6}$)cycloalkyl-($C_{1-3}$)alkyl wherein the ($C_{3-6}$)cycloalkyl optionally contains a ring oxygen atom; ($C_{1-3}$)fluoroalkyl, phenyl, or —$NH_2$;
[wherein in a sub-embodiment such group —$X^1$—CO—$R^{O1}$ represents especially —COOH, —CO—($C_{1-4}$)alkoxy, —O—$CH_2$—COOH, —NH—$CH_2$—COOH, —CO—NH—$SO_2$—($C_{1-4}$)alkyl, —CO—NH—$SO_2$—($C_{3-6}$)cycloalkyl, or —CO—NH—$SO_2$-phenyl; in particular, such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—$C(CH_3)_2$, —CO—NH—$SO_2$-cyclopropyl, or —CO—NH—$SO_2$-phenyl];
—CO—$CH_2$—CN;
hydroxy-($C_{1-4}$)alkyl (especially hydroxymethyl);
—$(CH_2)_m$—$NR^{N1}R^{N2}$, wherein m represents the integer 0 or 1 (especially 1); and wherein $R^{N1}$ and $R^{N2}$ independently represent hydrogen, ($C_{1-4}$)alkyl, ($C_{1-4}$)alkoxy-($C_{2-4}$)alkyl, or ($C_{3-6}$)cycloalkyl; or $R^{N1}$ and $R^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —$(CH_2)_m$—$NR^{N1}R^{N2}$ represents amino, amino-methyl, methylamino-methyl, isobutylamino-methyl, cyclopropylamino-methyl, cyclobutylamino-methyl, (2-methoxyethyl)amino-methyl, 2-oxo-pyrrolidin-1-yl, 1,1-dioxo-isothiazolidin-2-yl, or morpholin-4-yl);
—CO—$NR^{N3}R^{N4}$ wherein $R^{N3}$ and $R^{N4}$ independently represent hydrogen, ($C_{1-4}$)alkyl, hydroxy-($C_{2-4}$)alkyl, ($C_{1-3}$)alkoxy-($C_{2-4}$)alkyl, dimethylamino-($C_{2-4}$)alkyl, ($C_{1-4}$)alkoxy, or hydroxy-($C_{2-4}$)alkoxy (wherein preferably at least one of $R^{N3}$ and $R^{N4}$ represents hydrogen; and wherein particular examples of such group —CO—$NR^{N3}R^{N4}$ are —CO—$NH_2$, —CO—$NH(CH_3)$, —CO—$NH(C_2H_5)$, —CO—NH—O-methyl, —CO—NH—O-ethyl, —CO—NH—O-isopropyl, —CO—NH—$C_2H_4$—OH, —CO—NH—$C_2H_4$—$OCH_3$, —CO—NH—O—$C_2H_4$—OH, —CO—NH—$C_2H_4$—$N(CH_3)_2$);
—NH—CO—$NR^{N5}R^{N6}$ wherein $R^{N5}$ and $R^{N6}$ independently represent hydrogen or ($C_{1-4}$)alkyl (especially such group is —NH—CO—$NH_2$, —NH—CO—NH—$C_2H_5$);
—$SO_2$—$R^{S1}$ wherein $R^{S1}$ represents hydroxy, ($C_{1-4}$)alkyl (especially methyl), or —$NR^{N7}R^{N8}$ wherein $R^{N7}$ and $R^{N8}$ independently represent hydrogen or ($C_{1-3}$)alkyl (especially such group is —$SO_2$—$CH_3$, —$SO_2$—$NH_2$, —$SO_2$—OH, —$SO_2$—NH—$CH_3$);
5-oxo-4,5-dihydro-[1,2,4]oxadiazol-3-yl; or
5- or 6-membered heteroaryl (notably 5-membered heteroaryl, especially 1H-tetrazol-5-yl), wherein said 5- or 6-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, fluoro, 2-amino-2- oxo-ethyl, 2-carboxy-ethyl, or —NR$^{N9}$R$^{N10}$ wherein R$^{N9}$ and R$^{N10}$ independently represent hydrogen or (C$_{1-3}$)alkyl (especially amino, dimethylamino);

and (R$^6$)$_n$ represents one optional substituent (i.e. n represents the integer 0, or 1) independently selected from (C$_{1-6}$)alkyl (especially methyl, ethyl, propyl, isobutyl, 1-methyl-propan-1-yl, tert.-butyl, 3-methyl-butyl);

(C$_{1-4}$)alkoxy (especially methoxy, ethoxy, propoxy, isopropoxy, butoxy, isobutoxy);

(C$_{1-3}$)fluoroalkyl (especially trifluoromethyl);

(C$_{1-3}$)fluoroalkoxy (especially difluoromethoxy, trifluoromethoxy, 2,2,2-trifluoroethoxy);

halogen (especially fluoro or chloro);

(C$_{3-6}$)cycloalkyl (especially cyclopropyl);

(C$_{3-6}$)cycloalkyl-oxy (especially cyclobutyl-oxy, cyclopentyl-oxy);

hydroxy;

—(CH$_2$)$_m$—NR$^{N1}$R$^{N2}$, wherein m represents the integer 0 or 1 (especially 0); and wherein R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl (especially 2,2,2-trifluoro-ethyl), -or —SO$_2$—(C$_{1-4}$)alkyl; or R$^{N1}$ and R$^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —(CH$_2$)$_m$—NR$^{N1}$R$^{N2}$ represents amino, methylamino, ethylamino, propylamino, —NH—SO$_2$-methyl, —NH—SO$_2$-ethyl, or (2,2,2-trifluoro-ethyl)-amino; or pyrrolidin-1-yl); and —S—R$^{S2}$ wherein R$^{S2}$ represents (C$_{1-4}$)alkyl (especially methyl, ethyl, n-propyl, isopropyl, isobutyl), (C$_{3-6}$)cycloalkyl (especially cyclobutyl), or 2-fluoro-vinyl;

or Ar$^1$ represents 9- or 10-membered bicyclic heteroaryl (especially indazolyl, benzoimidazolyl, indolyl, benzotriazolyl, benzooxazolyl, quinoxalinyl, isoquinolinyl, quinolinyl; or pyrrolopyridinyl, or imidazopyridinyl); wherein said 9- or 10-membered bicyclic heteroaryl independently is unsubstituted, mono-, or di-substituted, wherein the substituents are independently selected from (C$_{1-4}$)alkyl (especially methyl); (C$_{1-3}$) fluoroalkyl (especially trifluoromethyl); or —COOH (especially such group is 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, quinolin-6-yl);

or Ar$^1$ represents a group of the structure (Ar-III):

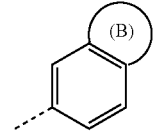

(Ar-III)

wherein ring (B) represents a non-aromatic 5- or 6-membered ring fused to the phenyl group, wherein ring (B) comprises one or two heteroatoms independently selected from nitrogen and oxygen (notably such group (Ar-III) is 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl; or 2,3-dihydro-benzooxazol-6-yl, or 2,3-dihydro-benzooxazol-5-yl, or 1,2,3,4-tetrahydro-quinazolin-6-yl, or 1,2,3,4-tetrahydro-quinazolin-7-yl, or 1,2,3,4-tetrahydro-isoquinolin-6-yl, or 1,2,3,4-tetrahydro-phthalazin-6-yl); wherein said ring (B) independently is unsubstituted, mono-, or di-substituted, wherein the substituents are independently selected from oxo and (C$_{1-6}$)alkyl (especially methyl, ethyl, propyl, butyl, isobutyl) (especially such group (Ar-III) is 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, or 2-isobutyl-1-oxo-2,3-dihydro-isoindol-5-yl).

9) Another embodiment relates to compounds according to any one of embodiments 1) to 5), wherein Ar$^1$ represents a phenyl group of the structure (Ar-I):

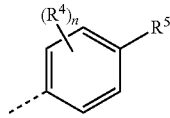

(Ar-I)

wherein
R$^5$ represents;
(C$_{1-4}$)alkoxy (especially methoxy);
(C$_{1-3}$)fluoroalkyl, wherein said (C$_{1-3}$)fluoroalkyl is optionally substituted with hydroxy (especially 2,2,2-trifluoro-1-hydroxy-ethyl);
(C$_{3-6}$)cycloalkyl, wherein said (C$_{3-6}$)cycloalkyl is unsubstituted or mono-substituted with amino (especially 1-amino-cyclopropyl);
(C$_{4-6}$)cycloalkyl containing a ring oxygen atom, wherein said (C$_{4-6}$)cycloalkyl containing a ring oxygen atom is unsubstituted or mono-substituted with fluoro, hydroxy, or methoxy (especially 3-fluoro-oxetan-3-yl, 3-hydroxy-oxetan-3-yl, 3-methoxy-oxetan-3-yl);
hydroxy;
—B(OH)$_2$;
2,2,2-trifluoro-1,1-dihydroxy-ethyl;

—X$^1$—CO—R$^{O1}$, wherein
X$^1$ represents a direct bond, (C$_{1-3}$)alkylene (especially —CH$_2$—, —CH$_2$—CH$_2$—), —O—(C$_{1-3}$)alkylene-* (especially —O—CH$_2$—*, —O—CH(CH$_3$)*, —O—CH$_2$—CH$_2$—*), —NH—(C$_{1-3}$)alkylene-* (especially —NH—CH$_2$—*, —NH—CH(CH$_3$)—*), —S—CH$_2$—*, —CF$_2$—, —CH=CH—, —CH—CH—, —NH—CO—*, —CO—, or (C$_{3-5}$)cycloalkylene; wherein the asterisks indicate the bond that is linked to the —CO—R$^{O1}$ group; and
R$^{O1}$ represents
—OH;
—O—(C$_{1-4}$)alkyl (especially ethoxy, methoxy);
—NH—SO$_2$—R$^{S3}$ wherein R$^{S3}$ represents (C$_{1-4}$)alkyl, (C$_{3-6}$)cycloalkyl wherein the (C$_{3-6}$)cycloalkyl optionally contains a ring oxygen atom, (C$_{3-6}$)cycloalkyl-(C$_{1-3}$)alkylene wherein the (C$_{3-6}$)cycloalkyl optionally contains a ring oxygen atom, (C$_{1-3}$)fluoroalkyl, phenyl, or —NH$_2$;
—O-phenyl;
—O—CH$_2$—CO—R$^{O4}$, wherein R$^{O4}$ represents hydroxy, or (C$_{1-4}$)alkoxy, or —N[(C$_{1-4}$)alkyl]$_2$;
—O—CH$_2$—O—CO—R$^{O5}$, wherein R$^{O5}$ represents (C$_{1-4}$)alkyl or (C$_{1-4}$)alkoxy; or
-O—CH$_2$—CH$_2$—N[(C$_{1-4}$)alkyl]$_2$ (especially —O—CH$_2$—CH$_2$—N(CH$_3$)$_2$);
(5-methyl-2-oxo-[1,3]dioxol-4-yl)-methyloxy-;
[wherein in particular such group —X$^1$—CO—R$^{O1}$ represents —COOH, —CO—O—C$_2$H$_5$, —O—CH$_2$—COOH, —NH—CH$_2$—COOH, —CO—NH—SO$_2$—CH$_3$, —CO—NH—SO$_2$—C(CH$_3$)$_2$, —CO—NH—SO$_2$-cyclopropyl, —CO—NH—SO$_2$-phenyl, —CO—O—CH$_3$, —CO—NH—SO$_2$-ethyl, —CO—NH—SO$_2$—NH$_2$, —COO—CH$_2$—COOH, —COO—CH$_2$—CH$_2$—N(CH$_3$)$_2$, —COO—CH$_2$—CO—N(CH$_3$)$_2$, —COO—CH$_2$—O—CO—O-ethyl, —COO—CH$_2$—O—CO-propyl, (5-methyl-2-oxo-[1,3]dioxol-4-yl)-methyl-O—CO—, —CH$_2$—COOH, —CH$_2$—CO—O-ethyl, —CH$_2$—CH$_2$—COOH, —CF$_2$—COOH, —CH=CH—COOH, —CH—CH—CO—O-ethyl, —NH—CO—COOH, —CO—COOH, —O—CH$_2$—CH$_2$—COOH, —O—CH(CH$_3$)—COOH, —NH—CH(CH$_3$)—COOH, —NH—CH$_2$—COO—CH$_3$, —COO-phenyl, 1-carboxy-cyclopropan-1-yl, 1-carboxy-cyclopentan-1-yl];
—CO—CH$_2$—CN;
—CO—CH$_2$—OH;
—CO—H;

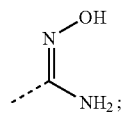
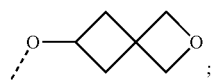

2-hydroxy-3,4-dioxo-cyclobut-1-enyl;
hydroxy-(C$_{1-4}$)alkyl (especially hydroxymethyl, 1-hydroxy-ethyl);
dihydroxy-(C$_{2-4}$)alkyl (especially 1,2-dihydroxyethyl);
hydroxy-(C$_{2-4}$)alkoxy (especially 2-hydroxyethoxy);
(C$_{1-4}$)alkoxy-(C$_{2-4}$)alkoxy (especially 2-methoxyethoxy);
—(CH$_2$)$_m$—NR$^{N1}$R$^{N2}$, wherein m represents the integer 0 or 1; and wherein
R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl, -or —SO$_2$—(C$_{1-4}$)alkyl (wherein preferably at least one of R$^{N1}$ and R$^{N2}$ represents hydrogen);
or R$^{N1}$ independently represents hydrogen or (C$_{1-4}$)alkyl, and R$^{N2}$ independently represents —CO—H, —CO—(C$_{1-3}$)alkyl, —CO—(C$_{1-3}$)alkylene-OH, or —CO—O—(C$_{1-3}$)alkyl;
or R$^{N1}$ and R$^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —(CH$_2$)$_m$—NR$^{N1}$R$^{N2}$ represents amino, methylamino, ethylamino, propylamino, aminomethyl, methylamino-methyl, isobutylaminomethyl, cyclopropylamino-methyl, cyclobutylamino-methyl, (2-methoxyethyl)amino-methyl, —NH—SO$_2$-methyl, —NH—SO$_2$-ethyl, or (2,2,2-trifluoro-ethyl)-amino; or —CH$_2$—NH—SO$_2$—CH$_3$; or —NH—CO—H, —N(C$_2$H$_5$)—CO—H, —NH—CO—C$_2$H$_5$, —NH—CO—CH$_2$—CH$_2$—OH, —NH—COO—CH$_3$, —N(CH$_3$)—COO—CH$_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl);
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, hydroxy-(C$_{2-4}$)alkoxy, benzyloxy, or hydroxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—C$_2$H$_4$—OCH$_3$, —CO—NH—O—C$_2$H$_4$—OH, —CO—NH—C$_2$H$_4$—N(CH$_3$)$_2$, —CO—NH—O-benzyl, or —CO—N(CH$_3$)$_2$, —CO—NH-isopropyl, or —CO—NH—OH);
—NH—CO—NR$^{N5}$R$^{N6}$ wherein R$^{N5}$ and R$^{N6}$ independently represent hydrogen or (C$_{1-4}$)alkyl (especially such group represents —NH—CO—NH$_2$, —NH—CO—NH—C$_2$H$_5$);
—SO$_2$—R$^{S1}$ wherein R$^{S1}$ represents hydroxy, (C$_{1-4}$)alkyl (especially methyl), or —NR$^{N7}$R$^{N8}$ wherein R$^{N7}$ and R$^{N8}$ independently represent hydrogen or (C$_{1-3}$)alkyl (especially such group represents —SO$_2$—CH$_3$, —SO$_2$—NH$_2$, —SO$_2$—OH, —SO$_2$—NH—CH$_3$);
5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);
benzooxazol-2-yl; or
—$(CH_2)_p$-HET, wherein p represents the integer 0 or 1 (especially 0); and wherein HET represents a 5- or 6-membered heteroaryl (especially oxazolyl, isoxazolyl, oxadiazolyl, thiazolyl, isothiazolyl, thiadiazolyl, imidazolyl, pyrazolyl, triazolyl, tetrazolyl, pyridinyl, pyrimidinyl, pyridazinyl, or pyrazinyl), wherein said 5- or 6-membered heteroaryl is unsubstituted, or mono- or di-substituted, wherein the substituents are independently selected from $(C_{1-4})$alkyl (especially methyl), $(C_{1-4})$alkoxy (especially methoxy), —COOH, hydroxy, fluoro, 2-amino-2-oxo-ethyl, 2-carboxyethyl, $(C_{3-5})$cycloalkyl (especially cyclopropyl), or —$NR^{N9}R^{N10}$ wherein $R^{N9}$ and $R^{N10}$ independently represent hydrogen or $(C_{1-3})$alkyl (especially amino, methylamino, dimethylamino); (especially such group —$(CH_2)_p$-HET is 1H-tetrazol-5-yl, 1H-pyrazol-1-yl, 1H-pyrazol-3-yl, 3-methylpyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, pyrazol-1-yl-methyl, 1H-imidazol-4-yl, 3H-[1,2,3]triazol-4-yl, 5-methyl-1H-imidazol-4-yl, 1,2-dimethyl-1H-imidazol-4-yl, 1,5-dimethyl-1H-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, or pyridin-2-yl);

and $(R^4)_n$ represents one or two optional substituents (i.e. n represents the integer 0, 1, or 2) independently selected from
$(C_{1-6})$alkyl (especially methyl, ethyl, n-propyl, isopropyl, n-butyl, isobutyl, 1-methyl-propan-1-yl, tert.-butyl, 3-methyl-butyl);
$(C_{1-4})$alkoxy (especially methoxy, ethoxy, n-propoxy, isopropoxy, n-butoxy, isobutoxy);
$(C_{1-3})$fluoroalkyl (especially trifluoromethyl);
$(C_{1-3})$fluoroalkoxy (especially difluoromethoxy, trifluoromethoxy, 2,2,2-trifluoroethoxy);
halogen (especially fluoro or chloro);
$(C_{3-6})$cycloalkyl (especially cyclopropyl);
$(C_{3-6})$cycloalkyl-oxy (especially cyclobutyl-oxy, cyclopentyl-oxy);
hydroxy;
nitro;
—$(CH_2)_m$—$NR^{N1}R^{N2}$, wherein m represents the integer 0 or 1 (especially 0); and wherein $R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl (especially 2,2,2-trifluoro-ethyl), -or —$SO_2$—$(C_{1-4})$alkyl; or $R^{N1}$ and $R^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —$(CH_2)_m$—$NR^{N1}R^{N2}$ represents amino, methylamino, ethylamino, propylamino, —NH—$SO_2$-methyl, —NH—$SO_2$-ethyl, or (2,2,2-trifluoro-ethyl)-amino; or pyrrolidin-1-yl);
—S—$R^{S2}$ wherein $R^{S2}$ represents $(C_{1-4})$alkyl (especially methyl, ethyl, n-propyl, isopropyl, isobutyl), $(C_{3-6})$cycloalkyl (especially cyclobutyl), or 2-fluoro-vinyl; or
phenyl-oxy, wherein the phenyl is optionally mono-substituted with halogen (especially 4-fluorophenoxy);
[wherein especially $(R^4)_n$ is absent, or $(R^4)_n$ represents one or two substituents, wherein one of said substituents is as defined above, and the other, if present, is fluoro or chloro];
or $R^5$ represents hydrogen, and $(R^4)$~ represents one or two substituents (i.e. n represents the integer 1 or 2), wherein
one of said substituents is selected from 1H-pyrazol-1-yl, and —$X^1$—COOH, wherein $X^1$ represents a direct bond, $(C_{1-3})$alkylene (especially —$CH_2$—, —$CH_2$—$CH_2$—), or —O—$(C_{1-3})$alkylene-* (especially —O—$CH_2$—*, —O—$CH_2$—$CH_2$—*), wherein the asterisks indicate the bond that is linked to the —COOH group [wherein in particular such group —$X^1$—COOH represents —COOH, —$CH_2$—COOH, —$CH_2$—$CH_2$—COOH, —O—$CH_2$—$CH_2$—COOH];
and the other of said substituents, if present, is selected from $(C_{1-4})$alkoxy (especially methoxy, ethoxy, n-propoxy); and —S—$(C_{1-4})$alkyl (especially —S-methyl, —S-ethyl, —S-n-propyl);
or $Ar^1$ represents a 5-membered heteroaryl group of the structure (Ar-II):

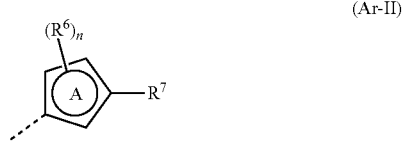

(Ar-II)

wherein in (Ar-II) the ring A represents a 5-membered heteroaryl ring (wherein it is well understood that in (Ar-II) the substituent $R^7$ is attached in meta-position with respect to the point of attachment of the rest of the molecule) (notably a thiophenyl or a thiazolyl ring;

especially thiophen-2-yl wherein $R^7$ is attached in position 5, or thiophen-2-yl wherein $R^7$ is attached in position 4; or thiazol-2-yl wherein $R^7$ is attached in position 5);
wherein
$R^7$ represents
- $(C_{1-4})$alkoxy (especially methoxy);
- $(C_{1-3})$fluoroalkyl, wherein said $(C_{1-3})$fluoroalkyl is optionally substituted with hydroxy (especially 2,2,2-trifluoro-1-hydroxy-ethyl);
- $(C_{3-6})$cycloalkyl, wherein said $(C_{3-6})$cycloalkyl is unsubstituted or mono-substituted with amino (especially 1-amino-cyclopropyl);
- $(C_{4-6})$cycloalkyl containing a ring oxygen atom, wherein said $(C_{4-6})$cycloalkyl containing a ring oxygen atom is unsubstituted or mono-substituted with fluoro, hydroxy, or methoxy (especially 3-fluoro-oxetan-3-yl, 3-hydroxy-oxetan-3-yl, 3-methoxy-oxetan-3-yl);
- hydroxy;
- 2,2,2-trifluoro-1,1-dihydroxy-ethyl;
- —$X^1$—CO—$R^{O1}$, wherein
  $X^1$ represents a direct bond, $(C_{1-3})$alkylene (especially —CH$_2$—, —CH$_2$—CH$_2$—), —O—$(C_{1-3})$alkylene-* (especially —O—CH$_2$—*, —O—CH(CH$_3$)—*, —O—CH$_2$—CH$_2$—*), —NH—$(C_{1-3})$alkylene-* (especially —NH—CH$_2$—*, —NH—CH(CH$_3$)—*), —S—CH$_2$—*, —CF$_2$—, —CH=CH—, —CH—CH—, —NH—CO—*, —CO—, or $(C_{3-5})$cycloalkylene; wherein the asterisks indicate the bond that is linked to the —CO—$R^{O1}$ group; and
  $R^{O1}$ represents
    - —OH;
    - —O—$(C_{1-4})$alkyl (especially ethoxy, methoxy);
    - —NH—SO$_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —NH$_2$;
    - —O-phenyl;
    - —O—CH$_2$—CO—$R^{O4}$, wherein $R^{O4}$ represents hydroxy, or $(C_{1-4})$alkoxy, or —N[$(C_{1-4})$alkyl]$_2$;
    - —O—CH$_2$—O—CO—$R^{O5}$, wherein $R^{O5}$ represents $(C_{1-4})$alkyl or $(C_{1-4})$alkoxy; or
    - —O—CH$_2$—CH$_2$—N[$(C_{1-4})$alkyl]$_2$ (especially —O—CH$_2$—CH$_2$—N(CH$_3$)$_2$);
    - (5-methyl-2-oxo-[1,3]dioxol-4-yl)-methyloxy-;
    - [wherein in particular, such group —$X^1$—CO—$R^{O1}$ represents —COOH, —CO—O—C$_2$H$_5$, —O—CH$_2$—COOH, —NH—CH$_2$—COOH, —CO—NH—SO$_2$—CH$_3$, —CO—NH—SO$_2$—C(CH$_3$)$_2$, —CO—NH—SO$_2$-cyclopropyl, —CO—NH—SO$_2$-phenyl, —COO—CH$_3$, —CO—NH—SO$_2$-ethyl, —CO—NH—SO$_2$—NH$_2$, —COO—CH$_2$—COOH, —COO—CH$_2$—CH$_2$—N(CH$_3$)$_2$, —COO—CH$_2$—CO—N(CH$_3$)$_2$, —COO—CH$_2$—O—CO—O-ethyl, —COO—CH$_2$—O—CO-propyl, (5-methyl-2-oxo-[1,3]dioxol-4-yl)-methyl-O—CO—, —CH$_2$—COOH, —CH$_2$—O—CO—O-ethyl, —CH$_2$—CH$_2$—COOH, —CF$_2$—COOH, —CH=CH—COOH, —CH=CH—CO—O-ethyl, —NH—CO—COOH, —CO—COOH, —O—CH$_2$—CH$_2$—COOH, —O—CH(CH$_3$)—COOH, —NH—CH(CH$_3$)—COOH, —NH—CH$_2$—COO—CH$_3$, —COO-phenyl, 1-carboxy-cyclopropan-1-yl, 1-carboxy-cyclopentan-1-yl];
- —CO—CH$_2$—CN;
- —CO—CH$_2$—OH;
- —CO—H;

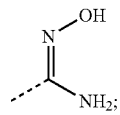

2-hydroxy-3,4-dioxo-cyclobut-1-enyl;
hydroxy-$(C_{1-4})$alkyl (especially hydroxymethyl, 1-hydroxy-ethyl);
dihydroxy-$(C_{2-4})$alkyl (especially 1,2-dihydroxy-ethyl);
hydroxy-$(C_{2-4})$alkoxy (especially 2-hydroxy-ethoxy);
$(C_{1-4})$alkoxy-$(C_{2-4})$alkoxy (especially 2-methoxy-ethoxy);
—NR$^{N1}$R$^{N2}$, wherein
  $R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl, -or —SO$_2$—$(C_{1-4})$alkyl (wherein preferably at least one of $R^{N1}$ and $R^{N2}$ represents hydrogen);
  or $R^{N1}$ independently represents hydrogen or $(C_{1-4})$alkyl, and $R^{N2}$ independently represents —CO—H, —CO—$(C_{1-3})$alkyl, —CO—$(C_{1-3})$alkylene-OH, or —CO—O—$(C_{1-3})$alkyl;
  or $R^{N1}$ and $R^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;
  (especially such group —NR$^{N1}$R$^{N2}$ represents amino, methylamino, ethylamino, propylamino, —NH—SO$_2$-methyl, —NH—SO$_2$-ethyl, or (2,2,2-trifluoro-ethyl)-amino; or —CH$_2$—NH—SO$_2$-methyl; or —NH—CO—H, —N(C$_2$H$_5$)—CO—H, —NH—CO—C$_2$H$_5$, —NH—CO—CH$_2$—CH$_2$—OH, —NH—COO—CH$_3$, —N(CH$_3$)—COO—CH$_3$; or pyrrolidin-1-yl, 2-oxo-pyrrolidin-1-yl, 1,1-dioxo-isothiazolidin-2-yl, morpholin-4-yl, azetidin-1-yl, or piperidin-1-yl);
—CO—NR$^{N3}$R$^{N4}$ wherein $R^{N3}$ and $R^{N4}$ independently represent hydrogen, $(C_{1-4})$alkyl, hydroxy-$(C_{2-4})$alkyl, $(C_{1-3})$alkoxy-$(C_{2-4})$alkyl, dimethylamino-$(C_{2-4})$alkyl, $(C_{1-4})$alkoxy, hydroxy-$(C_{2-4})$alkoxy, benzyloxy, or hydroxy (wherein preferably at least one of $R^{N3}$ and $R^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—C$_2$H$_4$—OCH$_3$, —CO—NH—O—C$_2$H$_4$—OH, —CO—NH—C$_2$H$_4$—N(CH$_3$)$_2$, —CO—NH—O-benzyl, or —CO—N(CH$_3$)$_2$, —CO—NH-isopropyl, or —CO—NH—OH);
—NH—CO—NR$^{N5}$R$^{N6}$ wherein R$^{N5}$ and R$^{N6}$ independently represent hydrogen or (C$_{1-4}$)alkyl (especially such group represents —NH—CO—NH$_2$, —NH—CO—NH—C$_2$H$_5$);
—SO$_2$—R$^{S1}$ wherein R$^{S1}$ represents hydroxy, (C$_{1-4}$)alkyl (especially methyl), or —NR$^{N7}$R$^{N8}$ wherein R$^{N7}$ and R$^{N8}$ independently represent hydrogen or (C$_{1-3}$)alkyl (especially such group represents —SO$_2$—CH$_3$, —SO$_2$—NH$_2$, —SO$_2$—OH, —SO$_2$—NH—CH$_3$);
5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);
HET, wherein HET represents a 5- or 6-membered heteroaryl (especially oxazolyl, isoxazolyl, oxadiazolyl, thiazolyl, isothiazolyl, thiadiazolyl, imidazolyl, pyrazolyl, triazolyl, tetrazolyl, pyridinyl, pyrimidinyl, pyridazinyl, or pyrazinyl, notably tetrazolyl, or isoxazolyl), wherein said 5- or 6-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, fluoro, 2-amino-2-oxo-ethyl, 2-carboxy-ethyl, (C$_{3-5}$)cycloalkyl (especially cyclopropyl), or —NR$^{N9}$R$^{N10}$ wherein R$^{N9}$ and R$^{N10}$ independently represent hydrogen or (C$_{1-3}$) alkyl (especially amino, dimethylamino); (especially such group HET is 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl, [1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, pyrazol-1-yl-methyl, 1H-imidazol-4-yl, 3H-[1,2,3]triazol-4-yl, 5-methyl-1H-imidazol-4-yl, 1,2-dimethyl-1H-imidazol-4-yl, 1,5-dimethyl-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, or pyridin-2-yl; notably HET is 1H-tetrazol-5-yl or 3-hydroxy-isoxazol-5-yl);

and (R$^6$)$_n$ represents one optional substituent (i.e. n represents the integer 0, or 1) independently selected from
(C$_{1-6}$)alkyl (especially methyl, ethyl, n-propyl, isopropyl, n-butyl, isobutyl, 1-methyl-propan-1-yl, tert.-butyl, 3-methyl-butyl);
(C$_{1-4}$)alkoxy (especially methoxy, ethoxy, n-propoxy, isopropoxy, n-butoxy, isobutoxy);
(C$_{1-3}$)fluoroalkyl (especially trifluoromethyl);
(C$_{1-3}$)fluoroalkoxy (especially difluoromethoxy, trifluoromethoxy, 2,2,2-trifluoroethoxy);
halogen (especially fluoro or chloro);
(C$_{3-6}$)cycloalkyl (especially cyclopropyl);
(C$_{3-6}$)cycloalkyl-oxy (especially cyclobutyl-oxy, cyclopentyl-oxy);
hydroxy;
pyridinyl;
—(CH$_2$)$_m$—NR$^{N1}$R$^{N2}$, wherein m represents the integer 0 or 1 (especially 0); and wherein R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl (especially 2,2,2-trifluoroethyl), -or —SO$_2$—(C$_{1-4}$)alkyl; or R$^{N1}$ and R$^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom; (especially such group —(CH$_2$)$_m$—NR$^{N1}$R$^{N2}$ represents amino, methylamino, ethylamino, propylamino, —NH—SO$_2$-methyl, —NH—SO$_2$-ethyl, or (2,2,2-trifluoro-ethyl)-amino; or pyrrolidin-1-yl); and
—S—R$^{S2}$ wherein R$^{S2}$ represents (C$_{1-4}$)alkyl (especially methyl, ethyl, n-propyl, isopropyl, isobutyl), (C$_{3-6}$)cycloalkyl (especially cyclobutyl), or 2-fluoro-vinyl;
[wherein, if present, such substituent R$^6$ is especially attached in the other meta-position with respect to the point of attachment of the rest of the molecule, i.e. especially ring A represents thiophen-2-yl wherein R$^7$ is attached in position 5 and R$^6$ is attached in position 4, or thiophen-2-yl wherein R$^7$ is attached in position 4 and R$^6$ is attached in position 5; or thiazol-2-yl wherein R$^7$ is attached in position 5 and R$^6$ is attached in position 4)];
or Ar$^1$ represents 9- or 10-membered bicyclic heteroaryl (especially indazolyl, benzoimidazolyl, indolyl, benzotriazolyl, benzooxazolyl, quinoxalinyl, isoquinolinyl, quinolinyl, pyrrolopyridinyl, or imidazopyridinyl); wherein said 9- or 10-membered bicyclic heteroaryl independently is unsubstituted, mono-, or di-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); (C$_{1-3}$)fluoroalkoxy (especially trifluoromethoxy); halogen; cyano; hydroxy, or —(C$_{0-3}$)alkylene-COOR$^{O2}$ wherein R$^{O2}$ represents hydrogen or (C$_{1-4}$)alkyl (especially methyl); (especially such 9- to 10-membered bicyclic heteroaryl is 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, quinolin-6-yl, 1H-indol-2-yl, 1H-indol-3-yl, 1H-indol-4-yl, 1H-indazol-5-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 3-methoxy-1H-indazol-6-yl, 6-methoxy-1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl; preferably such 9- to 10-membered bicyclic heteroaryl is 1H-benzoimidazol-5-yl, 1H-indol-6-yl, 1H-indol-5-yl, 1H-indol-2-yl, 1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl);

or $Ar^1$ represents a group of the structure (Ar-III):

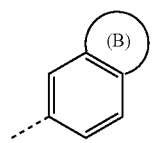

(Ar-III)

wherein ring (B) represents a non-aromatic 5- or 6-membered ring fused to the phenyl group, wherein ring (B) comprises one or two heteroatoms independently selected from nitrogen and oxygen (notably such group (Ar-III) is 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 2,3-dihydro-benzooxazolyl, 1,2,3,4-tetrahydro-quinazolinyl, 1,2,3,4-tetrahydro-isoquinolinyl, or 1,2,3,4-tetrahydro-phthalazinyl); wherein said ring (B) independently is unsubstituted, mono-, or di-substituted, wherein the substituents are independently selected from oxo, $(C_{1-6})$alkyl (especially methyl, ethyl, propyl, butyl, isobutyl) and —$(C_{0-3})$alkylene-$COOR^{O3}$ wherein $R^{O3}$ represents hydrogen or $(C_{1-3})$alkyl (especially such group (Ar-III) is 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, 2-isobutyl-1-oxo-2,3-dihydro-isoindol-5-yl, 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-methyl-2-oxo-1,2-dihydro-1H-indazol-6-yl, 1-(carboxymethyl)-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, 1-oxo-1,2,3,4-tetrahydro-isoquinolin-6-yl, or 1,4-dioxo-1,2,3,4-tetrahydro-phthalazin-6-yl; preferably such group (Ar-III) is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, or 1-oxo-1,2,3,4-tetrahydro-isoquinolin-6-yl).

10) Another embodiment relates to compounds according to any one of embodiments 1) to 5), wherein $Ar^1$ represents a phenyl group of the structure (Ar-IV):

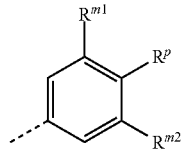

(Ar-IV)

wherein
$R^p$ represents;
hydroxy;
—COOH;
—CO—CH$_2$—CN;
—CO—$(C_{1-4})$alkoxy (especially —CO—O-ethyl);
—CO—NH—SO$_2$—$R^{S3}$ wherein $R^{S3}$ represents $R^{S3}$ represents $(C_{1-4})$alkyl, $(C_{3-6})$cycloalkyl; $(C_{3-6})$cycloalkyl-$(C_{1-3})$alkyl; $(C_{1-3})$fluoroalkyl, phenyl, or —NH$_2$ (especially $R^{S3}$ represents $(C_{1-4})$alkyl or cyclopropyl, in particular methyl, isopropyl, or cyclopropyl);
—X$^1$—CH$_2$—COOH, wherein X$^1$ represents O, or NH (especially —O—CH$_2$—COOH, or —NH—CH$_2$—COOH);
hydroxy-$(C_{1-4})$alkyl (especially hydroxymethyl);
—CO—NR$^{N3}$R$^{N4}$ wherein R$^{N3}$ and R$^{N4}$ independently represent hydrogen, $(C_{1-4})$alkyl, hydroxy-$(C_{2-4})$alkyl, $(C_{1-3})$alkoxy-$(C_{2-4})$alkyl, dimethylamino-$(C_{2-4})$alkyl, $(C_{1-4})$alkoxy, or hydroxy-$(C_{2-4})$alkoxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—O—C$_2$H$_4$—OH, —CO—NH—C$_2$H$_4$—OCH$_3$, —CO—NH—C$_2$H$_4$—N(CH$_3$)$_2$);
—NH—CO—NR$^{N5}$R$^{N6}$ wherein R$^{N5}$ and R$^{N6}$ independently represent hydrogen or $(C_{1-4})$alkyl (especially such group is —NH—CO—NH$_2$, —NH—CO—NH—C$_2$H$_5$);
—SO$_2$—R$^{S1}$ wherein R$^{S1}$ represents hydroxy, $(C_{1-4})$alkyl (especially methyl), or —NR$^{N7}$R$^{N8}$ wherein R$^{N7}$ and R$^{N8}$ independently represent hydrogen or $(C_{1-3})$alkyl (especially such group is —SO$_2$—CH$_3$, —SO$_2$—NH$_2$, —SO$_2$—OH, —SO$_2$—NH—CH$_3$);
5-oxo-4,5-dihydro-[1,2,4]oxadiazol-3-yl;
tetrazolyl (especially 1H-tetrazol-5-yl); or
5- or 6-membered heteroaryl selected from oxazolyl, isoxazolyl, oxadiazolyl, thiazolyl, isothiazolyl, thiadiazolyl, imidazolyl, pyrazolyl, triazolyl, pyridinyl, pyrimidinyl, pyridazinyl, or pyrazinyl; wherein said 5- or 6-membered heteroaryl is unsubstituted, or mono- or di-substituted, wherein the substituents are independently selected from (C$_{1-3}$)alkyl (especially methyl), (C$_{1-3}$)alkoxy (especially methoxy), —COOH, hydroxy, fluoro, 2-amino-2-oxo-ethyl, 2-carboxy-ethyl, or —NR$^{N9}$R$^{N10}$ wherein R$^{N9}$ and R$^{N10}$ independently represent hydrogen or (C$_{1-3}$)alkyl (especially amino, dimethylamino);

R$^{m1}$ represents
hydrogen;
(C$_{1-6}$)alkyl (especially methyl, ethyl, propyl, isobutyl, 1-methyl-propan-1-yl, tert.-butyl, 3-methyl-butyl);
(C$_{1-4}$)alkoxy (especially methoxy, ethoxy, propoxy, isopropoxy, butoxy, isobutoxy);
(C$_{1-3}$)fluoroalkyl (especially trifluoromethyl);
(C$_{1-3}$)fluoroalkoxy (especially difluoromethoxy, trifluoromethoxy, 2,2,2-trifluoroethoxy);
halogen (especially chloro, or fluoro);
(C$_{3-6}$)cycloalkyl (especially cyclopropyl);
(C$_{3-6}$)cycloalkyl-oxy (especially cyclobutyl-oxy, cyclopentyl-oxy);
hydroxy;
—(CH$_2$)$_m$—NR$^{N1}$R$^{N2}$, wherein m represents the integer 0 or 1 (especially 0); and wherein R$^{N1}$ and R$^{N2}$ independently represent hydrogen, (C$_{1-3}$)alkyl (especially methyl, ethyl), or (C$_{2-3}$)fluoroalkyl (especially 2,2,2-trifluoro-ethyl); or R$^{N1}$ and R$^{N2}$ together with the nitrogen to which they are attached form a pyrrolidinyl ring (especially such group —(CH$_2$)$_m$—NR$^{N1}$R$^{N2}$ represents amino, methylamino, ethylamino, propylamino, or (2,2,2-trifluoro-ethyl)-amino; or pyrrolidin-1-yl); or
—S—R$^{S2}$ wherein R$^{S2}$ represents (C$_{1-4}$)alkyl (especially methyl, ethyl, n-propyl, isopropyl, isobutyl), or (C$_{3-6}$)cycloalkyl (especially cyclobutyl);

and R$^{m2}$ represents
hydrogen; or
(C$_{1-6}$)alkyl (especially methyl, ethyl);
(C$_{1-3}$)alkoxy (especially methoxy, ethoxy); or
halogen (especially chloro, or fluoro);

or Ar$^1$ represents a 5-membered heteroaryl group of the structure (Ar-V):

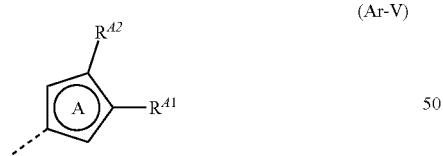

(Ar-V)

wherein in (Ar-V) the ring A represents a thiophenyl or a thiazolyl ring (especially thiophen-2-yl, or thiazol-2-yl); (wherein it is well understood that in (Ar-V) the substituent R$^{A1}$ is attached in meta-position with respect to the point of attachment of the rest of the molecule, especially in case the ring A represents a thiophen-2-yl, in position 5 of such thiophen-2-yl) wherein R$^{A1}$ represents
—COOH;
tetrazolyl (especially 1H-tetrazol-5-yl);
—CO—(C$_{1-4}$)alkoxy (especially —CO—O-ethyl);
—CO—NH—SO$_2$—R$^{S3}$ wherein R$^{S3}$ represents R$^{S3}$ represents (C$_{1-4}$)alkyl, (C$_{3-6}$)cycloalkyl; (C$_{3-6}$)cycloalkyl-(C$_{1-3}$)alkyl; (C$_{1-3}$)fluoroalkyl, phenyl, or —NH$_2$ (especially R$^{S3}$ represents (C$_{1-4}$)alkyl or cyclopropyl, in particular methyl, isopropyl, or cyclopropyl);
—X$^1$—CH$_2$—COOH, wherein X$^1$ represents O, or NH (especially —O—CH$_2$—COOH, or —NH—CH$_2$—COOH); or
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, or (C$_{1-3}$)alkoxy-(C$_{2-4}$)alkyl; (wherein preferably at least one of R$^{N3}$ and R$^{N4}$ represents hydrogen; and wherein particular examples of such group —CO—NR$^{N3}$R$^{N4}$ are —CO—NH(CH$_3$), —CO—NH(C$_2$H$_5$), —CO—NH—C$_2$H$_4$—OH, —CO—NH—C$_2$H$_4$—OCH$_3$);

and R$^{A2}$ represents
hydrogen;
(C$_{1-6}$)alkyl (especially methyl, ethyl);
(C$_{1-4}$)alkoxy (especially ethoxy, propoxy, isopropoxy, butoxy);
(C$_{1-3}$)fluoroalkyl (especially trifluoromethyl);
halogen (especially fluoro or chloro); or
hydroxy;

or Ar$^1$ represents 9- or 10-membered bicyclic heteroaryl selected from 1H-indol-5-yl, 1H-indol-4-yl, 1H-indol-6-yl, indazol-6-yl, 1H-benzoimidazol-5-yl, 1H-benzotriazol-5-yl, quinoxalin-6-yl, isoquinolin-7-yl, and quinolin-6-yl; wherein said 9- or 10-membered bicyclic heteroaryl independently is unsubstituted, mono-, or di-substituted, wherein the substituents are independently selected from (C$_{1-4}$)alkyl (especially methyl) or —COOH (especially such heteroaryl is 1H-indazol-6-yl, 1-methyl-1H-indazol-6-yl, 3-carboxy-1H-indazol-6-yl, 1H-benzoimidazol-5-yl, 2-methyl-1H-benzoimidazol-5-yl, 1H-indol-5-yl, 1-methyl-1H-indol-5-yl, 7-carboxy-1H-indol-4-yl, 1H-benzotriazol-5-yl, quinoxalin-6-yl, isoquinolin-7-yl, or quinolin-6-yl);

or Ar$^1$ represents a group of the structure (Ar-III):

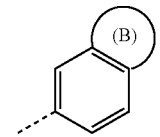

(Ar-III)

wherein ring (B) represents a non-aromatic 5-membered ring fused to the phenyl group, wherein ring (B) comprises one or two nitrogen ring atoms; wherein said ring (B) independently is unsubstituted, mono-, or di-substituted, wherein the substituents are independently selected from oxo and (C$_{1-6}$)alkyl (especially methyl, ethyl, propyl, butyl, isobutyl) (especially such group (Ar-III) is 2,3-dihydro-1H-indol-5-yl, 3-oxo-2,3-dihydro-1H-indazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl).

11) Another embodiment relates to compounds according to any one of embodiments 1) to 5), wherein Ar$^1$ represents a phenyl group of the structure (Ar-IV):

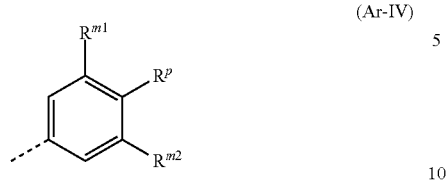
(Ar-IV)

wherein
$R^P$ represents;
($C_{4-6}$)cycloalkyl containing a ring oxygen atom, wherein said ($C_{4-6}$)cycloalkyl containing a ring oxygen atom is unsubstituted or mono-substituted with fluoro, hydroxy, or methoxy (especially 3-fluoro-oxetan-3-yl, 3-hydroxy-oxetan-3-yl, 3-methoxy-oxetan-3-yl);
hydroxy;
—$X^1$—CO—$R^{O1}$, wherein
$X^1$ represents a direct bond, ($C_{1-3}$)alkylene (especially —$CH_2$—, —$CH_2$—$CH_2$—), —O—($C_{1-3}$)alkylene-* (especially —O—$CH_2$—*, —O—CH($CH_3$)—*, —O—$CH_2$—$CH_2$—*), —NH—($C_{1-3}$)alkylene-* (especially —NH—$CH_2$—*, —NH—CH($CH_3$)*), —S—$CH_2$—*, —$CF_2$—, —CH=CH—, —CH=CH—, —NH—CO—*, —CO—, or ($C_{3-5}$)cycloalkylene; wherein the asterisks indicate the bond that is linked to the —CO—$R^{O1}$ group; and
$R^{O1}$ represents
—OH;
—O—($C_{1-4}$)alkyl (especially ethoxy, methoxy);
—NH—$SO_2$—$R^{S3}$ wherein $R^{S3}$ represents ($C_{1-4}$)alkyl, ($C_{3-6}$)cycloalkyl wherein the ($C_{3-6}$)cycloalkyl optionally contains a ring oxygen atom, ($C_{3-6}$)cycloalkyl-($C_{1-3}$)alkylene wherein the ($C_{3-6}$)cycloalkyl optionally contains a ring oxygen atom, ($C_{1-3}$)fluoroalkyl, phenyl, or —$NH_2$;
—O—$CH_2$—CO—$R^{O4}$, wherein $R^{O4}$ represents hydroxy, or ($C_{1-4}$)alkoxy, or —N[($C_{1-4}$)alkyl]$_2$;
—O—$CH_2$—O—CO—$R^{O5}$, wherein $R^{O5}$ represents ($C_{1-4}$)alkyl or ($C_{1-4}$)alkoxy; or
—O—$CH_2$—$CH_2$—N[($C_{1-4}$)alkyl]$_2$ (especially —O—$CH_2$—$CH_2$—N($CH_3$)$_2$);
(5-methyl-2-oxo-[1,3]dioxol-4-yl)-methyloxy-;
[wherein in particular such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—C($CH_3$)$_2$, —CO—NH—$SO_2$-cyclopropyl, —CO—NH—$SO_2$-phenyl, —COO—$CH_3$, —CO—NH—$SO_2$-ethyl, —CO—NH—$SO_2$—$NH_2$, —COO—$CH_2$—COOH, —COO—$CH_2$—$CH_2$—N($CH_3$)$_2$, —COO—$CH_2$—CO—N($CH_3$)$_2$, —COO—$CH_2$—O—CO—O-ethyl, —COO—$CH_2$—O—CO-propyl, (5-methyl-2-oxo-[1,3]dioxol-4-yl)-methyl-O—CO—, —$CH_2$—COOH, —$CH_2$—CO—O-ethyl, —$CH_2$—CO—COOH, —$CF_2$—COOH, —CH=CH—COOH, —CH—CH—CO—O-ethyl, —NH—CO—COOH, —CO—COOH, —O—$CH_2$—$CH_2$—COOH, —O—CH($CH_3$)—COOH, —NH—CH($CH_3$)—COOH, —NH—$CH_2$—COO—$CH_3$, —COO-phenyl, 1-carboxy-cyclopropan-1-yl, 1-carboxy-cyclopentan-1-yl];
—CO—H;

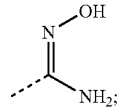

2-hydroxy-3,4-dioxo-cyclobut-1-enyl;
—$NR^{N1}R^{N2}$, wherein
$R^{N1}$ independently represents hydrogen or ($C_{1-4}$)alkyl, and $R^{N2}$ independently represents —CO—H, —CO—($C_{1-3}$)alkyl, or —CO—($C_{1-3}$)alkylene-OH;
(especially such group —($CH_2$)$_m$—$NR^{N1}R^{N2}$ represents-NH—CO—H, —N($C_2H_5$)—CO—H, —NH—CO—$C_2H_5$, —NH—CO—$CH_2$—$CH_2$—OH, or —NH—COO—$CH_3$);
—CO—$NR^{N3}R^{N4}$ wherein $R^{N3}$ and $R^{N4}$ independently represent hydrogen, ($C_{1-4}$)alkyl, hydroxy-($C_{2-4}$)alkyl, ($C_{1-3}$)alkoxy-($C_{2-4}$)alkyl, or hydroxy (wherein preferably at least one of $R^{N3}$ and $R^{N4}$ represents hydrogen; and wherein particular examples of such group —CO—$NR^{N3}R^{N4}$ are —CO—$NH_2$, —CO—NH($CH_3$), —CO—NH($C_2H_5$), —CO—NH—$C_2H_4$—OH, —CO—NH—$C_2H_4$—$OCH_3$, or —CO—N($CH_3$)$_2$, —CO—NH-isopropyl, or —CO—NH—OH);
—NH—CO—$NR^{N5}R^{N6}$ wherein $R^{N5}$ and $R^{N6}$ independently represent hydrogen or ($C_{1-4}$)alkyl (especially such group represents —NH—CO—$NH_2$, —NH—CO—NH—$C_2H_5$);
5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);
HET, wherein HET represents a 5- or 6-membered heteroaryl (especially 5-membered heteroaryl selected from oxazolyl, isoxazolyl, oxadiazolyl, thiazolyl, isothiazolyl, thiadiazolyl, imidazolyl, pyrazolyl, triazolyl, and tetrazolyl; or 6-membered heteroaryl selected from pyridinyl, pyrimidinyl, pyridazinyl, and pyrazinyl), wherein said 5- or 6-membered heteroaryl is unsubstituted, or mono- or di-substituted, wherein the substituents are independently selected from ($C_{1-4}$)alkyl (especially methyl), ($C_{1-4}$)alkoxy (especially methoxy), —COOH, hydroxy, fluoro, 2-amino-2-oxo-ethyl, 2-carboxy-ethyl, ($C_{3-5}$)cycloalkyl (especially cyclopropyl), or —$NR^{N9}R^{N10}$ wherein $R^{N9}$ and $R^{N10}$ independently represent hydrogen or ($C_{1-3}$)alkyl (especially amino, methylamino, dimethylamino) (especially the substituents are independently selected from ($C_{1-3}$)alkyl (especially methyl), and hydroxy); (in particular, such group HET is 1H-tetrazol-5-yl, 1H-pyrazol-1-yl, 1H-pyrazol-3-yl, 3-methyl-pyrazol-1-yl, 1-methyl-1H-pyrazol-3-yl, 5-methyl-1H-pyrazol-3-yl, 3,5-dimethyl-pyrazol-1-yl, 4-carboxy-1H-pyrazol-3-yl, 1H-imidazol-2-yl, 1H-imidazol-4-yl, 3-methyl-3H-imidazol-4-yl, 2-methyl-1H-imidazol-4-yl, 1,5-dimethyl-1H-imidazol-2-yl,

[1,2,4]oxadiazol-5-yl, 5-methyl-[1,2,4]oxadiazol-3-yl, 3-methyl-[1,2,4]oxadiazol-5-yl, 5-methyl-[1,3,4]oxadiazol-2-yl, isothiazol-5-yl, thiazol-2-yl, thiazol-4-yl, 4-methyl-thiazol-2-yl, 2-methyl-thiazol-4-yl, 2-amino-5-methyl-thiazol-4-yl, 4,5-dimethyl-thiazol-2-yl, 4-carboxy-thiazol-2-yl, 2-carboxy-thiazol-4-yl, 2-hydroxy-thiazol-4-yl, 2-amino-2-oxoethyl)thiazol-4-yl, isoxazol-3-yl, isoxazol-5-yl, 3-amino-isoxazol-5-yl, 3-hydroxy-isoxazol-5-yl, 3-methyl-isoxazol-5-yl, 4-methyl-isoxazol-5-yl, 4-carboxy-3-methyl-isoxazol-5-yl, oxazol-5-yl, 2-amino-oxazol-5-yl, 2-methyl-oxazol-5-yl, 2-(2-carboxyethyl)-oxazol-5-yl, 2-(2-carboxyethyl)-4-methyl-oxazol-5-yl, 5-amino-[1,3,4]thiadiazol-2-yl, 5-methylamino-[1,3,4]thiadiazol-2-yl, 4H-[1,2,4]triazol-3-yl, 1H-[1,2,4]triazol-1-yl, 2-methyl-2H-[1,2,4]triazol-3-yl, pyridin-2-yl, 4-fluoro-pyridin-2-yl, pyrimidin-2-yl, 5-fluoro-pyrimidin-2-yl, 5-methoxy-pyrimidin-2-yl, 4-methoxy-pyrimidin-2-yl, 6-methoxy-pyrimidin-4-yl, 6-dimethylamino-pyrimidin-4-yl, pyrazin-2-yl, 6-methoxy-pyrazin-2-yl, 6-methoxy-pyridazin-3-yl, pyrazol-1-yl-methyl, 1H-imidazol-4-yl, 3H-[1,2,3]triazol-4-yl, 5-methyl-1H-imidazol-4-yl, 1,2-dimethyl-1H-imidazol-4-yl, 1,5-dimethyl-1H-imidazol-4-yl, 2,5-dimethyl-1H-imidazol-4-yl, 2-cyclopropyl-1H-imidazol-4-yl, 2-cyclopropyl-1-methyl-1H-imidazol-4-yl, oxazol-2-yl, 4,5-dimethyl-oxazol-2-yl, or pyridin-2-yl; notably HET is 1H-tetrazol-5-yl, 3-hydroxy-isoxazol-5-yl, 1H-imidazol-4-yl, 5-methyl-1H-imidazol-4-yl, 2,5-dimethyl-1H-imidazol-4-yl);

$R^m$ represents
  $(C_{1-6})$alkyl (especially methyl, ethyl, n-propyl, isopropyl, n-butyl, isobutyl);
  $(C_{1-4})$alkoxy (especially methoxy, ethoxy, n-propoxy, isopropoxy, n-butoxy, isobutoxy);
  $(C_{1-3})$fluoroalkyl (especially trifluoromethyl);
  $(C_{1-3})$fluoroalkoxy (especially 2,2,2-trifluoroethoxy);
  halogen (especially fluoro or chloro);
  $(C_{3-6})$cycloalkyl (especially cyclopropyl);
  $(C_{3-6})$cycloalkyl-oxy (especially cyclobutyl-oxy, cyclopentyl-oxy);
  —$NR^{N1}R^{N2}$, wherein $R^{N1}$ and $R^{N2}$ independently represent hydrogen, $(C_{1-4})$alkyl, or $(C_{3-6})$cycloalkyl; (especially such group —$NR^{N1}R^{N2}$ represents amino, methylamino, ethylamino, or propylamino); or
  —S—$R^{S2}$ wherein $R^{S2}$ represents $(C_{1-4})$alkyl (especially methyl, ethyl, n-propyl, isopropyl, isobutyl), $(C_{3-6})$cycloalkyl (especially cyclobutyl), or 2-fluoro-vinyl; and $R^{m2}$ represents hydrogen, fluoro, or chloro;

or $R^p$ represents hydrogen;

$R^{m1}$ represents 1H-pyrazol-1-yl; or —$X^1$—COOH, wherein $X^1$ represents a direct bond, $(C_{1-3})$alkylene (especially —$CH_2$—, —$CH_2$—$CH_2$—), or —O—$(C_{1-3})$alkylene-* (especially —O—$CH_2$—*, —O—$CH_2$—$CH_2$—*), wherein the asterisks indicate the bond that is linked to the —COOH group [wherein in particular such group —$X^1$—COOH represents —COOH, —$CH_2$—COOH, —$CH_2$—$CH_2$—COOH, —O—$CH_2$—$CH_2$—COOH];

and $R^{m2}$ represents hydrogen, $(C_{1-4})$alkoxy (especially methoxy, ethoxy, n-propoxy); or —S—$(C_{1-4})$alkyl (especially —S-methyl, —S-ethyl, —S-n-propyl);

or $Ar^1$ represents a 5-membered heteroaryl group of the structure (Ar-II):

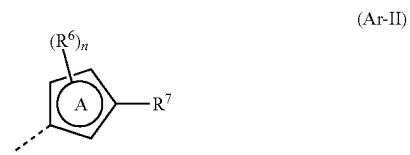

(Ar-II)

wherein in (Ar-II) the ring A represents a thiophenyl or a thiazolyl ring (wherein it is well understood that in (Ar-II) the substituent $R^7$ is attached in meta-position with respect to the point of attachment of the rest of the molecule) (especially ring A represents thiophen-2-yl wherein $R^7$ is attached in position 5, or thiophen-2-yl wherein $R^7$ is attached in position 4; or thiazol-2-yl wherein $R^7$ is attached in position 5);

wherein
$R^7$ represents
  3-hydroxy-oxetan-3-yl;
  hydroxy;
  2,2,2-trifluoro-1,1-dihydroxy-ethyl;
  —$X^1$—CO—$R^{O1}$, wherein
    $X^1$ represents a direct bond, $(C_{1-3})$alkylene (especially —$CH_2$—, —$CH_2$—$CH_2$—), —O—$(C_{1-3})$alkylene-* (especially —O—$CH_2$—*, —O—$CH(CH_3)$—*, —O—$CH_2$—$CH_2$—*), —NH—$(C_{1-3})$alkylene-* (especially —NH—$CH_2$—*, —NH—$CH(CH_3)$*), —S—$CH_2$—*, —$CF_2$—, —CH=CH—, —CH=CH—, —NH—CO—*, —CO—, or $(C_{3-5})$cycloalkylene; wherein the asterisks indicate the bond that is linked to the —CO—$R^{O1}$ group; and
    $R^{O1}$ represents
      —OH;
      —O—$(C_{1-4})$alkyl (especially ethoxy, methoxy);
      —NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —$NH_2$;
      —O-phenyl;
      —O—$CH_2$—CO—$R^{O4}$, wherein $R^{O4}$ represents hydroxy, or $(C_{1-4})$alkoxy, or —N[$(C_{1-4})$alkyl]$_2$;
      —O—$CH_2$—O—CO—$R^{O5}$, wherein $R^{O5}$ represents $(C_{1-4})$alkyl or $(C_{1-4})$alkoxy; or
      —O—$CH_2$—$CH_2$—N[$(C_{1-4})$alkyl]$_2$ (especially —O—$CH_2$—$CH_2$—N$(CH_3)_2$);
      (5-methyl-2-oxo-[1,3]dioxol-4-yl)-methyloxy-;
      [wherein in particular, such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—$C(CH_3)_2$, —CO—NH—$SO_2$-cyclopropyl, —CO—NH—$SO_2$-phenyl, —COO—$CH_3$, —CO—NH—$SO_2$-ethyl, —CO—NH—$SO_2$—$NH_2$, —COO—$CH_2$—COOH, —COO—$CH_2$—$CH_2$—N$(CH_3)_2$, —COO—$CH_2$—CO—

N(CH$_3$)$_2$, —COO—CH$_2$—O—CO—O-ethyl, —COO—CH$_2$—O—CO-propyl, (5-methyl-2-oxo-[1,3]dioxol-4-yl)-methyl-O—CO—, —CH$_2$—COOH, —CH$_2$—CO—O-ethyl, —CH$_2$—CH$_2$—COOH, —CF$_2$—COOH, —CH=CH—COOH, —CH—CH—CO—O-ethyl, —NH—CO—COOH, —CO—COOH, —O—CH$_2$—CH$_2$—COOH, —O—CH(CH$_3$)—COOH, —NH—CH(CH$_3$)—COOH, —NH—CH$_2$—COO—CH$_3$, —COO-phenyl, 1-carboxy-cyclopropan-1-yl, 1-carboxy-cyclopentan-1-yl];
—CO—CH$_2$—OH;
—CO—H;

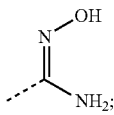

hydroxy-(C$_{1-4}$)alkyl (especially hydroxymethyl, 1-hydroxy-ethyl);
—NR$^{N1}$R$^{N2}$, wherein
R$^{N1}$ and R$^{N2}$ independently represent hydrogen, (C$_{1-4}$)alkyl, or (C$_{3-6}$)cycloalkyl (wherein preferably at least one of R$^{N1}$ and R$^{N2}$ represents hydrogen);
or R$^{N1}$ independently represents hydrogen or (C$_{1-4}$)alkyl, and R$^{N2}$ independently represents —CO—H, —CO—(C$_{1-3}$)alkyl, or —CO—(C$_{1-3}$)alkylene-OH;
(especially such group —NR$^{N1}$R$^{N2}$ represents amino, methylamino, ethylamino, propylamino, or —NH—CO—H, —N(C$_2$H$_5$)—CO—H, —NH—CO—C$_2$H$_5$, —NH—CO—CH$_2$—CH$_2$—OH, or —NH—COO—CH$_3$);
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, hydroxy-(C$_{2-4}$)alkoxy, benzyloxy, or hydroxy (wherein preferably at least one of R$^{N3}$ and R$^{N4}$ represents hydrogen; and wherein particular examples of such group —CO—NR$^{N3}$R$^{N4}$ are —CO—NH$_2$, —CO—NH(CH$_3$), —CO—NH(C$_2$H$_5$), —CO—NH—O-methyl, —CO—NH—O-ethyl, —CO—NH—O-isopropyl, —CO—NH—C$_2$H$_4$—OH, —CO—NH—C$_2$H$_4$—OCH$_3$, —CO—NH—O—C$_2$H$_4$—OH, —CO—NH—C$_2$H$_4$—N(CH$_3$)$_2$, —CO—NH—O-benzyl, or —CO—N(CH$_3$)$_2$, —CO—NH-isopropyl, or —CO—NH—OH);
—NH—CO—NR$^{N5}$R$^{N6}$ wherein R$^{N5}$ and R$^{N6}$ independently represent hydrogen or (C$_{1-4}$)alkyl (especially such group represents —NH—CO—NH$_2$, —NH—CO—NH—C$_2$H$_5$);
5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl); or
HET, wherein HET represents a 5- or 6-membered heteroaryl (especially 5-membered heteroaryl selected from oxazolyl, isoxazolyl, oxadiazolyl, thiazolyl, isothiazolyl, thiadiazolyl, imidazolyl, pyrazolyl, triazolyl, and tetrazolyl; or 6-membered heteroaryl selected from pyridinyl, pyrimidinyl, pyridazinyl, and pyrazinyl, notably tetrazolyl, imidazoloyl, or isoxazolyl), wherein said 5- or 6-membered heteroaryl is unsubstituted, or mono- or di-substituted, wherein the substituents are independently selected from (C$_{1-4}$)alkyl (especially methyl), (C$_{1-4}$)alkoxy (especially methoxy), —COOH, hydroxy, fluoro, 2-amino-2-oxo-ethyl, 2-carboxy-ethyl, (C$_{3-5}$)cycloalkyl (especially cyclopropyl), or —NR$^{N9}$R$^{N10}$ wherein R$^{N9}$ and R$^{N10}$ independently represent hydrogen or (C$_{1-3}$)alkyl (especially amino, dimethylamino) (especially the substituents are independently selected from (C$_{1-3}$)alkyl (especially methyl), and hydroxy); (in particular, such group HET is 1H-tetrazol-5-yl, 3-hydroxy-isoxazol-5-yl, 1H-imidazol-4-yl, 5-methyl-1H-imidazol-4-yl, or 2,5-dimethyl-1H-imidazol-4-yl; notably 1H-tetrazol-5-yl, or 3-hydroxy-isoxazol-5-yl);
and (R$^6$)$_n$ represents one optional substituent (i.e. n represents the integer 0, or 1) independently selected from
(C$_{1-6}$)alkyl (especially methyl, ethyl, n-propyl, isopropyl, n-butyl, isobutyl, 1-methyl-propan-1-yl, tert.-butyl, 3-methyl-butyl);
(C$_{1-4}$)alkoxy (especially methoxy, ethoxy, n-propoxy, isopropoxy, n-butoxy);
(C$_{1-3}$)fluoroalkyl (especially trifluoromethyl);
(C$_{1-3}$)fluoroalkoxy (especially difluoromethoxy, trifluoromethoxy, 2,2,2-trifluoroethoxy);
halogen (especially fluoro or chloro);
(C$_{3-6}$)cycloalkyl (especially cyclopropyl);
(C$_{3-6}$)cycloalkyl-oxy (especially cyclobutyl-oxy, cyclopentyl-oxy);
hydroxy;
pyridinyl; and
—NR$^{N1}$R$^{N2}$, wherein R$^{N1}$ and R$^{N2}$ independently represent hydrogen, (C$_{1-4}$)alkyl, or (C$_{3-6}$)cycloalkyl;
(especially such group —NR$^{N1}$R$^{N2}$ represents amino, methylamino, ethylamino, propylamino);
[wherein, if present, such substituent R$^6$ is especially attached in the other meta-position with respect to the point of attachment of the rest of the molecule, i.e. especially ring A represents thiophen-2-yl wherein R$^7$ is attached in position 5 and R$^6$ is attached in position 4, or thiophen-2-yl wherein R$^7$ is attached in position 4 and R$^6$ is attached in position 5; or thiazol-2-yl wherein R$^7$ is attached in position 5 and R$^6$ is attached in position 4)];
or Ar$^1$ represents 9- or 10-membered bicyclic heteroaryl (especially indazolyl, benzoimidazolyl, indolyl, benzotriazolyl, benzooxazolyl, quinoxalinyl, isoquinolinyl, quinolinyl, pyrrolopyridinyl, or imidazopyridinyl); wherein said 9- or 10-membered bicyclic heteroaryl independently is unsubstituted, mono-, or di-substituted, wherein the substituents are independently selected from (C$_{1-4}$)alkyl (especially methyl); (C$_{1-4}$)alkoxy (especially methoxy); (C$_{1-3}$)fluoroalkyl (especially trifluoromethyl); (C$_{1-3}$)fluoroalkoxy (especially trifluoromethoxy); halogen; cyano; hydroxy, or —(C$_{0-3}$)alkylene-COOR$^{O2}$ wherein R$^{O2}$ represents hydrogen or (C$_{1-4}$)alkyl (especially methyl); (especially such 9- to 10-membered bicyclic heteroaryl is 1H-indazol-6-yl, 1-methyl-1H-indazol-6-yl, 3-methyl-1H-indazol-6-yl, 3-carboxy-1H-indazol-6-yl, 1H-benzoimidazol-5-yl, 2-methyl-1H-benzoimidazol-5-yl, 2-trifluoromethyl-1H-benzoimidazol-5-yl, 1H-indol-6-yl, 1H-indol-5-yl, 1-methyl-1H-indol-5-yl, 2-carboxy-1H-indol-5-yl, 7-carboxy-1H-indol-4-yl, 7-carboxy-1-methyl-1H-indol-4-yl, 1H-benzotriazol-5-yl, 2-methyl-benzooxazol-5-yl, 2-methyl-benzooxazol-6-yl, quinoxalin-6-yl, isoquinolin-7-yl, quinolin-6-yl, 1H-indol-2-yl, 1H-indol-3-yl, 1H-indol-4-yl, 1H-indazol-5-yl, 1H-pyrrolo[2,3-c]pyridin-3-yl, 1H-pyrrolo[2,3-b]pyridin-3-yl, 1H-pyrrolo[2,3-b]pyridin-5-yl, 1-methyl-1H-pyrrolo[2,3-b]pyridin-5-yl, imidazo[1,2-a]pyridin-6-yl, 3-methoxy-1H-indazol-6-yl, 6-methoxy-1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl; preferably such 9- to 10-membered bicyclic heteroaryl is 1H-benzoimidazol-5-yl, 1H-indol-6-yl, 1H-indol-5-yl, 1H-indol-2-yl, 1H-indazol-5-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl);

or Ar$^1$ represents a group of the structure (Ar-III):

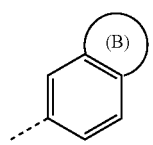

(Ar-III)

wherein ring (B) represents a non-aromatic 5- or 6-membered ring fused to the phenyl group, wherein ring (B) comprises one or two heteroatoms independently selected from nitrogen and oxygen (notably such group (Ar-III) is 2,3-dihydro-benzofuranyl, 2,3-dihydro-1H-indolyl, 2,3-dihydro-benzo[1,4]dioxinyl, 2,3-dihydro-1H-indazolyl, 2,3-dihydro-1H-benzo[d]imidazolyl, 2,3-dihydrobenzo[d]isoxazolyl, 2,3-dihydro-isoindolyl, 2,3-dihydro-benzooxazolyl, 1,2,3,4-tetrahydro-quinazolinyl, 1,2,3,4-tetrahydro-isoquinolinyl, or 1,2,3,4-tetrahydro-phthalazinyl); wherein said ring (B) independently is unsubstituted, mono-, or di-substituted, wherein the substituents are independently selected from oxo, (C$_{1-6}$)alkyl (especially methyl, ethyl, propyl, butyl, isobutyl) and —(C$_{0-3}$)alkylene-COOR$^{O3}$ wherein R$^{O3}$ represents hydrogen or (C$_{1-3}$) alkyl (especially such group (Ar-III) is 2,3-dihydro-benzofuran-5-yl, 2,3-dihydro-1H-indol-5-yl, 2,3-dihydro-benzo[1,4]dioxin-6-yl, 3-oxo-2,3-dihydro-1H-indazol-5-yl, 3-oxo-2,3-dihydro-1H-indazol-6-yl, 2-oxo-2,3-dihydro-1H-benzo[d]imidazol-5-yl, 3-oxo-2,3-dihydrobenzo[d]isoxazol-6-yl, 2-oxo-1,3-dihydro-indol-5-yl, 1-oxo-2,3-dihydro-isoindol-5-yl, 3-methyl-1-oxo-2,3-dihydro-isoindol-5-yl, 3-ethyl-1-oxo-2,3-dihydro-isoindol-5-yl, 3-propyl-1-oxo-2,3-dihydro-isoindol-5-yl, 3-isobutyl-1-oxo-2,3-dihydro-isoindol-5-yl, 2-methyl-1-oxo-2,3-dihydro-isoindol-5-yl, 2-ethyl-1-oxo-2,3-dihydro-isoindol-5-yl, 1-oxo-2-propyl-2,3-dihydro-isoindol-5-yl, 2-isobutyl-1-oxo-2,3-dihydro-isoindol-5-yl, 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-methyl-3-oxo-2,3-dihydro-1H-indazol-6-yl, 1-(carboxymethyl)-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, 1-oxo-1,2,3,4-tetrahydro-isoquinolin-6-yl, or 1,4-dioxo-1,2,3,4-tetrahydro-phthalazin-6-yl; preferably such group (Ar-III) is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, or 1-oxo-1,2,3,4-tetrahydro-isoquinolin-6-yl).

12) Another embodiment relates to compounds according to any one of embodiments 1) to 5), wherein Ar$^1$ represents a phenyl group selected from:

a)

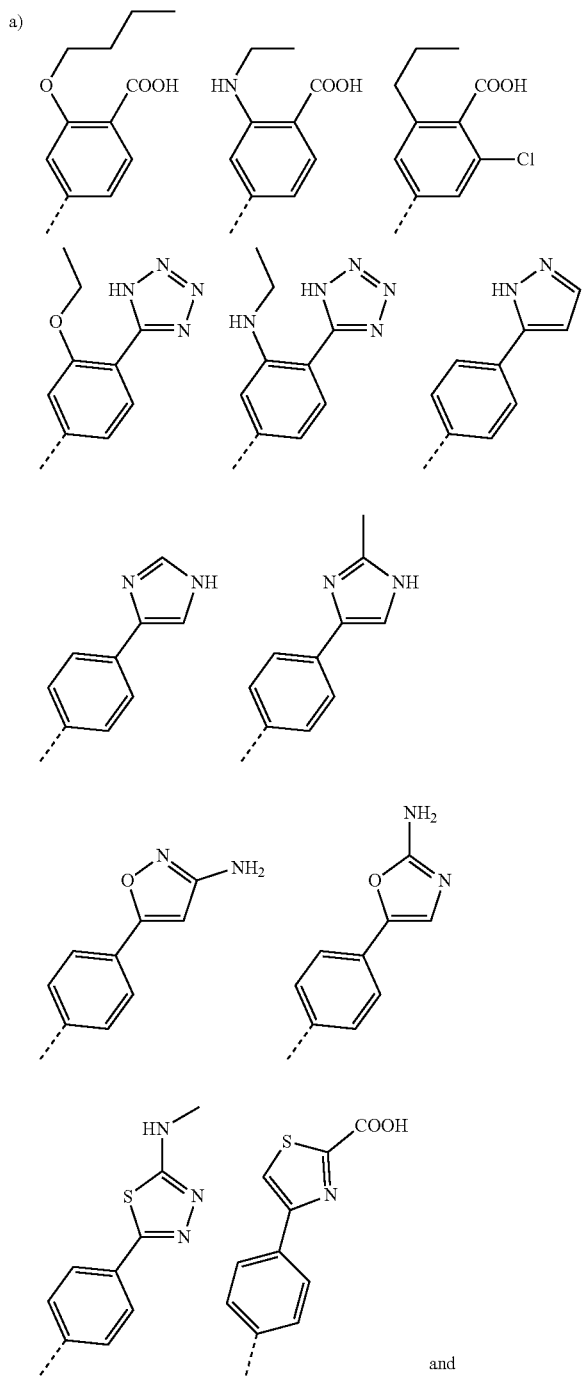

and

-continued
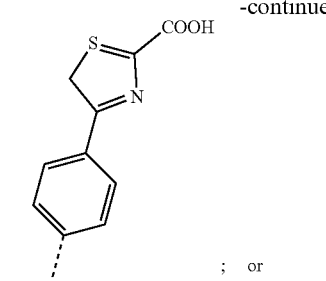
; or
b) 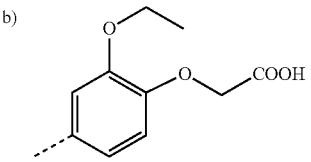
and
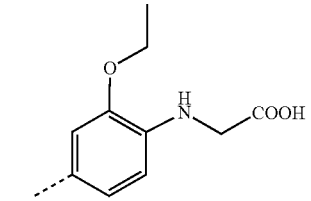
; or
c) 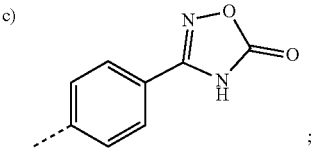
; or
d) 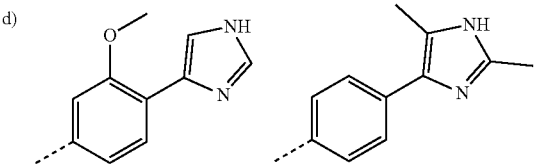
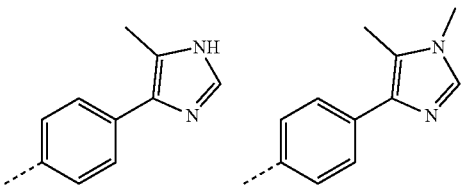
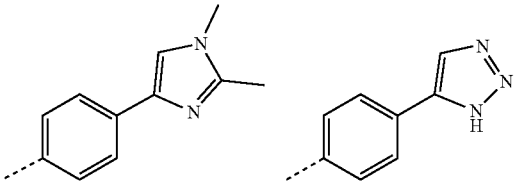
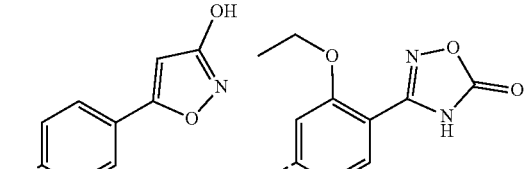
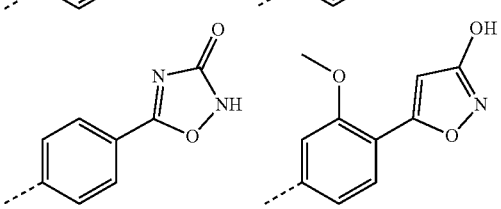
-continued
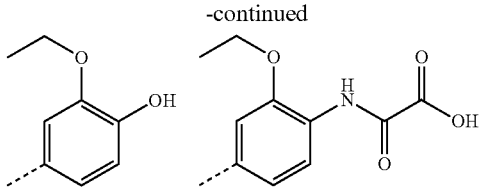
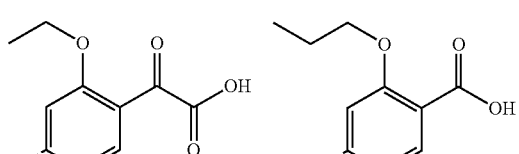
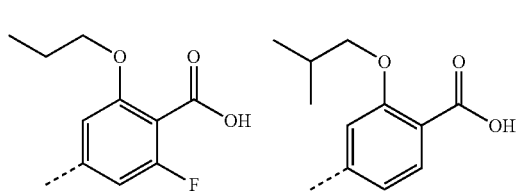
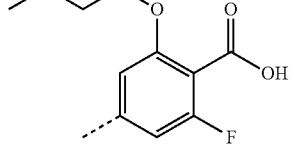
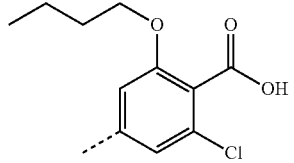
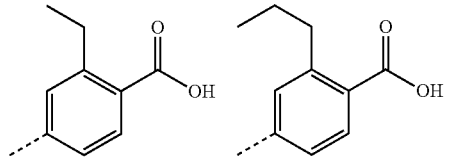
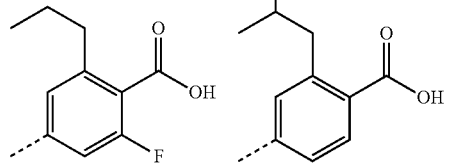
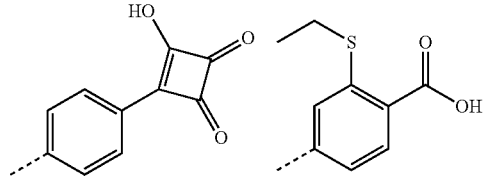
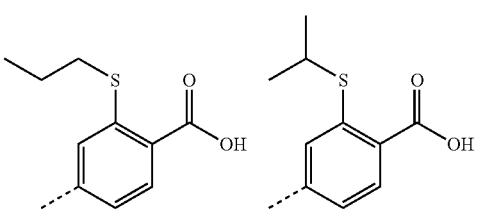

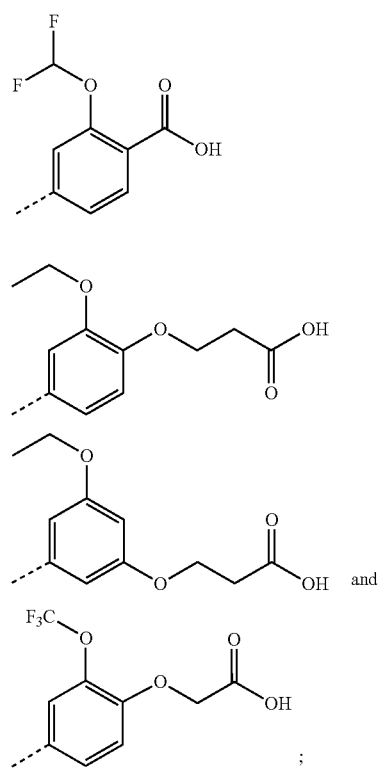
or Ar¹ represents a thiophenyl group selected from:
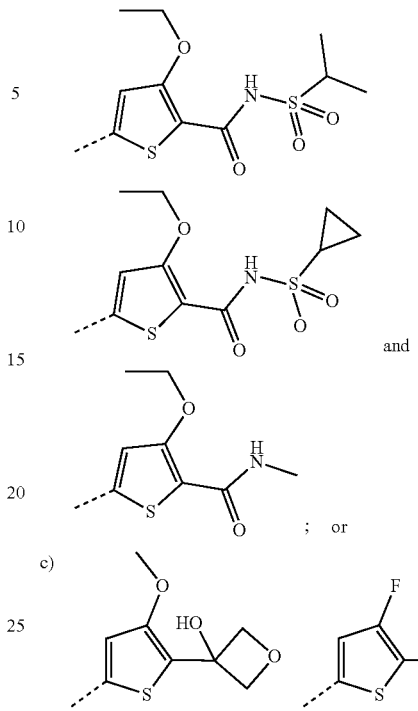
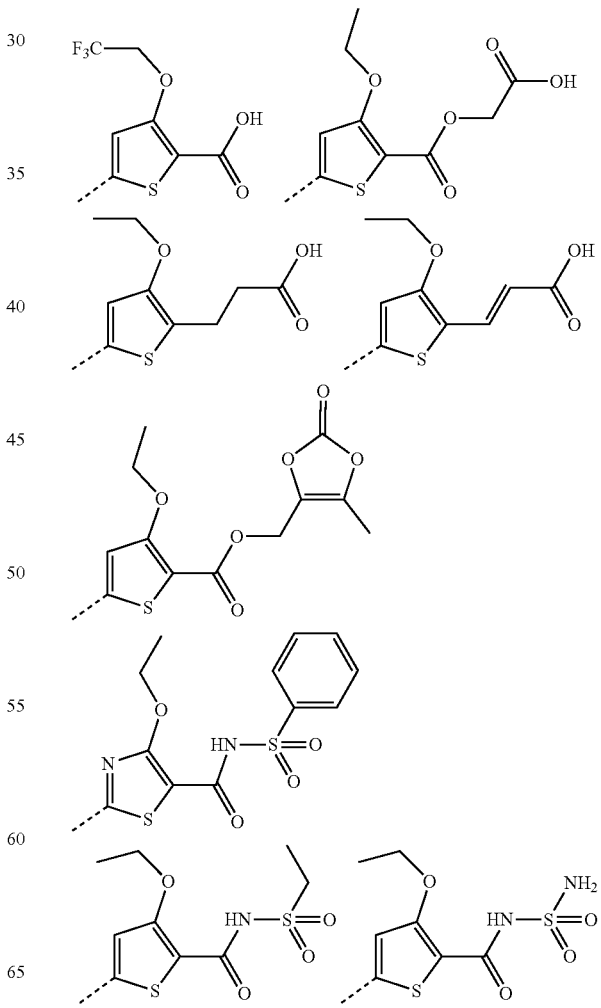

-continued
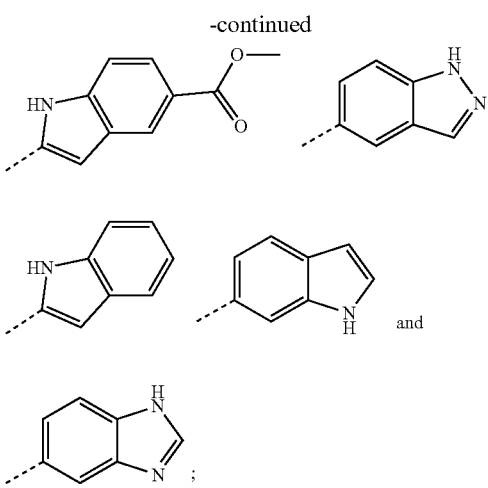
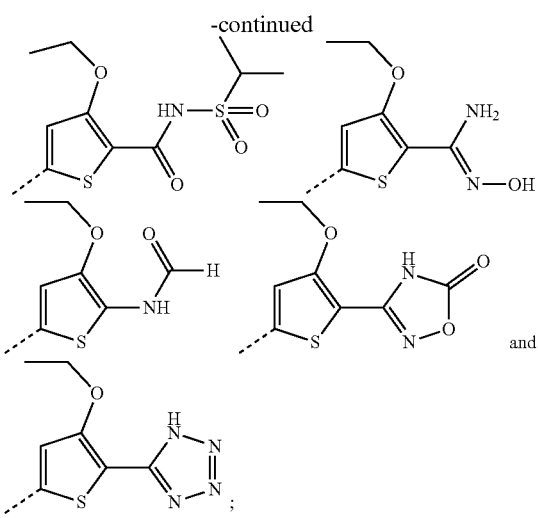
or Ar¹ represents a group selected from:
a)
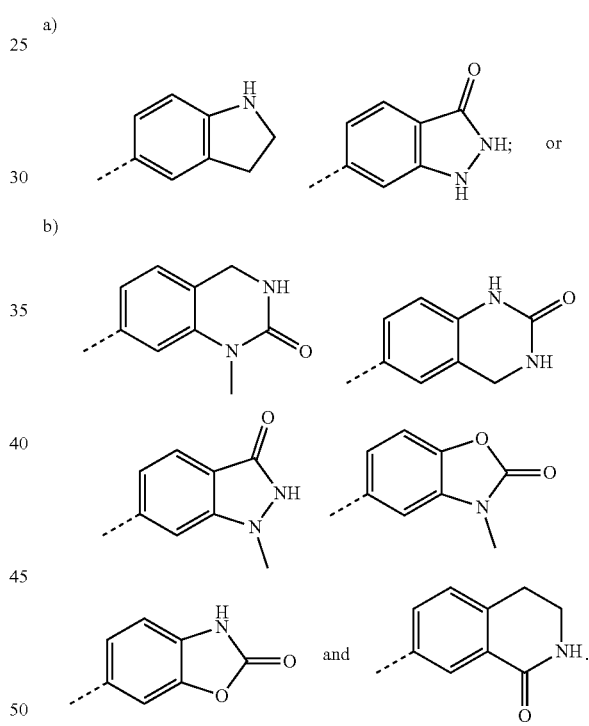
or Ar¹ represents a thiazoyl group selected from:
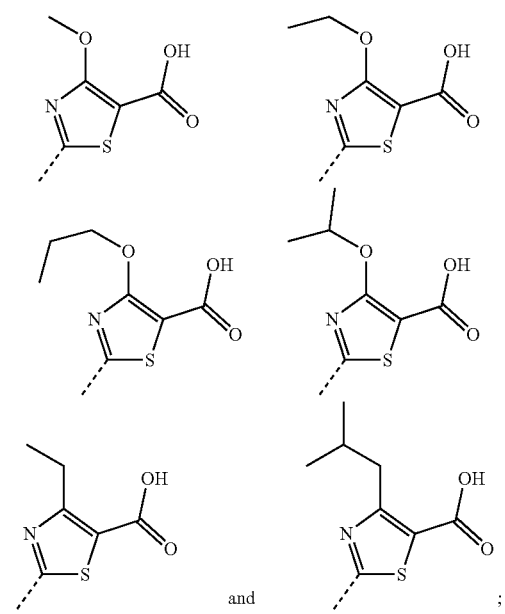
or Ar¹ represents 9- or 10-membered bicyclic heteroaryl selected from
a)
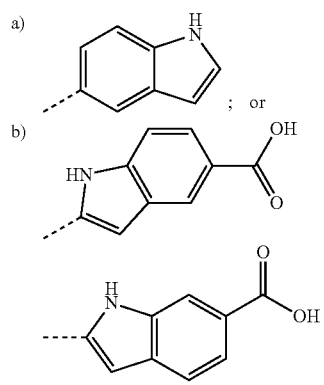; or
b)
13) Another embodiment relates to compounds according to any one of embodiments 1) to 5), wherein
Ar¹ represents a phenyl group selected from:
a)
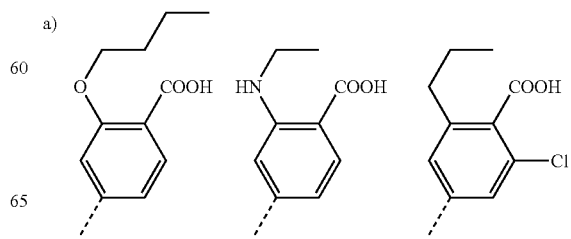

-continued
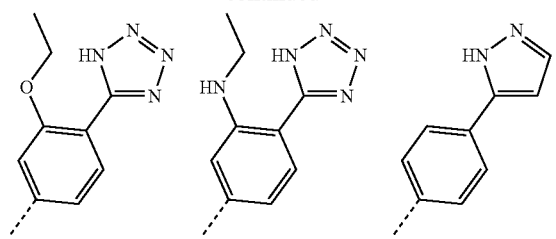
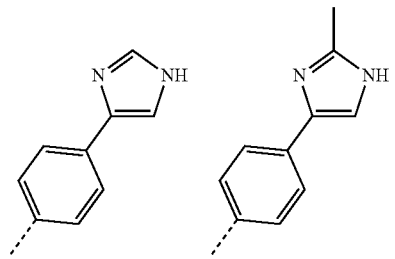
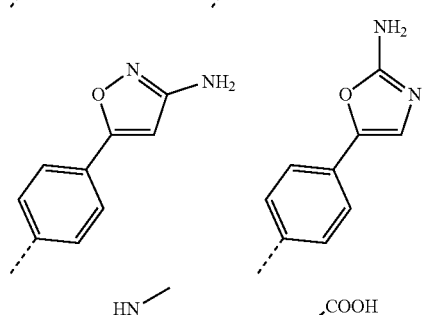
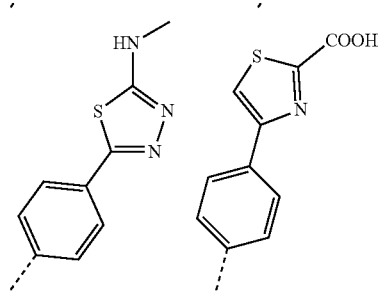
; or
b) 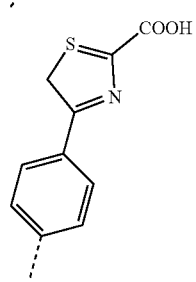
and
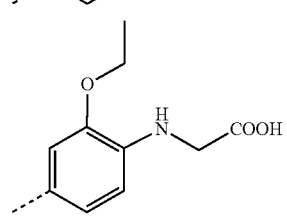
; or
-continued
c) 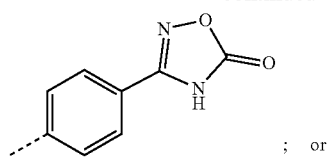
; or
d) 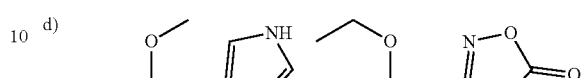
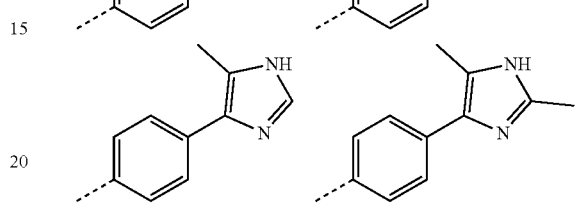
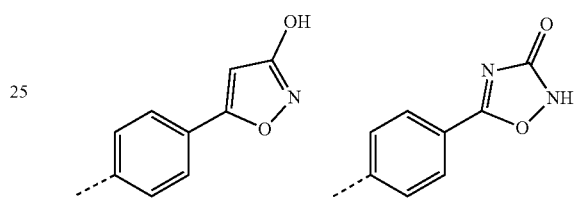
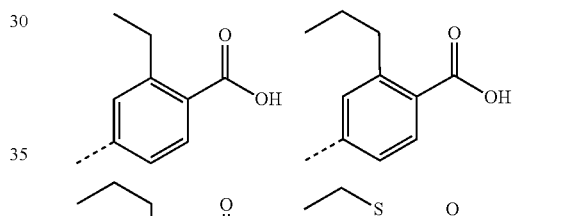
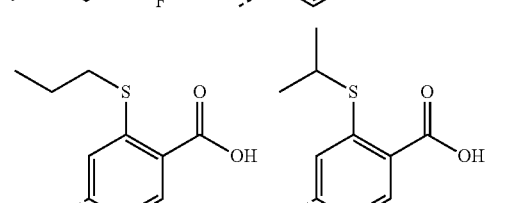
and
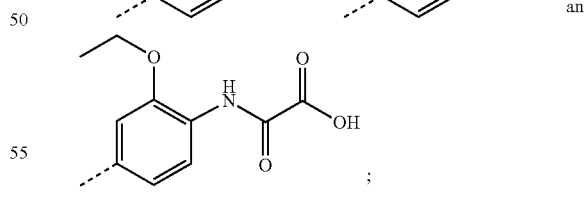
;
or Ar¹ represents a thiophenyl group selected from:
a) 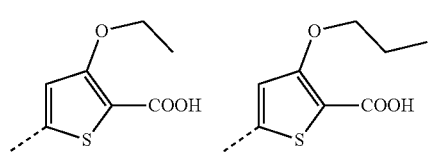

-continued
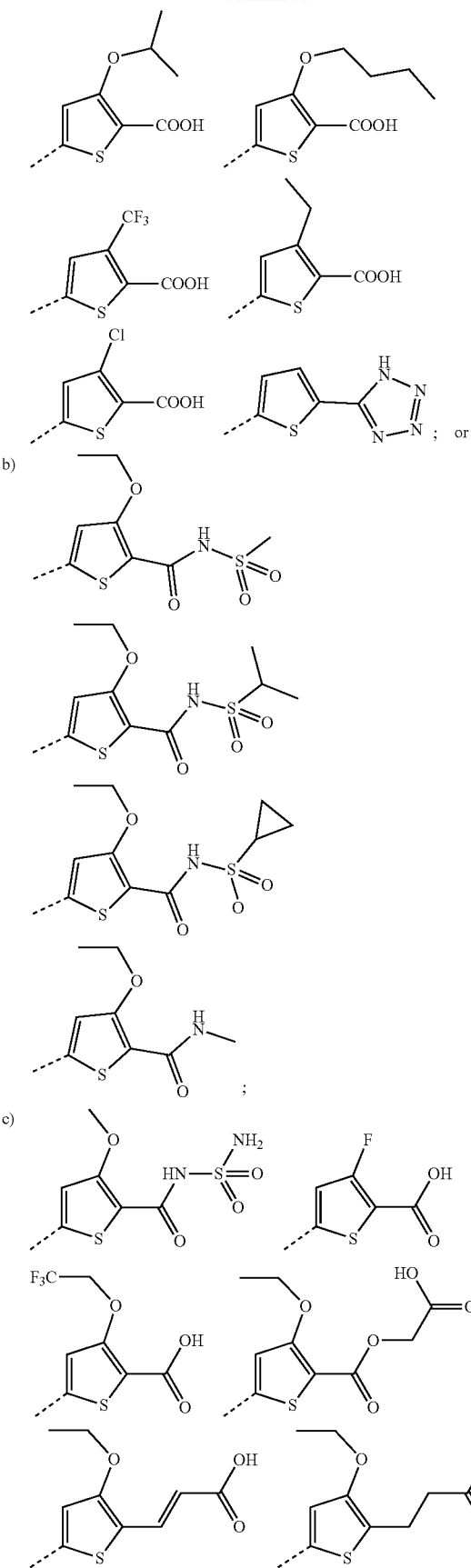
b)
c)
-continued
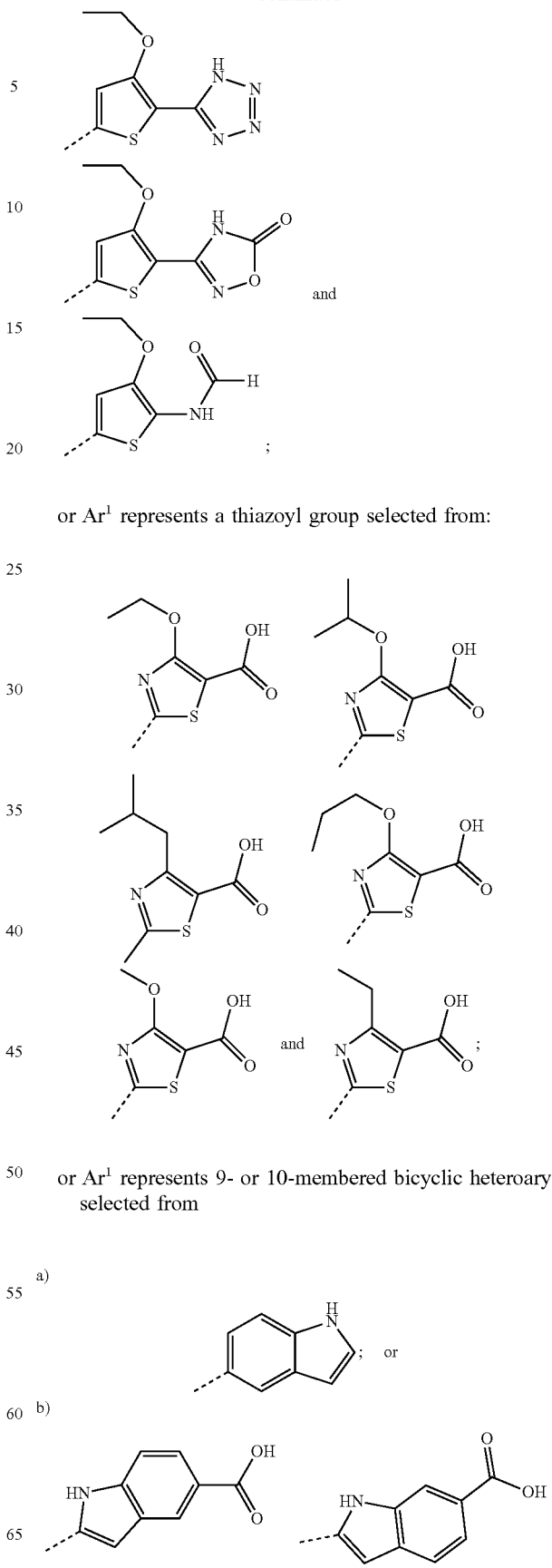
or Ar¹ represents a thiazoyl group selected from:
or Ar¹ represents 9- or 10-membered bicyclic heteroaryl selected from
a)
b)

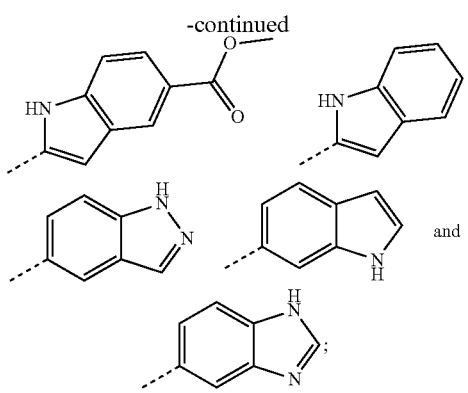

or Ar¹ represents a group of selected from:

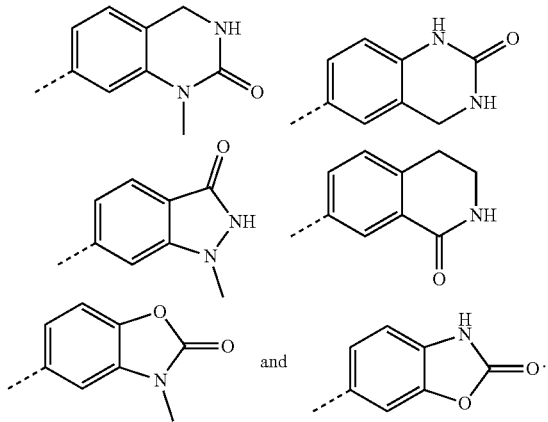

14) Another embodiment relates to compounds according to any one of embodiments 1) to 13), wherein
$(R^1)_n$ represents:
one, two or three optional substituents (i.e. n represents the integer 0, 1, 2, or 3); wherein said substituents are attached to the phenyl moiety of the indole ring; wherein said substituents are independently selected from $(C_{1-3})$alkyl (especially methyl), $(C_{1-3})$alkoxy (especially methoxy), halogen (especially fluoro, chloro, or bromo), $(C_{1-3})$fluoroalkyl (especially trifluoromethyl), $(C_{1-3})$fluoroalkoxy (especially trifluoromethoxy), or cyano;
or two $R^1$ together form a group —O—CH₂—O—, and the remaining $R^1$, if present, represents halogen (especially fluoro or chloro);
or $(R^1)_n$ represents:
one substituent in position 3 of the indole ring, wherein said substituent is selected from $(C_{1-3})$alkyl (especially methyl), $(C_{1-3})$alkoxy (especially methoxy), halogen (especially fluoro, chloro, or bromo), $(C_{1-3})$fluoroalkyl (especially trifluoromethyl), $(C_{1-3})$fluoroalkoxy (especially trifluoromethoxy), or cyano (especially such substituent is fluoro);
and, in addition, one or two optional substituents (i.e. 0, 1, or 2 additional substituents) attached to the phenyl moiety of the indole ring; wherein said substituents are independently selected from $(C_{1-3})$alkyl (especially methyl), $(C_{1-3})$alkoxy (especially methoxy), halogen (especially fluoro, chloro, or bromo), $(C_{1-3})$ fluoroalkyl (especially trifluoromethyl), $(C_{1-3})$fluoroalkoxy (especially trifluoromethoxy), or cyano;
or two $R^1$ together form a group —O—CH₂—O— attached to the phenyl moiety of the indole ring; and said substituent in position 3 of the indole moiety, if present, represents halogen (especially fluoro or chloro);
wherein it is understood that the indole ring is in addition substituted by the substituent $R^2$.

15) Another embodiment relates to compounds according to any one of embodiments 1) to 13), wherein the group

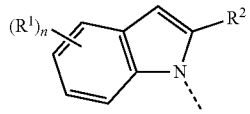

represents

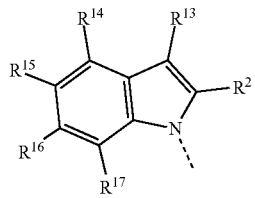

wherein
$R^2$ represents $(C_{1-3})$alkyl (especially methyl), halogen (especially chloro), or cyano; and
$R^{13}$ represents hydrogen; and
$R^{14}$, $R^{15}$, $R^{16}$, and $R^{17}$ independently represent the following:
$R^{14}$ represents hydrogen, $(C_{1-3})$alkyl (especially methyl, ethyl), $(C_{1-3})$alkoxy (especially methoxy), halogen (especially bromo, chloro, fluoro), $(C_{1-3})$ fluoroalkyl (especially trifluoromethyl), $(C_{1-3})$fluoroalkoxy (especially trifluoromethoxy), or cyano; (especially $R^{14}$ represents methyl, methoxy, halogen, or cyano);
$R^{15}$ represents hydrogen, $(C_{1-3})$alkyl (especially methyl), $(C_{1-3})$alkoxy (especially methoxy), halogen (especially chloro, fluoro), $(C_{1-3})$fluoroalkyl (especially trifluoromethyl), $(C_{1-3})$fluoroalkoxy (especially trifluoromethoxy), or cyano; (especially $R^{15}$ represents hydrogen, methyl, chloro, or fluoro);
$R^{16}$ represents hydrogen, $(C_{1-3})$alkyl (especially methyl), $(C_{1-3})$alkoxy (especially methoxy), halogen (especially fluoro), $(C_{1-3})$fluoroalkyl (especially trifluoromethyl), $(C_{1-3})$fluoroalkoxy (especially trifluoromethoxy), or cyano; (especially $R^{16}$ represents hydrogen, or fluoro); and
$R^{17}$ represents hydrogen, $(C_{1-3})$alkyl (especially methyl), $(C_{1-3})$alkoxy (especially methoxy), halogen (especially chloro, fluoro), $(C_{1-3})$fluoroalkyl (especially trifluoromethyl), $(C_{1-3})$fluoroalkoxy (especially trifluoromethoxy), or cyano; (especially $R^{17}$ represents hydrogen, chloro, or fluoro);
wherein at least one of $R^{14}$, $R^{15}$, $R^{16}$, and $R^{17}$ represents hydrogen; (and, preferably, at least one of $R^{14}$, $R^{15}$, $R^{16}$, and $R^{17}$ is different from hydrogen; especially one of $R^{14}$, $R^{16}$, and
$R^{17}$ is different from hydrogen);
or $R^{14}$ and $R^{15}$ together form a group —O—CH₂—O—, $R^{16}$ represents hydrogen and $R^{17}$ represents hydrogen or halogen (especially fluoro or chloro);
or
$R^2$ represents $(C_{1-3})$alkyl (especially methyl), halogen (especially chloro), or cyano; and
$R^{13}$ represents fluoro; and $R^{14}$, $R^{15}$, $R^{16}$, and $R^{17}$ independently represent the following:

$R^{14}$ represents hydrogen, $(C_{1-3})$alkyl (especially methyl, ethyl), $(C_{1-3})$alkoxy (especially methoxy), halogen (especially bromo, chloro, fluoro), $(C_{1-3})$fluoroalkyl (especially trifluoromethyl), $(C_{1-3})$fluoroalkoxy (especially trifluoromethoxy), or cyano; (especially $R^{14}$ represents hydrogen or methoxy);

$R^{15}$ represents hydrogen, $(C_{1-3})$alkyl (especially methyl), $(C_{1-3})$alkoxy (especially methoxy), halogen (especially chloro, fluoro), $(C_{1-3})$fluoroalkyl (especially trifluoromethyl), $(C_{1-3})$fluoroalkoxy (especially trifluoromethoxy), or cyano; (especially $R^{15}$ represents hydrogen);

$R^{16}$ represents hydrogen, $(C_{1-3})$alkyl (especially methyl), $(C_{1-3})$alkoxy (especially methoxy), halogen (especially fluoro), $(C_{1-3})$fluoroalkyl (especially trifluoromethyl), $(C_{1-3})$fluoroalkoxy (especially trifluoromethoxy), or cyano; (especially $R^{16}$ represents hydrogen); and $R^{17}$ represents hydrogen, $(C_{1-3})$alkyl (especially methyl), $(C_{1-3})$alkoxy (especially methoxy), halogen (especially chloro, fluoro), $(C_{1-3})$fluoroalkyl (especially trifluoromethyl), $(C_{1-3})$fluoroalkoxy (especially trifluoromethoxy), or cyano; (especially $R^{17}$ represents hydrogen or fluoro);

wherein at least two of $R^{14}$, $R^{15}$, $R^{16}$, and $R^{17}$ represent hydrogen.

16) Another embodiment relates to compounds according to any one of embodiments 1) to 13), wherein the group

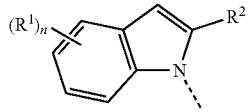

represents

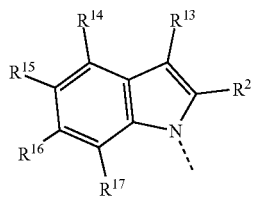

wherein $R^2$ represents methyl, chloro, or cyano; and
$R^{13}$ represents hydrogen; and $R^{14}$, $R^{15}$, R, and $R^{17}$ independently represent the following:

$R^{14}$ represents hydrogen, methyl, ethyl, methoxy, bromo, chloro, fluoro, trifluoromethyl, trifluoromethoxy, or cyano (especially $R^{14}$ represents methyl, methoxy, halogen, or cyano);

$R^{15}$ represents hydrogen, methyl, methoxy, chloro, fluoro (especially $R^{15}$ represents hydrogen, methyl, chloro, or fluoro);

$R^{16}$ represents hydrogen, methoxy, or fluoro; (especially $R^{16}$ represents hydrogen, or fluoro); and $R^{17}$ represents hydrogen, methyl, methoxy, chloro, fluoro, or cyano; (especially $R^{17}$ represents hydrogen, chloro, or fluoro);

wherein at least one of $R^{14}$, $R^{15}$, $R^{1}$, and $R^{17}$ represents hydrogen;

(and, preferably, at least one of $R^{14}$, $R^{15}$, $R^{16}$, and $R^{17}$ is different from hydrogen; especially at least one of $R^{14}$, $R^{16}$, and $R^{17}$ is different from hydrogen);

or $R^{14}$ and $R^{15}$ together form a group —O—CH$_2$—O—, $R^{16}$ represents hydrogen and $R^{17}$ represents hydrogen or halogen (especially fluoro or chloro);

or $R^2$ represents (Ca)alkyl (especially methyl), halogen (especially chloro), or cyano; and $R^{13}$ represents fluoro; and $R^{14}$, $R^{15}$, $R^{16}$, and $R^{17}$ independently represent the following:

$R^{14}$ represents hydrogen, methyl, ethyl, methoxy, bromo, chloro, fluoro, trifluoromethyl, trifluoromethoxy, or cyano (especially $R^{14}$ represents hydrogen or methoxy);

$R^{15}$ represents hydrogen, methyl, methoxy, chloro, fluoro (especially $R^{15}$ represents hydrogen);

$R^{16}$ represents hydrogen, methoxy, or fluoro; (especially $R^{16}$ represents hydrogen); and $R^{17}$ represents hydrogen, methyl, methoxy, chloro, fluoro, or cyano; (especially $R^{17}$ represents hydrogen or fluoro);

wherein at least two of $R^{14}$, $R^{15}$, $R^{16}$, and $R^{17}$ represent hydrogen.

17) Another embodiment relates to compounds according to any one of embodiments 1) to 13), wherein the group

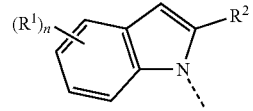

represents

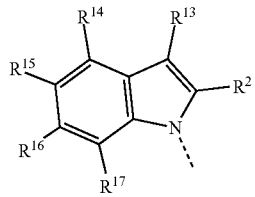

wherein $R^2$ represents methyl, chloro, or cyano; and
$R^{13}$ represents hydrogen; and $R^{14}$ represents hydrogen; $R^{17}$ represents hydrogen, chloro or fluoro; $R^{16}$ represents hydrogen, fluoro, chloro or methoxy; and $R^{15}$ represents hydrogen, methyl, chloro, fluoro or methoxy; wherein preferably at least one of $R^{15}$, $R^{16}$, and $R^{17}$ is different from hydrogen; especially $R^{16}$ and/or $R^{17}$ is/are different from hydrogen;

or $R^{14}$ represents methyl, $R^{17}$ represents hydrogen, chloro or fluoro; $R^{16}$ represents hydrogen, chloro or fluoro; and $R^{15}$ represents hydrogen or fluoro; wherein at least one of $R^{15}$, $R^{16}$, and $R^{17}$ represents hydrogen;

or $R^{14}$ represents methoxy, $R^7$ represents hydrogen, methyl, chloro or fluoro; $R^{15}$ represents hydrogen, chloro or fluoro; and $R^{15}$ represents hydrogen;

or $R^{14}$ represents halogen (especially bromo, chloro, fluoro), $R^{17}$ represents hydrogen, methyl, methoxy, chloro or fluoro; $R^{16}$ represents hydrogen, chloro or fluoro; and $R^{15}$ represents hydrogen or fluoro; wherein at least one of $R^{15}$, $R^{16}$, and $R^{17}$ represents hydrogen;

or $R^{14}$ represents cyano; $R^{17}$ represents hydrogen, or fluoro; $R^{16}$ represents hydrogen; and $R^{15}$ represents hydrogen;

or $R^{14}$ and $R^{15}$ together form a group —O—CH$_2$—O—, $R^{16}$ represents hydrogen and $R^{17}$ represents hydrogen or chloro;

or
$R^2$ represents methyl, chloro, or cyano; and
$R^{13}$ represents fluoro; and
$R^{14}$, $R^{17}$, $R^{16}$ and $R^{15}$ represent hydrogen;
or $R^{14}$ represents methoxy, $R^{17}$ represents fluoro; and $R^{16}$ and $R^{15}$ represent hydrogen.

18) Another embodiment relates to compounds according to any one of embodiments 1) to 13), wherein the group

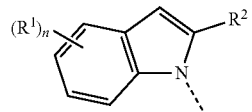

represents

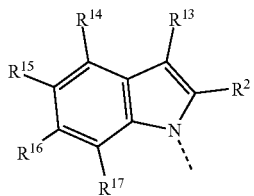

wherein
$R^2$ represents methyl, chloro, or cyano; and
$R^{13}$ represents hydrogen; and
$R^{14}$ represents hydrogen; $R^{17}$ represents hydrogen, chloro or fluoro; $R^{16}$ represents hydrogen, fluoro, chloro, or methoxy; and $R^{15}$ represents hydrogen, methyl, chloro, fluoro or methoxy; wherein preferably at least one of $R^{15}$, $R^{16}$, and $R^{17}$ is different from hydrogen; especially $R^{16}$ and/or $R^{17}$ is/are different from hydrogen;
or $R^{14}$ represents methyl, $R^{17}$ represents hydrogen, chloro or fluoro; $R^{16}$ represents hydrogen, chloro or fluoro; and $R^{15}$ represents hydrogen or fluoro; wherein at least one of $R^{15}$, $R^{16}$, and $R^{17}$ represents hydrogen;
or $R^{14}$ represents methoxy, $R^{17}$ represents hydrogen, methyl, chloro or fluoro; $R^{16}$ represents hydrogen, chloro or fluoro; and $R^{15}$ represents hydrogen;
or $R^{14}$ represents halogen (especially bromo, chloro, fluoro), $R^{17}$ represents hydrogen, methyl, methoxy, chloro or fluoro; $R^{16}$ represents hydrogen, chloro or fluoro; and $R^{15}$ represents hydrogen or fluoro; wherein at least one of $R^{15}$, $R^{16}$, and $R^{17}$ represents hydrogen;

or $R^{14}$ represents cyano; $R^{17}$ represents hydrogen, or fluoro; $R^{16}$ represents hydrogen; and $R^{15}$ represents hydrogen;

or $R^{14}$ and $R^{15}$ together form a group —O—CH$_2$—O—, $R^{16}$ represents hydrogen and $R^{17}$ represents hydrogen or chloro;

or
$R^2$ represents methyl, chloro, or cyano; and
$R^{13}$ represents fluoro; and
$R^{14}$, $R^{17}$, $R^{16}$ and $R^{15}$ represent hydrogen;
or $R^{14}$ represents methoxy, $R^{17}$ represents fluoro; and $R^{16}$ and $R^{15}$ represent hydrogen.

19) Another embodiment relates to compounds according to any one of embodiments 1) to 13), wherein the group

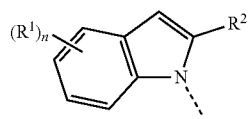

represents

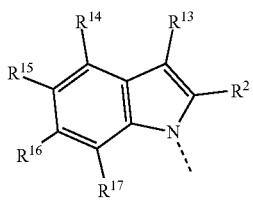

wherein
$R^2$ represents methyl, chloro, or cyano (especially methyl or cyano); and
$R^{13}$ represents hydrogen; and
$R^{14}$ represents hydrogen; $R^{17}$ represents hydrogen or fluoro; $R^{16}$ represents hydrogen, or fluoro; and $R^{15}$ represents hydrogen, methyl, chloro, or fluoro; wherein preferably at least one of $R^{15}$, $R^{16}$, and $R^{17}$ is different from hydrogen; especially $R^{16}$ and/or $R^{17}$ is/are different from hydrogen;
or $R^{14}$ represents methyl, $R^{17}$ represents hydrogen or fluoro; $R^{16}$ represents hydrogen, chloro or fluoro; and $R^{15}$ represents hydrogen or fluoro; wherein at least one of $R^{15}$, $R^1$, and $R^{17}$ represents hydrogen;
or $R^{14}$ represents methoxy, $R^{17}$ represents hydrogen, chloro or fluoro; $R^{16}$ represents hydrogen, chloro or fluoro; and $R^{15}$ represents hydrogen;
or $R^{14}$ represents halogen (especially bromo, chloro, fluoro), $R^{17}$ represents hydrogen or fluoro; $R^{16}$ represents hydrogen, chloro or fluoro; and $R^{15}$ represents hydrogen or fluoro; wherein at least one of $R^{15}$, $R^{16}$, and $R^{17}$ represents hydrogen.

20) Another embodiment relates to compounds according to any one of embodiments 1) to 19), wherein $R^2$ represents methyl.

21) Another embodiment relates to compounds according to any one of embodiments 1) to 19), wherein $R^2$ represents cyano.

22) Another embodiment relates to compounds according to any one of embodiments 1) to 13), wherein the group

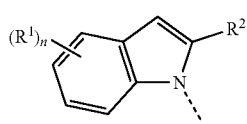
represents a group selected from the following groups A), B), C), D) and E):
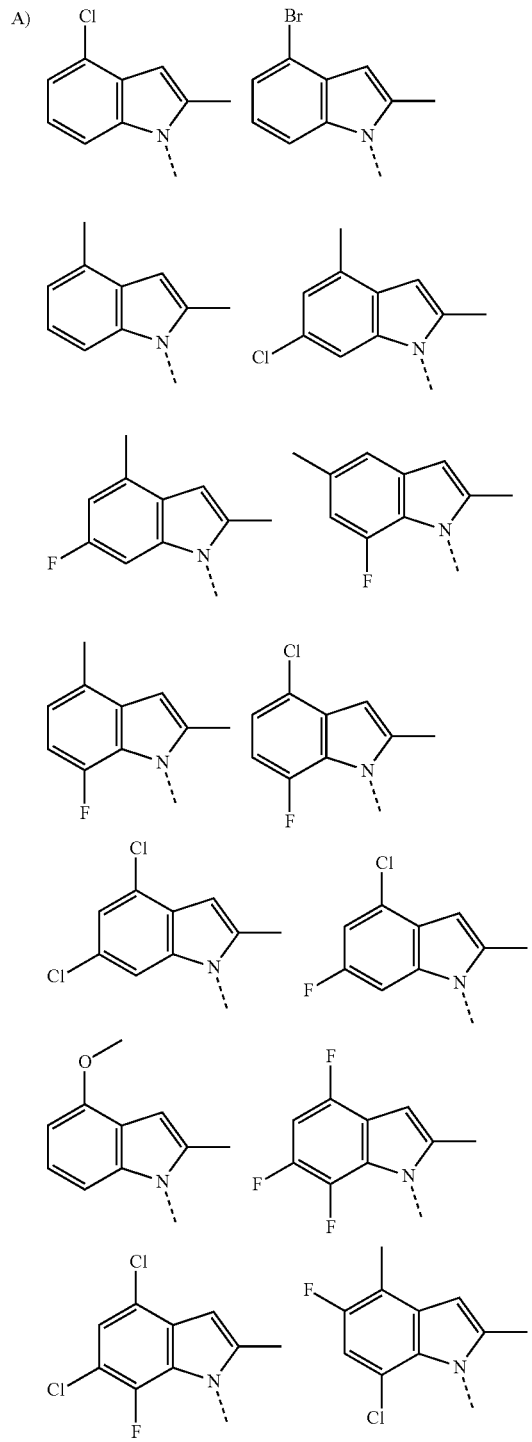
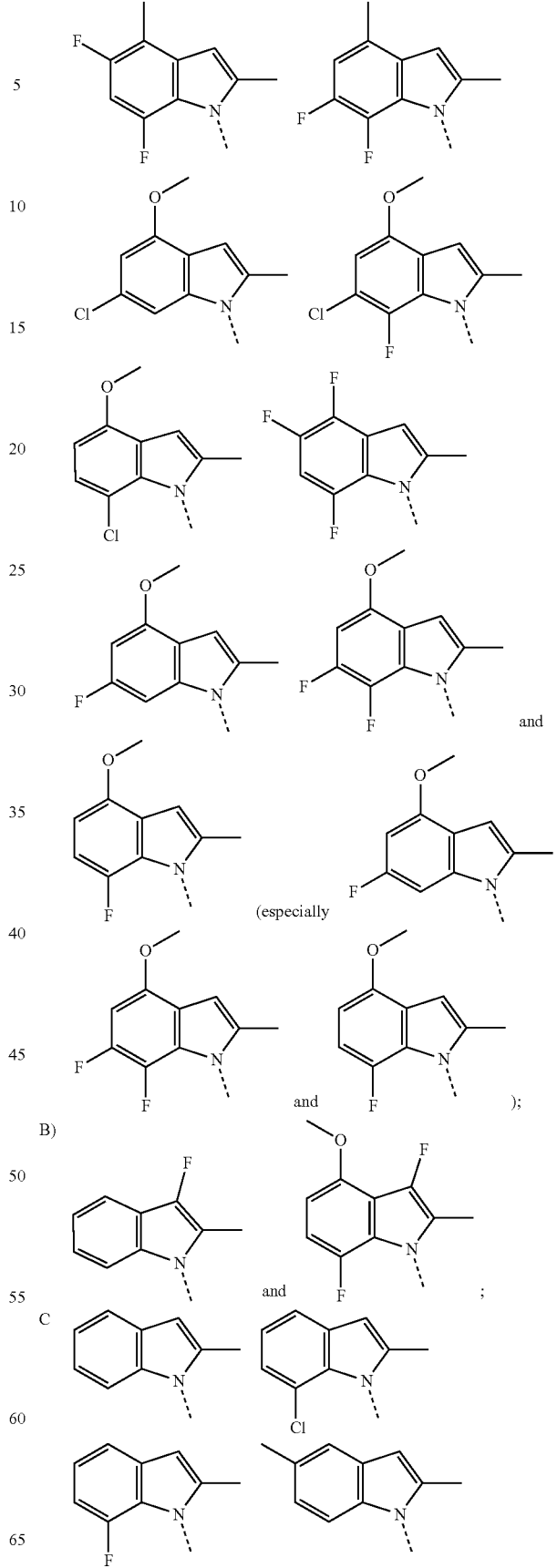

75
-continued
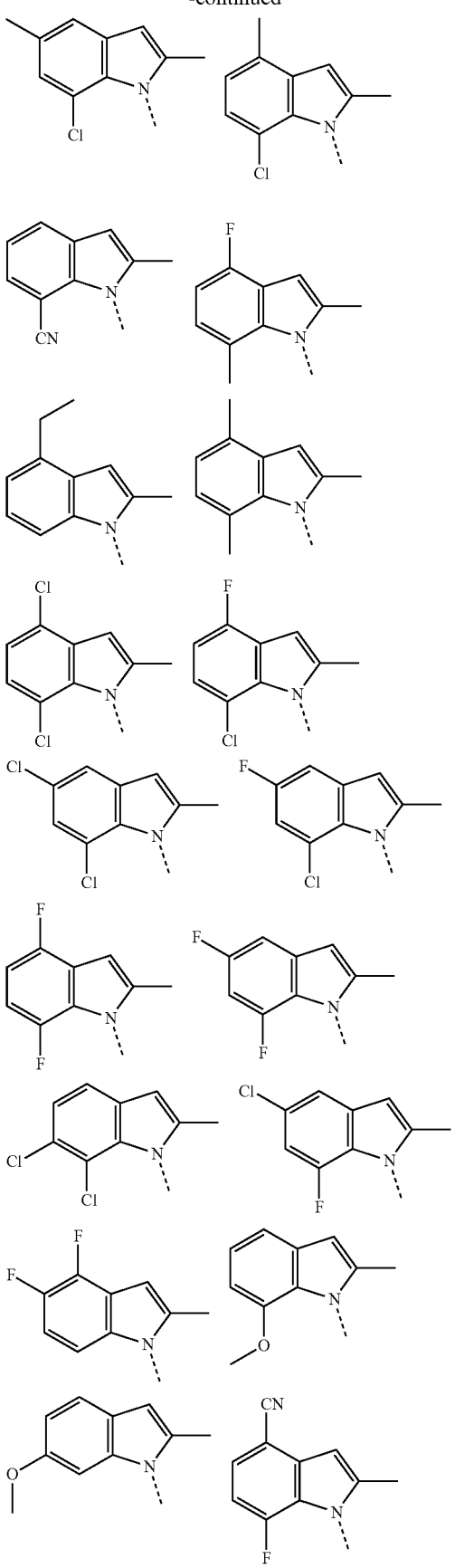
76
-continued
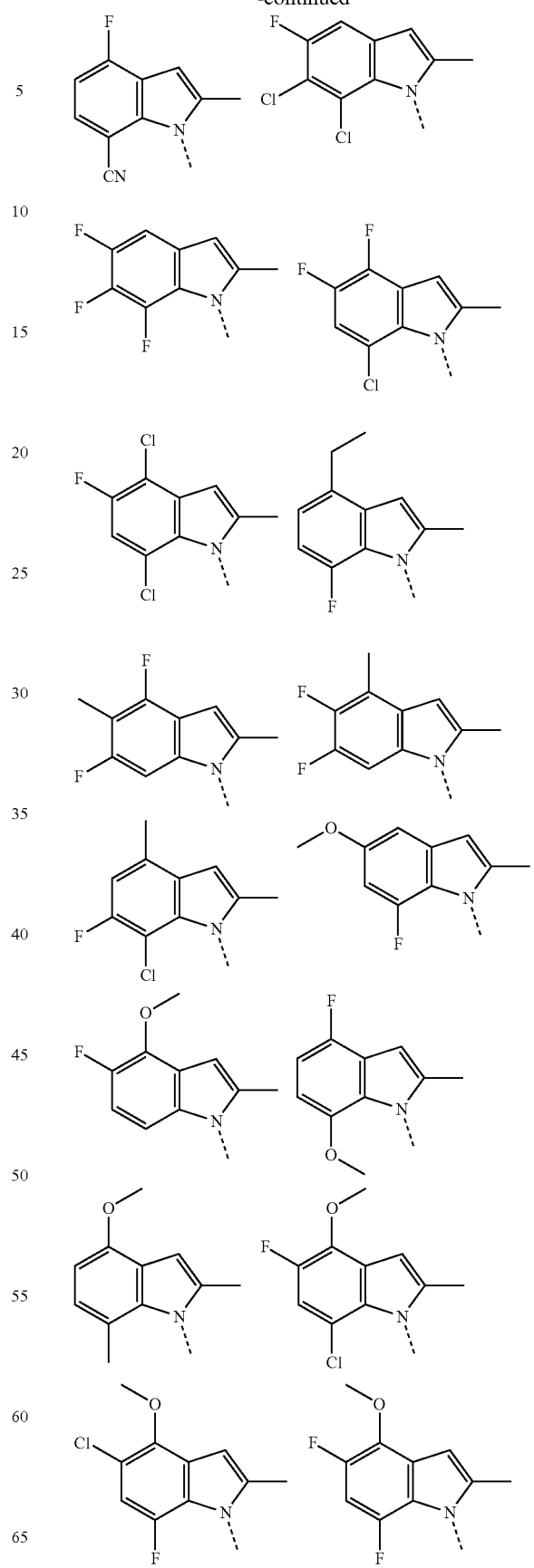

-continued

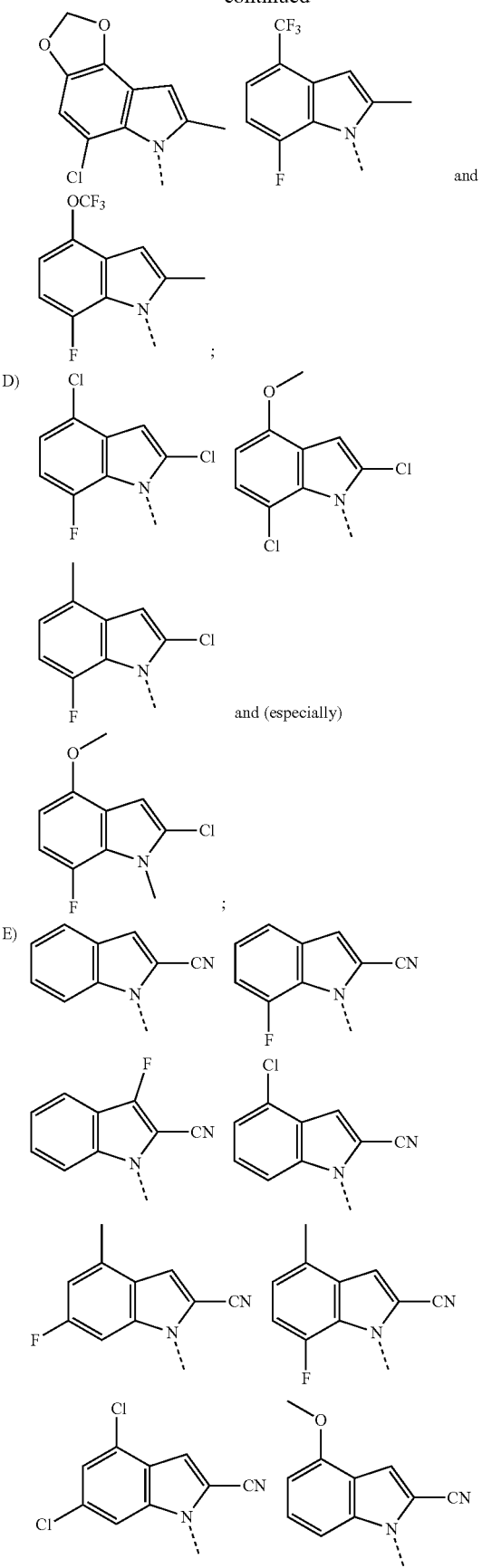

and (especially)

-continued

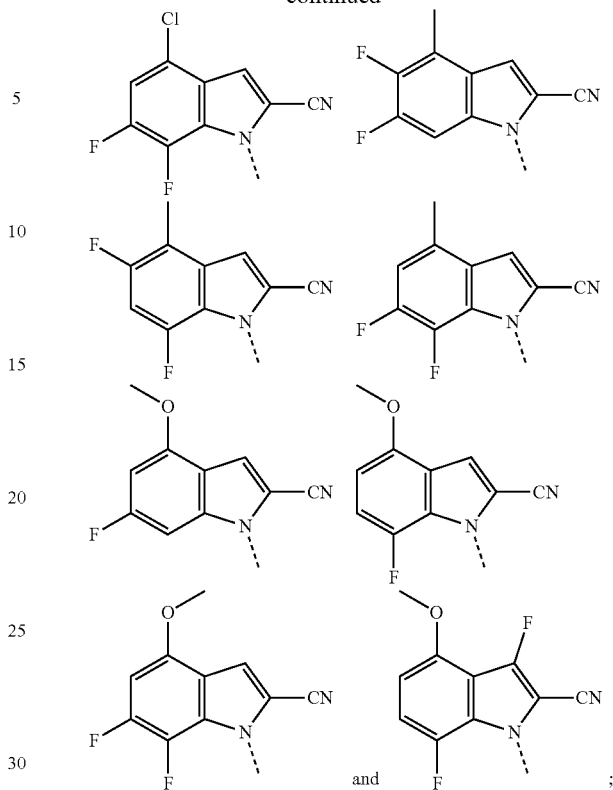

and wherein the groups of A), B) and E) are preferred groups.

23) The invention, thus, relates to compounds of the formula (I) as defined in embodiment 1), or to such compounds further limited by the characteristics of any one of embodiments 2) to 22), under consideration of their respective dependencies; to pharmaceutically acceptable salts thereof; and to the use of such compounds as medicaments especially in the prevention/prophylaxis or treatment of diseases which respond to the blockage of the EP2 receptors and/or the EP4 receptors as described herein below. For avoidance of any doubt, especially the following embodiments relating to the compounds of formula (I) are thus possible and intended and herewith specifically disclosed in individualized form:

1, 2+1, 4+1, 4+2+1, 5+1, 5+2+1, 5+4+1, 5+4+2+1, 7+1, 7+2+1, 7+4+1, 7+4+2+1, 7+5+1, 7+5+2+1, 7+5+4+1, 7+5+4+2+1, 9+1, 9+2+1, 9+4+1, 9+4+2+1, 9+5+1, 9+5+2+1, 9+5+4+1, 9+5+4+2+1, 11+1, 11+2+1, 11+4+1, 11+4+2+1, 11+5+1, 11+5+2+1, 11+5+4+1, 11+5+4+2+1, 12+1, 12+2+1, 12+4+1, 12+4+2+1, 12+5+1, 12+5+2+1, 12+5+4+1, 12+5+4+2+1, 13+1, 13+2+1, 13+4+1, 13+4+2+1, 13+5+1, 13+5+2+1, 13+5+4+1, 13+5+4+2+1, 15+1, 15+2+1, 15+4+1, 15+4+2+1, 15+5+1, 15+5+2+1, 15+5+4+1, 15+5+4+2+1, 15+7+1, 15+7+2+1, 15+7+4+1, 15+7+4+2+1, 15+7+5+1, 15+7+5+2+1, 15+7+5+4+1, 15+7+5+4+2+1, 15+9+1, 15+9+2+1, 15+9+4+1, 15+9+4+2+1, 15+9+5+1, 15+9+5+2+1, 15+9+5+4+1, 15+9+5+4+2+1, 15+11+1, 15+11+2+1, 15+11+4+1, 15+11+4+2+1, 15+11+5+1, 15+11+5+2+1, 15+11+5+4+1, 15+11+5+4+2+1, 15+12+1, 15+12+2+1, 15+12+4+1, 15+12+4+2+1, 15+12+5+1, 15+12+5+2+1, 15+12+5+4+1, 15+12+5+4+2+1, 15+13+1, 15+13+2+1, 15+13+4+1, 15+13+4+2+1, 15+13+5+1, 15+13+5+2+1, 15+13+5+4+1, 15+13+5+4+2+1, 16+1, 16+2+1, 16+4+1, 16+4+2+1, 16+5+1, 16+5+2+1, 16+5+4+1, 16+5+4+2+1,

16+7+1, 16+7+2+1, 16+7+4+1, 16+7+4+2+1, 16+7+5+1, 16+7+5+2+1, 16+7+5+4+1, 16+7+5+4+2+1, 16+9+1, 16+9+2+1, 16+9+4+1, 16+9+4+2+1, 16+9+5+1, 16+9+5+2+1, 16+9+5+4+1, 16+9+5+4+2+1, 16+11+1, 16+11+2+1, 16+11+4+1, 16+11+4+2+1, 16+11+5+1, 16+11+5+2+1, 16+11+5+4+1, 16+11+5+4+2+1, 16+12+1, 16+12+2+1, 16+12+4+1, 16+12+4+2+1, 16+12+5+1, 16+12+5+2+1, 16+12+5+4+1, 16+12+5+4+2+1, 16+13+1, 16+13+2+1, 16+13+4+1, 16+13+4+2+1, 16+13+5+1, 16+13+5+2+1, 16+13+5+4+1, 16+13+5+4+2+1, 20+1, 20+2+1, 20+4+1, 20+4+2+1, 20+5+1, 20+5+2+1, 20+5+4+1, 20+5+4+2+1, 20+7+1, 20+7+2+1, 20+7+4+1, 20+7+4+2+1, 20+7+5+1, 20+7+5+2+1, 20+7+5+4+1, 20+7+5+4+2+1, 20+15+1, 20+15+2+1, 20+15+4+1, 20+15+4+2+1, 20+15+5+1, 20+15+5+2+1, 20+15+5+4+1, 20+15+5+4+2+1, 20+15+7+1, 20+15+7+2+1, 20+15+7+4+1, 20+15+7+4+2+1, 20+15+7+5+1, 20+15+7+5+2+1, 20+15+7+5+4+1, 20+15+7+5+4+2+1, 20+15+9+1, 20+15+9+2+1, 20+15+9+4+1, 20+15+9+4+2+1, 20+15+9+5+1, 20+15+9+5+2+1, 20+15+9+5+4+1, 20+15+9+5+4+2+1, 20+15+11+1, 20+15+11+2+1, 20+15+11+4+1, 20+15+11+4+2+1, 20+15+11+5+1, 20+15+11+5+2+1, 20+15+11+5+4+1, 20+15+11+5+4+2+1, 20+15+12+1, 20+15+12+2+1, 20+15+12+4+1, 20+15+12+4+2+1, 20+15+12+5+1, 20+15+12+5+2+1, 20+15+12+5+4+1, 20+15+12+5+4+2+1, 20+15+13+1, 20+15+13+2+1, 20+15+13+4+1, 20+15+13+4+2+1, 20+15+13+5+1, 20+15+13+5+2+1, 20+15+13+5+4+1, 20+15+13+5+4+2+1, 20+16+1, 20+16+2+1, 20+16+4+1, 20+16+4+2+1, 20+16+5+1, 20+16+5+2+1, 20+16+5+4+1, 20+16+5+4+2+1, 20+16+7+1, 20+16+7+2+1, 20+16+7+4+1, 20+16+7+4+2+1, 20+16+7+5+1, 20+16+7+5+2+1, 20+16+7+5+4+1, 20+16+7+5+4+2+1, 20+16+9+1, 20+16+9+2+1, 20+16+9+4+1, 20+16+9+4+2+1, 20+16+9+5+1, 20+16+9+5+2+1, 20+16+9+5+4+1, 20+16+9+5+4+2+1, 20+16+11+1, 20+16+11+2+1, 20+16+11+4+1, 20+16+11+4+2+1, 20+16+11+5+1, 20+16+11+5+2+1, 20+16+11+5+4+1, 20+16+11+5+4+2+1, 20+16+12+1, 20+16+12+2+1, 20+16+12+4+1, 20+16+12+4+2+1, 20+16+12+5+1, 20+16+12+5+2+1, 20+16+12+5+4+1, 20+16+12+5+4+2+1, 20+16+13+1, 20+16+13+2+1, 20+16+13+4+1, 20+16+13+4+2+1, 20+16+13+5+1, 20+16+13+5+2+1, 20+16+13+5+4+1, 20+16+13+5+4+2+1, 21+1, 21+2+1, 21+4+1, 21+4+2+1, 21+5+1, 21+5+2+1, 21+5+4+1, 21+5+4+2+1, 21+7+1, 21+7+2+1, 21+7+4+1, 21+7+4+2+1, 21+7+5+1, 21+7+5+2+1, 21+7+5+4+1, 21+7+5+4+2+1, 21+15+1, 21+15+2+1, 21+15+4+1, 21+15+4+2+1, 21+15+5+1, 21+15+5+2+1, 21+15+5+4+1, 21+15+5+4+2+1, 21+15+7+1, 21+15+7+2+1, 21+15+7+4+1, 21+15+7+4+2+1, 21+15+7+5+1, 21+15+7+5+2+1, 21+15+7+5+4+1, 21+15+7+5+4+2+1, 21+15+9+1, 21+15+9+2+1, 21+15+9+4+1, 21+15+9+4+2+1, 21+15+9+5+1, 21+15+9+5+2+1, 21+15+9+5+4+1, 21+15+9+5+4+2+1, 21+15+11+1, 21+15+11+2+1, 21+15+11+4+1, 21+15+11+4+2+1, 21+15+11+5+1, 21+15+11+5+2+1, 21+15+11+5+4+1, 21+15+11+5+4+2+1, 21+15+12+1, 21+15+12+2+1, 21+15+12+4+1, 21+15+12+4+2+1, 21+15+12+5+1, 21+15+12+5+2+1, 21+15+12+5+4+1, 21+15+12+5+4+2+1, 21+15+13+1, 21+15+13+2+1, 21+15+13+4+1, 21+15+13+4+2+1, 21+15+13+5+1, 21+15+13+5+2+1, 21+15+13+5+4+1, 21+15+13+5+4+2+1, 21+16+1, 21+16+2+1, 21+16+4+1, 21+16+4+2+1, 21+16+5+1, 21+16+5+2+1, 21+16+5+4+1, 21+16+5+4+2+1, 21+16+7+1, 21+16+7+2+1, 21+16+7+4+1, 21+16+7+4+2+1, 21+16+7+5+1, 21+16+7+5+2+1, 21+16+7+5+4+1, 21+16+7+5+4+2+1, 21+16+9+1, 21+16+9+2+1, 21+16+9+4+1, 21+16+9+4+2+1, 21+16+9+5+1, 21+16+9+5+2+1, 21+16+9+5+4+1, 21+16+9+5+4+2+1, 21+16+11+1, 21+16+11+2+1, 21+16+11+4+1, 21+16+11+4+2+1, 21+16+11+5+1, 21+16+11+5+2+1, 21+16+11+5+4+1, 21+16+11+5+4+2+1, 21+16+12+1, 21+16+12+2+1, 21+16+12+4+1, 21+16+12+4+2+1, 21+16+12+5+1, 21+16+12+5+2+1, 21+16+12+5+4+1, 21+16+12+5+4+2+1, 21+16+13+1, 21+16+13+2+1, 21+16+13+4+1, 21+16+13+4+2+1, 21+16+13+5+1, 21+16+13+5+2+1, 21+16+13+5+4+1, 21+16+13+5+4+2+1, 22+1, 22+2+1, 22+4+1, 22+4+2+1, 22+5+1, 22+5+2+1, 22+5+4+1, 22+5+4+2+1, 22+7+1, 22+7+2+1, 22+7+4+1, 22+7+4+2+1, 22+7+5+1, 22+7+5+2+1, 22+7+5+4+1, 22+7+5+4+2+1, 22+9+1, 22+9+2+1, 22+9+4+1, 22+9+4+2+1, 22+9+5+1, 22+9+5+2+1, 22+9+5+4+1, 22+9+5+4+2+1, 22+11+1, 22+11+2+1, 22+11+4+1, 22+11+4+2+1, 22+11+5+1, 22+11+5+2+1, 22+11+5+4+1, 22+11+5+4+2+1, 22+12+1, 22+12+2+1, 22+12+4+1, 22+12+4+2+1, 22+12+5+1, 22+12+5+2+1, 22+12+5+4+1, 22+12+5+4+2+1, 22+13+1, 22+13+2+1, 22+13+4+1, 22+13+4+2+1, 22+13+5+1, 22+13+5+2+1, 22+13+5+4+1, 22+13+5+4+2+1.

In the list above the numbers refer to the embodiments according to their numbering provided hereinabove whereas "+" indicates the dependency from another embodiment. The different individualized embodiments are separated by commas. In other words, "16+13+4+1" for example refers to embodiment 16) depending on embodiment 13), depending on embodiment 4), depending on embodiment 1), i.e. embodiment "16+13+4+1" corresponds to the compounds of formula (I) according to embodiment 1) further limited by all the features of the embodiments 4), 13), and 16).

24) A second aspect of the invention relates to compounds of the formula (I) according to embodiment 1) which are also compounds of the formula (II)

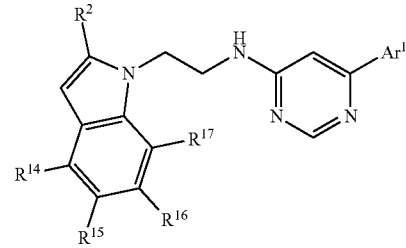

Formula (II)

wherein
$R^2$ represents (C-s)alkyl (especially methyl), halogen (especially chloro), or cyano; and
  $R^{14}$, $R^{15}$, $R^{16}$, and $R^{17}$ independently represent the following:
  $R^{14}$ represents hydrogen, methyl, ethyl, methoxy, bromo, chloro, fluoro, trifluoromethyl, trifluoromethoxy, or cyano (especially $R^{14}$ represents methyl, methoxy, halogen, or cyano);
  $R^{15}$ represents hydrogen, methyl, methoxy, chloro, fluoro (especially $R^{15}$ represents hydrogen, methyl, chloro, or fluoro);
  $R^{16}$ represents hydrogen, methoxy, or fluoro; (especially $R^{16}$ represents hydrogen, or fluoro); and
  $R^{17}$ represents hydrogen, methyl, methoxy, chloro, fluoro, or cyano; (especially $R^{17}$ represents hydrogen, chloro, or fluoro);
  wherein at least one of $R^{14}$, $R^{15}$, $R^{16}$, and $R^{17}$ represents hydrogen;
  (and, preferably, at least one of $R^{14}$, $R^{15}$, $R^{16}$, and $R^{17}$ is different from hydrogen; especially one of $R^{14}$, $R^{16}$, and $R^{17}$ is different from hydrogen);

or R$^{14}$ and R$^{15}$ together form a group —O—CH$_2$—O—, R$^{16}$ represents hydrogen and R$^{17}$ represents hydrogen or halogen (especially fluoro or chloro);

and Ar$^1$ is as defined in embodiment 10);

wherein the characteristics disclosed in embodiments 2) to 22) are intended to apply mutatis mutandis also to the compounds formula (II) according to embodiment 24); wherein especially the following embodiments are thus possible and intended and herewith specifically disclosed in individualized form:

24+12, 24+13, 24+17, 24+17+12, 24+17+13, 24+18, 24+18+12, 24+18+13, 24+19, 24+19+12, 24+19+13, 24+22, 24+22+12, 24+22+13, 24+20, 24+20+17, 24+20+17+12, 24+20+17+13, 24+20+18, 24+20+18+12, 24+20+18+13, 24+20+19, 24+20+19+12, 24+20+19+13, 24+21, 24+21+17, 24+21+17+12, 24+21+17+13, 24+21+18, 24+21+18+12, 24+21+18+13, 24+21+19, 24+21+19+12, 24+21+19+13.

In the list above the numbers refer to the embodiments according to their numbering provided hereinabove whereas "+" indicates the limitations as outlined above.

25) A third aspect of the invention relates to compounds of the formula (I) according to embodiment 1) which are also compounds of the formula (III)

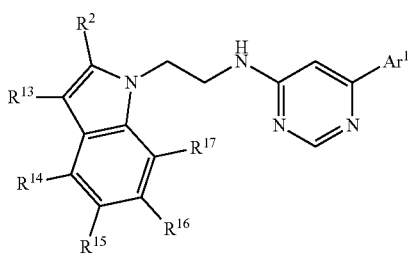

Formula (III)

wherein the group:

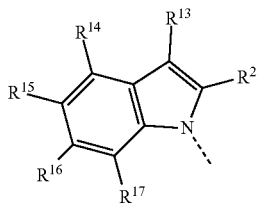

is as defined in embodiment 15); and

Ar$^1$ is as defined in embodiment 7);

wherein the characteristics disclosed in embodiments 2) to 22) are intended to apply mutatis mutandis also to the compounds formula (III) according to embodiment 25); wherein especially the following embodiments are thus possible and intended and herewith specifically disclosed in individualized form:

25, 25+9, 25+11, 25+12, 25+13, 25+16+9, 25+16+11, 25+16+12, 25+16+13, 25+16, 25+18+9, 25+18+11, 25+18+12, 25+18+13, 25+18, 25+20+9, 25+20+11, 25+20+12, 25+20+13, 25+20+16+9, 25+20+16+11, 25+20+16+12, 25+20+16+13, 25+20+16, 25+20+18+9, 25+20+18+11, 25+20+18+12, 25+20+18+13, 25+20+18, 25+20, 25+21+9, 25+21+11, 25+21+12, 25+21+13, 25+21+16+9, 25+21+16+11, 25+21+16+12, 25+21+16+13, 25+21+16, 25+21+18+9, 25+21+18+11, 25+21+18+12, 25+21+18+13, 25+21+18, 25+21, 25+22+9, 25+22+11, 25+22+12, 25+22+13, 25+22.

In the list above the numbers refer to the embodiments according to their numbering provided hereinabove whereas "+" indicates the limitations as outlined above.

26) Another embodiment relates to compounds of formula (III) according to embodiment 25), wherein the group:

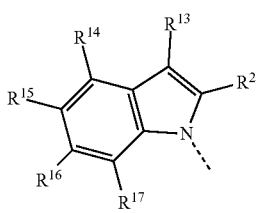

represents a group selected from the following groups A), B), C), D) and E):

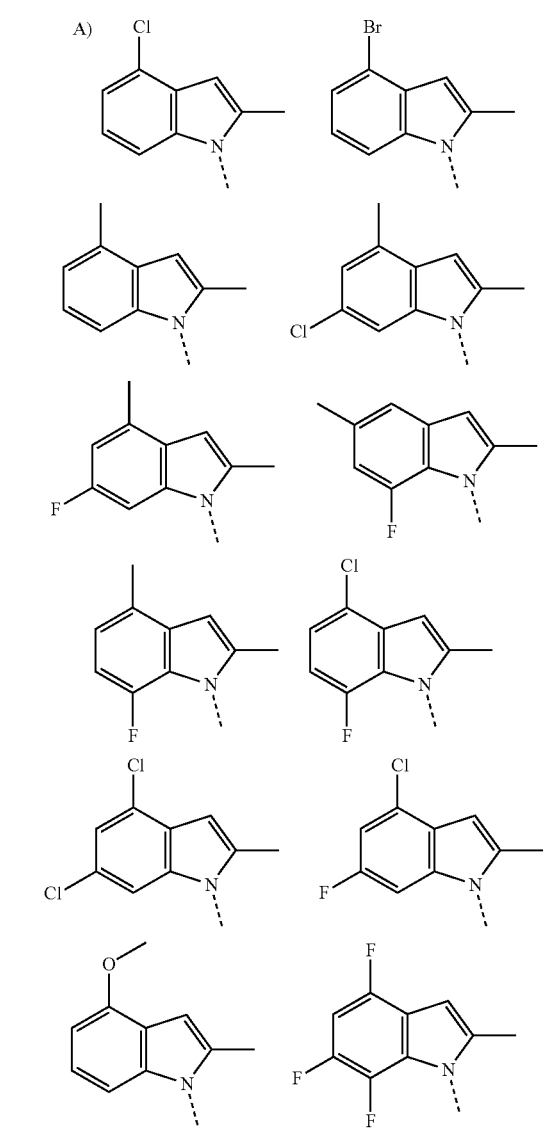

-continued
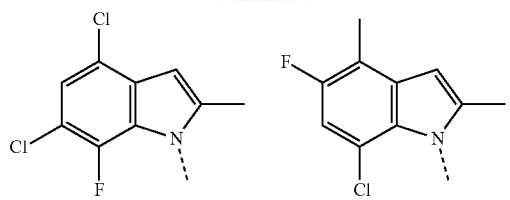
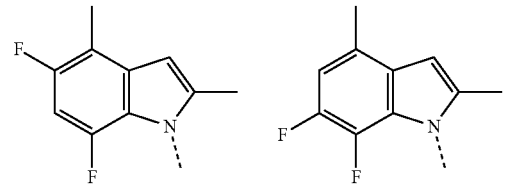
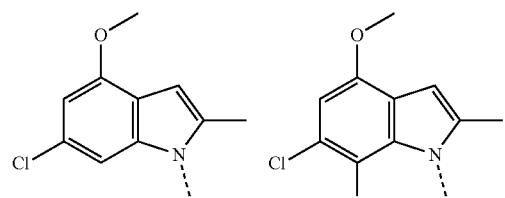
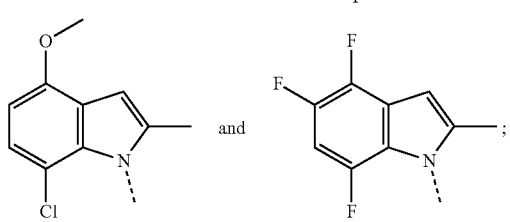
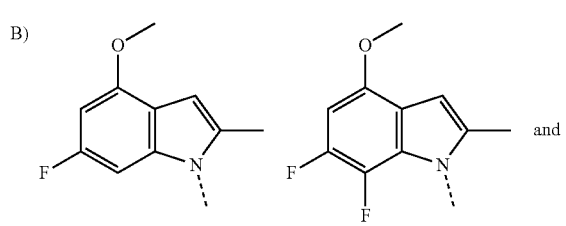
B)
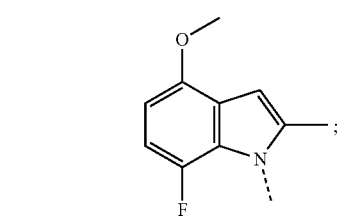
C)
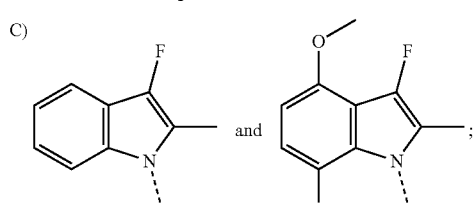
D)
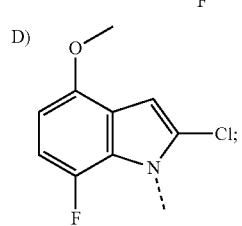
E)
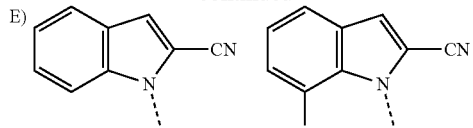
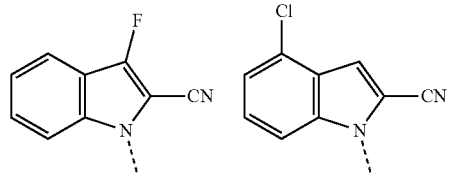
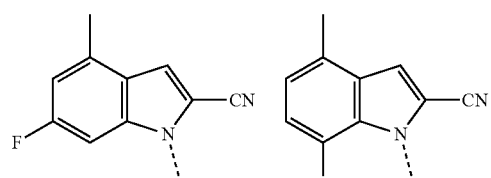
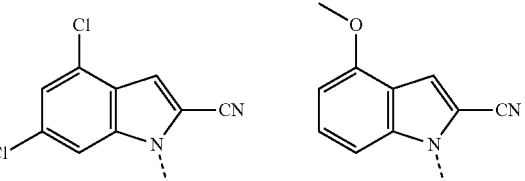
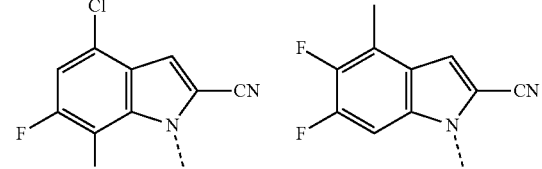
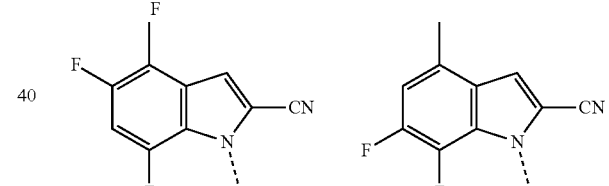
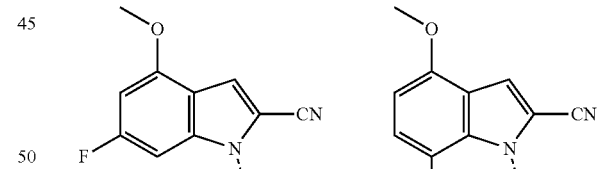
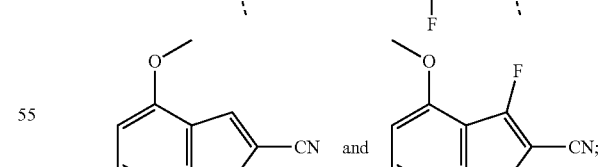
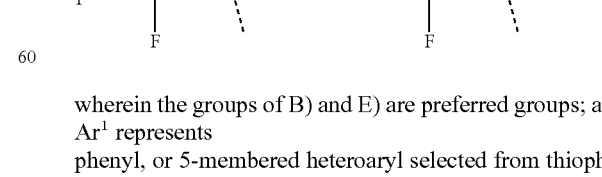
wherein the groups of B) and E) are preferred groups; and Ar[1] represents
phenyl, or 5-membered heteroaryl selected from thiophenyl and thiazolyl; wherein said phenyl or 5-membered heteroaryl independently is mono-, di- or tri-substituted;

wherein one of said substituents is selected from
—$X^1$—CO—$R^{O1}$, wherein
$X^1$ represents a direct bond, —$CH_2$—$CH_2$—, —O—$CH_2$—*, —NH—$CH_2$—*, —CH=CH—, or —NH—CO—*; wherein the asterisks indicate the bond that is linked to the —CO—$R^{O1}$ group; and $R^{O1}$ represents
- —OH;
- —O—$(C_{1-4})$alkyl (especially ethoxy, methoxy);
- —NH—$SO_2$—$R^{S3}$ wherein $R^{S3}$ represents $(C_{1-3})$alkyl, cyclopropyl, or —$NH_2$;
- —O—$CH_2$—CO—$R^{O4}$, wherein $R^{O4}$ represents hydroxy, or $(C_{1-4})$alkoxy; or
- —O—$CH_2$—O—CO—$R^{O5}$, wherein $R^{O5}$ represents $(C_{1-4})$alkyl or $(C_{1-4})$alkoxy;

[wherein in particular, such group —$X^1$—CO—$R^{O1}$ represents —COOH, —CO—O—$C_2H_5$, —O—$CH_2$—COOH, —NH—$CH_2$—COOH, —CO—NH—$SO_2$—$CH_3$, —CO—NH—$SO_2$—$C(CH_3)_2$, —CO—NH—$SO_2$-cyclopropyl, —COO—$CH_3$, —CO—NH—$SO_2$-ethyl, —CO—NH—$SO_2$—$NH_2$, —COO—$CH_2$—COOH, —COO—$CH_2$—O—CO—O-ethyl, —CO—O—$CH_2$—O—CO-propyl, —$CH_2$—$CH_2$—COOH, —CH=CH—COOH, —NH—CO—COOH, —NH—$CH_2$—COO—$CH_3$];

—$NR^{N1}R^{N2}$, wherein $R^{N1}$ independently represents hydrogen or $(C_{1-3})$alkyl, and $R^{N2}$ represents —CO—H (especially-NH—CO—H);

5-oxo-4,5-dihydro-[1,2,4]oxadiazol-3-yl (encompassing its tautomeric form 5-hydroxy-[1,2,4]oxadiazol-3-yl), or 3-oxo-2,3-dihydro-[1,2,4]oxadiazol-5-yl (encompassing its tautomeric form 3-hydroxy-[1,2,4]oxadiazol-5-yl);

1H-tetrazol-5-yl;

3-hydroxy-isoxazol-5-yl;

imidazolyl (especially 1H-imidazol-4-yl), which is unsubstituted, or mono- or di-substituted with methyl (in particular 1H-imidazol-4-yl, 5-methyl-1H-imidazol-4-yl, 2,5-dimethyl-1H-imidazol-4-yl);

pyrazolyl (especially 1H-pyrazol-3-yl);

isoxazolyl, oxazolyl, or thiadiazolyl; wherein said isoxazolyl, oxazolyl, or thiadiazolyl is mono-substituted with —$NR^{N9}R^{N10}$, wherein $R^{N9}$ represents hydrogen, and $R^{N10}$ represents hydrogen or methyl; (in particular 3-amino-isoxazol-5-yl, 2-amino-oxazol-5-yl, 5-methylamino-[1,3,4]thiadiazol-2-yl);

(wherein especially said 5-membered heteroaryl represents thiophen-2-yl wherein said substituent is attached in position 5, or thiophen-2-yl wherein said substituent is attached in position 4; or thiazol-2-yl wherein said substituent is attached in position 5)

and the remaining one or two of said substituents (if present) is/are independently selected from
- $(C_{1-4})$alkyl (especially ethyl, n-propyl, isobutyl);
- $(C_{1-4})$alkoxy (especially methoxy, ethoxy, n-propoxy, isopropoxy, n-butoxy);
- 2,2,2-trifluoroethoxy;
- halogen (especially fluoro or chloro);
- —$NR^{N1}R^{N2}$, wherein $R^{N1}$ represents hydrogen, and $R^{N2}$ represents $(C_{1-3})$alkyl;
- —S—$R^{S2}$ wherein $R^{S2}$ represents $(C_{1-4})$alkyl (especially methyl, ethyl, n-propyl, isopropyl);

or $Ar^1$ represents 8- to 10-membered bicyclic heteroaryl selected from unsubstituted benzimidazol (especially 1H-benzoimidazol-5-yl); unsubstituted indazolyl (especially 1H-indazol-5-yl), and indolyl which is unsubstituted or mono-substituted with —$COOR^{O2}$ wherein $R^{O2}$ represents hydrogen or $(C_{1-4})$alkyl (especially methyl) (in particular 1H-indol-6-yl, 1H-indol-5-yl, 1H-indol-2-yl, 5-carboxy-1H-indol-2-yl, 6-carboxy-1H-indol-2-yl, 5-(methoxycarbonyl)-1H-indol-2-yl, or 6-(methoxycarbonyl)-1H-indol-2-yl);

or $Ar^1$ represents oxo-substituted 8- to 10-membered partially aromatic fused bicyclic heterocyclyl selected from 2-oxo-2,3-dihydro-benzooxazolyl, 3-oxo-2,3-dihydro-1H-indazolyl, 2-oxo-1,2,3,4-tetrahydro-quinazolinyl, 1-oxo-1,2,3,4-tetrahydro-isoquinolinyl; wherein said oxo-substituted heterocyclyl is unsubstituted (i.e. it carries no further substituent in addition to the oxo substituent) or mono-substituted on a ring nitrogen atom with $(C_{1-3})$alkyl (especially methyl); (in particular such heterocyclyl is 2-oxo-2,3-dihydro-benzooxazol-6-yl, 3-methyl-2-oxo-2,3-dihydro-benzooxazol-5-yl, 1-methyl-3-oxo-2,3-dihydro-1H-indazol-6-yl, 2-oxo-1,2,3,4-tetrahydro-quinazolin-6-yl, 1-methyl-2-oxo-1,2,3,4-tetrahydro-quinazolin-7-yl, or 1-oxo-1,2,3,4-tetrahydro-isoquinolin-6-yl).

27) Another embodiment relates to most preferred compounds according to embodiment 1) which are selected from the following compounds:

3-Chloro-5-{6-[2-(6-fluoro-4-methoxy-2-methyl-indol-1-yl)-ethylamino]-pyrimidin-4-yl}-thiophene-2-carboxylic acid;

5-{6-[2-(2-Cyano-indol-1-yl)-ethylamino]-pyrimidin-4-yl}-3-ethoxy-thiophene-2-carboxylic acid;

[6-(2,3-Dihydro-1H-indol-5-yl)-pyrimidin-4-yl]-[2-(6-fluoro-4-methoxy-2-methyl-indol-1-yl)-ethyl]-amine;

[2-(7-Fluoro-2,4-dimethyl-indol-1-yl)-ethyl]-{6-[4-(1H-imidazol-4-yl)-phenyl]-pyrimidin-4-yl}-amine;

3-Ethyl-5-{6-[2-(6-fluoro-2,4-dimethyl-indol-1-yl)-ethylamino]-pyrimidin-4-yl}-thiophene-2-carboxylic acid;

5-{6-[2-(7-Fluoro-4-methoxy-2-methyl-indol-1-yl)-ethylamino]-pyrimidin-4-yl}-3-methyl-thiophene-2-carboxylic acid;

5-{6-[2-(4-Chloro-2-methyl-indol-1-yl)-ethylamino]-pyrimidin-4-yl}-3-ethoxy-thiophene-2-carboxylic acid;

3-Ethyl-5-{6-[2-(4-methoxy-2-methyl-indol-1-yl)-ethylamino]-pyrimidin-4-yl}-thiophene-2-carboxylic acid;

3-Chloro-5-{6-[2-(7-fluoro-4-methoxy-2-methyl-indol-1-yl)-ethylamino]-pyrimidin-4-yl}-thiophene-2-carboxylic acid;

4-{6-[2-(7-Fluoro-2,4-dimethyl-indol-1-yl)-ethylamino]-pyrimidin-4-yl}-2-methylamino-benzoic acid;

5-{6-[2-(5,7-Difluoro-2,4-dimethyl-indol-1-yl)-ethylamino]-pyrimidin-4-yl}-3-ethoxy-thiophene-2-carboxylic acid;

{6-[4-(3-Amino-isoxazol-5-yl)-phenyl]-pyrimidin-4-yl}-[2-(4-methoxy-2-methyl-indol-1-yl)-ethyl]-amine;

[2-(6-Fluoro-4-methoxy-2-methyl-indol-1-yl)-ethyl]-{6-[4-(1H-imidazol-4-yl)-phenyl]-pyrimidin-4-yl}-amine;

[2-(7-Fluoro-4-methoxy-2-methyl-indol-1-yl)-ethyl]-{6-[4-(1H-imidazol-4-yl)-phenyl]-pyrimidin-4-yl}-amine;

[2-(7-Fluoro-4-methoxy-2-methyl-indol-1-yl)-ethyl]-{6-[4-(2H-pyrazol-3-yl)-phenyl]-pyrimidin-4-yl}-amine;

3-Ethoxy-5-{6-[2-(4-methoxy-2-methyl-indol-1-yl)-ethylamino]-pyrimidin-4-yl}-thiophene-2-carboxylic acid;

5-{6-[2-(6-Chloro-2,4-dimethyl-indol-1-yl)-ethylamino]-pyrimidin-4-yl}-3-ethoxy-thiophene-2-carboxylic acid;

3-Ethoxy-5-{6-[2-(7-fluoro-2,4-dimethyl-indol-1-yl)-ethylamino]-pyrimidin-4-yl}-thiophene-2-carboxylic acid;

3-Ethoxy-5-{6-[2-(7-fluoro-2,5-dimethyl-indol-1-yl)-ethylamino]-pyrimidin-4-yl}-thiophene-2-carboxylic acid;

3-Ethoxy-5-{6-[2-(6-fluoro-2,4-dimethyl-indol-1-yl)-ethylamino]-pyrimidin-4-yl}-thiophene-2-carboxylic acid;

3-Ethyl-5-{6-[2-(7-fluoro-4-methoxy-2-methyl-indol-1-yl)-ethylamino]-pyrimidin-4-yl}-thiophene-2-carboxylic acid;

5-{6-[2-(4,6-Dichloro-2-methyl-indol-1-yl)-ethylamino]-pyrimidin-4-yl}-3-ethoxy-thiophene-2-carboxylic acid;

5-{6-[2-(4-Chloro-6-fluoro-2-methyl-indol-1-yl)-ethylamino]-pyrimidin-4-yl}-3-ethoxy-thiophene-2-carboxylic acid;

5-{6-[2-(4-Chloro-7-fluoro-2-methyl-indol-1-yl)-ethylamino]-pyrimidin-4-yl}-3-ethoxy-thiophene-2-carboxylic acid;

5-{6-[2-(2-Cyano-6-fluoro-4-methyl-indol-1-yl)-ethylamino]-pyrimidin-4-yl}-3-ethoxy-thiophene-2-carboxylic acid;

4-{6-[2-(7-Fluoro-4-methoxy-2-methyl-indol-1-yl)-ethylamino]-pyrimidin-4-yl}-2-methylamino-benzoic acid;

5-{6-[2-(7-Chloro-4-methoxy-2-methyl-indol-1-yl)-ethylamino]-pyrimidin-4-yl}-3-ethoxy-thiophene-2-carboxylic acid;

3-Ethoxy-5-{6-[2-(6-fluoro-4-methoxy-2-methyl-indol-1-yl)-ethylamino]-pyrimidin-4-yl}-thiophene-2-carboxylic acid;

3-Ethoxy-5-{6-[2-(7-fluoro-4-methoxy-2-methyl-indol-1-yl)-ethylamino]-pyrimidin-4-yl}-thiophene-2-carboxylic acid;

3-Ethoxy-5-{6-[2-(4,6,7-trifluoro-2-methyl-indol-1-yl)-ethylamino]-pyrimidin-4-yl}-thiophene-2-carboxylic acid;

3-Ethoxy-5-{6-[2-(4,5,7-trifluoro-2-methyl-indol-1-yl)-ethylamino]-pyrimidin-4-yl}-thiophene-2-carboxylic acid;

5-{6-[2-(6,7-Difluoro-2,4-dimethyl-indol-1-yl)-ethylamino]-pyrimidin-4-yl}-3-ethoxy-thiophene-2-carboxylic acid;

{6-[4-(3-Amino-isoxazol-5-yl)-phenyl]-pyrimidin-4-yl}-[2-(7-fluoro-4-methoxy-2-methyl-indol-1-yl)-ethyl]-amine;

[2-(6,7-Difluoro-4-methoxy-2-methyl-indol-1-yl)-ethyl]-{6-[4-(1H-imidazol-4-yl)-phenyl]-pyrimidin-4-yl}-amine;

[2-(7-Fluoro-2,4-dimethyl-indol-1-yl)-ethyl]-{6-[4-(5-methylamino-[1,3,4]thiadiazol-2-yl)-phenyl]-pyrimidin-4-yl}-amine;

5-{6-[2-(2-Cyano-6-fluoro-4-methoxy-indol-1-yl)-ethylamino]-pyrimidin-4-yl}-3-ethoxy-thiophene-2-carboxylic acid;

2-Ethylamino-4-{6-[2-(7-fluoro-4-methoxy-2-methyl-indol-1-yl)-ethylamino]-pyrimidin-4-yl}-benzoic acid;

5-{6-[2-(6,7-Difluoro-4-methoxy-2-methyl-indol-1-yl)-ethylamino]-pyrimidin-4-yl}-3-ethoxy-thiophene-2-carboxylic acid;

5-{6-[2-(6-Fluoro-2,4-dimethyl-indol-1-yl)-ethylamino]-2-methyl-pyrimidin-4-yl}-3-trifluoromethyl-thiophene-2-carboxylic acid;

5-{6-[2-(7-Fluoro-4-methoxy-2-methyl-indol-1-yl)-ethylamino]-pyrimidin-4-yl}-3-trifluoromethyl-thiophene-2-carboxylic acid;

5-{6-[2-(6-Fluoro-4-methoxy-2-methyl-indol-1-yl)-ethylamino]-pyrimidin-4-yl}-3-trifluoromethyl-thiophene-2-carboxylic acid;

[2-(7-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine;

4-(4-{6-[2-(7-Fluoro-4-methoxy-2-methyl-indol-1-yl)-ethylamino]-pyrimidin-4-yl}-phenyl)-thiazole-2-carboxylic acid;

2-Chloro-4-{6-[2-(6-chloro-4-methoxy-2-methyl-indol-1-yl)-ethylamino]-pyrimidin-4-yl}-6-propyl-benzoic acid;

2-Chloro-4-{6-[2-(6-fluoro-4-methoxy-2-methyl-indol-1-yl)-ethylamino]-pyrimidin-4-yl}-6-propyl-benzoic acid;

5-{6-[2-(6,7-Difluoro-4-methoxy-2-methyl-indol-1-yl)-ethylamino]-pyrimidin-4-yl}-3-trifluoromethyl-thiophene-2-carboxylic acid;

4-{6-[2-(6-Fluoro-4-methoxy-2-methyl-indol-1-yl)-ethylamino]-pyrimidin-4-yl}-2-isobutyl-benzoic acid;

5-{6-[2-(7-Fluoro-4-methoxy-2-methyl-indol-1-yl)-ethylamino]-2-methyl-pyrimidin-4-yl}-3-trifluoromethyl-thiophene-2-carboxylic acid;

5-{6-[2-(6-Fluoro-4-methoxy-2-methyl-indol-1-yl)-ethylamino]-2-methyl-pyrimidin-4-yl}-3-trifluoromethyl-thiophene-2-carboxylic acid;

1-Ethyl-3-(4-{6-[2-(7-fluoro-4-methoxy-2-methyl-indol-1-yl)-ethylamino]-pyrimidin-4-yl}-2-methoxy-phenyl)-urea;

{6-[4-(2-Amino-oxazol-5-yl)-phenyl]-pyrimidin-4-yl}-[2-(6-fluoro-4-methoxy-2-methyl-indol-1-yl)-ethyl]-amine;

{6-[4-(2-Amino-oxazol-5-yl)-phenyl]-pyrimidin-4-yl}-[2-(7-fluoro-4-methoxy-2-methyl-indol-1-yl)-ethyl]-amine;

2-(4-{6-[2-(6-Fluoro-4-methoxy-2-methyl-indol-1-yl)-ethylamino]-pyrimidin-4-yl}-phenyl)-thiazole-4-carboxylic acid;

2-(4-{6-[2-(7-Fluoro-4-methoxy-2-methyl-indol-1-yl)-ethylamino]-pyrimidin-4-yl}-phenyl)-thiazole-4-carboxylic acid;

[2-(6-Fluoro-4-methoxy-2-methyl-indol-1-yl)-ethyl]-{6-[4-(2-methyl-1H-imidazol-4-yl)-phenyl]-pyrimidin-4-yl}-amine;

[2-(6-Fluoro-2,4-dimethyl-indol-1-yl)-ethyl]-{6-[4-(5-methylamino-[1,3,4]thiadiazol-2-yl)-phenyl]-pyrimidin-4-yl}-amine;

4-{6-[2-(2-Cyano-6-fluoro-4-methoxy-indol-1-yl)-ethylamino]-pyrimidin-4-yl}-2-isobutyl-benzoic acid;

2-Chloro-4-{6-[2-(7-fluoro-4-methoxy-2-methyl-indol-1-yl)-ethylamino]-pyrimidin-4-yl}-6-propoxy-benzoic acid;

2-Butoxy-4-{6-[2-(7-fluoro-4-methoxy-2-methyl-indol-1-yl)-ethylamino]-pyrimidin-4-yl}-benzoic acid;

{6-[4-(2-Amino-oxazol-5-yl)-phenyl]-pyrimidin-4-yl}-[2-(6,7-difluoro-4-methoxy-2-methyl-indol-1-yl)-ethyl]-amine;

[2-(6,7-Difluoro-4-methoxy-2-methyl-indol-1-yl)-ethyl]-{6-[4-(2-methyl-1H-imidazol-4-yl)-phenyl]-pyrimidin-4-yl}-amine;

[2-(6-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine;

{6-[3-Ethoxy-4-(1H-tetrazol-5-yl)-phenyl]-pyrimidin-4-yl}-[2-(7-fluoro-4-methoxy-2-methyl-indol-1-yl)-ethyl]-amine;

{6-[3-Ethylamino-4-(1H-tetrazol-5-yl)-phenyl]-pyrimidin-4-yl}-[2-(7-fluoro-4-methoxy-2-methyl-indol-1-yl)-ethyl]-amine;

[2-(7-Chloro-4-methoxy-2-methyl-indol-1-yl)-ethyl]-{6-[3-ethylamino-4-(1H-tetrazol-5-yl)-phenyl]-pyrimidin-4-yl}-amine;

{6-[3-Ethylamino-4-(1H-tetrazol-5-yl)-phenyl]-pyrimidin-4-yl}-[2-(4-methoxy-2-methyl-indol-1-yl)-ethyl]-amine;

{6-[3-Ethylamino-4-(1H-tetrazol-5-yl)-phenyl]-pyrimidin-4-yl}-[2-(7-fluoro-2,4-dimethyl-indol-1-yl)-ethyl]-amine;

3-Butoxy-5-{6-[2-(6-fluoro-4-methoxy-2-methyl-indol-1-yl)-ethylamino]-pyrimidin-4-yl}-thiophene-2-carboxylic acid;

3-Butoxy-5-{6-[2-(7-fluoro-4-methoxy-2-methyl-indol-1-yl)-ethylamino]-pyrimidin-4-yl}-thiophene-2-carboxylic acid;

5-{6-[2-(6-Fluoro-4-methoxy-2-methyl-indol-1-yl)-ethylamino]-pyrimidin-4-yl}-3-propoxy-thiophene-2-carboxylic acid;

5-{6-[2-(7-Fluoro-4-methoxy-2-methyl-indol-1-yl)-ethylamino]-pyrimidin-4-yl}-3-isopropoxy-thiophene-2-carboxylic acid;

5-{6-[2-(6-Fluoro-4-methoxy-2-methyl-indol-1-yl)-ethylamino]-pyrimidin-4-yl}-3-isopropoxy-thiophene-2-carboxylic acid;

5-{6-[2-(7-Fluoro-4-methoxy-2-methyl-indol-1-yl)-ethylamino]-pyrimidin-4-yl}-3-propoxy-thiophene-2-carboxylic acid;

3-(4-{6-[2-(6,7-Difluoro-4-methoxy-2-methyl-indol-1-yl)-ethylamino]-pyrimidin-4-yl}-phenyl)-4H-[1,2,4]oxadiazol-5-one;

2-Chloro-4-{6-[2-(7-fluoro-4-methoxy-2-methyl-indol-1-yl)-ethylamino]-pyrimidin-4-yl}-6-isobutoxy-benzoic acid;

[2-(7-Fluoro-4-methoxy-2-methyl-indol-1-yl)-ethyl]-[6-(1H-indol-5-yl)-pyrimidin-4-yl]-amine;

[2-(6,7-Difluoro-4-methoxy-2-methyl-indol-1-yl)-ethyl]-[6-(1H-indol-5-yl)-pyrimidin-4-yl]-amine;

6-{6-[2-(7-Fluoro-4-methoxy-2-methyl-indol-1-yl)-ethylamino]-pyrimidin-4-yl}-1,2-dihydro-indazol-3-one;

4-{6-[2-(2-Chloro-7-fluoro-4-methoxy-indol-1-yl)-ethylamino]-pyrimidin-4-yl}-2-ethoxy-benzoic acid;

5-{6-[2-(2-Chloro-7-fluoro-4-methoxy-indol-1-yl)-ethylamino]-pyrimidin-4-yl}-3-ethoxy-thiophene-2-carboxylic acid;

5-{6-[2-(4-Bromo-2-methyl-indol-1-yl)-ethylamino]-pyrimidin-4-yl}-3-ethoxy-thiophene-2-carboxylic acid;

[2-(7-Fluoro-4-methoxy-2-methyl-indol-1-yl)-ethyl]-{6-[5-(1H-tetrazol-5-yl)-thiophen-2-yl]-pyrimidin-4-yl}-amine;

5-{6-[2-(6-Fluoro-4-methoxy-2-methyl-indol-1-yl)-ethylamino]-pyrimidin-4-yl}-3-hydroxy-thiophene-2-carboxylic acid;

5-{6-[2-(2-Cyano-7-fluoro-4-methoxy-indol-1-yl)-ethylamino]-pyrimidin-4-yl}-3-isopropoxy-thiophene-2-carboxylic acid;

1-(2-{6-[3-Ethoxy-4-(1H-tetrazol-5-yl)-phenyl]-pyrimidin-4-ylamino}-ethyl)-7-fluoro-4-methoxy-1H-indole-2-carbonitrile;

5-{6-[2-(2-Cyano-7-fluoro-4-methoxy-indol-1-yl)-ethylamino]-pyrimidin-4-yl}-3-trifluoromethyl-thiophene-2-carboxylic acid;

5-{6-[2-(2-cyano-7-fluoro-4-methoxy-indol-1-yl)-ethylamino]-pyrimidin-4-yl}-3-ethoxy-thiophene-2-carboxylic acid;

5-{6-[2-(2-Cyano-7-fluoro-4-methoxy-indol-1-yl)-ethylamino]-pyrimidin-4-yl}-3-fluoro-thiophene-2-carboxylic acid;

4-{6-[2-(2-Cyano-7-fluoro-4-methoxy-indol-1-yl)-ethylamino]-pyrimidin-4-yl}-2-ethoxy-benzoic acid;

(4-{6-[2-(2-Cyano-7-fluoro-4-methoxy-indol-1-yl)-ethylamino]-pyrimidin-4-yl}-2-ethoxy-phenoxy)-acetic acid;

N-(5-{6-[2-(2-Cyano-7-fluoro-4-methoxy-indol-1-yl)-ethylamino]-pyrimidin-4-yl}-3-ethoxy-thiophene-2-carbonyl)-methanesulfonamide;

(2-Ethoxy-4-{6-[2-(7-fluoro-4-methoxy-2-methyl-indol-1-yl)-ethylamino]-pyrimidin-4-yl}-phenoxy)-acetic acid;

(2-Ethoxy-4-{6-[2-(7-fluoro-4-methoxy-2-methyl-indol-1-yl)-ethylamino]-pyrimidin-4-yl}-phenylamino)-acetic acid;

5-{6-[2-(2-Cyano-4-methoxy-indol-1-yl)-ethylamino]-pyrimidin-4-yl}-3-ethoxy-thiophene-2-carboxylic acid;

N-(5-{6-[2-(2-Cyano-7-fluoro-4-methoxy-indol-1-yl)-ethylamino]-pyrimidin-4-yl}-3-ethoxy-thiophene-2-carbonyl)-benzenesulfonamide;

Propane-2-sulfonic acid (5-{6-[2-(2-cyano-7-fluoro-4-methoxy-indol-1-yl)-ethylamino]-pyrimidin-4-yl}-3-ethoxy-thiophene-2-carbonyl)-amide;

Cyclopropanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide; and 5-{6-[2-(2-Cyano-7-fluoro-4-methoxy-indol-1-yl)-ethylamino]-pyrimidin-4-yl}-3-ethoxy-thiophene-2-carboxylic acid methylamide.

28) In addition to the most preferred compounds listed in embodiment 27), further preferred compounds according to embodiment 1) are selected from the following compounds:

3-Chloro-5-{6-[2-(4-chloro-7-fluoro-2-methyl-indol-1-yl)-ethylamino]-pyrimidin-4-yl}-thiophene-2-carboxylic acid;

3-Chloro-5-{6-[2-(6-fluoro-2,4-dimethyl-indol-1-yl)-ethylamino]-pyrimidin-4-yl}-thiophene-2-carboxylic acid;

(2-Chloro-4-{6-[2-(7-fluoro-4-methoxy-2-methyl-indol-1-yl)-ethylamino]-pyrimidin-4-yl}-phenyl)-methanol;

5-{6-[2-(7-Fluoro-2,4-dimethyl-indol-1-yl)-ethylamino]-pyrimidin-4-yl}-3-methyl-thiophene-2-carboxylic acid;

[6-(2,3-Dihydro-1H-indol-5-yl)-pyrimidin-4-yl]-[2-(7-fluoro-4-methoxy-2-methyl-indol-1-yl)-ethyl]-amine;

[2-(6-Fluoro-2,4-dimethyl-indol-1-yl)-ethyl]-{6-[4-(1H-imidazol-4-yl)-phenyl]-pyrimidin-4-yl}-amine;

[2-(4-Methoxy-2-methyl-indol-1-yl)-ethyl]-{6-[4-(2H-pyrazol-3-yl)-phenyl]-pyrimidin-4-yl}-amine;

{6-[4-(1H-Imidazol-4-yl)-phenyl]-pyrimidin-4-yl}-[2-(4-methoxy-2-methyl-indol-1-yl)-ethyl]-amine;

[2-(7-Fluoro-4-methoxy-2-methyl-indol-1-yl)-ethyl]-[6-(2-methyl-1H-benzoimidazol-5-yl)-pyrimidin-4-yl]-amine;

3-Ethyl-5-{6-[2-(7-fluoro-2,4-dimethyl-indol-1-yl)-ethylamino]-pyrimidin-4-yl}-thiophene-2-carboxylic acid;

3-Fluoro-5-{6-[2-(7-fluoro-4-methoxy-2-methyl-indol-1-yl)-ethylamino]-pyrimidin-4-yl}-thiophene-2-carboxylic acid;

3-Fluoro-5-{6-[2-(6-fluoro-4-methoxy-2-methyl-indol-1-yl)-ethylamino]-pyrimidin-4-yl}-thiophene-2-carboxylic acid;

(4-{6-[2-(7-Fluoro-4-methoxy-2-methyl-indol-1-yl)-ethylamino]-pyrimidin-4-yl}-2-methoxy-phenyl)-methanol;

(2-Ethoxy-4-{6-[2-(7-fluoro-4-methoxy-2-methyl-indol-1-yl)-ethylamino]-pyrimidin-4-yl}-phenyl)-methanol;

[2-(6,7-Difluoro-2,4-dimethyl-indol-1-yl)-ethyl]-{6-[4-(1H-imidazol-4-yl)-phenyl]-pyrimidin-4-yl}-amine;

5-{6-[2-(4,5-Difluoro-2-methyl-indol-1-yl)-ethylamino]-pyrimidin-4-yl}-3-ethoxy-thiophene-2-carboxylic acid;

5-{6-[2-(5-Chloro-7-fluoro-2-methyl-indol-1-yl)-ethylamino]-pyrimidin-4-yl}-3-ethoxy-thiophene-2-carboxylic acid;

2-Ethylamino-4-{6-[2-(6-fluoro-2,4-dimethyl-indol-1-yl)-ethylamino]-pyrimidin-4-yl}-benzoic acid;

2-Ethylamino-4-{6-[2-(7-fluoro-2,4-dimethyl-indol-1-yl)-ethylamino]-pyrimidin-4-yl}-benzoic acid;

2-Ethylamino-4-{6-[2-(4-methoxy-2-methyl-indol-1-yl)-ethylamino]-pyrimidin-4-yl}-benzoic acid;

3-Ethoxy-5-{6-[2-(4-methoxy-2,7-dimethyl-indol-1-yl)-ethylamino]-pyrimidin-4-yl}-thiophene-2-carboxylic acid;

3-Ethoxy-5-{6-[2-(5,6,7-trifluoro-2-methyl-indol-1-yl)-ethylamino]-pyrimidin-4-yl}-thiophene-2-carboxylic acid;

[2-(6,7-Difluoro-4-methoxy-2-methyl-indol-1-yl)-ethyl]-[6-(4-[1,2,4]oxadiazol-5-yl-phenyl)-pyrimidin-4-yl]-amine;

[2-(6-Fluoro-4-methoxy-2-methyl-indol-1-yl)-ethyl]-{6-[4-(1-methyl-1H-pyrazol-3-yl)-phenyl]-pyrimidin-4-yl}-amine;

3-(4-{6-[2-(6-Fluoro-4-methoxy-2-methyl-indol-1-yl)-ethylamino]-pyrimidin-4-yl}-phenyl)-4H-[1,2,4]oxadiazol-5-one;

4-{6-[2-(7-Fluoro-4-methoxy-2-methyl-indol-1-yl)-ethylamino]-pyrimidin-4-yl}-2-propyl-benzoic acid;

1-Ethyl-3-(2-methoxy-4-{6-[2-(4-methoxy-2-methyl-indol-1-yl)-ethylamino]-pyrimidin-4-yl}-phenyl)-urea;

2-Chloro-6-ethylamino-4-{6-[2-(7-fluoro-4-methoxy-2-methyl-indol-1-yl)-ethylamino]-pyrimidin-4-yl}-benzoic acid;

[2-(7-Fluoro-4-methoxy-2-methyl-indol-1-yl)-ethyl]-(6-quinolin-6-yl-pyrimidin-4-yl)-amine;

2-Ethylamino-6-fluoro-4-{6-[2-(7-fluoro-2,4-dimethyl-indol-1-yl)-ethylamino]-pyrimidin-4-yl}-benzoic acid;

4-{6-[2-(7-Chloro-4-methoxy-2-methyl-indol-1-yl)-ethylamino]-pyrimidin-4-yl}-2-ethylamino-benzoic acid;

2-Chloro-4-{6-[2-(6-fluoro-2,4-dimethyl-indol-1-yl)-ethylamino]-pyrimidin-4-yl}-6-propyl-benzoic acid;

2-Chloro-4-{6-[2-(7-fluoro-2,4-dimethyl-indol-1-yl)-ethylamino]-pyrimidin-4-yl}-6-propyl-benzoic acid;

2-Fluoro-4-{6-[2-(7-fluoro-2,4-dimethyl-indol-1-yl)-ethylamino]-pyrimidin-4-yl}-6-propyl-benzoic acid;

4-{6-[2-(5,7-Difluoro-2,4-dimethyl-indol-1-yl)-ethylamino]-pyrimidin-4-yl}-2-ethoxy-benzoic acid;

2-Chloro-4-{6-[2-(4-methoxy-2-methyl-indol-1-yl)-ethylamino]-pyrimidin-4-yl}-6-propyl-benzoic acid;

{6-[4-(2-Amino-5-methyl-thiazol-4-yl)-phenyl]-pyrimidin-4-yl}-[2-(7-fluoro-4-methoxy-2-methyl-indol-1-yl)-ethyl]-amine;

5-{6-[2-(7-Fluoro-4-methoxy-2-methyl-indol-1-yl)-ethylamino]-pyrimidin-4-yl}-3-propyl-2,3-dihydro-isoindol-1-one;

2-Cyclobutoxy-4-{6-[2-(7-fluoro-4-methoxy-2-methyl-indol-1-yl)-ethylamino]-pyrimidin-4-yl}-benzoic acid;

4-{6-[2-(2-Cyano-6-fluoro-4-methoxy-indol-1-yl)-ethylamino]-pyrimidin-4-yl}-2-ethoxy-benzoic acid;

2-Ethylamino-6-fluoro-4-{6-[2-(7-fluoro-4-methoxy-2-methyl-indol-1-yl)-ethylamino]-pyrimidin-4-yl}-benzoic acid;

4-{6-[2-(6,7-Difluoro-4-methoxy-2-methyl-indol-1-yl)-ethylamino]-pyrimidin-4-yl}-2-ethoxy-benzoic acid;

4-{6-[2-(7-Fluoro-4-methoxy-2-methyl-indol-1-yl)-ethylamino]-pyrimidin-4-yl}-2-propoxy-benzoic acid;

4-{6-[2-(5,7-Difluoro-2,4-dimethyl-indol-1-yl)-ethylamino]-pyrimidin-4-yl}-2-isobutyl-benzoic acid;

2-Chloro-4-{6-[2-(7-fluoro-4-methoxy-2-methyl-indol-1-yl)-ethylamino]-pyrimidin-4-yl}-6-propyl-benzoic acid;

2-Fluoro-4-{6-[2-(7-fluoro-4-methoxy-2-methyl-indol-1-yl)-ethylamino]-pyrimidin-4-yl}-6-propyl-benzoic acid;

2-Fluoro-4-{6-[2-(6-fluoro-4-methoxy-2-methyl-indol-1-yl)-ethylamino]-pyrimidin-4-yl}-6-propyl-benzoic acid;

2-Butoxy-4-{6-[2-(7-fluoro-2,4-dimethyl-indol-1-yl)-ethylamino]-pyrimidin-4-yl}-benzoic acid;

4-{6-[2-(7-Fluoro-2,4-dimethyl-indol-1-yl)-ethylamino]-pyrimidin-4-yl}-2-isobutoxy-benzoic acid;

4-{6-[2-(7-Fluoro-4-methoxy-2-methyl-indol-1-yl)-ethylamino]-pyrimidin-4-yl}-2-isobutyl-benzoic acid;

2-(4-{6-[2-(7-Fluoro-2,4-dimethyl-indol-1-yl)-ethylamino]-pyrimidin-4-yl}-phenyl)-thiazole-4-carboxylic acid;

[2-(6-Fluoro-2,4-dimethyl-indol-1-yl)-ethyl]-{6-[4-(2-methyl-1H-imidazol-4-yl)-phenyl]-pyrimidin-4-yl}-amine;

2-(4-{6-[2-(4-Methoxy-2-methyl-indol-1-yl)-ethylamino]-pyrimidin-4-yl}-phenyl)-thiazole-4-carboxylic acid;

4-{6-[2-(7-Fluoro-4-methoxy-2-methyl-indol-1-yl)-ethylamino]-pyrimidin-4-yl}-2-trifluoromethyl-benzenesulfonamide;

{6-[4-(5-Amino-[1,3,4]thiadiazol-2-yl)-phenyl]-pyrimidin-4-yl}-[2-(6-fluoro-2,4-dimethyl-indol-1-yl)-ethyl]-amine;

[2-(6,7-Difluoro-2,4-dimethyl-indol-1-yl)-ethyl]-{6-[4-(2-methyl-1H-imidazol-4-yl)-phenyl]-pyrimidin-4-yl}-amine;

4-(4-{6-[2-(6-Fluoro-4-methoxy-2-methyl-indol-1-yl)-ethylamino]-pyrimidin-4-yl}-phenyl)-thiazole-2-carboxylic acid;

[2-(6-Fluoro-4-methoxy-2-methyl-indol-1-yl)-ethyl]-{6-[4-(5-methyl-1H-pyrazol-3-yl)-phenyl]-pyrimidin-4-yl}-amine;

4-{6-[2-(7-Fluoro-4-methoxy-2-methyl-indol-1-yl)-ethylamino]-pyrimidin-4-yl}-2-(2,2,2-trifluoro-ethylamino)-benzoic acid;

2-Cyclopentyloxy-4-{6-[2-(7-fluoro-4-methoxy-2-methyl-indol-1-yl)-ethylamino]-pyrimidin-4-yl}-benzoic acid;

2-Butoxy-4-{6-[2-(6-fluoro-4-methoxy-2-methyl-indol-1-yl)-ethylamino]-pyrimidin-4-yl}-benzoic acid;

4-{6-[2-(6-Fluoro-4-methoxy-2-methyl-indol-1-yl)-ethylamino]-pyrimidin-4-yl}-2-isobutoxy-benzoic acid;

4-{6-[2-(7-Fluoro-4-methoxy-2-methyl-indol-1-yl)-ethylamino]-pyrimidin-4-yl}-2-isobutoxy-benzoic acid;

4-{6-[2-(6,7-Difluoro-4-methoxy-2-methyl-indol-1-yl)-ethylamino]-pyrimidin-4-yl}-2-isobutyl-benzoic acid;

4-{6-[2-(7-Fluoro-4-methoxy-2-methyl-indol-1-yl)-ethylamino]-2-methyl-pyrimidin-4-yl}-2-isobutyl-benzoic acid;

2-Chloro-4-{6-[2-(5,7-difluoro-2,4-dimethyl-indol-1-yl)-ethylamino]-pyrimidin-4-yl}-6-propoxy-benzoic acid;

4-{6-[2-(6,7-Difluoro-4-methoxy-2-methyl-indol-1-yl)-ethylamino]-pyrimidin-4-yl}-2-fluoro-6-propoxy-benzoic acid;

4-{6-[2-(6,7-Difluoro-4-methoxy-2-methyl-indol-1-yl)-ethylamino]-pyrimidin-4-yl}-2-(2,2,2-trifluoro-ethylamino)-benzoic acid;

[2-(5-Chloro-7-methyl-[1,3]dioxolo[4,5-e]indol-6-yl)-ethyl]-{6-[3-ethylamino-4-(1H-tetrazol-5-yl)-phenyl]-pyrimidin-4-yl}-amine;

{6-[3-Ethoxy-4-(1H-tetrazol-5-yl)-phenyl]-pyrimidin-4-yl}-[2-(7-fluoro-2,4-dimethyl-indol-1-yl)-ethyl]-amine;

{6-[3-Ethoxy-4-(1H-tetrazol-5-yl)-phenyl]-pyrimidin-4-yl}-[2-(4-methoxy-2-methyl-indol-1-yl)-ethyl]-amine;

3-(4-{6-[2-(6-Chloro-4-methoxy-2-methyl-indol-1-yl)-ethylamino]-pyrimidin-4-yl}-phenyl)-4H-[1,2,4]oxadiazol-5-one;

2-Chloro-4-{6-[2-(6-fluoro-4-methoxy-2-methyl-indol-1-yl)-ethylamino]-pyrimidin-4-yl}-6-isobutoxy-benzoic acid;

[2-(6-Fluoro-2,4-dimethyl-indol-1-yl)-ethyl]-[6-(1H-indol-5-yl)-pyrimidin-4-yl]-amine;

[2-(7-Fluoro-2,4-dimethyl-indol-1-yl)-ethyl]-[6-(1H-indol-5-yl)-pyrimidin-4-yl]-amine;

[2-(6-Fluoro-4-methoxy-2-methyl-indol-1-yl)-ethyl]-[6-(1H-indol-5-yl)-pyrimidin-4-yl]-amine;

[2-(6-Fluoro-4-methoxy-2-methyl-indol-1-yl)-ethyl]-[6-(1-methyl-1H-indol-5-yl)-pyrimidin-4-yl]-amine;

[2-(7-Fluoro-4-methoxy-2-methyl-indol-1-yl)-ethyl]-[6-(1-methyl-1H-indol-5-yl)-pyrimidin-4-yl]-amine;

[2-(6,7-Difluoro-4-methoxy-2-methyl-indol-1-yl)-ethyl]-[6-(1-methyl-1H-indol-5-yl)-pyrimidin-4-yl]-amine;

2-Chloro-4-{6-[2-(6-fluoro-4-methoxy-2-methyl-indol-1-yl)-ethylamino]-pyrimidin-4-yl}-6-(2,2,2-trifluoro-ethoxy)-benzoic acid;

2-Chloro-4-{6-[2-(6,7-difluoro-4-methoxy-2-methyl-indol-1-yl)-ethylamino]-pyrimidin-4-yl}-6-(2,2,2-trifluoro-ethoxy)-benzoic acid;
2-Chloro-4-{6-[2-(7-fluoro-4-methoxy-2-methyl-indol-1-yl)-ethylamino]-pyrimidin-4-yl}-6-(2,2,2-trifluoro-ethoxy)-benzoic acid;
[2-(6-Fluoro-4-methoxy-2-methyl-indol-1-yl)-ethyl]-[6-(4-pyrazin-2-yl-phenyl)-pyrimidin-4-yl]-amine;
6-{6-[2-(7-Chloro-5-fluoro-4-methoxy-2-methyl-indol-1-yl)-ethylamino]-pyrimidin-4-yl}-1,2-dihydro-indazol-3-one;
3-Ethoxy-5-{6-[2-(7-fluoro-4-methoxy-2-methyl-indol-1-yl)-1-methyl-ethylamino]-pyrimidin-4-yl}-thiophene-2-carboxylic acid; and
5-{6-[2-(7-Fluoro-4-methoxy-2-methyl-indol-1-yl)-ethyl-amino]-pyrimidin-4-yl}-3-hydroxy-thiophene-2-carboxylic acid.

29) Further compounds according to embodiment 1) are selected from the following compounds:

[6-(4-Amino-phenyl)-pyrimidin-4-yl]-[2-(7-fluoro-2,4-dim-ethyl-indol-1-yl)-ethyl]-amine;
[6-(4-Amino-phenyl)-pyrimidin-4-yl]-[2-(7-fluoro-4-methoxy-2-methyl-indol-1-yl)-ethyl]-amine;
3-Chloro-5-{6-[2-(2-methyl-indol-1-yl)-ethylamino]-pyrimidin-4-yl}-thiophene-2-carboxylic acid;
3-Ethyl-5-{6-[2-(2-methyl-indol-1-yl)-ethylamino]-pyrimidin-4-yl}-thiophene-2-carboxylic acid;
[6-(1H-Benzoimidazol-5-yl)-pyrimidin-4-yl]-[2-(4-methoxy-2-methyl-indol-1-yl)-ethyl]-amine;
[6-(2,3-Dihydro-1H-indol-5-yl)-pyrimidin-4-yl]-[2-(6-fluoro-2,4-dimethyl-indol-1-yl)-ethyl]-amine;
[6-(2,3-Dihydro-1H-indol-5-yl)-pyrimidin-4-yl]-[2-(7-fluoro-2,4-dimethyl-indol-1-yl)-ethyl]-amine;
[6-(2,3-Dihydro-1H-indol-5-yl)-pyrimidin-4-yl]-[2-(4-methoxy-2-methyl-indol-1-yl)-ethyl]-amine;
(4-{6-[2-(4-Methoxy-2-methyl-indol-1-yl)-ethylamino]-pyrimidin-4-yl}-2-methyl-phenyl)-methanol;
(2-Chloro-4-{6-[2-(4-methoxy-2-methyl-indol-1-yl)-ethyl-amino]-pyrimidin-4-yl}-phenyl)-methanol;
(2-Fluoro-4-{6-[2-(4-methoxy-2-methyl-indol-1-yl)-ethyl-amino]-pyrimidin-4-yl}-phenyl)-methanol;
3-Chloro-5-{6-[2-(7-fluoro-2,4-dimethyl-indol-1-yl)-ethyl-amino]-pyrimidin-4-yl}-thiophene-2-carboxylic acid;
(2-Fluoro-4-{6-[2-(7-fluoro-2,4-dimethyl-indol-1-yl)-ethyl-amino]-pyrimidin-4-yl}-phenyl)-methanol;
3-Chloro-5-{6-[2-(4-methoxy-2-methyl-indol-1-yl)-ethyl-amino]-pyrimidin-4-yl}-thiophene-2-carboxylic acid;
4-{6-[2-(7-Fluoro-2,4-dimethyl-indol-1-yl)-ethylamino]-pyrimidin-4-yl}-benzamide;
4-{6-[2-(2,4-Dimethyl-indol-1-yl)-ethylamino]-pyrimidin-4-yl}-2-ethyl-benzoic acid;
(2-Fluoro-4-{6-[2-(7-fluoro-4-methoxy-2-methyl-indol-1-yl)-ethylamino]-pyrimidin-4-yl}-phenyl)-methanol;
2-Chloro-4-{6-[2-(7-fluoro-2,4-dimethyl-indol-1-yl)-ethyl-amino]-pyrimidin-4-yl}-benzoic acid;
(4-{6-[2-(7-Fluoro-2,4-dimethyl-indol-1-yl)-ethylamino]-pyrimidin-4-yl}-2-methoxy-phenyl)-methanol;
4-{6-[2-(7-Fluoro-2,4-dimethyl-indol-1-yl)-ethylamino]-pyrimidin-4-yl}-2-methyl-benzoic acid;
(4-{6-[2-(7-Fluoro-4-methoxy-2-methyl-indol-1-yl)-ethyl-amino]-pyrimidin-4-yl}-2-methyl-phenyl)-methanol;
2-Ethylsulfanyl-4-{6-[2-(2-methyl-indol-1-yl)-ethylamino]-pyrimidin-4-yl}-benzoic acid;
2,6-Difluoro-4-{6-[2-(7-fluoro-4-methoxy-2-methyl-indol-1-yl)-ethylamino]-pyrimidin-4-yl}-phenol;
4-{6-[2-(2,4-Dimethyl-indol-1-yl)-ethylamino]-pyrimidin-4-yl}-2-methoxy-benzoic acid;
(2-Methoxy-4-{6-[2-(4-methoxy-2-methyl-indol-1-yl)-eth-ylamino]-pyrimidin-4-yl}-phenyl)-methanol;
4-{6-[2-(7-Fluoro-2,4-dimethyl-indol-1-yl)-ethylamino]-pyrimidin-4-yl}-benzenesulfonic acid;
(4-{6-[2-(4-Methoxy-2-methyl-indol-1-yl)-ethylamino]-py-rimidin-4-yl}-phenyl)-urea;
4-{6-[2-(7-Fluoro-4-methoxy-2-methyl-indol-1-yl)-ethyl-amino]-pyrimidin-4-yl}-benzamide;
3-Chloro-5-{6-[2-(4,6-dichloro-2-methyl-indol-1-yl)-ethyl-amino]-pyrimidin-4-yl}-thiophene-2-carboxylic acid;
4-{6-[2-(4-Chloro-7-fluoro-2-methyl-indol-1-yl)-ethyl-amino]-pyrimidin-4-yl}-benzoic acid;
3-Fluoro-5-{6-[2-(7-fluoro-2,4-dimethyl-indol-1-yl)-ethyl-amino]-pyrimidin-4-yl}-thiophene-2-carboxylic acid;
3-Fluoro-5-{6-[2-(6-fluoro-2,4-dimethyl-indol-1-yl)-ethyl-amino]-pyrimidin-4-yl}-thiophene-2-carboxylic acid;
3-Fluoro-5-{6-[2-(4-methoxy-2-methyl-indol-1-yl)-ethyl-amino]-pyrimidin-4-yl}-thiophene-2-carboxylic acid;
3-Ethoxy-5-{6-[2-(2-methyl-indol-1-yl)-ethylamino]-py-rimidin-4-yl}-thiophene-2-carboxylic acid;
5-{6-[2-(4-Methoxy-2-methyl-indol-1-yl)-ethylamino]-py-rimidin-4-yl}-3-methyl-thiophene-2-carboxylic acid;
[6-(1H-Benzoimidazol-5-yl)-pyrimidin-4-yl]-[2-(7-fluoro-4-methoxy-2-methyl-indol-1-yl)-ethyl]-amine;
[2-(7-Fluoro-4-methoxy-2-methyl-indol-1-yl)-ethyl]-[6-(1H-indazol-6-yl)-pyrimidin-4-yl]-amine;
[2-(6-Fluoro-4-methoxy-2-methyl-indol-1-yl)-ethyl]-[6-(1H-indol-6-yl)-pyrimidin-4-yl]-amine;
5-{6-[2-(7-Fluoro-2,4-dimethyl-indol-1-yl)-ethylamino]-pyrimidin-4-yl}-1,3-dihydro-indol-2-one;
5-{6-[2-(7-Fluoro-2,4-dimethyl-indol-1-yl)-ethylamino]-pyrimidin-4-yl}-2,3-dihydro-isoindol-1-one;
[2-(7-Chloro-4-methoxy-2-methyl-indol-1-yl)-ethyl]-[6-(2,3-dihydro-1H-indol-5-yl)-pyrimidin-4-yl]-amine;
[2-(7-Fluoro-4-methoxy-2-methyl-indol-1-yl)-ethyl]-[6-(1H-indol-6-yl)-pyrimidin-4-yl]-amine;
[2-(7-Fluoro-2,4-dimethyl-indol-1-yl)-ethyl]-{6-[4-(2H-pyrazol-3-yl)-phenyl]-pyrimidin-4-yl}-amine;
5-{6-[2-(7-Fluoro-4-methoxy-2-methyl-indol-1-yl)-ethyl-amino]-pyrimidin-4-yl}-1,3-dihydro-2H-benzo[d]imida-zol-2-one;
{6-[4-(1H-Imidazol-2-yl)-phenyl]-pyrimidin-4-yl}-[2-(4-methoxy-2-methyl-indol-1-yl)-ethyl]-amine;
[2-(4-Methoxy-2-methyl-indol-1-yl)-ethyl]-[6-(4-pyrazol-1-yl-phenyl)-pyrimidin-4-yl]-amine;
[2-(7-Fluoro-2,4-dimethyl-indol-1-yl)-ethyl]-[6-(4-[1,2,4]oxadiazol-5-yl-phenyl)-pyrimidin-4-yl]-amine;
[2-(7-Fluoro-4-methoxy-2-methyl-indol-1-yl)-ethyl]-[6-(1-methyl-1H-indazol-6-yl)-pyrimidin-4-yl]-amine;
5-{6-[2-(4-Methoxy-2-methyl-indol-1-yl)-ethylamino]-py-rimidin-4-yl}-3-methyl-2,3-dihydro-isoindol-1-one;
5-{6-[2-(7-Fluoro-4-methoxy-2-methyl-indol-1-yl)-ethyl-amino]-pyrimidin-4-yl}-2,3-dihydro-isoindol-1-one;
5-{6-[2-(7-Fluoro-4-methoxy-2-methyl-indol-1-yl)-ethyl-amino]-pyrimidin-4-yl}-1,3-dihydro-indol-2-one;
[2-(6,7-Difluoro-4-methoxy-2-methyl-indol-1-yl)-ethyl]-[6-(1H-indol-6-yl)-pyrimidin-4-yl]-amine;
[2-(6-Fluoro-2,4-dimethyl-indol-1-yl)-ethyl]-[6-(4-isoxa-zol-3-yl-phenyl)-pyrimidin-4-yl]-amine;
5-{6-[2-(7-Fluoro-2,4-dimethyl-indol-1-yl)-ethylamino]-pyrimidin-4-yl}-3-methyl-2,3-dihydro-isoindol-1-one;
[2-(4-Methoxy-2-methyl-indol-1-yl)-ethyl]-[6-(4-thiazol-4-yl-phenyl)-pyrimidin-4-yl]-amine;
[2-(4-Methoxy-2-methyl-indol-1-yl)-ethyl]-{6-[4-(4H-[1,2,4]triazol-3-yl)-phenyl]-pyrimidin-4-yl}-amine;
(4-{6-[2-(7-Fluoro-4-methoxy-2-methyl-indol-1-yl)-ethyl-amino]-pyrimidin-4-yl}-thiophen-2-yl)-methanol;

2-Chloro-4-{6-[2-(6-fluoro-2,4-dimethyl-indol-1-yl)-ethyl-amino]-pyrimidin-4-yl}-benzoic acid;
4-{6-[2-(4-Chloro-7-fluoro-2-methyl-indol-1-yl)-ethyl-amino]-pyrimidin-4-yl}-2-methyl-benzoic acid;
4-{6-[2-(7-Fluoro-4-methoxy-2-methyl-indol-1-yl)-ethyl-amino]-pyrimidin-4-yl}-benzoic acid;
5-{6-[2-(7-Chloro-4-methoxy-2-methyl-indol-1-yl)-ethyl-amino]-pyrimidin-4-yl}-3-fluoro-thiophene-2-carboxylic acid;
4-{6-[2-(7-Fluoro-4-methoxy-2-methyl-indol-1-yl)-ethyl-amino]-pyrimidin-4-yl}-benzenesulfonic acid;
3-Ethoxy-5-{6-[2-(6-methoxy-2-methyl-indol-1-yl)-ethyl-amino]-pyrimidin-4-yl}-thiophene-2-carboxylic acid;
2-Isobutyl-4-{6-[2-(2-methyl-indol-1-yl)-ethylamino]-pyrimidin-4-yl}-benzoic acid;
4-{6-[2-(2,4-Dimethyl-indol-1-yl)-ethylamino]-pyrimidin-4-yl}-2-propyl-benzoic acid;
4-{6-[2-(4,7-Difluoro-2-methyl-indol-1-yl)-ethylamino]-pyrimidin-4-yl}-2-ethyl-benzoic acid;
4-{6-[2-(5,7-Difluoro-2-methyl-indol-1-yl)-ethylamino]-pyrimidin-4-yl}-2-ethyl-benzoic acid;
2-Chloro-4-{6-[2-(7-fluoro-2,4-dimethyl-indol-1-yl)-ethyl-amino]-pyrimidin-4-yl}-6-methyl-benzoic acid;
(2-Ethoxy-4-{6-[2-(7-fluoro-2,4-dimethyl-indol-1-yl)-ethylamino]-pyrimidin-4-yl}-phenyl)-methanol;
4-{6-[2-(7-Fluoro-2-methyl-indol-1-yl)-ethylamino]-pyrimidin-4-yl}-2-propyl-benzoic acid;
(2-Ethoxy-4-{6-[2-(4-methoxy-2-methyl-indol-1-yl)-ethyl-amino]-pyrimidin-4-yl}-phenyl)-methanol;
4-{6-[2-(2,4-Dimethyl-indol-1-yl)-ethylamino]-pyrimidin-4-yl}-2-ethoxy-benzoic acid;
4-{6-[2-(7-Fluoro-2,4-dimethyl-indol-1-yl)-ethylamino]-pyrimidin-4-yl}-2-methoxy-benzoic acid;
2-Chloro-4-{6-[2-(4-methoxy-2-methyl-indol-1-yl)-ethyl-amino]-pyrimidin-4-yl}-6-methyl-benzoic acid;
(4-{6-[2-(7-Fluoro-4-methoxy-2-methyl-indol-1-yl)-ethyl-amino]-pyrimidin-4-yl}-phenyl)-urea;
(6-Isoquinolin-7-yl-pyrimidin-4-yl)-[2-(2-methyl-indol-1-yl)-ethyl]-amine;
4-{6-[2-(4,7-Difluoro-2-methyl-indol-1-yl)-ethylamino]-pyrimidin-4-yl}-2-methylamino-benzoic acid;
4-{6-[2-(7-Chloro-2-methyl-indol-1-yl)-ethylamino]-pyrimidin-4-yl}-2-ethylamino-benzoic acid;
4-{6-[2-(2-Cyano-indol-1-yl)-ethylamino]-pyrimidin-4-yl}-2-ethoxy-benzoic acid;
4-{6-[2-(4-Methoxy-2-methyl-indol-1-yl)-ethylamino]-pyrimidin-4-yl}-2-methyl-benzenesulfonamide;
4-{6-[2-(2,4-Dimethyl-indol-1-yl)-ethylamino]-pyrimidin-4-yl}-2-isobutyl-benzoic acid;
4-{6-[2-(4,7-Dichloro-2-methyl-indol-1-yl)-ethylamino]-pyrimidin-4-yl}-2-fluoro-6-methylsulfanyl-benzoic acid;
2-Chloro-4-{6-[2-(4,7-dichloro-2-methyl-indol-1-yl)-ethyl-amino]-pyrimidin-4-yl}-6-methylsulfanyl-benzoic acid;
4-{6-[2-(7-Chloro-4-fluoro-2-methyl-indol-1-yl)-ethyl-amino]-pyrimidin-4-yl}-2-propyl-benzoic acid;
4-{6-[2-(4,7-Difluoro-2-methyl-indol-1-yl)-ethylamino]-pyrimidin-4-yl}-2-propyl-benzoic acid;
4-{6-[2-(5,7-Difluoro-2-methyl-indol-1-yl)-ethylamino]-pyrimidin-4-yl}-2-propyl-benzoic acid;
4-{6-[2-(7-Chloro-2,4-dimethyl-indol-1-yl)-ethylamino]-pyrimidin-4-yl}-2-ethylsulfanyl-benzoic acid;
4-{6-[2-(7-Fluoro-2,4-dimethyl-indol-1-yl)-ethylamino]-pyrimidin-4-yl}-2-propyl-benzoic acid;
4-{6-[2-(7-Fluoro-2-methyl-indol-1-yl)-ethylamino]-pyrimidin-4-yl}-2-isobutyl-benzoic acid;
4-{6-[2-(4,7-Dichloro-2-methyl-indol-1-yl)-ethylamino]-pyrimidin-4-yl}-2-ethylsulfanyl-benzoic acid;
4-{6-[2-(4,7-Dichloro-2-methyl-indol-1-yl)-ethylamino]-pyrimidin-4-yl}-2-ethoxy-benzoic acid;
4-{6-[2-(7-Chloro-4-fluoro-2-methyl-indol-1-yl)-ethyl-amino]-pyrimidin-4-yl}-2-ethoxy-benzoic acid;
4-{6-[2-(4,7-Difluoro-2-methyl-indol-1-yl)-ethylamino]-pyrimidin-4-yl}-2-ethoxy-benzoic acid;
4-{6-[2-(7-Chloro-2,4-dimethyl-indol-1-yl)-ethylamino]-pyrimidin-4-yl}-2-ethoxy-benzoic acid;
2-Ethoxy-4-{6-[2-(7-fluoro-2,4-dimethyl-indol-1-yl)-ethyl-amino]-pyrimidin-4-yl}-benzoic acid;
2-Chloro-6-ethyl-4-{6-[2-(4-methoxy-2-methyl-indol-1-yl)-ethylamino]-pyrimidin-4-yl}-benzoic acid;
4-{6-[2-(2-Cyano-indol-1-yl)-ethylamino]-pyrimidin-4-yl}-2-isobutyl-benzoic acid;
4-{6-[2-(5,7-Difluoro-2-methyl-indol-1-yl)-ethylamino]-pyrimidin-4-yl}-2-ethylamino-benzoic acid;
4-{6-[2-(4-Chloro-2-methyl-indol-1-yl)-ethylamino]-pyrimidin-4-yl}-2-cyclopropyl-benzoic acid;
2-Ethylamino-4-{6-[2-(6-methoxy-2-methyl-indol-1-yl)-ethylamino]-pyrimidin-4-yl}-benzoic acid;
2-Cyclopropyl-4-{6-[2-(4,7-difluoro-2-methyl-indol-1-yl)-ethylamino]-pyrimidin-4-yl}-benzoic acid;
2-Cyclopropyl-4-{6-[2-(7-fluoro-2,4-dimethyl-indol-1-yl)-ethylamino]-pyrimidin-4-yl}-benzoic acid;
2-Cyclopropyl-4-{6-[2-(4-methoxy-2-methyl-indol-1-yl)-ethylamino]-pyrimidin-4-yl}-benzoic acid;
[2-(6-Fluoro-2,4-dimethyl-indol-1-yl)-ethyl]-{6-[4-(1-methyl-1H-pyrazol-3-yl)-phenyl]-pyrimidin-4-yl}-amine;
[2-(6-Fluoro-2,4-dimethyl-indol-1-yl)-ethyl]-{6-[4-(5-methyl-1H-pyrazol-3-yl)-phenyl]-pyrimidin-4-yl}-amine;
[2-(4-Methoxy-2-methyl-indol-1-yl)-ethyl]-{6-[4-(5-methyl-[1,2,4]oxadiazol-3-yl)-phenyl]-pyrimidin-4-yl}-amine;
6-{6-[2-(6-Fluoro-2,4-dimethyl-indol-1-yl)-ethylamino]-pyrimidin-4-yl}-1H-indazole-3-carboxylic acid;
[2-(6-Fluoro-4-methoxy-2-methyl-indol-1-yl)-ethyl]-[6-(4-[1,2,4]oxadiazol-5-yl-phenyl)-pyrimidin-4-yl]-amine;
3-(4-{6-[2-(7-Fluoro-2,4-dimethyl-indol-1-yl)-ethylamino]-pyrimidin-4-yl}-phenyl)-4H-[1,2,4]oxadiazol-5-one;
[2-(7-Fluoro-4-methoxy-2-methyl-indol-1-yl)-ethyl]-[6-(4-[1,2,4]oxadiazol-5-yl-phenyl)-pyrimidin-4-yl]-amine;
[2-(6,7-Difluoro-2,4-dimethyl-indol-1-yl)-ethyl]-[6-(4-[1,2,4]oxadiazol-5-yl-phenyl)-pyrimidin-4-yl]-amine;
{6-[4-(3-Amino-isoxazol-5-yl)-phenyl]-pyrimidin-4-yl}-[2-(7-fluoro-2,4-dimethyl-indol-1-yl)-ethyl]-amine;
[2-(7-Fluoro-4-methoxy-2-methyl-indol-1-yl)-ethyl]-{6-[4-(1H-imidazol-2-yl)-phenyl]-pyrimidin-4-yl}-amine;
3-(4-{6-[2-(4-Methoxy-2-methyl-indol-1-yl)-ethylamino]-pyrimidin-4-yl}-phenyl)-4H-[1,2,4]oxadiazol-5-one;
3-Ethyl-5-{6-[2-(4-methoxy-2-methyl-indol-1-yl)-ethyl-amino]-pyrimidin-4-yl}-2,3-dihydro-isoindol-1-one;
2-Ethyl-5-{6-[2-(4-methoxy-2-methyl-indol-1-yl)-ethyl-amino]-pyrimidin-4-yl}-2,3-dihydro-isoindol-1-one;
5-(4-{6-[2-(6-Fluoro-2,4-dimethyl-indol-1-yl)-ethylamino]-pyrimidin-4-yl}-phenyl)-isoxazol-3-ol;
[2-(7-Fluoro-4-methoxy-2-methyl-indol-1-yl)-ethyl]-[6-(4-oxazol-5-yl-phenyl)-pyrimidin-4-yl]-amine;
5-{6-[2-(7-Fluoro-4-methoxy-2-methyl-indol-1-yl)-ethyl-amino]-pyrimidin-4-yl}-3-methyl-2,3-dihydro-isoindol-1-one;
5-{6-[2-(7-Fluoro-4-methoxy-2-methyl-indol-1-yl)-ethyl-amino]-pyrimidin-4-yl}-2-methyl-2,3-dihydro-isoindol-1-one;
[2-(6-Fluoro-4-methoxy-2-methyl-indol-1-yl)-ethyl]-[6-(4-isothiazol-5-yl-phenyl)-pyrimidin-4-yl]-amine;

3-Ethyl-5-{6-[2-(7-fluoro-2,4-dimethyl-indol-1-yl)-ethylamino]-pyrimidin-4-yl}-2,3-dihydro-isoindol-1-one;

[2-(7-Fluoro-4-methoxy-2-methyl-indol-1-yl)-ethyl]-{6-[4-(4H-[1,2,4]triazol-3-yl)-phenyl]-pyrimidin-4-yl}-amine;

4-{6-[2-(6-Fluoro-2,4-dimethyl-indol-1-yl)-ethylamino]-pyrimidin-4-yl}-2-methylamino-benzoic acid;

4-{6-[2-(4-Fluoro-2,7-dimethyl-indol-1-yl)-ethylamino]-pyrimidin-4-yl}-2-methylamino-benzoic acid;

4-{6-[2-(4-Chloro-2-methyl-indol-1-yl)-ethylamino]-pyrimidin-4-yl}-2-ethylamino-benzoic acid;

4-{6-[2-(4-Methoxy-2-methyl-indol-1-yl)-ethylamino]-pyrimidin-4-yl}-2-methylamino-benzoic acid;

2-Amino-4-{6-[2-(7-fluoro-4-methoxy-2-methyl-indol-1-yl)-ethylamino]-pyrimidin-4-yl}-benzoic acid;

4-{6-[2-(7-Chloro-2,4-dimethyl-indol-1-yl)-ethylamino]-pyrimidin-4-yl}-2-methylsulfanyl-benzoic acid;

2-Fluoro-4-{6-[2-(7-fluoro-2,4-dimethyl-indol-1-yl)-ethylamino]-pyrimidin-4-yl}-6-methyl-benzoic acid;

2-Ethyl-4-{6-[2-(6-fluoro-2,4-dimethyl-indol-1-yl)-ethylamino]-pyrimidin-4-yl}-benzoic acid;

2-Ethyl-4-{6-[2-(7-fluoro-2,4-dimethyl-indol-1-yl)-ethylamino]-pyrimidin-4-yl}-benzoic acid;

4-{6-[2-(4,7-Dichloro-2-methyl-indol-1-yl)-ethylamino]-pyrimidin-4-yl}-2-methylsulfanyl-benzoic acid;

2,6-Dichloro-4-{6-[2-(7-fluoro-2,4-dimethyl-indol-1-yl)-ethylamino]-pyrimidin-4-yl}-benzoic acid;

2-Ethyl-4-{6-[2-(4-methoxy-2-methyl-indol-1-yl)-ethylamino]-pyrimidin-4-yl}-benzoic acid;

5-{6-[2-(7-Chloro-4-methoxy-2-methyl-indol-1-yl)-ethylamino]-pyrimidin-4-yl}-3-ethyl-thiophene-2-carboxylic acid;

2,6-Dichloro-4-{6-[2-(4-methoxy-2-methyl-indol-1-yl)-ethylamino]-pyrimidin-4-yl}-benzoic acid;

4-{6-[2-(6-Fluoro-2,4-dimethyl-indol-1-yl)-ethylamino]-pyrimidin-4-yl}-2-methoxy-benzoic acid;

4-{6-[2-(4-Chloro-2-methyl-indol-1-yl)-ethylamino]-pyrimidin-4-yl}-2-ethoxy-benzoic acid;

5-{6-[2-(6,7-Dichloro-2-methyl-indol-1-yl)-ethylamino]-pyrimidin-4-yl}-3-ethoxy-thiophene-2-carboxylic acid;

3-Ethyl-5-{6-[2-(7-fluoro-2,5-dimethyl-indol-1-yl)-ethylamino]-pyrimidin-4-yl}-thiophene-2-carboxylic acid;

4-{6-[2-(4,7-Difluoro-2-methyl-indol-1-yl)-ethylamino]-pyrimidin-4-yl}-2-ethylamino-benzoic acid;

2-Ethylamino-4-{6-[2-(4-fluoro-2,7-dimethyl-indol-1-yl)-ethylamino]-pyrimidin-4-yl}-benzoic acid;

2-Ethylamino-4-{6-[2-(7-methoxy-2-methyl-indol-1-yl)-ethylamino]-pyrimidin-4-yl}-benzoic acid;

4-{6-[2-(7-Chloro-4-methoxy-2-methyl-indol-1-yl)-ethylamino]-pyrimidin-4-yl}-2-methylamino-benzoic acid;

2-Ethoxy-4-{6-[2-(4-methoxy-2-methyl-indol-1-yl)-ethylamino]-pyrimidin-4-yl}-benzoic acid;

2-Ethoxy-4-{6-[2-(6-methoxy-2-methyl-indol-1-yl)-ethylamino]-pyrimidin-4-yl}-benzoic acid;

3-Ethoxy-5-{6-[2-(7-fluoro-5-methoxy-2-methyl-indol-1-yl)-ethylamino]-pyrimidin-4-yl}-thiophene-2-carboxylic acid;

4-{6-[2-(7-Fluoro-4-methoxy-2-methyl-indol-1-yl)-ethylamino]-pyrimidin-4-yl}-2-methoxy-benzoic acid;

4-{6-[2-(2,5-Dimethyl-indol-1-yl)-ethylamino]-pyrimidin-4-yl}-2-isobutyl-benzoic acid;

2-Ethyl-6-fluoro-4-{6-[2-(7-fluoro-2,4-dimethyl-indol-1-yl)-ethylamino]-pyrimidin-4-yl}-benzoic acid;

4-{6-[2-(7-Fluoro-2,5-dimethyl-indol-1-yl)-ethylamino]-pyrimidin-4-yl}-2-propyl-benzoic acid;

4-{6-[2-(4-Chloro-2-methyl-indol-1-yl)-ethylamino]-pyrimidin-4-yl}-2-isobutyl-benzoic acid;

4-{6-[2-(7-Chloro-5-fluoro-2,4-dimethyl-indol-1-yl)-ethylamino]-pyrimidin-4-yl}-2-methylsulfanyl-benzoic acid;

4-{6-[2-(4-Methoxy-2-methyl-indol-1-yl)-ethylamino]-pyrimidin-4-yl}-2-propyl-benzoic acid;

5-{6-[2-(6,7-Dichloro-5-fluoro-2-methyl-indol-1-yl)-ethylamino]-pyrimidin-4-yl}-3-ethoxy-thiophene-2-carboxylic acid;

2-Fluoro-4-{6-[2-(7-fluoro-4-methoxy-2-methyl-indol-1-yl)-ethylamino]-pyrimidin-4-yl}-6-methyl-benzoic acid;

4-{6-[2-(4,5-Difluoro-2-methyl-indol-1-yl)-ethylamino]-pyrimidin-4-yl}-2-ethoxy-benzoic acid;

4-{6-[2-(4,6-Dichloro-2-methyl-indol-1-yl)-ethylamino]-pyrimidin-4-yl}-2-ethoxy-benzoic acid;

4-{6-[2-(4-Chloro-6-fluoro-2-methyl-indol-1-yl)-ethylamino]-pyrimidin-4-yl}-2-ethoxy-benzoic acid;

4-{6-[2-(4-Chloro-7-fluoro-2-methyl-indol-1-yl)-ethylamino]-pyrimidin-4-yl}-2-ethoxy-benzoic acid;

2-Ethoxy-4-{6-[2-(6-fluoro-2,4-dimethyl-indol-1-yl)-ethylamino]-pyrimidin-4-yl}-benzoic acid;

2-Ethyl-4-{6-[2-(6-fluoro-4-methoxy-2-methyl-indol-1-yl)-ethylamino]-pyrimidin-4-yl}-benzoic acid;

4-{6-[2-(7-Chloro-2,5-dimethyl-indol-1-yl)-ethylamino]-pyrimidin-4-yl}-2-ethoxy-benzoic acid;

2-Ethoxy-4-{6-[2-(7-fluoro-2,5-dimethyl-indol-1-yl)-ethylamino]-pyrimidin-4-yl}-benzoic acid;

4-{6-[2-(7-Fluoro-2,4-dimethyl-indol-1-yl)-ethylamino]-pyrimidin-4-yl}-2-methoxy-6-methyl-benzoic acid;

4-{6-[2-(7-Chloro-4-methoxy-2-methyl-indol-1-yl)-ethylamino]-pyrimidin-4-yl}-2-ethyl-benzoic acid;

2-Ethyl-4-{6-[2-(7-fluoro-4-methoxy-2-methyl-indol-1-yl)-ethylamino]-pyrimidin-4-yl}-benzoic acid;

2,6-Dichloro-4-{6-[2-(6-fluoro-4-methoxy-2-methyl-indol-1-yl)-ethylamino]-pyrimidin-4-yl}-benzoic acid;

2,6-Dichloro-4-{6-[2-(7-fluoro-4-methoxy-2-methyl-indol-1-yl)-ethylamino]-pyrimidin-4-yl}-benzoic acid;

4-{6-[2-(5-Chloro-7-methyl-[1,3]dioxolo[4,5-e]indol-6-yl)-ethylamino]-pyrimidin-4-yl}-2-ethyl-benzoic acid;

2-Cyclopropyl-4-{6-[2-(7-fluoro-4-methoxy-2-methyl-indol-1-yl)-ethylamino]-pyrimidin-4-yl}-benzoic acid;

{6-[4-(2-Amino-5-methyl-thiazol-4-yl)-phenyl]-pyrimidin-4-yl}-[2-(7-fluoro-2,4-dimethyl-indol-1-yl)-ethyl]-amine;

{6-[3-Fluoro-4-(5-methyl-[1,3,4]oxadiazol-2-yl)-phenyl]-pyrimidin-4-yl}-[2-(4-methoxy-2-methyl-indol-1-yl)-ethyl]-amine;

[2-(7-Fluoro-4-methoxy-2-methyl-indol-1-yl)-ethyl]-{6-[4-(3-methyl-[1,2,4]oxadiazol-5-yl)-phenyl]-pyrimidin-4-yl}-amine;

[2-(7-Fluoro-4-methoxy-2-methyl-indol-1-yl)-ethyl]-{6-[4-(5-methyl-[1,2,4]oxadiazol-3-yl)-phenyl]-pyrimidin-4-yl}-amine;

[2-(7-Fluoro-4-methoxy-2-methyl-indol-1-yl)-ethyl]-{6-[4-(3-methyl-pyrazol-1-yl)-phenyl]-pyrimidin-4-yl}-amine;

{6-[4-(2-Amino-5-methyl-thiazol-4-yl)-phenyl]-pyrimidin-4-yl}-[2-(4-methoxy-2-methyl-indol-1-yl)-ethyl]-amine;

3-(4-{6-[2-(7-Fluoro-4-methoxy-2-methyl-indol-1-yl)-ethylamino]-pyrimidin-4-yl}-phenyl)-4H-[1,2,4]oxadiazol-5-one;

5-{6-[2-(4-Methoxy-2-methyl-indol-1-yl)-ethylamino]-pyrimidin-4-yl}-3-propyl-2,3-dihydro-isoindol-1-one;

5-{6-[2-(4-Methoxy-2-methyl-indol-1-yl)-ethylamino]-pyrimidin-4-yl}-2-propyl-2,3-dihydro-isoindol-1-one;

3-Ethyl-5-{6-[2-(7-fluoro-4-methoxy-2-methyl-indol-1-yl)-ethylamino]-pyrimidin-4-yl}-2,3-dihydro-isoindol-1-one;

4-{6-[2-(7-Fluoro-4-methoxy-2-methyl-indol-1-yl)-ethylamino]-pyrimidin-4-yl}-1H-indole-7-carboxylic acid;

2-Ethoxy-4-{6-[2-(7-fluoro-4-methoxy-2-methyl-indol-1-yl)-ethylamino]-pyrimidin-4-yl}-benzoic acid;

4-{6-[2-(2,4-Dimethyl-indol-1-yl)-ethylamino]-pyrimidin-4-yl}-2-(3-methyl-butyl)-benzoic acid;
4-{6-[2-(4,7-Difluoro-2-methyl-indol-1-yl)-ethylamino]-pyrimidin-4-yl}-2-isobutyl-benzoic acid;
4-{6-[2-(5,7-Difluoro-2-methyl-indol-1-yl)-ethylamino]-pyrimidin-4-yl}-2-isobutyl-benzoic acid;
4-{6-[2-(7-Chloro-2,4-dimethyl-indol-1-yl)-ethylamino]-pyrimidin-4-yl}-2-propylsulfanyl-benzoic acid;
4-{6-[2-(7-Fluoro-2,4-dimethyl-indol-1-yl)-ethylamino]-pyrimidin-4-yl}-2-isobutyl-benzoic acid;
2-Chloro-4-{6-[2-(7-chloro-4,5-difluoro-2-methyl-indol-1-yl)-ethylamino]-pyrimidin-4-yl}-6-methylsulfanyl-benzoic acid;
4-{6-[2-(7-Chloro-4-fluoro-2-methyl-indol-1-yl)-ethylamino]-pyrimidin-4-yl}-2-fluoro-6-propyl-benzoic acid;
4-{6-[2-(7-Chloro-5-fluoro-2,4-dimethyl-indol-1-yl)-ethylamino]-pyrimidin-4-yl}-2-ethylsulfanyl-benzoic acid;
2-Chloro-4-{6-[2-(7-chloro-4-fluoro-2-methyl-indol-1-yl)-ethylamino]-pyrimidin-4-yl}-6-propyl-benzoic acid;
2-Isobutyl-4-{6-[2-(6-methoxy-2-methyl-indol-1-yl)-ethylamino]-pyrimidin-4-yl}-benzoic acid;
4-{6-[2-(7-Chloro-5-fluoro-2,4-dimethyl-indol-1-yl)-ethylamino]-pyrimidin-4-yl}-2-ethoxy-benzoic acid;
2-Ethoxy-4-{6-[2-(7-fluoro-2,4-dimethyl-indol-1-yl)-ethylamino]-pyrimidin-4-yl}-6-methyl-benzoic acid;
4-{6-[2-(6-Chloro-2,4-dimethyl-indol-1-yl)-ethylamino]-pyrimidin-4-yl}-2-difluoromethoxy-benzoic acid;
4-{6-[2-(7-Chloro-4,5-difluoro-2-methyl-indol-1-yl)-ethylamino]-pyrimidin-4-yl}-2-ethoxy-benzoic acid;
[2-(4-Methoxy-2-methyl-indol-1-yl)-ethyl]-[6-(2-methyl-1H-benzoimidazol-5-yl)-pyrimidin-4-yl]-amine;
2-Chloro-6-ethylamino-4-{6-[2-(7-fluoro-2,4-dimethyl-indol-1-yl)-ethylamino]-pyrimidin-4-yl}-benzoic acid;
2-Cyclopropyl-4-{6-[2-(6-fluoro-2,4-dimethyl-indol-1-yl)-ethylamino]-pyrimidin-4-yl}-benzoic acid;
[2-(7-Fluoro-2,4-dimethyl-indol-1-yl)-ethyl]-(6-quinolin-6-yl-pyrimidin-4-yl)-amine;
4-{6-[2-(7-Fluoro-2,4-dimethyl-indol-1-yl)-ethylamino]-pyrimidin-4-yl}-2-propylamino-benzoic acid;
2,6-Difluoro-4-{6-[2-(7-fluoro-4-methoxy-2-methyl-indol-1-yl)-ethylamino]-pyrimidin-4-yl}-benzenesulfonamide;
2-Chloro-6-ethylamino-4-{6-[2-(4-methoxy-2-methyl-indol-1-yl)-ethylamino]-pyrimidin-4-yl}-benzoic acid;
{6-[4-(5-Amino-[1,3,4]thiadiazol-2-yl)-phenyl]-pyrimidin-4-yl}-[2-(2-methyl-indol-1-yl)-ethyl]-amine;
4-{6-[2-(7-Chloro-4-methoxy-2-methyl-indol-1-yl)-ethylamino]-pyrimidin-4-yl}-2-ethoxy-6-methyl-benzoic acid;
2-Ethoxy-4-{6-[2-(7-fluoro-4-methoxy-2-methyl-indol-1-yl)-ethylamino]-pyrimidin-4-yl}-6-methyl-benzoic acid;
4-{6-[2-(4,7-Difluoro-2-methyl-indol-1-yl)-ethylamino]-pyrimidin-4-yl}-2-(3-methyl-butyl)-benzoic acid;
4-{6-[2-(4,7-Dichloro-2-methyl-indol-1-yl)-ethylamino]-pyrimidin-4-yl}-2-isobutylsulfanyl-benzoic acid;
[2-(7-Fluoro-4-methoxy-2-methyl-indol-1-yl)-ethyl]-(6-quinoxalin-6-yl-pyrimidin-4-yl)-amine;
2-Cyclopropyl-4-{6-[2-(6-fluoro-4-methoxy-2-methyl-indol-1-yl)-ethylamino]-pyrimidin-4-yl}-benzoic acid;
[2-(7-Fluoro-4-methoxy-2-methyl-indol-1-yl)-ethyl]-(6-isoquinolin-7-yl-pyrimidin-4-yl)-amine;
1-(2-Fluoro-4-{6-[2-(4-methoxy-2-methyl-indol-1-yl)-ethylamino]-pyrimidin-4-yl}-phenyl)-cyclopropanecarboxylic acid;
{6-[4-(5-Methylamino-[1,3,4]thiadiazol-2-yl)-phenyl]-pyrimidin-4-yl}-[2-(2-methyl-indol-1-yl)-ethyl]-amine;
6-{6-[2-(7-Chloro-4-methoxy-2-methyl-indol-1-yl)-ethylamino]-pyrimidin-4-yl}-1H-indazole-3-carboxylic acid;
6-{6-[2-(7-Fluoro-4-methoxy-2-methyl-indol-1-yl)-ethylamino]-pyrimidin-4-yl}-1H-indazole-3-carboxylic acid;
2,6-Dichloro-4-{6-[2-(6-fluoro-2,4-dimethyl-indol-1-yl)-ethylamino]-pyrimidin-4-yl}-benzoic acid;
4-{6-[2-(4-Cyano-7-fluoro-2-methyl-indol-1-yl)-ethylamino]-pyrimidin-4-yl}-2-propyl-benzoic acid;
4-{6-[2-(7-Fluoro-4-methoxy-2-methyl-indol-1-yl)-ethylamino]-pyrimidin-4-yl}-2-nitro-benzoic acid;
4-{6-[2-(2-Cyano-6-fluoro-4-methyl-indol-1-yl)-ethylamino]-pyrimidin-4-yl}-2-ethoxy-benzoic acid;
2-Ethylamino-6-fluoro-4-{6-[2-(4-methoxy-2-methyl-indol-1-yl)-ethylamino]-pyrimidin-4-yl}-benzoic acid;
2-Ethylamino-4-{6-[2-(4-fluoro-7-methoxy-2-methyl-indol-1-yl)-ethylamino]-pyrimidin-4-yl}-benzoic acid;
4-{6-[2-(4-Methoxy-2-methyl-indol-1-yl)-ethylamino]-pyrimidin-4-yl}-2-propoxy-benzoic acid;
2-Chloro-4-{6-[2-(7-fluoro-4-methoxy-2-methyl-indol-1-yl)-ethylamino]-pyrimidin-4-yl}-6-methoxy-benzoic acid;
4-{6-[2-(6-Chloro-4-methoxy-2-methyl-indol-1-yl)-ethylamino]-pyrimidin-4-yl}-2-ethoxy-benzoic acid;
2-Ethoxy-4-{6-[2-(6-fluoro-4-methoxy-2-methyl-indol-1-yl)-ethylamino]-pyrimidin-4-yl}-benzoic acid;
4-{6-[2-(7-Chloro-4-methoxy-2-methyl-indol-1-yl)-ethylamino]-pyrimidin-4-yl}-2-ethoxy-benzoic acid;
4-{6-[2-(7-Fluoro-4-methoxy-2-methyl-indol-1-yl)-ethylamino]-pyrimidin-4-yl}-2-methoxy-6-methyl-benzoic acid;
2-Ethoxy-6-fluoro-4-{6-[2-(4-methoxy-2-methyl-indol-1-yl)-ethylamino]-pyrimidin-4-yl}-benzoic acid;
4-{6-[2-(4,5-Difluoro-2-methyl-indol-1-yl)-ethylamino]-pyrimidin-4-yl}-2-isobutyl-benzoic acid;
2-Chloro-4-{6-[2-(7-fluoro-2,5-dimethyl-indol-1-yl)-ethylamino]-pyrimidin-4-yl}-6-propyl-benzoic acid;
2-Fluoro-4-{6-[2-(7-fluoro-2,5-dimethyl-indol-1-yl)-ethylamino]-pyrimidin-4-yl}-6-propyl-benzoic acid;
4-{6-[2-(6-Fluoro-2,4-dimethyl-indol-1-yl)-ethylamino]-pyrimidin-4-yl}-2-isobutyl-benzoic acid;
4-{6-[2-(4,7-Dichloro-2-methyl-indol-1-yl)-ethylamino]-pyrimidin-4-yl}-2-isopropylsulfanyl-benzoic acid;
2-Chloro-4-{6-[2-(7-chloro-5-fluoro-2-methyl-indol-1-yl)-ethylamino]-pyrimidin-4-yl}-6-propyl-benzoic acid;
2-Isobutyl-4-{6-[2-(4-methoxy-2-methyl-indol-1-yl)-ethylamino]-pyrimidin-4-yl}-benzoic acid;
4-{6-[2-(7-Chloro-4-methoxy-2-methyl-indol-1-yl)-ethylamino]-pyrimidin-4-yl}-2-ethyl-6-fluoro-benzoic acid;
2-Chloro-6-ethoxy-4-{6-[2-(6-fluoro-2,4-dimethyl-indol-1-yl)-ethylamino]-pyrimidin-4-yl}-benzoic acid;
2-Chloro-6-ethoxy-4-{6-[2-(7-fluoro-2,5-dimethyl-indol-1-yl)-ethylamino]-pyrimidin-4-yl}-benzoic acid;
2-Ethoxy-6-fluoro-4-{6-[2-(7-fluoro-2,4-dimethyl-indol-1-yl)-ethylamino]-pyrimidin-4-yl}-benzoic acid;
2-Ethoxy-6-fluoro-4-{6-[2-(7-fluoro-2,5-dimethyl-indol-1-yl)-ethylamino]-pyrimidin-4-yl}-benzoic acid;
2-Ethyl-6-fluoro-4-{6-[2-(7-fluoro-4-methoxy-2-methyl-indol-1-yl)-ethylamino]-pyrimidin-4-yl}-benzoic acid;
4-{6-[2-(6-Fluoro-2,4-dimethyl-indol-1-yl)-ethylamino]-pyrimidin-4-yl}-2-propoxy-benzoic acid;
4-{6-[2-(7-Fluoro-2,4-dimethyl-indol-1-yl)-ethylamino]-pyrimidin-4-yl}-2-propoxy-benzoic acid;
4-{6-[2-(7-Chloro-4-methoxy-2-methyl-indol-1-yl)-ethylamino]-pyrimidin-4-yl}-2-propyl-benzoic acid;
2-Fluoro-4-{6-[2-(4-methoxy-2-methyl-indol-1-yl)-ethylamino]-pyrimidin-4-yl}-6-propyl-benzoic acid;
4-{6-[2-(7-Chloro-5-fluoro-4-methoxy-2-methyl-indol-1-yl)-ethylamino]-pyrimidin-4-yl}-2-methylsulfanyl-benzoic acid;

2-Ethoxy-4-{6-[2-(4,5,7-trifluoro-2-methyl-indol-1-yl)-ethylamino]-pyrimidin-4-yl}-benzoic acid;
2-Chloro-4-{6-[2-(4-chloro-7-fluoro-2-methyl-indol-1-yl)-ethylamino]-pyrimidin-4-yl}-6-ethoxy-benzoic acid;
4-{6-[2-(4-Cyano-7-fluoro-2-methyl-indol-1-yl)-ethylamino]-pyrimidin-4-yl}-2-ethylamino-benzoic acid;
4-{6-[2-(7-Chloro-2,4-dimethyl-indol-1-yl)-ethylamino]-pyrimidin-4-yl}-2-cyclobutylsulfanyl-benzoic acid;
2-Cyclobutylsulfanyl-4-{6-[2-(4,7-dichloro-2-methyl-indol-1-yl)-ethylamino]-pyrimidin-4-yl}-benzoic acid;
4-{6-[2-(5-Chloro-7-methyl-[1,3]dioxolo[4,5-e]indol-6-yl)-ethylamino]-pyrimidin-4-yl}-2-ethoxy-benzoic acid;
4-{6-[2-(5-Chloro-7-methyl-[1,3]dioxolo[4,5-e]indol-6-yl)-ethylamino]-pyrimidin-4-yl}-2-ethylamino-benzoic acid;
3-Isobutyl-5-{6-[2-(4-methoxy-2-methyl-indol-1-yl)-ethylamino]-pyrimidin-4-yl}-2,3-dihydro-isoindol-1-one;
4-{6-[2-(7-Fluoro-2,4-dimethyl-indol-1-yl)-ethylamino]-pyrimidin-4-yl}-2-pyrrolidin-1-yl-benzoic acid;
5-{6-[2-(7-Fluoro-4-methoxy-2-methyl-indol-1-yl)-ethylamino]-pyrimidin-4-yl}-2-propyl-2,3-dihydro-isoindol-1-one;
5-{6-[2-(7-Fluoro-4-methoxy-2-methyl-indol-1-yl)-ethylamino]-pyrimidin-4-yl}-3-isobutyl-2,3-dihydro-isoindol-1-one;
4-{6-[2-(7-Fluoro-4-methoxy-2-methyl-indol-1-yl)-ethylamino]-pyrimidin-4-yl}-2-pyrrolidin-1-yl-benzoic acid;
2-Butoxy-4-{6-[2-(4-methoxy-2-methyl-indol-1-yl)-ethylamino]-pyrimidin-4-yl}-benzoic acid;
2-Isobutoxy-4-{6-[2-(4-methoxy-2-methyl-indol-1-yl)-ethylamino]-pyrimidin-4-yl}-benzoic acid;
2-Chloro-6-ethoxy-4-{6-[2-(7-fluoro-4-methoxy-2-methyl-indol-1-yl)-ethylamino]-pyrimidin-4-yl}-benzoic acid;
2-Ethoxy-6-fluoro-4-{6-[2-(7-fluoro-4-methoxy-2-methyl-indol-1-yl)-ethylamino]-pyrimidin-4-yl}-benzoic acid;
4-{6-[2-(6-Fluoro-4-methoxy-2-methyl-indol-1-yl)-ethylamino]-pyrimidin-4-yl}-2-propoxy-benzoic acid;
2-Ethoxy-4-{6-[2-(7-fluoro-4-methoxy-2-methyl-indol-1-yl)-ethylamino]-2-methyl-pyrimidin-4-yl}-benzoic acid;
4-{6-[2-(7-Chloro-4-methoxy-2-methyl-indol-1-yl)-ethylamino]-pyrimidin-4-yl}-2-propoxy-benzoic acid;
2-Chloro-4-{6-[2-(4-methoxy-2-methyl-indol-1-yl)-ethylamino]-pyrimidin-4-yl}-6-propoxy-benzoic acid;
2-Fluoro-4-{6-[2-(4-methoxy-2-methyl-indol-1-yl)-ethylamino]-pyrimidin-4-yl}-6-propoxy-benzoic acid;
4-{6-[2-(4-Methoxy-2-methyl-indol-1-yl)-ethylamino]-pyrimidin-4-yl}-2-trifluoromethoxy-benzoic acid;
4-{6-[2-(7-Chloro-4,5-difluoro-2-methyl-indol-1-yl)-ethylamino]-pyrimidin-4-yl}-2-isopropylsulfanyl-benzoic acid;
2-Isobutyl-4-{6-[2-(4,6,7-trifluoro-2-methyl-indol-1-yl)-ethylamino]-pyrimidin-4-yl}-benzoic acid;
2-Isobutyl-4-{6-[2-(4,5,7-trifluoro-2-methyl-indol-1-yl)-ethylamino]-pyrimidin-4-yl}-benzoic acid;
2-Isobutyl-4-{6-[2-(4-methoxy-2,7-dimethyl-indol-1-yl)-ethylamino]-pyrimidin-4-yl}-benzoic acid;
4-{6-[2-(7-Fluoro-2,4-dimethyl-indol-1-yl)-ethylamino]-pyrimidin-4-yl}-2-trifluoromethoxy-benzoic acid;
4-{6-[2-(5,7-Difluoro-2,4-dimethyl-indol-1-yl)-ethylamino]-pyrimidin-4-yl}-2-difluoromethoxy-benzoic acid;
4-{6-[2-(6-Chloro-4-methoxy-2-methyl-indol-1-yl)-ethylamino]-pyrimidin-4-yl}-2-fluoro-6-propyl-benzoic acid;
4-{6-[2-(7-Chloro-4-methoxy-2-methyl-indol-1-yl)-ethylamino]-pyrimidin-4-yl}-2-fluoro-6-propyl-benzoic acid;
2-Chloro-4-{6-[2-(7-chloro-4-methoxy-2-methyl-indol-1-yl)-ethylamino]-pyrimidin-4-yl}-6-propyl-benzoic acid;
2-Chloro-4-{6-[2-(6-chloro-2,4-dimethyl-indol-1-yl)-ethylamino]-pyrimidin-4-yl}-6-propoxy-benzoic acid;
2-Chloro-4-{6-[2-(6-fluoro-2,4-dimethyl-indol-1-yl)-ethylamino]-pyrimidin-4-yl}-6-propoxy-benzoic acid;
2-Fluoro-4-{6-[2-(6-fluoro-2,4-dimethyl-indol-1-yl)-ethylamino]-pyrimidin-4-yl}-6-propoxy-benzoic acid;
4-{6-[2-(6-Fluoro-2,4-dimethyl-indol-1-yl)-ethylamino]-pyrimidin-4-yl}-2-isobutoxy-benzoic acid;
2-Butoxy-4-{6-[2-(6-fluoro-2,4-dimethyl-indol-1-yl)-ethylamino]-pyrimidin-4-yl}-benzoic acid;
4-{6-[2-(6-Chloro-4-methoxy-2-methyl-indol-1-yl)-ethylamino]-pyrimidin-4-yl}-2-isobutyl-benzoic acid;
4-{6-[2-(7-Fluoro-2,4-dimethyl-indol-1-yl)-ethylamino]-pyrimidin-4-yl}-2-methoxy-6-propyl-benzoic acid;
2-Ethoxy-6-ethyl-4-{6-[2-(7-fluoro-2,4-dimethyl-indol-1-yl)-ethylamino]-pyrimidin-4-yl}-benzoic acid;
4-{6-[2-(7-Chloro-4-methoxy-2-methyl-indol-1-yl)-ethylamino]-pyrimidin-4-yl}-2-isobutyl-benzoic acid;
4-{6-[2-(7-Chloro-5-fluoro-4-methoxy-2-methyl-indol-1-yl)-ethylamino]-pyrimidin-4-yl}-2-ethylsulfanyl-benzoic acid;
4-(4-{6-[2-(6-Fluoro-2,4-dimethyl-indol-1-yl)-ethylamino]-pyrimidin-4-yl}-phenyl)-thiazole-2-carboxylic acid;
2-(4-{6-[2-(6-Fluoro-2,4-dimethyl-indol-1-yl)-ethylamino]-pyrimidin-4-yl}-phenyl)-thiazole-4-carboxylic acid;
4-(4-{6-[2-(4,6-Dichloro-2-methyl-indol-1-yl)-ethylamino]-pyrimidin-4-yl}-phenyl)-thiazole-2-carboxylic acid;
2-(4-{6-[2-(4,6-Dichloro-2-methyl-indol-1-yl)-ethylamino]-pyrimidin-4-yl}-phenyl)-thiazole-4-carboxylic acid;
{6-[4-(2-Amino-oxazol-5-yl)-phenyl]-pyrimidin-4-yl}-[2-(6-fluoro-2,4-dimethyl-indol-1-yl)-ethyl]-amine;
[2-(6-Fluoro-4-methoxy-2-methyl-indol-1-yl)-ethyl]-[6-(4-isoxazol-3-yl-phenyl)-pyrimidin-4-yl]-amine;
4-{6-[2-(6-Fluoro-2,4-dimethyl-indol-1-yl)-ethylamino]-pyrimidin-4-yl}-2-(2,2,2-trifluoro-ethylamino)-benzoic acid;
4-{6-[2-(7-Fluoro-2,4-dimethyl-indol-1-yl)-ethylamino]-pyrimidin-4-yl}-2-(2,2,2-trifluoro-ethylamino)-benzoic acid;
[2-(4-Methoxy-2-methyl-indol-1-yl)-ethyl]-{6-[4-(2-methyl-thiazol-4-yl)-phenyl]-pyrimidin-4-yl}-amine;
4-{6-[2-(4-Methoxy-2-methyl-indol-1-yl)-ethylamino]-pyrimidin-4-yl}-2-(2,2,2-trifluoro-ethylamino)-benzoic acid;
[2-(7-Fluoro-4-methoxy-2-methyl-indol-1-yl)-ethyl]-{6-[4-(5-methyl-[1,3,4]oxadiazol-2-yl)-phenyl]-pyrimidin-4-yl}-amine;
[2-(6-Fluoro-4-methoxy-2-methyl-indol-1-yl)-ethyl]-{6-[4-(3-methyl-3H-imidazol-4-yl)-phenyl]-pyrimidin-4-yl}-amine;
[2-(7-Fluoro-4-methoxy-2-methyl-indol-1-yl)-ethyl]-{6-[4-(3-methyl-3H-imidazol-4-yl)-phenyl]-pyrimidin-4-yl}-amine;
[2-(6-Fluoro-4-methoxy-2-methyl-indol-1-yl)-ethyl]-{6-[4-(2-methyl-oxazol-4-yl)-phenyl]-pyrimidin-4-yl}-amine;
4-{6-[2-(6-Fluoro-4-methoxy-2-methyl-indol-1-yl)-ethylamino]-pyrimidin-4-yl}-2-(2,2,2-trifluoro-ethylamino)-benzoic acid;
[2-(7-Fluoro-4-methoxy-2-methyl-indol-1-yl)-ethyl]-[6-(4-pyridin-2-yl-phenyl)-pyrimidin-4-yl]-amine;
4-{6-[2-(7-Fluoro-4-methoxy-2-methyl-indol-1-yl)-ethylamino]-pyrimidin-4-yl}-N-methyl-2-trifluoromethyl-benzenesulfonamide;
5-(4-{6-[2-(7-Fluoro-4-methoxy-2-methyl-indol-1-yl)-ethylamino]-pyrimidin-4-yl}-phenyl)-3-methyl-isoxazole-4-carboxylic acid;

2-Difluoromethoxy-4-{6-[2-(4-methoxy-2-methyl-indol-1-yl)-ethylamino]-pyrimidin-4-yl}-benzoic acid;
2-Chloro-6-ethoxy-4-{6-[2-(4-methoxy-2-methyl-indol-1-yl)-ethylamino]-pyrimidin-4-yl}-benzoic acid;
2-Difluoromethoxy-4-{6-[2-(6-fluoro-2,4-dimethyl-indol-1-yl)-ethylamino]-pyrimidin-4-yl}-benzoic acid;
2-Difluoromethoxy-4-{6-[2-(7-fluoro-2,4-dimethyl-indol-1-yl)-ethylamino]-pyrimidin-4-yl}-benzoic acid;
4-{6-[2-(6-Fluoro-4-methoxy-2-methyl-indol-1-yl)-ethylamino]-pyrimidin-4-yl}-2-trifluoromethoxy-benzoic acid;
4-{6-[2-(7-Chloro-4-methoxy-2-methyl-indol-1-yl)-ethylamino]-pyrimidin-4-yl}-2-trifluoromethoxy-benzoic acid;
4-{6-[2-(7-Fluoro-4-methoxy-2-methyl-indol-1-yl)-ethylamino]-pyrimidin-4-yl}-2-trifluoromethoxy-benzoic acid;
2-Chloro-4-{6-[2-(6-fluoro-4-methoxy-2-methyl-indol-1-yl)-ethylamino]-pyrimidin-4-yl}-6-propoxy-benzoic acid;
2-Fluoro-4-{6-[2-(6-fluoro-4-methoxy-2-methyl-indol-1-yl)-ethylamino]-pyrimidin-4-yl}-6-propoxy-benzoic acid;
2-Fluoro-4-{6-[2-(7-fluoro-4-methoxy-2-methyl-indol-1-yl)-ethylamino]-pyrimidin-4-yl}-6-propoxy-benzoic acid;
2-Butoxy-4-{6-[2-(7-chloro-4-methoxy-2-methyl-indol-1-yl)-ethylamino]-pyrimidin-4-yl}-benzoic acid;
4-{6-[2-(7-Chloro-4-methoxy-2-methyl-indol-1-yl)-ethylamino]-pyrimidin-4-yl}-2-isobutoxy-benzoic acid;
2-Ethoxy-6-ethyl-4-{6-[2-(7-fluoro-4-methoxy-2-methyl-indol-1-yl)-ethylamino]-pyrimidin-4-yl}-benzoic acid;
4-{6-[2-(7-Fluoro-4-methoxy-2-methyl-indol-1-yl)-ethylamino]-pyrimidin-4-yl}-2-methoxy-6-propyl-benzoic acid;
2-Chloro-6-propoxy-4-{6-[2-(4,6,7-trifluoro-2-methyl-indol-1-yl)-ethylamino]-pyrimidin-4-yl}-benzoic acid;
4-{6-[2-(6-Fluoro-4-methoxy-2-methyl-indol-1-yl)-ethylamino]-2-methyl-pyrimidin-4-yl}-2-isobutyl-benzoic acid;
2-Ethoxy-4-{6-[2-(7-fluoro-2,4-dimethyl-indol-1-yl)-ethylamino]-pyrimidin-4-yl}-6-propyl-benzoic acid;
4-{6-[2-(6,7-Difluoro-2,4-dimethyl-indol-1-yl)-ethylamino]-pyrimidin-4-yl}-2-fluoro-6-propoxy-benzoic acid;
2-Difluoromethoxy-4-{6-[2-(6-fluoro-4-methoxy-2-methyl-indol-1-yl)-ethylamino]-pyrimidin-4-yl}-benzoic acid;
4-{6-[2-(7-Chloro-4-methoxy-2-methyl-indol-1-yl)-ethylamino]-pyrimidin-4-yl}-2-difluoromethoxy-benzoic acid;
2-Difluoromethoxy-4-{6-[2-(7-fluoro-4-methoxy-2-methyl-indol-1-yl)-ethylamino]-pyrimidin-4-yl}-benzoic acid;
2-Ethoxy-4-{6-[2-(7-fluoro-4-methoxy-2-methyl-indol-1-yl)-ethylamino]-pyrimidin-4-yl}-6-propyl-benzoic acid;
3-Ethoxy-5-{6-[2-(6-fluoro-4-methoxy-2-methyl-indol-1-yl)-ethylamino]-2-trifluoromethyl-pyrimidin-4-yl}-thiophene-2-carboxylic acid;
3-{5-(4-{6-[2-(7-Fluoro-4-methoxy-2-methyl-indol-1-yl)-ethylamino]-pyrimidin-4-yl}-phenyl)-oxazol-2-yl]-propionic acid;
2-(4-Fluoro-phenoxy)-4-{6-[2-(4-methoxy-2-methyl-indol-1-yl)-ethylamino]-pyrimidin-4-yl}-benzoic acid;
4-{6-[2-(7-Fluoro-4-methoxy-2-methyl-indol-1-yl)-ethylamino]-pyrimidin-4-yl}-2-(4-fluoro-phenoxy)-benzoic acid;
{6-[3-Ethoxy-5-fluoro-4-(1H-tetrazol-5-yl)-phenyl]-pyrimidin-4-yl}-[2-(6-fluoro-4-methoxy-2-methyl-indol-1-yl)-ethyl]-amine;
{6-[3-Ethoxy-5-fluoro-4-(1H-tetrazol-5-yl)-phenyl]-pyrimidin-4-yl}-[2-(6-fluoro-2,4-dimethyl-indol-1-yl)-ethyl]-amine;
[2-(7-Chloro-4-methoxy-2-methyl-indol-1-yl)-ethyl]-{6-[3-ethoxy-4-(1H-tetrazol-5-yl)-phenyl]-pyrimidin-4-yl}-amine;
{6-[3-Ethoxy-4-(1H-tetrazol-5-yl)-phenyl]-pyrimidin-4-yl}-[2-(2-methyl-indol-1-yl)-ethyl]-amine;
[2-(4-Methoxy-2-methyl-indol-1-yl)-ethyl]-{6-[3-methoxy-4-(1H-tetrazol-5-yl)-phenyl]-pyrimidin-4-yl}-amine;
{6-[3-Ethylamino-4-(1H-tetrazol-5-yl)-phenyl]-pyrimidin-4-yl}-[2-(2-methyl-indol-1-yl)-ethyl]-amine;
3-(4-{6-[2-(4,6-Dichloro-2-methyl-indol-1-yl)-ethylamino]-pyrimidin-4-yl}-phenyl)-4H-[1,2,4]oxadiazol-5-one;
3-(4-{6-[2-(4,5,7-Trifluoro-2-methyl-indol-1-yl)-ethylamino]-pyrimidin-4-yl}-phenyl)-4H-[1,2,4]oxadiazol-5-one;
[2-(7-Fluoro-4-methoxy-2-methyl-indol-1-yl)-ethyl]-{6-[3-methoxy-4-(1H-tetrazol-5-yl)-phenyl]-pyrimidin-4-yl}-amine;
[2-(7-Chloro-4-methoxy-2-methyl-indol-1-yl)-ethyl]-{6-[3-methoxy-4-(1H-tetrazol-5-yl)-phenyl]-pyrimidin-4-yl}-amine;
[2-(6-Fluoro-2,4-dimethyl-indol-1-yl)-ethyl]-[6-(4-[1,2,4]oxadiazol-5-yl-phenyl)-pyrimidin-4-yl]-amine;
2-Chloro-6-isobutoxy-4-{6-[2-(4-methoxy-2-methyl-indol-1-yl)-ethylamino]-pyrimidin-4-yl}-benzoic acid;
2-Chloro-4-{6-[2-(6-fluoro-2,4-dimethyl-indol-1-yl)-ethylamino]-pyrimidin-4-yl}-6-isobutoxy-benzoic acid;
2-Chloro-4-{6-[2-(6,7-difluoro-2,4-dimethyl-indol-1-yl)-ethylamino]-pyrimidin-4-yl}-6-isobutoxy-benzoic acid;
[6-(1H-Indol-5-yl)-pyrimidin-4-yl]-[2-(2-methyl-indol-1-yl)-ethyl]-amine;
[2-(6,7-Difluoro-2,4-dimethyl-indol-1-yl)-ethyl]-[6-(1H-indol-5-yl)-pyrimidin-4-yl]-amine;
[2-(6-Fluoro-2,4-dimethyl-indol-1-yl)-ethyl]-[6-(1-methyl-1H-indol-5-yl)-pyrimidin-4-yl]-amine;
[2-(7-Fluoro-2,4-dimethyl-indol-1-yl)-ethyl]-[6-(1-methyl-1H-indol-5-yl)-pyrimidin-4-yl]-amine;
3-(4-{6-[2-(7-Fluoro-2,4-dimethyl-indol-1-yl)-ethylamino]-pyrimidin-4-yl}-phenyl)-3-oxo-propionitrile;
3-(4-{6-[2-(6-Fluoro-4-methoxy-2-methyl-indol-1-yl)-ethylamino]-pyrimidin-4-yl}-phenyl)-3-oxo-propionitrile;
3-(4-{6-[2-(7-Fluoro-4-methoxy-2-methyl-indol-1-yl)-ethylamino]-pyrimidin-4-yl}-phenyl)-3-oxo-propionitrile;
3-(4-{6-[2-(6,7-Difluoro-4-methoxy-2-methyl-indol-1-yl)-ethylamino]-pyrimidin-4-yl}-phenyl)-3-oxo-propionitrile;
[2-(2-Methyl-indol-1-yl)-ethyl]-{6-[4-(3-methyl-isoxazol-5-yl)-phenyl]-pyrimidin-4-yl}-amine;
[2-(6-Fluoro-4-methoxy-2-methyl-indol-1-yl)-ethyl]-{6-[4-(3-methyl-isoxazol-5-yl)-phenyl]-pyrimidin-4-yl}-amine;
[2-(7-Fluoro-4-methoxy-2-methyl-indol-1-yl)-ethyl]-{6-[4-(3-methyl-isoxazol-5-yl)-phenyl]-pyrimidin-4-yl}-amine;
4-{6-[2-(7-Chloro-5-fluoro-2,4-dimethyl-indol-1-yl)-ethylamino]-pyrimidin-4-yl}-2-propoxy-benzoic acid;
2-Chloro-4-{6-[2-(4-methoxy-2-methyl-indol-1-yl)-ethylamino]-pyrimidin-4-yl}-6-(2,2,2-trifluoro-ethoxy)-benzoic acid;
2-Chloro-4-{6-[2-(6-fluoro-2,4-dimethyl-indol-1-yl)-ethylamino]-pyrimidin-4-yl}-6-(2,2,2-trifluoro-ethoxy)-benzoic acid;
[2-(6-Fluoro-4-methoxy-2-methyl-indol-1-yl)-ethyl]-[6-(3-pyrazol-1-yl-phenyl)-pyrimidin-4-yl]-amine;

[2-(6-Fluoro-4-methoxy-2-methyl-indol-1-yl)-ethyl]-[6-(4-pyridin-2-yl-phenyl)-pyrimidin-4-yl]-amine;
[2-(6-Fluoro-4-methoxy-2-methyl-indol-1-yl)-ethyl]-(6-isoquinolin-7-yl-pyrimidin-4-yl)-amine;
[2-(6-Fluoro-2,4-dimethyl-indol-1-yl)-ethyl]-[6-(3-pyrazol-1-yl-phenyl)-pyrimidin-4-yl]-amine;
[2-(6-Fluoro-2,4-dimethyl-indol-1-yl)-ethyl]-[6-(4-pyridin-2-yl-phenyl)-pyrimidin-4-yl]-amine;
[2-(6-Fluoro-2,4-dimethyl-indol-1-yl)-ethyl]-(6-isoquinolin-7-yl-pyrimidin-4-yl)-amine;
[2-(6-Fluoro-2,4-dimethyl-indol-1-yl)-ethyl]-(6-quinolin-6-yl-pyrimidin-4-yl)-amine;
[2-(6-Fluoro-4-methoxy-2-methyl-indol-1-yl)-ethyl]-{6-[4-(4-methyl-isoxazol-5-yl)-phenyl]-pyrimidin-4-yl}-amine;
[2-(7-Fluoro-4-methoxy-2-methyl-indol-1-yl)-ethyl]-{6-[4-(4-methyl-isoxazol-5-yl)-phenyl]-pyrimidin-4-yl}-amine;
[6-(3H-Benzotriazol-5-yl)-pyrimidin-4-yl]-[2-(7-fluoro-2,4-dimethyl-indol-1-yl)-ethyl]-amine;
[2-(7-Fluoro-2,4-dimethyl-indol-1-yl)-ethyl]-[6-(4-[1,2,4]triazol-1-yl-phenyl)-pyrimidin-4-yl]-amine;
[2-(6-Fluoro-4-methoxy-2-methyl-indol-1-yl)-ethyl]-[6-(4-isoxazol-5-yl-phenyl)-pyrimidin-4-yl]-amine;
[2-(7-Fluoro-4-methoxy-2-methyl-indol-1-yl)-ethyl]-[6-(4-isoxazol-5-yl-phenyl)-pyrimidin-4-yl]-amine;
[2-(6,7-Difluoro-4-methoxy-2-methyl-indol-1-yl)-ethyl]-[6-(4-isoxazol-5-yl-phenyl)-pyrimidin-4-yl]-amine;
{6-[3-Methoxy-4-(1H-tetrazol-5-yl)-phenyl]-pyrimidin-4-yl}-[2-(2-methyl-indol-1-yl)-ethyl]-amine;
[2-(4,7-Difluoro-2-methyl-indol-1-yl)-ethyl]-{6-[3-methoxy-4-(1H-tetrazol-5-yl)-phenyl]-pyrimidin-4-yl}-amine;
[2-(6-Fluoro-4-methoxy-2-methyl-indol-1-yl)-ethyl]-[6-(4-thiazol-2-yl-phenyl)-pyrimidin-4-yl]-amine;
[2-(6-Fluoro-4-methoxy-2-methyl-indol-1-yl)-ethyl]-{6-[4-(4-methoxy-pyrimidin-2-yl)-phenyl]-pyrimidin-4-yl}-amine;
[2-(6-Fluoro-4-methoxy-2-methyl-indol-1-yl)-ethyl]-[6-(4-pyrimidin-2-yl-phenyl)-pyrimidin-4-yl]-amine;
[2-(6-Fluoro-4-methoxy-2-methyl-indol-1-yl)-ethyl]-{6-[4-(5-methoxy-pyrimidin-2-yl)-phenyl]-pyrimidin-4-yl}-amine;
[2-(6-Fluoro-4-methoxy-2-methyl-indol-1-yl)-ethyl]-{6-[4-(4-methyl-thiazol-2-yl)-phenyl]-pyrimidin-4-yl}-amine;
[2-(6-Fluoro-4-methoxy-2-methyl-indol-1-yl)-ethyl]-{6-[4-(6-methoxy-pyrazin-2-yl)-phenyl]-pyrimidin-4-yl}-amine;
6-(4-(6-((2-(6-fluoro-4-methoxy-2-methyl-1H-indol-1-yl)ethyl)amino)pyrimidin-4-yl)phenyl)-N,N-dimethylpyrimidin-4-amine;
[2-(2-Methyl-indol-1-yl)-ethyl]-[6-(4-thiazol-2-yl-phenyl)-pyrimidin-4-yl]-amine;
2-Ethoxy-4-{6-[2-(7-fluoro-4-methoxy-2-methyl-indol-1-yl)-ethylamino]-pyrimidin-4-yl}-N-methoxy-benzamide;
2,N-Diethoxy-4-{6-[2-(7-fluoro-4-methoxy-2-methyl-indol-1-yl)-ethylamino]-pyrimidin-4-yl}-benzamide;
N-Benzyloxy-2-ethoxy-4-{6-[2-(7-fluoro-2,4-dimethyl-indol-1-yl)-ethylamino]-pyrimidin-4-yl}-benzamide;
2-Ethoxy-4-{6-[2-(7-fluoro-4-methoxy-2-methyl-indol-1-yl)-ethylamino]-pyrimidin-4-yl}-N-(2-hydroxy-ethoxy)-benzamide;
2-Ethoxy-4-{6-[2-(7-fluoro-4-methoxy-2-methyl-indol-1-yl)-ethylamino]-pyrimidin-4-yl}-N-isopropoxy-benzamide;
2-Ethoxy-4-{6-[2-(7-fluoro-2,4-dimethyl-indol-1-yl)-ethylamino]-pyrimidin-4-yl}-N-(2-hydroxy-ethoxy)-benzamide;
6-{6-[2-(2-Methyl-indol-1-yl)-ethylamino]-pyrimidin-4-yl}-1,2-dihydro-indazol-3-one;
6-{6-[2-(2-Methyl-indol-1-yl)-ethylamino]-pyrimidin-4-yl}-benzo[d]isoxazol-3-one;
4-{6-[2-(2,7-Dichloro-4-methoxy-indol-1-yl)-ethylamino]-pyrimidin-4-yl}-2-ethoxy-benzoic acid;
4-{6-[2-(2,4-Dichloro-7-fluoro-indol-1-yl)-ethylamino]-pyrimidin-4-yl}-2-ethoxy-benzoic acid;
4-{6-[2-(2-Chloro-7-fluoro-4-methyl-indol-1-yl)-ethylamino]-pyrimidin-4-yl}-2-ethoxy-benzoic acid;
4-{6-[2-(4-Bromo-2-methyl-indol-1-yl)-ethylamino]-pyrimidin-4-yl}-2-ethoxy-benzoic acid;
2-[4-(4-{6-[2-(4-Methoxy-2-methyl-indol-1-yl)-ethylamino]-pyrimidin-4-yl}-phenyl)-thiazol-2-yl]-acetamide;
2-[4-(4-{6-[2-(7-Fluoro-4-methoxy-2-methyl-indol-1-yl)-ethylamino]-pyrimidin-4-yl}-phenyl)-thiazol-2-yl]-acetamide;
4-{6-[2-(5,6-Difluoro-2,4-dimethyl-indol-1-yl)-ethylamino]-pyrimidin-4-yl}-2-ethoxy-benzoic acid;
4-{6-[2-(7-Chloro-2,4-dimethyl-indol-1-yl)-ethylamino]-pyrimidin-4-yl}-2-((E)-2-fluoro-vinylsulfanyl)-benzoic acid;
5-{6-[2-(2-Methyl-indol-1-yl)-ethylamino]-pyrimidin-4-yl}-2-(1H-tetrazol-5-yl)-phenol;
3-Ethoxy-5-{6-[2-(7-fluoro-4-methoxy-2-methyl-indol-1-yl)-ethylamino]-pyrimidin-4-yl}-thiophene-2-carboxylic acid ethyl ester;
[2-(2-Methyl-indol-1-yl)-ethyl]-{6-[5-(1H-tetrazol-5-yl)-thiophen-2-yl]-pyrimidin-4-yl}-amine;
3-Ethoxy-5-{6-[2-(7-fluoro-4-methoxy-2-methyl-indol-1-yl)-propylamino]-pyrimidin-4-yl}-thiophene-2-carboxylic acid;
4-(4-{6-[2-(7-Fluoro-4-methoxy-2-methyl-indol-1-yl)-ethylamino]-pyrimidin-4-yl}-phenyl)-thiazol-2-ol;
5-{6-[2-(6-Fluoro-4-methoxy-2-methyl-indol-1-yl)-ethylamino]-pyrimidin-4-yl}-thiophen-3-ol; and
2-Ethoxy-4-{6-[2-(4-fluoro-2,7-dimethyl-indol-1-yl)-ethylamino]-pyrimidin-4-yl}-benzoic acid. 30) In addition to the most preferred compounds listed in embodiment 27), further most preferred compounds compounds according to embodiment 1) are selected from the following compounds:
Ethanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide;
7-Fluoro-1-(2-{6-[4-(1H-imidazol-4-yl)-3-methoxy-phenyl]-pyrimidin-4-ylamino}-ethyl)-4-methoxy-1H-indole-2-carbonitrile;
7-Fluoro-4-methoxy-1-(2-{6-[4-(5-methyl-1H-imidazol-4-yl)-phenyl]-pyrimidin-4-ylamino}-ethyl)-1H-indole-2-carbonitrile;
1-(2-{6-[3-Ethoxy-4-((5-oxo-4,5-dihydro-[1,2,4]oxadiazol-3-yl)-phenyl]-pyrimidin-4-ylamino}-ethyl)-7-fluoro-4-methoxy-1H-indole-2-carbonitrile;
1-(2-{6-[4-(2,5-Dimethyl-1H-imidazol-4-yl)-phenyl]-pyrimidin-4-ylamino}-ethyl)-7-fluoro-4-methoxy-1H-indole-2-carbonitrile;
1-{2-[6-(3-Ethyl-4-hydroxy-phenyl)-pyrimidin-4-ylamino]-ethyl}-7-fluoro-4-methoxy-1H-indole-2-carbonitrile;
1-(2-{6-[4-(1,5-Dimethyl-1H-imidazol-4-yl)-phenyl]-pyrimidin-4-ylamino}-ethyl)-7-fluoro-4-methoxy-1H-indole-2-carbonitrile;

1-(2-{6-[4-(1,2-Dimethyl-1H-imidazol-4-yl)-phenyl]-pyrimidin-4-ylamino}-ethyl)-7-fluoro-4-methoxy-1H-indole-2-carbonitrile;
7-Fluoro-1-(2-{6-[4-((5-oxo-4,5-dihydro-[1,2,4]oxadiazol-3-yl)-phenyl]-pyrimidin-4-ylamino}-ethyl)-4-methoxy-1H-indole-2-carbonitrile;
7-Fluoro-1-(2-{6-[5-(3-hydroxy-oxetan-3-yl)-4-methoxy-thiophen-2-yl]-pyrimidin-4-ylamino}-ethyl)-4-methoxy-1H-indole-2-carbonitrile;
1-(2-{6-[4-(2-Cyclopropyl-1-methyl-1H-imidazol-4-yl)-phenyl]-pyrimidin-4-ylamino}-ethyl)-7-fluoro-4-methoxy-1H-indole-2-carbonitrile;
(4-{6-[2-(2-Cyano-7-fluoro-4-methoxy-indol-1-yl)-ethylamino]-pyrimidin-4-yl}-2-trifluoromethoxy-phenoxy)-acetic acid;
7-Fluoro-1-(2-{6-[4-(3H-imidazol-4-yl)-phenyl]-pyrimidin-4-ylamino}-ethyl)-4-methoxy-1H-indole-2-carbonitrile;
3-(2-Ethoxy-4-{6-[2-(7-fluoro-4-methoxy-2-methyl-indol-1-yl)-ethylamino]-pyrimidin-4-yl}-phenyl)-[1,2,4]oxadiazol-5(4H)-one;
7-Fluoro-1-(2-{6-[4-(3-oxo-2,3-dihydro-1,2,4-oxadiazol-5-yl)-phenyl]-pyrimidin-4-ylamino}-ethyl)-4-methoxy-1H-indole-2-carbonitrile;
5-{6-[2-(7-Fluoro-4-methoxy-2-methyl-indol-1-yl)-ethylamino]-pyrimidin-4-yl}-3-(2,2,2-trifluoro-ethoxy)-thiophene-2-carboxylic acid;
(4-{6-[2-(2-Cyano-7-fluoro-4-methoxy-indol-1-yl)-ethylamino]-pyrimidin-4-yl}-2-ethyl-phenoxy)-acetic acid;
3-(2-Ethoxy-4-{6-[2-(6-fluoro-2,4-dimethyl-indol-1-yl)-ethylamino]-pyrimidin-4-yl}-phenyl)-[1,2,4]oxadiazol-5(4H)-one;
2-butoxy-6-chloro-4-(6-((2-(7-fluoro-4-methoxy-2-methyl-1H-indol-1-yl)ethyl-1,1,2,2-d4)amino)pyrimidin-4-yl)benzoic acid;
5-{6-[2-(7-Chloro-5-fluoro-2,4-dimethyl-indol-1-yl)-ethylamino]-pyrimidin-4-yl}-3-ethoxy-thiophene-2-carboxylic acid;
5-{6-[2-(6-Fluoro-4-methoxy-2-methyl-indol-1-yl)-ethylamino]-pyrimidin-4-yl}-3-(2,2,2-trifluoro-ethoxy)-thiophene-2-carboxylic acid;
2-(2-Ethoxy-4-{6-[2-(7-fluoro-4-methoxy-2-methyl-indol-1-yl)-ethylamino]-pyrimidin-4-yl}-phenylamino)-propionic acid;
5-{6-[2-(2-Cyano-3-fluoro-indol-1-yl)-ethylamino]-pyrimidin-4-yl}-3-trifluoromethyl-thiophene-2-carboxylic acid;
5-{6-[2-(2-Cyano-7-fluoro-4-methyl-indol-1-yl)-ethylamino]-pyrimidin-4-yl}-3-fluoro-thiophene-2-carboxylic acid;
7-Fluoro-1-(2-{6-[4-(3-hydroxy-isoxazol-5-yl)-phenyl]-pyrimidin-4-ylamino}-ethyl)-4-methoxy-1H-indole-2-carbonitrile;
N-(4-{6-[2-(2-Cyano-7-fluoro-4-methoxy-indol-1-yl)-ethylamino]-pyrimidin-4-yl}-2-ethoxy-phenyl)-oxalamic acid;
7-Fluoro-1-(2-{6-[4-(3-hydroxy-isoxazol-5-yl)-3-methoxy-phenyl]-pyrimidin-4-ylamino}-ethyl)-4-methoxy-1H-indole-2-carbonitrile;
5-{6-[2-(2-Cyano-7-fluoro-4-methyl-indol-1-yl)-ethylamino]-pyrimidin-4-yl}-3-trifluoromethyl-thiophene-2-carboxylic acid;
(4-{6-[2-(2-Cyano-7-fluoro-4-methoxy-indol-1-yl)-ethylamino]-pyrimidin-4-yl}-2-ethoxy-phenylamino)-acetic acid;
1-(2-{6-[4-(2-Cyclopropyl-1H-imidazol-4-yl)-phenyl]-pyrimidin-4-ylamino}-ethyl)-7-fluoro-4-methoxy-1H-indole-2-carbonitrile;
5-{6-[2-(6-Chloro-7-fluoro-4-methoxy-2-methyl-indol-1-yl)-ethylamino]-pyrimidin-4-yl}-3-ethoxy-thiophene-2-carboxylic acid;
(4-{6-[2-(2-Cyano-4-methoxy-indol-1-yl)-ethylamino]-pyrimidin-4-yl}-2-ethoxy-phenylamino)-acetic acid;
7-Fluoro-1-{2-[6-(4-hydroxy-3-trifluoromethoxy-phenyl)-pyrimidin-4-ylamino]-ethyl}-4-methoxy-1H-indole-2-carbonitrile;
1-{2-[6-(3-Chloro-4-hydroxy-phenyl)-pyrimidin-4-ylamino]-ethyl}-7-fluoro-4-methoxy-1H-indole-2-carbonitrile;
5-{6-[2-(4,6-Dichloro-7-fluoro-2-methyl-indol-1-yl)-ethylamino]-pyrimidin-4-yl}-3-ethoxy-thiophene-2-carboxylic acid;
5-{6-[2-(6-Chloro-4-methoxy-2-methyl-indol-1-yl)-ethylamino]-pyrimidin-4-yl}-3-isopropoxy-thiophene-2-carboxylic acid;
(4-{6-[2-(2-Cyano-4-methoxy-indol-1-yl)-ethylamino]-pyrimidin-4-yl}-2-ethoxy-phenoxy)-acetic acid;
5-{6-[2-(6-Chloro-4-methoxy-2-methyl-indol-1-yl)-ethylamino]-pyrimidin-4-yl}-3-ethoxy-thiophene-2-carboxylic acid;
2-Butoxy-4-{6-[2-(2-cyano-7-fluoro-4-methoxy-indol-1-yl)-ethylamino]-pyrimidin-4-yl}-benzoic acid;
4-{6-[2-(7-Fluoro-4-methoxy-2-methyl-indol-1-yl)-ethylamino]-pyrimidin-4-yl}-2-trifluoromethoxy-phenol;
3-Ethoxy-5-{6-[2-(3-fluoro-2-methyl-indol-1-yl)-ethylamino]-pyrimidin-4-yl}-thiophene-2-carboxylic acid;
5-{6-[2-(2-Cyano-3-fluoro-indol-1-yl)-ethylamino]-pyrimidin-4-yl}-3-ethoxy-thiophene-2-carboxylic acid;
(2-Ethoxy-4-{6-[2-(7-fluoro-2,4-dimethyl-indol-1-yl)-ethylamino]-pyrimidin-4-yl}-phenylamino)-acetic acid;
2-Butoxy-4-{6-[2-(6,7-difluoro-4-methoxy-2-methyl-indol-1-yl)-ethylamino]-pyrimidin-4-yl}-benzoic acid;
5-{6-[2-(2,4-Dimethyl-indol-1-yl)-ethylamino]-pyrimidin-4-yl}-3-isopropoxy-thiophene-2-carboxylic acid;
5-{6-[2-(2,4-Dimethyl-indol-1-yl)-ethylamino]-pyrimidin-4-yl}-3-ethoxy-thiophene-2-carboxylic acid;
3-(2-Ethoxy-4-{6-[2-(4-methoxy-2-methyl-indol-1-yl)-ethylamino]-pyrimidin-4-yl}-phenyl)-[1,2,4]oxadiazol-5(4H)-one;
5-{6-[2-(4,6-Dichloro-2-cyano-indol-1-yl)-ethylamino]-pyrimidin-4-yl}-3-ethoxy-thiophene-2-carboxylic acid;
5-{6-[2-(2-Cyano-5,6-difluoro-4-methyl-indol-1-yl)-ethylamino]-pyrimidin-4-yl}-3-ethoxy-thiophene-2-carboxylic acid;
5-{6-[2-(2-Cyano-7-fluoro-4-methyl-indol-1-yl)-ethylamino]-pyrimidin-4-yl}-3-ethoxy-thiophene-2-carboxylic acid;
5-{6-[2-(2-Cyano-7-fluoro-indol-1-yl)-ethylamino]-pyrimidin-4-yl}-3-ethoxy-thiophene-2-carboxylic acid;
(4-{6-[2-(2-Cyano-7-fluoro-4-methyl-indol-1-yl)-ethylamino]-pyrimidin-4-yl}-2-ethoxy-phenoxy)-acetic acid;
(4-{6-[2-(2-Cyano-7-fluoro-indol-1-yl)-ethylamino]-pyrimidin-4-yl}-2-ethoxy-phenylamino)-acetic acid;
1-{2-[6-(3-Ethoxy-4-hydroxy-phenyl)-pyrimidin-4-ylamino]-ethyl}-7-fluoro-4-methoxy-1H-indole-2-carbonitrile;
5-{6-[2-(2-Cyano-7-fluoro-4-methoxy-indol-1-yl)-ethylamino]-pyrimidin-4-yl}-thiophene-2-carboxylic acid amide;
5-{6-[2-(2-Cyano-4-methoxy-indol-1-yl)-ethylamino]-pyrimidin-4-yl}-3-fluoro-thiophene-2-carboxylic acid;
5-{6-[2-(4-Chloro-2-cyano-6,7-difluoro-indol-1-yl)-ethylamino]-pyrimidin-4-yl}-3-fluoro-thiophene-2-carboxylic acid;

2-Butoxy-4-{6-[2-(2-cyano-7-fluoro-4-methoxy-indol-1-yl)-ethylamino]-pyrimidin-4-yl}-6-fluoro-benzoic acid;
2-Butoxy-6-chloro-4-{6-[2-(2-cyano-7-fluoro-4-methoxy-indol-1-yl)-ethylamino]-pyrimidin-4-yl}-benzoic acid;
2-Chloro-4-{6-[2-(2-cyano-7-fluoro-4-methoxy-indol-1-yl)-ethylamino]-pyrimidin-4-yl}-6-propoxy-benzoic acid;
4-{6-[2-(2-Cyano-7-fluoro-4-methoxy-indol-1-yl)-ethylamino]-pyrimidin-4-yl}-2-fluoro-6-propoxy-benzoic acid;
5-{6-[2-(4-Chloro-2-cyano-indol-1-yl)-ethylamino]-pyrimidin-4-yl}-3-ethoxy-thiophene-2-carboxylic acid;
5-{6-[2-(2-Cyano-4-methoxy-indol-1-yl)-ethylamino]-pyrimidin-4-yl}-3-trifluoromethyl-thiophene-2-carboxylic acid;
5-{6-[2-(4-Chloro-2-cyano-indol-1-yl)-ethylamino]-pyrimidin-4-yl}-3-trifluoromethyl-thiophene-2-carboxylic acid;
5-{6-[2-(4-Chloro-2-cyano-6,7-difluoro-indol-1-yl)-ethylamino]-pyrimidin-4-yl}-3-trifluoromethyl-thiophene-2-carboxylic acid;
2-Chloro-4-{6-[2-(2-cyano-7-fluoro-4-methoxy-indol-1-yl)-ethylamino]-pyrimidin-4-yl}-6-isobutoxy-benzoic acid;
(4-{6-[2-(4-Chloro-2-cyano-indol-1-yl)-ethylamino]-pyrimidin-4-yl}-2-ethoxy-phenylamino)-acetic acid;
(4-{6-[2-(4-Chloro-2-cyano-6,7-difluoro-indol-1-yl)-ethylamino]-pyrimidin-4-yl}-2-ethoxy-phenylamino)-acetic acid;
4-{6-[2-(2-Cyano-7-fluoro-4-methoxy-indol-1-yl)-ethylamino]-pyrimidin-4-yl}-2-difluoromethoxy-benzoic acid;
7-Fluoro-4-methoxy-1-{2-[6-(1-methyl-2-oxo-1,2,3,4-tetrahydro-quinazolin-7-yl)-pyrimidin-4-ylamino]-ethyl}-1H-indole-2-carbonitrile;
7-Fluoro-4-methoxy-1-{2-[6-(1-methyl-3-oxo-2,3-dihydro-1H-indazol-6-yl)-pyrimidin-4-ylamino]-ethyl}-1H-indole-2-carbonitrile;
3-{6-[2-(2-Cyano-7-fluoro-4-methoxy-indol-1-yl)-ethylamino]-pyrimidin-4-yl}-5-ethylsulfanyl-benzoic acid;
7-Fluoro-4-methoxy-1-(2-{6-[4-(3H-[1,2,3]triazol-4-yl)-phenyl]-pyrimidin-4-ylamino}-ethyl)-1H-indole-2-carbonitrile;
3-(3-{6-[2-(2-Cyano-7-fluoro-4-methoxy-indol-1-yl)-ethylamino]-pyrimidin-4-yl}-5-ethoxy-phenoxy)-propionic acid;
3-(4-{6-[2-(2-Cyano-7-fluoro-4-methoxy-indol-1-yl)-ethylamino]-pyrimidin-4-yl}-2-ethoxy-phenoxy)-propionic acid;
4-{6-[2-(2-Cyano-7-fluoro-4-methoxy-indol-1-yl)-ethylamino]-pyrimidin-4-yl}-2-ethoxy-3-fluoro-benzoic acid;
4-{6-[2-(2-Cyano-7-fluoro-4-methoxy-indol-1-yl)-ethylamino]-pyrimidin-4-yl}-2-ethoxy-benzenesulfonamide;
1-(2-{6-[3-Ethoxy-4-(3H-[1,2,3]triazol-4-yl)-phenyl]-pyrimidin-4-ylamino}-ethyl)-7-fluoro-4-methoxy-1H-indole-2-carbonitrile;
3-(5-{6-[2-(2-Cyano-7-fluoro-4-methoxy-indol-1-yl)-ethylamino]-pyrimidin-4-yl}-3-ethoxy-thiophen-2-yl)-propionic acid;
7-Fluoro-1-(2-{6-[4-(2-hydroxy-3,4-dioxo-cyclobut-1-enyl)-phenyl]-pyrimidin-4-ylamino}-ethyl)-4-methoxy-1H-indole-2-carbonitrile;
(4-{6-[2-(2-Cyano-7-fluoro-4-methoxy-indol-1-yl)-ethylamino]-pyrimidin-4-yl}-2-ethoxy-phenyl)-oxo-acetic acid;
4-{6-[2-(2-Cyano-7-fluoro-4-methoxy-indol-1-yl)-ethylamino]-pyrimidin-4-yl}-2-propylsulfanyl-benzoic acid;
4-{6-[2-(2-Cyano-6-fluoro-4-methoxy-indol-1-yl)-ethylamino]-pyrimidin-4-yl}-2-propylsulfanyl-benzoic acid;
4-{6-[2-(2-Cyano-7-fluoro-4-methoxy-indol-1-yl)-ethylamino]-pyrimidin-4-yl}-2-isopropylsulfanyl-benzoic acid;
4-{6-[2-(2-Cyano-6-fluoro-4-methoxy-indol-1-yl)-ethylamino]-pyrimidin-4-yl}-2-isopropylsulfanyl-benzoic acid;
4-{6-[2-(2-Cyano-7-fluoro-4-methoxy-indol-1-yl)-ethylamino]-pyrimidin-4-yl}-2-fluoro-6-propyl-benzoic acid;
5-{6-[2-(2-Cyano-5,7-difluoro-4-methyl-indol-1-yl)-ethylamino]-pyrimidin-4-yl}-3-ethoxy-thiophene-2-carboxylic acid;
5-{6-[2-(2-Cyano-6,7-difluoro-4-methyl-indol-1-yl)-ethylamino]-pyrimidin-4-yl}-3-ethoxy-thiophene-2-carboxylic acid;
5-{6-[2-(2-Cyano-6,7-difluoro-4-methoxy-indol-1-yl)-ethylamino]-pyrimidin-4-yl}-3-ethoxy-thiophene-2-carboxylic acid;
(4-{6-[2-(2-Cyano-6,7-difluoro-4-methoxy-indol-1-yl)-ethylamino]-pyrimidin-4-yl}-2-ethoxy-phenoxy)-acetic acid;
(4-{6-[2-(2-Cyano-6,7-difluoro-4-methoxy-indol-1-yl)-ethylamino]-pyrimidin-4-yl}-2-ethoxy-phenylamino)-acetic acid;
4-{6-[2-(2-Cyano-7-fluoro-4-methoxy-indol-1-yl)-ethylamino]-pyrimidin-4-yl}-2-propyl-benzoic acid;
4-{6-[2-(2-Cyano-7-fluoro-4-methoxy-indol-1-yl)-ethylamino]-pyrimidin-4-yl}-2-ethyl-benzoic acid;
4-{6-[2-(2-Cyano-7-fluoro-4-methoxy-indol-1-yl)-ethylamino]-pyrimidin-4-yl}-2-isobutoxy-benzoic acid;
4-{6-[2-(2-Cyano-7-fluoro-4-methoxy-indol-1-yl)-ethylamino]-pyrimidin-4-yl}-2-propoxy-benzoic acid;
4-{6-[2-(2-Cyano-7-fluoro-4-methyl-indol-1-yl)-ethylamino]-pyrimidin-4-yl}-2-ethylsulfanyl-benzoic acid;
4-{6-[2-(2-Cyano-4-methoxy-indol-1-yl)-ethylamino]-pyrimidin-4-yl}-2-ethylsulfanyl-benzoic acid;
4-{6-[2-(2-Cyano-7-fluoro-4-methoxy-indol-1-yl)-ethylamino]-pyrimidin-4-yl}-2-ethylsulfanyl-benzoic acid;
4-{6-[2-(2-Cyano-6-fluoro-4-methoxy-indol-1-yl)-ethylamino]-pyrimidin-4-yl}-2-ethylsulfanyl-benzoic acid;
4-{6-[2-(2-Cyano-6,7-difluoro-4-methoxy-indol-1-yl)-ethylamino]-pyrimidin-4-yl}-2-ethylsulfanyl-benzoic acid;
4-{6-[2-(2-Cyano-6,7-difluoro-4-methyl-indol-1-yl)-ethylamino]-pyrimidin-4-yl}-2-ethoxy-benzoic acid;
4-{6-[2-(2-Cyano-4-methoxy-indol-1-yl)-ethylamino]-pyrimidin-4-yl}-2-methylamino-benzoic acid;
2-{6-[2-(2-Cyano-7-fluoro-4-methoxy-indol-1-yl)-ethylamino]-pyrimidin-4-yl}-1H-indole-5-carboxylic acid;
7-Fluoro-1-{2-[6-(1H-indol-2-yl)-pyrimidin-4-ylamino]-ethyl}-4-methoxy-1H-indole-2-carbonitrile;
2-{6-[2-(2-Cyano-7-fluoro-4-methoxy-indol-1-yl)-ethylamino]-pyrimidin-4-yl}-1H-indole-5-carboxylic acid methyl ester;
7-Fluoro-1-(2-{6-[4-(2-hydroxy-ethoxy)-phenyl]-pyrimidin-4-ylamino}-ethyl)-4-methoxy-1H-indole-2-carbonitrile;
7-Fluoro-1-{2-[6-(1H-indol-6-yl)-pyrimidin-4-ylamino]-ethyl}-4-methoxy-1H-indole-2-carbonitrile;
7-Fluoro-4-methoxy-1-{2-[6-(1H-pyrrolo[2,3-c]pyridin-3-yl)-pyrimidin-4-ylamino]-ethyl}-1H-indole-2-carbonitrile;
7-Fluoro-1-{2-[6-(1H-indol-3-yl)-pyrimidin-4-ylamino]-ethyl}-4-methoxy-1H-indole-2-carbonitrile;
7-Fluoro-4-methoxy-1-{2-[6-(2-oxo-1,2,3,4-tetrahydro-quinazolin-6-yl)-pyrimidin-4-ylamino]-ethyl}-1H-indole-2-carbonitrile;
N-(4-{6-[2-(2-Cyano-7-fluoro-4-methoxy-indol-1-yl)-ethylamino]-pyrimidin-4-yl}-phenyl)-formamide;

7-Fluoro-4-methoxy-1-{2-[6-(2-oxo-2,3-dihydro-benzooxazol-6-yl)-pyrimidin-4-ylamino]-ethyl}-1H-indole-2-carbonitrile;

7-Fluoro-4-methoxy-1-{2-[6-(3-methyl-2-oxo-2,3-dihydro-benzooxazol-5-yl)-pyrimidin-4-ylamino]-ethyl}-1H-indole-2-carbonitrile;

7-Fluoro-1-{2-[6-(1H-indazol-5-yl)-pyrimidin-4-ylamino]-ethyl}-4-methoxy-1H-indole-2-carbonitrile;

7-Fluoro-4-methoxy-1-{2-[6-(1H-pyrrolo[2,3-b]pyridin-3-yl)-pyrimidin-4-ylamino]-ethyl}-1H-indole-2-carbonitrile;

7-Fluoro-4-methoxy-1-{2-[6-(1H-pyrrolo[2,3-b]pyridin-5-yl)-pyrimidin-4-ylamino]-ethyl}-1H-indole-2-carbonitrile;

7-Fluoro-4-methoxy-1-{2-[6-(1-methyl-1H-pyrrolo[2,3-b]pyridin-5-yl)-pyrimidin-4-ylamino]-ethyl}-1H-indole-2-carbonitrile;

1-(4-{6-[2-(2-Cyano-7-fluoro-4-methoxy-indol-1-yl)-ethylamino]-pyrimidin-4-yl}-2-methoxy-phenyl)-3-ethyl-urea;

1-{2-[6-(1H-Benzoimidazol-5-yl)-pyrimidin-4-ylamino]-ethyl}-7-fluoro-4-methoxy-1H-indole-2-carbonitrile;

1-{2-[6-(3H-Benzotriazol-5-yl)-pyrimidin-4-ylamino]-ethyl}-7-fluoro-4-methoxy-1H-indole-2-carbonitrile;

7-Fluoro-4-methoxy-1-{2-[6-(1-oxo-1,2,3,4-tetrahydro-isoquinolin-6-yl)-pyrimidin-4-ylamino]-ethyl}-1H-indole-2-carbonitrile;

1-{2-[6-(3-Ethoxy-4-formyl-phenyl)-pyrimidin-4-ylamino]-ethyl}-7-fluoro-4-methoxy-1H-indole-2-carbonitrile;

7-Fluoro-1-{2-[6-(1H-indol-5-yl)-pyrimidin-4-ylamino]-ethyl}-4-methoxy-1H-indole-2-carbonitrile;

4-{6-[2-(2-Cyano-7-fluoro-4-methoxy-indol-1-yl)-ethylamino]-pyrimidin-4-yl}-2-fluoro-benzoic acid methyl ester;

7-Fluoro-1-{2-[6-(4-hydroxy-3-trifluoromethyl-phenyl)-pyrimidin-4-ylamino]-ethyl}-4-methoxy-1H-indole-2-carbonitrile;

3-{6-[2-(2-Cyano-7-fluoro-4-methoxy-indol-1-yl)-ethylamino]-pyrimidin-4-yl}-5-ethoxy-benzoic acid;

5-{6-[2-(2-Cyano-7-fluoro-4-methoxy-indol-1-yl)-ethylamino]-pyrimidin-4-yl}-thiophene-3-carboxylic acid ethyl ester;

4-{6-[2-(2-Cyano-7-fluoro-4-methoxy-indol-1-yl)-ethylamino]-pyrimidin-4-yl}-2-methylamino-benzoic acid;

4-{6-[2-(5,7-Difluoro-2,4-dimethyl-indol-1-yl)-ethylamino]-pyrimidin-4-yl}-2-methylamino-benzoic acid;

3-(5-{6-[2-(7-Fluoro-4-methoxy-2-methyl-indol-1-yl)-ethylamino]-pyrimidin-4-yl}-3-isopropoxy-thiophen-2-yl)-propionic acid;

3-(3-Ethoxy-5-{6-[2-(7-fluoro-4-methoxy-2-methyl-indol-1-yl)-ethylamino]-pyrimidin-4-yl}-thiophen-2-yl)-propionic acid;

(E)-3-(3-Ethoxy-5-{6-[2-(7-fluoro-4-methoxy-2-methyl-indol-1-yl)-ethylamino]-pyrimidin-4-yl}-thiophen-2-yl)-acrylic acid;

4-{6-[2-(6-Fluoro-4-methoxy-2-methyl-indol-1-yl)-ethylamino]-pyrimidin-4-yl}-2-methylamino-benzoic acid;

3-Chloro-5-{6-[2-(4-chloro-2-cyano-indol-1-yl)-ethylamino]-pyrimidin-4-yl}-thiophene-2-carboxylic acid;

3-Chloro-5-{6-[2-(4-chloro-2-cyano-6,7-difluoro-indol-1-yl)-ethylamino]-pyrimidin-4-yl}-thiophene-2-carboxylic acid;

N-(3-Ethoxy-5-{6-[2-(7-fluoro-4-methoxy-2-methyl-indol-1-yl)-ethylamino]-pyrimidin-4-yl}-thiophene-2-carbonyl)-methanesulfonamide;

5-{6-[2-(2-Cyano-7-fluoro-4-methoxy-indol-1-yl)-ethylamino]-pyrimidin-4-yl}-3-ethoxy-thiophene-2-carboxylic acid ethylamide;

5-{6-[2-(2-Cyano-7-fluoro-4-methoxy-indol-1-yl)-ethylamino]-pyrimidin-4-yl}-3-ethoxy-thiophene-2-carboxylic acid dimethylamide;

5-{6-[2-(2-Cyano-7-fluoro-4-methoxy-indol-1-yl)-ethylamino]-pyrimidin-4-yl}-3-ethoxy-thiophene-2-carboxylic acid (2-hydroxy-ethyl)-amide;

5-{6-[2-(2-Cyano-7-fluoro-4-methoxy-indol-1-yl)-ethylamino]-pyrimidin-4-yl}-3-ethoxy-thiophene-2-carboxylic acid isopropylamide;

5-{6-[2-(2-Cyano-7-fluoro-4-methoxy-indol-1-yl)-ethylamino]-pyrimidin-4-yl}-3-ethoxy-thiophene-2-carboxylic acid (2-methoxy-ethyl)-amide;

5-(6-((2-(2-cyano-7-fluoro-4-methoxy-1H-indol-1-yl)ethyl)amino)pyrimidin-4-yl)-3-ethoxy-N-sulfamoylthiophene-2-carboxamide;

5-{6-[2-(2-Cyano-7-fluoro-4-methoxy-indol-1-yl)-ethylamino]-pyrimidin-4-yl}-3-ethoxy-thiophene-2-carboxylic acid hydroxyamide;

(3-Ethoxy-5-{6-[2-(7-fluoro-4-methoxy-2-methyl-indol-1-yl)-ethylamino]-pyrimidin-4-yl}-thiophen-2-yl)-methanol;

2-{6-[2-(7-Fluoro-4-methoxy-2-methyl-indol-1-yl)-ethylamino]-pyrimidin-4-yl}-4-isopropoxy-thiazole-5-carboxylic acid;

2-{6-[2-(7-Fluoro-4-methoxy-2-methyl-indol-1-yl)-ethylamino]-pyrimidin-4-yl}-4-methoxy-thiazole-5-carboxylic acid;

4-Ethoxy-2-{6-[2-(7-fluoro-4-methoxy-2-methyl-indol-1-yl)-ethylamino]-pyrimidin-4-yl}-thiazole-5-carboxylic acid;

2-{6-[2-(7-Fluoro-4-methoxy-2-methyl-indol-1-yl)-ethylamino]-pyrimidin-4-yl}-4-propoxy-thiazole-5-carboxylic acid;

2-{6-[2-(7-Fluoro-4-methoxy-2-methyl-indol-1-yl)-ethylamino]-pyrimidin-4-yl}-4-isobutyl-thiazole-5-carboxylic acid;

5-{6-[2-(2-Cyano-7-fluoro-4-methoxy-indol-1-yl)-ethylamino]-pyrimidin-4-yl}-3-ethoxy-thiophene-2-carboxylic acid carboxymethyl ester;

5-{6-[2-(2-Cyano-7-fluoro-4-methoxy-indol-1-yl)-ethylamino]-pyrimidin-4-yl}-3-ethoxy-thiophene-2-carboxylic acid dimethylcarbamoylmethyl ester;

5-{6-[2-(2-Cyano-7-fluoro-4-methoxy-indol-1-yl)-ethylamino]-pyrimidin-4-yl}-3-ethoxy-thiophene-2-carboxylic acid butyryloxymethyl ester;

5-{6-[2-(2-Cyano-7-fluoro-4-methoxy-indol-1-yl)-ethylamino]-pyrimidin-4-yl}-3-ethoxy-thiophene-2-carboxylic acid ethoxycarbonyloxymethyl ester;

5-{6-[2-(2-Cyano-7-fluoro-4-methoxy-indol-1-yl)-ethylamino]-pyrimidin-4-yl}-3-ethoxy-thiophene-2-carboxylic acid 5-methyl-2-oxo-[1,3]dioxol-4-ylmethyl ester;

5-{6-[2-(2-Cyano-7-fluoro-4-methoxy-indol-1-yl)-ethylamino]-pyrimidin-4-yl}-3-ethoxy-thiophene-2-carboxylic acid 2-dimethylamino-ethyl ester;

5-{6-[2-(2-Cyano-7-fluoro-4-methoxy-indol-1-yl)-ethylamino]-pyrimidin-4-yl}-3-ethoxy-thiophene-2-carboxylic acid phenyl ester;

(4-{6-[2-(2-Cyano-7-fluoro-4-methoxy-indol-1-yl)-ethylamino]-pyrimidin-4-yl}-2-methoxy-phenyl)-propynoic acid ethyl ester;

{6-[4-Ethoxy-5-(1H-tetrazol-5-yl)-thiophen-2-yl]-pyrimidin-4-yl}-[2-(7-fluoro-4-methoxy-2-methyl-indol-1-yl)-ethyl]-amine;

3-Ethoxy-5-{6-[2-(7-fluoro-4-methoxy-2-methyl-indol-1-yl)-ethylamino]-pyrimidin-4-yl}-N-hydroxy-thiophene-2-carboxamidine;

3-(3-Ethoxy-5-{6-[2-(7-fluoro-4-methoxy-2-methyl-indol-1-yl)-ethylamino]-pyrimidin-4-yl}-thiophen-2-yl)-[1,2,4]oxadiazol-5(4H)-one;

5-{6-[2-(3,7-Difluoro-4-methoxy-2-methyl-indol-1-yl)-ethylamino]-pyrimidin-4-yl}-3-ethoxy-thiophene-2-carboxylic acid;

[2-(7-Fluoro-4-methoxy-2-methyl-indol-1-yl)-ethyl]-{6-[5-(2H-tetrazol-5-yl)-4-trifluoromethyl-thiophen-2-yl]-pyrimidin-4-yl}-amine;

5-{6-[2-(7-Fluoro-4-methoxy-2-methyl-indol-1-yl)-ethylamino]-pyrimidin-4-yl}-N-hydroxy-3-trifluoromethyl-thiophene-2-carboxamidine;

3-(5-{6-[2-(7-Fluoro-4-methoxy-2-methyl-indol-1-yl)-ethylamino]-pyrimidin-4-yl}-3-trifluoromethyl-thiophen-2-yl)-[1,2,4]oxadiazol-5(4H)-one;

4-{6-[2-(2-Cyano-7-fluoro-4-methoxy-indol-1-yl)-ethylamino]-pyrimidin-4-yl}-2-ethoxy-N-hydroxy-benzamide;

5-(3-Ethoxy-5-{6-[2-(7-fluoro-4-methoxy-2-methyl-indol-1-yl)-ethylamino]-pyrimidin-4-yl}-thiophen-2-yl)-isoxazol-3-ol;

5-{6-[2-(7-Fluoro-4-methoxy-2-methyl-indol-1-yl)-ethylamino]-pyrimidin-4-yl}-3-pyridin-2-yl-thiophene-2-carboxylic acid;

[6-(4-Ethylamino-thiophen-2-yl)-pyrimidin-4-yl]-[2-(7-fluoro-2,4-dimethyl-indol-1-yl)-ethyl]-amine;

[6-(4-Ethylamino-thiophen-2-yl)-pyrimidin-4-yl]-[2-(6-fluoro-2,4-dimethyl-indol-1-yl)-ethyl]-amine;

[6-(4-Ethylamino-thiophen-2-yl)-pyrimidin-4-yl]-[2-(6-fluoro-4-methoxy-2-methyl-indol-1-yl)-ethyl]-amine;

N-Ethyl-N-(5-{6-[2-(7-fluoro-4-methoxy-2-methyl-indol-1-yl)-ethylamino]-pyrimidin-4-yl}-thiophen-3-yl)-formamide;

N-(3-Ethoxy-5-{6-[2-(7-fluoro-4-methoxy-2-methyl-indol-1-yl)-ethylamino]-pyrimidin-4-yl}-thiophen-2-yl)-formamide;

N-(3-Ethoxy-5-{6-[2-(7-fluoro-4-methoxy-2-methyl-indol-1-yl)-ethylamino]-pyrimidin-4-yl}-thiophen-2-yl)-propionamide;

N-(3-Ethoxy-5-{6-[2-(7-fluoro-4-methoxy-2-methyl-indol-1-yl)-ethylamino]-pyrimidin-4-yl}-thiophen-2-yl)-3-hydroxy-propionamide;

(3-Ethoxy-5-{6-[2-(7-fluoro-4-methoxy-2-methyl-indol-1-yl)-ethylamino]-pyrimidin-4-yl}-thiophen-2-yl)-urea; and 5-{6-[2-(2-Cyano-3,7-difluoro-4-methoxy-indol-1-yl)-ethylamino]-pyrimidin-4-yl}-3-trifluoromethyl-thiophene-2-carboxylic acid.

31) In addition to the preferred compounds listed in embodiment 28), further preferred compounds according to embodiment 1) are selected from the following compounds:

1-(3-Ethoxy-5-{6-[2-(7-fluoro-4-methoxy-2-methyl-indol-1-yl)-ethylamino]-pyrimidin-4-yl}-thiophen-2-yl)-ethanol;

(2-Ethoxy-4-{6-[2-(7-fluoro-4-methoxy-2-methyl-indol-1-yl)-ethylamino]-pyrimidin-4-yl}-phenylamino)-acetic acid methyl ester;

7-Fluoro-4-methoxy-1-{2-[6-(2-trifluoromethyl-pyridin-4-yl)-pyrimidin-4-ylamino]-ethyl}-1H-indole-2-carbonitrile;

3-{6-[2-(2-Cyano-7-fluoro-4-methoxy-indol-1-yl)-ethylamino]-pyrimidin-4-yl}-5-methoxy-benzoic acid;

7-Fluoro-4-methoxy-1-{2-[6-(2-oxo-2,3-dihydro-1H-benzoimidazol-5-yl)-pyrimidin-4-ylamino]-ethyl}-1H-indole-2-carbonitrile;

4-{6-[2-(2-Cyano-7-fluoro-4-methoxy-indol-1-yl)-ethylamino]-pyrimidin-4-yl}-N-(2-methoxy-ethyl)-benzamide;

7-Fluoro-1-[2-(6-imidazo[1,2-a]pyridin-6-yl-pyrimidin-4-ylamino)-ethyl]-4-methoxy-1H-indole-2-carbonitrile;

7-Fluoro-1-{2-[6-(2-oxo-2,3-dihydro-1H-benzo[d]imidazol-5-yl)-pyrimidin-4-ylamino]-ethyl}-4-methoxy-1H-indole-2-carbonitrile;

1-{2-[6-(2-Cyclopropyl-pyridin-4-yl)-pyrimidin-4-ylamino]-ethyl}-7-fluoro-4-methoxy-1H-indole-2-carbonitrile;

1-{2-[6-(2-Azetidin-1-yl-pyridin-4-yl)-pyrimidin-4-ylamino]-ethyl}-7-fluoro-4-methoxy-1H-indole-2-carbonitrile;

4-{6-[2-(2-Cyano-7-fluoro-4-methoxy-indol-1-yl)-ethylamino]-pyrimidin-4-yl}-benzoic acid;

7-Fluoro-4-methoxy-1-{2-[6-(2-methyl-3-oxo-2,3-dihydro-1H-indazol-6-yl)-pyrimidin-4-ylamino]-ethyl}-1H-indole-2-carbonitrile;

7-Fluoro-4-methoxy-1-{2-[6-(3-methoxy-1H-indazol-6-yl)-pyrimidin-4-ylamino]-ethyl}-1H-indole-2-carbonitrile;

(4-{6-[2-(4-Chloro-2-cyano-6,7-difluoro-indol-1-yl)-ethylamino]-pyrimidin-4-yl}-2-ethoxy-phenoxy)-acetic acid;

5-{6-[2-(4-Chloro-2-cyano-indol-1-yl)-ethylamino]-pyrimidin-4-yl}-3-fluoro-thiophene-2-carboxylic acid;

5-{6-[2-(2-Cyano-7-fluoro-indol-1-yl)-ethylamino]-pyrimidin-4-yl}-3-fluoro-thiophene-2-carboxylic acid;

(4-{6-[2-(2-Cyano-5,6-difluoro-4-methyl-indol-1-yl)-ethylamino]-pyrimidin-4-yl}-2-ethoxy-phenylamino)-acetic acid;

5-{6-[2-(7-Chloro-5-fluoro-4-methoxy-2-methyl-indol-1-yl)-ethylamino]-pyrimidin-4-yl}-3-ethoxy-thiophene-2-carboxylic acid;

2-Butoxy-4-{6-[2-(6-chloro-7-fluoro-4-methoxy-2-methyl-indol-1-yl)-ethylamino]-pyrimidin-4-yl}-benzoic acid;

5-{6-[2-(4,7-Dichloro-5-fluoro-2-methyl-indol-1-yl)-ethylamino]-pyrimidin-4-yl}-3-ethoxy-thiophene-2-carboxylic acid;

(2-Ethoxy-4-{6-[2-(6-fluoro-4-methoxy-2-methyl-indol-1-yl)-ethylamino]-pyrimidin-4-yl}-phenylamino)-acetic acid;

5-{6-[2-(2-Cyano-7-fluoro-indol-1-yl)-ethylamino]-pyrimidin-4-yl}-3-trifluoromethyl-thiophene-2-carboxylic acid;

5-{6-[2-(4,6-Dichloro-2-cyano-indol-1-yl)-ethylamino]-pyrimidin-4-yl}-3-trifluoromethyl-thiophene-2-carboxylic acid;

5-{6-[2-(4,6-Dichloro-2-cyano-indol-1-yl)-ethylamino]-pyrimidin-4-yl}-3-fluoro-thiophene-2-carboxylic acid;

[6-(3-Ethoxy-4-oxazol-2-yl-phenyl)-pyrimidin-4-yl]-[2-(7-fluoro-4-methoxy-2-methyl-indol-1-yl)-ethyl]-amine; and (2-Chloro-4-{6-[2-(2-cyano-7-fluoro-4-methoxy-indol-1-yl)-ethylamino]-pyrimidin-4-yl}-phenoxy)-acetic acid.

The compounds of formula (I) according to embodiments 1) to 31) and their pharmaceutically acceptable salts can be used as medicaments, e.g. in the form of pharmaceutical compositions for enteral (such especially oral e.g. in form of a tablet or a capsule) or parenteral administration (including topical application or inhalation).

The production of the pharmaceutical compositions can be effected in a manner which will be familiar to any person skilled in the art (see for example Remington, *The Science*

*and Practice of Pharmacy,* 21st Edition (2005), Part 5, "Pharmaceutical Manufacturing" [published by Lippincott Williams & Wilkins]) by bringing the described compounds of formula (I) or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

The present invention also relates to a method for the prevention/prophylaxis or treatment of a disease or disorder mentioned herein comprising administering to a subject a pharmaceutically active amount of a compound of formula (I) according to embodiments 1) to 31).

In a preferred embodiment of the invention, the administered amount is comprised between 1 mg and 2000 mg per day, particularly between 5 mg and 1000 mg per day, more particularly between 25 mg and 500 mg per day, especially between 50 mg and 200 mg per day.

Whenever the word "between" is used to describe a numerical range, it is to be understood that the end points of the indicated range are explicitly included in the range. For example: if a temperature range is described to be between 40° C. and 80° C., this means that the end points 40° C. and 80° C. are included in the range; or if a variable is defined as being an integer between 1 and 4, this means that the variable is the integer 1, 2, 3, or 4.

Unless used regarding temperatures, the term "about" placed before a numerical value "X" refers in the current application to an interval extending from X minus 10% of X to X plus 10% of X, and preferably to an interval extending from X minus 5% of X to X plus 5% of X. In the particular case of temperatures, the term "about" placed before a temperature "Y" refers in the current application to an interval extending from the temperature Y minus 10° C. to Y plus 10° C., and preferably to an interval extending from Y minus 5° C. to Y plus 5° C.

For avoidance of any doubt, if compounds are described as useful for the prevention/prophylaxis or treatment of certain diseases, such compounds are likewise suitable for use in the preparation of a medicament for the prevention/prophylaxis or treatment of said diseases. Likewise, such compounds are also suitable in a method for the prevention/prophylaxis or treatment of such diseases, comprising administering to a subject (mammal, especially human) in need thereof, an effective amount of such compound.

The compounds of formula (I) according to embodiments 1) to 31) are useful for the prevention/prophylaxis or treatment of disorders relating to the EP2 and/or EP4 receptors.

Certain compounds of formula (I) according to embodiments 1) to 31) exhibit their biological activity as modulators of the prostaglandin 2 receptors EP2 and/or EP4 in a biological environment, (i.e. in the presence of one or more enzymes capable of breaking a covalent bond linked to a carbonyl group such as an amidase, an esterase or any suitable equivalent thereof capable of removing a prodrug group from a carboxylic acid group.

Diseases or disorders relating to the EP2 and/or EP4 receptors are especially cancer (notably melanoma including metastatic melanoma; lung cancer including non-small cell lung cancer; bladder cancer including urinary bladder cancer, urothelial cell carcinoma; renal carcinomas including renal cell carcinoma, metastatic renal cell carcinoma, metastatic renal clear cell carcinoma; gastro-intestinal cancers including colorectal cancer, metastatic colorectal cancer, familial adenomatous polyposis (FAP), oesophageal cancer, gastric cancer, gallbladder cancer, cholangiocarcinoma, hepatocellular carcinoma, and pancreatic cancer such as pancreatic adenocarcinoma or pancreatic ductal carcinoma; endometrial cancer; ovarian cancer; cervical cancer; neuroblastoma; prostate cancer including castrate-resistant prostate cancer; brain tumors including brain metastases, malignant gliomas, glioblastoma multiforme, medulloblastoma, meningiomas; breast cancer including triple negative breast carcinoma; oral tumors; nasopharyngeal tumors; thoracic cancer; head and neck cancer; leukemias including acute myeloid leukemia, adult T-cell leukemia; carcinomas; adenocarcinomas; thyroid carcinoma including papillary thyroid carcinoma; choriocarcinoma; Ewing's sarcoma; osteosarcoma; rhabdomyosarcoma; Kaposi's sarcoma; lymphoma including Burkitt's lymphoma, Hodgkin's lymphoma, MALT lymphoma; multiple myelomas; and virally induced tumors; especially melanoma; lung cancer; bladder cancer; renal carcinomas; gastro-intestinal cancers; endometrial cancer; ovarian cancer; cervical cancer; and neuroblastoma);

as well as further diseases or disorders relating to the EP2 and/or EP4 receptors such as:

pain (notably inflammatory pain and painful menstruation);

endometriosis;

autosomal dominant polycystic kidney disease;

acute ischemic syndromes in atherosclerotic patients;

pneumonia; and neurodegenerative diseases including amyotrophic lateral sclerosis, stroke; Parkinson disease, Alzheimer's disease and HIV associated dementia;

and EP2 and/or EP4 antagonists may further be used to control female fertility.

Further diseases or disorders relating to the EP2 and/or EP4 receptors are autoimmune disorders such as especially multiple sclerosis, rheumatoid arthritis and osteoarthritis; and osteoporosis.

The compounds of formula (I) according to any one of embodiments 1) to 31) are in particular useful as therapeutic agents for the prevention/prophylaxis or treatment of a cancer. They can be used as single therapeutic agents or in combination with one or more chemotherapy agents and/or radiotherapy and/or targeted therapy. Such combined treatment may be effected simultaneously, separately, or over a period of time.

The invention, thus, also relates to pharmaceutical compositions comprising a pharmaceutically acceptable carrier material, and:

a compound of formula (I) according to any one of embodiments 1) to 31);

and one or more cytotoxic chemotherapy agents.

The invention, thus, further relates to a kit comprising a pharmaceutical composition, said composition comprising a pharmaceutically acceptable carrier material, and:

a compound of formula (I) according to any one of embodiments 1) to 31);

and instructions how to use said pharmaceutical composition for the prevention/prophylaxis or the treatment of a cancer, in combination with chemotherapy and/or radiotherapy and/or targeted therapy.

The terms "radiotherapy" or "radiation therapy" or "radiation oncology", refer to the medical use of ionizing radiation in the prevention/prophylaxis (adjuvant therapy) and/or treatment of cancer; including external and internal radiotherapy.

The term "targeted therapy" refers to the prevention/prophylaxis (adjuvant therapy) and/or treatment of cancer with one or more anti-neoplastic agents such as small molecules or antibodies which act on specific types of cancer cells or stromal cells. Some targeted therapies block the action of certain enzymes, proteins, or other molecules involved in the growth and spread of cancer cells. Other types of targeted therapies help the immune system kill cancer cells (immunotherapies); or inhibit angiogenesis, the growth and formation of new blood vessels in the tumor; or deliver toxic substances directly to cancer cells and kill them. An example of a targeted therapy which is in particular suitable to be combined with the compounds of the present invention is immunotherapy, especially immunotherapy targeting the programmed cell death receptor 1 (PD-1 receptor) or its ligand PD-L1 (Zelenay et al., 2015, Cell 162, 1-14; Yongkui Li et al., Oncoimmunology 2016, 5(2):e1074374).

When used in combination with the compounds of formula (I), the term "targeted therapy" especially refers to agents such as:

a) Epidermal growth factor receptor (EGFR) inhibitors or blocking antibodies (for example Gefitinib, Erlotinib, Afatinib, Icotinib, Lapatinib, Panitumumab, Zalutumumab, Nimotuzumab, Matuzumab and Cetuximab);

b) RAS/RAF/MEK pathway inhibitors (for example Vemurafenib, Sorafenib, Dabrafenib, GDC-0879, PLX-4720, LGX818, RG7304, Trametinib (GSK1120212), Cobimetinib (GDC-0973/XL518), Binimetinib (MEK162, ARRY-162), Selumetinib (AZD6244));

c) Aromatase inhibitors (for example Exemestane, Letrozole, Anastrozole, Vorozole, Formestane, Fadrozole);

d) Angiogenesis inhibitors, especially VEGF signalling inhibitors such as Bevacuzimab (Avastin), Ramucirumab, Sorafenib or Axitinib;

e) Immune Checkpoint inhibitors (for example: anti-PD1 antibodies such as Pembrolizumab (Lambrolizumab, MK-3475), Nivolumab, Pidilizumab (CT-011), AMP-514/MED10680, PDR001, SHR-1210; REGN2810, BGBA317; fusion proteins targeting PD-1 such as AMP-224; small molecule anti-PD1 agents such as for example compounds disclosed in WO2015/033299, WO2015/044900 and WO2015/034820; anti-PD1L antibodies, such as BMS-936559, atezolizumab (MPDL3280A, RG7446), MED14736, avelumab (MSB0010718C), durvalumab (MED14736); anti-PDL2 antibodies, such as AMP224; anti-CTLA-4 antibodies, such as ipilimumab, tremilmumab; anti-Lymphocyte-activation gene 3 (LAG-3) antibodies, such as BMS-986016, IMP701, MK-4280, ImmuFact IMP321; anti T cell immunoglobulin mucin-3 (TIM-3) antibodies, such as MBG453; anti-CD137/4-1BB antibodies, such as BMS-663513/urelumab, PF-05082566; anti T cell immunoreceptor with Ig and ITIM domains (TIGIT) antibodies, such as RG6058 (anti-TIGIT, MTIG7192A);

f) Vaccination approaches (for example dendritic cell vaccination, peptide or protein vaccination (for example with gp100 peptide or MAGE-A3 peptide);

g) Re-introduction of patient derived or allogenic (non-self) cancer cells genetically modified to secrete immunomodulatory factors such as granulocyte monocyte colony stimulating factor (GMCSF) gene-transfected tumor cell vaccine (GVAX) or Fms-related tyrosine kinase 3 (Flt-3) ligand gene-transfected tumor cell vaccine (FVAX), or Toll like receptor enhanced GM-CSF tumor based vaccine (TEGVAX);

h) T-cell based adoptive immunotherapies, including chimeric antigen receptor (CAR) engineered T-cells (for example CTL019);

i) Cytokine or immunocytokine based therapy (for example Interferon alpha, interferon beta, interferon gamma, interleukin 2, interleukin 15);

j) Toll-like receptor (TLR) agonists (for example resiquimod, imiquimod, glucopyranosyl lipid A, CpG oligodesoxynucleotides);

k) Thalidomide analogues (for example Lenalidomide, Pomalidomide);

l) Indoleamin-2,3-Dioxgenase (IDO) and/or Tryptophane-2,3-Dioxygenase (TDO) inhibitors (for example RG6078/NLG919/GDC-0919; Indoximod/1MT (1-methyltryptophan), INCB024360/Epacadostat, PF-06840003 (EOS200271), F001287);

m) Activators of T-cell co-stimulatory receptors (for example anti-OX40/CD134 (Tumor necrosis factor receptor superfamily, member 4, such as RG7888 (MOXR0916), 9B12; MED16469, GSK3174998, MED10562), anti OX40-Ligand/CD252; anti-glucocorticoid-induced TNFR family related gene (GITR) (such as TRX518, MED11873, MK-4166, BMS-986156), anti-CD40 (TNF receptor superfamily member 5) antibodies (such as Dacetuzumab (SGN-40), HCD122, CP-870,893, RG7876, ADC-1013, APX005M, SEA-CD40); anti-CD40-Ligand antibodies (such as BG9588); anti-CD27 antibodies such as Varlilumab);

n) Molecules binding a tumor specific antigen as well as a T-cell surface marker such as bispecific antibodies (for example RG7802 targeting CEA and CD3) or antibody fragments, antibody mimetic proteins such as designed ankyrin repeat proteins (DARPINS), bispecific T-cell engager (BITE, for example AMG103, AMG330);

o) Antibodies or small molecular weight inhibitors targeting colony-stimulating factor-1 receptor (CSF-1R) (for example Emactuzumab (RG7155), Cabiralizumab (FPA-008), PLX3397);

p) Agents targeting immune cell check points on natural killer cells such as antibodies against Killer-cell immunoglobulin-like receptors (KIR) for example Lirilumab (IPH2102/BMS-986015);

q) Agents targeting the Adenosine receptors or the ectonucleases CD39 and CD73 that convert ATP to Adenosine, such as MED19447 (anti-CD73 antibody), PBF-509; CPI-444 (Adenosine A2a receptor antagonist).

When used in combination with the compounds of formula (I), immune checkpoint inhibitors such as those listed under d), and especially those targeting the programmed cell death receptor 1 (PD-1 receptor) or its ligand PD-L1, are preferred.

The term "chemotherapy" refers to the treatment of cancer with one or more cytotoxic anti-neoplastic agents ("cytotoxic chemotherapy agents"). Chemotherapy is often used in conjunction with other cancer treatments, such as radiation therapy or surgery. The term especially refers to conventional cytotoxic chemotherapeutic agents which act by killing cells that divide rapidly, one of the main properties of most cancer cells. Chemotherapy may use one drug at a time (single-agent chemotherapy) or several drugs at once (combination chemotherapy or polychemotherapy). Chemotherapy using drugs that convert to cytotoxic activity only upon light exposure is called photochemotherapy or photodynamic therapy.

The term "cytotoxic chemotherapy agent" or "chemotherapy agent" as used herein refers to an active antineoplastic agent inducing apoptosis or necrotic cell death. When used in combination with the compounds of formula (I), the term especially refers to conventional cytotoxic chemotherapy agents such as:

a) alkylating agents (for example mechlorethamine, chlorambucil, cyclophosphamide, ifosfamide, streptozocin, carmustine, lomustine, melphalan, dacarbazine, temozolomide, fotemustine, thiotepa or altretamine; especially cyclophosphamide, carmustine, melphalan, dacarbazine, or temozolomide);

b) platinum drugs (especially cisplatin, carboplatin or oxaliplatin);

c) antimetabolite drugs (for example 5-fluorouracil, folic acid/leucovorin, capecitabine, 6-mercaptopurine, methotrexate, gemcitabine, cytarabine, fludarabine or pemetrexed; especially 5-fluorouracil, folic acid/leucovorin, capecitabine, methotrexate, gemcitabine or pemetrexed);

d) anti-tumor antibiotics (for example daunorubicin, doxorubicin, epirubicin, idarubicin, actinomycin-D, bleomycin, mitomycin-C or mitoxantrone; especially doxorubicin);

e) mitotic inhibitors (for example paclitaxel, docetaxel, ixabepilone, vinblastine, vincristine, vinorelbine, vindesine or estramustine; especially paclitaxel, docetaxel, ixabepilone or, vincristine); or f) topoisomerase inhibitors (for example etoposide, teniposide, topotecan, irinotecan, diflomotecan or elomotecan; especially etoposide or irinotecan).

When used in combination with the compounds of formula (I), preferred cytotoxic chemotherapy agents are the above-mentioned alkylating agents (notably fotemustine, cyclophosphamide, ifosfamide, carmustine, dacarbazine and prodrugs thereof such as especially temozolomide or pharmaceutically acceptable salts of these compounds; in particular temozolomide); mitotic inhibitors (notably paclitaxel, docetaxel, ixabepilone; or pharmaceutically acceptable salts of these compounds; in particular paclitaxel); platinum drugs (notably cisplatin, oxaliplatin and carboplatin); as well etoposide and gemcitabine.

Chemotherapy may be given with a curative intent or it may aim to prolong life or to palliate symptoms.

Combined modality chemotherapy is the use of drugs with other cancer treatments, such as radiation therapy or surgery.

Induction chemotherapy is the first line treatment of cancer with a chemotherapeutic drug. This type of chemotherapy is used for curative intent.

Consolidation chemotherapy is the given after remission in order to prolong the overall disease free time and improve overall survival. The drug that is administered is the same as the drug that achieved remission.

Intensification chemotherapy is identical to consolidation chemotherapy but a different drug than the induction chemotherapy is used.

Combination chemotherapy involves treating a patient with a number of different drugs simultaneously. The drugs differ in their mechanism and side effects. The biggest advantage is minimising the chances of resistance developing to any one agent. Also, the drugs can often be used at lower doses, reducing toxicity.

Neoadjuvant chemotherapy is given prior to a local treatment such as surgery, and is designed to shrink the primary tumor. It is also given to cancers with a high risk of micrometastatic disease.

Adjuvant chemotherapy is given after a local treatment (radiotherapy or surgery). It can be used when there is little evidence of cancer present, but there is risk of recurrence. It is also useful in killing any cancerous cells that have spread to other parts of the body. These micrometastases can be treated with adjuvant chemotherapy and can reduce relapse rates caused by these disseminated cells.

Maintenance chemotherapy is a repeated low-dose treatment to prolong remission.

Salvage chemotherapy or palliative chemotherapy is given without curative intent, but simply to decrease tumor load and increase life expectancy. For these regimens, a better toxicity profile is generally expected.

"Simultaneously", when referring to an administration type, means in the present application that the administration type concerned consists in the administration of two or more active ingredients and/or treatments at approximately the same time; wherein it is understood that a simultaneous administration will lead to exposure of the subject to the two or more active ingredients and/or treatments at the same time. When administered simultaneously, said two or more active ingredients may be administered in a fixed dose combination, or in an equivalent non-fixed dose combination (e.g. by using two or more different pharmaceutical compositions to be administered by the same route of administration at approximately the same time), or by a non-fixed dose combination using two or more different routes of administration; wherein said administration leads to essentially simultaneous exposure of the subject to the two or more active ingredients and/or treatments. For example, when used in combination with chemotherapy and/or suitable targeted therapy, the present EP2/EP4 antagonists would possibly be used "simultaneously".

"Fixed dose combination", when referring to an administration type, means in the present application that the administration type concerned consists in the administration of one single pharmaceutical composition comprising the two or more active ingredients.

"Separately", when referring to an administration type, means in the present application that the administration type concerned consists in the administration of two or more active ingredients and/or treatments at different points in time; wherein it is understood that a separate administration will lead to a treatment phase (e.g. at least 1 hour, notably at least 6 hours, especially at least 12 hours) where the subject is exposed to the two or more active ingredients and/or treatments at the same time; but a separate administration may also lead to a treatment phase where for a certain period of time (e.g. at least 12 hours, especially at least one day) the subject is exposed to only one of the two or more active ingredients and/or treatments. Separate administration especially refers to situations wherein at least one of the active ingredients and/or treatments is given with a periodicity substantially different from daily (such as once or twice daily) administration (e.g. wherein one active ingredient and/or treatment is given e.g. once or twice a day, and another is given e.g. every other day, or once a week or at even longer distances). For example, when used in combination with radiotherapy, the present EP2/EP4 antagonists would possibly be used "separately".

By administration "over a period of time" is meant in the present application the subsequent administration of two or more active ingredients and/or treatments at different times. The term in particular refers to an administration method according to which the entire administration of one of the active ingredients and/or treatments is completed before the administration of the other/the others begins. In this way it is possible to administer one of the active ingredients and/or treatments for several months before administering the other active ingredient(s) and/or treatment(s).

Administration "over a period of time" also encompasses situations wherein the compound of formula (I) would be used in a treatment that starts after termination of an initial chemotherapeutic (for example an induction chemotherapy) and/or radiotherapeutic treatment and/or targeted therapy treatment, wherein optionally said treatment would be in combination with a further/an ongoing chemotherapeutic and/or radiotherapeutic treatment and/or targeted therapy treatment (for example in combination with a consolidation chemotherapy, an intensification chemotherapy, an adjuvant chemotherapy, or a maintenance chemotherapy; or radiotherapeutic equivalents thereof); wherein such further/ongoing chemotherapeutic and/or radiotherapeutic treatment and/or targeted therapy treatment would be simultaneously, separately, or over a period of time in the sense of "not given with the same periodicity".

The compounds of formula (I) as defined in embodiments 1) to 31) are also useful in a method of modulating an immune response in a subject having a tumor, comprising the administration of an effective amount of the compound of formula (I); wherein said effective amount reactivates the immune system in the tumor of said subject; wherein especially said effective amount:
  counteracts the polarization of tumor-associated macrophages towards tumor-promoting M2 macrophages; and/or
  down-regulates the activation, expansion and/or the effector function of immunosuppressive cells that have accumulated in a tumor (especially of regulatory T cells (Tregs) and/or myeloid derived suppressor cells (MDSC)); and/or
  up-regulates IFN-γ and/or TNF-α and/or IL-12 and/or IL-2 expression in immune cells such as natural killer cells, T-cells, dendritic cells and macrophages (leading to the induction of tumor cell apoptosis and/or restrained tumorigenesis); and/or
  directly or indirectly counteracts the suppressed activation, IL-2 responsiveness and expansion of cytotoxic T-cells (thereby decreasing local immunosuppression).

The compounds of formula (I) as defined in embodiments 1) to 31) are also useful in a method of diminishing tumor growth and/or reducing tumor size in a subject having a tumor, comprising the administration of an effective amount of the compound of formula (I); wherein said effective amount down-regulates tumor angiogenesis (especially by decreasing endothelial cell motility and/or survival, and/or by decreasing the expression of VEGF (vascular endothelial growth factor)); and/or wherein said effective amount diminishes tumor cell survival and/or induces tumor cell apoptosis (especially via inhibition of PI3K/AKT and MAPK signalling).

The compounds of formula (I) as defined in embodiments 1) to 31) are also useful in a method of modulating an immune response in a subject having a tumor, comprising the administration of an effective amount of the compound of formula (I); wherein said effective amount reactivates the immune system in the tumor of said subject; wherein said effective amount activates the cytotoxicity and cytokine production of natural killer cells and/or cytotoxic T-cells.

Besides, any preferences and (sub-)embodiments indicated for the compounds of formula (I) (whether for the compounds themselves, salts thereof, compositions containing the compounds or salts thereof, or uses of the compounds or salts thereof, etc.) apply mutatis mutandis to compounds of formula (II) and formula (III).

Preparation of Compounds of Formula (I)

The compounds of formula (I) can be prepared by well-known literature methods, by the methods given below, by the methods given in the experimental part below or by analogous methods. Optimum reaction conditions may vary with the particular reactants or solvents used, but such conditions can be determined by a person skilled in the art by routine optimisation procedures. In some cases the order of carrying out the following reaction schemes, and/or reaction steps, may be varied to facilitate the reaction or to avoid unwanted reaction products. In the general sequence of reactions outlined below, the generic groups $R^1$, $R^2$, $R^3$, $R^{4a}$, $R^{4b}$, $R^{5a}$, $R^{5b}$ and $Ar^1$ are as defined for formula (I). Other abbreviations used herein are explicitly defined, or are as defined in the experimental section. In some instances the generic groups $R^1$, $R^2$, $R^3$, $R^{4a}$, $R^{4b}$, $R^{5a}$, $R^{5b}$ and $Ar^1$ might be incompatible with the assembly illustrated in the schemes below and so will require the use of protecting groups (PG). The use of protecting groups is well known in the art (see for example "Protective Groups in Organic Synthesis", T. W. Greene, P. G. M. Wuts, Wiley-Interscience, 1999). For the purposes of this discussion, it will be assumed that such protecting groups as necessary are in place. In some cases the final product may be further modified, for example, by manipulation of substituents to give a new final product. These manipulations may include, but are not limited to, reduction, oxidation, alkylation, acylation, hydrolysis and transition-metal catalysed cross-coupling reactions which are commonly known to those skilled in the art. The compounds obtained may also be converted into salts, especially pharmaceutically acceptable salts, in a manner known per se.

Compounds of formula (I) of the present invention can be prepared according to the general sequence of reactions outlined below.

Generally, compounds of Formula (I) can be obtained by reaction of a compound of Structure (2), wherein X is a chlorine, a bromine or an iodine, with a compound of Structure (3), wherein M represents a boronic acid or a boronic ester, in a typical Suzuki cross-coupling reaction, in the presence of a base such as $K_2CO_3$, $Cs_2CO_3$, $Na_2CO_3$, $K_3PO_4$, or CsF and a catalyst such as $Pd(PPh_3)_4$, $PdCl_2$(dppf) or $Pd(OAc)_2$, in a solvent like ethanol, THF, water, or mixtures thereof, typically at elevated temperatures. Alternatively, a Negishi cross-coupling reaction can be performed, when M represents a zinc halide, with a catalyst such as $Pd(PPh_3)_4$, in a solvent such as THF or DMF, at RT or at elevated temperatures. A Stille cross-coupling reaction can also be carried out, when M represents a tin residue, typically trimethyltin or tributyltin, with a catalyst such as $Pd(PPh_3)_4$, in a solvent like THF, dioxane or DMF, at RT or elevated temperatures.

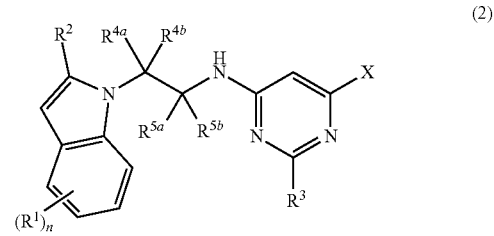

(2)

$$M—Ar^1 \quad (3)$$

Alternatively, compounds of Formula (I) can be obtained by Stille coupling of a compound of structure (4), wherein $R^{Sn}$ is typically methyl or n-butyl, with a compound of structure (5), wherein X is iodine, bromine or chlorine, in the presence of a catalyst such as $Pd(PPh_3)_4$, in a solvent like THF, dioxane or DMF, at RT or elevated temperatures.

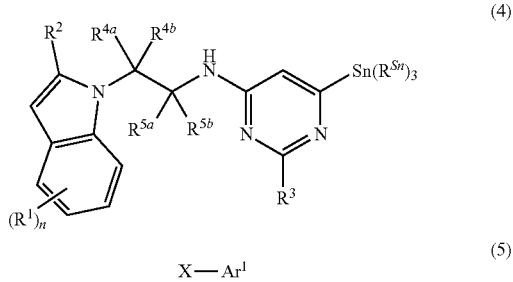

(4)

$$X—Ar^1 \quad (5)$$

Compounds of formula (2) can be formed by a nucleophilic aromatic substitution of compound of structure (6), wherein X represents Cl, Br or I, and Y represents Cl, Br, I or F, with a compound of structure (7), in the presence of a base such as TEA, DIPEA or $K_2CO_3$, in a solvent such as isopropanol, butanol, DMF or THF, at RT or at elevated temperatures.

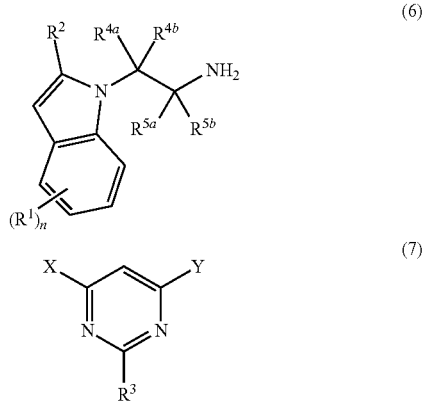

(6)

(7)

Compounds of formula (3) can be obtained from commercial sources, or synthesized by methods described in the literature, or by methods known by a person skilled in the art. A boronic acid derivative can be formed by the Miyaura borylation reaction, by cross-coupling of bis(pinacolato) diboron with aryl halides or triflates, in the presence of a base such as potassium acetate and a catalyst such as $PdCl_2(dppf)$. Alternatively, a boronic acid derivative can be formed by a lithiation/borylation sequence, typically at low temperatures, using butyllithium or lithium diisopropylamide as the base, and tri-isopropylborate or isopropoxyboronic acid pinacol ester, in a solvent such as diethyl ether or THF.

Compounds of formula (4) can be formed by reacting a compound of formula (2) with a stannane derivative such as hexamethyltin or hexabutyltin, in the presence of a catalyst such as $PdCl_2(PPh_3)_2$, sometimes with a ligand such as triphenylarsine, in a solvent such as dioxane, typically at elevated temperatures.

Compounds of formula (5) can be obtained from commercial sources, or synthesized by methods described in the literature, or by methods known by a person skilled in the art.

Compounds of formula (6) can be obtained by the reaction of an indole of formula (8) with a compound of structure (9), wherein X is a chlorine or a bromine, with a base like sodium hydroxide, in presence of a phase-transfer agent like tetrabutyl ammonium hydrogen sulfate, in a solvent like toluene, at RT or at elevated temperatures.

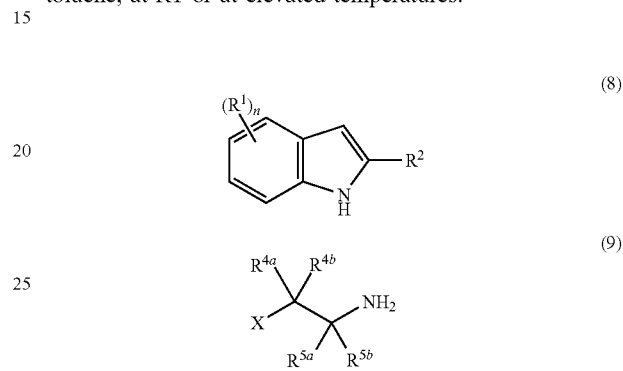

(8)

(9)

Alternatively, the amino group in compounds of formula (9) can be protected, for example with a tert-butyloxycarbonyl group, or as a phthalimide. X can then be a leaving group such as chlorine, bromine, iodine, mesylate, tosylate or triflate group. The reaction with the indole of formula (8) can be carried out in presence of a base such as NaH, in a solvent such as DMF, at low temperatures, or at RT or at elevated temperatures. Subsequent deprotection of the amino group to afford compounds of formula (6) can be carried with an acid such as 4N HCl in dioxane or TFA in a solvent like DCM in the case of a tert-butyloxycarbonyl protecting group, with hydrazine in a solvent like methanol or ethanol in the case of a phthalimide protecting group.

Indole compounds of formula (8) can be obtained from commercial sources, or synthesized by methods described in the literature, or by methods known by a person skilled in the art.

When $R^2$ is a nitrile, the following sequence can be applied (scheme 1). The nitrile moiety can be formed by dehydration of the corresponding primary amide (8-c), by using for instance cyanuric chloride in a solvent such as DMF, at low temperatures or at RT, or at elevated temperatures. The primary amide of formula (8-c) can be formed by reacting the corresponding carboxylic acid of formula (8-b) with a reagent such as thionyl chloride or oxalyl chloride, in a solvent such as DCM, eventually with a catalytic amount of DMF, at low temperatures, or at RT, or at elevated temperatures, and then reacting the intermediate acid chloride with 25% aq. ammonium hydroxide solution, preferably at low temperature. The carboxylic acid of formula (8-b) can be formed by hydrolysis of the ester of formula (8-a), wherein R is an alkyl group such as methyl or ethyl, with a base such as NaOH, or KOH or LiOH, in a solvent like MeOH, EtOH, THF, or water, or a mixture of them, at low temperature or at RT or at elevated temperatures.

Scheme 1

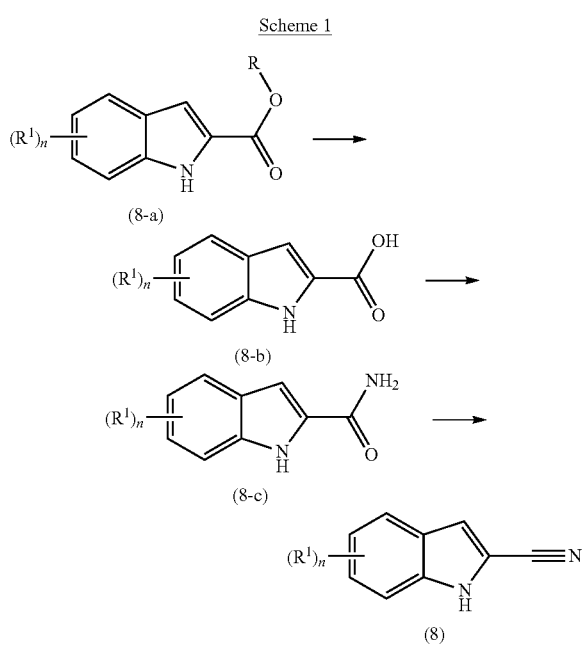

Compounds of formula (8-a) can be purchased from commercial suppliers, or synthesized according to known literature procedures. For example, compounds of formula (8-a) can be synthesized using a Hemetsberger-Knittel indole synthesis, as outlined in Scheme 2. Benzaldehyde derivatives of formula (8-d) are reacted with alkyl azidoacetate (8-e), wherein R is typically methyl or ethyl, in a solvent such as MeOH or EtOH, in presence of a base such as sodium methoxide or sodium ethoxide, at low temperatures or at RT. This affords the derivative of formula (8-f), which can be transformed into the compound of formula (8-a) when heated at elevated temperatures, in a solvent such as xylene.

Scheme 2

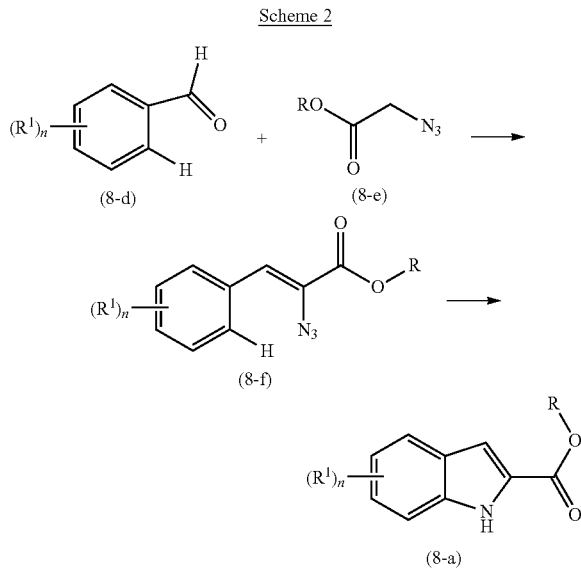

Compounds of formula (8-a) can also be synthesized using a Fischer indole synthesis, as outlined in Scheme 3. An hydrazine compound of formula (8-g) can be reacted with a pyruvate derivative of formula (8-h), wherein R is typically methyl or ethyl, in a solvent like MeOH, EtOH, water, or a mixture thereof, usually in presence of an acid such as glacial acetic acid, hydrochloric acid, or sulphuric acid, at RT or elevated temperatures. The intermediate hydrazone can be isolated, or transformed directly further into the indole of formula (8-a), in presence of an acid such as polyphosphoric acid, hydrochloric acid, zinc dichloride, para-toluenesulfonic acid or TFA, in a solvent like toluene, ethanol or ethylene glycol, or neat, typically at elevated temperatures.

Scheme 3

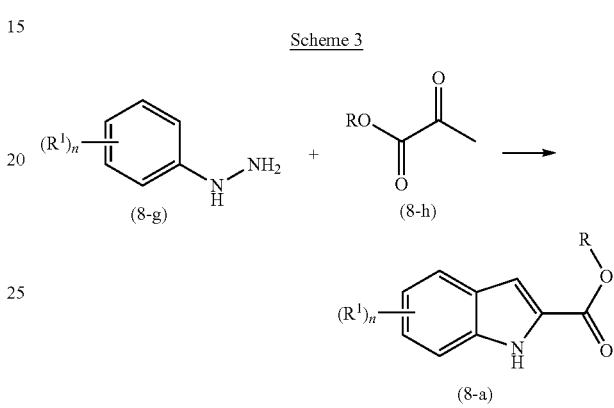

Compounds of formula (8), wherein $R^2$ is a methyl group, can be synthesized using a Bartoli indole synthesis (Scheme 4), wherein a nitrobenzene of formula (8-i) is reacted with an isopropenylmagnesium halide of formula (8-j), wherein X is bromine or chlorine, in a solvent like THF, typically at low temperatures to RT.

Scheme 4

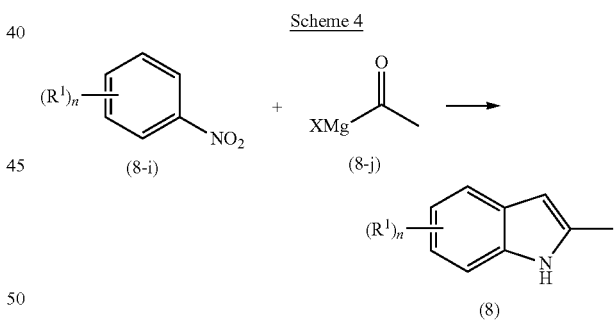

Alternatively, compounds of formula (8) can be formed via a Fischer indole synthesis, wherein a hydrazine of formula (VIII-g) can be reacted with acetone, to form the corresponding hydrazone intermediate, which can be transformed into the indole of formula (8), in presence of an acid such as polyphosphoric acid, hydrochloric acid, zinc dichloride, para-toluenesulfonic acid or TFA, in a solvent like toluene, EtOH or ethylene glycol, or neat, typically at elevated temperatures.

Alternatively, compounds of formula (8), wherein $R^2$ is a methyl group, can be derived from compounds of formula (8-a), as outlined in Scheme 5. Ester derivatives of formula (8-a) can be reduced to their corresponding alcohol derivatives of formula (8-k), using a reducing agent such as LiAlH$_4$, in a solvent like THF, at low, ambient or elevated temperatures. Alcohol derivatives of formula (8-k) can be oxidized to their corresponding aldehyde derivatives of formula (8-1), using an oxidizing agent such as manganese dioxide, in a solvent like DCM, at RT or elevated temperatures. The aldehydes of formula (8-1) can be reduced to the compounds of formula (8) using for example the Huang-Minlon modification of the Wolff-Kishner Reduction, by using hydrazine and KOH, in diethylene glycol, at elevated temperatures.

Scheme 5

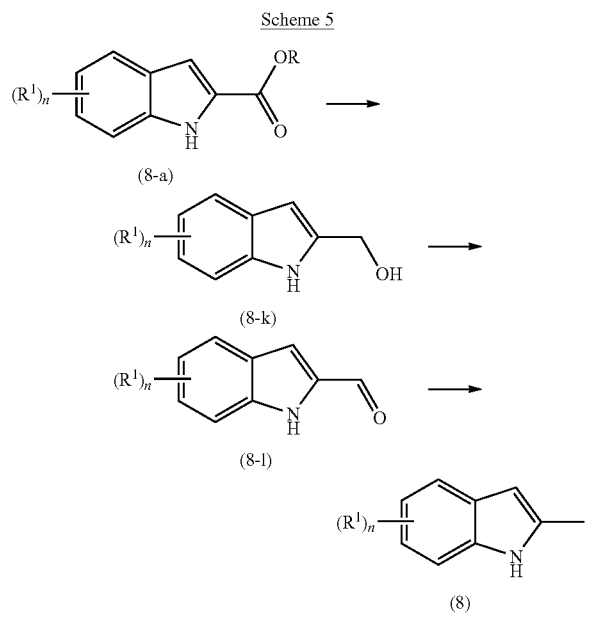

Alternatively, compounds of formula (8), wherein $R^2$ is a methyl group, can be derived from compounds of formula (8-m), which can be purchased from commercial suppliers, or synthesized by methods described in the literature or by methods known by a person skilled in the art (Scheme 6). The nitrogen in the compounds of formula (8-m) can be protected by a protecting group PG such as a tosyl group, or a benzenesulfonyl group, by reaction with tosyl chloride or benzenesulfonyl chloride, in presence of a base such as NaH, in a solvent such as DMF, at low, or ambient or elevated temperatures. Compounds of formula (8-n) can then be reacted with a base such as butyl lithium, in a solvent such as THF, preferably at low temperatures, and then with a methylating agent, such as iodomethane, at low temperature or at RT, to yield the compound of formula (8-0). The protecting group PG can then be removed to afford the compound of formula (8). When PG is a benzenesulfonyl or a tosyl group, the deprotection reaction can be carried out in presence of a base such as NaOH in a solvent such as MeOH, typically at elevated temperatures, or with a reagent such as tetrabutylammonium fluoride, in a solvent like THF, at elevated temperatures.

Scheme 6

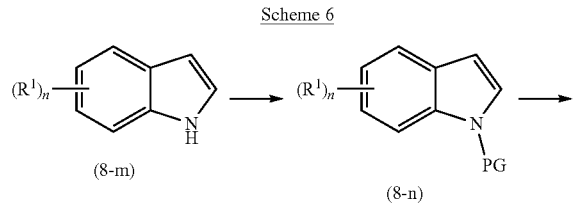

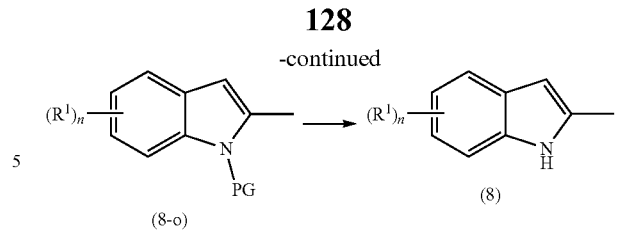

In some cases, the compounds of formula (8) may be further modified, for example, by manipulation of substituents to give a new compound of formula (8). These manipulations may include, but are not limited to, reduction, oxidation, alkylation, acylation, hydrolysis and transition-metal catalysed cross-coupling reactions which are commonly known to those skilled in the art.

Compounds of formula (I), wherein $R^2$ is a chlorine group, can be synthesized by chlorination of the corresponding oxindole of formula (10) (Scheme 7), in presence of a chlorinating agent such as phosphorous oxychloride, preferably at elevated temperatures. Compounds of formula (10) can be in turn synthesized by a Suzuki cross-coupling reaction of a compound of formula (11) with an aryl boronic acid derivative of formula (3), wherein M represents a boronic acid or a boronic ester, in the presence of a base such as $K_2CO_3$, $Cs_2CO_3$, $Na_2CO_3$, $K_3PO_4$, or CsF and a catalyst such as $Pd(PPh_3)_4$, $PdCl_2(dppf)$ or $Pd(OAc)_2$, in a solvent like EtOH, THF, water, or mixtures thereof, typically at elevated temperatures. Compounds of formula (11) can be synthesized by a nucleophilic aromatic substitution of compound of structure (6), wherein X represents Cl, Br or I, and Y represents Cl, Br, I or F, with a compound of structure (12), in the presence of a base such as TEA, DIPEA or $K_2CO_3$, in a solvent such as isopropanol, butanol, DMF or THF, at RT or at elevated temperatures. Compounds of formula (12) can be formed by the reduction of compounds of formula (13) with a reagent like hydrazine, in a solvent like ethanol, typically at elevated temperatures. Compounds of formula (13) can be synthesized by the reaction of compounds of formula (14), wherein X is a leaving group such as a bromine or a chlorine, with a compound of formula (15), in presence of a base such as NaH, in a solvent such as DMF, at low temperatures, or at RT or at elevated temperatures.

Scheme 7

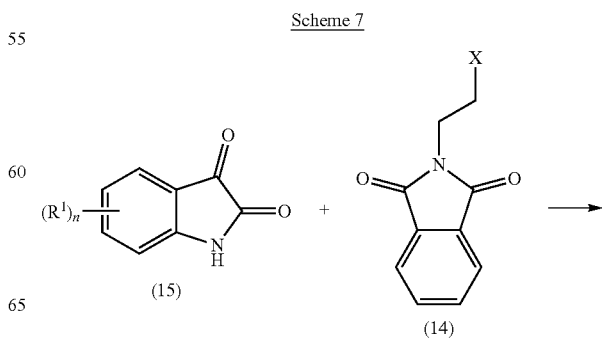

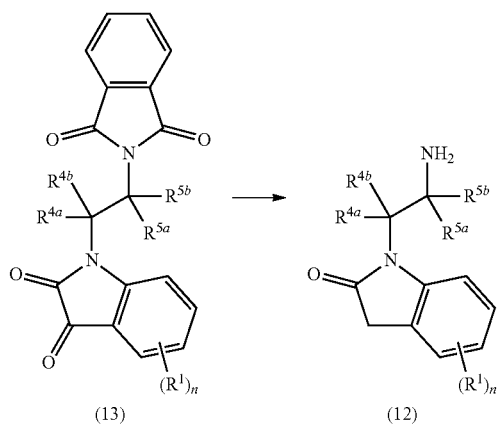

(13) (12)

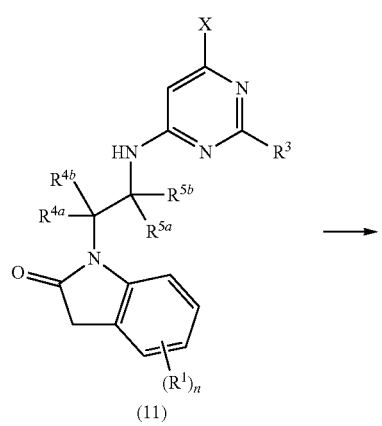

(11)

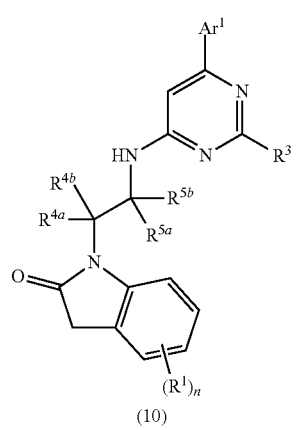

(10)

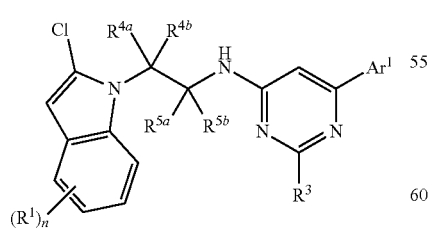

Compounds of formula (15) can be synthesized by the reaction of a compound of formula (16) with a strong acid such as for example concentrated sulphuric acid, preferably at elevated temperatures.

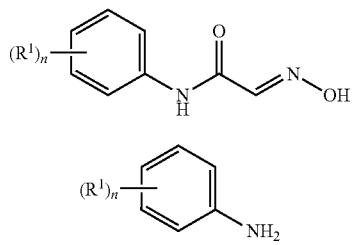

(16)

(17)

Compounds of formula (16) can be synthesized by reacting the aniline of formula (17) with an acid such as concentrated hydrochloric acid, in a solvent such as water, together with chloral hydrate, sodium sulphate and hydroxylamine, preferably at elevated temperatures.

The compounds of formula (I) can be alternatively accessed by carrying out the reaction steps and/or the reactions schemes described previously in a different order. For example, compounds of formula (I) can be formed by the reaction of a compound of formula (6) with a compound of formula (18), in presence of a base such as TEA, DIPEA, or $K_2CO_3$, in a solvent such as EtOH, isopropanol, butanol or DMF, preferably at elevated temperatures. Alternatively, compounds of formula (I) can be synthesized by reacting a compound of formula (6) with a compound of formula (19), in presence of a coupling agent such as (Benzotriazol-1-yloxy)-tris(dimethylamino)-phosphonium hexafluorophosphate (BOP), (benzotriazol-1-yl-oxy)-tripyrrolidino-phosphonium hexafluorophosphate (PyBOP) or hexachlorocyclotriphosphazene, in presence of a base such as DBU, DIPEA or TEA in a solvent such as THF, MeCN or DMF, at low temperatures, or at RT or at elevated temperatures.

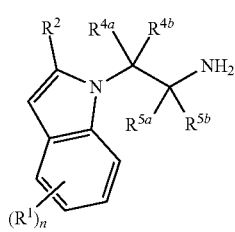

(6)

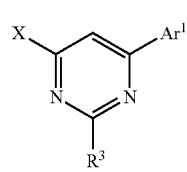

(18)

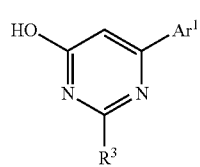

(19)

The compounds of formula (18) can be synthesized by the coupling of a compound of formula (7), wherein X and Y represent a chlorine, a bromine or an iodine, with a compound of formula (3), wherein M represents a boronic acid or a boronic ester, in a typical Suzuki cross-coupling reaction, in the presence of a base such as $K_2CO_3$, $Cs_2CO_3$, Na₂CO₃, K₃PO₄, or CsF and a catalyst such as Pd(PPh₃)₄, PdCl₂(dppf) or Pd(OAc)₂, in a solvent like ethanol, THF, water, or mixtures thereof, typically at elevated temperatures. Alternatively, a Negishi cross-coupling reaction can be performed, when M represents a zinc halide, with a catalyst such as Pd(PPh₃)₄, in a solvent such as THF or DMF, at RT or at elevated temperatures. A Stille cross-coupling reaction can also be carried out, when M represents a tin residue, typically trimethyltin or tributyltin, with a catalyst such as Pd(PPh₃)₄, in a solvent like THF, dioxane or DMF, at RT or elevated temperatures.

The compounds of formula (19) can be synthesized by the coupling of a compound of formula (7), wherein X represents a chlorine, a bromine or an iodine, and Y represents an hydroxyl, with a compound of formula (3), wherein M represents a boronic acid or a boronic ester, in a typical Suzuki cross-coupling reaction, in the presence of a base such as K₂CO₃, C₂CO₃, Na₂CO₃, K₃PO₄, or CsF and a catalyst such as Pd(PPh₃)₄, PdCl₂(dppf) or Pd(OAc)₂, in a solvent like ethanol, THF, water, or mixtures thereof, typically at elevated temperatures. Alternatively, a Negishi cross-coupling reaction can be performed, when M represents a zinc halide, with a catalyst such as Pd(PPh₃)₄, in a solvent such as THF or DMF, at RT or at elevated temperatures. A Stille cross-coupling reaction can also be carried out, when M represents a tin residue, typically trimethyltin or tributyltin, with a catalyst such as Pd(PPh₃)₄, in a solvent like THF, dioxane or DMF, at RT or elevated temperatures. Alternatively, the compound of formula (19) can be formed by alkoxy cleavage of a compound of formula (20), wherein R is an alkyl group such as methyl, ethyl or benzyl, under acidic conditions, such as HCl in a solvent such as dioxane, at RT or at elevated temperatures.

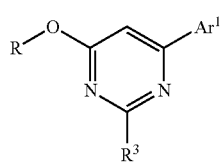

(20)

The compounds of formula (20) can be synthesized by the coupling of a compound of formula (7), wherein X represents a chlorine, a bromine or an iodine, and Y represents an alkoxy group, typically methoxy or ethoxy, with a compound of formula (3), wherein M represents a boronic acid or a boronic ester, in a typical Suzuki cross-coupling reaction, in the presence of a base such as K₂CO₃, Cs₂CO₃, Na₂CO₃, K₃PO₄, or CsF and a catalyst such as Pd(PPh₃)₄, PdCl₂(dppf) or Pd(OAc)₂, in a solvent like ethanol, THF, water, or mixtures thereof, typically at elevated temperatures. Alternatively, a Negishi cross-coupling reaction can be performed, when M represents a zinc halide, with a catalyst such as Pd(PPh₃)₄, in a solvent such as THF or DMF, at RT or at elevated temperatures. A Stille cross-coupling reaction can also be carried out, when M represents a tin residue, typically trimethyltin or tributyltin, with a catalyst such as Pd(PPh₃)₄, in a solvent like THF, dioxane or DMF, at RT or elevated temperatures.

Compounds of formula (8), wherein $R^1$ is a fluorine atom at position 3 and $R^2$ is a methyl, can be synthesized using the sequence described in Scheme 8. The compound of formula (15) can be fluorinated with a fluorinating agent such as diethyl aminosulfur trifluoride (DAST) in a solvent such as DCM, at low temperature or at RT. The resulting compound (8-p) can be reduced with a reducing agent such as borane, in a solvent such as THF, at low temperature or RT, to afford compound of formula (8-q). The nitrogen in the compounds of formula (8-q) can be protected by a protecting group PG such as a tosyl group, or a benzenesulfonyl group, by reaction with tosyl chloride or benzenesulfonyl chloride, in presence of a base such as NaH, in a solvent such as DMF, at low, or ambient or elevated temperatures. Compounds of formula (8-r) can then be reacted with a base such as butyl lithium, in a solvent such as THF, preferably at low temperatures, and then with a methylating agent, such as iodomethane, at low temperature or at RT, to yield the compound of formula (8-s). The protecting group PG can then be removed to afford the compound of formula (8). When PG is a benzenesulfonyl or a tosyl group, the deprotection reaction can be carried out in presence of a base such as NaOH in a solvent such as MeOH, typically at elevated temperatures, or with a reagent such as tetrabutylammonium fluoride, in a solvent like THF, at elevated temperatures. Alternatively, Compounds of formula (8-r) can then be reacted with a base such as butyl lithium, in a solvent such as THF, preferably at low temperatures, and then with a carboxylic acid source, such as carbon dioxide, at low temperature or at RT, to yield the compound of formula (8-t). The primary amide of formula (8-u) can be formed by reacting (8-t) with a reagent such as thionyl chloride, oxalyl chloride or carbonyl di-imidazole (CDI), in a solvent such as DCM, eventually with a catalytic amount of DMF, at low temperatures, or at RT, or at elevated temperatures, and then reacting the intermediate acid chloride with 25% aq. ammonium hydroxide solution, preferably at low temperature. The nitrile moiety in (8-v) can be formed by dehydration of the corresponding primary amide (8-u), by using for instance cyanuric chloride in a solvent such as DMF, at low temperatures or at RT, or at elevated temperatures. The protecting group PG can then be removed to afford the compound of formula (8). When PG is a benzenesulfonyl or a tosyl group, the deprotection reaction can be carried out in presence of a base such as NaOH in a solvent such as MeOH, typically at elevated temperatures, or with a reagent such as tetrabutylammonium fluoride, in a solvent like THF, at elevated temperatures.

Scheme 8

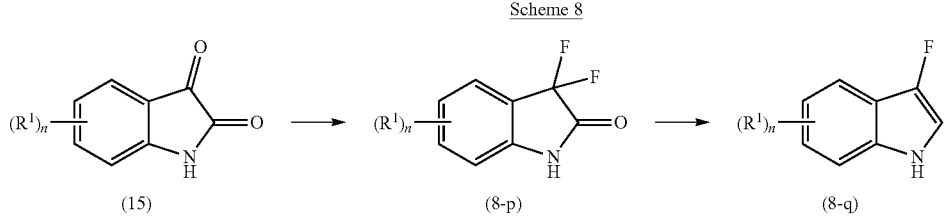

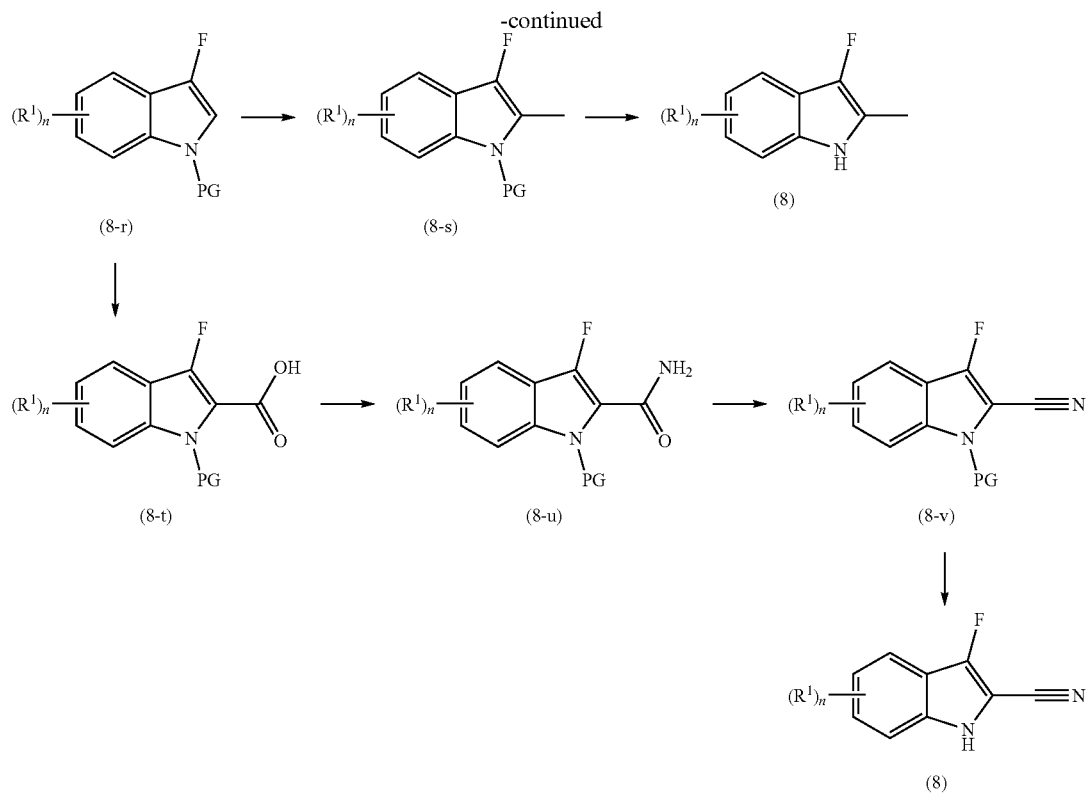

The following examples are provided to illustrate the invention. These examples are illustrative only and should not be construed as limiting the invention in any way.

EXPERIMENTAL PART

I. Chemistry

All temperatures are stated in ° C. Commercially available starting materials were used as received without further purification. Unless otherwise specified, all reactions were carried out in oven-dried glassware under an atmosphere of nitrogen. Compounds were purified by flash column chromatography on silica gel or by preparative HPLC. Compounds described in the invention are characterised by LC-MS data (retention time $t_R$ is given in min; molecular weight obtained from the mass spectrum is given in g/mol) using the conditions listed below. In cases where compounds of the present invention appear as a mixture of conformational isomers, particularly visible in their LC-MS spectra, the retention time of the most abundant conformer is given. In some cases compounds are isolated after purification in form of the corresponding ammonium salt (*1), or the respective formic acid salt (*2); such compounds are marked accordingly.

Analytical LC-MS Equipment:

HPLC pump: Binary gradient pump, Agilent G4220A or equivalent

Autosampler: Gilson LH215 (with Gilson 845z injector) or equivalent

Column compartment: Dionex TCC-3000RS or equivalent

Degasser: Dionex SRD-3200 or equivalent

Make-up pump: Dionex HPG-3200SD or equivalent

DAD detector: Agilent G4212A or equivalent

MS detector: Single quadrupole mass analyzer, Thermo Finnigan MSQPlus or equivalent ELS detector: Sedere SEDEX 90 or equivalent LC-MS with Acidic Conditions Method A: Column: Zorbax SB-aq (3.5 μm, 4.6×50 mm). Conditions: MeCN [eluent A]; water+0.04% TFA [eluent B]. Gradient: 95% B→5% B over 1.5 min (flow: 4.5 mL/min). Detection: UV/Vis+MS.

Method B: Column: Waters XBridge C18 (2.5 μm, 4.6×30 mm). Conditions: MeCN [eluent A]; water+0.04% TFA [eluent B]. Gradient: 95% B→5% B over 1.5 min (flow: 4.5 mL/min). Detection: UV/Vis+MS.

Method C: Waters Acquity Binary, Solvent Manager, MS: Waters SQ Detector, DAD: Acquity UPLC PDA Detector, ELSD: Acquity UPLC ELSD. Column: Acquity UPLC BEH $C_{18}$ 1.7 μm 2.1×50 mm from Waters, thermostated in the Acquity UPLC Column Manager at 60° C. Eluents: $H_2O$+ 0.05% TFA; B2: MeCN+0.045% TFA. Method: Gradient: 2% B 98% B over 2.0 min. Flow: 1.2 mL/min. Detection: UV 214 nm and ELSD, and MS, $t_R$ is given in min.

LC-MS with Basic Conditions

Method D: Column: Ascentis 2.1*50 mm 5 μm, Eluents: A:$H_2O$+0.05% $NH_4OH$, B: MeCN, Method: 5% B to 95% B in 1.1 min, Flow 1.8 ml/min, Detection UV: 214 nm Method E: Column: Waters BEH $C_{18}$, 3.0×50 mm, 2.5 m, Eluents: A: Water/$NH_3$ [c($NH_3$)=13 mmol/l], B: MeCN, Method: 5% B to 95% B in 1.2 min, Flow 1.6 ml/min, Detection UV: 214 nm Method F: Column: Agilent Zorbax Extend $C_13$, 4.6×50 mm, 5 m, Eluents: A: Water/$NH_3$ [c($NH_3$)=13 mmol/l], B: MeCN, Method: 5% B to 95% B in 0.75 min; Flow 4.5 ml/min, Detection UV: 214 nm Preparative HPLC Equipment:

Gilson 333/334 HPLC pump equipped with Gilson LH215, Dionex SRD-3200 degasser,

Dionex ISO-3100A make-up pump, Dionex DAD-3000 DAD detector, Single quadrupole mass analyzer MS detector, Thermo Finnigan MSQ Plus, MRA100-000 flow splitter, Polymer Laboratories PL-ELS1000 ELS detector Preparative HPLC with Basic Conditions Column: Waters XBridge (10 μm, 75×30 mm). Conditions: MeCN [eluent A]; water+0.5% NH$_4$OH (25% aq.) [eluent B]; Gradient see Table 1 (flow: 75 mL/min), the starting percentage of Eluent A (x) is determined depending on the polarity of the compound to purify. Detection: UV/Vis+MS

TABLE 1

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Preparative HPLC with Acidic Conditions

Column: Waters Atlantis T3 (10 μm, 75×30 mm). Conditions: MeCN [eluent A]; water+0.5% HCO$_2$H [eluent B]; Gradient see Table 2 (flow: 75 mL/min), the starting percentage of Eluent A (x) is determined depending on the polarity of the compound to purify. Detection: UV/Vis+MS

TABLE 2

| t (min) | 0 | 0.01 | 4.0 | 6.0 | 6.2 | 6.6 |
|---|---|---|---|---|---|---|
| Eluent A (%) | x | x | 95 | 95 | x | x |
| Eluent B (%) | 100-x | 100-x | 5 | 5 | 100-x | 100-x |

Abbreviations (as Used Hereinbefore or Hereinafter)

aq. aqueous
atm atmosphere
d days
DCM dichloromethane
DIPEA diisopropyl-ethylamine, Hünig's base
DMF dimethylformamide
DMSO dimethylsulfoxide
dppf 1,1'-bis(diphenylphosphino)ferrocene
Et ethyl
Et$_2$O diethylether
EtOAc ethyl acetate
EtOH ethanol
Ex. example
FC flash chromatography on silica gel
h hour(s)
hept heptane(s)
HPLC high performance liquid chromatography
HV high vacuum conditions
$^i$Bu isobutyl
$^i$Pr isopropyl
LC-MS liquid chromatography-mass spectrometry
Lit. Literature
Me methyl
MeCN acetonitrile
MeOH methanol
mL milliliter
min minute(s)
MW microwave
$^n$Pr n-propyl
OAc acetate
Pd$_2$dba$_3$ Tris(dibenzylideneacetone)dipalladium(0)
Pd(dppf)Cl$_2$·DCM [1,1'-bis(diphenylphosphino)-ferrocene]dichloropalladium (II) complex with dichloromethane
Ph phenyl
PPh$_3$ triphenyl phosphine
prep. Preparative
rac racemic
RM reaction mixture
RT room temperature
s second(s)
sat. saturated (if not indicated otherwise: sat. aq.)
tBu tert-butyl=tertiary butyl
TEA triethylamine
TFA trifluoroacetic acid
THF tetrahydrofuran
TLC thin layer chromatography
tosyl p-toluene-sulfonyl
$t_R$ retention time
triflate trifluoromethanesulfonate A—Preparation of Precursors and Intermediates A.1. Synthesis of Pyrimidine Halide Derivatives of Formula (III)

A.1.1. 6-Chloro-N-(2-(2-methyl-1H-indol-1-yl)ethyl)pyrimidin-4-amine

To a solution of 4,6-dichloropyrimidine (3.00 g, 20.1 mmol) in 2-propanol (50 mL) at RT is added 2-(2-methyl-1H-indol-1-yl)ethan-1-amine (3.68 g, 21.1 mmol) and TEA (3.08 mL, 22.2 mmol). The resulting mixture is refluxed for 2 h, then allowed to cool to RT and concentrated under reduced pressure. The residue is partitioned between sat. aq. NaHCO$_3$ solution and EtOAc. The layers are separated and the aqueous layer is extracted once more with EtOAc. The combined organic layers are washed with water, brine, dried over MgSO$_4$, filtered and the solvent is removed in vacuo yielding the desired product as a yellow powder (5.45 g, 94%). LC-MS A: $t_R$=0.87 min; [M+H]$^+$=287.13.

A.1.1.1. 2-(2-Methyl-1H-indol-1-yl)ethan-1-amine

To a solution of 2-methylindole (10.04 g, 75 mmol) in toluene (200 mL) are added 2-chloroethylamine hydrochloride (17.4 g, 150 mmol), freshly powdered NaOH (21.00 g, 525 mmol) and tetrabutyl ammonium hydrogen sulfate (2.037 g, 6 mmol). The resulting mixture is heated up to reflux and stirred for 17 h. It is then cooled down to RT, and filtered through a filter paper. The residue is triturated twice with toluene, and filtrated. The filtrate is concentrated under reduced pressure, and the residue is purified by FC, using a gradient of DCM/MeOH from 100:0 to 95:5. After concentration of the product containing fractions, the title compound (13.2 g, 99%) is obtained as a yellow resin: LC-MS A: $t_R$=0.54 min; [M+H]$^+$=175.31.

In analogy to example A.1.1., the following halo-pyrimidines are prepared:

A.1.2. 6-Chloro-N-(2-(4-chloro-2-methyl-1H-indol-1-yl)ethyl)pyrimidin-4-amine

The title compound is prepared according to the synthesis of A.1.1. described above using 2-(4-chloro-2-methyl-1H-indol-1-yl)ethan-1-amine; LC-MS A: $t_R$=0.92 min; [M+H]$^+$=320.99.

A.1.2.1. 2-(4-Chloro-2-methyl-1H-indol-1-yl)ethan-1-amine

The title compound is prepared according to the synthesis of A.1.1.1. described above using 4-chloro-2-methyl-1H-indole; LC-MS A: $t_R$=0.61 min; $[M+H]^+$=209.12.

A.1.3. 6-Chloro-N-(2-(2,4-dimethyl-1H-indol-1-yl)ethyl)pyrimidin-4-amine

The title compound is prepared according to the synthesis of A.1.1. described above using 2-(2,4-dimethyl-1H-indol-1-yl)ethan-1-amine; LC-MS A: $t_R$=0.90 min; $[M+H]^+$=301.09.

A.1.3.1. 2-(2,4-Dimethyl-1H-indol-1-yl)ethan-1-amine

The title compound is prepared according to the synthesis of A.1.1.1. described above using 2,4-dimethyl-1H-indole; LC-MS A: $t_R$=0.58 min; $[M+H]^+$=189.25.

A.1.4. 6-Chloro-N-(2-(6-fluoro-2,4-dimethyl-1H-indol-1-yl)ethyl)pyrimidin-4-amine The title compound is prepared according to the synthesis of A.1.1. described above using 2-(6-fluoro-2,4-dimethyl-1H-indol-1-yl)ethan-1-amine; LC-MS A: $t_R$=0.92 min; $[M+H]^+$=319.21.

A.1.4.1. 2-(6-Fluoro-2,4-dimethyl-1H-indol-1-yl)ethan-1-amine

The title compound is prepared according to the synthesis of A.1.1.1. described above using 6-fluoro-2,4-dimethyl-1H-indole; LC-MS A: $t_R$=0.60 min; $[M+H]^+$=207.33.

A.1.5. 6-Chloro-N-(2-(7-chloro-2,5-dimethyl-1H-indol-1-yl)ethyl)pyrimidin-4-amine The title compound is prepared according to the synthesis of A.1.1. described above using 2-(7-chloro-2,5-dimethyl-1H-indol-1-yl)ethan-1-amine; LC-MS A: $t_R$=0.97 min; $[M+H]^+$=334.93.

A.1.5.1. 2-(7-Chloro-2,5-dimethyl-1H-indol-1-yl)ethan-1-amine

The title compound is prepared according to the synthesis of A.1.1.1. described above using 7-chloro-2,5-dimethyl-1H-indole; LC-MS A: $t_R$=0.63 min; $[M+H]^+$=222.97.

A.1.6. 6-Chloro-N-(2-(7-chloro-2,4-dimethyl-1H-indol-1-yl)ethyl)pyrimidin-4-amine The title compound is prepared according to the synthesis of A.1.1. described above using 2-(7-chloro-2,4-dimethyl-1H-indol-1-yl)ethan-1-amine; LC-MS A: $t_R$=0.97 min; $[M+H]^+$=335.04.

A.1.6.1. 2-(7-Chloro-2,4-dimethyl-1H-indol-1-yl)ethan-1-amine

The title compound is prepared according to the synthesis of A.1.1.1. described above using 7-chloro-2,4-dimethyl-1H-indole; LC-MS A: $t_R$=0.63 min; $[M+H]^+$=222.93.

A.1.7. 6-Chloro-N-(2-(7-fluoro-2,5-dimethyl-1H-indol-1-yl)ethyl)pyrimidin-4-amine The title compound is prepared according to the synthesis of A.1.1. described above using 2-(7-fluoro-2,5-dimethyl-1H-indol-1-yl)ethan-1-amine; LC-MS A: $t_R$=0.93 min; $[M+H]^+$=319.02.

A.1.7.1. 2-(7-Fluoro-2,5-dimethyl-1H-indol-1-yl)ethan-1-amine

The title compound is prepared according to the synthesis of A.1.1.1. described above using 7-fluoro-2,5-dimethyl-1H-indole; LC-MS A: $t_R$=0.61 min; $[M+H]^+$=207.17.

A.1.8. 6-Chloro-N-(2-(7-fluoro-2,4-dimethyl-1H-indol-1-yl)ethyl)pyrimidin-4-amine The title compound is prepared according to the synthesis of A.1.1. described above using 2-(7-fluoro-2,4-dimethyl-1H-indol-1-yl)ethan-1-amine; LC-MS A: $t_R$=0.93 min; $[M+H]^+$=319.08.

A.1.8.1. 2-(7-Fluoro-2,4-dimethyl-1H-indol-1-yl)ethan-1-amine

The title compound is prepared according to the synthesis of A.1.1.1. described above using 7-fluoro-2,4-dimethyl-1H-indole; LC-MS A: $t_R$=0.60 min; $[M+H]^+$=207.17.

A.1.9. 6-Chloro-N-(2-(4,7-dichloro-2-methyl-1H-indol-1-yl)ethyl)pyrimidin-4-amine The title compound is prepared according to the synthesis of A.1.1. described above using 2-(4,7-dichloro-2-methyl-1H-indol-1-yl)ethan-1-amine; LC-MS A: $t_R$=0.98 min; $[M+H]^+$=355.06.

A.1.9.1. 2-(4,7-Dichloro-2-methyl-1H-indol-1-yl)ethan-1-amine

The title compound is prepared according to the synthesis of A.1.1.1. described above using 4,7-dichloro-2-methyl-1H-indole; LC-MS A: $t_R$=0.65 min; $[M+H]^+$=243.04.

A.1.10. 6-Chloro-N-(2-(4,7-difluoro-2-methyl-1H-indol-1-yl)ethyl)pyrimidin-4-amine The title compound is prepared according to the synthesis of A.1.1. described above using 2-(4,7-difluoro-2-methyl-1H-indol-1-yl)ethan-1-amine; LC-MS A: $t_R$=0.89 min; $[M+H]^+$=323.09.

A.1.10.1. 2-(4,7-Difluoro-2-methyl-1H-indol-1-yl)ethan-1-amine

The title compound is prepared according to the synthesis of A.1.1.1. described above using 4,7-difluoro-2-methyl-1H-indole; LC-MS A: $t_R$=0.59 min; $[M+H]^+$=211.14.

A.1.11. 6-Chloro-N-(2-(5,7-difluoro-2-methyl-1H-indol-1-yl)ethyl)pyrimidin-4-amine The title compound is prepared according to the synthesis of A.1.1. described above using 2-(5,7-difluoro-2-methyl-1H-indol-1-yl)ethan-1-amine; LC-MS A: $t_R$=0.91 min; [M+H]$^+$=322.95.

A.1.11.1. 2-(4,7-Difluoro-2-methyl-1H-indol-1-yl)ethan-1-amine

The title compound is prepared according to the synthesis of A.1.1.1. described above using 5,7-difluoro-2-methyl-1H-indole; LC-MS A: $t_R$=0.59 min; [M+H]$^+$=211.13.

A.1.12. 6-Chloro-N-(2-(6,7-dichloro-2-methyl-1H-indol-1-yl)ethyl)pyrimidin-4-amine The title compound is prepared according to the synthesis of A.1.1. described above using 2-(6,7-dichloro-2-methyl-1H-indol-1-yl)ethan-1-amine; LC-MS A: $t_R$=0.97 min; [M+H]$^+$=355.03.

A.1.12.1. 2-(6,7-Dichloro-2-methyl-1H-indol-1-yl)ethan-1-amine

The title compound is prepared according to the synthesis of A.1.1.1. described above using 6,7-dichloro-2-methyl-1H-indole; LC-MS A: $t_R$=0.64 min; [M+H]$^+$=243.05.

A.1.13. 6-Chloro-N-(2-(5-chloro-7-fluoro-2-methyl-1H-indol-1-yl)ethyl)pyrimidin-4-amine The title compound is prepared according to the synthesis of A.1.1. described above using 2-(5-chloro-7-fluoro-2-methyl-1H-indol-1-yl)ethan-1-amine; LC-MS A: $t_R$=0.95 min; [M+H]$^+$=339.13.

A.1.13.1. 2-(5-Chloro-7-fluoro-2-methyl-1H-indol-1-yl)ethan-1-amine

The title compound is prepared according to the synthesis of A.1.1.1. described above using 5-chloro-7-fluoro-2-methyl-1H-indole; LC-MS A: $t_R$=0.63 min; [M+H]$^+$=227.01.

A.1.14. 6-Chloro-N-(2-(4,5-difluoro-2-methyl-1H-indol-1-yl)ethyl)pyrimidin-4-amine The title compound is prepared according to the synthesis of A.1.1. described above using 2-(4,5-difluoro-2-methyl-1H-indol-1-yl)ethan-1-amine; LC-MS A: $t_R$=0.91 min; [M+H]$^+$=324.42.

A.1.14.1. 2-(4,5-Difluoro-2-methyl-1H-indol-1-yl)ethan-1-amine

The title compound is prepared according to the synthesis of A.1.1.1. described above using 4,5-difluoro-2-methyl-1H-indole; LC-MS A: $t_R$=0.60 min; [M+H]$^+$=211.13.

A.1.15. 6-Chloro-N-(2-(4-chloro-7-fluoro-2-methyl-1H-indol-1-yl)ethyl)pyrimidin-4-amine The title compound is prepared according to the synthesis of A.1.1. described above using 2-(4-chloro-7-fluoro-2-methyl-1H-indol-1-yl)ethan-1-amine; LC-MS A: $t_R$=0.95 min; [M+H]$^+$=339.02.

A.1.15.1. 2-(4-Chloro-7-fluoro-2-methyl-1H-indol-1-yl)ethan-1-amine

The title compound is prepared according to the synthesis of A.1.1.1. described above using 4-chloro-7-fluoro-2-methyl-1H-indole; LC-MS A: $t_R$=0.62 min; [M+H]$^+$=227.10.

A.1.16. 6-Chloro-N-(2-(4,6-dichloro-2-methyl-1H-indol-1-yl)ethyl)pyrimidin-4-amine The title compound is prepared according to the synthesis of A.1.1. described above using 2-(4,6-dichloro-2-methyl-1H-indol-1-yl)ethan-1-amine; LC-MS A: $t_R$=0.97 min; [M+H]$^+$=354.85.

A.1.16.1. 2-(4,6-Dichloro-2-methyl-1H-indol-1-yl)ethan-1-amine

The title compound is prepared according to the synthesis of A.1.1.1. described above using 4,6-dichloro-2-methyl-1H-indole; LC-MS A: $t_R$=0.66 min; [M+H]$^+$=243.00.

A.1.17. 6-Chloro-N-(2-(4-chloro-6-fluoro-2-methyl-1H-indol-1-yl)ethyl)pyrimidin-4-amine The title compound is prepared according to the synthesis of A.1.1. described above using 2-(4-chloro-6-fluoro-2-methyl-1H-indol-1-yl)ethan-1-amine; LC-MS A: $t_R$=0.94 min; [M+H]$^+$=338.94.

A.1.17.1. 2-(4-Chloro-6-fluoro-2-methyl-1H-indol-1-yl)ethan-1-amine

The title compound is prepared according to the synthesis of A.1.1.1. described above using 4-chloro-6-fluoro-2-methyl-1H-indole; LC-MS A: $t_R$=0.63 min; [M+H]$^+$=227.04.

A.1.18. 6-Chloro-N-(2-(4-methoxy-2-methyl-1H-indol-1-yl)ethyl)pyrimidin-4-amine The title compound is prepared according to the synthesis of A.1.1. described above using 2-(4-methoxy-2-methyl-1H-indol-1-yl)ethan-1-amine; LC-MS A: $t_R$=0.86 min; [M+H]$^+$=317.07.

A.1.18.1. 2-(4-Methoxy-2-methyl-1H-indol-1-yl)ethan-1-amine

The title compound is prepared according to the synthesis of A.1.1.1. described above using 4-methoxy-2-methyl-1H-indole; LC-MS A: $t_R$=0.54 min; [M+H]$^+$=205.34.

A.1.19. 6-Chloro-N-(2-(6-methoxy-2-methyl-1H-indol-1-yl)ethyl)pyrimidin-4-amine The title compound is prepared according to the synthesis of A.1.1. described above using 2-(6-methoxy-2-methyl-1H-indol-1-yl)ethan-1-amine; LC-MS A: $t_R$=0.86 min; [M+H]$^+$= 317.34.

A.1.19.1. 2-(6-Methoxy-2-methyl-1H-indol-1-yl)ethan-1-amine

The title compound is prepared according to the synthesis of A.1.1.1. described above using 6-methoxy-2-methyl-1H-indole; LC-MS A: $t_R$=0.56 min; [M+H]$^+$=205.19.

A.1.20. 1-(2-((6-Chloropyrimidin-4-yl)amino)ethyl)-7-fluoro-2-methyl-1H-indole-4-carbonitrile The title compound is prepared according to the synthesis of A.1.1. described above using 1-(2-aminoethyl)-7-fluoro-2-methyl-1H-indole-4-carbonitrile; LC-MS A: $t_R$=0.87 min; [M+H]$^+$=330.07.

A.1.20.1. 1-(2-Aminoethyl)-7-fluoro-2-methyl-1H-indole-4-carbonitrile

The title compound is prepared according to the synthesis of A.1.1.1. described above 7-fluoro-2-methyl-1H-indole-4-carbonitrile; LC-MS A: $t_R$=0.55 min; [M+H]$^+$= 218.13.

A.1.21. 6-Chloro-N-(2-(4,5,7-trifluoro-2-methyl-1H-indol-1-yl)ethyl)pyrimidin-4-amine The title compound is prepared according to the synthesis of A.1. described above using 2-(4,5,7-trifluoro-2-methyl-1H-indol-1-yl)ethan-1-amine; LC-MS A: $t_R$=0.93 min; [M+H]$^+$=340.99.

A.1.21.1. 2-(4,5,7-Trifluoro-2-methyl-1H-indol-1-yl)ethan-1-amine

The title compound is prepared according to the synthesis of A.1.1.1. described above 4,5,7-trifluoro-2-methyl-1H-indole; LC-MS A: $t_R$=0.61 min; [M+H]$^+$=229.13.

A.1.22. 6-Chloro-N-(2-(7-chloro-5-fluoro-2,4-dimethyl-1H-indol-1-yl)ethyl)pyrimidin-4-amine The title compound is prepared according to the synthesis of A.1.1. described above using 2-(7-chloro-5-fluoro-2,4-dimethyl-1H-indol-1-yl)ethan-1-amine; LC-MS A: $t_R$=0.98 min; [M+H]$^+$=354.28.

A.1.22.1. 2-(7-Chloro-5-fluoro-2,4-dimethyl-1H-indol-1-yl)ethan-1-amine

The title compound is prepared according to the synthesis of A.1.1.1. described above 7-chloro-5-fluoro-2,4-dimethyl-1H-indole; LC-MS A: $t_R$=0.64 min; [M+H]$^+$= 241.14.

A.1.23. 6-Chloro-N-(2-(6-fluoro-4-methoxy-2-methyl-1H-indol-1-yl)ethyl)pyrimidin-4-amine The title compound is prepared according to the synthesis of A.1. described above using 2-(6-fluoro-4-methoxy-2-methyl-1H-indol-1-yl)ethan-1-amine; LC-MS A: $t_R$=0.89 min; [M+H]$^+$=335.02.

A.1.23.1. 2-(6-Fluoro-4-methoxy-2-methyl-1H-indol-1-yl)ethan-1-amine

The title compound is prepared according to the synthesis of A.1.1.1. described above 6-fluoro-4-methoxy-2-methyl-1H-indole; LC-MS A: $t_R$=0.57 min; [M+H]$^+$= 223.13.

A.1.24. 6-Chloro-N-(2-(7-chloro-4-methoxy-2-methyl-1H-indol-1-yl)ethyl)pyrimidin-4-amine The title compound is prepared according to the synthesis of A.1.1. described above using 2-(7-chloro-4-methoxy-2-methyl-1H-indol-1-yl)ethan-1-amine; LC-MS A: $t_R$=0.93 min; [M+H]$^+$=350.97.

A.1.24.1. 2-(7-Chloro-4-methoxy-2-methyl-1H-indol-1-yl)ethan-1-amine

The title compound is prepared according to the synthesis of A.1.1.1. described above 7-chloro-4-methoxy-2-methyl-1H-indole; LC-MS A: $t_R$=0.59 min; [M+H]$^+$= 239.11.

A.1.25. 6-Chloro-N-(2-(7-fluoro-4-methoxy-2-methyl-1H-indol-1-yl)ethyl)pyrimidin-4-amine The title compound is prepared according to the synthesis of A.1.1. described above using 2-(7-fluoro-4-methoxy-2-methyl-1H-indol-1-yl)ethan-1-amine; LC-MS A: $t_R$=0.89 min; [M+H]$^+$=335.04.

A.1.25.1. 2-(7-Fluoro-4-methoxy-2-methyl-1H-indol-1-yl)ethan-1-amine

The title compound is prepared according to the synthesis of A.1.1.1. described above 7-fluoro-4-methoxy-2-methyl-1H-indole; LC-MS A: $t_R$=0.56 min; [M+H]$^+$= 223.10.

A.1.26. 6-Chloro-N-(2-(7-fluoro-5-methoxy-2-methyl-1H-indol-1-yl)ethyl)pyrimidin-4-amine The title compound is prepared according to the synthesis of A.1.1. described above using 2-(7-fluoro-5-methoxy-2-methyl-1H-indol-1-yl)ethan-1-amine; LC-MS A: $t_R$=0.89 min; [M+H]$^+$=335.00.

A.1.26.1. 2-(7-Fluoro-5-methoxy-2-methyl-1H-indol-1-yl)ethan-1-amine

The title compound is prepared according to the synthesis of A.1.1.1. described above 7-fluoro-5-methoxy-2-methyl-1H-indole; LC-MS A: $t_R$=0.57 min; [M+H]$^+$= 223.11.

A.1.27. 6-Chloro-N-(2-(5-fluoro-4-methoxy-2-methyl-1H-indol-1-yl)ethyl)pyrimidin-4-amine The title compound is prepared according to the synthesis of A.1.1. described above using 2-(5-fluoro-4-methoxy-2-methyl-1H-indol-1-yl)ethan-1-amine; LC-MS A: $t_R$=0.86 min; [M+H]$^+$=335.09.

A.1.27.1. 2-(5-Fluoro-4-methoxy-2-methyl-1H-indol-1-yl)ethan-1-amine

The title compound is prepared according to the synthesis of A.1.1.1. described above 5-fluoro-4-methoxy-2-methyl-1H-indole; LC-MS A: $t_R$=0.55 min; [M+H]$^+$=222.99.

A.1.28. 6-Chloro-N-(2-(4-fluoro-7-methoxy-2-methyl-1H-indol-1-yl)ethyl)pyrimidin-4-amine The title compound is prepared according to the synthesis of A.1.1. described above using 2-(4-fluoro-7-methoxy-2-methyl-1H-indol-1-yl)ethan-1-amine; LC-MS A: $t_R$=0.92 min; [M+H]$^+$=335.13.

A.1.28.1. 2-(4-Fluoro-7-methoxy-2-methyl-1H-indol-1-yl)ethan-1-amine

The title compound is prepared according to the synthesis of A.1.1.1. described above 4-fluoro-7-methoxy-2-methyl-1H-indole; LC-MS A: $t_R$=0.61 min; [M+H]$^+$=223.08.

A.1.29. 6-Chloro-N-(2-(4-methoxy-2,7-dimethyl-1H-indol-1-yl)ethyl)pyrimidin-4-amine The title compound is prepared according to the synthesis of A.1. described above using 2-(4-methoxy-2,7-dimethyl-1H-indol-1-yl)ethan-1-amine; LC-MS A: $t_R$=0.88 min; [M+H]$^+$=331.1.

A.1.29.1. 2-(4-Methoxy-2,7-dimethyl-1H-indol-1-yl)ethan-1-amine

The title compound is prepared according to the synthesis of A.1.1.1. described above 4-methoxy-2,7-dimethyl-1H-indole; LC-MS A: $t_R$=0.57 min; [M+H]$^+$=219.17.

A.1.30. 6-Chloro-N-(2-(7-chloro-2-methyl-1H-indol-1-yl)ethyl)pyrimidin-4-amine The title compound is prepared according to the synthesis of A.1.1. described above using 2-(7-chloro-2-methyl-1H-indol-1-yl)ethan-1-amine; LC-MS A: $t_R$=0.93 min; [M+H]$^+$= 321.17

A.1.30.1. 2-(7-Chloro-2-methyl-1H-indol-1-yl)ethan-1-amine

The title compound is prepared according to the synthesis of A.1.1.1. described above 7-chloro-2-methyl-1H-indole; LC-MS A: $t_R$=0.58 min; [M+H]$^+$=209.24.

A.1.31. 6-Chloro-N-(2-(7-fluoro-2-methyl-1H-indol-1-yl)ethyl)pyrimidin-4-amine The title compound is prepared according to the synthesis of A.1.1. described above using 2-(7-fluoro-2-methyl-1H-indol-1-yl)ethan-1-amine; LC-MS A: $t_R$=0.88 min; [M+H]$^+$= 305.11

A.1.31.1. 2-(7-Fluoro-2-methyl-1H-indol-1-yl)ethan-1-amine

The title compound is prepared according to the synthesis of A.1.1.1. described above 7-fluoro-2-methyl-1H-indole; LC-MS A: $t_R$=0.58 min; [M+H]$^+$=193.27.

A.1.32. 6-Chloro-N-(2-(2,5-dimethyl-1H-indol-1-yl)ethyl)pyrimidin-4-amine

The title compound is prepared according to the synthesis of A.1.1. described above using 2-(2,5-dimethyl-1H-indol-1-yl)ethan-1-amine; LC-MS A: $t_R$=0.91 min; [M+H]$^+$=301.18.

A.1.32.1. 2-(2,5-Dimethyl-1H-indol-1-yl)ethan-1-amine

The title compound is prepared according to the synthesis of A.1.1.1. described above 2,5-dimethyl-1H-indole; LC-MS A: $t_R$=0.59 min; [M+H]$^+$=189.32.

A.1.33. 1-(2-((6-Chloropyrimidin-4-yl)amino)ethyl)-2-methyl-1H-indole-7-carbonitrile The title compound is prepared according to the synthesis of A.1.1. described above using 1-(2-aminoethyl)-2-methyl-1H-indole-7-carbonitrile; LC-MS A: $t_R$=0.86 min; [M+H]$^+$=312.10.

A.1.33.1. 1-(2-Aminoethyl)-2-methyl-1H-indole-7-carbonitrile

The title compound is prepared according to the synthesis of A.1.1.1. described above using 2-methyl-1H-indole-7-carbonitrile; LC-MS A: $t_R$=0.55 min; [M+H]+=200.19.

A.1.34. 6-Chloro-N-(2-(4-ethyl-2-methyl-1H-indol-1-yl)ethyl)pyrimidin-4-amine The title compound is prepared according to the synthesis of A.1.1. described above using 2-(4-ethyl-2-methyl-1H-indol-1-yl)ethan-1-amine; LC-MS A: $t_R$=0.94 min; [M+H]$^+$= 315.11.

A.1.34.1. 2-(4-Ethyl-2-methyl-1H-indol-1-yl)ethan-1-amine

The title compound is prepared according to the synthesis of A.1.1.1. described above using 4-ethyl-2-methyl-1H-indole; LC-MS A: $t_R$=0.63 min; [M+H]$^+$=203.24.

A.1.35. 6-Chloro-N-(2-(2,4,7-trimethyl-1H-indol-1-yl)ethyl)pyrimidin-4-amine The title compound is prepared according to the synthesis of A.1.1. described above using 2-(2,4,7-trimethyl-1H-indol-1-yl)ethan-1-amine; LC-MS A: $t_R$=0.94 min; [M+H]$^+$=315.00.

A.1.35.1. 2-(2,4,7-Trimethyl-1H-indol-1-yl)ethan-1-amine

The title compound is prepared according to the synthesis of A.1.1.1. described above using 2,4,7-trimethyl-1H-indole; LC-MS A: $t_R$=0.62 min; [M+H]$^+$=203.21.

A.1.36. 6-Chloro-N-(2-(7-chloro-4-fluoro-2-methyl-1H-indol-1-yl)ethyl)pyrimidin-4-amine The title compound is prepared according to the synthesis of A.1.1. described above using 2-(7-chloro-4-fluoro-2-methyl-1H-indol-1-yl)ethan-1-amine; LC-MS A: $t_R$=0.94 min; [M+H]$^+$=338.84.

A.1.36.1. 2-(7-Chloro-4-fluoro-2-methyl-1H-indol-1-yl)ethan-1-amine

The title compound is prepared according to the synthesis of A.1.1.1. described above using 7-chloro-4-fluoro-2-methyl-1H-indole; LC-MS A: $t_R$=0.61 min; [M+H]$^+$=227.06.

A.1.37. 6-Chloro-N-(2-(5,7-dichloro-2-methyl-1H-indol-1-yl)ethyl)pyrimidin-4-amine The title compound is prepared according to the synthesis of A.1.1. described above using 2-(5,7-dichloro-2-methyl-1H-indol-1-yl)ethan-1-amine; LC-MS A: $t_R$=0.98 min; [M+H]$^+$=356.89.

A.1.37.1. 2-(5,7-Dichloro-2-methyl-1H-indol-1-yl)ethan-1-amine

The title compound is prepared according to the synthesis of A.1.1.1. described above using 5,7-dichloro-2-methyl-1H-indole; LC-MS A: $t_R$=0.65 min; [M+H]$^+$=243.01.

A.1.38. 6-Chloro-N-(2-(7-chloro-5-fluoro-2-methyl-1H-indol-1-yl)ethyl)pyrimidin-4-amine The title compound is prepared according to the synthesis of A.1.1. described above using 2-(7-chloro-5-fluoro-2-methyl-1H-indol-1-yl)ethan-1-amine; LC-MS A: $t_R$=0.94 min; [M+H]$^+$=338.87.

A.1.38.1. 2-(7-Chloro-5-fluoro-2-methyl-1H-indol-1-yl)ethan-1-amine

The title compound is prepared according to the synthesis of A.1.1.1. described above using 7-chloro-5-fluoro-2-methyl-1H-indole; LC-MS A: $t_R$=0.61 min; [M+H]$^+$=227.04.

A.1.39. 6-Chloro-N-(2-(7-methoxy-2-methyl-1H-indol-1-yl)ethyl)pyrimidin-4-amine The title compound is prepared according to the synthesis of A.1.1. described above using 2-(7-methoxy-2-methyl-1H-indol-1-yl)ethan-1-amine; LC-MS A: $t_R$=0.89 min; [M+H]$^+$= 317.28.

A.1.39.1. 2-(7-Methoxy-2-methyl-1H-indol-1-yl)ethan-1-amine

The title compound is prepared according to the synthesis of A.1.1.1. described above using 7-methoxy-2-methyl-1H-indole; LC-MS A: $t_R$=0.81 min; [M+H]$^+$=205.18.

A.1.40. 6-Chloro-N-(2-(7-methoxy-2-methyl-1H-indol-1-yl)ethyl)pyrimidin-4-amine The title compound is prepared according to the synthesis of A.1.1. described above using 2-(7-methoxy-2-methyl-1H-indol-1-yl)ethan-1-amine; LC-MS A: $t_R$=0.89 min; [M+H]$^+$= 317.28.

A.1.40.1. 2-(7-Methoxy-2-methyl-1H-indol-1-yl)ethan-1-amine

The title compound is prepared according to the synthesis of A.1.1.1. described above using 7-methoxy-2-methyl-1H-indole; LC-MS A: $t_R$=0.81 min; [M+H]$^+$=205.18.

A.1.41. 1-(2-((6-Chloropyrimidin-4-yl)amino)ethyl)-1H-indole-2-carbonitrile

The title compound is prepared according to the synthesis of A.1.1. described above using 2-(2-cyano-1H-indol-1-yl)ethan-1-aminium 2,2,2-trifluoroacetate; LC-MS A: $t_R$=0.85 min; [M+H]$^+$=298.05.

A.1.41.1. 2-(2-Cyano-1H-indol-1-yl)ethan-1-aminium 2,2,2-trifluoroacetate

A solution of tert-butyl (2-(2-cyano-1H-indol-1-yl)ethyl) carbamate (2.08 g, 6.56 mmol) in DCM (20 mL) is treated with TFA (20 mL) and the RM is stirred for 1 h at RT. The solvents are removed under vacuum. The residue is triturated three times in Et$_2$O, affording the title compound as a beige powder (1.56 g, 81%). LC-MS A: $t_R$=0.82 min; [M+H]$^+$=186.25.

A.1.41.2. Tert-butyl (2-(2-cyano-1H-indol-1-yl)ethyl)carbamate

NaH (0.27 g, 6.75 mmol) is added portionwise to a solution of 1H-indole-2-carbonitrile (0.80 g, 5.63 mmol) in DMF (25 mL) and the RM is stirred at RT for 15 min. A solution of N-Boc-2-bromoethyl-amine (1.30 g, 5.63 mmol) in DMF (10 mL) is added dropwise, and the RM is heated up to 85° C. and stirred at this temperature for 17 h, then cooled at RT and partitioned between Et$_2$O and H$_2$O. The aqueous layer is re-extracted with Et$_2$O (×3). The combined organic layers are dried over MgSO$_4$, filtered and concentrated under reduced pressure, affording the title compound as a brown oil. LC-MS A: $t_R$=0.90 min; [M+H-Boc]$^+$=186.27.

A.1.42. 6-Chloro-N-(2-(5,6,7-trifluoro-2-methyl-1H-indol-1-yl)ethyl)pyrimidin-4-amine The title compound is prepared according to the synthesis of A.1.1. described above using 2-(5,6,7-trifluoro-2-methyl-1H-indol-1-yl)ethan-1-amine; LC-MS A: $t_R$=0.93 min; [M+H]$^+$=341.00.

A.1.42.1. 2-(5,6,7-Trifluoro-2-methyl-1H-indol-1-yl)ethan-1-amine

The title compound is prepared according to the synthesis of A.1.1.1. described above using 5,6,7-trifluoro-2-methyl-1H-indole; LC-MS A: $t_R$=0.60 min; [M+H]$^+$=229.14.

A.1.42.2. 5,6,7-Trifluoro-2-methyl-1H-indole (Bartoli reaction)

A solution of isopropenylmagnesium bromide (0.5M in THF, 225 mL, 112 mmol) is cooled at −50° C. A solution of 2,3,4-trifluoronitrobenzene (6.28 g, 35.5 mmol) in THF (50 mL) is added dropwise over 30 min. After the addition, the reaction is stirred at −50° C. for 1 h. 100 mL of a saturated ammonium chloride solution is added dropwise to the RM at −40° C. before allowing the mixture to warm to RT. The mixture is diluted with 100 mL of water and extracted with Et$_2$O, then dried over MgSO$_4$ and concentrated. The crude material is purified by FC, eluting with heptane/EtOAc 1:0 to 95:5, affording the title compound as a yellow liquid (2.26 g, 34%). LC-MS A: t$_R$=0.87 min; no ionization.

A.1.43. 6-Chloro-N-(2-(7-chloro-4,5-difluoro-2-methyl-1H-indol-1-yl)ethyl)pyrimidin-4-amine The title compound is prepared according to the synthesis of A.1. described above using 2-(7-chloro-4,5-difluoro-2-methyl-1H-indol-1-yl)ethan-1-amine; LC-MS A: t$_R$=0.97 min; [M+H]$^+$=357.03.

A.1.43.1. 2-(7-Chloro-4,5-difluoro-2-methyl-1H-indol-1-yl)ethan-1-amine

The title compound is prepared according to the synthesis of A.1.1.1. described above using 7-chloro-4,5-difluoro-2-methyl-1H-indole; LC-MS A: t$_R$=0.63 min; [M+H]$^+$=245.10.

A.1.43.2. 7-Chloro-4,5-Difluoro-2-methyl-1H-indole

The title compound is prepared according to the Bartoli reaction described above for the preparation of A.1.42.2., using 2-Chloro-4,5-difluoronitrobenzene; LC-MS A: t$_R$=0.90 min; no ionization.

A.1.44. 6-Chloro-N-(2-(4,7-dichloro-5-fluoro-2-methyl-1H-indol-1-yl)ethyl)pyrimidin-4-amine The title compound is prepared according to the synthesis of A.1. described above using 2-(4,7-dichloro-5-fluoro-2-methyl-1H-indol-1-yl)ethan-1-amine; LC-MS A: t$_R$=0.99 min; [M+H]$^+$=372.97.

A.1.44.1. 2-(4,7-Dichloro-5-fluoro-2-methyl-1H-indol-1-yl)ethan-1-amine

The title compound is prepared according to the synthesis of A.1.1.1. described above using 4,7-dichloro-5-fluoro-2-methyl-1H-indole; LC-MS A: t$_R$=0.64 min; [M+H]$^+$=261.07.

A.1.44.2. 4,7-Dichloro-5-fluoro-2-methyl-1H-indole

The title compound is prepared according to the Bartoli reaction described above for the preparation of A.1.42.2., using 1,4-dichloro-2-fluoro-5-nitrobenzene; LC-MS A: t$_R$=0.93 min; no ionization.

A.1.45. 6-Chloro-N-(2-(6,7-difluoro-2,4-dimethyl-1H-indol-1-yl)ethyl)pyrimidin-4-amine The title compound is prepared according to the synthesis of A.1.1. described above using 2-(6,7-difluoro-2,4-dimethyl-1H-indol-1-yl)ethan-1-amine; LC-MS A: t$_R$=0.94 min; [M+H]$^+$=337.12.

A.1.45.1. 2-(6,7-Difluoro-2,4-dimethyl-1H-indol-1-yl)ethan-1-amine

The title compound is prepared according to the synthesis of A.1.1.1. described above using 6,7-difluoro-2,4-dimethyl-1H-indole; LC-MS A: t$_R$=0.62 min; [M+H]$^+$=225.23.

A.1.45.2. 6,7-Difluoro-2,4-dimethyl-1H-indole

To a solution of 4-bromo-6,7-difluoro-2-methyl-1H-indole (1.36 g, 5.53 mmol) and bis(tri-tert-butylphosphine)palladium(0) (169 mg, 0.332 mmol) in THF (12 mL) is added dropwise methylzinc chloride (2.0M solution in THF, 5.3 mL, 16.6 mmol). The mixture is heated at 80° C. in the microwave for 30 min. It is then partitioned between HCl 2N (25 mL) and DCM. The aqueous layer is re-extracted with DCM. The organic layer is dried over MgSO$_4$, concentrated and purified by FC, eluting with heptane/EtOAc 100:0 to 97:3. This afforded the title compound as a yellow oil (0.573 g, 57%); LC-MS A: t$_R$=0.88 min; [M+H]$^+$=182.32.

A.1.45.3. 4-Bromo-6,7-difluoro-2-methyl-1H-indole

The title compound is prepared according to the Bartoli reaction described above for the preparation of A.1.42.2., using 5-Bromo-1,2-difluoro-3-nitrobenzene; LC-MS A: t$_R$=0.91 min; no ionization.

A.1.46. 6-Chloro-N-(2-(6,7-difluoro-4-methoxy-2-methyl-1H-indol-1-yl)ethyl)pyrimidin-4-amine The title compound is prepared according to the synthesis of A.1.1. described above using 2-(6,7-difluoro-4-methoxy-2-methyl-1H-indol-1-yl)ethan-1-amine; LC-MS A: t$_R$=0.91 min; [M+H]$^+$=353.08.

A.1.46.1. 2-(6,7-Difluoro-4-methoxy-2-methyl-1H-indol-1-yl)ethan-1-amine

The title compound is prepared according to the synthesis of A.1.1.1. described above using 6,7-difluoro-4-methoxy-2-methyl-1H-indole; LC-MS A: t$_R$=0.59 min; [M+H]$^+$=241.19.

A.1.46.2. 6,7-Difluoro-4-methoxy-2-methyl-1H-indole

To a solution of 4-bromo-6,7-difluoro-2-methyl-1H-indole (1.69 g, 5.09 mmol) in DMF (10 mL) are added sodium methoxide (5.4M in MeOH, 9.45 mL, 50.9 mmol) and copper(I) iodide (1.938 g, 10.2 mmol). The RM is heated at 120° C. for 30 min in the microwave. It is then filtered over celite and rinsed with DCM. The filtrate is washed with water, the aqueous phase is extracted twice with DCM and the combined organic layers are dried over MgSO$_4$ and concentrated under reduced pressure. The residue is purified by FC, eluting with using Heptane/EtOAc 100:0 to 93:7. This afforded the title compound as a orange oil (0.52 g, 48%); LC-MS A: t$_R$=0.59 min; [M+H]$^+$=241.19.

A.1.46.3. 4-Bromo-6,7-difluoro-2-methyl-1H-indole

The title compound is prepared according to the Bartoli reaction described above for the preparation of

A.1.47. 6-Chloro-N-(2-(5-chloro-7-fluoro-4-methoxy-2-methyl-1H-indol-1-yl)ethyl)pyrimidin-4-amine The title compound is prepared according to the synthesis of A.1.1. described above using 2-(5-chloro-7-fluoro-4-methoxy-2-methyl-1H-indol-1-yl)ethan-1-amine; LC-MS A: $t_R$=0.92 min; [M+H]$^+$=368.91.

A.1.47.1. 2-(5-Chloro-7-fluoro-4-methoxy-2-methyl-1H-indol-1-yl)ethan-1-amine The title compound is prepared according to the synthesis of A.1.1.1. described above using 5-chloro-7-fluoro-4-methoxy-2-methyl-1H-indole; LC-MS A: $t_R$=0.61 min; [M+H]$^+$=257.06.

A.1.47.2. 5-Chloro-7-fluoro-4-methoxy-2-methyl-1H-indole

The title compound is prepared according to the Bartoli reaction described above for the preparation of A.1.42.2., using 1-chloro-5-fluoro-2-methoxy-4-nitrobenzene; LC-MS A: $t_R$=0.86 min; [M+H]$^+$=214.08.

A.1.48. 6-Chloro-N-(2-(5,7-difluoro-4-methoxy-2-methyl-1H-indol-1-yl)ethyl)pyrimidin-4-amine The title compound is prepared according to the synthesis of A.1.1. described above using 2-(5,7-difluoro-4-methoxy-2-methyl-1H-indol-1-yl)ethan-1-amine; LC-MS A: $t_R$=0.90 min; [M+H]$^+$=352.95.

A.1.48.1. 2-(5,7-Difluoro-4-methoxy-2-methyl-1H-indol-1-yl)ethan-1-amine

The title compound is prepared according to the synthesis of A.1.1.1. described above using 5,7-difluoro-4-methoxy-2-methyl-1H-indole; LC-MS A: $t_R$=0.59 min; [M+H]$^+$=241.11.

A.1.48.2. 5,7-Difluoro-4-methoxy-2-methyl-1H-indole

The title compound is prepared according to the Bartoli reaction described above for the preparation of A.1.42.2., using 1,5-difluoro-2-methoxy-4-nitrobenzene; LC-MS A: $t_R$=0.83 min; [M+H]$^+$=198.44.

A.1.49. 6-Chloro-N-(2-(5-chloro-7-methyl-6H-[1,3]dioxolo[4,5-e]indol-6-yl)ethyl)pyrimidin-4-amine The title compound is prepared according to the synthesis of A.1.1. described above using 2-(5-chloro-7-methyl-6H-[1,3]dioxolo[4,5-e]indol-6-yl)ethan-1-amine; LC-MS A: $t_R$=0.92 min; [M+H]$^+$=366.87.

A.1.49.1. 2-(5-Chloro-7-methyl-6H-[1,3]dioxolo[4,5-e]indol-6-yl)ethan-1-amine The title compound is prepared according to the synthesis of A.1.1.1. described above using 5-chloro-7-methyl-6H-[1,3]dioxolo[4,5-e]indole; LC-MS A: $t_R$=0.59 min; [M+H]$^+$=253.09.

A.1.49.2. 5-Chloro-7-methyl-6H-[1,3]dioxolo[4,5-e]indole

The title compound is prepared according to the Bartoli reaction described above for the preparation of A.1.42.2., using 5-chloro-6-nitrobenzo[d][1,3]dioxole; LC-MS A: $t_R$=0.85 min; [M+H]$^+$=210.26.

A.1.50. 6-Chloro-N-(2-(7-chloro-5-fluoro-4-methoxy-2-methyl-1H-indol-1-yl)ethyl)pyrimidin-4-amine The title compound is prepared according to the synthesis of A.1.1. described above using 2-(7-chloro-5-fluoro-4-methoxy-2-methyl-1H-indol-1-yl)ethan-1-amine; LC-MS A: $t_R$=0.94 min; [M+H]$^+$=369.08.

A.1.50.1. 2-(7-Chloro-5-fluoro-4-methoxy-2-methyl-1H-indol-1-yl)ethan-1-amine The title compound is prepared according to the synthesis of A.1.1.1. described above using 7-chloro-5-fluoro-4-methoxy-2-methyl-1H-indole; LC-MS A: $t_R$=0.61 min; [M+H]$^+$=257.15.

A.1.50.2. 7-Chloro-5-fluoro-4-methoxy-2-methyl-1H-indole

The title compound is prepared according to the Bartoli reaction described above for the preparation of A.1.42.2., using 1-chloro-5-fluoro-4-methoxy-2-nitrobenzene; LC-MS A: $t_R$=0.87 min; [M+H]$^+$=214.22.

A.1.51. 6-Chloro-N-(2-(7-fluoro-2-methyl-4-(trifluoromethyl)-1H-indol-1-yl)ethyl)pyrimidin-4-amine The title compound is prepared according to the synthesis of A.1.1. described above using 2-(7-fluoro-2-methyl-4-(trifluoromethyl)-1H-indol-1-yl)ethan-1-amine; LC-MS A: $t_R$=0.96 min; [M+H]$^+$=373.02.

A.1.51.1. 2-(7-Fluoro-2-methyl-4-(trifluoromethyl)-1H-indol-1-yl)ethan-1-amine The title compound is prepared according to the synthesis of A.1.1.1. described above using 7-fluoro-2-methyl-4-(trifluoromethyl)-1H-indole; LC-MS A: $t_R$=0.66 min; [M+MeCN]$^+$=302.24.

A.1.51.2. 7-Fluoro-2-methyl-4-(trifluoromethyl)-1H-indole

The title compound is prepared according to the Bartoli reaction described above for the preparation of A.1.42.2., using 1-fluoro-2-nitro-4-(trifluoromethyl)benzene; LC-MS A: $t_R$=0.91 min; [M+H]$^+$=218.17.

A.1.52. 6-Chloro-N-(2-(7-fluoro-2-methyl-4-(trifluoromethoxy)-1H-indol-1-yl)ethyl)pyrimidin-4-amine The title compound is prepared according to the synthesis of A.1.1. described above using 2-(7-fluoro-2-methyl-4-(trifluoromethoxy)-1H-indol-1-yl)ethan-1-amine; LC-MS A: $t_R$=0.97 min; [M+H]$^+$=388.79.

A.1.52.1. 2-(7-Fluoro-2-methyl-4-(trifluoromethoxy)-1H-indol-1-yl)ethan-1-amine The title compound is prepared according to the synthesis of A.1.1.1. described above using 7-fluoro-2-methyl-4-(trifluoromethoxy)-1H-indole; LC-MS A: $t_R$=0.68 min; [M+MeCN]$^+$=317.90.

A.1.52.2. 7-Fluoro-2-methyl-4-(trifluoromethoxy)-1H-indole

The title compound is prepared according to the Bartoli reaction described above for the preparation of A.1.42.2., using 1-fluoro-2-nitro-4-(trifluoromethoxy) benzene; LC-MS A: $t_R$=0.92 min; [M+MeCN]$^+$=274.26.

A.1.53. 6-Chloro-N-(2-(6,7-dichloro-5-fluoro-2-methyl-1H-indol-1-yl)ethyl)pyrimidin-4-amine The title compound is prepared according to the synthesis of A.1.1. described above using 2-(6,7-dichloro-5-fluoro-2-methyl-1H-indol-1-yl)ethan-1-amine; LC-MS A: $t_R$=0.98 min; [M+H]$^+$=373.07.

A.1.53.1. 2-(6,7-Dichloro-5-fluoro-2-methyl-1H-indol-1-yl)ethan-1-amine

The title compound is prepared according to the synthesis of A.1.1.1. described above using 6,7-dichloro-5-fluoro-2-methyl-1H-indole; LC-MS A: $t_R$=0.65 min; [M+MeCN]$^+$=261.08.

A.1.53.2. 6,7-Dichloro-5-fluoro-2-methyl-1H-indole

Acetone (7.95 mL, 107 mmol) is added to a solution of 2,3-dichloro-4-fluoroaniline (1.93 g, 10.7 mmol) in DMSO (20 mL). Palladium(II)acetate (0.481 g, 2.14 mmol) and copper(II) acetate (5.84 g, 32.2 mmol) are added, and the mixture is heated at 85° C. for 17 h. The mixture is concentrated, filtered over a plug of silica and rinsed with DCM. The filtrate is washed with HCl 2N and brine, dried over MgSO$_4$ and concentrated. The residue is purified by FC, eluting with heptane/EtOAc from 100:0 to 95:5, affording the title compound as an orange solid (0.52 g, 23%). LC-MS A: $t_R$=0.92 min; [M+H]$^+$=218.07.

A.1.54. 6-Chloro-N-(2-(6-chloro-4-methoxy-2-methyl-1H-indol-1-yl)ethyl)pyrimidin-4-amine The title compound is prepared according to the synthesis of A.1.1. described above using 2-(6-chloro-4-methoxy-2-methyl-1H-indol-1-yl)ethan-1-amine; LC-MS A: $t_R$=0.91 min; [M+H]$^+$=351.08.

A.1.54.1. 2-(6-Chloro-4-methoxy-2-methyl-1H-indol-1-yl)ethan-1-amine

The title compound is prepared according to the synthesis of A.1.1.1. described above using 6-chloro-4-methoxy-2-methyl-1H-indole; LC-MS A: $t_R$=0.62 min; [M+H]$^+$=239.16.

A.1.55. 6-Chloro-N-(2-(4-ethyl-7-fluoro-2-methyl-1H-indol-1-yl)ethyl)pyrimidin-4-amine The title compound is prepared according to the synthesis of A.1.1. described above using 2-(4-ethyl-7-fluoro-2-methyl-1H-indol-1-yl)ethan-1-amine; LC-MS A: $t_R$=0.96 min; [M+H]$^+$=332.93.

A.1.55.1. 2-(4-Ethyl-7-fluoro-2-methyl-1H-indol-1-yl)ethan-1-amine

The title compound is prepared according to the synthesis of A.1.1.1. described above using 4-ethyl-7-fluoro-2-methyl-1H-indole; LC-MS A: $t_R$=0.65 min; [M+H]$^+$=221.06.

A.1.55.2. 4-Ethyl-7-fluoro-2-methyl-1H-indole

Pd(dppf)Cl$_2$·DCM (39 mg, 0.047 mmol) is added to a degassed solution of 4-bromo-7-fluoro-2-methyl-1H-indole (0.432 g, 1.89 mmol), triethylborane (1M in THF, 2.27 mL, 2.27 mmol) and Cs$_2$CO$_3$ (1.85 g, 5.68 mmol) in THE (15 mL). After stirring 24 h at reflux under an argon atmosphere. the RM is cooled to RT and filtered through a Whatmann GF/A filter. The filtrate is concentrated in vacuo, and the residue is purified by FC, eluting with heptane/EtOAc 100:0 to 95:5. This afforded the title compound as a yellow oil (0.21 g, 62%); LC-MS A: $t_R$=0.90 min; [M+H]$^+$=178.24.

A.1.56. 6-Chloro-N-(2-(6-fluoro-2,4-dimethyl-1H-indol-1-yl)ethyl)-2-methylpyrimidin-4-amine The title compound is prepared according to the synthesis of A.1.1. described above using 2-(6-fluoro-2,4-dimethyl-1H-indol-1-yl)ethan-1-amine (see A.1.4.) and 4,6-dichloro-2-methylpyrimidine; LC-MS A: $t_R$=0.91 min; [M+H]$^+$=333.11.

A.1.57. 6-Chloro-N-(2-(6-fluoro-4-methoxy-2-methyl-1H-indol-1-yl)ethyl)-2-methylpyrimidin-4-amine The title compound is prepared according to the synthesis of A.1.1. described above using 2-(6-fluoro-4-methoxy-2-methyl-1H-indol-1-yl)ethan-1-amine (see A.1.23.) and 4,6-dichloro-2-methylpyrimidine; LC-MS A: $t_R$=0.88 min; [M+H]$^+$=349.12.

A.1.58. 6-Chloro-N-(2-(7-fluoro-4-methoxy-2-methyl-1H-indol-1-yl)ethyl)-2-methylpyrimidin-4-amine The title compound is prepared according to the synthesis of A.1.1. described above using 2-(7-fluoro-4-methoxy-2-methyl-1H-indol-1-yl)ethan-1-amine (see A.1.25.) and 4,6-dichloro-2-methylpyrimidine; LC-MS A: $t_R$ 0.86 min; [M+H]$^+$=349.13.

A.1.59. 6-Chloro-N-(2-(6-chloro-2,4-dimethyl-1H-indol-1-yl)ethyl)pyrimidin-4-amine The title compound is prepared according to the synthesis of A.1.1. described above using 2-(6-chloro-2,4-dimethyl-1H-indol-1-yl)ethan-1-amine; LC-MS A: $t_R$=0.94 min; [M+H]$^+$=334.95.

A.1.59.1. 2-(6-Chloro-2,4-dimethyl-1H-indol-1-yl)ethan-1-amine

The title compound is prepared according to the synthesis of A.1.1.1. described above using 6-chloro-2,4-dimethyl-1H-indole; LC-MS A: $t_R$=0.64 min; $[M+H]^+$=223.18.

A.1.59.2. 6-Chloro-2,4-dimethyl-1H-indole

To a solution of 5-chloro-2-iodo-3-methylaniline (325 mg, 1.21 mmol), PEPPSI-IPr (50.5 mg, 0.0729 mmol) and sodium tert-butoxide (193 mg, 1.94 mmol) in toluene (4 mL) is added 2-bromopropene (0.136 mL, 1.52 mmol). The mixture is heated at 175° C. for 15 min in the microwave, then at 215° C. for 20 min. The RM is concentrated under reduced pressure, and purified by FC, eluting with heptane/DCM 1:0 to 3:1. This afforded the title compound as a yellow solid (71 mg, 33%). LC-MS A: $t_R$=0.89 min; $[M+H]^+$=180.29.

A.1.60. 6-Chloro-N-(2-(5,7-difluoro-2,4-dimethyl-1H-indol-1-yl)ethyl)pyrimidin-4-amine The title compound is prepared according to the synthesis of A.1.1. described above using 2-(5,7-difluoro-2,4-dimethyl-1H-indol-1-yl)ethan-1-amine; LC-MS A: $t_R$=0.94 min; $[M+H]^+$=336.96.

A.1.60.1. 2-(5,7-Difluoro-2,4-dimethyl-1H-indol-1-yl)ethan-1-amine

The title compound is prepared according to the synthesis of A.1.1.1. described above using 5,7-difluoro-2,4-dimethyl-1H-indole; LC-MS A: $t_R$=0.62 min; $[M+H]^+$=226.20.

A.1.60.2. 5,7-Difluoro-2,4-dimethyl-1H-indole

The title compound is prepared according to the Bartoli reaction described above for the preparation of A.1.42.2., using 2,4-difluoro-5-nitrotoluene; LC-MS A: $t_R$=0.88 min; no ionization.

A.1.61. 6-Chloro-N-(2-(4,6,7-trifluoro-2-methyl-1H-indol-1-yl)ethyl)pyrimidin-4-amine The title compound is prepared according to the synthesis of A.1.1. described above using 2-(4,6,7-trifluoro-2-methyl-1H-indol-1-yl)ethan-1-amine; LC-MS A: $t_R$=0.92 min; $[M+H]^+$=341.10.

A.1.61.1. 2-(4,6,7-Trifluoro-2-methyl-1H-indol-1-yl)ethan-1-amine

The title compound is prepared according to the synthesis of A.1.1.1. described above using 4,6,7-trifluoro-2-methyl-1H-indole; LC-MS A: $t_R$=0.61 min; $[M+H]^+$=229.07.

A.1.61.2. 4,6,7-Trifluoro-2-methyl-1H-indole

The title compound is prepared according to the Bartoli reaction described above for the preparation of A.1.42.2., using 1,2,5-Trifluoro-3-nitrobenzene; LC-MS A: $t_R$=0.87 min; no ionization.

A.1.62. 6-Chloro-N-(2-(6-fluoro-4-methoxy-2-methyl-1H-indol-1-yl)ethyl)-2-(trifluoromethyl)pyrimidin-4-amine The title compound is prepared according to the synthesis of A.1.1. described above using 2-(6-fluoro-4-methoxy-2-methyl-1H-indol-1-yl)ethan-1-amine (see A.1.23.) and 4,6-dichloro-2-trifluoromethylpyrimidine; LC-MS A: $t_R$=1.00 min; $[M+H]^+$=403.07.

A.1.63. 6-Chloro-N-(2-(6-fluoro-2,4-dimethyl-1H-indol-1-yl)ethyl)-2-(trifluoromethyl)pyrimidin-4-amine The title compound is prepared according to the synthesis of A.1.1. described above using 2-(6-fluoro-2,4-dimethyl-1H-indol-1-yl)ethan-1-amine (see A.1.4.) and 4,6-dichloro-2-trifluoromethylpyrimidine; LC-MS A: $t_R$=1.01 min; $[M+H]^+$=386.87.

A.1.64. 1-(2-((6-Chloropyrimidin-4-yl)amino)ethyl)-6-fluoro-4-methoxy-1H-indole-2-carbonitrile The title compound is prepared according to the synthesis of A.1.1. described above using 1-(2-aminoethyl)-6-fluoro-4-methoxy-1H-indole-2-carbonitrile; LC-MS A: $t_R$=0.87 min; $[M+H]^+$=346.09.

A.1.64.1. 1-(2-Aminoethyl)-6-fluoro-4-methoxy-1H-indole-2-carbonitrile

A solution of tert-butyl (2-(2-cyano-6-fluoro-4-methoxy-1H-indol-1-yl)ethyl)carbamate (330 mg, 0.99 mmol) in DCM (5 mL) is treated with TFA (0.77 mL, 9.9 mmol), at RT. The RM is stirred at RT for 1 h, then concentrated under vacuum, affording the title compound as the trifluoro acetate salt (0.235 g, 100%); LC-MS A: $t_R$=0.57 min; $[M+H]^+$=234.19.

A.1.64.2. Tert-butyl (2-(2-cyano-6-fluoro-4-methoxy-1H-indol-1-yl)ethyl)carbamate A solution of 6-fluoro-4-methoxy-1H-indole-2-carbonitrile (1.12 g, 5.59 mmol) in DMF (25 mL) is treated at 0° C. with NaH (60% in oil, 269 mg, 6.72 mmol). The RM is stirred at RT for 15 min, then a solution of N-Boc-2-bromoethyl-amine (1.36 g, 5.87 mmol) in DMF (10 mL) is added dropwise, and the RM is heated at 85° C. for 16 h. The mixture is allowed to cool down to RT, quenched with water, and concentrated to dryness. The residue is purified by FC, eluting with heptane/EtOAc 100:0 to 70:30, affording the title compound as a white solid (330 mg, 18%); LC-MS A: $t_R$=0.92 min; $[M+H]^+$=334.15.

A.1.64.3. 6-Fluoro-4-methoxy-1H-indole-2-carbonitrile

To a solution of 6-fluoro-4-methoxy-1H-indole-2-carboxamide (2.65 g, 12.7 mmol) in DMF (40 mL) at 0° C. is added dropwise a solution of cyanuric chloride (3.59 g, 19.1 mmol) in DMF (10 mL). The RM is stirred for 1.5 h while reaching RT, then it is treated with water (50 mL), and stirred for 30 min. It is diluted with water, and extracted with EtOAc (3×). The combined organic extracts are washed with sat. $Na_2CO_3$, brine and dried over $MgSO_4$. The solvent is removed under reduced pressure to afford the title compound as a white solid (2.32 g, 96%). LC-MS A: $t_R$=0.94 min; [M+H]$^+$= 189.13.

A.1.64.4. 6-Fluoro-4-methoxy-1H-indole-2-carboxamide

6-Fluoro-4-methoxy-1H-indole-2-carboxylic acid (2.79 g, 13.3 mmol) is dissolved in DCM (60 mL) under $N_2$. DMF (1 drop) and thionyl chloride (3.5 mL, 48 mmol) are added at RT and the resulting RM is refluxed for 1 h, then cooled at RT, then at 0° C. 25% Ammonia solution (20 mL) is added dropwise and the RM is stirred for 20 min. The solvents are evaporated under reduced pressure. The solid residue is washed with water, and dried under high vacuum, yielding the title compound as a white solid (2.65 g, 95%). LC-MS A: $t_R$=0.72 min; [M+H]$^+$=207.11.

A.1.65. 1-(2-((6-Chloropyrimidin-4-yl)amino)ethyl)-6-fluoro-4-methyl-1H-indole-2-carbonitrile The title compound is prepared according to the synthesis of A.1.1. described above using 1-(2-aminoethyl)-6-fluoro-4-methyl-1H-indole-2-carbonitrile; LC-MS A: $t_R$=0.89 min; [M+H]$^+$=330.15.

A.1.65.1. 1-(2-Aminoethyl)-6-fluoro-4-methyl-1H-indole-2-carbonitrile

A solution of tert-butyl (2-(2-cyano-6-fluoro-4-methoxy-1H-indol-1-yl)ethyl)carbamate (1.75 g, 5.51 mmol) in DCM (20 mL) is treated with TFA (4.27 mL, 55.1 mmol), at RT. The RM is stirred at RT for 1 h, then concentrated under vacuum, affording the title compound as the trifluoro acetate salt (1.2 g, 100%); LC-MS A: $t_R$=0.58 min; [M+H]$^+$=218.24.

A.1.65.2. Tert-butyl (2-(2-cyano-6-fluoro-4-methyl-1H-indol-1-yl)ethyl)carbamate The title compound is prepared according to the synthesis of tert-butyl (2-(2-cyano-6-fluoro-4-methoxy-1H-indol-1-yl)ethyl)carbamate (see A.1.64.2.) using 6-fluoro-4-methyl-1H-indole-2-carbonitrile; LC-MS A: $t_R$=0.97 min; [M+H]$^+$=318.15.

A.1.65.3. 6-Fluoro-4-methyl-1H-indole-2-carbonitrile

The title compound is prepared according to the synthesis of 6-fluoro-4-methoxy-1H-indole-2-carbonitrile (see A.1.64.3.) using 6-fluoro-4-methyl-1H-indole-2-carboxamide; LC-MS D: $t_R$=1.00 min; [M−H]$^+$=172.96.

A.1.65.4. 6-Fluoro-4-methyl-1H-indole-2-carboxamide

The title compound is prepared according to the synthesis of 6-fluoro-4-methoxy-1H-indole-2-carboxamide (see A.1.64.4.) using 6-fluoro-4-methyl-1H-indole-2-carboxylic acid; LC-MS D: $t_R$=0.77 min; [M−H]$^+$=191.14.

A.1.66. 6-Chloro-N-(2-(4,6-difluoro-2,5-dimethyl-1H-indol-1-yl)ethyl)pyrimidin-4-amine The title compound is prepared according to the synthesis of A.1.1. described above using 2-(4,6-difluoro-2,5-dimethyl-1H-indol-1-yl)ethan-1-amine; LC-MS A: $t_R$=0.95 min; [M+H]$^+$=336.99.

A.1.66.1. 2-(4,6-Difluoro-2,5-dimethyl-1H-indol-1-yl)ethan-1-amine

The title compound is prepared according to the synthesis of A.1.1.1. described above using 4,6-difluoro-2,5-dimethyl-1H-indole; LC-MS A: $t_R$=0.65 min; [M+H]$^+$=225.32.

A.1.66.2. 4,6-Difluoro-2,5-dimethyl-1H-indole

A solution of 4,6-difluoro-2,5-dimethyl-1-(phenylsulfonyl)-1H-indole (9.50 g, 23.7 mmol) in MeOH (80 mL) is treated with NaOH 32% (7 mL, 237 mmol). The RM is refluxed o/n, cooled down to RT, and concentrated under reduced pressure. The crude residue is partioned between water and EtOAc, the aqueous layer is re-extracted with EtOAc. The combined organic extracts are dried (MgSO$_4$), and concentrated under reduced pressure. The crude product is purified by FC, eluting with heptane/toluene 1:0 to 3:2, affording the title compound as a light brown solid (4.29 g, 99%); LC-MS A: $t_R$=0.89 min; [M+H]$^+$=182.23.

A.1.66.3. 4,6-Difluoro-2,5-dimethyl-1-(phenylsulfonyl)-1H-indole

Diisopropylamine (5.82 mL, 41.2 mmol) is dissolved in dry THF (125 mL) at RT under Argon. The solution is cooled to 0° C. and n-butyllithium (2.5M solution in hexanes, 17.2 ml, 42.9 mmol) is added dropwise. The solution is stirred at RT for 30 min, then cooled to −78° C. 4,6-Difluoro-1-(phenylsulfonyl)-1H-indole (10.6 g, 34.3 mmol) is dissolved in dry THF (80 mL) and this solution is added dropwise at −78° C. in the freshly prepared solution of LDA over a 30 min period of time. It is then allowed to warm up to 0° C. over 30 min. The solution is cooled again to −78° C. and iodomethane (4.32 mL, 68.7 mmol) is added dropwise and it is slowly allowed to reach RT, overnight. The mixture is poured over ice and treated with saturated NH$_4$Cl solution. The THF is removed under reduced pressure, the residue is extracted with EtOAc (2×). The combined organic layers are washed with brine, dried over MgSO$_4$, filtered and concentrated under vacuum. The residue is purified by FC, eluting with heptane/DCM 1:0 to 17:3, affording the title compound as a white solid (9.50 g, 80%); LC-MS A: $t_R$=0.91 min; [M+H]$^+$= 322.65.

A.1.66.4. 4,6-Difluoro-1-(phenylsulfonyl)-1H-indole

NaH (1.55 g, 38.8 mmol) is added portionwise to a solution of 4,6-difluoroindole (5.00 g, 31 mmol) in THF dry (120 mL) at 0° C., and the mixture is stirred for 15 min at this temperature. Then benzenesulfonyl chloride (4.81 mL, 37.2 mmol) is added dropwise and the mixture is stirred overnight at RT. A few mL of ice-cold water are added to neutralize residual NaH and PhSO$_2$Cl, then it is concentrated in vacuo. The residue is diluted in EtOAc and washed with 1N NaHCO$_3$ and brine, dried over MgSO$_4$, filtered and concentrated under vacuum. Finally the crude product is filtered through a pad of silica gel using DCM as solvent, affording the title compound as a white solid (9.08 g, 100%). LC-MS A: $t_R$=0.96 min; no ionization

A.1.67. 6-Chloro-N-(2-(7-chloro-6-fluoro-2,4-dimethyl-1H-indol-1-yl)ethyl)pyrimidin-4-amine The title compound is prepared according to the synthesis of A.1.1. described above using 2-(7-chloro-6-fluoro-2,4-dimethyl-1H-indol-1-yl)ethan-1-amine; LC-MS A: $t_R$=0.98 min; [M+H]$^+$=353.05.

A.1.67.1. 2-(7-Chloro-6-fluoro-2,4-dimethyl-1H-indol-1-yl)ethan-1-amine

The title compound is prepared according to the synthesis of A.1.1.1. described above using 7-chloro-6-fluoro-2,4-dimethyl-1H-indole; LC-MS A: $t_R$=0.64 min; [M+H]$^+$=241.13.

A.1.67.2. 7-Chloro-6-fluoro-2,4-dimethyl-1H-indole

The title compound is prepared according to the synthesis of A.1.42.2. described above using 2-chloro-1-fluoro-5-methyl-3-nitrobenzene; LC-MS A: $t_R$=0.91 min; [M+H]$^+$=198.24.

A.1.67.3. 2-Chloro-1-fluoro-5-methyl-3-nitrobenzene

C2CsO$_3$ (487 mg, 1.48 mmol) and K$_2$CO$_3$ (409 mg, 2.96 mmol) are added to a degassed solution of 5-bromo-2-chloro-1-fluoro-3-nitrobenzene (380 mg, 1.48 mmol) in 1,4-dioxane (50 mL) at RT under a N$_2$ atmosphere. Then Pd(PPh$_3$)$_4$ (171 mg, 0.15 mmol) and trimethylboroxine (0.21 mL, 1.48 mmol) are added. The resulting orange heterogeneous mixture is stirred at reflux for 7 h. The RM is cooled to RT and concentrated. The residue is diluted with water (30 mL) and extracted with DCM (2×30 mL). The combined extracts are washed with brine (50 mL), dried over MgSO$_4$, filtered and concentrated under reduced pressure. The crude material is purified by FC, eluting with heptane/DCM from 90/10 to 0/100. This afforded the title compound as an orange solid (187 mg, 63%). LC-MS A: $t_R$=0.88 min; no ionization.

A.1.67.4. 5-Bromo-2-chloro-1-fluoro-3-nitrobenzene

To a solution of 4-Bromo-2-fluoro-6-nitrophenol (500 mg, 2.06 mmol) in anhydrous DMF (5 mL) at −30/40° C. is added oxalyl chloride (0.35 mL, 4.11 mmol, 2 eq), dropwise. The resulting white heterogeneous mixture is then stirred for 15 min at −40° C. and heated up to 80° C. for 4 h 30. The RM is cooled to RT. Ice and water (20 mL) are successively added and the mixture is stirred further for 20 min. The yellow precipitate is collected by filtration and dried under HV to afford the title compound as a yellow solid (418 mg, 79%). LC-MS A: $t_R$=0.89 min; no ionization.

A.1.68. 1-(2-(((6-Chloropyrimidin-4-yl)amino)ethyl)-7-fluoro-4-methoxy-1H-indole-2-carbonitrile A solution of tert-butyl (6-chloropyrimidin-4-yl)(2-(2-cyano-7-fluoro-4-methoxy-1H-indol-1-yl)ethyl)carbamate (7.98 g, 17.9 mmol) in HCl (4N in dioxane, 75 mL) is stirred at RT for 17 h. The RM is concentrated under reduced pressure and the residue is partioned between DCM and aqueous sat. Na$_2$CO$_3$ solution. The organic layer is separated and the aqueous layer is extracted with EtOAc. The combined organic layers are dried over MgSO$_4$ and concentrated, affording the title compound as a light yellow solid (6.3 g, quantitative); LC-MS A: $t_R$=0.87 min; [M+H]$^+$=346.08.

A.1.68.1. Tert-butyl (6-chloropyrimidin-4-yl)(2-(2-cyano-7-fluoro-4-methoxy-1H-indol-1-yl)ethyl)carbamate To a solution of tert-butyl (2-(2-cyano-7-fluoro-4-methoxy-1H-indol-1-yl)ethyl)carbamate (9.00 g, 27 mmol) in dioxane (220 mL) at RT is added portionwise NaH (60% in oil, 4.86 g, 121 mmol). The RM is stirred at RT for 10 min, then 4,6-dichloropyrimidine (9.25 g, 62.1 mmol) is added portionwise and the mixture is heated and stirred at 95° C. overnight. Under ice bath cooling, the mixture is carefully quenched by dropwise addition of water (50 mL). The organic solvent is removed under vacuum, then the aqueous residue is extracted once with DCM then twice with EtOAc. The organic layer is washed with brine, dried over MgSO4, filtered and concentrated. The crude product is purified by FC, eluting with Hept/EtOAc 19:1 to 9:1, to afford the title compound as a white solid (7.98 g, 66%); LC-MS A: $t_R$=1.05 min; [M+H]$^+$=446.05.

A.1.68.2. Tert-butyl (2-(2-cyano-7-fluoro-4-methoxy-1H-indol-1-yl)ethyl)carbamate The title compound is prepared according to the synthesis of tert-butyl (2-(2-cyano-6-fluoro-4-methoxy-1H-indol-1-yl)ethyl)carbamate (see A.1.64.2.) using 7-fluoro-4-methoxy-1H-indole-2-carbonitrile; LC-MS A: $t_R$=0.91 min; [M+H]$^+$=334.14.

A.1.68.3. 7-Fluoro-4-methoxy-1H-indole-2-carbonitrile

The title compound is prepared according to the synthesis of 6-fluoro-4-methoxy-1H-indole-2-carbonitrile (see A.1.64.3.) using 7-fluoro-4-methoxy-1H-indole-2-carboxamide; LC-MS DA: $t_R$=0.81 min; no ionization.

A.1.68.4. 7-Fluoro-4-methoxy-1H-indole-2-carboxamide

The title compound is prepared according to the synthesis of 6-fluoro-4-methoxy-1H-indole-2-carboxamide (see A.1.64.4.) using 7-fluoro-4-methoxy-1H-indole-2-carboxylic acid; LC-MS D: $t_R$=0.63 min; [M+MeCN]+=250.21.

A.1.69. 1-(2-(((6-Chloropyrimidin-4-yl)amino)ethyl)-4-methoxy-1H-indole-2-carbonitrile The title compound is prepared according to the synthesis of A.1.68. using tert-butyl (6-chloropyrimidin-4-yl)(2-(2-cyano-4-methoxy-1H-indol-1-yl)ethyl)carbamate; LC-MS A: $t_R$=0.85 min; [M+H]$^+$=328.08.

A.1.69.1. Tert-butyl (6-chloropyrimidin-4-yl)(2-(2-cyano-7-4-methoxy-1H-indol-1-yl)ethyl)carbamate The title compound is prepared according to the synthesis of tert-butyl (6-chloropyrimidin-4-yl)(2-(2-cyano-7-fluoro-4-methoxy-1H-indol-1-yl)ethyl)carbamate (see A.1.68.1.) using tert-butyl (2-(2-cyano-4-methoxy-1H-indol-1-yl)ethyl)carbamate; LC-MS A: $t_R$=1.03 min; [M+H]$^+$=428.08.

A.1.69.2. tert-butyl (2-(2-cyano-4-methoxy-1H-indol-1-yl)ethyl)carbamate

The title compound is prepared according to the synthesis of tert-butyl (2-(2-cyano-6-fluoro-4-methoxy-1H-indol-1-yl)ethyl)carbamate (see A.1.64.2.) using 4-methoxy-1H-indole-2-carbonitrile; LC-MS A: $t_R$ 0.90 min; [M+H]$^+$=316.08.

A.1.70. 6-chloro-N-(2-(6-chloro-7-fluoro-4-methoxy-2-methyl-1H-indol-1-yl)ethyl)pyrimidin-4-amine The title compound is prepared according to the synthesis of A.1.1. described above using 2-(6-chloro-7-fluoro-4-methoxy-2-methyl-1H-indol-1-yl)ethan-1-amine; LC-MS A: $t_R$=0.94 min; [M+H]$^+$=369.07.

A.1.70.1. 2-(6-chloro-7-fluoro-4-methoxy-2-methyl-1H-indol-1-yl)ethan-1-amine The title compound is prepared according to the synthesis of A.1.1.1. described above using 6-chloro-7-fluoro-4-methoxy-2-methyl-1H-indole; LC-MS A: $t_R$=0.63 min; [M+H]+=257.19.

A.1.70.2. 6-chloro-7-fluoro-4-methoxy-2-methyl-1H-indole

6-Chloro-7-fluoro-4-methoxy-1H-indole-2-carbaldehyde (355 mg, 1.56 mmol) is dissolved in DEG (16 mL). Then potassium hydroxide (438 mg, 7.8 mmol) and hydrazine monohydrate (0.247 mL, 7.8 mmol) are added and the RM is heated at 120° C. for 1 h. The mixture is cooled to RT, diluted with water, extracted with EtOAc (×3) and the organic layer is washed with brine and dried over MgSO$_4$. The solvents are removed under vacuum. The residue is purified by FC (Hept/EtOAc from 1:0 to 90:10), affording the title compound as a light yellow oil (233 mg, 70%). LC-MS E: $t_R$=1.06 min; [M–H]$^+$=212.07.

A.1.70.3. 6-Chloro-7-fluoro-4-methoxy-1H-indole-2-carbaldehyde (6-Chloro-7-fluoro-4-methoxy-1H-indol-2-yl)methanol (406 mg, 1.77 mmol) is dissolved in DCM (10 mL) and manganese(IV) oxide (1367 mg, 14.1 mmol) is added portionwise. The mixture is refluxed overnight. It is then filtered over a pad of celite and very well washed with hot AcOEt (60° C.). The filtrate is evaporated, the residue is dried under vacuum, affording the title compound as a light brown solid (355 mg, 88%). LC-MS E: $t_R$=0.97 min; [M–H]$^+$=226.02.

A.1.70.4. (6-Chloro-7-fluoro-4-methoxy-1H-indol-2-yl)methanol

Methyl 6-chloro-7-fluoro-4-methoxy-1H-indole-2-carboxylate (211 mg, 0.82 mmol) is dissolved in dry THF (4 mL) and cooled down to −20° C., then Lithium aluminum hydride (solution 2M in THF, 0.82 mL, 1.64 mmol) is added dropwise and the mixtures is stirred overnight, letting the temperature rise slowly to RT. The mixture is cooled at 0° C. and carefully quenched with 66.4 uL of water, 132.8 uL of 10% NaOH and then 199.2 uL of water. The mixture is filtered over a pad of celite, rinsed with DCM and concentrated, affording the title compound as a white solid. LC-MS E: $t_R$=0.86 min; [M–H]$^+$=228.08.

A.1.70.5. Methyl 6-chloro-7-fluoro-4-methoxy-1H-indole-2-carboxylate

To a solution of dry methanol (10 mL) and sodium methoxide (30% solution in methanol, 5.4M, 4.48 mL, 20.1 mmol) at −20° C. is added dropwise a solution of 4-chloro-5-fluoro-2-methoxybenzaldehyde (1013 mg, 5.03 mmol) and methyl 2-azidoacetate (2.02 mL, 20.1 mmol) in dry methanol (5 mL). The mixture is stirred at −20° C. for 3 h, then at 0° C. for 2 h, and at RT overnight. The reaction solvent is removed under reduced pressure. The residue is partitioned between xylenes (20 mL) and water. The aqueous phase is re-extracted once with xylenes. The combined organic layers are washed with brine, dried over MgSO$_4$ and filtered. The filtrate is refluxed overnight. (170° C.), cooled down to room temperature and an ice bath is placed to help the product precipitating. The product is filtered, and dried under high vacuum (white solid, 636 mg, 49%). LC-MS E: $t_R$=1.05 min; [M–H]$^+$=256.04.

A.1.71. 6-Chloro-N-(2-(4,6-dichloro-7-fluoro-2-methyl-1H-indol-1-yl)ethyl)pyrimidin-4-amine The title compound is prepared according to the synthesis of A.1. described above using 2-(4,6-dichloro-7-fluoro-2-methyl-1H-indol-1-yl)ethan-1-amine; LC-MS A: $t_R$=0.99 min; [M+H]$^+$=373.06.

A.1.71.1. 2-(4,6-Dichloro-7-fluoro-2-methyl-1H-indol-1-yl)ethan-1-amine

The title compound is prepared according to the synthesis of A.1.1.1. described above using 4,6-dichloro-7-fluoro-2-methyl-1H-indole; LC-MS A: $t_R$=0.67 min; [M+MeCN]$^+$=302.12.

A.1.71.2. 4,6-Dichloro-7-fluoro-2-methyl-1H-indole

The title compound is prepared according to the synthesis of A.1.70.2. described above using 4,6-dichloro-7-fluoro-1H-indole-2-carbaldehyde; LC-MS E: $t_R$=1.19 min; [M–H]$^+$=216.02.

A.1.71.3. 4,6-Dichloro-7-fluoro-1H-indole-2-carbaldehyde

The title compound is prepared according to the synthesis of A.1.70.3. described above using (4,6-dichloro-7-fluoro-1H-indol-2-yl)methanol; LC-MS E: $t_R$=1.06 min; [M–H]$^+$=229.97.

A.1.71.4. (4,6-Dichloro-7-fluoro-1H-indol-2-yl)methanol

The title compound is prepared according to the synthesis of A.1.70.4. described above using methyl 4,6-dichloro-7-fluoro-1H-indole-2-carboxylate; LC-MS E: $t_R$=0.98 min; [M−H]$^+$=232.02.

A.1.71.5. Methyl 4,6-dichloro-7-fluoro-1H-indole-2-carboxylate

The title compound is prepared according to the synthesis of A.1.70.5. described above using 2,4-dichloro-5-fluorobenzaldehyde; LC-MS E: $t_R$=1.18 min; [M−H]$^+$=260.01.

A.1.72. 1-(2-((6-Chloropyrimidin-4-yl)amino)ethyl)-7-fluoro-4-methyl-1H-indole-2-carbonitrile The title compound is prepared according to the synthesis of A.1.68. using tert-butyl (6-chloropyrimidin-4-yl)(2-(2-cyano-7-fluoro-4-methyl-1H-indol-1-yl)ethyl)carbamate; LC-MS A: $t_R$=0.89 min; [M+H]$^+$=330.10.

A.1.72.1. Tert-butyl (6-chloropyrimidin-4-yl)(2-(2-cyano-7-fluoro-4-methyl-1H-indol-1-yl)ethyl)carbamate The title compound is prepared according to the synthesis of A.1.68.1. using tert-butyl (2-(2-cyano-7-fluoro-4-methyl-1H-indol-1-yl)ethyl)carbamate; LC-MS A: $t_R$=1.06 min; [M+H]$^+$=430.07.

A.1.72.2. Tert-butyl (2-(2-cyano-7-fluoro-4-methyl-1H-indol-1-yl)ethyl)carbamate The title compound is prepared according to the synthesis of A.1.68.2. using 7-fluoro-4-methyl-1H-indole-2-carbonitrile; LC-MS A: $t_R$=0.94 min; [M+H]$^+$=318.13.

A.1.72.3. 7-Fluoro-4-methyl-1H-indole-2-carbonitrile

The title compound is prepared according to the synthesis of 6-fluoro-4-methoxy-1H-indole-2-carbonitrile (see A.1.64.3.) using 7-fluoro-4-methyl-1H-indole-2-carboxamide; LC-MS A: $t_R$=0.84 min; no ionization.

A.1.72.4. 7-Fluoro-4-methyl-1H-indole-2-carboxamide

The title compound is prepared according to the synthesis of A.1.64.4. using 7-fluoro-4-methyl-1H-indole-2-carboxylic acid; LC-MS D: $t_R$=0.67 min; [M+MeCN]$^+$=234.19.

A.1.73. 1-(2-((6-Chloropyrimidin-4-yl)amino)ethyl)-7-fluoro-1H-indole-2-carbonitrile The title compound is prepared according to the synthesis of A.1.68. using tert-butyl (6-chloropyrimidin-4-yl)(2-(2-cyano-7-fluoro-1H-indol-1-yl)ethyl)carbamate; LC-MS A: $t_R$=0.85 min; [M+H]$^+$=316.07.

A.1.73.1. Tert-butyl (6-chloropyrimidin-4-yl)(2-(2-cyano-7-fluoro-1H-indol-1-yl)ethyl)carbamate The title compound is prepared according to the synthesis of A.1.68.1. using tert-butyl (2-(2-cyano-7-fluoro-1H-indol-1-yl)ethyl)carbamate; LC-MS A: $t_R$=1.04 min; [M+H]$^+$=416.05.

A.1.73.2. Tert-butyl (2-(2-cyano-7-fluoro-1H-indol-1-yl)ethyl)carbamate

The title compound is prepared according to the synthesis of A.1.68.2. using 7-fluoro-1H-indole-2-carbonitrile; LC-MS A: $t_R$=0.91 min; [M+H]$^+$=304.12.

A.1.73.3. 7-Fluoro-1H-indole-2-carbonitrile

The title compound is prepared according to the synthesis of A.1.64.3. using 7-fluoro-1H-indole-2-carboxamide; LC-MS E: $t_R$=0.91 min; [M−H]$^+$=159.05.

A.1.73.4. 7-Fluoro-1H-indole-2-carboxamide

The title compound is prepared according to the synthesis of A.1.64.4. using 7-fluoro-1H-indole-2-carboxylic acid; LC-MS A: $t_R$=0.61 min; [M+MeCN]$^+$=220.19.

A.1.74. 4,6-dichloro-1-(2-((6-chloropyrimidin-4-yl)amino)ethyl)-1H-indole-2-carbonitrile The title compound is prepared according to the synthesis of A.1.68. using tert-butyl (6-chloropyrimidin-4-yl)(2-(4,6-dichloro-2-cyano-1H-indol-1-yl)ethyl)carbamate; LC-MS A: $t_R$=0.94 min; [M+H]$^+$=365.95.

A.1.74.1. Tert-butyl (6-chloropyrimidin-4-yl)(2-(4,6-dichloro-2-cyano-1H-indol-1-yl)ethyl)carbamate The title compound is prepared according to the synthesis of A.1.68.1. using tert-butyl (2-(4,6-dichloro-2-cyano-1H-indol-1-yl)ethyl)carbamate; LC-MS A: $t_R$=0.98 min; [M+H]$^+$=353.90.

A.1.74.2. Tert-butyl (2-(4,6-dichloro-2-cyano-1H-indol-1-yl)ethyl)carbamate The title compound is prepared according to the synthesis of A.1.68.2. using 4,6-dichloro-1H-indole-2-carbonitrile; LC-MS A: $t_R$=0.91 min; [M+H]$^+$=304.12.

A.1.74.3. 4,6-Dichloro-1H-indole-2-carbonitrile

The title compound is prepared according to the synthesis of A.1.64.3. using 4,6-dichloro-1H-indole-2-carboxamide; LC-MS A: $t_R$=0.90 min; no ionization.

A.1.74.4. 4,6-Dichloro-1H-indole-2-carboxamide

The title compound is prepared according to the synthesis of A.1.64.4. using 4,6-dichloro-1H-indole-2-carboxylic acid; LC-MS A: $t_R$=0.76 min; [M+MeCN]$^+$=270.07.

A.1.75. 1-(2-((6-Chloropyrimidin-4-yl)amino)ethyl)-5,6-difluoro-4-methyl-1H-indole-2-carbonitrile The title compound is prepared according to the synthesis of A.1.68. using tert-butyl (6-chloropyrimidin-4-yl)(2-(2-cyano-5,6-difluoro-4-methyl-1H-indol-1-yl)ethyl)carbamate; LC-MS A: $t_R$=0.91 min; [M+H]$^+$=348.05.

A.1.75.1. Tert-butyl (6-chloropyrimidin-4-yl)(2-(2-cyano-5,6-difluoro-4-methyl-1H-indol-1-yl)ethyl)carbamate The title compound is prepared according to the synthesis of A.1.68.1. using tert-butyl (2-(2-cyano-5,6-difluoro- 4-methyl-1H-indol-1-yl)ethyl)carbamate; LC-MS A: $t_R$=1.07 min; [M+H]$^+$=448.03.

A.1.75.2. Tert-butyl (2-(2-cyano-5,6-difluoro-4-methyl-1H-indol-1-yl)ethyl)carbamate The title compound is prepared according to the synthesis of A.1.68.2. using 5,6-difluoro-4-methyl-1H-indole-2-carbonitrile; LC-MS A: $t_R$=0.95 min; [M+H]$^+$=336.12.

A.1.75.3. 5,6-Difluoro-4-methyl-1H-indole-2-carbonitrile

The title compound is prepared according to the synthesis of A.1.64.3. using 5,6-difluoro-4-methyl-1H-indole-2-carboxamide; LC-MS A: $t_R$=0.85 min; no ionization.

A.1.75.4. 5,6-Difluoro-4-methyl-1H-indole-2-carboxamide

The title compound is prepared according to the synthesis of A.1.64.4. using 5,6-difluoro-4-methyl-1H-indole-2-carboxylic acid; LC-MS A: $t_R$=0.71 min; [M+MeCN]$^+$= 252.16.

A.1.75.5. 5,6-Difluoro-4-methyl-1H-indole-2-carboxylic acid

A solution of methyl 5,6-difluoro-4-methyl-1H-indole-2-carboxylate (2200 mg, 9.77 mmol) in THF (25 mL) and MeOH (25 mL) is treated at RT with 1N NaOH (25 mL). The RM is stirred at RT for 2 h 30, then the organic solvents are removed under reduced pressure. The residue is extracted with EtOAc (3×). The aqueous phase is then acidified with 2N HCl, and it is extracted with EtOAc (3×). The combined organic extracts are washed with water, brine, dried (MgSO$_4$), and concentrated under reduced pressure, yielding the title compound as a pale ochre powder (1.50 g, 73%); LC-MS E: $t_R$=0.48 min; [M−H]$^+$=210.06.

A.1.75.6. Methyl 5,6-difluoro-4-methyl-1H-indole-2-carboxylate

The title compound is prepared according to the synthesis of A.1.70.5. using 3,4-difluoro-2-methylbenzaldehyde; LC-MS A: $t_R$=0.87 min; no ionization.

A.1.76. 6-Chloro-N-(2-(3-fluoro-2-methyl-1H-indol-1-yl)ethyl)pyrimidin-4-amine The title compound is prepared according to the synthesis of A.1.1. described above using 2-(3-fluoro-2-methyl-1H-indol-1-yl)ethan-1-amine; LC-MS A: $t_R$=0.89 min; [M+H]$^+$=305.05.

A.1.76.1. 2-(3-Fluoro-2-methyl-1H-indol-1-yl)ethan-1-amine

The title compound is prepared according to the synthesis of A.1.1.1. described above using 3-fluoro-2-methyl-1H-indole; LC-MS A: $t_R$=0.55 min; [M+H]$^+$=193.29.

A.1.77. 1-(2-((6-Chloropyrimidin-4-yl)amino)ethyl)-3-fluoro-1H-indole-2-carbonitrile The title compound is prepared according to the synthesis of A.1.68. using tert-butyl (6-chloropyrimidin-4-yl)(2-(2-cyano-3-fluoro-1H-indol-1-yl)ethyl)carbamate; LC-MS A: $t_R$=0.87 min; [M+H]$^+$=316.06.

A.1.77.1. Tert-butyl (6-chloropyrimidin-4-yl)(2-(2-cyano-3-fluoro-1H-indol-1-yl)ethyl)carbamate The title compound is prepared according to the synthesis of A.1.68.1. using tert-butyl (2-(2-cyano-3-fluoro-1H-indol-1-yl)ethyl)carbamate; LC-MS A: $t_R$=1.05 min; [M+H]$^+$=416.11.

A.1.77.2. Tert-butyl (2-(2-cyano-3-fluoro-1H-indol-1-yl)ethyl)carbamate

The title compound is prepared according to the synthesis of A.1.68.2. using 3-fluoro-1H-indole-2-carbonitrile; LC-MS A: $t_R$=0.92 min; [M+H]$^+$=304.13.

A.1.77.3. 3-Fluoro-1H-indole-2-carbonitrile

To a solution of 3-fluoro-1-tosyl-1H-indole-2-carbonitrile (1782 mg, 5.67 mmol, 1 eq) in THF (57 mL) is added a solution of Tetrabutylammonium fluoride (1M in THF, 8.5 mL, 8.5 mmol). The resulting mixture is refluxed for 45 min, cooled to rt, diluted with ethyl acetate (50 mL), washed with saturated aqueous NaHCO$_3$ (50 mL) and brine, dried over MgSO$_4$, filtered and concentrated to dryness. The residue is purified by FC (EA-Hept 0:1 to 1:4) to afford the title compound as an off-white solid (655 mg, 72%); LC-MS A: $t_R$=0.81 min; no ionization.

A.1.77.4. 3-Fluoro-1-tosyl-1H-indole-2-carbonitrile

The title compound is prepared according to the synthesis of A.1.64.3. using 3-fluoro-1-tosyl-1H-indole-2-carboxamide; LC-MS A: $t_R$=0.97 min; no ionization.

A.1.77.5. 3-Fluoro-1-tosyl-1H-indole-2-carboxamide

The title compound is prepared according to the synthesis of A.1.64.4. using 3-Fluoro-1-tosyl-1H-indole-2-carboxylic acid; LC-MS A: $t_R$=0.80 min; [M−H]$^+$=333.10.

A.1.77.6. 3-Fluoro-1-tosyl-1H-indole-2-carboxylic acid n-Butyllithium (1.6 M in hexanes, 4.3 mL, 6.9 mmol) is added dropwise to a cold solution of 3-fluoroindole tosylate (2000 mg, 6.57 mmol) in THF (24 mL) at −75° C. The resulting mixture is stirred at this temperature for 30 min. Then an excess of dry CO2 gas (prepared by adding dry ice on toluene and the formed gas is added to the mixture via a needle) is bubbled through the RM for 15 min at −75° C. Then the cooling bath is removed and the mixture is slowly warmed to rt. The mixture is concentrated to dryness. The white solid obtained is dissolved in water (25 mL) and the aqueous solution extracted with EtOAc (25 mL). The aqueous layer is acidified (to pH=1) with 2N HCl and extracted twice with EtOAc (2×15 mL). The combined organic layers are dried over MgSO$_4$, filtered and concentrated to dryness to give the title crude acid as an off-white solid (2.124 g, 97%); LC-MS A: $t_R$=0.84 min; [M−H]$^+$= 333.99.

A.1.78. 6-Chloro-N-(2-(7-fluoro-4-methoxy-2-methyl-1H-indol-1-yl)ethyl-1,1,2,2-d4)pyrimidin-4-amine The title compound is prepared according to the synthesis of A.1.1. described above using 2-(7-fluoro-4-methoxy-2-methyl-1H-indol-1-yl)ethan-1,1,2,2-d4-1-amine; LC-MS A: $t_R$=0.88 min; $[M+H]^+$=339.12.

A.1.78.1. 2-(7-Fluoro-4-methoxy-2-methyl-1H-indol-1-yl)ethan-1,1,2,2-d4-1-amine 1-(2-Bromoethyl-1,1,2,2-d4)-7-fluoro-4-methoxy-2-methyl-1H-indole (373 mg, 1.18 mmol) is dissolved in ammoniac (7 N in MeOH, 4.5 mL, 29.6 mmol) and the RM is stirred at 100° C. for 2 h in the microwave. NH4OH (25%, 2 mL) and EtOH (3 mL) are added and the mixture is heated at 140° C. for 3 h. After cooling the crude product is treated with brine (15 mL) and extracted with EtOAc (3×20 mL). The organic phase is dried with MgSO₄ and concentrated under vacuum. Purification by FC (DCM/MeOH (0.5% NH₃) 1:0 to 19:1) afforded the title compound as a beige solid (258 mg, 96%). LC-MS A: $t_R$=0.56 min; $[M+H]^+$=227.25.

A.1.78.2. 1-(2-Bromoethyl-1,1,2,2-d4)-7-fluoro-4-methoxy-2-methyl-1H-indole NaH (100 mg, 2.51 mmol) is added portionwise to a solution of 7-fluoro-4-methoxy-2-methyl-1H-indole (300 mg, 1.67 mmol) in 7 mL of DMF at 0° C. The mixture is stirred for 15 min then 1,2-dibromoethane-d4 (0.219 mL, 2.51 mmol) in DMF (3 mL) is added dropwise. The RM is stirred at RT overnight. NaH (100 mg, 2.51 mmol) is added and after 15 min at RT 1,2-dibromoethane-d4 (0.51 mL, 5.86 mmol) is added. and the mixture is stirred at RT for 3 h. NaH (100 mg, 2.51 mmol) is added and after 15 min at RT 1,2-dibromoethane-d4 (0.51 mL, 5.86 mmol, 3.5 eq) is added and the mixture is stirred at RT for 3 h. It is then quenched at 0° C. with H2O (20 mL) and extracted twice with DCM, dried over MgSO₄ and concentrated. The crude is purified by FC (Hept/EtOAc 1:0 to 19:1), affording the title compound as a white solid (373 mg, 77%); LC-MS A: $t_R$=0.94 min; $[M+H]^+$=292.21.

A.1.79. 4-Chloro-1-(2-((6-chloropyrimidin-4-yl)amino)ethyl)-6,7-difluoro-1H-indole-2-carbonitrile The title compound is prepared according to the synthesis of A.1.68. using tert-butyl (2-(4-chloro-2-cyano-6,7-difluoro-1H-indol-1-yl)ethyl)(6-chloropyrimidin-4-yl)carbamate; LC-MS A: $t_R$=0.92 min; $[M+H]^+$=368.02.

A.1.79.1. Tert-butyl (2-(4-chloro-2-cyano-6,7-difluoro-1H-indol-1-yl)ethyl)(6-chloropyrimidin-4-yl)carbamate The title compound is prepared according to the synthesis of A.1.68.1. using tert-butyl (2-(4-chloro-2-cyano-6,7-difluoro-1H-indol-1-yl)ethyl)carbamate; LC-MS A: $t_R$=1.08 min; $[M+H]^+$=467.99.

A.1.79.2. Tert-butyl (2-(4-chloro-2-cyano-6,7-difluoro-1H-indol-1-yl)ethyl)carbamate The title compound is prepared according to the synthesis of A.1.68.2. using 4-chloro-6,7-difluoro-1H-indole-2-carbonitrile; LC-MS A: $t_R$=0.96 min; $[M+MeCN]^+$=381.97.

A.1.79.3. 4-Chloro-6,7-difluoro-1H-indole-2-carbonitrile

The title compound is prepared according to the synthesis of A.1.64.3. using 4-chloro-6,7-difluoro-1H-indole-2-carboxamide; LC-MS A: $t_R$=0.87 min; no ionization.

A.1.79.4. 4-Chloro-6,7-difluoro-1H-indole-2-carboxamide

To a solution of methyl 4-chloro-6,7-difluoro-1H-indole-2-carboxylate (500 mg, 2.04 mmol) in THE (5 mL) is added ammonia (7 N solution in MeOH, 8.73 mL, 61.1 mmol) and NaCN (9.98 mg, 0.204 mmol) and this solution is heated in a sealed vial at 130° C. for 10 hour in the microwave. The solvents are removed under reduced pressure. Affording the title compound as a light brown powder (0.510 g, quant.); LC-MS A: $t_R$=0.73 min; $[M+MeCN]^+$=271.93.

A.1.79.5. Methyl 4-chloro-6,7-difluoro-1H-indole-2-carboxylate

The title compound is prepared according to the synthesis of A.1.70.5. using 2-chloro-4,5-difluorobenzaldehyde; LC-MS A: $t_R$=0.89 min; no ionization.

A.1.80. 4-Chloro-1-(2-((6-chloropyrimidin-4-yl)amino)ethyl)-1H-indole-2-carbonitrile The title compound is prepared according to the synthesis of A.1.68. using tert-butyl (2-(4-chloro-2-cyano-1H-indol-1-yl)ethyl)(6-chloropyrimidin-4-yl)carbamate; LC-MS A: $t_R$ 0.89 min; $[M+H]^+$=332.03.

A.1.80.1. Tert-butyl (2-(4-chloro-2-cyano-1H-indol-1-yl)ethyl)(6-chloropyrimidin-4-yl)carbamate The title compound is prepared according to the synthesis of A.1.68.1. using tert-butyl (2-(4-chloro-2-cyano-1H-indol-1-yl)ethyl)carbamate; LC-MS A: $t_R$=1.06 min; $[M+H]^+$=432.02.

A.1.80.2. Tert-butyl (2-(4-chloro-2-cyano-1H-indol-1-yl)ethyl)carbamate

The title compound is prepared according to the synthesis of A.1.68.2. using 4-chloro-1H-indole-2-carbonitrile; LC-MS A: $t_R$=0.94 min; $[M+H]^+$=320.08.

A.1.80.3. 4-Chloro-1H-indole-2-carbonitrile

The title compound is prepared according to the synthesis of A.1.64.3. using 4-chloro-1H-indole-2-carboxamide; LC-MS A: $t_R$=0.83 min; no ionization.

A.1.80.4. 4-Chloro-1H-indole-2-carboxamide

The title compound is prepared according to the synthesis of A.1.64.4. using 4-chloro-1H-indole-2-carboxylic acid; LC-MS A: $t_R$=0.68 min; [M+MeCN]$^+$=236.14.

A.1.81. 1-(2-((6-Chloropyrimidin-4-yl)amino)ethyl)-6,7-difluoro-4-methyl-1H-indole-2-carbonitrile The title compound is prepared according to the synthesis of A.1.68. using tert-butyl (6-chloropyrimidin-4-yl)(2-(2-cyano-6,7-difluoro-4-methyl-1H-indol-1-yl)ethyl)carbamate; LC-MS A: $t_R$=0.91 min; [M+H]$^+$=348.11.

A.1.81.1. Tert-butyl (6-chloropyrimidin-4-yl)(2-(2-cyano-6,7-difluoro-4-methyl-1H-indol-1-yl)ethyl) carbamate The title compound is prepared according to the synthesis of A.1.68.1. using tert-butyl (2-(2-cyano-6,7-difluoro-4-methyl-1H-indol-1-yl)ethyl)carbamate; LC-MS A: $t_R$=1.07 min; [M+H]$^+$=448.11.

A.1.81.2. Tert-butyl (2-(2-cyano-6,7-difluoro-4-methyl-1H-indol-1-yl)ethyl)carbamate The title compound is prepared according to the synthesis of A.1.68.2. using 6,7-difluoro-4-methyl-1H-indole-2-carbonitrile; LC-MS A: $t_R$=0.95 min; [M+H]+=336.12.

A.1.81.3. 6,7-Difluoro-4-methyl-1H-indole-2-carbonitrile

The title compound is prepared according to the synthesis of A.1.64.3. using 6,7-difluoro-4-methyl-1H-indole-2-carboxamide; LC-MS E: $t_R$=1.01 min; [M–H]$^+$=191.15.

A.1.81.4. 6,7-Difluoro-4-methyl-1H-indole-2-carboxamide

The title compound is prepared according to the synthesis of A.1.64.4. using 6,7-difluoro-4-methyl-1H-indole-2-carboxylic acid; LC-MS A: $t_R$=0.70 min; [M+MeCN]$^+$= 252.23

A.1.81.5. 6,7-Difluoro-4-methyl-1H-indole-2-carboxylic acid

The title compound is prepared according to the synthesis of A.1.75.5. using methyl 6,7-difluoro-4-methyl-1H-indole-2-; LC-MS E: $t_R$=0.47 min; [M–H]$^+$=210.08

A.1.81.6. Methyl 6,7-difluoro-4-methyl-1H-indole-2-carboxylate

The title compound is prepared according to the synthesis of A.1.70.5. using 4,5-difluoro-2-methylbenzaldehyde; LC-MS E: $t_R$=1.04 min; [M–H]$^+$=224.10

A.1.82. 1-(2-((6-Chloropyrimidin-4-yl)amino)ethyl)-6,7-difluoro-4-methoxy-1H-indole-2-carbonitrile The title compound is prepared according to the synthesis of A.1.68. using tert-butyl (6-chloropyrimidin-4-yl)(2-(2-cyano-6,7-difluoro-4-methoxy-1H-indol-1-yl)ethyl)carbamate; LC-MS A: $t_R$=0.90 min; [M+H]$^+$=364.12.

A.1.82.1. Tert-butyl (6-chloropyrimidin-4-yl)(2-(2-cyano-6,7-difluoro-4-methoxy-1H-indol-1-yl)ethyl) carbamate The title compound is prepared according to the synthesis of A.1.68.1. using tert-butyl (2-(2-cyano-6,7-difluoro-4-methoxy-1H-indol-1-yl)ethyl)carbamate; LC-MS A: $t_R$=1.06 min; [M+H]$^+$=464.1.

A.1.82.2. Tert-butyl (2-(2-cyano-6,7-difluoro-4-methoxy-1H-indol-1-yl)ethyl)carbamate The title compound is prepared according to the synthesis of A.1.68.2. using 6,7-difluoro-4-methoxy-1H-indole-2-carbonitrile; LC-MS A: $t_R$=0.94 min; [M+H]$^+$= 352.16.

A.1.82.3. 6,7-Difluoro-4-methoxy-1H-indole-2-carbonitrile

The title compound is prepared according to the synthesis of A.1.64.3. using 6,7-difluoro-4-methoxy-1H-indole-2-carboxamide; LC-MS A: $t_R$=0.84 min; no ionization.

A.1.82.4. 6,7-Difluoro-4-methoxy-1H-indole-2-carboxamide

The title compound is prepared according to the synthesis of A.1.64.4. using 6,7-difluoro-4-methyl-1H-indole-2-carboxylic acid; LC-MS A: $t_R$=0.68 min; [M+MeCN]$^+$= 268.23

A.1.82.5. 6,7-Difluoro-4-methoxy-1H-indole-2-carboxylic acid

The title compound is prepared according to the synthesis of A.1.75.5. using methyl 6,7-difluoro-4-methyl-1H-indole-2-; LC-MS A: $t_R$=0.72 min; no ionization

A.1.82.6. Methyl 6,7-difluoro-4-methoxy-1H-indole-2-carboxylate

The title compound is prepared according to the synthesis of A.1.70.5. using 4,5-difluoro-2-methoxybenzaldehyde; LC-MS A: $t_R$=0.84 min; no ionization

A.2. Synthesis of Boronic Acid Derivatives of Formula (III)

A.2.1. (4-Fluoro-5-(methoxycarbonyl)thiophen-2-yl)boronic acid

To a solution of diisopropylamine (0.815 mL, 5.76 mmol) in THF (20 mL) at −78° C. is added dropwise n-butyllithium (2.5M in hexanes, 2.3 mL, 5.76 mmol). The RM is stirred for 15 min at −78° C. then warmed to 0° C. for 30 min then cooled again to −78° C. A solution of methyl 3-fluoro-2-thiophenecarboxylate (615 mg, 3.84 mmol) in THF (10 mL) is added dropwise, and the resulting RM is stirred for 10 min at −78° C., then a solution of 2-isopropoxy-4,4,5,5-tetramethyl-1,3,2-dioxaborolane (1.2 mL, 5.76 mmol) in THF (10 mL) is added dropwise and the RM is kept stirring for 15 min at −78° C., then is allowed to warm to RT and stirred for 1 h. HCl 1N (30 mL) is added and the mixture is extracted with EtOAc 3 times. The combined organic layers are washed with brine, dried over MgSO$_4$ and the solvent is removed in vacuo yielding a pale yellow solid (800 mg, 100%). LC-MS A: $t_R$=0.62 min; no ionization.

A.2.2. (4-Ethyl-5-(methoxycarbonyl)thiophen-2-yl)boronic acid

The title compound is prepared according to the synthesis of (4-fluoro-5-(methoxycarbonyl)thiophen-2-yl)boronic acid (see A.2.1.) using methyl 3-ethylthiophene-2-carboxylate; LC-MS A: $t_R$=0.70 min; no ionization.

A.2.3. 4-(4-(4,4,5,5-Tetramethyl-1,3,2-dioxaborolan-2-yl)phenyl)-1H-imidazole

A solution of 4-(4-bromophenyl)-1H-imidazole (1.72 g, 7.71 mmol), bis(pinacolato)diboron (2.94 g, 11.6 mmol), potassium acetate (2.27 g, 23.1 mmol) and dichloro(1,1′-bis (diphenylphosphino) ferrocene) palladium (II) dichloromethane adduct (378 mg, 0.463 mmol) in DMF (30 mL) is heated at 110° C. for 17 h. The RM is filtered through a pad of celite, the filtrate is concentrated and purified via FC, eluting with DCM/MeOH (100:0 to 97:3), affording the title compound as a greenish powder (1.01 g, 48%). LC-MS A: $t_R$=0.63 min; [M+H]$^+$=271.14.

Following the procedure described for the synthesis of A.2.3. described above, the following boronic acid derivatives are synthesized, starting from the corresponding commercially available halides (see table 3).

TABLE 3

Boronic acid derivatives A.2.4.-A.2.44.

| No. | Compound | $t_R$ [min] (LC-MS) | MS Data m/z [M + H]$^+$ |
|---|---|---|---|
| A.2.4. | 1-Methyl-4-(4,4,5,5-tetramethyl-1,3,2-dioxaborolan-2-yl)-1H-indole-7-carboxylic acid | 0.97 (A) | 316.27 |
| A.2.5. | 2-Chloro-6-methoxy-4-(4,4,5,5-tetramethyl-1,3,2-dioxaborolan-2-yl)benzoic acid | 0.83 (A) | 312.97 |
| A.2.6. | 2-(Difluoromethoxy)-4-(4,4,5,5-tetramethyl-1,3,2-dioxaborolan-2-yl)benzoic acid | 0.37 (E) | 313.11 |
| A.2.7. | 2-Methyl-4-(4-(4,4,5,5-tetramethyl-1,3,2-dioxaborolan-2-yl)phenyl)-1H-imidazole | 0.65 (A) | 285.22 |
| A.2.8. | 3-(5-(4-(4,4,5,5-Tetramethyl-1,3,2-dioxaborolan-2-yl)phenyl)oxazol-2-yl)propanoic acid | 0.83 (A) | 344.05 |
| A.2.9. | 3-(4-Methyl-5-(4-(4,4,5,5-tetramethyl-1,3,2-dioxaborolan-2-yl)phenyl)oxazol-2-yl)propanoic acid | 0.83 (A) | 358.12 |
| A.2.10. | 1-Methyl-5-(4-(4,4,5,5-tetramethyl-1,3,2-dioxaborolan-2-yl)phenyl)-1H-imidazole | 0.63 (A) | 284.92 |
| A.2.11. | 5-(4-(4,4,5,5-Tetramethyl-1,3,2-dioxaborolan-2-yl)phenyl)isothiazole | 0.97 (A) | 288.11 |
| A.2.12. | 2-Methyl-4-(4-(4,4,5,5-tetramethyl-1,3,2-dioxaborolan-2-yl)phenyl)oxazole | 0.92 (A) | 286.18 |
| A.2.13. | 5-Methyl-3-(4-(4,4,5,5-tetramethyl-1,3,2-dioxaborolan-2-yl)phenyl)-1H-pyrazole | 0.84 (A) | 285.21 |
| A.2.14. | 3-(4-(4,4,5,5-Tetramethyl-1,3,2-dioxaborolan-2-yl)phenyl)isoxazole | 0.92 (A) | 272.16 |
| A.2.15. | 1-Methyl-3-(4-(4,4,5,5-tetramethyl-1,3,2-dioxaborolan-2-yl)phenyl)-1H-pyrazole | 0.89 (A) | 285.26 |
| A.2.16. | 5-(4,4,5,5-Tetramethyl-1,3,2-dioxaborolan-2-yl)-2-(trifluoromethyl)-1H-benzo[d]imidazole | 0.85 (A) | 313.21 |
| A.2.17. | 2-(Ethylamino)-4-(4,4,5,5-tetramethyl-1,3,2-dioxaborolan-2-yl)benzoic acid | 0.84 (A) | 292.26 |
| A.2.18. | 2-(Pyrrolidin-1-yl)-4-(4,4,5,5-tetramethyl-1,3,2-dioxaborolan-2-yl)benzoic acid | 0.72 (A) | 318.14 |
| A.2.19. | 2-(4-Fluorophenoxy)-4-(4,4,5,5-tetramethyl-1,3,2-dioxaborolan-2-yl)benzoic acid | 0.91 (A) | 359.08 |
| A.2.20. | 2-Methyl-5-(4,4,5,5-tetramethyl-1,3,2-dioxaborolan-2-yl)isoindolin-1-one | 0.84 (A) | 274.11 |
| A.2.21. | 2-Ethyl-5-(4,4,5,5-tetramethyl-1,3,2-dioxaborolan-2-yl)isoindolin-1-one | 0.87 (A) | 288.16 |
| A.2.22. | 2-Propyl-5-(4,4,5,5-tetramethyl-1,3,2-dioxaborolan-2-yl)isoindolin-1-one | 0.90 (A) | 302.14 |
| A.2.23. | 2-Isobutyl-5-(4,4,5,5-tetramethyl-1,3,2-dioxaborolan-2-yl)isoindolin-1-one | 0.93 (A) | 316.14 |
| A.2.24. | 2,6-Difluoro-4-(4,4,5,5-tetramethyl-1,3,2-dioxaborolan-2-yl)benzenesulfonamide | 0.47 (F) | No ionization |
| A.2.25. | 2-Chloro-6-methyl-4-(4,4,5,5-tetramethyl-1,3,2-dioxaborolan-2-yl)benzoic acid | 0.85 (A) | No ionization |
| A.2.26. | 2-Chloro-6-ethyl-4-(4,4,5,5-tetramethyl-1,3,2-dioxaborolan-2-yl)benzoic acid | 0.38 (E) | 309.05 |
| A.2.27. | 2-(Tert-butyl)-4-(4,4,5,5-tetramethyl-1,3,2-dioxaborolan-2-yl)benzoic acid | 0.61 (E) | 303.21 |
| A.2.28. | 4-(4,4,5,5-Tetramethyl-1,3,2-dioxaborolan-2-yl)-2-((2,2,2-trifluoroethyl)amino)benzoic acid | 0.90 (A) | 346.18 |
| A.2.29. | 3-(4-(4,4,5,5-Tetramethyl-1,3,2-dioxaborolan-2-yl)phenyl)-[1,2,4]oxadiazol-5(4H)-one | 0.83 (A) | 330.01 |
| A.2.30. | 2-ethyl-6-fluoro-4-(4,4,5,5-tetramethyl-1,3,2-dioxaborolan-2-yl)benzoic acid | 0.87 (A) | No ionization |
| A.2.31. | 2-Fluoro-6-methyl-4-(4,4,5,5-tetramethyl-1,3,2-dioxaborolan-2-yl)benzoic acid | 0.84 (A) | No ionization |
| A.2.32. | 2-Methoxy-6-methyl-4-(4,4,5,5-tetramethyl-1,3,2-dioxaborolan-2-yl)benzoic acid | 0.80 (A) | 293.16 |
| A.2.33. | 4-(4,4,5,5-Tetramethyl-1,3,2-dioxaborolan-2-yl)-2-(trifluoromethyl)benzenesulfonamide | 0.86 (A) | No ionization |
| A.2.34. | N-Methyl-4-(4,4,5,5-tetramethyl-1,3,2-dioxaborolan-2-yl)-2-(trifluoromethyl)benzenesulfonamide | 0.92 (A) | No ionization |
| A.2.35. | N,2-Dimethyl-4-(4,4,5,5-tetramethyl-1,3,2-dioxaborolan-2-yl)benzenesulfonamide | 0.92 (A) | No ionization |
| A.2.36. | 5-(4-(4,4,5,5-Tetramethyl-1,3,2-dioxaborolan-2-yl)phenyl)isoxazol-3-amine | 0.84 (A) | 287.11 |
| A.2.37. | 3-Methoxy-4-(4,4,5,5-tetramethyl-1,3,2-dioxaborolan-2-yl)thiophene-2-carboxylic acid | 0.89 (A) | 299.08 |
| A.2.38. | 2-Cyclopropyl-4-(4,4,5,5-tetramethyl-1,3,2-dioxaborolan-2-yl)benzoic acid | 0.86 (A) | 330.18 |
| A.2.39. | 5-(4-(4,4,5,5-Tetramethyl-1,3,2-dioxaborolan-2-yl)phenyl)oxazol-2-amine | 0.68 (A) | 287.20 |
| A.2.40. | 2-(Methylthio)-4-(4,4,5,5-tetramethyl-1,3,2-dioxaborolan-2-yl)benzoic acid | 0.96 (A) | 309.18 |
| A.2.41. | 2-Cyclobutoxy-5-(4,4,5,5-tetramethyl-1,3,2-dioxaborolan-2-yl)benzoic acid | 0.91 (A) | 319.11 |

TABLE 3-continued

Boronic acid derivatives A.2.4.-A.2.44.

| No. | Compound | $t_R$ [min] (LC-MS) | MS Data m/z [M + H]$^+$ |
|---|---|---|---|
| A.2.42. | Ethyl 4-(4-(4,4,5,5-tetramethyl-1,3,2-dioxaborolan-2-yl)phenyl)thiazole-2-carboxylate | 1.01 (A) | 360.00 |
| A.2.43. | Methyl 3-methyl-5-(4-(4,4,5,5-tetramethyl-1,3,2-dioxaborolan-2-yl)phenyl)isoxazole-4-carboxylate | 1.00 (A) | 344.17 |
| A.2.44. | Methyl 4-(4,4,5,5-tetramethyl-1,3,2-dioxaborolan-2-yl)-1H-indole-7-carboxylate | 0.95 (A) | 302.23 |

A.2.45. Propyl 2-(propylthio)-4-(4,4,5,5-tetramethyl-1,3,2-dioxaborolan-2-yl)benzoate The title compound is prepared according to the procedure described for A.2.3., starting with propyl 4-bromo-2-(propylthio)benzoate. LC-MS A: $t_R$=1.06 min; [M+H]+= 365.04.

A.2.45.1. Propyl 4-bromo-2-(propylthio)benzoate

Propyl iodide (1.51 mL, 15.3 mmol) is added dropwise to a 0° C. solution of 4-bromo-2-sulfanylbenzoic acid (1.50 g, 6.11 mmol) and Cs$_2$CO$_3$ (4.18 g, 12.8 mmol) in DMF (60 mL). The RM is stirred for 15 min at 0° C. and then at RT for 16 h. The RM is quenched with water, then EtOAc is added and layers are separated. The aqueous layer is extracted twice with EtOAc. The combined organic layers are washed with brine, dried (MgSO$_4$), and concentrated under reduced pressure. The residue is purified by FC, eluting with Heptane to give the title compound as a pale yellow solid (1.66 g, 86%). LC-MS A: $t_R$=1.04 min; no ionization.

A.2.46. Isopropyl 2-(isopropylthio)-4-(4,4,5,5-tetramethyl-1,3,2-dioxaborolan-2-yl)benzoate The title compound is prepared according to the procedure described for A.2.3., starting with isopropyl 4-bromo-2-(isopropylthio)benzoate. LC-MS A: $t_R$=1.06 min; [M+H]+= 365.21.

A.2.46.1. Isopropyl 4-bromo-2-(isopropylthio)benzoate

The title compound is prepared according to the procedure described for A.2.45.1., using isopropyl iodide. LC-MS A: $t_R$=1.04 min; no ionization.

A.2.47. Isobutyl 2-(isobutylthio)-4-(4,4,5,5-tetramethyl-1,3,2-dioxaborolan-2-yl)benzoate The title compound is prepared according to the procedure described for A.2.3., starting with isobutyl 4-bromo-2-(isobutylthio)benzoate. LC-MS A: $t_R$=1.12 min; [M+H]+= 393.26.

A.2.47.1. Isobutyl 4-bromo-2-(isobutylthio)benzoate

The title compound is prepared according to the procedure described for A.2.45.1., using 1-iodo-2-methylpropane. LC-MS A: $t_R$=1.09 min; [M+H]+=345.06.

A.2.48 Cyclobutyl 2-(cyclobutylthio)-4-(4,4,5,5-tetramethyl-1,3,2-dioxaborolan-2-yl)benzoate The title compound is prepared according to the procedure described for A.2.3., starting with cyclobutyl 4-bromo-2-(cyclobutylthio)benzoate. LC-MS A: $t_R$=1.10 min; [M+H]+=389.26.

A.2.48.1. Cyclobutyl 4-bromo-2-(cyclobutylthio)benzoate

The title compound is prepared according to the procedure described for A.2.45.1., using bromocyclobutane. LC-MS A: $t_R$=1.07 min; no ionization.

A.2.49. 2-Isobutyl-4-(4,4,5,5-tetramethyl-1,3,2-dioxaborolan-2-yl)benzoic acid The title compound is prepared according to the procedure described for A.2.3., starting with 4-bromo-2-isobutylbenzoic acid. LC-MS F: $t_R$=0.48 min; [M−H]+=303.26.

A.2.49.1. 4-Bromo-2-isobutylbenzoic acid

4-Bromo-2-fluorobenzoic acid (2.00 g, 9.13 mmol) is dissolved in dry THF (15 mL) in a 100 mL heat-gun-dried round-bottom flask under N$_2$. The solution is cooled down to 0° C. and isobutylmagnesium bromide (2M in Et$_2$O, 13.7 mL, 27.4 mmol) is added dropwise over 5 min. The RM is stirred at 0° C. for 1 h and at RT for 4 h. EtOH (10 mL) is added dropwise. After stirring for 5 min, the solvents are removed under reduced pressure. The residue is partitioned between EtOAc and 1N NaOH. The aqueous phase is re-extracted with EtOAc (2×). The aqueous phase is then acidified with 1N HCl and extracted 3× with EtOAc. these extracts are dried (MgSO$_4$) and concentrated under reduced pressure. The residue is triturated in EtOAc, the solid is filtered, washed with EtOAc and dried, affording the title compound as an off-white solid (0.756 g, 32%). LC-MS F: $t_R$=0.51 min; [M−H]+=257.15.

A.2.50. 2-Isopentyl-4-(4,4,5,5-tetramethyl-1,3,2-dioxaborolan-2-yl)benzoic acid The title compound is prepared according to the procedure described for A.2.3., starting with 4-bromo-2-isopentylbenzoic acid. LC-MS F: $t_R$ 0.52 min; [M−H]+=317.25.

A.2.50.1. 4-Bromo-2-isopentylbenzoic acid

The title compound is prepared according to the procedure described for A.2.49.1., starting with isopentylmagnesium bromide. LC-MS A: $t_R$=0.84 min; no ionization.

A.2.51. 2-Chloro-6-propyl-4-(4,4,5,5-tetramethyl-1,3,2-dioxaborolan-2-yl)benzoic acid The title compound is prepared according to the procedure described for A.2.3., starting with 4-bromo-2-chloro-6-propylbenzoic acid. LC-MS A: $t_R$=0.92 min; no ionization.

A.2.51.1. 4-Bromo-2-chloro-6-propylbenzoic acid

The title compound is prepared according to the procedure described for A.2.49.1., starting with 4-bromo-2-fluoro-6-chlorobenzoic acid and propylmagnesium chloride. LC-MS A: $t_R$=0.85 min; no ionization.

A.2.52. 2-Fluoro-6-propyl-4-(4,4,5,5-tetramethyl-1,3,2-dioxaborolan-2-yl)benzoic acid The title compound is prepared according to the procedure described for A.2.3., starting with 4-bromo-2-fluoro-6-propylbenzoic acid. LC-MS E: $t_R$=0.48 min; [M−H]+=307.11.

A.2.52.1. 4-Bromo-2-fluoro-6-propylbenzoic acid

The title compound is prepared according to the procedure described for A.2.49.1., starting with 4-bromo-2,6-difluorobenzoic acid and propylmagnesium chloride. LC-MS A: $t_R$=0.84 min; no ionization.

A.2.53. 2-Chloro-6-ethoxy-4-(4,4,5,5-tetramethyl-1,3,2-dioxaborolan-2-yl)benzoic acid The title compound is prepared according to the procedure described for A.2.3., starting with 4-bromo-2-chloro-6-ethoxybenzoic acid. LC-MS A: $t_R$=0.87 min; [M+H]+=327.03.

A.2.53.1. 4-Bromo-2-chloro-6-ethoxybenzoic acid

To a solution of 4-bromo-2-fluoro-6-chlorobenzoic acid (1.175 g, 4.64 mmol) in dry DMF (8 mL) is added NaH (60% suspension in oil, 408 mg, 10.2 mmol) portionwise. Once the gas evolution is finished, a solution of dry EtOH (0.297 mL, 5.1 mmol) in 3 mL of dry DMF is added dropwise. The RM is heated up to 100° C., stirred for 1 h, then cooled to RT and poured into water. The pH is adjusted to 3 with HCl 1N and then extracted three times with EtOAc. The combined org. phases are washed with water, brine, dried over $MgSO_4$, filtered and concentrated in vacuo yielding quantitatively the desired product as a beige solid. LC-MS F: $t_R$=0.43 min; [M−H]+=278.97.

A.2.54. 2-Ethoxy-6-fluoro-4-(4,4,5,5-tetramethyl-1,3,2-dioxaborolan-2-yl)benzoic acid The title compound is prepared according to the procedure described for A.2.3., starting with 4-bromo-2-ethoxy-6-fluorobenzoic acid. LC-MS A: $t_R$=0.84 min; [M+H]+=311.03.

A.2.54.1. 4-Bromo-2-ethoxy-6-fluorobenzoic acid

The title compound is prepared according to the procedure described for A.2.53.1., starting with 4-bromo-2,6-difluorobenzoic acid. LC-MS F: $t_R$=0.49 min; [M−H]+=261.07.

A.2.55. 2-Chloro-6-propoxy-4-(4,4,5,5-tetramethyl-1,3,2-dioxaborolan-2-yl)benzoic acid The title compound is prepared according to the procedure described for A.2.3., starting with 4-bromo-2-chloro-6-propoxybenzoic acid. LC-MS A: $t_R$=0.90 min; [M+H]+=341.21.

A.2.55.1. 4-Bromo-2-chloro-6-propoxybenzoic acid

The title compound is prepared according to the procedure described for A.2.53.1., propanol instead of ethanol. LC-MS A: $t_R$=0.83 min; no ionization.

A.2.56. 2-Fluoro-6-propoxy-4-(4,4,5,5-tetramethyl-1,3,2-dioxaborolan-2-yl)benzoic acid The title compound is prepared according to the procedure described for A.2.3., starting with 4-bromo-2-fluoro-6-propoxybenzoic acid. LC-MS A: $t_R$=0.87 min; [M+H]+=325.14.

A.2.56.1. 4-Bromo-2-fluoro-6-propoxybenzoic acid

The title compound is prepared according to the procedure described for A.2.55.1., starting with 4-bromo-2,6-difluorobenzoic acid. LC-MS E: $t_R$=0.45 min; [M−H]+=274.93.

A.2.57. 2-Ethoxy-6-methyl-4-(4,4,5,5-tetramethyl-1,3,2-dioxaborolan-2-yl)benzoic acid The title compound is prepared according to the procedure described for A.2.3., starting with 4-bromo-2-ethoxy-6-methylbenzoic acid. LC-MS A: $t_R$=0.80 min; [M+H]+=293.16.

A.2.57.1. 4-Bromo-2-ethoxy-6-methylbenzoic acid

The title compound is prepared according to the procedure described for A.2.53.1., starting with 4-bromo-2-fluoro-6-methylbenzoic acid. LC-MS A: $t_R$=0.72 min; no ionization.

A.2.58. 2-Ethoxy-6-ethyl-4-(4,4,5,5-tetramethyl-1,3,2-dioxaborolan-2-yl)benzoic acid The title compound is prepared according to the procedure described for A.2.3., starting with 4-bromo-2-ethoxy-6-ethylbenzoic acid. LC-MS A: $t_R$=0.87 min; [M+H]+=321.08.

A.2.58.1. 4-Bromo-2-ethoxy-6-ethylbenzoic acid

The title compound is prepared according to the procedure described for A.2.53.1., starting with 4-bromo-2-ethyl-6-fluorobenzoic acid. LC-MS A: $t_R$=0.77 min; no ionization.

A.2.59. 2-Ethoxy-6-propyl-4-(4,4,5,5-tetramethyl-1,3,2-dioxaborolan-2-yl)benzoic acid The title compound is prepared according to the procedure described for A.2.3., starting with 4-bromo-2-ethoxy-6-propylbenzoic acid. LC-MS A: $t_R$=0.90 min; [M+H]+=335.11.

A.2.59.1. 4-Bromo-2-ethoxy-6-propylbenzoic acid

The title compound is prepared according to the procedure described for A.2.53.1., starting with 4-bromo-2-fluoro-6-propylbenzoic acid. LC-MS A: $t_R$=0.86 min; [M+H]+=286.98.

A.2.60. 2-Methoxy-6-propyl-4-(4,4,5,5-tetramethyl-1,3,2-dioxaborolan-2-yl)benzoic acid The title compound is prepared according to the procedure described for A.2.3., starting with 4-bromo-2-methoxy-6-propylbenzoic acid. LC-MS A: $t_R$=0.87 min; [M+H]+=321.12.

A.2.60.1. 4-Bromo-2-methoxy-6-propylbenzoic acid

The title compound is prepared according to the procedure described for A.2.53.1., starting with 4-bromo-2-fluoro-6-propylbenzoic acid and methanol. LC-MS A: $t_R$=0.86 min; [M+MeCN]+=315.99.

A.2.61. Methyl 2-(cyclopentyloxy)-5-(4,4,5,5-tetramethyl-1,3,2-dioxaborolan-2-yl)benzoate The title compound is prepared according to the procedure described for A.2.3., starting with methyl 5-bromo-2-(cyclopentyloxy)benzoate. LC-MS A: $t_R$=1.01 min; [M+H]+= 347.15.

A.2.61.1. Methyl 5-bromo-2-(cyclopentyloxy)benzoate

To a solution of methyl 4-bromo-2-hydroxybenzoate (2.00 g, 8.4 mmol) in DMF (20 mL), bromocyclobutane (1.01 mL, 9.24 mmol) and $K_2CO_3$ (1.74 g, 12.6 mmol) are added. The RM is stirred at 80° C. for 19 h, cooled to RT, and partitioned between water and $Et_2O$. Organic layers are combined and washed with additional water, dried over $MgSO_4$ and concentrated to dryness. The crude product is purified by FC, eluting with Heptane/DCM (100:0 to 40:60) to the product as a colourless oil (1.88 g, 75%). LC-MS A: $t_R$=0.97 min; [M+H]+=298.89.

A.2.62. 2-Chloro-6-(ethylamino)-4-(4,4,5,5-tetramethyl-1,3,2-dioxaborolan-2-yl)benzoic acid The title compound is prepared according to the procedure described for A.2.3., starting with 4-bromo-2-chloro-6-(ethylamino)benzoic acid. LC-MS A: $t_R$=0.87 min; [M+H]+=326.07.

A.2.62.1. 4-Bromo-2-chloro-6-(ethylamino)benzoic acid

A MW vial is charged with 4-bromo-2-fluoro-6-chlorobenzoic acid (2.00 g, 7.89 mmol), ethylamine hydrochloride (3.25 g, 39.5 mmol), TEA (5.49 mL, 39.5 mmol) and pyridine (12 mL). It is purged with $N_2$, capped and heated in the MW apparatus at 150° C. for 2.5 h. The RM is concentrated under reduced pressure. The residue is acidified with 1N HCl. The precipitate is collected by filtration as a beige solid. LC-MS A: $t_R$=0.90 min; no ionization.

A.2.63. 2-(Ethylamino)-6-fluoro-4-(4,4,5,5-tetramethyl-1,3,2-dioxaborolan-2-yl)benzoic acid The title compound is prepared according to the procedure described for A.2.3., starting with 4-bromo-2-(ethylamino)-6-fluorobenzoic acid. LC-MS F: $t_R$=0.17 min; [M−H]+=308.28.

A.2.63.1. 4-Bromo-2-(ethylamino)-6-fluorobenzoic acid

The title compound is prepared according to the procedure described for A.2.62.1., starting with 4-bromo-2,6-difluoro-benzoic acid. LC-MS A: $t_R$=0.84 min; [M+H]+=262.00.

A.2.64. 2-Ethoxy-4-(4,4,5,5-tetramethyl-1,3,2-dioxaborolan-2-yl)benzenesulfonamide The title compound is prepared according to the procedure described for A.2.3., starting with 4-bromo-2-ethoxybenzenesulfonamide. LC-MS A: $t_R$=0.81 min; [M+H]+= 328.03.

A.2.64.1. 4-Bromo-2-ethoxybenzenesulfonamide

To a suspension of NaH (60%, suspension in oil, 220 mg, 5.51 mmol) in DMF (7 mL) is added a solution of dry EtOH (0.505 mL, 8.66 mmol) in DMF (2 mL) for 30 minutes at RT. The suspension is stirred for 30 minutes at RT. A solution of 4-bromo-2-fluorobenzenesulfonamide (1.00 g, 3.94 mmol) in DMF (4 mL) is added dropwise over 30 minutes at RT. The suspension is stirred at RT for 1 hour and at 70° C. for 4 hours. The suspension is poured into aq. HCl solution (1N, 20 mL) at 0° C., and the mixture is stirred at RT for 1 hour. The mixture is filtered to collect precipitate and the precipitate is washed with water and hexane, then dried and purified via FC, using heptane/EtOAc with a gradient from 100:0 to 70:30. This afforded the title compound as a white powder (305 mg, 28%). LC-MS F: $t_R$=0.74 min; [M−H]+=280.02.

A.2.65. 1-(2-Ethoxy-4-(4,4,5,5-tetramethyl-1,3,2-dioxaborolan-2-yl)phenyl)-2,2,2-trifluoroethan-1-ol The title compound is prepared according to the procedure described for A.2.3., starting with 1-(4-bromo-2-ethoxyphenyl)-2,2,2-trifluoroethan-1-ol. LC-MS A: $t_R$=0.94 min; no ionization.

A.2.65.1. 1-(4-Bromo-2-ethoxyphenyl)-2,2,2-trifluoroethan-1-ol

A solution of 4-bromo-2-ethoxybenzaldehyde (500 mg, 2.18 mmol) and (trifluoromethyl)trimethylsilane (0.395 mL, 2.62 mmol) in THF (5 mL) is cooled to 0° C. and treated with tetrabutylammonium fluoride (1 M in THF, 0.327 mL, 0.327 mmol). The resulting solution is allowed to warm to RT and stirred at this temperature for 2 h and quenched with 1N HCl (10 mL, 10 mmol, 1 eq. The mixture is extracted with $Et_2O$. The organic layer is dried over $MgSO_4$, filtered and concentrated under reduced pressure. The crude material is purified by flash chromatography using Hept/EtOAc 100:0 to 90:10. This afforded the title compound as a colourless oil (610 mg, 93%). LC-MS F: $t_R$=0.93 min; [M–H]+=342.95.

A.2.66. 3-Ethoxy-5-(4,4,5,5-tetramethyl-1,3,2-dioxaborolan-2-yl)thiophene-2-carboxylic acid Lithium diisopropylamide (2.0 M in THF/hexanes, 25 mL, 49.6 mmol) is added dropwise to a solution of 3-ethoxythiophene-2-carboxylic acid (4.00 g, 22.5 mmol) in dry THF (130 mL) at −78° C. The resulting mixture is stirred for 30 min at −78° C. then at 0° C. for 10 min. Back at −78° C., a solution of 2-isopropoxy-4,4,5,5-tetramethyl-1,3,2-dioxaborolane (9.38 mL, 45.1 mmol) in dry THF (30 mL) is added dropwise and the mixture is slowly allowed to warm to RT overnight. HCl 2N (50 mL) is added dropwise at 0° C., then the THF is removed in vacuo and the mixture is extracted twice with EtOAc. The combined organic layers are washed with brine, dried over MgSO$_4$ and the solvent is removed. The crude product is purified by FC using Hept/DCM/EtOAc 1:0:0 to 0:9:1 as the eluent. This afforded the title compound as a white solid (5.26 g, 78%). LC-MS A: $t_R$=0.48 min; [M+H]+=217.07 (boronic acid, from hydrolysis of the pinacol ester on the LCMS-column).

A.2.67. 5-(4-(4,4,5,5-Tetramethyl-1,3,2-dioxaborolan-2-yl)phenyl)-[1,2,4]oxadiazole The title compound is prepared according to the procedure described for A.2.3., starting with 5-(4-bromophenyl)-[1,2,4]oxadiazole. LC-MS A: $t_R$=0.81 min; no ionization.

A.2.68. 5-(4,4,5,5-Tetramethyl-1,3,2-dioxaborolan-2-yl)-3-(trifluoromethyl)thiophene-2-carboxylic acid The title compound is prepared according to the procedure described for A.2.66., starting with 3-(trifluoromethyl)thiophene-2-carboxylic acid. LC-MS A: $t_R$=0.59 min; no ionization.

A.2.68.1. 3-(Trifluoromethyl)thiophene-2-carboxylic acid

To a −78° C. solution of 3-(trifluoromethyl)thiophene (0.4 mL, 3.68 mmol) in dry THE (10 mL) is added dropwise a solution of butyllithium (1.38M in hexane, 2.93 mL, 4.05 mmol) and the RM is stirred for 30 min. The RM is then poured over an excess of freshly crushed dry ice carbon dioxide. Once the RM is back at RT, HCl 1N is added until pH<3 and the mixture is extracted with DCM (3×). The organic layer is dried over MgSO$_4$ and concentrated under vacuum, affording the title compound as a pale yellow solid (0.72 g, quantitative). LC-MS A: $t_R$=0.69 min; no ionization.

A.2.69. rac-Tert-butyl (R)-3-methyl-1-oxo-5-(4,4,5,5-tetramethyl-1,3,2-dioxaborolan-2-yl)isoindoline-2-carboxylate To a solution of tert-butyl 1-oxo-5-(4,4,5,5-tetramethyl-1,3,2-dioxaborolan-2-yl)isoindoline-2-carboxylate (500 mg, 1.39 mmol) in THE (8 mL) at −78° C. is added dropwise sodium bis(trimethylsilyl)amide (0.6M in toluene, 2.8 mL, 1.67 mmol) and the RM is stirred for 15 min. Iodomethane (0.13 mL, 2.09 mmol) is added and the mixture is slowly allowed to reach RT overnight. The mixture is treated with water and extracted with DCM. The organic extracts are dried (MgSO$_4$), and concentrated under reduced pressure. The residue is purified by FC, eluting with a slow gradient of Hept/EtOAc 0 to 15%. This afforded the title compound as a yellow solid (175 mg, 34%). LC-MS A: $t_R$=0.99 min; no ionization.

A.2.69.1. Tert-butyl 1-oxo-5-(4,4,5,5-tetramethyl-1,3,2-dioxaborolan-2-yl)isoindoline-2-carboxylate The title compound is prepared according to the procedure described for A.2.3., starting with tert-butyl 5-bromo-1-oxoisoindoline-2-carboxylate. LC-MS A: $t_R$=0.96 min; [M+H]+=360.06.

A.2.70. rac-Tert-butyl (R)-3-ethyl-1-oxo-5-(4,4,5,5-tetramethyl-1,3,2-dioxaborolan-2-yl)isoindoline-2-carboxylate The title compound is prepared according to the procedure described for A.2.69., using ethyl iodide. LC-MS A: $t_R$=1.01 min; [M+H]+=388.13.

A.2.71. rac-Tert-butyl (R)-1-oxo-3-propyl-5-(4,4,5,5-tetramethyl-1,3,2-dioxaborolan-2-yl)isoindoline-2-carboxylate The title compound is prepared according to the procedure described for A.2.69., using propyl iodide. LC-MS A: $t_R$=1.03 min; [M+H]+=401.99.

A.2.72. rac-Tert-butyl (R)-3-isobutyl-1-oxo-5-(4,4,5,5-tetramethyl-1,3,2-dioxaborolan-2-yl)isoindoline-2-carboxylate The title compound is prepared according to the procedure described for A.2.69., using 1-iodo-2-methylpropane. LC-MS F: $t_R$=0.58 min; no ionization.

A.2.73. Methyl 2-fluoro-6-(methylthio)-4-(4,4,5,5-tetramethyl-1,3,2-dioxaborolan-2-yl)benzoate The title compound is prepared according to the procedure described for A.2.3., using methyl 4-bromo-2-fluoro-6-(methylthio)benzoate. LC-MS A: $t_R$=0.98 min; [M+H]+=327.11.

A.2.73.1. Methyl 4-bromo-2-fluoro-6-(methylthio)benzoate

Iodomethane (0.113 mL, 1.81 mmol) was added dropwise to a solution of 4-bromo-2-fluoro-6-(methylthio)benzoic acid (500 mg, 1.51 mmol) and Cs$_2$CO$_3$ (492 mg, 1.51 mmol) in anhydrous DMF (20 mL) at 0° C. The RM was stirred for 15 min at 0° C. and then at RT for 1 h. It was quenched with water, then EtOAc was added and layers were separated. The aqueous layer was extracted twice with EtOAc. The organic layers were combined and washed with brine, dried over anhydrous MgSO$_4$, filtered and concentrated under reduced. The crude product was purified by FC, eluting with heptane to give the title compound as a colorless oil (173 mg, 41%). LC-MS A: $t_R$=0.90 min; no ionization.

A.2.73.2. 4-Bromo-2-fluoro-6-(methylthio)benzoic acid

To a suspension of freshly powdered sodium hydroxide (397 mg, 9.92 mmol) in DMF (20 mL) at 0° is added 4-bromo-2,6-difluorobenzoic acid (2.00 g, 8.27 mmol, 1 eq) and the RM is stirred at 0° C. for 10 min. Sodium thiomethoxide (732 mg, 9.92 mmol) is added and the resulting RM is allowed to warm up to RT and stirred for 2 h. It is quenched with 2N HCl, and extracted with EtOAc (3×). The combined organic layers are washed with brine, dried over anhydrous MgSO$_4$, filtered and concentrated under reduced pressure to give the crude product quantitatively as a yellow oil. LC-MS A: $t_R$=0.76 min; no ionization.

A.2.74. Methyl 2-chloro-6-(methylthio)-4-(4,4,5,5-tetramethyl-1,3,2-dioxaborolan-2-yl)benzoate The title compound is prepared according to the procedure described for A.2.3., using methyl 4-bromo-2-fluoro-6-(methylthio)benzoate. LC-MS A: $t_R$=1.00 min; [M+H]+=343.14.

A.2.74.1. Methyl 4-bromo-2-chloro-6-(methylthio)benzoate

The title compound is prepared according to the procedure described for A.2.73.1., using 4-bromo-2-chloro-6-(methylthio)benzoic acid. LC-MS A: $t_R$=0.93 min; no ionization.

A.2.74.2. 4-Bromo-2-chloro-6-(methylthio)benzoic acid

The title compound is prepared according to the procedure described for A.2.73.2., using 4-bromo-2-fluoro-6-chlorobenzoic acid. LC-MS A: $t_R$=0.77 min; no ionization.

A.2.75. 1-(2-Ethoxy-4-(4,4,5,5-tetramethyl-1,3,2-dioxaborolan-2-yl)phenyl)-N-methylmethanamine A mixture of 2-ethoxy-4-(4,4,5,5-tetramethyl-1,3,2-dioxaborolan-2-yl)benzaldehyde (300 mg, 1.09 mmol) and methylamine (2M in MeOH, 1.65 mL, 3.3 mmol) is stirred at 65° C. for 4 hours. After cooling to RT, sodium borohydride (64 mg, 1.63 mmol) is added and the RM is stirred for 30 min, then concentrated in vacuo. The resulting residue is dissolved in EtOAc and washed by a sat. NaHCO$_3$ solution. The aq phase is basified with two drops of 1N NaOH (pH=13) and extracted with EtOAc. The combined organic extracts are washed with brine, dried (MgSO$_4$), filtered, concentrate, affording the title compound as a white powder. LC-MS A: $t_R$=0.66 min; [M+H]+=292.15.

A.2.75.1. 2-Ethoxy-4-(4,4,5,5-tetramethyl-1,3,2-dioxaborolan-2-yl)benzaldehyde To a mixture of (2-ethoxy-4-(4,4,5,5-tetramethyl-1,3,2-dioxaborolan-2-yl)phenyl)methanol (957 mg, 3.23 mmol) in DCM (15 mL) at 0° C. is added Dess-Martin periodinane (2.06 g, 4.85 mmol). The RM is stirred at 0° C. for 2 h, then diluted with DCM, washed with 10% aq Na2S2O3, sat aq NaHCO$_3$ and brine. The organic layer is dried (MgSO$_4$), concentrated, and purified via FC using heptane/EtOAc from 100:0 to 80:20. This afforded the title compound as a white solid (700 mg, 78%). LC-MS A: $t_R$=0.96 min; [M+H]+=277.13.

A.2.75.2. (2-Ethoxy-4-(4,4,5,5-tetramethyl-1,3,2-dioxaborolan-2-yl)phenyl)methanol The title compound is prepared according to the procedure described for A.2.3., using (4-bromo-2-ethoxyphenyl)methanol. LC-MS A: $t_R$=0.84 min; no ionization.

A.2.76. N-(2-Ethoxy-4-(4,4,5,5-tetramethyl-1,3,2-dioxaborolan-2-yl)benzyl)cyclopropanamine The title compound is prepared according to the procedure described for A.2.75., using cyclopropylamine. LC-MS A: $t_R$=0.70 min; [M+H]+=318.12.

A.2.77. N-(2-Ethoxy-4-(4,4,5,5-tetramethyl-1,3,2-dioxaborolan-2-yl)benzyl)-2-methoxyethan-1-amine The title compound is prepared according to the procedure described for A.2.75., using 2-methoxyethylamine. LC-MS A: $t_R$=0.70 min; [M+H]+=336.10.

A.2.78. N-(2-Ethoxy-4-(4,4,5,5-tetramethyl-1,3,2-dioxaborolan-2-yl)benzyl)-2-methylpropan-1-amine The title compound is prepared according to the procedure described for A.2.75., using isobutylamine. LC-MS A: $t_R$=0.75 min; [M+H]+=334.13.

A.2.79. N-(2-Ethoxy-4-(4,4,5,5-tetramethyl-1,3,2-dioxaborolan-2-yl)benzyl)cyclobutanamine The title compound is prepared according to the procedure described for A.2.75., using cyclobutylamine. LC-MS A: $t_R$=0.74 min; [M+H]+=332.08.

A.2.80. Methyl 2-(methylsulfonamido)-4-(4,4,5,5-tetramethyl-1,3,2-dioxaborolan-2-yl)benzoate Methylsulfonyl chloride (141 mg, 1.22 mmol) is added to a solution of methyl 2-amino-4-(4,4,5,5-tetramethyl-1,3,2-dioxaborolan-2-yl)benzoate (75 mg, 0.271 mmol) and pyridine (0.131 mL, 1.62 mmol) in DCM (3 mL). The mixture is stirred at 50° C. for 3 days. It is treated at RT with 1 mL of 1N NaHCO$_3$, passed through a phase separator and rinsed with DCM. The solvent is evaporated under reduced pressure, to afford the title compound, which is used as such in the coupling step. LC-MS A: $t_R$=0.93 min; no ionization.

A.2.81. Methyl 2-(ethylsulfonamido)-4-(4,4,5,5-tetramethyl-1,3,2-dioxaborolan-2-yl)benzoate The title compound is prepared according to the procedure described for A.2.80., using ethylsulfonyl chloride. LC-MS A: $t_R$=0.96 min; [M+H]+=370.03.

A.2.82. Methyl 2-(butylamino)-4-(4,4,5,5-tetramethyl-1,3,2-dioxaborolan-2-yl)benzoate A solution of methyl 2-amino-4-(4,4,5,5-tetramethyl-1,3,2-dioxaborolan-2-yl)benzoate (50 mg, 0.18 mmol) and propionaldehyde (0.020 mL, 0.271 mmol) in dry THF (3 mL) is stirred for 15 min at RT. Sodium triacetoxyborohydride (115 mg, 0.541 mmol) is added. The RM is stirred at RT overnight. The RM is treated with 1N aq. NaHCO$_3$ (1 mL) and extracted with DCM using a phase separator. Evapora-

A.2.83. 5-(4-(4,4,5,5-Tetramethyl-1,3,2-dioxaborolan-2-yl)phenyl)isoxazol-3-ol To a solution of ethyl 3-(4-(4,4,5,5-tetramethyl-1,3,2-dioxaborolan-2-yl)phenyl)propiolate (477 mg, 1.59 mmol) in dry MeOH (10 mL) are added at RT hydroxylamine hydrochloride (442 mg, 6.36 mmol) and potassium hydroxide (5M in MeOH, 1.91 mL, 9.53 mmol). The RM is stirred overnight at RT. It is then concentrated in vacuo and the resulting mixture is partitioned between EtOAc and water. The pH of the aqueous layer is adjusted to pH3 by adding HCl 1N. Both phases are separated. The aqueous layer is extracted twice with EtOAc then the combined organic layers are washed with water, brine, dried over $MgSO_4$, filtered and concentrated in vacuo. The residue is purified via FC, eluting with a gradient from Heptane:EtOAc 100:0 to 60:40. This afforded the title compound as a pinkish solid (58 mg, 13%). LC-MS A: $t_R$=0.85 min; [M+H]+=288.34.

A.2.83.1. Ethyl 3-(4-(4,4,5,5-tetramethyl-1,3,2-dioxaborolan-2-yl)phenyl)propiolate A solution of 4-Iodophenylboronic acid, pinacol ester (495 mg, 1.5 mmol) in TEA (6.19 mL, 43.5 mmol) is degassed 3 times (vacuum/argon), then are added successively Tetrakis-(triphenylphosphine)-palladium (173 mg, 0.15 mmol), Copper (I) iodide (85.7 mg, 0.45 mmol) and ethyl propiolate (0.155 mL, 1.5 mmol). The RM is flushed with argon and heated at 70° C. overnight, then concentrated in vacuo. The residue which is purified by FC, eluting with a gradient of Heptane:EtOAc from 100:0 to 80:20. This afforded the title compound as a yellow oil (482 mg, 54%). LC-MS A: $t_R$=1.02 min; [M+H]+=301.19.

A.2.84. 5-(2-Ethoxy-4-(4,4,5,5-tetramethyl-1,3,2-dioxaborolan-2-yl)phenyl)-1H-tetrazole A mixture of 2-ethoxy-4-(4,4,5,5-tetramethyl-1,3,2-dioxaborolan-2-yl)benzonitrile (500 mg, 1.83 mmol), Azidotributyltin(IV) (0.768 mL, 2.75 mmol), and dry toluene (4 mL) is heated at 180° C. for 1 h. The mixture is cooled to RT, treated with HCl 0.1N and extracted with EtOAc. The organic layer is dried over $MgSO_4$ and concentrated under vacuum. The residue is purified via FC, eluting with a gradient from Heptane:EtOAc 100:0 to 10:90. This afforded the title compound as a white solid (135 mg, 23%). LC-MS A: $t_R$=0.87 min; [M+H]+=317.14.

A.2.84.1. 2-Ethoxy-4-(4,4,5,5-tetramethyl-1,3,2-dioxaborolan-2-yl)benzonitrile A solution of 2-hydroxy-4-(4,4,5,5-tetramethyl-1,3,2-dioxaborolan-2-yl)benzonitrile (1.50 g, 6.12 mmol), $K_2CO_3$ (1.69 g, 12.2 mmol) in DMF (4 mL) and iodoethane (0.596 mL, 7.34 mmol) is heated at 120° C. for 30 min. The RM is cooled down to RT, partitioned between DCM and 1N $NaHCO_3$. The aqueous layer is re-extracted with DCM, the combined organics are dried ($MgSO_4$), and concentrated under reduced pressure. This afforded the title compound as a beige solid (1.31 g, 78%). LC-MS A: $t_R$=0.96 min; [M+CH3CN+H]+=315.10

A.2.85. 5-(2-Ethoxy-6-fluoro-4-(4,4,5,5-tetramethyl-1,3,2-dioxaborolan-2-yl)phenyl)-1H-tetrazole The title compound is prepared according to the procedure described for A.2.3., using 5-(4-bromo-2-ethoxy-6-fluorophenyl)-1H-tetrazole. LC-MS A: $t_R$=0.83 min; [M+H]+=335.03.

A.2.85.1. 5-(4-Bromo-2-ethoxy-6-fluorophenyl)-1H-tetrazole

The title compound is prepared according to the procedure described for A.2.84., using 4-bromo-2-ethoxy-6-fluorobenzonitrile. LC-MS A: $t_R$=0.75 min; [M+H]+=288.96.

A.2.85.2. 4-Bromo-2-ethoxy-6-fluorobenzonitrile

To a solution of 4-bromo-2,6-difluorobenzonitrile (1.00 g, 4.59 mmol) in dry THF (10 mL) is added portionwise at RT sodium ethoxide (375 mg, 5.5 mmol). The RM is stirred at RT overnight. The RM is poured into sat. aq. NH4Cl, extracted with DCM (3×). The combined extracts are dried ($MgSO_4$) and concentrated in vacuo, affording the title compound as a white solid (1.10 g, 98%). LC-MS A: $t_R$=0.90 min; no ionization.

A.2.86. N-Ethyl-5-(4,4,5,5-tetramethyl-1,3,2-dioxaborolan-2-yl)-2-(1H-tetrazol-5-yl)aniline The title compound is prepared according to the procedure described for A.2.3., using 5-bromo-N-ethyl-2-(1H-tetrazol-5-yl)aniline. LC-MS A: $t_R$=0.88 min; [M+H]+=316.14.

A.2.86.1. 5-Bromo-N-ethyl-2-(1H-tetrazol-5-yl)aniline

A solution of 4-bromo-2-(ethylamino)benzonitrile (387 mg, 1.72 mmol) in EtOH (12 mL) is treated with sodium azide (374 mg, 5.76 mmol) and zinc bromide (465 mg, 2.06 mmol) and the mixture is heated by MW in a sealed tube at 150° C. for 4 h. The RM is diluted with HCl 0.1N and extracted twice with DCM. The extracts are dried over $MgSO_4$ and the solvent is evaporated. Purification by FC, eluting with Heptane/DCM/EtOAc 1:0:0 to 0:3:1 afforded the title compound as a white solid (363 mg, 79%). LC-MS A: $t_R$=0.84 min; [M+H]+=268.02.

A.2.87. Methyl 3-propoxy-5-(4,4,5,5-tetramethyl-1,3,2-dioxaborolan-2-yl)thiophene-2-carboxylate The title compound is prepared according to the procedure described for A.2.66., using methyl 3-propoxythiophene-2-carboxylate. LC-MS A: $t_R$=0.68 min; [M+H]+=245.11 (boronic acid, from hydrolysis of the pinacol ester on the LCMS-column).

A.2.87.1. Methyl 3-propoxythiophene-2-carboxylate

To a solution of methyl 3-hydroxythiophene-2-carboxylate (1.00 g, 6.32 mmol) in dry DMF (12 mL), cooled at 0° C. is added NaH (60% suspension in oil, 316 mg, 7.9 mmol), portionwise. Once the gas evolution is finished, 1-bromopropane (0.64 mL, 6.95 mmol) is added dropwise. After 5 minutes at 0° C. the RM is Also the crude title compound. LC-MS A: $t_R$=0.83 min; no ionization.

allowed to warm to RT, then at 40° C. overnight. The RM is cooled down to RT, poured into water and extracted three times with Ethyl acetate. The combined org. phases are washed with water, brine, dried over MgSO$_4$, filtered and concentrated in vacuo, yielding the desired product as a white solid (1.17 g, 92%). LC-MS A: $t_R$=0.79 min; [M+H]+=201.12.

A.2.88. Methyl 3-butoxy-5-(4,4,5,5-tetramethyl-1,3, 2-dioxaborolan-2-yl)thiophene-2-carboxylate The title compound is prepared according to the procedure described for A.2.66., using methyl 3-butoxythiophene-2-carboxylate. LC-MS A: $t_R$=0.65 min; [M+H]+=245.16 (boronic acid, from hydrolysis of the pinacol ester on the LCMS-column).

A.2.88.1. Methyl 3-butoxythiophene-2-carboxylate

The title compound is prepared according to the procedure described for A.2.87.1., using butyl bromide. LC-MS A: $t_R$=0.85 min; [M+H]+=215.11.

A.2.89. Methyl 3-isopropoxy-5-(4,4,5,5-tetramethyl-1,3,2-dioxaborolan-2-yl)thiophene-2-carboxylate The title compound is prepared according to the procedure described for A.2.66., using methyl 3-isopropoxythiophene-2-carboxylate. LC-MS A: $t_R$=0.73 min; [M+H]+=259.12 (boronic acid, from hydrolysis of the pinacol ester on the LCMS-column).

A.2.89.1. Methyl 3-isopropoxythiophene-2-carboxylate

The title compound is prepared according to the procedure described for A.2.87.1., using 2-bromopropane. LC-MS A: $t_R$=0.79 min; [M+H]+=201.16.

A.2.90. 5-(2-Methoxy-4-(4,4,5,5-tetramethyl-1,3,2-dioxaborolan-2-yl)phenyl)-1H-tetrazole The title compound is prepared according to the procedure described for A.2.84., using 2-methoxy-4-(4,4,5,5-tetramethyl-1,3,2-dioxaborolan-2-yl)benzonitrile. LC-MS A: $t_R$=0.83 min; [M+H]+=303.12.

A.2.90.1. 2-Methoxy-4-(4,4,5,5-tetramethyl-1,3,2-dioxaborolan-2-yl)benzonitrile

To a solution of 2-hydroxy-4-(4,4,5,5-tetramethyl-1,3,2-dioxaborolan-2-yl)benzonitrile (1.00 g, 4.08 mmol), K$_2$CO$_3$ (1.13 g, 8.16 mmol) in DMF (4 mL) is added iodomethane (0.305 mL, 4.9 mmol) is added and the mixture is heated at 120° C. for 30 min. The RM is cooled to RT, partitioned between DCM and 1N NaHCO$_3$. The aqueous layer is re-extracted with DCM, the combined organics are dried (MgSO$_4$), and concentrated under reduced. This afforded the title compound as a beige solid (0.93 g, 88%). LC-MS A: $t_R$=0.93 min; [M+MeCN+H]+=301.13.

A.2.91. 1-(4-(4,4,5,5-Tetramethyl-1,3,2-dioxaborolan-2-yl)phenyl)-1H-[1,2,4]triazole The title compound is prepared according to the procedure described for A.2.3., using 1-(4-bromophenyl)-1H-[1,2,4]triazole. LC-MS A: $t_R$=0.86 min; [M+H]+=272.25.

A.2.92. 5-(4-(4,4,5,5-Tetramethyl-1,3,2-dioxaborolan-2-yl)phenyl)isoxazole

The title compound is prepared according to the procedure described for A.2.3., using 5-(4-bromophenyl)isoxazole. LC-MS A: $t_R$=0.93 min; [M+MeCN+H]+=313.24.

A.2.93. 4-Methyl-5-(4-(4,4,5,5-tetramethyl-1,3,2-dioxaborolan-2-yl)phenyl)isoxazole The title compound is prepared according to the procedure described for A.2.3., using 5-(4-bromophenyl)-4-methylisoxazole. LC-MS A: $t_R$=0.96 min; [M+H]+=286.21.

A.2.94. 3-Methyl-5-(4-(4,4,5,5-tetramethyl-1,3,2-dioxaborolan-2-yl)phenyl)isoxazole The title compound is prepared according to the procedure described for A.2.3., using 5-(4-bromophenyl)-3-methylisoxazole. LC-MS A: $t_R$=0.96 min; [M+H]+=286.21.

A.2.95. 3-Methyl-5-(4-(4,4,5,5-tetramethyl-1,3,2-dioxaborolan-2-yl)phenyl)isoxazole The title compound is prepared according to the procedure described for A.2.3., using 5-(4-Bromophenyl)isoxazole-3-carboxylic acid. LC-MS E: $t_R$=0.96 min; [M−H]+=270.16.

A.2.96. 2-Chloro-6-isobutoxy-4-(4,4,5,5-tetramethyl-1,3,2-dioxaborolan-2-yl)benzoic acid The title compound is prepared according to the procedure described for A.2.3., using 4-bromo-2-chloro-6-isobutoxybenzoic acid. LC-MS A: $t_R$=0.93 min; [M+H]+=355.12.

A.2.96.1. 4-Bromo-2-chloro-6-isobutoxybenzoic acid

The title compound is prepared according to the procedure described for A.2.53.1., using 2-methyl-1-propanol. LC-MS A: $t_R$=0.87 min; no ionization.

A.2.97. 2-Chloro-4-(4,4,5,5-tetramethyl-1,3,2-dioxaborolan-2-yl)-6-(2,2,2-trifluoroethoxy)benzoic acid The title compound is prepared according to the procedure described for A.2.3., using 4-bromo-2-chloro-6-(2,2,2-trifluoroethoxy)benzoic acid. LC-MS A: $t_R$=0.90 min; no ionization.

A.2.97.1. 4-Bromo-2-chloro-6-(2,2,2-trifluoroethoxy)benzoic acid

The title compound is prepared according to the procedure described for A.2.53.1., using 2,2,2-trifluoroethanol. LC-MS A: $t_R$=0.82 min; no ionization.

A.2.98. 2-(2-Ethoxy-4-(4,4,5,5-tetramethyl-1,3,2-dioxaborolan-2-yl)phenoxy)acetic acid A solution of ethyl 2-(2-ethoxy-4-(4,4,5,5-tetramethyl-1,3,2-dioxaborolan-2-yl)phenoxy)acetate (1.285 g, 3.82 mmol) in EtOH (15 mL) is treated with NaOH 10% (7.64 mL, 19.1 mmol) and the RM is stirred at 50° C. for 30 min. The RM is cooled to RT and diluted with EtOAc. HCl 2N (15 mL) is added to reach acidic pH (<1). The aqueous layer is extracted twice with EtOAc. The resulting organic phase is dried over MgSO4 and concentrated, affording the title compound as an orange paste. LC-MS A: $t_R$=0.80 min; [M+H]=323.12.

A.2.98.1. Ethyl 2-(2-ethoxy-4-(4,4,5,5-tetramethyl-1,3,2-dioxaborolan-2-yl)phenoxy)acetate A solution of 2-ethoxy-4-(4,4,5,5-tetramethyl-1,3,2-dioxaborolan-2-yl)phenol (3.47 g, 12.5 mmol) in anhydrous DMF (50 mL) is treated successively with Cs$_2$CO$_3$ (6.10 g, 18.7 mmol) and ethyl bromoacetate (1.48 mL, 13.1 mmol). The RM is stirred at RT for 1 h. Water is added, and the mixture is extracted with Et2O (×3). The combined organic layers are then washed successively with water (×2) and brine, dried over MgSO4, filtered, and concentrated to dryness under reduced pressure to afford the pure product as a colorless oil (1.46 g, 77%). LC-MS A: $t_R$=0.94 min; [M+H]=351.18.

A.2.99. (2-Ethoxy-4-(4,4,5,5-tetramethyl-1,3,2-dioxaborolan-2-yl)phenyl)glycine To a solution of methyl (2-ethoxy-4-(4,4,5,5-tetramethyl-1,3,2-dioxaborolan-2-yl)phenyl)glycinate (207 mg, 0.61 mmol) in THF/H2O (4:1) (5 mL) is added LiOH·H2O (51 mg, 1.21 mmol) and the mixture is stirred at RT for 2 h. The mixture is treated with HCl 1 N (1 mL) and extracted with EtOAc, dried over MgSO4 and concentrated, affording the title compound as a brown oil (0.151 g, 78%). LC-MS A: $t_R$=0.82 min; [M+H]=322.07.

A.2.99.1. Methyl (2-ethoxy-4-(4,4,5,5-tetramethyl-1,3,2-dioxaborolan-2-yl)phenyl)glycinate The title compound is prepared according to the procedure described for A.2.3., starting with methyl (4-bromo-2-ethoxyphenyl)glycinate. LC-MS A: $t_R$=0.93 min; [M+H]+=336.28.

A.2.99.2. Methyl (4-bromo-2-ethoxyphenyl)glycinate

To a solution of 4-bromo-2-ethoxyaniline (0.60 g, 2.64 mmol) in DMF (2.5 mL) is added DiPEA (0.673 mL, 3.96 mmol) followed by methyl bromoacetate (0.275 mL, 2.9 mmol). The mixture is stirred at 90° C. for 1 h in the microwave apparatus. The DMF is evaporated under high vacuum and the residue is purified by FC, eluting with Hept/EtOAc 1:0 to 17:3 affording the title compound as a dark red oil (0.71 g, 94%). LC-MS A: $t_R$=0.89 min; [M+H]+=288.08.

Following the procedure described for the synthesis of A.2.3. described above, the following boronic acid derivatives are synthesized, starting from the corresponding commercially available halides (see table 4).

TABLE 4

Boronic acid derivatives A.2.100.-A.2.109.

| No. | Compound | $t_R$ [min] (LC-MS) | MS Data m/z [M + H]+ |
|---|---|---|---|
| A.2.100. | 2-Ethoxy-4-(4,4,5,5-tetramethyl-1,3,2-dioxaborolan-2-yl)aniline | 0.73 (A) | 264.25 |
| A.2.101. | 4,4-Dimethyl-2-(4-(4,4,5,5-tetramethyl-1,3,2-dioxaborolan-2-yl)phenyl)-4,5-dihydrooxazole | 0.73 (A) | 302.22 |
| A.2.102. | 2-Ethyl-4-(4,4,5,5-tetramethyl-1,3,2-dioxaborolan-2-yl)phenol | 0.87 (A) | No ionization |
| A.2.103. | 5-(4-(4,4,5,5-Tetramethyl-1,3,2-dioxaborolan-2-yl)phenyl)-[1,2,4]oxadiazol-3-ol | 0.82 (A) | 290.10 |
| A.2.104. | 3-(4-(4,4,5,5-Tetramethyl-1,3,2-dioxaborolan-2-yl)phenyl)-[1,2,4]oxadiazol-5(4H)-one | 0.38 (E) | 287.14 |
| A.2.105. | 1,2-Dimethyl-4-(4-(4,4,5,5-tetramethyl-1,3,2-dioxaborolan-2-yl)phenyl)-1H-imidazole | 0.67 (A) | 299.20 |
| A.2.106. | 5-Methyl-4-(4-(4,4,5,5-tetramethyl-1,3,2-dioxaborolan-2-yl)phenyl)-1H-imidazole | 0.66 (A) | 285.24 |
| A.2.107. | 2,5-Dimethyl-4-(4-(4,4,5,5-tetramethyl-1,3,2-dioxaborolan-2-yl)phenyl)-1H-imidazole | 0.68 (A) | 299.22 |
| A.2.108. | 2-Cyclopropyl-1-methyl-4-(4-(4,4,5,5-tetramethyl-1,3,2-dioxaborolan-2-yl)phenyl)-1H-imidazole | 0.70 (A) | 325.16 |
| A.2.109. | 5-(4-(4,4,5,5-Tetramethyl-1,3,2-dioxaborolan-2-yl)phenyl)isoxazol-3-ol | 0.85 (A) | 288.17 |

Following the procedure described for the synthesis of A.2.98.1. described above, the following boronic acid derivatives are synthesized, starting from the corresponding commercially available boronic acid derivatives and alkyl halides (see table 5).

TABLE 5

Boronic acid derivatives A.2.110.-A.2.114.

| No. | Compound | $t_R$ [min] (LC-MS) | MS Data m/z [M + H]+ |
|---|---|---|---|
| A.2.110. | Methyl 2-(4-(4,4,5,5-tetramethyl-1,3,2-dioxaborolan-2-yl)-2-(trifluoromethoxy)phenoxy)acetate | 0.98 (A) | 376.99 |

TABLE 5-continued

Boronic acid derivatives A.2.110.-A.2.114.

| No. | Compound | $t_R$ [min] (LC-MS) | MS Data m/z [M + H]$^+$ |
|---|---|---|---|
| A.2.111. | Methyl 2-(2-ethyl-4-(4,4,5,5-tetramethyl-1,3,2-dioxaborolan-2-yl)phenoxy)acetate | 0.96 (A) | 321.17 |
| A.2.112. | Methyl 2-(2-ethoxy-4-(4,4,5,5-tetramethyl-1,3,2-dioxaborolan-2-yl)phenoxy)propanoate | 0.94 (A) | 351.23 |
| A.2.113. | Ethyl 2-(2-ethoxy-4-(4,4,5,5-tetramethyl-1,3,2-dioxaborolan-2-yl)phenoxy)-2-fluoroacetate | 0.99 (A) | 369.12 |
| A.2.114. | Methyl 2-(2-chloro-4-(4,4,5,5-tetramethyl-1,3,2-dioxaborolan-2-yl)phenoxy)acetate | 0.94 (A) | 327.10 |

A.2.115. 2-(2-Propoxy-4-(4,4,5,5-tetramethyl-1,3,2-dioxaborolan-2-yl)phenyl)acetic acid To a solution of propyl 2-(2-propoxy-4-(4,4,5,5-tetramethyl-1,3,2-dioxaborolan-2-yl)phenyl)acetate (308 mg, 0.85 mmol) in EtOH (9 mL) is added NaOH (10% aq. Solution, 3.4 mL) and the mixture is stirred at RT for 2 h. EtOH is removed in vacuo. pH of the resulting basic aqueous layer is adjusted to pH=3-4 using HCl 1N and extracted twice with EtOAc. The combined organic layers are washed with water, brine, dried over MgSO$_4$, filtered and solvent is removed in vacuo, yielding the title compound as a white powder (0.238 g, 87%). LC-MS A: $t_R$=0.88 min; [M+H]=321.08.

A.2.115.1. Propyl 2-(2-propoxy-4-(4,4,5,5-tetramethyl-1,3,2-dioxaborolan-2-yl)phenyl)acetate The title compound is prepared according to the procedure described for A.2.3., starting with propyl 2-(4-bromo-2-propoxyphenyl)acetate. LC-MS A: $t_R$=1.04 min; [M+H]+=363.12.

A.2.115.2. Propyl 2-(4-bromo-2-propoxyphenyl)acetate

To a solution of 4-bromo-2-hydroxyphenylacetic acid (1.50 g, 6.37 mmol) in DMF (50 mL) is added 1-Iodopropane (1.38 mL, 14 mmol, 2.2 eq) and Cs2CO3 (6.23 g, 19.1 mmol). The RM is stirred at 100° C. over night, then cooled to RT. Water is added, and the DMF is removed under reduced pressure. The residue is partitioned between EtOAc and water. The aqueous layer is re-extracted twice with EtOAc. The combined organic extracts are washed with brine, dried (MgSO$_4$) and concentrated in vacuo. The residue is purified by FC (H:EE 100:0 to 90:10), affording the title compound as a colourless oil (0.775 g, 39%). LC-MS A: $t_R$=1.00 min; [M+H]+=315.07.

Following the procedure described for the synthesis of A.2.115. described above, the following boronic acid derivatives are synthesized, using the corresponding alkyl iodide (see Table 6).

TABLE 6

Boronic acid derivatives A.2.116.-A.2.117.

| No. | Compound | $t_R$ [min] (LC-MS) | MS Data m/z [M + H]$^+$ |
|---|---|---|---|
| A.2.116. | 2-(2-Butoxy-4-(4,4,5,5-tetramethyl-1,3,2-dioxaborolan-2-yl)phenyl)acetic acid | 0.92 (A) | 335.18 |
| A.2.117. | 2-(2-Cyclobutoxy-4-(4,4,5,5-tetramethyl-1,3,2-dioxaborolan-2-yl)phenyl)acetic acid | 0.88 (A) | 333.15 |

A.2.118. 2-Butoxy-6-fluoro-4-(4,4,5,5-tetramethyl-1,3,2-dioxaborolan-2-yl)benzoic acid The title compound is prepared according to the procedure described for A.2.3., starting with 4-bromo-2-butoxy-6-fluorobenzoic acid. LC-MS A: $t_R$=0.92 min; [M+H]=339.21.

A.2.118.1. 4-Bromo-2-butoxy-6-fluorobenzoic acid

The title compound is prepared according to the procedure described for A.2.115., starting with methyl 4-bromo-2-butoxy-6-fluorobenzoate. LC-MS E: $t_R$=0.52 min; [M−H]+=290.89.

A.2.118.2. methyl 4-bromo-2-butoxy-6-fluorobenzoate

To a solution of methyl 4-bromo-2-fluoro-6-hydroxybenzoate (1.00 g, 4.02 mmol) in DMF (10 mL), is added Cs2CO3 (2.62 g, 8.03 mmol) followed by 1-iodobutane (0.685 mL, 6.02 mmol). The RM is stirred at 120° C. for 2 h in the microwave. The RM is concentrated under reduced pressure, the residue is partitioned between DCM and water. The aqueous layer is re-extracted with DCM, the combined organics are dried (MgSO$_4$), and concentrated under reduced pressure. Purification by FC (Hept/EtOAc 1:0 to 19:1) afforded the title compound as a colourless oil (1.24 g, 99%). LC-MS A: $t_R$=0.98 min; [M+H]+=306.84.

A.2.119. 2-Butoxy-6-chloro-4-(4,4,5,5-tetramethyl-1,3,2-dioxaborolan-2-yl)benzoic acid The title compound is prepared according to the procedure described for A.2.3., starting with 4-bromo-2-butoxy-6-chlorobenzoic acid. LC-MS A: $t_R$=0.93 min; [M+H]=355.16.

A.2.119.1. 4-Bromo-2-butoxy-6-chlorobenzoic acid

To a solution of 4-bromo-2-fluoro-6-chlorobenzoic acid (1.00 g, 3.95 mmol) in dry DMF (7 mL) at 0° C. is added NaH (347 mg, 8.68 mmol) portionwise. Once the gas evolution is finished, a solution of 1-butanol (0.397 mL, 4.34 mmol) in dry DMF (3 mL) is added dropwise. Once the gas evolution is finished, it is heated up to 90° C. for 1 h. The mixture is poured into water. pH is adjusted to 1 with HCl 1N and then extracted three times with DCM. The organic phase is washed with water, brine, dried over MgSO$_4$, filtered and concentrated under vacuum, yielding quantitatively the desired product as a light orange solid. LC-MS A: $t_R$=0.88 min; [M+MeCN]+=349.99

A.2.120. Methyl methyl(4-(4,4,5,5-tetramethyl-1,3,2-dioxaborolan-2-yl)phenyl)carbamate To a solution of 4-(methylamino)phenylboronic acid pinacol ester (100 mg, 0.416 mmol) in dry DCM (3.6 mL) are added DIPEA (0.214 mL, 1.25 mmol) and methyl chloroformate (0.039 mL, 0.499 mmol). The resulting mixture is stirred at room temperature for 30 min. The mixture is partitioned between water (5 mL) and DCM (5 mL). The organic layer is separated, dried over MgSO$_4$, filtered, and concentrated to dryness. The residue is purified by FC (EtOAc-Heptane 2:8) to obtain the title compound as an off-white solid (92 mg, 63%). LC-MS A: $t_R$=0.90 min; [M+H]=292.21.

A.2.121. 2-(4-(3-Methoxyoxetan-3-yl)phenyl)-4,4,5,5-tetramethyl-1,3,2-dioxaborolane To a solution of 3-(4-(4,4,5,5-tetramethyl-1,3,2-dioxaborolan-2-yl)phenyl)oxetan-3-ol (150 mg, 0.543 mmol) in DMF (3.2 mL) is added NaH, 60% (26.1 mg, 0.652 mmol). The grey suspension is stirred for 30 min at RT. Iodomethane (0.169 mL, 2.72 mmol) is added and the RM is stirred at RT for 3 h. NaH, 60% (26.1 mg, 0.652 mmol) is added to the RM at RT. After 30 min, iodomethane (0.0845 mL, 1.36 mmol) is added and the RM is stirred overnight at RT. NaH, 60% (52.1 mg, 1.3 mmol) is added to the RM at RT. After 1 h stirring at RT iodomethane (0.169 mL, 2.72 mmol) is added and the RM is stirred for 45 min at RT. The grey suspension is quenched by the addition of 12 mL water. The mixture is extracted two times with DCM. The combined extracts are washed sequentially with water and brine, dried (MgSO$_4$) and concentrated under vacuum. Purification by FC (gradient Heptane/AcOEt) afforded the title compound as a white solid (20 mg, 13%). LC-MS A: $t_R$=0.90 min; no ionization.

A.2.122. Ethyl 2-((2-ethoxy-4-(4,4,5,5-tetramethyl-1,3,2-dioxaborolan-2-yl)phenyl)amino)-2-oxoacetate The title compound is prepared according to the procedure described for A.2.3., starting with ethyl 2-((4-bromo-2-ethoxyphenyl)amino)-2-oxoacetate. LC-MS A: $t_R$=0.98 min; [M+H]=364.21.

A.2.122.1. Ethyl 2-((4-bromo-2-ethoxyphenyl)amino)-2-oxoacetate

To a solution of 4-bromo-2-ethoxyaniline (1.10 g, 4.84 mmol) in DCM (35 mL) is added TEA (0.748 mL, 5.32 mmol) at RT. The RM is cooled to 0° C. and ethyl oxalyl chloride (0.61 mL, 5.32 mmol) is added dropwise. The RM is stirred for 30 min at 0° C. then allowed to warm to RT and stirred for 30 min. The RM is partitioned between ethyl acetate and saturated aqueous solution of NaHCO$_3$. The two layers are separated and the organic layers washed with water, brine then dried over MgSO$_4$, filtered and solvent removed under vacuo, affording the title compound as a brown solid (1.52 g, 99%). LC-MS A: $t_R$=0.92 min; [M+MeCN]+=316.04.

A.2.123. Methyl (2-ethoxy-4-(4,4,5,5-tetramethyl-1,3,2-dioxaborolan-2-yl)phenyl)alaninate The title compound is prepared according to the procedure described for A.2.3., starting with methyl (4-bromo-2-ethoxyphenyl)alaninate. LC-MS A: $t_R$=0.96 min; [M+H]+=350.25.

A.2.123.1. Methyl (4-bromo-2-ethoxyphenyl)alaninate

The title compound is prepared according to the procedure described for A.2.99.2. using methyl 2-bromopropionate. LC-MS A: $t_R$=0.93 min; [M+H]+=304.12.

A.2.124. 2-(2-Ethoxy-4-(4,4,5,5-tetramethyl-1,3,2-dioxaborolan-2-yl)phenyl)benzo[d]oxazole The title compound is prepared according to the procedure described for A.2.3., starting with 2-(4-bromo-2-ethoxyphenyl)benzo[d]oxazole. LC-MS A: $t_R$=1.02 min; [M+H]+=366.20.

A.2.124.1. 2-(4-Bromo-2-ethoxyphenyl)benzo[d]oxazole

To a solution of 4-bromo-2-ethoxybenzaldehyde (1.00 g, 4.37 mmol) in MeOH (25 mL) at RT under argon is added 2-aminophenol (481 mg, 4.37 mmol). The resulting solution is stirred over night at 45° C., then concentrated in vacuo. The residue is dissolved in THF (5 mL) and DCM (22.5 mL) and DDQ (2,3-Dichloro-5,6-dicyano-1,4-Benzoquinone) (991 mg, 4.37 mmol) is added. The RM is stirred at RT, then diluted with aq. sat. NaHCO$_3$ and extracted with EtOAc (twice). The combined organic layers are washed with brine, dried over MgSO$_4$, filtered and evaporated to dryness yielding the title compound as a yellow residue (1.40 g, 99%). LC-MS A: $t_R$=0.97 min; [M+H]+=318.09.

A.2.125. 2-(2-Ethoxy-4-(4,4,5,5-tetramethyl-1,3,2-dioxaborolan-2-yl)phenyl)-4,5-dimethyloxazole The title compound is prepared according to the procedure described for A.2.3., starting with 2-(4-bromo-2-ethoxyphenyl)-4,5-dimethyloxazole. LC-MS A: $t_R$=0.92 min; [M+H]+=344.27.

A.2.125.1. 2-(4-Bromo-2-ethoxyphenyl)-4,5-dimethyloxazole

To a solution of acetyl methyl carbinol (379 mg, 4 mmol) and 4-DMAP (125 mg, 1 mmol) in DCM (25 mL) at RT under argon are added DCC (1042 mg, 5 mmol). The resulting mixture is stirred 2 h at RT then filtered. The filtrate is concentrated in vacuo. The residue is treated with AcOH (15 mL) and ammonium acetate (1573 mg, 20 mmol). The resulting mixture is heated for 1 h 30 at reflux then is kept stirring at RT over night. It is then partitioned between EtOAc and water. Phases are separated and the aqueous layer is extracted once more with EtOAc. The combined organic layers are washed with water, brine, dried over $MgSO_4$, filtered and evaporated in vacuo to yield the title compound as a yellow residue (1.40 g, 99%). LC-MS A: $t_R$=0.88 min; [M+H]+=295.99.

A.2.126. 2-(2-Ethoxy-4-(4,4,5,5-tetramethyl-1,3,2-dioxaborolan-2-yl)phenyl)oxazole The title compound is prepared according to the procedure described for A.2.3., starting with 2-(4-bromo-2-ethoxyphenyl)oxazole. LC-MS A: $t_R$=0.93 min; [M+H]+=316.25.

A.2.126.1. 2-(4-Bromo-2-ethoxyphenyl)oxazole

To 4-bromo-N-(2,2-dimethoxyethyl)-2-ethoxybenzamide (550 mg, 1.66 mmol) at RT under argon is added Eaton's Reagent (Phosphorus pentoxide, 7.7 wt. % in methanesulfonic acid) (13.6 mL, 6.62 mmol). The resulting mixture is stirred at 145° C. using a pre warmed plate during 6 hours then heating is stopped and RM is allowed to cool to RT over night. The RM is poured onto ice-water and the resulting mixture is stirred 30 min then extracted with EtOAc (twice). The combined organic layers are washed with water, brine, dried over $MgSO_4$, filtered and evaporated to dryness yielding the title compound as a black oil (475 mg, 100%). LC-MS A: $t_R$=0.86 min; [M+H]+=268.1.

A.2.126.2. 4-Bromo-N-(2,2-dimethoxyethyl)-2-ethoxybenzamide

4-Bromo-2-ethoxybenzoic acid (500 mg, 2 mmol) is dissolved in DMF (14 mL) at RT under argon. The resulting solution is cooled to 0° C. and 1-(3-dimethylaminopropyl)-3-ethylcarbodiimide hydrochloride (587 mg, 3 mmol), HOBT Hydrate (461 mg, 3 mmol) and DIPEA (1.37 mL, 8 mmol) are added. The RM is stirred 5 min at 0° C. then allowed to warm up to RT and aminoacetaldehyde dimethyl acetal (0.242 mL, 2.2 mmol) is added followed by 4-DMAP (62.3 mg, 0.5 mmol). The RM is stirred at RT overnight, then concentrated under reduced pressure. The residue is diluted in EtOAc, washed with HCl 0.1N, $NaHCO_3$ aq. sat.solution, water, brine, dried over $MgSO_4$, filtered and solvent is removed in vacuo yielding the title compound as a pale yellow powder (550 mg, 83%). LC-MS A: $t_R$=0.84 min; [M+H]+=302.11.

A.2.127.5-(4,4,5,5-Tetramethyl-1,3,2-dioxaborolan-2-yl)-3-(2,2,2-trifluoroethoxy)thiophene-2-carboxylic acid The title compound is prepared according to the procedure described for A.2.1., starting with 3-(2,2,2-trifluoroethoxy)thiophene-2-carboxylic acid. LC-MS A: $t_R$=0.86 min; no ionization.

A.2.127.1. 3-(2,2,2-trifluoroethoxy)thiophene-2-carboxylic acid

To a solution of 3-fluorothiophene-2-carboxylic acid (678 mg, 4.64 mmol) in dry DMF (11 mL) at 0° C. is added NaH (60% suspension in oil, 408 mg, 10.2 mmol) portionwise. Once the gas evolution is finished, 2,2,2-trifluoroethanol (0.391 mL, 5.1 mmol) is added dropwise. After 10 minutes at 0° C. the RM is heated at 90° C. overnight. It is then cooled to 0° C. and quenched with water, and concentrated under reduced pressure. The residue is partitioned between water and EtOAc. The aqueous layer is re-extracted twice with EtOAc. The combined org. phases are washed with water, brine, dried over $MgSO_4$, filtered and concentrated in vacuo. The residue is purified by FC (H:EE 100:0 to 70:30), affording the title compound as a white powder (365 mg, 35%). LC-MS A: $t_R$=0.67 min, no ionization.

A.2.128. Methyl 4-(4,4,5,5-tetramethyl-1,3,2-dioxaborolan-2-yl)-2-(2,2,2-trifluoroethoxy)benzoate The title compound is prepared according to the procedure described for A.2.3., starting with methyl 4-bromo-2-(2,2,2-trifluoroethoxy)benzoate. LC-MS A: $t_R$=0.97 min; [M+H]+=361.13.

A.2.128.1. Methyl 4-bromo-2-(2,2,2-trifluoroethoxy)benzoate

A solution of methyl 4-bromo-2-hydroxybenzoate (300 mg, 1.3 mmol) and $K_2CO_3$ (549 mg, 3.9 mmol) in DMF (6 mL) is treated 1,1,1-trifluoro-2-iodoethane (0.384 mL, 3.9 mmol). The mixture is then stirred at 150° C. overnight, cooled to RT and treated with water, extracted with DCM, and concentrated affording the crude title compound as an orange solid (186 mg, 46%). LC-MS A: $t_R$=0.91 min, no ionization.

A.2.129. 3-(2-Ethoxy-4-(4,4,5,5-tetramethyl-1,3,2-dioxaborolan-2-yl)phenyl)-[1,2,4]oxadiazol-5(4H)-one The title compound is prepared according to the procedure described for A.2.3., starting with 3-(4-bromo-2-ethoxyphenyl)-[1,2,4]oxadiazol-5(4H)-one. LC-MS A: $t_R$=0.89 min; [M+H]+=333.06.

A.2.129.1. 3-(4-Bromo-2-ethoxyphenyl)-[1,2,4]oxadiazol-5(4H)-one

The solution of (Z)-4-bromo-2-ethoxy-N'-hydroxybenzimidamide (1.395 g, 5.38 mmol), 1,1'-carbonyldiimidazole (1.31 g, 8.08 mmol) and 1,8-diazabicyclo[5.4.0]undec-7-ene (1.23 mL, 8.08 mmol) in dioxane (20 mL) is stirred at 90° C. for 4 h 30 min. Once at rt, the product precipitated upon addition of HCl 1M. Dioxane is partially evaporated via N2 stream prior to filtering off the solid under vacuum, washing with water. The title compound is obtained as a white solid (1.375 g, 90%). LC-MS A: $t_R$=0.81 min, [M+MeCN]+=325.89.

A.2.129.2. (Z)-4-Bromo-2-ethoxy-N'-hydroxybenzimidamide

A suspension of 4-bromo-2-ethoxybenzonitrile (1.50 g, 6.5 mmol), hydroxylamine hydrochloride (913 mg, 13 mmol) and NaHCO$_3$ (1.365 g, 16.3 mmol) in water (1.32 mL) and EtOH (26.6 mL) is stirred in a sealed tube at 90° C. for 3 h. Once at RT, the product precipitated from the rxn mix upon addition of water. The solid is filtered off under high vacuum, washing with water and some Et2O. A first crop of pure title compound (947 mg) was thus obtained as white solid. The filtrate is extracted with AcOEt. The organic layer is then washed twice with brine, dried over MgSO$_4$, filtered and concentrated. The residue is purified by FC (hept/AcOEt 5:5) to yield another crop of the pure title compound as a white solid (448 mg), merged with the first batch from precipitation. The title compound is obtained as a white solid (1.395 g, 83%). LC-MS A: $t_R$=0.53 min, [M+H]+=259.03.

A.2.130. 2-(3-Ethoxy-5-(4,4,5,5-tetramethyl-1,3,2-dioxaborolan-2-yl)thiophen-2-yl)acetic acid The title compound is prepared according to the procedure described for A.2.3., starting with 2-(5-bromo-3-ethoxythiophen-2-yl)acetic acid. LC-MS A: $t_R$=0.89 min; [M+H]+=333.06.

A.2.130.1. 2-(5-Bromo-3-ethoxythiophen-2-yl)acetic acid

To a solution of 2-(3-ethoxythiophen-2-yl)acetic acid (205 mg, 1.1 mmol) in DMF (3 mL) is added portionwise N-bromsuccinimide (237 mg, 1.32 mmol). The mixture is stirred at 70° C. overnight. N-Bromsuccinimide (237 mg, 1.32 mmol) is added and the mixture is stirred at 80° C. for 2 h, then cooled to RT. The mixture is treated with 1 N HCl (5 mL) and extracted with EtOAc. The organic layer is dried over MgSO$_4$ and concentrated. The residue is purified by FC (Hept/DCM 1:0 to 0:1), affording the title compound as a brown oil (0.195 g, 67%). LC-MS E: $t_R$=0.47 min, [M−H]+=262.95.

A.2.130.2. 2-(3-Ethoxythiophen-2-yl)acetic acid

Sodium (65.2 mg, 2.84 mmol) is carefully added at 0° C. into EtOH (3.76 mL, 64.5 mmol) under stirring and N2 atm. Then CuO (51.3 mg, 0.645 mmol) and KI (21.4 mg, 0.129 mmol) are added, followed by 2-(3-bromothiophen-2-yl)acetic acid (300 mg, 1.29 mmol). The RM is stirred at 120° C. for 1 h in the microwave, then at 130° C. for 1 h and at 150° C. for 1 h. The mixture is poured into HCl 2N (5 mL) and extracted with EtOAc. The organic layer is dried over MgSO$_4$ and concentrated. The crude product is purified by FC (Hept/DCM 1:0 to 0:1), affording the title compound as a brown oil (1.395 g, 83%). LC-MS E: $t_R$=0.35 min, [M−H]+=185.10.

A.2.131. 4-(2-Methoxy-4-(4,4,5,5-tetramethyl-1,3,2-dioxaborolan-2-yl)phenyl)-1H-imidazole The title compound is prepared according to the procedure described for A.2.3., starting with 4-(4-bromo-2-methoxyphenyl)-1H-imidazole. LC-MS A: $t_R$=0.66 min; [M+H]+=301.19.

A.2.131.1. 4-(4-Bromo-2-methoxyphenyl)-1H-imidazole

A mixture of 2-bromo-1-(4-bromo-2-methoxyphenyl)ethan-1-one (2.30 g, 7.47 mmol) in formamide (25 mL, 314 mmol) is stirred at 165° C. for 8 h, then cooled to RT, diluted with EtOAc and washed with sat. aq. NaHCO$_3$ and brine. The organic layer is dried over MgSO$_4$, filtered and concentrated. The residue is purified by FC (Hept→100% AcOEt) to give the product as a sticky beige solid, which is further triturated with some heptane to obtain a beige powder (0.84 g, 44%). LC-MS A: $t_R$=0.58 min, [M+H]+=253.09.

A.2.131.2. 2-Bromo-1-(4-bromo-2-methoxyphenyl)ethan-1-one

A solution of 1-(4-bromo-2-methoxyphenyl)ethan-1-one (3.04 g, 13.3 mmol) and copper(II) bromide (4.50 g, 19.9 mmol) in EtOAc (30 mL) is stirred at 100° C. overnight. Once at RT, the RM is pour onto iced water. The biphasic mixture is filtered, then the pH is adjusted with sat. aq. NaHCO$_3$ and the phases are separated. The organic layer is washed twice with brine, dried over MgSO$_4$, filtered and evaporated. The residue is triturated with MeOH, filtered off and dried under vacuum (brown solid, 2.40 g, 59%). LC-MS A: $t_R$=0.89 min, no ionization.

A.2.132. Methyl 1-ethyl-3-(4,4,5,5-tetramethyl-1,3,2-dioxaborolan-2-yl)-1H-pyrazole-5-carboxylate The title compound is prepared according to the procedure described for A.2.3., starting with methyl 1-ethyl-3-(((trifluoromethyl)sulfonyl)oxy)-1H-pyrazole-5-carboxylate. LC-MS A: $t_R$=0.54 min; [M+H]+=199.26 (mass of boronic acid from hydrolysis of boronate on LCMS).

A.2.132.1. Methyl 1-ethyl-3-(((trifluoromethyl)sulfonyl)oxy)-1H-pyrazole-5-carboxylate To a solution of methyl 2-ethyl-5-oxo-2,5-dihydro-1H-pyrazole-3-carboxylate (814 mg, 4.54 mmol) and N-phenyl-bis(trifluoromethanesulfonimide) (2153 mg, 5.91 mmol) in DCM (15 mL) at 0° C. is added TEA (6.32 mL, 45.4 mmol). The RM is stirred at 0° C. during 10 min then allowed to warm up to RT and stirred for 1 h. The RM is concentrated under reduced pressure, the residue is purified by FC (Hept:EtOAc 1:0 to 9:1), affording the title compound as a colorless liquid (1.061 g, 77%). LC-MS A: $t_R$=0.93 min, no ionization.

A.2.132.2. Methyl 2-ethyl-5-oxo-2,5-dihydro-1H-pyrazole-3-carboxylate

To a solution of dimethyl acetylenedicarboxylate (1.75 mL, 14.1 mmol) in toluene (20 mL) and AcOH (20 mL) at 0° C. is added ethylhydrazine oxalate (2.00 g, 12.8 mmol). The RM is stirred at RT for 1 hour, then refluxed for 4 h, and cooled to RT. It is concentrated in vacuo, partitioned between EtOAC and sat. NaHCO$_3$. The organic layer is washed with NaHCO$_3$.sat and brine, dried over MgSO$_4$, filtered and concentrated in vacuo, yielding the title compound as a yellow paste (863 mg, 40%). LC-MS A: $t_R$=0.57 min, [M+H]+=171.03.

A.2.133. 5-(2-Methoxy-4-(4,4,5,5-tetramethyl-1,3,2-dioxaborolan-2-yl)phenyl)isoxazol-3-ol Butyllithium (1.6M in hexane, 1.1 mL, 1.76 mmol) is added dropwise, at −78° C. under nitrogen, to a stirred solution of 5-(4-bromo-2-methoxyphenyl)isoxazol-3-ol (158 mg, 0.585 mmol) in dry THF (4 mL). The RM is stirred at −78° C. for 25 min, then isopropoxyboronic acid, pinacol ester (0.418 mL, 2.05 mmol) is added dropwise and the RM is stirred at −78° C. for 45 min then at RT for 40 min. The RM is quenched with sat. aq. NH$_4$Cl and extracted with EtOAc. The organic layer is washed twice with brine, dried over MgSO$_4$, filtered and concentrated. The residue is purified by FC (Hept→Hept/EtOAc 9:1 to 8:2) to afford the expected product as a white solid (42 mg, 23%). LC-MS A: $t_R$=0.86 min; [M+H]+=318.14.

A.2.133.1.
5-(4-Bromo-2-methoxyphenyl)isoxazol-3-ol

HCl conc. (6.8 mL) is added dropwise at RT to a stirred suspension of 3-(4-bromo-2-methoxyphenyl)-3-oxo-N-((tetrahydro-2H-pyran-2-yl)oxy)propanamide (284 mg, 0.763 mmol) in MeOH (1.7 mL). The RM is stirred at rt for 30 min. Water (4 mL) is added and the precipitate is filtered off, washing with 1.2 mL water to afford the expected product as a white solid (169 mg, 82%) LC-MS A: $t_R$=0.79 min, [M+H]+=271.99.

A.2.133.2. 3-(4-Bromo-2-methoxyphenyl)-3-oxo-N-((tetrahydro-2H-pyran-2-yl)oxy)propanamide To a solution of ethyl 3-(4-bromo-2-methoxyphenyl)-3-oxopropanoate (971 mg, 1.33 mmol) in dry NMP (15.7 mL) are sequentially added O-(tetrahydro-2H-pyran-2-yl)hydroxylamine (512 mg, 4.19 mmol) and DMAP (433 mg, 3.55 mmol) at RT. The RM is heated to 115° C. and stirred overnight, then cooled to RT. The mixture is partitioned between 40 mL HCl 0.5M (pH 2) and 40 mL EtOAc. The organic layer is washed three times with 40 ml NaCl sat. The aqueous layer is reextracted with 40 ml EA. The organic layers are combined, dried over MgSO$_4$, filtered and concentrated. The residue is purified by FC (Hept-EtOAc), affording the title compound as a white solid (301 mg, 25%). LC-MS A: $t_R$=0.76 min, [M+H]+=373.98.

A.2.133.3. Ethyl 3-(4-bromo-2-methoxyphenyl)-3-oxopropanoate 1-(4-bromo-2-methoxyphenyl)ethanone (1.00 g, 4.37 mmol) is dissolved in diethyl carbonate (5.6 mL, 46.2 mmol). NaH (66% suspension in oil, 384 mg, 9.6 mmol) is added carefully. The RM is stirred overnight at RT. Water is added carefully and the mixture is extracted two times with EtOAc. The organic layers are washed with water, brine, dried over MgSO$_4$, filtered and concentrated. The residue is purified by FC (Hept-EtOAc, affording the title compound as a light yellow oil (933 mg, 71%). LC-MS A: $t_R$=0.87 min, [M+H]+=303.01

A.2.134. 1,5-Dimethyl-4-(4-(4,4,5,5-tetramethyl-1,3,2-dioxaborolan-2-yl)phenyl)-1H-imidazole The title compound is prepared according to the procedure described for A.2.3., starting with 4-(4-bromophenyl)-1,5-dimethyl-1H-imidazole. LC-MS A: $t_R$=0.68 min; [M+H]+=299.19.

A.2.134.1.
4-(4-Bromophenyl)-1,5-dimethyl-1H-imidazole

NaH (60% suspension in oil, 25.3 mg, 0.633 mmol) is added at 0° C., under nitrogen, to a stirred solution of 5-methyl-4-(4-(4,4,5,5-tetramethyl-1,3,2-dioxaborolan-2-yl)phenyl)-1H-imidazole (100 mg, 0.422 mmol) in DMF (2 mL). The RM is stirred at 0° C. for 15 min, then iodomethane (0.032 mL, 0.506 mmol) is added and the RM is stirred at RT for 2 h. It is quenched with sat. aq. NH$_4$Cl and extracted with AcOEt. The organic layer is washed twice with brine, dried over MgSO$_4$, filtered and concentrated to afford the title compound (4:1 ratio of regio-isomers) as a beige solid (99 mg, 93%). LC-MS A: $t_R$=0.58 min, [M+H]+=251.10.

A.2.135. 3-(5-(4,4,5,5-Tetramethyl-1,3,2-dioxaborolan-2-yl)thiophen-2-yl)oxetan-3-ol The title compound is prepared according to the procedure described for A.2.1., starting with 3-(thiophen-2-yl)oxetan-3-ol. LC-MS A: $t_R$=0.75 min; no ionization.

A.2.135.1. 3-(Thiophen-2-yl)oxetan-3-ol

To a solution of 2-bromothiophene (0.0594 mL, 0.601 mmol) in Et2O (2.1 mL) cooled at −78° C. is added butyllithium (1.6M in hexane, 0.45 mL, 0.721 mmol). The RM is stirred at −78° C. for 1 h, then 3-oxetanone (0.0533 mL, 0.902 mmol) in Et2O (0.7 mL) is added dropwise and the RM is stirred at −78° C. and allowed to warm up to RT and stirred for 2 h. The solution is diluted with water, the aqueous layer is extracted three times with EtOAc and the combined organic layers are dried over MgSO$_4$, filtered and concentrated under reduced pressure. The residue is purified with FC (Hept to Hept/EtOAc 8:2) to give the title compound as a colorless oil (62 mg, 66%). LC-MS A: $t_R$=0.49 min, no ionization

A.2.136. 3-(3-Methoxy-5-(4,4,5,5-tetramethyl-1,3,2-dioxaborolan-2-yl)thiophen-2-yl)oxetan-3-ol The title compound is prepared according to the procedure described for A.2.1., starting with 3-(3-methoxythiophen-2-yl)oxetan-3-ol. LC-MS A: $t_R$=0.78 min; [M−H2O]+= 295.12.

A.2.136.1. 3-(3-Methoxythiophen-2-yl)oxetan-3-ol

To a stirred solution of 3-methoxythiophene (1.00 g, 8.58 mmol) and N,N,N',N'-tetramethylethylenediamine (1.55 mL, 10.3 mmol) in Et2O (30 mL) is added butyllithium (1.6M in Hexane, 6.4 mL, 10.3 mmol) dropwise at 0° C. The RM is stirred at RT for 30 min, then 3-oxetanone (0.761 mL, 12.9 mmol) is added dropwise and the RM is stirred at RT for 35 min, then diluted with water, the aqueous layer is extracted three times with EtOAc and the combined organic layers are dried over MgSO$_4$, filtered and concentrated under reduced pressure. The residue is purified by FC (Hept to Hept/EtOAc 8:2) to give the title compound as a light-yellow oil (1-123 g, 70%). LC-MS A: $t_R$=0.53 min; [M−H2O]+=169.04.

A.2.137. 2-(5-(3-Methoxyoxetan-3-yl)thiophen-2-yl)-4,4,5,5-tetramethyl-1,3,2-dioxaborolane The title compound is prepared according to the procedure described for A.2.1., starting with 3-methoxy-3-(thiophen-2-yl)oxetane. LC-MS A: $t_R$=0.88 min; no ionization.

A.2.137.1. 3-Methoxy-3-(thiophen-2-yl)oxetane

To a solution of 3-(thiophen-2-yl)oxetan-3-ol (A.2.135.1) (242 mg, 1.55 mmol) in DMF (12.1 mL) at 0° C. is added NaH (60% dispersion in mineral oil, 0.062 mg, 1.86 mmol) and the RM is stirred for 1 h at 0° C. Iodomethane (0.145 mL, 2.32 mmol) is added and the RM is stirred and monitored by LCMS/TLC until complete. EtOAc is added and the RM is washed with NaHCO$_3$ solution. The organic layer is dried, filtered and concentrated under reduced pressure. The residue is purified by FC (Hept to Hept/EtOAc 9:1) to give the title compound as a colorless oil (187 mg, 71%). LC-MS A: $t_R$=0.67 min; no ionization.

Following the procedure described for the synthesis of A.2.3. described above, the following boronic acid derivatives are synthesized, starting from the corresponding commercially available halides (see table 7).

TABLE 7

Boronic acid derivatives A.2.138.-A.2.144.

| No. | Compound | $t_R$ [min] (LC-MS) | MS Data m/z [M + H]+ |
|---|---|---|---|
| A.2.138. | 3-Methoxy-6-(4,4,5,5-tetramethyl-1,3,2-dioxaborolan-2-yl)-1H-indazole | 0.86 (A) | 275.21 |
| A.2.139. | 1-Methyl-7-(4,4,5,5-tetramethyl-1,3,2-dioxaborolan-2-yl)-3,4-dihydroquinazolin-2(1H)-one | 0.80 (A) | 289.18 |
| A.2.140. | 2-Methyl-6-(4,4,5,5-tetramethyl-1,3,2-dioxaborolan-2-yl)-1,2-dihydro-3H-indazol-3-one | 0.76 (A) | 275.23 |
| A.2.141. | 1-Methyl-6-(4,4,5,5-tetramethyl-1,3,2-dioxaborolan-2-yl)-1,2-dihydro-3H-indazol-3-one | 0.77 (A) | 275.27 |
| A.2.142. | 3-(Ethylthio)-5-(4,4,5,5-tetramethyl-1,3,2-dioxaborolan-2-yl)benzoic acid | 0.42 (E) | 307.15 |
| A.2.143. | 5-(4-(4,4,5,5-Tetramethyl-1,3,2-dioxaborolan-2-yl)phenyl)-1H-[1,2,3]triazole | 0.80 (A) | 272.26 |
| A.2.144. | 3-(2-Ethoxy-4-(4,4,5,5-tetramethyl-1,3,2-dioxaborolan-2-yl)phenyl)propanoic acid | 0.87 (A) | 321.18 |

A.2.145. Ethyl 2-(3-oxo-6-(4,4,5,5-tetramethyl-1,3,2-dioxaborolan-2-yl)-2,3-dihydro-1H-indazol-1-yl)acetate The title compound is prepared according to the procedure described for A.2.3., starting with 3-(3-bromo-5-ethoxyphenoxy)propanoic acid. LC-MS E: $t_R$=0.49 min; [M−H]$^+$=335.14.

A.2.145.1. 3-(3-Bromo-5-ethoxyphenoxy)propanoic acid

To a mixture of 6-bromo-1,2-dihydro-3H-indazol-3-one (1.00 g, 4.69 mmol), potassium carbonate (1.97 g, 14.1 mmol) and DMF (16 mL) is added ethyl bromoacetate (0.557 mL, 4.69 mmol). The RM is stirred at RT for 60 h. The RM is poured into water (260 mL), acidified with HCl 2N and extracted twice with EtOAc. The combined organic layers are dried over MgSO$_4$ and concentrated under reduced pressure. The residue is triturated in DCM to afford a white precipitate corresponding to unreacted 6-bromo-1,2-dihydro-3H-indazol-3-one and the filtrate is further purified by FC (heptane/AcOEt 6:4) to afford the expected product as a white solid (744 mg, 26%). LC-MS A: $t_R$=0.74 min; [M+H]$^+$=300.91.

A.2.146. 3-(3-Ethoxy-5-(4,4,5,5-tetramethyl-1,3,2-dioxaborolan-2-yl)phenoxy)propanoic acid The title compound is prepared according to the procedure described for A.2.3., starting with 3-(4-bromo-3-ethoxyphenoxy)propanoic acid. LC-MS A: $t_R$=0.81 min; [M+H]$^+$=337.17.

A.2.146.1. 3-(4-Bromo-3-ethoxyphenoxy)propanoic acid

A microwave vial is charged with 3-bromo-5-ethoxyphenol (600 mg, 2.76 mmol), H2O (2 mL), NaOH 32% (0.615 mL, 6.63 mmol) and 3-chloropropionic acid (337 mg, 3.04 mmol). It is sealed and irradiated at 120° C., for 15 min at high energy level. The RM is diluted in water and pH is decreased to pH9 with HCl 2N then is extracted twice with EtOAc. The basic aqueous layer is then acidified to pH2 and extracted twice with EtOAc: the combined organic extracts are washed with water, brine, dried over MgSO$_4$, filtered and evaporated to dryness, yielding the title compound as an orange solid (187 mg, 23%). LC-MS E: $t_R$=0.51 min; [M−H]$^+$=287.05.

A.2.147. 3-(2-Ethoxy-5-(4,4,5,5-tetramethyl-1,3,2-dioxaborolan-2-yl)phenoxy)propanoic acid The title compound is prepared according to the procedure described for A.2.3., starting with 3-(4-bromo-2-ethoxyphenoxy)propanoic acid. LC-MS E: $t_R$=0.45 min; [M−H]$^+$=335.18.

A.2.147.1. 3-(4-Bromo-2-ethoxyphenoxy)propanoic acid

The title compound is prepared according to the procedure described for A.2.146.1., starting with (4-bromo-2-ethoxyphenol. LC-MS E: $t_R$=0.48 min; [M−H]$^+$=287.01.

A.2.148. 2-Ethoxy-3-fluoro-4-(4,4,5,5-tetramethyl-1,3,2-dioxaborolan-2-yl)benzoic acid Ethyl 2-ethoxy-3-fluoro-4-(4,4,5,5-tetramethyl-1,3,2-dioxaborolan-2-yl)benzoate (960 mg, 2.38 mmol) is dissolved in MeOH/THF (1:1) (10 mL). NaOH 10% (4.77 mL, 11.9 mmol) is added and the RM is stirred at RT for 4 h, treated with HCl 2N to reach acidic pH (<2) and extracted with EtOAc. The resulting organic phase is dried over $MgSO_4$ and concentrated, to afford the title compound as a yellow solid (735 mg, 99%). LC-MS A: $t_R$=0.91 min; $[M+MeCN]^+$= 352.2.

A.2.148.1. Ethyl 2-ethoxy-3-fluoro-4-(4,4,5,5-tetramethyl-1,3,2-dioxaborolan-2-yl)benzoate The title compound is prepared according to the procedure described for A.2.3, starting with ethyl 4-bromo-2-ethoxy-3-fluorobenzoate. LC-MS A: $t_R$=1.10 min; $[M+H]^+$=339.26

A.2.148.2. Ethyl 4-bromo-2-ethoxy-3-fluorobenzoate

To a solution of 4-bromo-3-fluoro-2-hydroxybenzoic acid (750 mg, 3.1 mmol) and K2CO3 (1.07 g, 7.74 mmol) in DMF (6 mL), is added ethyl iodide (0.508 mL, 6.35 mmol). The reaction is stirred for 60 h at RT. It is partitioned between DCM and brine. The aqueous layer is re-extracted with DCM, the combined organics are washed with brine then dried ($MgSO_4$), and concentrated under reduced pressure to afford the title compound as a dark orange oil. LC-MS A: $t_R$=1.03 min; $[M+H]^+$=291.01

A.2.149. 2-Ethoxy-4-(4,4,5,5-tetramethyl-1,3,2-dioxaborolan-2-yl)benzensulfonamide The title compound is prepared according to the procedure described for A.2.3., starting with 4-bromo-2-ethoxybenzenesulfonamide. LC-MS A: $t_R$=0.90 min; $[M+H]^+$= 328.26.

A.2.149.1. 4-Bromo-2-ethoxybenzenesulfonamide

Sodium ethoxide (0.546 mL, 6.61 mmol) is dissolved in DMF (11 mL). 4-Bromo-2-fluorobenzenesulphonamide (1.20 g, 4.72 mmol) in DMF (5 mL) is added dropwise. The RM is stirred at RT for 1 h, then the temperature is raised to 60° C. for 2 h. Sodium ethoxide (0.39 mL, 4.72 mmol) is added and the RM is stirred for another hour. The RM is partitioned between EtOAc and water. The organic phase is washed with water and brine, dried over $MgSO_4$, filtered and evaporated under reduced pressure. The crude is purified by FC (H/EtOAc from 0:100 to 50:50), to afford the title compound as a white powder (841 mg, 64%). LC-MS A: $t_R$=0.78 min; no ionization.

A.2.150. 5-(2-Ethoxy-4-(4,4,5,5-tetramethyl-1,3,2-dioxaborolan-2-yl)phenyl)-1H-[1,2,3]triazole Azidotrimethylsilane (0.136 mL, 0.97 mmol) is added to a solution of copper(I) iodide (6.22 mg, 0.0323 mmol) and 2-(3-ethoxy-4-ethynylphenyl)-4,4,5,5-tetramethyl-1,3,2-dioxaborolane (176 mg, 0.647 mmol) in DMF/MeOH (9:1) (2 mL) under Ar in a MW vial. The RM is stirred at 130° C. for 20 min in the microwave, then cooled to RT and filtered through a 0.45 um Whatman filter and concentrated. The residue is purified by FC (Hept/EtOAc, 1:0 to 7:3) to afford the title compound as a yellow solid. LC-MS A: $t_R$=0.97 min; $[M+H]^+$=316.32.

A.2.150.1. 2-(3-Ethoxy-4-ethynylphenyl)-4,4,5,5-tetramethyl-1,3,2-dioxaborolane Dimethyl (1-diazo-2-oxopropyl)phosphonate (10% solution in MeCN, 4.67 mL, 2.06 mmol) is added at RT to a solution of 2-ethoxy-4-(tetramethyl-1,3,2-dioxaborolan-2-yl)benzaldehyde (500 mg, 1.72 mmol) and K2CO3 (475 mg, 3.44 mmol) in MeOH (7 mL) and the RM is stirred at 50° C. for 2 days. The RM is concentrated, DCM and water are added. The layers are separated and the aqueous layer extracted with DCM (2×). The combined org. extracts are washed with brine (1×), dried ($MgSO_4$), filtered and concentrated. The crude is purified by FC (Hept/DCM 0 to 25%) to afford the title compound as a colourless oil (176 mg, 38%). LC-MS A: $t_R$=1.09 min; $[M+H]^+$=273.36.

A.2.151. Methyl (E)-3-(3-ethoxy-5-(4,4,5,5-tetramethyl-1,3,2-dioxaborolan-2-yl)thiophen-2-yl)acrylate The title compound is prepared according to the procedure described for A.2.1., starting with methyl (E)-3-(3-ethoxythiophen-2-yl)acrylate. LC-MS A: $t_R$=1.02 min; $[M+H]^+$=339.14.

A.2.151.1. Methyl (E)-3-(3-ethoxythiophen-2-yl)acrylate

A suspension of 3-ethoxythiophene-2-carbaldehyde (2.90 g, 18.6 mmol), methyl bromoacetate (3.07 mL, 33.4 mmol), and triphenylphosphine (7.305 g, 27.8 mmol) in aq saturated $NaHCO_3$ (100 mL) is stirred at RT for 5 h. THF (30 mL) is added and the RM is stirred overnight at RT. It is then extracted twice with DCM. The combined organic layers are dried over $MgSO_4$, filtered, and concentrated under vacuum. The crude is purified by FC (Hept/EtOAc 9:1) to afford the title compound as a dark orange oil (2.9 g, 100%). LC-MS A: $t_R$=0.69 min; $[M+MeCN]^+$=198.26.

A.2.152. 3-(3-Ethoxy-5-(4,4,5,5-tetramethyl-1,3,2-dioxaborolan-2-yl)thiophen-2-yl)propanoic acid To a solution of methyl (E)-3-(3-ethoxy-5-(4,4,5,5-tetramethyl-1,3,2-dioxaborolan-2-yl)thiophen-2-yl)acrylate [A.2.151.] (250 mg, 0.786 mmol) in MeOH (15 mL) is added Pd/C 5% wet (50 mg). Then the vessel is inertized with N2 and flushed with $H_2$. The mixture is placed in a autoclave and it is stirred overnight at RT under 4 Bar of $H_2$, then for 1 d at 50° C. under 4 bar of $H_2$. After filtration on whatman filter, NaOH 10% (1.18 mL, 11.8 mmol) is added and the RM is stirred for 1 h at RT. It is then treated with HCl 2N until pH<1 and extracted twice with EtOAc. The organic layer is dried over $MgSO_4$ and concentrated, to afford the title compound as a dark yellow oil (287 mg, 74%). LC-MS A: $t_R$=0.86 min; [M+H]+=327.09.

A.2.153. 3-Ethoxy-4-(4-(4,4,5,5-tetramethyl-1,3,2-dioxaborolan-2-yl)phenyl)cyclobut-3-ene-1,2-dione 3-Ethoxy-4-(tributylstannyl)cyclobut-3-ene-1,2-dione (335 mg, 0.807 mmol) and 4-iodophenylboronic acid, pinacol ester (298 mg, 0.904 mmol) are dissolved in DMF (4 mL) with N2 bubbling for 5 min. Trans-Benzyl(chloro)bis (triphenylphosphine)palladium(II) (36.7 mg, 0.0484 mmol) and CuI (15.4 mg, 0.0807 mmol) are added and the RM is stirred at RT for 3 h., then filtered over a microglass filter, concentrated under vacuum and purified by FC (H:EtOAc 100:0 to 80:20) to obtain the title compound as a yellow solid (127 mg, 48%). LC-MS A: $t_R$=0.97 min; [M+MeCN]+= 370.07.

A.2.154. Ethyl 2-(2-ethoxy-4-(4,4,5,5-tetramethyl-1,3,2-dioxaborolan-2-yl)phenyl)-2-oxoacetate The title compound is prepared according to the procedure described for A.2.3., starting with ethyl 2-(4-bromo-2-ethoxyphenyl)-2-oxoacetate. LC-MS A: $t_R$=0.98 min; [M+H]+=349.19.

A.2.154.1. Ethyl 2-(4-bromo-2-ethoxyphenyl)-2-oxoacetate

To a solution of 2-(4-bromo-2-hydroxyphenyl)-2-oxoacetic acid (1.00 g, 3.88 mmol) and K2CO3 (1.605 g) in DMF (10 mL) is added iodethane (0.799 mL, 9.69 mmol) and the RM is stirred at 50° C. for 2 d. K2CO3 (1.605 g, 11.6 mmol) and iodethane (0.799 mL, 9.69 mmol) are added and the RM is stirred at 60° C. for 20 h. The RM is filtered, rinsed with DCM and concentrated under reduced. The residue is purified by FC (Hept/EtOAc 1:0 to 4:1) to afford the title compound as a beige solid (0.921 g, 79%). LC-MS A: $t_R$=0.92 min; [M+H]$^+$=303.03.

A.2.155. Methyl 3-(3-isopropoxy-5-(4,4,5,5-tetramethyl-1,3,2-dioxaborolan-2-yl)thiophen-2-yl)propanoate In a dry 20 mL microwave vial under argon are added methyl 3-(3-isopropoxythiophen-2-yl)propanoate (476 mg, 1.88 mmol), bis(pinacolato)diboron (389 mg, 1.5 mmol), (1,5-cyclooctadiene)(methoxy)iridium(I) dimer (62.2 mg, 0.0938 mmol), 4,4'-di-tert-butyl-2,2'-dipyridyl (40.3 mg, 0.15 mmol) in cyclohexane (15 mL) and the RM is heated at 125° C. for 15 min in the microwave. The mixture is washed with HCl 2N, filtered on a 0.45 um whatman filter, rinsed with DCM and concentrated. Purification by FC (Hept/EtOAc 1:0 to 4:1) affords the title compound as a colourless oil (518 mg, 78%). LC-MS A: $t_R$=1.10 min; [M+H]+=355.22.

A.2.155.1. Methyl 3-(3-isopropoxythiophen-2-yl)propanoate

To a solution of methyl (E)-3-(3-isopropoxythiophen-2-yl)acrylate (870 mg, 3.84 mmol) in EtOH (30 mL) is added Pd/C 10% wet (200 mg). Then the vessel is inertized with N2 and flushed with H2. The mixture is stirred under 5 Bar of H2. The mixture is filtered on Whatman 0.45 um, rinsed and concentrated, to afford the title compound as an orange oil (2.9 g, 100%). LC-MS A: $t_R$=0.95 min; [M+H]$^+$=229.26.

A.2.155.2. Methyl (E)-3-(3-isopropoxythiophen-2-yl)acrylate

The title compound is prepared according to the procedure described for A.2.151.1., starting with 3-isopropoxythiophene-2-carbaldehyde. LC-MS A: $t_R$=1.02 min; [M+H]+=339.14. LC-MS A: $t_R$=0.89 min; [M+H]$^+$=227.18.

A.2.156. Ethyl 3-ethoxy-5-(4,4,5,5-tetramethyl-1,3,2-dioxaborolan-2-yl)-1H-pyrrole-2-carboxylate The title compound is prepared according to the procedure described for A.2.155., starting with ethyl 3-ethoxy-1H-pyrrole-2-carboxylate. LC-MS A: $t_R$=0.87 min; [M+H]+= 310.28.

A.2.157. Methyl 3-(N-ethyl-2,2,2-trifluoroacetamido)-5-(4,4,5,5-tetramethyl-1,3,2-dioxaborolan-2-yl)thiophene-2-carboxylate The title compound is prepared according to the procedure described for A.2.155., starting with methyl 3-(N-ethyl-2,2,2-trifluoroacetamido)thiophene-2-carboxylate. LC-MS A: $t_R$=0.73 min; no ionization.

A.2.157.1. Methyl 3-(N-ethyl-2,2,2-trifluoroacetamido)thiophene-2-carboxylate To a solution of methyl 3-(2,2,2-trifluoroacetamido)thiophene-2-carboxylate (330 mg, 1.3 mmol) in DMF (5 mL) are added K2CO3 (450 mg, 1.95 mmol) and iodoethane (0.159 mL, 1.95 mmol). The RM is stirred overnight at RT. It is then quenched with water and extracted with DCM. The organic layer is washed twice with brine, dried over MgSO$_4$ and concentrated. The residue is purified by FC (Hept/EtOAc 0 to 15%) to afford the title compound as an orange solid (510 mg, 100%). LC-MS A: $t_R$=0.83 min; [M+MeCN]$^+$=323.00.

B—Preparation of Examples

General Procedure A: Suzuki Coupling with Pd(PPh$_3$)$_4$

A mixture of the respective pyrimidine halide derivative (II) (0.15 mmol), the respective boronic acid derivative (III) (0.18 mmol), and K$_2$CO$_3$ 2M (0.3 mL, 0.6 mmol) in ethanol (3 mL) is purged with argon, tetrakis-(triphenylphosphine)-palladium (0.0075 mmol) is added, and the RM is heated at 90° C. overnight. Alternatively, the reaction can be performed in a microwave apparatus, at 120° C. for 15-30 min. The RM is filtered through a 0.45 um Glass MicroFiber filter, washed with EtOH/MeCN and DMF. The filtrate is purified either by preparative HPLC or FC. Alternatively, it is diluted with water, if needed the pH is adjusted, and extracted with EtOAc (3×). The combined organic extracts are dried (MgSO$_4$) and concentrated under reduced pressure. The residue is purified by preparative HPLC or by FC.

General Procedure B: Suzuki Coupling with Pd(PPh$_3$)$_4$ Followed by Ester Hydrolysis A mixture of the respective pyrimidine halide derivative (II) (0.15 mmol), the respective boronic acid derivative (III) (0.18 mmol), and K$_2$CO$_3$ 2M (0.3 mL, 0.6 mmol) in EtOH (3 mL) is purged with argon, Pd(PPh$_3$)$_4$ (0.0075 mmol) is added, and the RM is heated at 90° C. overnight. Alternatively, the reaction can be performed in a microwave apparatus, at 120° C. for 15-30 min. NaOH (32% solution, 0.5 mL) is added, and the RM is stirred at RT for 2-20 h or at 90° C. for 0.5-20 h. It is then filtered through a 0.45 um Glass MicroFiber filter, washed with EtOH and water. The filtrate is either purified directly by preparative HPLC or diluted with 1N HCl, and extracted 3× with EtOAc. The combined organic extracts are dried (MgSO$_4$) and concentrated under reduced pressure. The residue is purified by preparative HPLC or by FC.

General Procedure C: Suzuki Coupling with PdCl$_2$(Dppf) Followed by Ester Hydrolysis A mixture of the respective pyrimidine halide derivative (II) (0.15 mmol), the respective boronic acid derivative (III) (0.18-0.3 mmol), and Cs$_2$CO$_3$ (0.75 mmol) in THE (4 mL) and water (0.5 mL) is purged with argon, [1,1'-bis(diphenylphosphino)ferrocene]dichloropalladium(II) complex with DCM (0.015 mmol) is added, and the RM is heated at 80° C. overnight. NaOH (32% solution, 0.5 mL) is added, and the RM is stirred at 80° C. for 2 h. It is then filtered through a 0.45 um Glass MicroFiber filter, washed with EtOH and water. The filtrate is either purified directly by preparative HPLC or diluted with 1N HCl, and extracted 3× with EtOAc. The combined organic extracts are dried (MgSO$_4$) and concentrated under reduced pressure. The residue is purified by preparative HPLC or by FC.

Compounds of Examples 1-745 listed in Table 8 below are prepared by applying either one of the above-mentioned procedures A, B or C to the pyrimidine halide derivatives A.1.1.-A.1.67. coupled with commercially available boronic acid derivatives or with boronic acid derivatives A.2.1.-A.2.97.

TABLE 8

Examples 1-745

| Ex. | Compound | $t_R$ [min] (LC-MS) | MS Data m/z [M + H]$^+$ |
|---|---|---|---|
| 1 | [6-(4-Amino-phenyl)-pyrimidin-4-yl]-[2-(7-fluoro-2,4-dimethyl-indol-1-yl)-ethyl]-amine | 0.73 (C) | 376.3 |
| 2 | [2-(7-Fluoro-4-methoxy-2-methyl-indol-1-yl)-ethyl]-[6-(2-methoxy-thiazol-4-yl)-pyrimidin-4-yl]-amine | 1.07 (C) | 414.3 |
| 3 | [2-(7-Fluoro-4-methoxy-2-methyl-indol-1-yl)-ethyl]-[6-(2-methoxy-thiazol-5-yl)-pyrimidin-4-yl]-amine | 0.95 (C) | 414.3 |
| 4 | [6-(4-Amino-phenyl)-pyrimidin-4-yl]-[2-(7-fluoro-4-methoxy-2-methyl-indol-1-yl)-ethyl]-amine | 0.67 (C) | 392.3 |
| 5 | 3-Chloro-5-{6-[2-(2-methyl-indol-1-yl)-ethylamino]-pyrimidin-4-yl}-thiophene-2-carboxylic acid (*1) | 1.13 (C) | 413.2 |
| 6 | 3-Ethyl-5-{6-[2-(2-methyl-indol-1-yl)-ethylamino]-pyrimidin-4-yl}-thiophene-2-carboxylic acid (*1) | 1.11 (C) | 407.3 |
| 7 | [2-(6-Fluoro-2,4-dimethyl-indol-1-yl)-ethyl]-[6-(1H-indazol-6-yl)-pyrimidin-4-yl]-amine | 0.83 (C) | 401.3 |
| 8 | [6-(1H-Benzoimidazol-5-yl)-pyrimidin-4-yl]-[2-(4-methoxy-2-methyl-indol-1-yl)-ethyl]-amine | 0.56 (C) | 399.3 |
| 9 | [6-(2,3-Dihydro-1H-indol-5-yl)-pyrimidin-4-yl]-[2-(6-fluoro-2,4-dimethyl-indol-1-yl)-ethyl]-amine | 0.77 (C) | 402.4 |
| 10 | [2-(6-Fluoro-2,4-dimethyl-indol-1-yl)-ethyl]-[6-(1H-indol-6-yl)-pyrimidin-4-yl]-amine | 0.83 (C) | 400.3 |
| 11 | [6-(2,3-Dihydro-1H-indol-5-yl)-pyrimidin-4-yl]-[2-(7-fluoro-2,4-dimethyl-indol-1-yl)-ethyl]-amine | 0.78 (C) | 402.4 |
| 12 | [6-(2,3-Dihydro-1H-indol-5-yl)-pyrimidin-4-yl]-[2-(4-methoxy-2-methyl-indol-1-yl)-ethyl]-amine | 0.68 (C) | 400.4 |
| 13 | (4-{6-[2-(4-Methoxy-2-methyl-indol-1-yl)-ethylamino]-pyrimidin-4-yl}-2-methyl-phenyl)-methanol | 0.68 (C) | 403.4 |
| 14 | 3-Chloro-5-{6-[2-(4-chloro-7-fluoro-2-methyl-indol-1-yl)-ethylamino]-pyrimidin-4-yl}-thiophene-2-carboxylic acid | 1.25 (C) | 465.2 |
| 15 | 4-{6-[2-(7-Fluoro-2,4-dimethyl-indol-1-yl)-ethylamino]-pyrimidin-4-yl}-benzoic acid | 0.72 (A) | 404.95 |
| 16 | (2-Chloro-4-{6-[2-(4-methoxy-2-methyl-indol-1-yl)-ethylamino]-pyrimidin-4-yl}-phenyl)-methanol | 0.82 (C) | 423.3 |
| 17 | (2-Fluoro-4-{6-[2-(4-methoxy-2-methyl-indol-1-yl)-ethylamino]-pyrimidin-4-yl}-phenyl)-methanol | 0.76 (C) | 407.3 |
| 18 | 3-Chloro-5-{6-[2-(7-fluoro-2,4-dimethyl-indol-1-yl)-ethylamino]-pyrimidin-4-yl}-thiophene-2-carboxylic acid | 0.88 (A) | 445.0 |
| 19 | 3-Chloro-5-{6-[2-(6-fluoro-2,4-dimethyl-indol-1-yl)-ethylamino]-pyrimidin-4-yl}-thiophene-2-carboxylic acid | 1.19 (C) | 445.3 |
| 20 | (2-Chloro-4-{6-[2-(7-fluoro-2,4-dimethyl-indol-1-yl)-ethylamino]-pyrimidin-4-yl}-phenyl)-methanol | 0.97 (C) | 425.3 |
| 21 | (2-Fluoro-4-{6-[2-(7-fluoro-2,4-dimethyl-indol-1-yl)-ethylamino]-pyrimidin-4-yl}-phenyl)-methanol | 0.90 (C) | 409.4 |
| 22 | (4-{6-[2-(7-Fluoro-2,4-dimethyl-indol-1-yl)-ethylamino]-pyrimidin-4-yl}-2-methyl-phenyl)-methanol | 0.80 (C) | 405.4 |
| 23 | 3-Chloro-5-{6-[2-(4-methoxy-2-methyl-indol-1-yl)-ethylamino]-pyrimidin-4-yl}-thiophene-2-carboxylic acid | 0.81 (A) | 443.1 |
| 24 | [6-(4-Aminomethyl-3-fluoro-phenyl)-pyrimidin-4-yl]-[2-(4-methoxy-2-methyl-indol-1-yl)-ethyl]-amine | 0.53 (C) | 406.4 |
| 25 | 4-{6-[2-(7-Fluoro-2,4-dimethyl-indol-1-yl)-ethylamino]-pyrimidin-4-yl}-benzamide | 0.79 (C) | 404.3 |
| 26 | 4-{6-[2-(2,4-Dimethyl-indol-1-yl)-ethylamino]-pyrimidin-4-yl}-2-ethyl-benzoic acid | 0.93 (C) | 415.4 |
| 27 | (2-Chloro-4-{6-[2-(7-fluoro-4-methoxy-2-methyl-indol-1-yl)-ethylamino]-pyrimidin-4-yl}-phenyl)-methanol | 0.89 (C) | 441.3 |
| 28 | (2-Fluoro-4-{6-[2-(7-fluoro-4-methoxy-2-methyl-indol-1-yl)-ethylamino]-pyrimidin-4-yl}-phenyl)-methanol | 0.82 (C) | 425.3 |
| 29 | 2-Chloro-4-{6-[2-(7-fluoro-2,4-dimethyl-indol-1-yl)-ethylamino]-pyrimidin-4-yl}-benzoic acid | 1.04 (C) | 439.3 |
| 30 | (4-{6-[2-(7-Fluoro-2,4-dimethyl-indol-1-yl)-ethylamino]-pyrimidin-4-yl}-2-methoxy-phenyl)-methanol | 0.81 (C) | 421.4 |
| 31 | 4-{6-[2-(7-Fluoro-2,4-dimethyl-indol-1-yl)-ethylamino]-pyrimidin-4-yl}-2-methyl-benzoic acid | 0.93 (C) | 419.4 |

TABLE 8-continued

Examples 1-745

| Ex. | Compound | $t_R$ [min] (LC-MS) | MS Data m/z [M + H]⁺ |
|---|---|---|---|
| 32 | (4-{6-[2-(7-Fluoro-4-methoxy-2-methyl-indol-1-yl)-ethylamino]-pyrimidin-4-yl}-2-methyl-phenyl)-methanol | 0.73 (C) | 421.4 |
| 33 | 2-Ethylsulfanyl-4-{6-[2-(2-methyl-indol-1-yl)-ethylamino]-pyrimidin-4-yl}-benzoic acid | 0.96 (C) | 433.3 |
| 34 | 2,6-Difluoro-4-{6-[2-(7-fluoro-4-methoxy-2-methyl-indol-1-yl)-ethylamino]-pyrimidin-4-yl}-phenol | 0.91 (C) | 429.3 |
| 35 | 4-{6-[2-(2,4-Dimethyl-indol-1-yl)-ethylamino]-pyrimidin-4-yl}-2-methoxy-benzoic acid | 0.86 (C) | 417.3 |
| 36 | (2-Methoxy-4-{6-[2-(4-methoxy-2-methyl-indol-1-yl)-ethylamino]-pyrimidin-4-yl}-phenyl)-methanol | 0.70 (C) | 419.4 |
| 37 | 4-{6-[2-(7-Fluoro-2,4-dimethyl-indol-1-yl)-ethylamino]-pyrimidin-4-yl}-benzenesulfonic acid | 0.83 (C) | 441.3 |
| 38 | 3-Chloro-5-{6-[2-(6-fluoro-4-methoxy-2-methyl-indol-1-yl)-ethylamino]-pyrimidin-4-yl}-thiophene-2-carboxylic acid | 1.11 (C) | 461.3 |
| 39 | (4-{6-[2-(4-Methoxy-2-methyl-indol-1-yl)-ethylamino]-pyrimidin-4-yl}-phenyl)-urea | 0.60 (C) | 417.3 |
| 40 | (4-{6-[2-(7-Fluoro-2,4-dimethyl-indol-1-yl)-ethylamino]-pyrimidin-4-yl}-phenyl)-urea | 0.70 (C) | 419.4 |
| 41 | 2-Amino-4-{6-[2-(7-fluoro-2,4-dimethyl-indol-1-yl)-ethylamino]-pyrimidin-4-yl}-benzoic acid | 0.84 (C) | 420.3 |
| 42 | 4-{6-[2-(7-Fluoro-4-methoxy-2-methyl-indol-1-yl)-ethylamino]-pyrimidin-4-yl}-benzamide | 0.72 (C) | 420.3 |
| 43 | 5-{6-[2-(2-Cyano-indol-1-yl)-ethylamino]-pyrimidin-4-yl}-3-ethoxy-thiophene-2-carboxylic acid | 0.66 (A) | 433.9 |
| 44 | 3-Chloro-5-{6-[2-(4,6-dichloro-2-methyl-indol-1-yl)-ethylamino]-pyrimidin-4-yl}-thiophene-2-carboxylic acid (*1) | 1.31 (C) | 481.2 |
| 45 | 5-{6-[2-(7-Fluoro-2,4-dimethyl-indol-1-yl)-ethylamino]-pyrimidin-4-yl}-3-methyl-thiophene-2-carboxylic acid (*1) | 1.14 (C) | 425.3 |
| 46 | 4-{6-[2-(4-Chloro-7-fluoro-2-methyl-indol-1-yl)-ethylamino]-pyrimidin-4-yl}-benzoic acid (*1) | 0.97 (C) | 425.3 |
| 47 | 3-Fluoro-5-{6-[2-(7-fluoro-2,4-dimethyl-indol-1-yl)-ethylamino]-pyrimidin-4-yl}-thiophene-2-carboxylic acid (*1) | 1.16 (C) | 429.3 |
| 48 | 3-Fluoro-5-{6-[2-(6-fluoro-2,4-dimethyl-indol-1-yl)-ethylamino]-pyrimidin-4-yl}-thiophene-2-carboxylic acid (*1) | 1.14 (C) | 429.3 |
| 49 | 3-Fluoro-5-{6-[2-(4-methoxy-2-methyl-indol-1-yl)-ethylamino]-pyrimidin-4-yl}-thiophene-2-carboxylic acid (*1) | 1.02 (C) | 427.3 |
| 50 | 3-Ethoxy-5-{6-[2-(2-methyl-indol-1-yl)-ethylamino]-pyrimidin-4-yl}-thiophene-2-carboxylic acid (*1) | 1.03 (C) | 423.3 |
| 51 | 5-{6-[2-(4-Methoxy-2-methyl-indol-1-yl)-ethylamino]-pyrimidin-4-yl}-3-methyl-thiophene-2-carboxylic acid (*1) | 0.99 (C) | 423.3 |
| 52 | [2-(6-Fluoro-2,4-dimethyl-indol-1-yl)-ethyl]-[6-(3-methyl-1H-indazol-6-yl)-pyrimidin-4-yl]-amine | 0.86 (C) | 415.4 |
| 53 | [2-(6-Fluoro-2,4-dimethyl-indol-1-yl)-ethyl]-[6-(1-methyl-1H-indazol-6-yl)-pyrimidin-4-yl]-amine | 0.91 (C) | 415.4 |
| 54 | [2-(7-Fluoro-2,4-dimethyl-indol-1-yl)-ethyl]-[6-(2-methyl-1H-benzoimidazol-5-yl)-pyrimidin-4-yl]-amine | 0.64 (C) | 415.4 |
| 55 | [2-(7-Fluoro-2,4-dimethyl-indol-1-yl)-ethyl]-(6-quinoxalin-6-yl-pyrimidin-4-yl)-amine | 0.75 (A) | 413.20 |
| 56 | [6-(1H-Benzoimidazol-5-yl)-pyrimidin-4-yl]-[2-(7-chloro-4-methoxy-2-methyl-indol-1-yl)-ethyl]-amine | 0.67 (C) | 433.3 |
| 57 | [6-(1H-Benzoimidazol-5-yl)-pyrimidin-4-yl]-[2-(7-fluoro-4-methoxy-2-methyl-indol-1-yl)-ethyl]-amine | 0.61 (C) | 417.3 |
| 58 | [2-(7-Fluoro-4-methoxy-2-methyl-indol-1-yl)-ethyl]-[6-(1H-indazol-6-yl)-pyrimidin-4-yl]-amine | 0.76 (C) | 417.3 |
| 59 | [2-(6,7-Difluoro-2,4-dimethyl-indol-1-yl)-ethyl]-[6-(1H-indol-6-yl)-pyrimidin-4-yl]-amine | 0.87 (C) | 418.4 |
| 60 | [2-(4-Methoxy-2-methyl-indol-1-yl)-ethyl]-[6-(2-methyl-benzooxazol-6-yl)-pyrimidin-4-yl]-amine | 0.80 (C) | 414.4 |
| 61 | 5-{6-[2-(6-Fluoro-2,4-dimethyl-indol-1-yl)-ethylamino]-pyrimidin-4-yl}-1,3-dihydro-indol-2-one | 0.72 (C) | 416.3 |
| 62 | [6-(2,3-Dihydro-1H-indol-5-yl)-pyrimidin-4-yl]-[2-(6-fluoro-4-methoxy-2-methyl-indol-1-yl)-ethyl]-amine | 0.72 (C) | 418.4 |
| 63 | [2-(6-Fluoro-4-methoxy-2-methyl-indol-1-yl)-ethyl]-[6-(1H-indol-6-yl)-pyrimidin-4-yl]-amine | 0.78 (C) | 416.3 |
| 64 | 5-{6-[2-(7-Fluoro-2,4-dimethyl-indol-1-yl)-ethylamino]-pyrimidin-4-yl}-1,3-dihydro-indol-2-one | 0.73 (C) | 416.3 |
| 65 | 5-{6-[2-(7-Fluoro-2,4-dimethyl-indol-1-yl)-ethylamino]-pyrimidin-4-yl}-2,3-dihydro-isoindol-1-one | 0.81 (C) | 414.3 |
| 66 | [2-(7-Chloro-4-methoxy-2-methyl-indol-1-yl)-ethyl]-[6-(2,3-dihydro-1H-indol-5-yl)-pyrimidin-4-yl]-amine | 0.77 (C) | 434.3 |
| 67 | [6-(2,3-Dihydro-1H-indol-5-yl)-pyrimidin-4-yl]-[2-(7-fluoro-4-methoxy-2-methyl-indol-1-yl)-ethyl]-amine | 0.72 (C) | 418.4 |
| 68 | [2-(7-Fluoro-4-methoxy-2-methyl-indol-1-yl)-ethyl]-[6-(1H-indol-6-yl)-pyrimidin-4-yl]-amine | 0.78 (C) | 416.3 |
| 69 | [2-(6-Fluoro-2,4-dimethyl-indol-1-yl)-ethyl]-{6-[4-(1H-imidazol-4-yl)-phenyl]-pyrimidin-4-yl}-amine | 0.63 (C) | 427.4 |
| 70 | [2-(7-Fluoro-2,4-dimethyl-indol-1-yl)-ethyl]-{6-[4-(2H-pyrazol-3-yl)-phenyl]-pyrimidin-4-yl}-amine | 0.86 (C) | 427.4 |
| 71 | [2-(7-Fluoro-2,4-dimethyl-indol-1-yl)-ethyl]-{6-[4-(1H-imidazol-2-yl)-phenyl]-pyrimidin-4-yl}-amine | 0.65 (C) | 427.4 |

TABLE 8-continued

Examples 1-745

| Ex. | Compound | $t_R$ [min] (LC-MS) | MS Data m/z [M + H]+ |
|---|---|---|---|
| 72 | [2-(7-Fluoro-2,4-dimethyl-indol-1-yl)-ethyl]-{6-[4-(1H-imidazol-4-yl)-phenyl]-pyrimidin-4-yl}-amine | 0.64 (C) | 427.4 |
| 73 | [2-(7-Fluoro-2,4-dimethyl-indol-1-yl)-ethyl]-[6-(4-pyrazol-1-yl-phenyl)-pyrimidin-4-yl]-amine | 0.99 (C) | 427.4 |
| 74 | 5-{6-[2-(7-Fluoro-4-methoxy-2-methyl-indol-1-yl)-ethylamino]-pyrimidin-4-yl}-1,3-dihydro-2H-benzo[d]imidazol-2-one | 0.64 (C) | 433.3 |
| 75 | [2-(4-Methoxy-2-methyl-indol-1-yl)-ethyl]-{6-[4-(2H-pyrazol-3-yl)-phenyl]-pyrimidin-4-yl}-amine | 0.74 (C) | 425.4 |
| 76 | {6-[4-(1H-Imidazol-2-yl)-phenyl]-pyrimidin-4-yl}-[2-(4-methoxy-2-methyl-indol-1-yl)-ethyl]-amine | 0.55 (C) | 425.4 |
| 77 | {6-[4-(1H-Imidazol-4-yl)-phenyl]-pyrimidin-4-yl}-[2-(4-methoxy-2-methyl-indol-1-yl)-ethyl]-amine | 0.53 (C) | 425.4 |
| 78 | [2-(4-Methoxy-2-methyl-indol-1-yl)-ethyl]-[6-(4-pyrazol-1-yl-phenyl)-pyrimidin-4-yl]-amine | 0.85 (C) | 425.4 |
| 79 | [2-(7-Fluoro-2,4-dimethyl-indol-1-yl)-ethyl]-[6-(4-[1,2,4]oxadiazol-5-yl-phenyl)-pyrimidin-4-yl]-amine | 0.90 (C) | 429.3 |
| 80 | [2-(7-Chloro-4-methoxy-2-methyl-indol-1-yl)-ethyl]-[6-(2-methyl-1H-benzoimidazol-5-yl)-pyrimidin-4-yl]-amine | 0.64 (C) | 447.3 |
| 81 | [2-(7-Fluoro-4-methoxy-2-methyl-indol-1-yl)-ethyl]-[6-(2-methyl-1H-benzoimidazol-5-yl)-pyrimidin-4-yl]-amine | 0.59 (C) | 431.4 |
| 82 | [2-(7-Chloro-4-methoxy-2-methyl-indol-1-yl)-ethyl]-[6-(1-methyl-1H-indazol-6-yl)-pyrimidin-4-yl]-amine | 0.91 (C) | 447.3 |
| 83 | [2-(7-Fluoro-4-methoxy-2-methyl-indol-1-yl)-ethyl]-[6-(1-methyl-1H-indazol-6-yl)-pyrimidin-4-yl]-amine | 0.84 (C) | 431.4 |
| 84 | [2-(6-Fluoro-2,4-dimethyl-indol-1-yl)-ethyl]-[6-(4-isothiazol-5-yl-phenyl)-pyrimidin-4-yl]-amine | 0.80 (A) | 444.10 |
| 85 | [2-(7-Fluoro-2,4-dimethyl-indol-1-yl)-ethyl]-[6-(4-thiazol-4-yl-phenyl)-pyrimidin-4-yl]-amine | 0.98 (C) | 444.3 |
| 86 | rac-5-{6-[2-(4-Methoxy-2-methyl-indol-1-yl)-ethylamino]-pyrimidin-4-yl}-3-methyl-2,3-dihydro-isoindol-1-one | 0.72 (C) | 428.4 |
| 87 | 5-{6-[2-(4-Methoxy-2-methyl-indol-1-yl)-ethylamino]-pyrimidin-4-yl}-2-methyl-2,3-dihydro-isoindol-1-one | 0.73 (C) | 428.4 |
| 88 | 5-{6-[2-(6-Fluoro-4-methoxy-2-methyl-indol-1-yl)-ethylamino]-pyrimidin-4-yl}-1,3-dihydro-indol-2-one | 0.67 (C) | 432.4 |
| 89 | [2-(7-Fluoro-4-methoxy-2-methyl-indol-1-yl)-ethyl]-[6-(2-methyl-benzooxazol-6-yl)-pyrimidin-4-yl]-amine | 0.87 (C) | 432.4 |
| 90 | 5-{6-[2-(7-Fluoro-4-methoxy-2-methyl-indol-1-yl)-ethylamino]-pyrimidin-4-yl}-2,3-dihydro-isoindol-1-one | 0.73 (C) | 432.4 |
| 91 | 5-{6-[2-(7-Fluoro-4-methoxy-2-methyl-indol-1-yl)-ethylamino]-pyrimidin-4-yl}-1,3-dihydro-indol-2-one | 0.67 (C) | 432.3 |
| 92 | [2-(6,7-Difluoro-4-methoxy-2-methyl-indol-1-yl)-ethyl]-[6-(1H-indol-6-yl)-pyrimidin-4-yl]-amine | 0.82 (C) | 434.3 |
| 93 | 5-{6-[2-(6,7-Difluoro-2,4-dimethyl-indol-1-yl)-ethylamino]-pyrimidin-4-yl}-1,3-dihydro-indol-2-one | 0.77 (C) | 434.3 |
| 94 | [2-(6-Fluoro-2,4-dimethyl-indol-1-yl)-ethyl]-[6-(4-isoxazol-3-yl-phenyl)-pyrimidin-4-yl]-amine | 0.79 (A) | 428.24 |
| 95 | 5-{6-[2-(7-Fluoro-2,4-dimethyl-indol-1-yl)-ethylamino]-pyrimidin-4-yl}-2-methyl-2,3-dihydro-isoindol-1-one | 0.87 (C) | 430.4 |
| 96 | rac-5-{6-[2-(7-Fluoro-2,4-dimethyl-indol-1-yl)-ethylamino]-pyrimidin-4-yl}-3-methyl-2,3-dihydro-isoindol-1-one | 0.86 (C) | 430.4 |
| 97 | [2-(7-Fluoro-2,4-dimethyl-indol-1-yl)-ethyl]-[6-(4-oxazol-5-yl-phenyl)-pyrimidin-4-yl]-amine | 0.96 (C) | 428.4 |
| 98 | [2-(4-Methoxy-2-methyl-indol-1-yl)-ethyl]-[6-(4-thiazol-4-yl-phenyl)-pyrimidin-4-yl]-amine | 0.85 (C) | 442.3 |
| 99 | [2-(7-Fluoro-2,4-dimethyl-indol-1-yl)-ethyl]-{6-[4-(4H-[1,2,4]triazol-3-yl)-phenyl]-pyrimidin-4-yl}-amine | 0.79 (C) | 428.4 |
| 100 | [2-(4-Methoxy-2-methyl-indol-1-yl)-ethyl]-{6-[4-(4H-[1,2,4]triazol-3-yl)-phenyl]-pyrimidin-4-yl}-amine | 0.67 (C) | 426.4 |
| 101 | (4-{6-[2-(7-Fluoro-4-methoxy-2-methyl-indol-1-yl)-ethylamino]-pyrimidin-4-yl}-thiophen-2-yl)-methanol (*2) | 0.70 (C) | 413.3 |
| 102 | 4-{6-[2-(4,6-Difluoro-2,5-dimethyl-indol-1-yl)-ethylamino]-pyrimidin-4-yl}-2-isobutyl-benzoic acid | 0.81 (A) | 479.19 |
| 103 | 3-Ethyl-5-{6-[2-(7-fluoro-2,4-dimethyl-indol-1-yl)-ethylamino]-pyrimidin-4-yl}-thiophene-2-carboxylic acid (*1) | 1.20 (C) | 439.3 |
| 104 | 3-Ethyl-5-{6-[2-(6-fluoro-2,4-dimethyl-indol-1-yl)-ethylamino]-pyrimidin-4-yl}-thiophene-2-carboxylic acid (*1) | 1.17 (C) | 439.3 |
| 105 | 2-Chloro-4-{6-[2-(6-fluoro-2,4-dimethyl-indol-1-yl)-ethylamino]-pyrimidin-4-yl}-benzoic acid (*1) | 1.02 (C) | 439.3 |
| 106 | 4-{6-[2-(4-Chloro-7-fluoro-2-methyl-indol-1-yl)-ethylamino]-pyrimidin-4-yl}-2-methyl-benzoic acid (*1) | 0.98 (C) | 439.3 |
| 107 | 5-{6-[2-(7-Fluoro-4-methoxy-2-methyl-indol-1-yl)-ethylamino]-pyrimidin-4-yl}-3-methyl-thiophene-2-carboxylic acid (*1) | 1.05 (C) | 441.3 |
| 108 | 5-{6-[2-(4-Chloro-2-methyl-indol-1-yl)-ethylamino]-pyrimidin-4-yl}-3-ethoxy-thiophene-2-carboxylic acid (*1) | 1.11 (C) | 457.3 |

TABLE 8-continued

Examples 1-745

| Ex. | Compound | $t_R$ [min] (LC-MS) | MS Data m/z [M + H]+ |
|---|---|---|---|
| 109 | 4-{6-[2-(7-Fluoro-4-methoxy-2-methyl-indol-1-yl)-ethylamino]-pyrimidin-4-yl}-benzoic acid (*1) | 0.84 (C) | 421.3 |
| 110 | 3-Ethyl-5-{6-[2-(4-methoxy-2-methyl-indol-1-yl)-ethylamino]-pyrimidin-4-yl}-thiophene-2-carboxylic acid (*1) | 1.06 (C) | 437.3 |
| 111 | 5-{6-[2-(7-Chloro-4-methoxy-2-methyl-indol-1-yl)-ethylamino]-pyrimidin-4-yl}-3-fluoro-thiophene-2-carboxylic acid (*1) | 1.15 (C) | 461.2 |
| 112 | 3-Fluoro-5-{6-[2-(7-fluoro-4-methoxy-2-methyl-indol-1-yl)-ethylamino]-pyrimidin-4-yl}-thiophene-2-carboxylic acid (*1) | 1.07 (C) | 445.3 |
| 113 | 3-Fluoro-5-{6-[2-(6-fluoro-4-methoxy-2-methyl-indol-1-yl)-ethylamino]-pyrimidin-4-yl}-thiophene-2-carboxylic acid (*1) | 1.06 (C) | 445.3 |
| 114 | 3-Chloro-5-{6-[2-(7-fluoro-4-methoxy-2-methyl-indol-1-yl)-ethylamino]-pyrimidin-4-yl}-thiophene-2-carboxylic acid (*1) | 1.13 (C) | 461.2 |
| 115 | 5-{6-[2-(7-Fluoro-4-methoxy-2-methyl-indol-1-yl)-ethylamino]-pyrimidin-4-yl}-1,3-dihydro-benzoimidazol-2-one | 0.63 (A) | 433.08 |
| 116 | 4-{6-[2-(7-Fluoro-4-methoxy-2-methyl-indol-1-yl)-ethylamino]-pyrimidin-4-yl}-benzenesulfonic acid | 0.75 (C) | 457.3 |
| 117 | 3-Ethoxy-5-{6-[2-(6-methoxy-2-methyl-indol-1-yl)-ethylamino]-pyrimidin-4-yl}-thiophene-2-carboxylic acid | 1.01 (C) | 453.3 |
| 118 | 2-Ethyl-4-{6-[2-(4-ethyl-2-methyl-indol-1-yl)-ethylamino]-pyrimidin-4-yl}-benzoic acid | 0.99 (C) | 429.4 |
| 119 | 2-Isobutyl-4-{6-[2-(2-methyl-indol-1-yl)-ethylamino]-pyrimidin-4-yl}-benzoic acid | 1.00 (C) | 429.4 |
| 120 | 4-{6-[2-(2,4-Dimethyl-indol-1-yl)-ethylamino]-pyrimidin-4-yl}-2-propyl-benzoic acid | 0.99 (C) | 429.4 |
| 121 | 4-{6-[2-(4,7-Difluoro-2-methyl-indol-1-yl)-ethylamino]-pyrimidin-4-yl}-2-ethyl-benzoic acid | 0.97 (C) | 437.4 |
| 122 | 4-{6-[2-(5,7-Difluoro-2-methyl-indol-1-yl)-ethylamino]-pyrimidin-4-yl}-2-ethyl-benzoic acid | 0.96 (C) | 437.4 |
| 123 | 2-Chloro-4-{6-[2-(7-fluoro-2,4-dimethyl-indol-1-yl)-ethylamino]-pyrimidin-4-yl}-6-methyl-benzoic acid | 0.99 (C) | 453.3 |
| 124 | (2-Ethoxy-4-{6-[2-(7-fluoro-2,4-dimethyl-indol-1-yl)-ethylamino]-pyrimidin-4-yl}-phenyl)-methanol | 0.88 (C) | 435.4 |
| 125 | 4-{6-[2-(7-Fluoro-2-methyl-indol-1-yl)-ethylamino]-pyrimidin-4-yl}-2-propyl-benzoic acid | 1.00 (C) | 433.4 |
| 126 | 2-Bromo-5-fluoro-4-{6-[2-(7-fluoro-2,4-dimethyl-indol-1-yl)-ethylamino]-pyrimidin-4-yl}-benzoic acid | 1.14 (C) | 501.2 |
| 127 | (2-Ethoxy-4-{6-[2-(4-methoxy-2-methyl-indol-1-yl)-ethylamino]-pyrimidin-4-yl}-phenyl)-methanol | 0.76 (C) | 433.4 |
| 128 | 4-{6-[2-(2,4-Dimethyl-indol-1-yl)-ethylamino]-pyrimidin-4-yl}-2-ethoxy-benzoic acid | 0.94 (C) | 431.4 |
| 129 | 4-{6-[2-(7-Fluoro-2,4-dimethyl-indol-1-yl)-ethylamino]-pyrimidin-4-yl}-2-methoxy-benzoic acid | 0.91 (C) | 435.4 |
| 130 | (4-{6-[2-(7-Fluoro-4-methoxy-2-methyl-indol-1-yl)-ethylamino]-pyrimidin-4-yl}-2-methoxy-phenyl)-methanol | 0.75 (C) | 437.4 |
| 131 | 2-Chloro-4-{6-[2-(4-methoxy-2-methyl-indol-1-yl)-ethylamino]-pyrimidin-4-yl}-6-methyl-benzoic acid | 0.83 (C) | 451.3 |
| 132 | (4-{6-[2-(7-Fluoro-4-methoxy-2-methyl-indol-1-yl)-ethylamino]-pyrimidin-4-yl}-phenyl)-urea | 0.64 (C) | 435.4 |
| 133 | (6-Isoquinolin-7-yl-pyrimidin-4-yl)-[2-(2-methyl-indol-1-yl)-ethyl]-amine (*2) | 0.63 (A) | 380.21 |
| 134 | 4-{6-[2-(4,7-Difluoro-2-methyl-indol-1-yl)-ethylamino]-pyrimidin-4-yl}-2-methylamino-benzoic acid | 0.90 (C) | 438.3 |
| 135 | 4-{6-[2-(7-Fluoro-2,4-dimethyl-indol-1-yl)-ethylamino]-pyrimidin-4-yl}-2-methyl-benzenesulfonamide | 0.90 (C) | 454.3 |
| 136 | 4-{6-[2-(7-Fluoro-2,4-dimethyl-indol-1-yl)-ethylamino]-pyrimidin-4-yl}-2-methylamino-benzoic acid | 0.91 (C) | 434.4 |
| 137 | 4-{6-[2-(7-Chloro-2-methyl-indol-1-yl)-ethylamino]-pyrimidin-4-yl}-2-ethylamino-benzoic acid | 1.00 (C) | 450.3 |
| 138 | 4-{6-[2-(2-Cyano-indol-1-yl)-ethylamino]-pyrimidin-4-yl}-2-ethoxy-benzoic acid | 0.88 (C) | 428.4 |
| 139 | 4-{6-[2-(4-Methoxy-2-methyl-indol-1-yl)-ethylamino]-pyrimidin-4-yl}-2-methyl-benzenesulfonamide | 0.76 (C) | 452.3 |
| 140 | 4-{6-[2-(2,4-Dimethyl-indol-1-yl)-ethylamino]-pyrimidin-4-yl}-2-isobutyl-benzoic acid | 1.05 (C) | 443.4 |
| 141 | 4-{6-[2-(4,7-Dichloro-2-methyl-indol-1-yl)-ethylamino]-pyrimidin-4-yl}-2-fluoro-6-methylsulfanyl-benzoic acid | 1.17 (C) | 505.2 |
| 142 | 2-Chloro-4-{6-[2-(4,7-dichloro-2-methyl-indol-1-yl)-ethylamino]-pyrimidin-4-yl}-6-methylsulfanyl-benzoic acid | 1.19 (C) | 521.2 |
| 143 | 4-{6-[2-(7-Chloro-4-fluoro-2-methyl-indol-1-yl)-ethylamino]-pyrimidin-4-yl}-2-propyl-benzoic acid | 1.11 (C) | 467.3 |
| 144 | 4-{6-[2-(4,7-Difluoro-2-methyl-indol-1-yl)-ethylamino]-pyrimidin-4-yl}-2-propyl-benzoic acid | 1.03 (C) | 451.4 |
| 145 | 4-{6-[2-(5,7-Difluoro-2-methyl-indol-1-yl)-ethylamino]-pyrimidin-4-yl}-2-propyl-benzoic acid | 1.02 (C) | 451.4 |
| 146 | 4-{6-[2-(7-Chloro-2,4-dimethyl-indol-1-yl)-ethylamino]-pyrimidin-4-yl}-2-ethylsulfanyl-benzoic acid | 1.13 (C) | 481.3 |
| 147 | 4-{6-[2-(7-Fluoro-2,4-dimethyl-indol-1-yl)-ethylamino]-pyrimidin-4-yl}-2-propyl-benzoic acid | 1.05 (C) | 447.4 |
| 148 | 4-{6-[2-(7-Fluoro-2-methyl-indol-1-yl)-ethylamino]-pyrimidin-4-yl}-2-isobutyl-benzoic acid | 1.06 (C) | 447.4 |

TABLE 8-continued

Examples 1-745

| Ex. | Compound | $t_R$ [min] (LC-MS) | MS Data m/z [M + H]+ |
|---|---|---|---|
| 149 | 4-{6-[2-(4,7-Dichloro-2-methyl-indol-1-yl)-ethylamino]-pyrimidin-4-yl}-2-ethylsulfanyl-benzoic acid | 1.19 (C) | 501.3 |
| 150 | 2-Chloro-4-{6-[2-(7-chloro-2,4-dimethyl-indol-1-yl)-ethylamino]-pyrimidin-4-yl}-6-methylsulfanyl-benzoic acid | 0.78 (A) | 501.07 |
| 151 | 4-{6-[2-(4,7-Dichloro-2-methyl-indol-1-yl)-ethylamino]-pyrimidin-4-yl}-2-ethoxy-benzoic acid | 0.78 (A) | 485.17 |
| 152 | 4-{6-[2-(7-Chloro-4-fluoro-2-methyl-indol-1-yl)-ethylamino]-pyrimidin-4-yl}-2-ethoxy-benzoic acid | 1.05 (C) | 469.3 |
| 153 | 4-{6-[2-(5,7-Dichloro-2-methyl-indol-1-yl)-ethylamino]-pyrimidin-4-yl}-2-ethoxy-benzoic acid | 1.12 (C) | 485.3 |
| 154 | 4-{6-[2-(4,7-Difluoro-2-methyl-indol-1-yl)-ethylamino]-pyrimidin-4-yl}-2-ethoxy-benzoic acid | 0.98 (C) | 453.3 |
| 155 | 2-Chloro-4-{6-[2-(7-chloro-4-methoxy-2-methyl-indol-1-yl)-ethylamino]-pyrimidin-4-yl}-6-methyl-benzoic acid | 0.98 (C) | 485.3 |
| 156 | 2-Chloro-4-{6-[2-(7-fluoro-4-methoxy-2-methyl-indol-1-yl)-ethylamino]-pyrimidin-4-yl}-6-methyl-benzoic acid | 0.90 (C) | 469.3 |
| 157 | 4-{6-[2-(7-Chloro-2,4-dimethyl-indol-1-yl)-ethylamino]-pyrimidin-4-yl}-2-ethoxy-benzoic acid | 1.06 (C) | 465.4 |
| 158 | 2-Ethoxy-4-{6-[2-(7-fluoro-2,4-dimethyl-indol-1-yl)-ethylamino]-pyrimidin-4-yl}-benzoic acid | 0.99 (C) | 449.4 |
| 159 | (2-Ethoxy-4-{6-[2-(7-fluoro-4-methoxy-2-methyl-indol-1-yl)-ethylamino]-pyrimidin-4-yl}-phenyl)-methanol | 0.81 (C) | 451.4 |
| 160 | 2-Chloro-6-ethyl-4-{6-[2-(4-methoxy-2-methyl-indol-1-yl)-ethylamino]-pyrimidin-4-yl}-benzoic acid | 0.90 (C) | 465.3 |
| 161 | [6-(3-Fluoro-4-methanesulfonyl-phenyl)-pyrimidin-4-yl]-[2-(7-fluoro-4-methoxy-2-methyl-indol-1-yl)-ethyl]-amine | 1.04 (C) | 473.3 |
| 162 | 5-{6-[2-(5,7-Difluoro-2,4-dimethyl-indol-1-yl)-ethylamino]-pyrimidin-4-yl}-3-ethoxy-thiophene-2-carboxylic acid | 0.82 (A) | 473.10 |
| 163 | 4-{6-[2-(7-Cyano-2-methyl-indol-1-yl)-ethylamino]-pyrimidin-4-yl}-2-ethylamino-benzoic acid | 0.92 (C) | 441.4 |
| 164 | [6-(1H-Benzoimidazol-5-yl)-pyrimidin-4-yl]-[2-(7-fluoro-2,4-dimethyl-indol-1-yl)-ethyl]-amine (*2) | 0.67 (C) | 401.3 |
| 165 | 4-{6-[2-(2-Cyano-indol-1-yl)-ethylamino]-pyrimidin-4-yl}-2-isobutyl-benzoic acid | 1.00 (C) | 440.4 |
| 166 | 2,6-Difluoro-4-{6-[2-(7-fluoro-2,4-dimethyl-indol-1-yl)-ethylamino]-pyrimidin-4-yl}-benzenesulfonamide | 1.06 (C) | 476.3 |
| 167 | 4-{6-[2-(5,7-Difluoro-2-methyl-indol-1-yl)-ethylamino]-pyrimidin-4-yl}-2-ethylamino-benzoic acid | 0.96 (C) | 452.4 |
| 168 | 4-{6-[2-(7-Fluoro-2,4-dimethyl-indol-1-yl)-ethylamino]-pyrimidin-4-yl}-N-(2-hydroxy-ethyl)-benzamide | 0.77 (C) | 448.4 |
| 169 | 4-{6-[2-(4-Chloro-2-methyl-indol-1-yl)-ethylamino]-pyrimidin-4-yl}-2-cyclopropyl-benzoic acid (*1) | 0.97 (C) | 447.3 |
| 170 | 2-Ethylamino-4-{6-[2-(6-methoxy-2-methyl-indol-1-yl)-ethylamino]-pyrimidin-4-yl}-benzoic acid | 0.87 (C) | 446.4 |
| 171 | 4-{6-[2-(7-Fluoro-4-methoxy-2-methyl-indol-1-yl)-ethylamino]-pyrimidin-4-yl}-2-methyl-benzenesulfonamide | 0.83 (C) | 470.3 |
| 172 | 2-Chloro-4-{6-[2-(7-fluoro-4-methoxy-2-methyl-indol-1-yl)-ethylamino]-pyrimidin-4-yl}-benzenesulfonamide | 0.95 (C) | 490.3 |
| 173 | 2-Cyclopropyl-4-{6-[2-(4,7-difluoro-2-methyl-indol-1-yl)-ethylamino]-pyrimidin-4-yl}-benzoic acid | 0.96 (C) | 449.3 |
| 174 | 2-Cyclopropyl-4-{6-[2-(7-fluoro-2,4-dimethyl-indol-1-yl)-ethylamino]-pyrimidin-4-yl}-benzoic acid | 0.98 (C) | 445.4 |
| 175 | 2-Cyclopropyl-4-{6-[2-(4-methoxy-2-methyl-indol-1-yl)-ethylamino]-pyrimidin-4-yl}-benzoic acid | 0.84 (C) | 443.4 |
| 176 | [2-(6,7-Difluoro-2,4-dimethyl-indol-1-yl)-ethyl]-{6-[4-(1H-imidazol-4-yl)-phenyl]-pyrimidin-4-yl}-amine | 0.67 (C) | 445.4 |
| 177 | [2-(6-Fluoro-2,4-dimethyl-indol-1-yl)-ethyl]-{6-[4-(1-methyl-1H-pyrazol-3-yl)-phenyl]-pyrimidin-4-yl}-amine | 0.77 (A) | 441.28 |
| 178 | [2-(6-Fluoro-2,4-dimethyl-indol-1-yl)-ethyl]-{6-[4-(5-methyl-1H-pyrazol-3-yl)-phenyl]-pyrimidin-4-yl}-amine | 0.74 (A) | 441.00 |
| 179 | [2-(4-Methoxy-2-methyl-indol-1-yl)-ethyl]-{6-[4-(5-methyl-[1,2,4]oxadiazol-3-yl)-phenyl]-pyrimidin-4-yl}-amine | 0.93 (C) | 441.4 |
| 180 | {6-[4-(3-Amino-isoxazol-5-yl)-phenyl]-pyrimidin-4-yl}-[2-(4-methoxy-2-methyl-indol-1-yl)-ethyl]-amine | 0.77 (C) | 441.4 |
| 181 | [2-(7-Fluoro-4-methoxy-2-methyl-indol-1-yl)-ethyl]-[6-(2-morpholin-4-yl-thiazol-5-yl)-pyrimidin-4-yl]-amine | 0.90 (C) | 469.4 |
| 182 | 3-(4-{6-[2-(6-Fluoro-2,4-dimethyl-indol-1-yl)-ethylamino]-pyrimidin-4-yl}-phenyl)-4H-[1,2,4]oxadiazol-5-one | 0.74 (A) | 445.08 |
| 183 | 6-{6-[2-(6-Fluoro-2,4-dimethyl-indol-1-yl)-ethylamino]-pyrimidin-4-yl}-1H-indazole-3-carboxylic acid | 0.80 (C) | 445.3 |
| 184 | [2-(6-Fluoro-4-methoxy-2-methyl-indol-1-yl)-ethyl]-[6-(4-[1,2,4]oxadiazol-5-yl-phenyl)-pyrimidin-4-yl]-amine | 0.83 (C) | 445.3 |
| 185 | 3-(4-{6-[2-(7-Fluoro-2,4-dimethyl-indol-1-yl)-ethylamino]-pyrimidin-4-yl}-phenyl)-4H-[1,2,4]oxadiazol-5-one | 0.97 (C) | 445.3 |

TABLE 8-continued

Examples 1-745

| Ex. | Compound | $t_R$ [min] (LC-MS) | MS Data m/z [M + H]⁺ |
|---|---|---|---|
| 186 | [2-(7-Fluoro-4-methoxy-2-methyl-indol-1-yl)-ethyl]-[6-(4-[1,2,4]oxadiazol-5-yl-phenyl)-pyrimidin-4-yl]-amine | 0.83 (C) | 445.4 |
| 187 | [2-(6,7-Difluoro-2,4-dimethyl-indol-1-yl)-ethyl]-[6-(4-[1,2,4]oxadiazol-5-yl-phenyl)-pyrimidin-4-yl]-amine | 0.95 (C) | 447.3 |
| 188 | [2-(6-Fluoro-4-methoxy-2-methyl-indol-1-yl)-ethyl]-{6-[4-(1H-imidazol-4-yl)-phenyl]-pyrimidin-4-yl}-amine | 0.58 (C) | 443.4 |
| 189 | {6-[4-(3-Amino-isoxazol-5-yl)-phenyl]-pyrimidin-4-yl}-[2-(7-fluoro-2,4-dimethyl-indol-1-yl)-ethyl]-amine | 0.89 (C) | 443.4 |
| 190 | [2-(7-Fluoro-4-methoxy-2-methyl-indol-1-yl)-ethyl]-[6-(4-pyrazol-1-yl-phenyl)-pyrimidin-4-yl]-amine | 0.91 (C) | 443.4 |
| 191 | [2-(7-Fluoro-4-methoxy-2-methyl-indol-1-yl)-ethyl]-{6-[4-(1H-imidazol-4-yl)-phenyl]-pyrimidin-4-yl}-amine | 0.58 (A) | 443.02 |
| 192 | [2-(7-Fluoro-4-methoxy-2-methyl-indol-1-yl)-ethyl]-{6-[4-(1H-imidazol-2-yl)-phenyl]-pyrimidin-4-yl}-amine | 0.60 (C) | 443.4 |
| 193 | [2-(7-Fluoro-4-methoxy-2-methyl-indol-1-yl)-ethyl]-{6-[4-(2H-pyrazol-3-yl)-phenyl]-pyrimidin-4-yl}-amine | 0.79 (C) | 443.4 |
| 194 | 3-(4-{6-[2-(4-Methoxy-2-methyl-indol-1-yl)-ethylamino]-pyrimidin-4-yl}-phenyl)-4H-[1,2,4]oxadiazol-5-one | 0.84 (C) | 443.3 |
| 195 | [2-(7-Fluoro-2,4-dimethyl-indol-1-yl)-ethyl]-{6-[4-(2-methyl-thiazol-4-yl)-phenyl]-pyrimidin-4-yl}-amine | 1.05 (C) | 458.4 |
| 196 | rac-3-Ethyl-5-{6-[2-(4-methoxy-2-methyl-indol-1-yl)-ethylamino]-pyrimidin-4-yl}-2,3-dihydro-isoindol-1-one | 0.78 (C) | 442.4 |
| 197 | 2-Ethyl-5-{6-[2-(4-methoxy-2-methyl-indol-1-yl)-ethylamino]-pyrimidin-4-yl}-2,3-dihydro-isoindol-1-one | 0.79 (C) | 442.4 |
| 198 | 5-{6-[2-(4,7-Dichloro-2-methyl-indol-1-yl)-ethylamino]-pyrimidin-4-yl}-1H-indole-2-carboxylic acid | 0.87 (C) | 480.3 |
| 199 | 5-{6-[2-(6,7-Difluoro-4-methoxy-2-methyl-indol-1-yl)-ethylamino]-pyrimidin-4-yl}-1,3-dihydro-indol-2-one | 0.72 (C) | 450.3 |
| 200 | 5-(4-{6-[2-(6-Fluoro-2,4-dimethyl-indol-1-yl)-ethylamino]-pyrimidin-4-yl}-phenyl)-isoxazol-3-ol | 0.73 (A) | 444.08 |
| 201 | 5-{6-[2-(7-Chloro-2,4-dimethyl-indol-1-yl)-ethylamino]-pyrimidin-4-yl}-1H-indole-2-carboxylic acid | 0.83 (C) | 460.3 |
| 202 | [2-(7-Fluoro-4-methoxy-2-methyl-indol-1-yl)-ethyl]-[6-(4-oxazol-5-yl-phenyl)-pyrimidin-4-yl]-amine | 0.88 (C) | 444.4 |
| 203 | rac-5-{6-[2-(7-Fluoro-4-methoxy-2-methyl-indol-1-yl)-ethylamino]-pyrimidin-4-yl}-3-methyl-2,3-dihydro-isoindol-1-one | 0.78 (C) | 446.4 |
| 204 | 5-{6-[2-(7-Fluoro-4-methoxy-2-methyl-indol-1-yl)-ethylamino]-pyrimidin-4-yl}-2-methyl-2,3-dihydro-isoindol-1-one | 0.79 (C) | 446.4 |
| 205 | [2-(6-Fluoro-4-methoxy-2-methyl-indol-1-yl)-ethyl]-[6-(4-isothiazol-5-yl-phenyl)-pyrimidin-4-yl]-amine | 0.79 (A) | 460.22 |
| 206 | 2-Ethyl-5-{6-[2-(7-fluoro-2,4-dimethyl-indol-1-yl)-ethylamino]-pyrimidin-4-yl}-2,3-dihydro-isoindol-1-one | 0.93 (C) | 444.4 |
| 207 | rac-3-Ethyl-5-{6-[2-(7-fluoro-2,4-dimethyl-indol-1-yl)-ethylamino]-pyrimidin-4-yl}-2,3-dihydro-isoindol-1-one | 0.91 (C) | 444.4 |
| 208 | [2-(7-Fluoro-4-methoxy-2-methyl-indol-1-yl)-ethyl]-{6-[4-(4H-[1,2,4]triazol-3-yl)-phenyl]-pyrimidin-4-yl}-amine | 0.73 (C) | 444.4 |
| 209 | 4-{6-[2-(6-Fluoro-2,4-dimethyl-indol-1-yl)-ethylamino]-pyrimidin-4-yl}-2-methylamino-benzoic acid (*1) | 0.90 (C) | 434.4 |
| 210 | 4-{6-[2-(7-Chloro-6-fluoro-2,4-dimethyl-indol-1-yl)-ethylamino]-pyrimidin-4-yl}-2-ethoxy-benzoic acid | 0.78 (A) | 483.08 |
| 211 | 4-{6-[2-(4-Fluoro-2,7-dimethyl-indol-1-yl)-ethylamino]-pyrimidin-4-yl}-2-methylamino-benzoic acid (*1) | 0.92 (C) | 434.4 |
| 212 | 4-{6-[2-(4-Chloro-2-methyl-indol-1-yl)-ethylamino]-pyrimidin-4-yl}-2-ethylamino-benzoic acid (*1) | 0.98 (C) | 450.3 |
| 213 | 4-{6-[2-(4-Methoxy-2-methyl-indol-1-yl)-ethylamino]-pyrimidin-4-yl}-2-methylamino-benzoic acid (*1) | 0.78 (C) | 432.4 |
| 214 | 2-Amino-4-{6-[2-(7-fluoro-4-methoxy-2-methyl-indol-1-yl)-ethylamino]-pyrimidin-4-yl}-benzoic acid (*1) | 0.77 (C) | 434.3 |
| 215 | 4-{6-[2-(7-Fluoro-4-methoxy-2-methyl-indol-1-yl)-ethylamino]-pyrimidin-4-yl}-3-methoxy-thiophene-2-carboxylic acid (*1) | 0.77 (C) | 457.3 |
| 216 | 3-Ethoxy-5-{6-[2-(4-methoxy-2-methyl-indol-1-yl)-ethylamino]-pyrimidin-4-yl}-thiophene-2-carboxylic acid (*1) | 0.98 (C) | 453.3 |
| 217 | 4-{6-[2-(7-Chloro-2,4-dimethyl-indol-1-yl)-ethylamino]-pyrimidin-4-yl}-2-methylsulfanyl-benzoic acid (*1) | 1.06 (C) | 467.3 |
| 218 | 2-Fluoro-4-{6-[2-(7-fluoro-2,4-dimethyl-indol-1-yl)-ethylamino]-pyrimidin-4-yl}-6-methyl-benzoic acid (*1) | 0.97 (C) | 437.3 |
| 219 | 2-Ethyl-4-{6-[2-(6-fluoro-2,4-dimethyl-indol-1-yl)-ethylamino]-pyrimidin-4-yl}-benzoic acid (*1) | 0.96 (C) | 433.4 |
| 220 | 2-Ethyl-4-{6-[2-(7-fluoro-2,4-dimethyl-indol-1-yl)-ethylamino]-pyrimidin-4-yl}-benzoic acid (*1) | 0.98 (C) | 433.4 |
| 221 | 4-{6-[2-(4,7-Dichloro-2-methyl-indol-1-yl)-ethylamino]-pyrimidin-4-yl}-2-methylsulfanyl-benzoic acid (*1) | 1.12 (C) | 487.2 |
| 222 | 2,6-Dichloro-4-{6-[2-(7-fluoro-2,4-dimethyl-indol-1-yl)-ethylamino]-pyrimidin-4-yl}-benzoic acid (*1) | 1.10 (C) | 473.3 |

TABLE 8-continued

Examples 1-745

| Ex. | Compound | $t_R$ [min] (LC-MS) | MS Data m/z [M + H]+ |
|---|---|---|---|
| 223 | 2-Ethyl-4-{6-[2-(4-methoxy-2-methyl-indol-1-yl)-ethylamino]-pyrimidin-4-yl}-benzoic acid (*1) | 0.84 (C) | 431.4 |
| 224 | 5-{6-[2-(6-Chloro-2,4-dimethyl-indol-1-yl)-ethylamino]-pyrimidin-4-yl}-3-ethoxy-thiophene-2-carboxylic acid (*1) | 0.83 (A) | 471.07 |
| 225 | 5-{6-[2-(7-Chloro-4-methoxy-2-methyl-indol-1-yl)-ethylamino]-pyrimidin-4-yl}-3-ethyl-thiophene-2-carboxylic acid (*1) | 1.19 (C) | 471.3 |
| 226 | 2,6-Dichloro-4-{6-[2-(4-methoxy-2-methyl-indol-1-yl)-ethylamino]-pyrimidin-4-yl}-benzoic acid (*1) | 0.91 (C) | 471.3 |
| 227 | 3-Ethoxy-5-{6-[2-(7-fluoro-2,4-dimethyl-indol-1-yl)-ethylamino]-pyrimidin-4-yl}-thiophene-2-carboxylic acid (*1) | 1.12 (C) | 455.3 |
| 228 | 3-Ethoxy-5-{6-[2-(7-fluoro-2,5-dimethyl-indol-1-yl)-ethylamino]-pyrimidin-4-yl}-thiophene-2-carboxylic acid (*1) | 1.13 (C) | 455.3 |
| 229 | 3-Ethoxy-5-{6-[2-(6-fluoro-2,4-dimethyl-indol-1-yl)-ethylamino]-pyrimidin-4-yl}-thiophene-2-carboxylic acid (*1) | 1.10 (C) | 455.3 |
| 230 | 3-Ethyl-5-{6-[2-(7-fluoro-4-methoxy-2-methyl-indol-1-yl)-ethylamino]-pyrimidin-4-yl}-thiophene-2-carboxylic acid (*1) | 1.11 (C) | 455.3 |
| 231 | 3-Ethyl-5-{6-[2-(7-fluoro-5-methoxy-2-methyl-indol-1-yl)-ethylamino]-pyrimidin-4-yl}-thiophene-2-carboxylic acid (*1) | 1.12 (C) | 455.3 |
| 232 | 4-{6-[2-(6-Fluoro-2,4-dimethyl-indol-1-yl)-ethylamino]-pyrimidin-4-yl}-2-methoxy-benzoic acid (*1) | 0.90 (C) | 435.3 |
| 233 | 4-{6-[2-(7-Fluoro-4-methoxy-2-methyl-indol-1-yl)-ethylamino]-pyrimidin-4-yl}-2-methyl-benzoic acid (*1) | 0.85 (C) | 435.3 |
| 234 | 4-{6-[2-(4-Chloro-2-methyl-indol-1-yl)-ethylamino]-pyrimidin-4-yl}-2-ethoxy-benzoic acid (*1) | 0.99 (C) | 451.3 |
| 235 | 5-{6-[2-(4,5-Difluoro-2-methyl-indol-1-yl)-ethylamino]-pyrimidin-4-yl}-3-ethoxy-thiophene-2-carboxylic acid (*1) | 1.07 (C) | 459.3 |
| 236 | 5-{6-[2-(6,7-Dichloro-2-methyl-indol-1-yl)-ethylamino]-pyrimidin-4-yl}-3-ethoxy-thiophene-2-carboxylic acid (*1) | 1.21 (C) | 491.3 |
| 237 | 5-{6-[2-(5-Chloro-7-fluoro-2-methyl-indol-1-yl)-ethylamino]-pyrimidin-4-yl}-3-ethoxy-thiophene-2-carboxylic acid (*1) | 1.16 (C) | 475.3 |
| 238 | 5-{6-[2-(4,6-Dichloro-2-methyl-indol-1-yl)-ethylamino]-pyrimidin-4-yl}-3-ethoxy-thiophene-2-carboxylic acid (*1) | 1.22 (C) | 491.3 |
| 239 | 5-{6-[2-(4-Chloro-6-fluoro-2-methyl-indol-1-yl)-ethylamino]-pyrimidin-4-yl}-3-ethoxy-thiophene-2-carboxylic acid (*1) | 1.15 (C) | 475.3 |
| 240 | 5-{6-[2-(4-Chloro-7-fluoro-2-methyl-indol-1-yl)-ethylamino]-pyrimidin-4-yl}-3-ethoxy-thiophene-2-carboxylic acid (*1) | 1.15 (C) | 475.3 |
| 241 | 3-Ethyl-5-{6-[2-(7-fluoro-2,5-dimethyl-indol-1-yl)-ethylamino]-pyrimidin-4-yl}-thiophene-2-carboxylic acid (*2) | 1.22 (C) | 439.3 |
| 242 | 5-{6-[2-(5-Chloro-7-fluoro-2-methyl-indol-1-yl)-ethylamino]-pyrimidin-4-yl}-3-ethyl-thiophene-2-carboxylic acid (*2) | 1.24 (C) | 459.3 |
| 243 | 4-{6-[2-(4,7-Difluoro-2-methyl-indol-1-yl)-ethylamino]-pyrimidin-4-yl}-2-ethylamino-benzoic acid (*1) | 0.97 (C) | 452.4 |
| 244 | 2-Ethylamino-4-{6-[2-(6-fluoro-2,4-dimethyl-indol-1-yl)-ethylamino]-pyrimidin-4-yl}-benzoic acid (*1) | 0.96 (C) | 448.4 |
| 245 | 2-Ethylamino-4-{6-[2-(7-fluoro-2,4-dimethyl-indol-1-yl)-ethylamino]-pyrimidin-4-yl}-benzoic acid (*1) | 0.98 (C) | 448.4 |
| 246 | 2-Ethylamino-4-{6-[2-(4-fluoro-2,7-dimethyl-indol-1-yl)-ethylamino]-pyrimidin-4-yl}-benzoic acid (*1) | 0.99 (C) | 448.4 |
| 247 | 2-Ethylamino-4-{6-[2-(7-methoxy-2-methyl-indol-1-yl)-ethylamino]-pyrimidin-4-yl}-benzoic acid (*1) | 0.91 (C) | 446.4 |
| 248 | 2-Ethylamino-4-{6-[2-(4-methoxy-2-methyl-indol-1-yl)-ethylamino]-pyrimidin-4-yl}-benzoic acid (*1) | 0.85 (C) | 446.4 |
| 249 | 5-{6-[2-(2-Cyano-6-fluoro-4-methyl-indol-1-yl)-ethylamino]-pyrimidin-4-yl}-3-ethoxy-thiophene-2-carboxylic acid (*1) | 0.81 (A) | 465.86 |
| 250 | 4-{6-[2-(7-Chloro-4-methoxy-2-methyl-indol-1-yl)-ethylamino]-pyrimidin-4-yl}-2-methylamino-benzoic acid (*1) | 0.90 (C) | 466.3 |
| 251 | 4-{6-[2-(7-Fluoro-4-methoxy-2-methyl-indol-1-yl)-ethylamino]-pyrimidin-4-yl}-2-methylamino-benzoic acid (*1) | 0.84 (C) | 450.4 |
| 252 | 4-{6-[2-(4-Fluoro-7-methoxy-2-methyl-indol-1-yl)-ethylamino]-pyrimidin-4-yl}-2-methylamino-benzoic acid (*1) | 0.88 (C) | 450.4 |
| 253 | 2-Ethoxy-4-{6-[2-(4-methoxy-2-methyl-indol-1-yl)-ethylamino]-pyrimidin-4-yl}-benzoic acid (*1) | 0.85 (C) | 447.4 |
| 254 | 2-Methoxy-4-{6-[2-(4-methoxy-2-methyl-indol-1-yl)-ethylamino]-pyrimidin-4-yl}-6-methyl-benzoic acid (*1) | 0.74 (C) | 447.4 |
| 255 | 2-Ethoxy-4-{6-[2-(6-methoxy-2-methyl-indol-1-yl)-ethylamino]-pyrimidin-4-yl}-benzoic acid (*1) | 0.87 (C) | 447.4 |
| 256 | 5-{6-[2-(7-Chloro-4-methoxy-2-methyl-indol-1-yl)-ethylamino]-pyrimidin-4-yl}-3-ethoxy-thiophene-2-carboxylic acid (*1) | 1.10 (C) | 487.3 |
| 257 | 3-Ethoxy-5-{6-[2-(6-fluoro-4-methoxy-2-methyl-indol-1-yl)-ethylamino]-pyrimidin-4-yl}-thiophene-2-carboxylic acid (*1) | 1.03 (C) | 471.3 |
| 258 | 3-Ethoxy-5-{6-[2-(7-fluoro-4-methoxy-2-methyl-indol-1-yl)-ethylamino]-pyrimidin-4-yl}-thiophene-2-carboxylic acid (*1) | 1.03 (C) | 471.3 |
| 259 | 3-Ethoxy-5-{6-[2-(7-fluoro-5-methoxy-2-methyl-indol-1-yl)-ethylamino]-pyrimidin-4-yl}-thiophene-2-carboxylic acid (*1) | 1.04 (C) | 471.3 |

TABLE 8-continued

Examples 1-745

| Ex. | Compound | $t_R$ [min] (LC-MS) | MS Data m/z [M + H]$^+$ |
|---|---|---|---|
| 260 | 4-{6-[2-(7-Fluoro-4-methoxy-2-methyl-indol-1-yl)-ethylamino]-pyrimidin-4-yl}-2-methoxy-benzoic acid (*1) | 0.83 (C) | 451.3 |
| 261 | 3-Ethoxy-5-{6-[2-(4-methoxy-2,7-dimethyl-indol-1-yl)-ethylamino]-pyrimidin-4-yl}-thiophene-2-carboxylic acid (*1) | 1.04 (C) | 467.3 |
| 262 | 4-{6-[2-(2,5-Dimethyl-indol-1-yl)-ethylamino]-pyrimidin-4-yl}-2-isobutyl-benzoic acid (*1) | 1.06 (C) | 443.4 |
| 263 | 4-{6-[2-(5-Chloro-7-fluoro-2-methyl-indol-1-yl)-ethylamino]-pyrimidin-4-yl}-2-propyl-benzoic acid (*1) | 1.10 (C) | 467.3 |
| 264 | 2-Chloro-6-ethyl-4-{6-[2-(6-fluoro-2,4-dimethyl-indol-1-yl)-ethylamino]-pyrimidin-4-yl}-benzoic acid (*1) | 1.04 (C) | 467.3 |
| 265 | 2-Ethyl-6-fluoro-4-{6-[2-(7-fluoro-2,4-dimethyl-indol-1-yl)-ethylamino]-pyrimidin-4-yl}-benzoic acid (*1) | 1.04 (C) | 451.4 |
| 266 | 4-{6-[2-(7-Chloro-2,5-dimethyl-indol-1-yl)-ethylamino]-pyrimidin-4-yl}-2-propyl-benzoic acid (*1) | 1.13 (C) | 463.4 |
| 267 | 4-{6-[2-(7-Fluoro-2,5-dimethyl-indol-1-yl)-ethylamino]-pyrimidin-4-yl}-2-propyl-benzoic acid (*1) | 1.05 (C) | 447.4 |
| 268 | 4-{6-[2-(4-Chloro-2-methyl-indol-1-yl)-ethylamino]-pyrimidin-4-yl}-2-isobutyl-benzoic acid (*1) | 1.10 (C) | 463.4 |
| 269 | 5-{6-[2-(6-Fluoro-2,4-dimethyl-indol-1-yl)-ethylamino]-pyrimidin-4-yl}-3-trifluoromethyl-thiophene-2-carboxylic acid (*1) | 1.27 (C) | 479.3 |
| 270 | 4-{6-[2-(7-Chloro-5-fluoro-2,4-dimethyl-indol-1-yl)-ethylamino]-pyrimidin-4-yl}-2-methylsulfanyl-benzoic acid (*1) | 1.09 (C) | 485.3 |
| 271 | 4-{6-[2-(4-Methoxy-2-methyl-indol-1-yl)-ethylamino]-pyrimidin-4-yl}-2-propyl-benzoic acid (*1) | 0.91 (C) | 445.4 |
| 272 | 5-{6-[2-(6,7-Dichloro-5-fluoro-2-methyl-indol-1-yl)-ethylamino]-pyrimidin-4-yl}-3-ethoxy-thiophene-2-carboxylic acid (*1) | 1.22 (C) | 509.2 |
| 273 | 3-Ethoxy-5-{6-[2-(5,6,7-trifluoro-2-methyl-indol-1-yl)-ethylamino]-pyrimidin-4-yl}-thiophene-2-carboxylic acid (*1) | 1.12 (C) | 477.3 |
| 274 | 3-Ethoxy-5-{6-[2-(4,6,7-trifluoro-2-methyl-indol-1-yl)-ethylamino]-pyrimidin-4-yl}-thiophene-2-carboxylic acid (*1) | 0.83 (A) | 477.04 |
| 275 | 3-Ethoxy-5-{6-[2-(4,5,7-trifluoro-2-methyl-indol-1-yl)-ethylamino]-pyrimidin-4-yl}-thiophene-2-carboxylic acid (*1) | 1.12 (C) | 477.3 |
| 276 | 4-{6-[2-(7-Chloro-4-methoxy-2-methyl-indol-1-yl)-ethylamino]-pyrimidin-4-yl}-2-fluoro-6-methyl-benzoic acid (*1) | 0.96 (C) | 469.3 |
| 277 | 2-Fluoro-4-{6-[2-(7-fluoro-4-methoxy-2-methyl-indol-1-yl)-ethylamino]-pyrimidin-4-yl}-6-methyl-benzoic acid (*1) | 0.88 (C) | 453.3 |
| 278 | 4-{6-[2-(4,5-Difluoro-2-methyl-indol-1-yl)-ethylamino]-pyrimidin-4-yl}-2-ethoxy-benzoic acid (*1) | 0.96 (C) | 453.4 |
| 279 | 4-{6-[2-(4,6-Dichloro-2-methyl-indol-1-yl)-ethylamino]-pyrimidin-4-yl}-2-ethoxy-benzoic acid (*1) | 1.13 (C) | 485.3 |
| 280 | 4-{6-[2-(4-Chloro-6-fluoro-2-methyl-indol-1-yl)-ethylamino]-pyrimidin-4-yl}-2-ethoxy-benzoic acid (*1) | 1.05 (C) | 469.3 |
| 281 | 4-{6-[2-(4-Chloro-7-fluoro-2-methyl-indol-1-yl)-ethylamino]-pyrimidin-4-yl}-2-ethoxy-benzoic acid (*1) | 1.04 (C) | 469.3 |
| 282 | 2-Ethoxy-4-{6-[2-(6-fluoro-2,4-dimethyl-indol-1-yl)-ethylamino]-pyrimidin-4-yl}-benzoic acid (*1) | 0.98 (C) | 449.4 |
| 283 | 2-Ethyl-4-{6-[2-(6-fluoro-4-methoxy-2-methyl-indol-1-yl)-ethylamino]-pyrimidin-4-yl}-benzoic acid (*1) | 0.90 (C) | 449.4 |
| 284 | 4-{6-[2-(7-Chloro-2,5-dimethyl-indol-1-yl)-ethylamino]-pyrimidin-4-yl}-2-ethoxy-benzoic acid (*1) | 1.07 (C) | 465.4 |
| 285 | 2-Ethoxy-4-{6-[2-(7-fluoro-2,5-dimethyl-indol-1-yl)-ethylamino]-pyrimidin-4-yl}-benzoic acid (*1) | 1.00 (C) | 449.4 |
| 286 | 4-{6-[2-(7-Fluoro-2,4-dimethyl-indol-1-yl)-ethylamino]-pyrimidin-4-yl}-2-methoxy-6-methyl-benzoic acid (*1) | 0.87 (C) | 449.4 |
| 287 | 4-{6-[2-(7-Chloro-4-methoxy-2-methyl-indol-1-yl)-ethylamino]-pyrimidin-4-yl}-2,6-dimethyl-benzoic acid (*1) | 0.86 (C) | 465.4 |
| 288 | 4-{6-[2-(7-Chloro-4-methoxy-2-methyl-indol-1-yl)-ethylamino]-pyrimidin-4-yl}-2-ethyl-benzoic acid (*1) | 0.97 (C) | 465.4 |
| 289 | 4-{6-[2-(7-Fluoro-4-methoxy-2-methyl-indol-1-yl)-ethylamino]-pyrimidin-4-yl}-2,6-dimethyl-benzoic acid (*1) | 0.80 (C) | 449.4 |
| 290 | 2-Ethyl-4-{6-[2-(7-fluoro-4-methoxy-2-methyl-indol-1-yl)-ethylamino]-pyrimidin-4-yl}-benzoic acid (*1) | 0.90 (C) | 449.4 |
| 291 | 2,6-Dichloro-4-{6-[2-(6-fluoro-4-methoxy-2-methyl-indol-1-yl)-ethylamino]-pyrimidin-4-yl}-benzoic acid (*1) | 0.99 (C) | 489.3 |
| 292 | 2,6-Dichloro-4-{6-[2-(7-chloro-4-methoxy-2-methyl-indol-1-yl)-ethylamino]-pyrimidin-4-yl}-benzoic acid (*1) | 1.09 (C) | 505.2 |
| 293 | 2,6-Dichloro-4-{6-[2-(7-fluoro-4-methoxy-2-methyl-indol-1-yl)-ethylamino]-pyrimidin-4-yl}-benzoic acid (*1) | 0.99 (C) | 489.3 |
| 294 | 5-{6-[2-(6,7-Difluoro-2,4-dimethyl-indol-1-yl)-ethylamino]-pyrimidin-4-yl}-3-ethoxy-thiophene-2-carboxylic acid (*1) | 1.14 (C) | 473.3 |
| 295 | 4-{6-[2-(5-Chloro-7-methyl-[1,3]dioxolo[4,5-e]indol-6-yl)-ethylamino]-pyrimidin-4-yl}-2-ethyl-benzoic acid | 0.95 (C) | 479.3 |
| 296 | 2-Cyclopropyl-4-{6-[2-(7-fluoro-4-methoxy-2-methyl-indol-1-yl)-ethylamino]-pyrimidin-4-yl}-benzoic acid | 0.90 (C) | 461.4 |

TABLE 8-continued

Examples 1-745

| Ex. | Compound | $t_R$ [min] (LC-MS) | MS Data m/z [M + H]$^+$ |
|---|---|---|---|
| 297 | [2-(6-Fluoro-2,4-dimethyl-indol-1-yl)-ethyl]-[6-(2-trifluoromethyl-1H-benzoimidazol-5-yl)-pyrimidin-4-yl]-amine | 0.76 (A) | 469.27 |
| 298 | {6-[4-(2-Amino-5-methyl-thiazol-4-yl)-phenyl]-pyrimidin-4-yl}-[2-(7-fluoro-2,4-dimethyl-indol-1-yl)-ethyl]-amine | 0.82 (C) | 473.4 |
| 299 | [2-(6,7-Difluoro-4-methoxy-2-methyl-indol-1-yl)-ethyl]-[6-(4-[1,2,4]oxadiazol-5-yl-phenyl)-pyrimidin-4-yl]-amine | 0.89 (C) | 463.3 |
| 300 | {6-[3-Fluoro-4-(5-methyl-[1,3,4]oxadiazol-2-yl)-phenyl]-pyrimidin-4-yl}-[2-(4-methoxy-2-methyl-indol-1-yl)-ethyl]-amine | 0.96 (C) | 459.4 |
| 301 | [2-(6-Fluoro-4-methoxy-2-methyl-indol-1-yl)-ethyl]-{6-[4-(3-methyl-[1,2,4]oxadiazol-5-yl)-phenyl]-pyrimidin-4-yl}-amine | 1.06 (C) | 459.4 |
| 302 | [2-(7-Fluoro-4-methoxy-2-methyl-indol-1-yl)-ethyl]-{6-[4-(3-methyl-[1,2,4]oxadiazol-5-yl)-phenyl]-pyrimidin-4-yl}-amine | 1.07 (C) | 459.4 |
| 303 | [2-(7-Fluoro-4-methoxy-2-methyl-indol-1-yl)-ethyl]-{6-[4-(5-methyl-[1,2,4]oxadiazol-3-yl)-phenyl]-pyrimidin-4-yl}-amine | 1.00 (C) | 459.4 |
| 304 | {6-[4-(3-Amino-isoxazol-5-yl)-phenyl]-pyrimidin-4-yl}-[2-(7-fluoro-4-methoxy-2-methyl-indol-1-yl)-ethyl]-amine | 0.82 (C) | 459.4 |
| 305 | [2-(6-Fluoro-2,4-dimethyl-indol-1-yl)-ethyl]-{6-[3-fluoro-4-(5-methyl-[1,3,4]oxadiazol-2-yl)-phenyl]-pyrimidin-4-yl}-amine | 1.09 (C) | 461.4 |
| 306 | [2-(7-Fluoro-2,4-dimethyl-indol-1-yl)-ethyl]-{6-[3-fluoro-4-(5-methyl-[1,3,4]oxadiazol-2-yl)-phenyl]-pyrimidin-4-yl}-amine | 1.11 (C) | 461.4 |
| 307 | [2-(6,7-Difluoro-4-methoxy-2-methyl-indol-1-yl)-ethyl]-{6-[4-(1H-imidazol-4-yl)-phenyl]-pyrimidin-4-yl}-amine | 0.63 (C) | 461.4 |
| 308 | [6-(3-Fluoro-4-pyrazol-1-ylmethyl-phenyl)-pyrimidin-4-yl]-[2-(4-methoxy-2-methyl-indol-1-yl)-ethyl]-amine | 0.93 (C) | 457.4 |
| 309 | [2-(6-Fluoro-4-methoxy-2-methyl-indol-1-yl)-ethyl]-{6-[4-(1-methyl-1H-pyrazol-3-yl)-phenyl]-pyrimidin-4-yl}-amine | 0.74 (A) | 457.06 |
| 310 | [2-(7-Fluoro-4-methoxy-2-methyl-indol-1-yl)-ethyl]-{6-[4-(3-methyl-pyrazol-1-yl)-phenyl]-pyrimidin-4-yl}-amine | 0.95 (C) | 457.4 |
| 311 | {6-[4-(2-Amino-5-methyl-thiazol-4-yl)-phenyl]-pyrimidin-4-yl}-[2-(4-methoxy-2-methyl-indol-1-yl)-ethyl]-amine | 0.71 (C) | 471.4 |
| 312 | 3-(4-{6-[2-(6-Fluoro-4-methoxy-2-methyl-indol-1-yl)-ethylamino]-pyrimidin-4-yl}-phenyl)-4H-[1,2,4]oxadiazol-5-one | 0.72 (A) | 461.04 |
| 313 | 3-(4-{6-[2-(7-Fluoro-4-methoxy-2-methyl-indol-1-yl)-ethylamino]-pyrimidin-4-yl}-phenyl)-4H-[1,2,4]oxadiazol-5-one | 0.90 (C) | 461.4 |
| 314 | rac-5-{6-[2-(4-Methoxy-2-methyl-indol-1-yl)-ethylamino]-pyrimidin-4-yl}-3-propyl-2,3-dihydro-isoindol-1-one | 0.85 (C) | 456.4 |
| 315 | 5-{6-[2-(4-Methoxy-2-methyl-indol-1-yl)-ethylamino]-pyrimidin-4-yl}-2-propyl-2,3-dihydro-isoindol-1-one | 0.86 (C) | 456.4 |
| 316 | {6-[4-(1,1-Dioxo-1l6-isothiazolidin-2-yl)-phenyl]-pyrimidin-4-yl}-[2-(7-fluoro-2,4-dimethyl-indol-1-yl)-ethyl]-amine | 0.84 (C) | 480.4 |
| 317 | 1-(4-{6-[2-(6-Fluoro-4-methoxy-2-methyl-indol-1-yl)-ethylamino]-pyrimidin-4-yl}-phenyl)-pyrrolidin-2-one | 0.79 (C) | 460.4 |
| 318 | 1-(4-{6-[2-(7-Fluoro-4-methoxy-2-methyl-indol-1-yl)-ethylamino]-pyrimidin-4-yl}-phenyl)-pyrrolidin-2-one | 0.79 (C) | 460.4 |
| 319 | rac-3-Ethyl-5-{6-[2-(7-fluoro-4-methoxy-2-methyl-indol-1-yl)-ethylamino]-pyrimidin-4-yl}-2,3-dihydro-isoindol-1-one | 0.84 (C) | 460.4 |
| 320 | 2-Ethyl-5-{6-[2-(7-fluoro-4-methoxy-2-methyl-indol-1-yl)-ethylamino]-pyrimidin-4-yl}-2,3-dihydro-isoindol-1-one | 0.85 (C) | 460.4 |
| 321 | [2-(7-Fluoro-4-methoxy-2-methyl-indol-1-yl)-ethyl]-{6-[4-(2-methyl-thiazol-4-yl)-phenyl]-pyrimidin-4-yl}-amine | 0.97 (C) | 474.4 |
| 322 | rac-5-{6-[2-(7-Fluoro-2,4-dimethyl-indol-1-yl)-ethylamino]-pyrimidin-4-yl}-3-propyl-2,3-dihydro-isoindol-1-one | 0.98 (C) | 458.4 |
| 323 | 4-{6-[2-(7-Fluoro-4-methoxy-2-methyl-indol-1-yl)-ethylamino]-pyrimidin-4-yl}-1H-indole-7-carboxylic acid | 0.77 (C) | 460.4 |
| 324 | [2-(7-Fluoro-2,4-dimethyl-indol-1-yl)-ethyl]-{6-[4-(5-methylamino-[1,3,4]thiadiazol-2-yl)-phenyl]-pyrimidin-4-yl}-amine | 0.74 (A) | 474.20 |
| 325 | [6-(2,3-Dihydro-benzofuran-5-yl)-pyrimidin-4-yl]-[2-(7-fluoro-4-methoxy-2-methyl-indol-1-yl)-ethyl]-amine (*2) | 0.80 (C) | 419.4 |
| 326 | 2-Ethoxy-4-{6-[2-(7-fluoro-4-methoxy-2-methyl-indol-1-yl)-ethylamino]-pyrimidin-4-yl}-benzoic acid | 0.91 (C) | 465.4 |
| 327 | 4-{6-[2-(4-Ethyl-2-methyl-indol-1-yl)-ethylamino]-pyrimidin-4-yl}-2-isobutyl-benzoic acid | 1.11 (C) | 457.4 |
| 328 | 2-Isobutyl-4-{6-[2-(2,4,7-trimethyl-indol-1-yl)-ethylamino]-pyrimidin-4-yl}-benzoic acid | 1.12 (C) | 457.4 |
| 329 | 4-{6-[2-(2,4-Dimethyl-indol-1-yl)-ethylamino]-pyrimidin-4-yl}-2-(3-methyl-butyl)-benzoic acid | 1.13 (C) | 457.4 |
| 330 | 4-{6-[2-(7-Chloro-5-fluoro-2,4-dimethyl-indol-1-yl)-ethylamino]-pyrimidin-4-yl}-2-fluoro-6-methylsulfanyl-benzoic acid | 1.15 (C) | 503.3 |
| 331 | 2-Chloro-4-{6-[2-(7-chloro-5-fluoro-2,4-dimethyl-indol-1-yl)-ethylamino]-pyrimidin-4-yl}-6-methylsulfanyl-benzoic acid | 1.17 (C) | 519.3 |
| 332 | 4-{6-[2-(4,7-Difluoro-2-methyl-indol-1-yl)-ethylamino]-pyrimidin-4-yl}-2-isobutyl-benzoic acid | 1.09 (C) | 465.4 |
| 333 | 4-{6-[2-(5,7-Difluoro-2-methyl-indol-1-yl)-ethylamino]-pyrimidin-4-yl}-2-isobutyl-benzoic acid | 1.09 (C) | 465.4 |

TABLE 8-continued

Examples 1-745

| Ex. | Compound | $t_R$ [min] (LC-MS) | MS Data m/z $[M + H]^+$ |
|---|---|---|---|
| 334 | 4-{6-[2-(7-Chloro-2,4-dimethyl-indol-1-yl)-ethylamino]-pyrimidin-4-yl}-2-propylsulfanyl-benzoic acid | 1.20 (C) | 495.3 |
| 335 | 2-Chloro-4-{6-[2-(7-chloro-2,5-dimethyl-indol-1-yl)-ethylamino]-pyrimidin-4-yl}-6-propyl-benzoic acid | 1.23 (C) | 497.3 |
| 336 | 4-{6-[2-(7-Fluoro-2,4-dimethyl-indol-1-yl)-ethylamino]-pyrimidin-4-yl}-2-isobutyl-benzoic acid | 1.11 (C) | 461.4 |
| 337 | rac-2-sec-Butyl-4-{6-[2-(7-fluoro-2,4-dimethyl-indol-1-yl)-ethylamino]-pyrimidin-4-yl}-benzoic acid | 1.08 (C) | 461.4 |
| 338 | 4-{6-[2-(4-Ethyl-7-fluoro-2-methyl-indol-1-yl)-ethylamino]-pyrimidin-4-yl}-2-propyl-benzoic acid | 1.11 (C) | 461.4 |
| 339 | 2-Chloro-4-{6-[2-(7-chloro-4,5-difluoro-2-methyl-indol-1-yl)-ethylamino]-pyrimidin-4-yl}-6-methylsulfanyl-benzoic acid | 1.17 (C) | 523.2 |
| 340 | 4-{6-[2-(7-Chloro-4-fluoro-2-methyl-indol-1-yl)-ethylamino]-pyrimidin-4-yl}-2-fluoro-6-propyl-benzoic acid | 1.17 (C) | 485.3 |
| 341 | 4-{6-[2-(7-Chloro-5-fluoro-2,4-dimethyl-indol-1-yl)-ethylamino]-pyrimidin-4-yl}-2-ethylsulfanyl-benzoic acid | 1.16 (C) | 499.3 |
| 342 | 2-Chloro-4-{6-[2-(7-chloro-4-fluoro-2-methyl-indol-1-yl)-ethylamino]-pyrimidin-4-yl}-6-propyl-benzoic acid | 1.20 (C) | 501.3 |
| 343 | 2-Isobutyl-4-{6-[2-(6-methoxy-2-methyl-indol-1-yl)-ethylamino]-pyrimidin-4-yl}-benzoic acid | 0.98 (C) | 459.4 |
| 344 | 4-{6-[2-(7-Chloro-5-fluoro-2,4-dimethyl-indol-1-yl)-ethylamino]-pyrimidin-4-yl}-2-ethoxy-benzoic acid | 1.09 (C) | 483.3 |
| 345 | 2-Chloro-4-{6-[2-(7-chloro-4-methoxy-2-methyl-indol-1-yl)-ethylamino]-pyrimidin-4-yl}-6-ethyl-benzoic acid | 1.05 (C) | 499.3 |
| 346 | 2-Chloro-6-ethyl-4-{6-[2-(7-fluoro-4-methoxy-2-methyl-indol-1-yl)-ethylamino]-pyrimidin-4-yl}-benzoic acid | 0.97 (C) | 483.4 |
| 347 | 2-Ethoxy-4-{6-[2-(7-fluoro-2,4-dimethyl-indol-1-yl)-ethylamino]-pyrimidin-4-yl}-6-methyl-benzoic acid | 0.92 (C) | 463.4 |
| 348 | 4-{6-[2-(7-Fluoro-4-methoxy-2-methyl-indol-1-yl)-ethylamino]-pyrimidin-4-yl}-2-propyl-benzoic acid | 0.97 (C) | 463.4 |
| 349 | 4-{6-[2-(6-Chloro-2,4-dimethyl-indol-1-yl)-ethylamino]-pyrimidin-4-yl}-2-difluoromethoxy-benzoic acid | 0.78 (A) | 487.03 |
| 350 | 4-{6-[2-(7-Chloro-4,5-difluoro-2-methyl-indol-1-yl)-ethylamino]-pyrimidin-4-yl}-2-ethoxy-benzoic acid | 1.09 (C) | 487.3 |
| 351 | 4-{6-[2-(4,7-Dichloro-5-fluoro-2-methyl-indol-1-yl)-ethylamino]-pyrimidin-4-yl}-2-ethoxy-benzoic acid | 1.14 (C) | 503.3 |
| 352 | [2-(4-Methoxy-2-methyl-indol-1-yl)-ethyl]-[6-(2-methyl-1H-benzoimidazol-5-yl)-pyrimidin-4-yl]-amine (*2) | 0.54 (C) | 413.3 |
| 353 | 2-Chloro-6-ethylamino-4-{6-[2-(7-fluoro-2,4-dimethyl-indol-1-yl)-ethylamino]-pyrimidin-4-yl}-benzoic acid | 1.04 (C) | 482.4 |
| 354 | 2-Cyclopropyl-4-{6-[2-(6-fluoro-2,4-dimethyl-indol-1-yl)-ethylamino]-pyrimidin-4-yl}-benzoic acid (*1) | 0.96 (C) | 445.4 |
| 355 | [2-(7-Fluoro-2,4-dimethyl-indol-1-yl)-ethyl]-(6-quinolin-6-yl-pyrimidin-4-yl)-amine (*2) | 0.72 (A) | 412.11 |
| 356 | 4-{6-[2-(7-Fluoro-2,4-dimethyl-indol-1-yl)-ethylamino]-pyrimidin-4-yl}-2-propylamino-benzoic acid | 1.05 (C) | 462.4 |
| 357 | [2-(7-Fluoro-2,4-dimethyl-indol-1-yl)-ethyl]-(6-isoquinolin-7-yl-pyrimidin-4-yl)-amine (*2) | 0.68 (A) | 412.06 |
| 358 | [6-(3-Ethoxy-4-methylaminomethyl-phenyl)-pyrimidin-4-yl]-[2-(7-fluoro-4-methoxy-2-methyl-indol-1-yl)-ethyl]-amine | 0.62 (C) | 464.4 |
| 359 | 2,6-Difluoro-4-{6-[2-(7-fluoro-4-methoxy-2-methyl-indol-1-yl)-ethylamino]-pyrimidin-4-yl}-benzenesulfonamide | 0.98 (C) | 492.3 |
| 360 | 4-{6-[2-(7-Fluoro-4-methoxy-2-methyl-indol-1-yl)-ethylamino]-pyrimidin-4-yl}-2,N-dimethyl-benzenesulfonamide | 0.93 (C) | 484.4 |
| 361 | 4-{6-[2-(7-Fluoro-4-methoxy-2-methyl-indol-1-yl)-ethylamino]-pyrimidin-4-yl}-N-(2-hydroxy-ethyl)-benzamide | 0.71 (C) | 464.4 |
| 362 | 2-Chloro-6-ethylamino-4-{6-[2-(4-methoxy-2-methyl-indol-1-yl)-ethylamino]-pyrimidin-4-yl}-benzoic acid | 0.89 (C) | 480.3 |
| 363 | {6-[4-(5-Amino-[1,3,4]thiadiazol-2-yl)-phenyl]-pyrimidin-4-yl}-[2-(2-methyl-indol-1-yl)-ethyl]-amine (*2) | 0.66 (A) | 428.14 |
| 364 | 4-{6-[2-(5,7-Difluoro-4-methoxy-2-methyl-indol-1-yl)-ethylamino]-pyrimidin-4-yl}-2-ethoxy-benzoic acid | 0.95 (C) | 483.4 |
| 365 | 4-{6-[2-(7-Chloro-4-methoxy-2-methyl-indol-1-yl)-ethylamino]-pyrimidin-4-yl}-2-ethoxy-6-methyl-benzoic acid | 0.91 (C) | 495.4 |
| 366 | 2-Ethoxy-4-{6-[2-(7-fluoro-4-methoxy-2-methyl-indol-1-yl)-ethylamino]-pyrimidin-4-yl}-6-methyl-benzoic acid | 0.85 (C) | 479.4 |
| 367 | 4-{6-[2-(4,7-Difluoro-2-methyl-indol-1-yl)-ethylamino]-pyrimidin-4-yl}-2-(3-methyl-butyl)-benzoic acid | 1.17 (C) | 479.4 |
| 368 | 4-{6-[2-(7-Chloro-2,4-dimethyl-indol-1-yl)-ethylamino]-pyrimidin-4-yl}-2-isobutylsulfanyl-benzoic acid | 1.26 (C) | 509.3 |
| 369 | 4-{6-[2-(7-Fluoro-2,4-dimethyl-indol-1-yl)-ethylamino]-pyrimidin-4-yl}-2-(3-methyl-butyl)-benzoic acid | 1.18 (C) | 475.4 |
| 370 | 4-{6-[2-(4,7-Dichloro-2-methyl-indol-1-yl)-ethylamino]-pyrimidin-4-yl}-2-isobutylsulfanyl-benzoic acid | 1.32 (C) | 529.3 |

TABLE 8-continued

Examples 1-745

| Ex. | Compound | t_R [min] (LC-MS) | MS Data m/z [M + H]+ |
|---|---|---|---|
| 371 | 4-{6-[2-(7-Chloro-5-fluoro-2,4-dimethyl-indol-1-yl)-ethylamino]-pyrimidin-4-yl}-2-propylsulfanyl-benzoic acid | 1.22 (C) | 513.3 |
| 372 | 2-Chloro-4-{6-[2-(7-fluoro-5-methoxy-2-methyl-indol-1-yl)-ethylamino]-pyrimidin-4-yl}-6-propyl-benzoic acid | 1.05 (C) | 497.4 |
| 373 | 4-{6-[2-(5,7-Difluoro-4-methoxy-2-methyl-indol-1-yl)-ethylamino]-pyrimidin-4-yl}-2-propyl-benzoic acid | 1.01 (C) | 481.4 |
| 374 | 1-Ethyl-3-(4-{6-[2-(7-fluoro-2,4-dimethyl-indol-1-yl)-ethylamino]-pyrimidin-4-yl}-2-methoxy-phenyl)-urea | 0.84 (C) | 477.4 |
| 375 | 1-Ethyl-3-(2-methoxy-4-{6-[2-(4-methoxy-2-methyl-indol-1-yl)-ethylamino]-pyrimidin-4-yl}-phenyl)-urea | 0.74 (C) | 475.4 |
| 376 | [2-(7-Fluoro-4-methoxy-2-methyl-indol-1-yl)-ethyl]-(6-quinoxalin-6-yl-pyrimidin-4-yl)-amine (*2) | 0.70 (A) | 429.25 |
| 377 | 2-Ethoxy-4-{6-[2-(7-fluoro-4-methoxy-2-methyl-indol-1-yl)-ethylamino]-pyrimidin-4-yl}-benzenesulfonamide | 0.89 (C) | 500.4 |
| 378 | 1-(2-Fluoro-4-{6-[2-(7-fluoro-2,4-dimethyl-indol-1-yl)-ethylamino]-pyrimidin-4-yl}-phenyl)-cyclopropanecarboxylic acid (*1) | 1.01 (C) | 463.4 |
| 379 | 4-{6-[2-(7-Fluoro-2,4-dimethyl-indol-1-yl)-ethylamino]-pyrimidin-4-yl}-2-trifluoromethyl-benzenesulfonamide | 1.10 (C) | 508.3 |
| 380 | 4-{6-[2-(4-Methoxy-2-methyl-indol-1-yl)-ethylamino]-pyrimidin-4-yl}-2-trifluoromethyl-benzenesulfonamide | 0.98 (C) | 506.3 |
| 381 | 2-Chloro-6-ethylamino-4-{6-[2-(7-fluoro-4-methoxy-2-methyl-indol-1-yl)-ethylamino]-pyrimidin-4-yl}-benzoic acid | 0.95 (C) | 498.4 |
| 382 | 2-Cyclopropyl-4-{6-[2-(6-fluoro-4-methoxy-2-methyl-indol-1-yl)-ethylamino]-pyrimidin-4-yl}-benzoic acid (*1) | 0.89 (C) | 461.4 |
| 383 | [2-(7-Fluoro-4-methoxy-2-methyl-indol-1-yl)-ethyl]-(6-isoquinolin-7-yl-pyrimidin-4-yl)-amine (*2) | 0.64 (A) | 428.17 |
| 384 | [2-(7-Fluoro-4-methoxy-2-methyl-indol-1-yl)-ethyl]-(6-quinolin-6-yl-pyrimidin-4-yl)-amine (*2) | 0.68 (A) | 428.20 |
| 385 | {6-[4-(1-Amino-cyclopropyl)-phenyl]-pyrimidin-4-yl}-[2-(7-fluoro-4-methoxy-2-methyl-indol-1-yl)-ethyl]-amine (*2) | 0.56 (C) | 432.4 |
| 386 | 1-(2-Fluoro-4-{6-[2-(4-methoxy-2-methyl-indol-1-yl)-ethylamino]-pyrimidin-4-yl}-phenyl)-cyclopropanecarboxylic acid (*1) | 0.88 (C) | 461.4 |
| 387 | {6-[4-(5-Methylamino-[1,3,4]thiadiazol-2-yl)-phenyl]-pyrimidin-4-yl}-[2-(2-methyl-indol-1-yl)-ethyl]-amine (*2) | 0.69 (A) | 442.17 |
| 388 | 6-{6-[2-(7-Chloro-4-methoxy-2-methyl-indol-1-yl)-ethylamino]-pyrimidin-4-yl}-1H-indazole-3-carboxylic acid (*1) | 0.80 (C) | 477.3 |
| 389 | 6-{6-[2-(7-Fluoro-4-methoxy-2-methyl-indol-1-yl)-ethylamino]-pyrimidin-4-yl}-1H-indazole-3-carboxylic acid (*1) | 0.74 (C) | 461.3 |
| 390 | 2,6-Dichloro-4-{6-[2-(6-fluoro-2,4-dimethyl-indol-1-yl)-ethylamino]-pyrimidin-4-yl}-benzoic acid (*2) | 1.08 (C) | 473.3 |
| 391 | 5-{6-[2-(2-Cyano-6-fluoro-4-methoxy-indol-1-yl)-ethylamino]-pyrimidin-4-yl}-3-ethoxy-thiophene-2-carboxylic acid (*1) | 0.79 (A) | 481.81 |
| 392 | 2-Ethylamino-6-fluoro-4-{6-[2-(7-fluoro-2,4-dimethyl-indol-1-yl)-ethylamino]-pyrimidin-4-yl}-benzoic acid (*1) | 1.08 (C) | 466.4 |
| 393 | 4-{6-[2-(4-Cyano-7-fluoro-2-methyl-indol-1-yl)-ethylamino]-pyrimidin-4-yl}-2-propyl-benzoic acid (*1) | 0.95 (C) | 458.4 |
| 394 | 4-{6-[2-(7-Fluoro-4-methoxy-2-methyl-indol-1-yl)-ethylamino]-pyrimidin-4-yl}-2-nitro-benzoic acid (*1) | 0.98 (C) | 466.3 |
| 395 | 4-{6-[2-(2-Cyano-6-fluoro-4-methoxy-indol-1-yl)-ethylamino]-pyrimidin-4-yl}-2-ethoxy-benzoic acid (*1) | 0.73 (A) | 460.08 |
| 396 | 4-{6-[2-(7-Chloro-4-methoxy-2-methyl-indol-1-yl)-ethylamino]-pyrimidin-4-yl}-2-ethylamino-benzoic acid (*1) | 0.97 (C) | 480.4 |
| 397 | 2-Ethylamino-4-{6-[2-(7-fluoro-4-methoxy-2-methyl-indol-1-yl)-ethylamino]-pyrimidin-4-yl}-benzoic acid (*1) | 0.91 (C) | 464.4 |
| 398 | 2-Ethylamino-6-fluoro-4-{6-[2-(4-methoxy-2-methyl-indol-1-yl)-ethylamino]-pyrimidin-4-yl}-benzoic acid (*1) | 0.93 (C) | 464.4 |
| 399 | 2-Ethylamino-4-{6-[2-(4-fluoro-7-methoxy-2-methyl-indol-1-yl)-ethylamino]-pyrimidin-4-yl}-benzoic acid (*1) | 0.94 (C) | 464.4 |
| 400 | 4-{6-[2-(4-Methoxy-2-methyl-indol-1-yl)-ethylamino]-pyrimidin-4-yl}-2-propoxy-benzoic acid (*1) | 0.93 (C) | 461.4 |
| 401 | 2-Chloro-4-{6-[2-(7-fluoro-4-methoxy-2-methyl-indol-1-yl)-ethylamino]-pyrimidin-4-yl}-6-methoxy-benzoic acid (*1) | 0.90 (C) | 485.3 |
| 402 | 4-{6-[2-(6-Chloro-4-methoxy-2-methyl-indol-1-yl)-ethylamino]-pyrimidin-4-yl}-2-ethoxy-benzoic acid (*1) | 0.97 (C) | 481.3 |
| 403 | 2-Ethoxy-4-{6-[2-(6-fluoro-4-methoxy-2-methyl-indol-1-yl)-ethylamino]-pyrimidin-4-yl}-benzoic acid (*1) | 0.91 (C) | 465.4 |
| 404 | 4-{6-[2-(7-Chloro-4-methoxy-2-methyl-indol-1-yl)-ethylamino]-pyrimidin-4-yl}-2-methoxy-6-methyl-benzoic acid (*1) | 0.86 (C) | 481.3 |
| 405 | 4-{6-[2-(7-Chloro-4-methoxy-2-methyl-indol-1-yl)-ethylamino]-pyrimidin-4-yl}-2-ethoxy-benzoic acid (*1) | 0.99 (C) | 481.3 |
| 406 | 4-{6-[2-(7-Fluoro-4-methoxy-2-methyl-indol-1-yl)-ethylamino]-pyrimidin-4-yl}-2-methoxy-6-methyl-benzoic acid (*1) | 0.80 (C) | 465.4 |
| 407 | 2-Ethoxy-6-fluoro-4-{6-[2-(4-methoxy-2-methyl-indol-1-yl)-ethylamino]-pyrimidin-4-yl}-benzoic acid (*1) | 0.88 (C) | 465.4 |

TABLE 8-continued

Examples 1-745

| Ex. | Compound | $t_R$ [min] (LC-MS) | MS Data m/z [M + H]$^+$ |
|---|---|---|---|
| 408 | 5-{6-[2-(6,7-Difluoro-4-methoxy-2-methyl-indol-1-yl)-ethylamino]-pyrimidin-4-yl}-3-ethoxy-thiophene-2-carboxylic acid (*1) | 1.08 (C) | 489.3 |
| 409 | 5-{6-[2-(5-Chloro-7-fluoro-4-methoxy-2-methyl-indol-1-yl)-ethylamino]-pyrimidin-4-yl}-3-ethoxy-thiophene-2-carboxylic acid (*1) | 1.10 (C) | 505.3 |
| 410 | 4-{6-[2-(7-Chloro-2,4-dimethyl-indol-1-yl)-ethylamino]-pyrimidin-4-yl}-2-isopropylsulfanyl-benzoic acid (*1) | 1.19 (C) | 495.3 |
| 411 | 4-{6-[2-(4,5-Difluoro-2-methyl-indol-1-yl)-ethylamino]-pyrimidin-4-yl}-2-isobutyl-benzoic acid (*1) | 1.07 (C) | 465.4 |
| 412 | 2-Chloro-4-{6-[2-(6-fluoro-2,4-dimethyl-indol-1-yl)-ethylamino]-pyrimidin-4-yl}-6-propyl-benzoic acid (*1) | 1.11 (C) | 481.4 |
| 413 | 2-Chloro-4-{6-[2-(7-fluoro-2,4-dimethyl-indol-1-yl)-ethylamino]-pyrimidin-4-yl}-6-propyl-benzoic acid (*1) | 1.14 (C) | 481.4 |
| 414 | 2-Chloro-4-{6-[2-(7-fluoro-2,5-dimethyl-indol-1-yl)-ethylamino]-pyrimidin-4-yl}-6-propyl-benzoic acid (*1) | 1.15 (C) | 481.4 |
| 415 | 2-Fluoro-4-{6-[2-(6-fluoro-2,4-dimethyl-indol-1-yl)-ethylamino]-pyrimidin-4-yl}-6-propyl-benzoic acid (*1) | 1.09 (C) | 465.4 |
| 416 | 2-Fluoro-4-{6-[2-(7-fluoro-2,4-dimethyl-indol-1-yl)-ethylamino]-pyrimidin-4-yl}-6-propyl-benzoic acid (*1) | 1.11 (C) | 465.4 |
| 417 | 2-Fluoro-4-{6-[2-(7-fluoro-2,5-dimethyl-indol-1-yl)-ethylamino]-pyrimidin-4-yl}-6-propyl-benzoic acid (*1) | 1.13 (C) | 465.4 |
| 418 | 4-{6-[2-(4,6-Dichloro-2-methyl-indol-1-yl)-ethylamino]-pyrimidin-4-yl}-2-isobutyl-benzoic acid (*1) | 1.23 (C) | 497.3 |
| 419 | 4-{6-[2-(4-Chloro-6-fluoro-2-methyl-indol-1-yl)-ethylamino]-pyrimidin-4-yl}-2-isobutyl-benzoic acid (*1) | 1.16 (C) | 481.4 |
| 420 | 5-{6-[2-(6,7-Difluoro-2,4-dimethyl-indol-1-yl)-ethylamino]-pyrimidin-4-yl}-3-trifluoromethyl-thiophene-2-carboxylic acid (*1) | 1.31 (C) | 497.3 |
| 421 | 4-{6-[2-(6-Chloro-2,4-dimethyl-indol-1-yl)-ethylamino]-pyrimidin-4-yl}-2-isobutyl-benzoic acid (*1) | 0.80 (A) | 477.17 |
| 422 | 4-{6-[2-(6-Fluoro-2,4-dimethyl-indol-1-yl)-ethylamino]-pyrimidin-4-yl}-2-isobutyl-benzoic acid (*1) | 1.09 (C) | 461.4 |
| 423 | 5-{6-[2-(6-Fluoro-2,4-dimethyl-indol-1-yl)-ethylamino]-2-methyl-pyrimidin-4-yl}-3-trifluoromethyl-thiophene-2-carboxylic acid (*1) | 1.24 (C) | 493.3 |
| 424 | 4-{6-[2-(4,7-Dichloro-2-methyl-indol-1-yl)-ethylamino]-pyrimidin-4-yl}-2-isopropylsulfanyl-benzoic acid (*1) | 1.24 (C) | 515.3 |
| 425 | 4-{6-[2-(5-Chloro-7-fluoro-2-methyl-indol-1-yl)-ethylamino]-pyrimidin-4-yl}-2-fluoro-6-propyl-benzoic acid (*1) | 1.17 (C) | 485.3 |
| 426 | 2-Chloro-4-{6-[2-(7-chloro-5-fluoro-2-methyl-indol-1-yl)-ethylamino]-pyrimidin-4-yl}-6-propyl-benzoic acid (*1) | 1.19 (C) | 501.3 |
| 427 | 2-Chloro-4-{6-[2-(5-chloro-7-fluoro-2-methyl-indol-1-yl)-ethylamino]-pyrimidin-4-yl}-6-propyl-benzoic acid (*1) | 1.20 (C) | 501.3 |
| 428 | 2-Isobutyl-4-{6-[2-(4-methoxy-2-methyl-indol-1-yl)-ethylamino]-pyrimidin-4-yl}-benzoic acid (*1) | 0.97 (C) | 459.4 |
| 429 | 4-{6-[2-(7-Chloro-4-methoxy-2-methyl-indol-1-yl)-ethylamino]-pyrimidin-4-yl}-2-ethyl-6-fluoro-benzoic acid (*1) | 1.03 (C) | 483.4 |
| 430 | 4-{6-[2-(5,7-Difluoro-2,4-dimethyl-indol-1-yl)-ethylamino]-pyrimidin-4-yl}-2-ethoxy-benzoic acid (*1) | 0.75 (A) | 466.90 |
| 431 | 4-{6-[2-(6,7-Difluoro-2,4-dimethyl-indol-1-yl)-ethylamino]-pyrimidin-4-yl}-2-ethoxy-benzoic acid (*1) | 1.03 (C) | 467.4 |
| 432 | 2-Chloro-6-ethoxy-4-{6-[2-(6-fluoro-2,4-dimethyl-indol-1-yl)-ethylamino]-pyrimidin-4-yl}-benzoic acid (*1) | 1.03 (C) | 483.3 |
| 433 | 2-Chloro-6-ethoxy-4-{6-[2-(7-fluoro-2,4-dimethyl-indol-1-yl)-ethylamino]-pyrimidin-4-yl}-benzoic acid (*1) | 1.05 (C) | 483.3 |
| 434 | 2-Chloro-6-ethoxy-4-{6-[2-(7-fluoro-2,5-dimethyl-indol-1-yl)-ethylamino]-pyrimidin-4-yl}-benzoic acid (*1) | 1.07 (C) | 483.3 |
| 435 | 2-Ethoxy-6-fluoro-4-{6-[2-(7-fluoro-2,4-dimethyl-indol-1-yl)-ethylamino]-pyrimidin-4-yl}-benzoic acid (*1) | 1.03 (C) | 467.4 |
| 436 | 2-Ethoxy-6-fluoro-4-{6-[2-(7-fluoro-2,5-dimethyl-indol-1-yl)-ethylamino]-pyrimidin-4-yl}-benzoic acid (*1) | 1.04 (C) | 467.4 |
| 437 | 2-Ethyl-6-fluoro-4-{6-[2-(7-fluoro-4-methoxy-2-methyl-indol-1-yl)-ethylamino]-pyrimidin-4-yl}-benzoic acid (*1) | 0.95 (C) | 467.4 |
| 438 | 2-Chloro-6-ethyl-4-{6-[2-(6-fluoro-4-methoxy-2-methyl-indol-1-yl)-ethylamino]-pyrimidin-4-yl}-benzoic acid (*1) | 0.96 (C) | 483.3 |
| 439 | 4-{6-[2-(6-Fluoro-2,4-dimethyl-indol-1-yl)-ethylamino]-pyrimidin-4-yl}-2-propoxy-benzoic acid (*1) | 1.05 (C) | 463.4 |
| 440 | 2-Ethoxy-4-{6-[2-(6-fluoro-2,4-dimethyl-indol-1-yl)-ethylamino]-2-methyl-pyrimidin-4-yl}-benzoic acid (*1) | 0.83 (C) | 463.4 |
| 441 | 4-{6-[2-(7-Fluoro-2,4-dimethyl-indol-1-yl)-ethylamino]-pyrimidin-4-yl}-2-propoxy-benzoic acid (*1) | 1.07 (C) | 463.4 |
| 442 | 4-{6-[2-(7-Chloro-4-methoxy-2-methyl-indol-1-yl)-ethylamino]-pyrimidin-4-yl}-2-propyl-benzoic acid (*1) | 1.04 (C) | 479.4 |
| 443 | 4-{6-[2-(7-Fluoro-5-methoxy-2-methyl-indol-1-yl)-ethylamino]-pyrimidin-4-yl}-2-propyl-benzoic acid (*1) | 0.97 (C) | 463.4 |
| 444 | 2-Chloro-4-{6-[2-(4-methoxy-2-methyl-indol-1-yl)-ethylamino]-pyrimidin-4-yl}-6-propyl-benzoic acid (*1) | 0.98 (C) | 479.4 |

TABLE 8-continued

Examples 1-745

| Ex. | Compound | t_R [min] (LC-MS) | MS Data m/z [M + H]+ |
|---|---|---|---|
| 445 | 2-Fluoro-4-{6-[2-(4-methoxy-2-methyl-indol-1-yl)-ethylamino]-pyrimidin-4-yl}-6-propyl-benzoic acid (*1) | 0.96 (C) | 463.4 |
| 446 | 5-{6-[2-(7-Fluoro-4-methoxy-2-methyl-indol-1-yl)-ethylamino]-pyrimidin-4-yl}-3-trifluoromethyl-thiophene-2-carboxylic acid (*1) | 1.21 (C) | 495.3 |
| 447 | 5-{6-[2-(6-Fluoro-4-methoxy-2-methyl-indol-1-yl)-ethylamino]-pyrimidin-4-yl}-3-trifluoromethyl-thiophene-2-carboxylic acid (*1) | 1.19 (C) | 495.3 |
| 448 | 4-{6-[2-(7-Chloro-5-fluoro-4-methoxy-2-methyl-indol-1-yl)-ethylamino]-pyrimidin-4-yl}-2-methylsulfanyl-benzoic acid (*1) | 1.03 (C) | 501.3 |
| 449 | 2-Ethoxy-4-{6-[2-(4,5,7-trifluoro-2-methyl-indol-1-yl)-ethylamino]-pyrimidin-4-yl}-benzoic acid (*1) | 1.02 (C) | 471.3 |
| 450 | 2-Chloro-4-{6-[2-(4-chloro-7-fluoro-2-methyl-indol-1-yl)-ethylamino]-pyrimidin-4-yl}-6-ethoxy-benzoic acid (*1) | 1.11 (C) | 503.3 |
| 451 | 4-{6-[2-(4-Cyano-7-fluoro-2-methyl-indol-1-yl)-ethylamino]-pyrimidin-4-yl}-2-ethylamino-benzoic acid (*1) | 0.89 (C) | 459.4 |
| 452 | 4-{6-[2-(7-Chloro-2,4-dimethyl-indol-1-yl)-ethylamino]-pyrimidin-4-yl}-2-cyclobutylsulfanyl-benzoic acid | 1.24 (C) | 507.3 |
| 453 | 2-Cyclobutylsulfanyl-4-{6-[2-(4,7-dichloro-2-methyl-indol-1-yl)-ethylamino]-pyrimidin-4-yl}-benzoic acid | 1.30 (C) | 527.3 |
| 454 | 4-{6-[2-(5-Chloro-7-methyl-[1,3]dioxolo[4,5-e]indol-6-yl)-ethylamino]-pyrimidin-4-yl}-2-ethoxy-benzoic acid | 0.96 (C) | 495.3 |
| 455 | [2-(7-Fluoro-4-methoxy-2-methyl-indol-1-yl)-ethyl]-{6-[3-fluoro-4-(5-methyl-[1,3,4]oxadiazol-2-yl)-phenyl]-pyrimidin-4-yl}-amine | 1.02 (C) | 477.4 |
| 456 | 3-(4-{6-[2-(7-Fluoro-2,4-dimethyl-indol-1-yl)-ethylamino]-pyrimidin-4-yl}-phenyl)-1H-pyrazole-4-carboxylic acid | 0.77 (C) | 471.4 |
| 457 | [2-(7-Fluoro-4-methoxy-2-methyl-indol-1-yl)-ethyl]-[6-(3-fluoro-4-pyrazol-1-ylmethyl-phenyl)-pyrimidin-4-yl]-amine | 0.99 (C) | 475.4 |
| 458 | {6-[4-(2-Amino-5-methyl-thiazol-4-yl)-phenyl]-pyrimidin-4-yl}-[2-(7-fluoro-4-methoxy-2-methyl-indol-1-yl)-ethyl]-amine | 0.76 (C) | 489.3 |
| 459 | {6-[4-(3,5-Dimethyl-pyrazol-1-yl)-phenyl]-pyrimidin-4-yl}-[2-(7-fluoro-4-methoxy-2-methyl-indol-1-yl)-ethyl]-amine | 0.99 (C) | 471.4 |
| 460 | 4-{6-[2-(5-Chloro-7-methyl-[1,3]dioxolo[4,5-e]indol-6-yl)-ethylamino]-pyrimidin-4-yl}-2-ethylamino-benzoic acid | 0.95 (C) | 494.3 |
| 461 | rac-3-Isobutyl-5-{6-[2-(4-methoxy-2-methyl-indol-1-yl)-ethylamino]-pyrimidin-4-yl}-2,3-dihydro-isoindol-1-one | 0.92 (C) | 470.5 |
| 462 | 2-Isobutyl-5-{6-[2-(4-methoxy-2-methyl-indol-1-yl)-ethylamino]-pyrimidin-4-yl}-2,3-dihydro-isoindol-1-one | 0.93 (C) | 470.4 |
| 463 | [6-(4-Cyclopropylaminomethyl-3-ethoxy-phenyl)-pyrimidin-4-yl]-[2-(4-methoxy-2-methyl-indol-1-yl)-ethyl]-amine | 0.62 (C) | 472.4 |
| 464 | 4-{6-[2-(7-Fluoro-2,4-dimethyl-indol-1-yl)-ethylamino]-pyrimidin-4-yl}-2-pyrrolidin-1-yl-benzoic acid | 0.89 (C) | 474.4 |
| 465 | rac-5-{6-[2-(7-Fluoro-4-methoxy-2-methyl-indol-1-yl)-ethylamino]-pyrimidin-4-yl}-3-propyl-2,3-dihydro-isoindol-1-one | 0.91 (C) | 474.4 |
| 466 | 5-{6-[2-(7-Fluoro-4-methoxy-2-methyl-indol-1-yl)-ethylamino]-pyrimidin-4-yl}-2-propyl-2,3-dihydro-isoindol-1-one | 0.92 (C) | 474.4 |
| 467 | 5-{6-[2-(7-Fluoro-2,4-dimethyl-indol-1-yl)-ethylamino]-pyrimidin-4-yl}-2-isobutyl-2,3-dihydro-isoindol-1-one | 1.07 (C) | 472.4 |
| 468 | rac-5-{6-[2-(7-Fluoro-2,4-dimethyl-indol-1-yl)-ethylamino]-pyrimidin-4-yl}-3-isobutyl-2,3-dihydro-isoindol-1-one | 1.05 (C) | 472.4 |
| 469 | {6-[4-(1,1-Dioxo-1l6-isothiazolidin-2-yl)-phenyl]-pyrimidin-4-yl}-[2-(7-fluoro-4-methoxy-2-methyl-indol-1-yl)-ethyl]-amine | 0.78 (C) | 496.4 |
| 470 | 4-{6-[2-(7-Fluoro-4-methoxy-2-methyl-indol-1-yl)-ethylamino]-pyrimidin-4-yl}-1-methyl-1H-indole-7-carboxylic acid | 0.77 (C) | 474.4 |
| 471 | [2-(7-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine | 0.71 (A) | 490.18 |
| 472 | 2-Cyclobutoxy-4-{6-[2-(7-fluoro-4-methoxy-2-methyl-indol-1-yl)-ethylamino]-pyrimidin-4-yl}-benzoic acid | 0.76 (A) | 491.07 |
| 473 | [6-(4-Cyclopropylaminomethyl-3-ethoxy-phenyl)-pyrimidin-4-yl]-[2-(7-fluoro-4-methoxy-2-methyl-indol-1-yl)-ethyl]-amine | 0.66 (C) | 490.5 |
| 474 | rac-5-{6-[2-(7-Fluoro-4-methoxy-2-methyl-indol-1-yl)-ethylamino]-pyrimidin-4-yl}-3-isobutyl-2,3-dihydro-isoindol-1-one | 0.97 (C) | 488.4 |
| 475 | 5-{6-[2-(7-Fluoro-4-methoxy-2-methyl-indol-1-yl)-ethylamino]-pyrimidin-4-yl}-2-isobutyl-2,3-dihydro-isoindol-1-one | 0.99 (C) | 488.4 |
| 476 | 4-(4-{6-[2-(7-Fluoro-4-methoxy-2-methyl-indol-1-yl)-ethylamino]-pyrimidin-4-yl}-phenyl)-thiazole-2-carboxylic acid | 0.85 (C) | 504.3 |
| 477 | 5-(4-{6-[2-(7-Fluoro-2,4-dimethyl-indol-1-yl)-ethylamino]-pyrimidin-4-yl}-phenyl)-3-methyl-isoxazole-4-carboxylic acid | 1.03 (C) | 486.4 |
| 478 | 4-{6-[2-(7-Fluoro-4-methoxy-2-methyl-indol-1-yl)-ethylamino]-pyrimidin-4-yl}-2-pyrrolidin-1-yl-benzoic acid | 0.81 (C) | 490.4 |
| 479 | 4-{6-[2-(7-Fluoro-2,4-dimethyl-indol-1-yl)-ethylamino]-pyrimidin-4-yl}-2-methanesulfonylamino-benzoic acid (*1) | 0.99 (C) | 498.3 |
| 480 | 4-{6-[2-(2-Cyano-6-fluoro-4-methoxy-indol-1-yl)-ethylamino]-pyrimidin-4-yl}-2-ethoxy-benzoic acid (*1) | 0.73 (A) | 476.07 |
| 481 | 4-{6-[2-(2-Cyano-6-fluoro-4-methyl-indol-1-yl)-ethylamino]-pyrimidin-4-yl}-2-isobutyl-benzoic acid (*1) | 0.79 (A) | 472.09 |

TABLE 8-continued

Examples 1-745

| Ex. | Compound | $t_R$ [min] (LC-MS) | MS Data m/z [M + H]$^+$ |
|---|---|---|---|
| 482 | 4-{6-[2-(7-Cyano-4-fluoro-2-methyl-indol-1-yl)-ethylamino]-pyrimidin-4-yl}-2-isobutyl-benzoic acid (*1) | 1.09 (C) | 472.4 |
| 483 | 2-Ethylamino-6-fluoro-4-{6-[2-(7-fluoro-4-methoxy-2-methyl-indol-1-yl)-ethylamino]-pyrimidin-4-yl}-benzoic acid (*1) | 0.99 (C) | 482.4 |
| 484 | 2-Butoxy-4-{6-[2-(4-methoxy-2-methyl-indol-1-yl)-ethylamino]-pyrimidin-4-yl}-benzoic acid (*1) | 1.01 (C) | 475.4 |
| 485 | 2-Isobutoxy-4-{6-[2-(4-methoxy-2-methyl-indol-1-yl)-ethylamino]-pyrimidin-4-yl}-benzoic acid (*1) | 1.00 (C) | 475.4 |
| 486 | 4-{6-[2-(7-Chloro-5-fluoro-4-methoxy-2-methyl-indol-1-yl)-ethylamino]-pyrimidin-4-yl}-2-ethoxy-benzoic acid (*1) | 1.03 (C) | 499.3 |
| 487 | 4-{6-[2-(6,7-Difluoro-4-methoxy-2-methyl-indol-1-yl)-ethylamino]-pyrimidin-4-yl}-2-ethoxy-benzoic acid (*1) | 0.97 (C) | 483.4 |
| 488 | 2-Chloro-4-{6-[2-(7-chloro-4-methoxy-2-methyl-indol-1-yl)-ethylamino]-pyrimidin-4-yl}-6-ethoxy-benzoic acid (*1) | 1.04 (C) | 515.3 |
| 489 | 2-Chloro-6-ethoxy-4-{6-[2-(7-fluoro-4-methoxy-2-methyl-indol-1-yl)-ethylamino]-pyrimidin-4-yl}-benzoic acid (*1) | 0.97 (C) | 499.3 |
| 490 | 2-Ethoxy-6-fluoro-4-{6-[2-(7-fluoro-4-methoxy-2-methyl-indol-1-yl)-ethylamino]-pyrimidin-4-yl}-benzoic acid (*1) | 0.94 (C) | 483.4 |
| 491 | 4-{6-[2-(5-Chloro-7-fluoro-4-methoxy-2-methyl-indol-1-yl)-ethylamino]-pyrimidin-4-yl}-2-ethoxy-benzoic acid (*1) | 1.01 (C) | 499.3 |
| 492 | 2-Ethoxy-4-{6-[2-(6-fluoro-4-methoxy-2-methyl-indol-1-yl)-ethylamino]-2-methyl-pyrimidin-4-yl}-benzoic acid (*1) | 0.78 (C) | 479.4 |
| 493 | 4-{6-[2-(6-Fluoro-4-methoxy-2-methyl-indol-1-yl)-ethylamino]-pyrimidin-4-yl}-2-propoxy-benzoic acid (*1) | 0.98 (C) | 479.4 |
| 494 | 2-Ethoxy-4-{6-[2-(7-fluoro-4-methoxy-2-methyl-indol-1-yl)-ethylamino]-2-methyl-pyrimidin-4-yl}-benzoic acid (*1) | 0.78 (C) | 479.4 |
| 495 | 4-{6-[2-(7-Chloro-4-methoxy-2-methyl-indol-1-yl)-ethylamino]-pyrimidin-4-yl}-2-propoxy-benzoic acid (*1) | 1.06 (C) | 495.4 |
| 496 | 4-{6-[2-(7-Fluoro-4-methoxy-2-methyl-indol-1-yl)-ethylamino]-pyrimidin-4-yl}-2-propoxy-benzoic acid (*1) | 0.99 (C) | 479.4 |
| 497 | 2-Chloro-4-{6-[2-(4-methoxy-2-methyl-indol-1-yl)-ethylamino]-pyrimidin-4-yl}-6-propoxy-benzoic acid (*1) | 0.98 (C) | 495.4 |
| 498 | 2-Fluoro-4-{6-[2-(4-methoxy-2-methyl-indol-1-yl)-ethylamino]-pyrimidin-4-yl}-6-propoxy-benzoic acid (*1) | 0.96 (C) | 479.4 |
| 499 | 4-{6-[2-(4-Methoxy-2-methyl-indol-1-yl)-ethylamino]-pyrimidin-4-yl}-2-trifluoromethoxy-benzoic acid (*1) | 1.03 (C) | 487.3 |
| 500 | 4-{6-[2-(7-Chloro-4,5-difluoro-2-methyl-indol-1-yl)-ethylamino]-pyrimidin-4-yl}-2-isopropylsulfanyl-benzoic acid (*1) | 1.21 (C) | 517.3 |
| 501 | 4-{6-[2-(5,7-Difluoro-2,4-dimethyl-indol-1-yl)-ethylamino]-pyrimidin-4-yl}-2-isobutyl-benzoic acid (*1) | 0.80 (A) | 479.12 |
| 502 | 4-{6-[2-(6,7-Difluoro-2,4-dimethyl-indol-1-yl)-ethylamino]-pyrimidin-4-yl}-2-isobutyl-benzoicacid (*1) | 1.14 (C) | 479.4 |
| 503 | 4-{6-[2-(6-Fluoro-2,4-dimethyl-indol-1-yl)-ethylamino]-2-methyl-pyrimidin-4-yl}-2-isobutyl-benzoic acid (*1) | 0.93 (C) | 475.4 |
| 504 | 4-{6-[2-(7-Chloro-5-fluoro-2,4-dimethyl-indol-1-yl)-ethylamino]-pyrimidin-4-yl}-2-isopropylsulfanyl-benzoic acid (*1) | 1.22 (C) | 513.3 |
| 505 | 2-Isobutyl-4-{6-[2-(4,6,7-trifluoro-2-methyl-indol-1-yl)-ethylamino]-pyrimidin-4-yl}-benzoic acid (*1) | 0.81 (A) | 483.02 |
| 506 | 2-Isobutyl-4-{6-[2-(4,5,7-trifluoro-2-methyl-indol-1-yl)-ethylamino]-pyrimidin-4-yl}-benzoic acid (*1) | 1.13 (C) | 483.4 |
| 507 | 2-Isobutyl-4-{6-[2-(4-methoxy-2,7-dimethyl-indol-1-yl)-ethylamino]-pyrimidin-4-yl}-benzoic acid (*1) | 1.04 (C) | 473.5 |
| 508 | 4-{6-[2-(7-Fluoro-2,4-dimethyl-indol-1-yl)-ethylamino]-pyrimidin-4-yl}-2-trifluoromethoxy-benzoic acid (*1) | 1.18 (C) | 489.3 |
| 509 | 4-{6-[2-(7-Chloro-5-fluoro-4-methoxy-2-methyl-indol-1-yl)-ethylamino]-pyrimidin-4-yl}-2-fluoro-6-methylsulfanyl-benzoic acid (*1) | 1.08 (C) | 519.3 |
| 510 | 4-{6-[2-(5,7-Difluoro-2,4-dimethyl-indol-1-yl)-ethylamino]-pyrimidin-4-yl}-2-difluoromethoxy-benzoic acid (*1) | 0.77 (A) | 489.11 |
| 511 | 4-{6-[2-(6-Chloro-4-methoxy-2-methyl-indol-1-yl)-ethylamino]-pyrimidin-4-yl}-2-fluoro-6-propyl-benzoic acid (*1) | 1.09 (C) | 497.4 |
| 512 | 4-{6-[2-(7-Chloro-4-methoxy-2-methyl-indol-1-yl)-ethylamino]-pyrimidin-4-yl}-2-fluoro-6-propyl-benzoic acid (*1) | 1.11 (C) | 497.4 |
| 513 | 2-Chloro-4-{6-[2-(7-chloro-4-methoxy-2-methyl-indol-1-yl)-ethylamino]-pyrimidin-4-yl}-6-propyl-benzoic acid (*1) | 1.13 (C) | 513.3 |
| 514 | 2-Chloro-4-{6-[2-(7-fluoro-4-methoxy-2-methyl-indol-1-yl)-ethylamino]-pyrimidin-4-yl}-6-propyl-benzoic acid (*1) | 1.05 (C) | 497.4 |
| 515 | 2-Fluoro-4-{6-[2-(7-fluoro-4-methoxy-2-methyl-indol-1-yl)-ethylamino]-pyrimidin-4-yl}-6-propyl-benzoic acid (*1) | 0.76 (A) | 480.93 |
| 516 | 2-Fluoro-4-{6-[2-(7-fluoro-5-methoxy-2-methyl-indol-1-yl)-ethylamino]-pyrimidin-4-yl}-6-propyl-benzoic acid (*1) | 1.03 (C) | 481.4 |
| 517 | 2-Chloro-4-{6-[2-(5-fluoro-4-methoxy-2-methyl-indol-1-yl)-ethylamino]-pyrimidin-4-yl}-6-propyl-benzoic acid (*1) | 1.02 (C) | 497.4 |
| 518 | 2-Chloro-4-{6-[2-(6-chloro-4-methoxy-2-methyl-indol-1-yl)-ethylamino]-pyrimidin-4-yl}-6-propyl-benzoic acid (*1) | 1.11 (C) | 513.3 |

TABLE 8-continued

Examples 1-745

| Ex. | Compound | $t_R$ [min] (LC-MS) | MS Data m/z [M + H]$^+$ |
|---|---|---|---|
| 519 | 2-Chloro-4-{6-[2-(6-fluoro-4-methoxy-2-methyl-indol-1-yl)-ethylamino]-pyrimidin-4-yl}-6-propyl-benzoic acid (*1) | 1.04 (C) | 497.4 |
| 520 | 2-Fluoro-4-{6-[2-(5-fluoro-4-methoxy-2-methyl-indol-1-yl)-ethylamino]-pyrimidin-4-yl}-6-propyl-benzoic acid (*1) | 1.00 (C) | 481.4 |
| 521 | 2-Fluoro-4-{6-[2-(6-fluoro-4-methoxy-2-methyl-indol-1-yl)-ethylamino]-pyrimidin-4-yl}-6-propyl-benzoic acid (*1) | 1.02 (C) | 481.4 |
| 522 | 2-Chloro-4-{6-[2-(6-chloro-2,4-dimethyl-indol-1-yl)-ethylamino]-pyrimidin-4-yl}-6-propoxy-benzoic acid (*1) | 0.80 (A) | 512.99 |
| 523 | 2-Chloro-4-{6-[2-(6-fluoro-2,4-dimethyl-indol-1-yl)-ethylamino]-pyrimidin-4-yl}-6-propoxy-benzoic acid (*1) | 1.11 (C) | 497.4 |
| 524 | 2-Fluoro-4-{6-[2-(6-fluoro-2,4-dimethyl-indol-1-yl)-ethylamino]-pyrimidin-4-yl}-6-propoxy-benzoic acid (*1) | 1.09 (C) | 481.4 |
| 525 | 5-{6-[2-(6,7-Difluoro-4-methoxy-2-methyl-indol-1-yl)-ethylamino]-pyrimidin-4-yl}-3-trifluoromethyl-thiophene-2-carboxylic acid (*1) | 1.24 (C) | 513.3 |
| 526 | 4-{6-[2-(6-Fluoro-2,4-dimethyl-indol-1-yl)-ethylamino]-pyrimidin-4-yl}-2-isobutoxy-benzoic acid (*1) | 1.12 (C) | 477.4 |
| 527 | 2-Butoxy-4-{6-[2-(6-fluoro-2,4-dimethyl-indol-1-yl)-ethylamino]-pyrimidin-4-yl}-benzoic acid (*1) | 1.13 (C) | 477.4 |
| 528 | 2-tert-Butyl-4-{6-[2-(6-fluoro-4-methoxy-2-methyl-indol-1-yl)-ethylamino]-pyrimidin-4-yl}-benzoic acid (*1) | 0.94 (C) | 477.4 |
| 529 | 4-{6-[2-(6-Chloro-4-methoxy-2-methyl-indol-1-yl)-ethylamino]-pyrimidin-4-yl}-2-isobutyl-benzoic acid (*1) | 1.08 (C) | 493.4 |
| 530 | 4-{6-[2-(6-Fluoro-4-methoxy-2-methyl-indol-1-yl)-ethylamino]-pyrimidin-4-yl}-2-isobutyl-benzoic acid (*1) | 1.02 (C) | 477.4 |
| 531 | 4-{6-[2-(7-Fluoro-2,4-dimethyl-indol-1-yl)-ethylamino]-pyrimidin-4-yl}-2-methoxy-6-propyl-benzoic acid (*1) | 0.98 (C) | 477.4 |
| 532 | 2-Ethoxy-6-ethyl-4-{6-[2-(7-fluoro-2,4-dimethyl-indol-1-yl)-ethylamino]-pyrimidin-4-yl}-benzoic acid (*1) | 0.97 (C) | 477.4 |
| 533 | 2-Butoxy-4-{6-[2-(7-fluoro-2,4-dimethyl-indol-1-yl)-ethylamino]-pyrimidin-4-yl}-benzoic acid (*1) | 1.15 (C) | 477.4 |
| 534 | 4-{6-[2-(7-Fluoro-2,4-dimethyl-indol-1-yl)-ethylamino]-pyrimidin-4-yl}-2-isobutoxy-benzoic acid (*1) | 1.14 (C) | 477.4 |
| 535 | 2-tert-Butyl-4-{6-[2-(7-fluoro-4-methoxy-2-methyl-indol-1-yl)-ethylamino]-pyrimidin-4-yl}-benzoic acid (*1) | 0.95 (C) | 475.4 |
| 536 | 4-{6-[2-(7-Chloro-4-methoxy-2-methyl-indol-1-yl)-ethylamino]-pyrimidin-4-yl}-2-isobutyl-benzoic acid (*1) | 1.1 (C) | 493.4 |
| 537 | 4-{6-[2-(7-Fluoro-4-methoxy-2-methyl-indol-1-yl)-ethylamino]-pyrimidin-4-yl}-2-isobutyl-benzoic acid (*1) | 1.02 (C) | 477.4 |
| 538 | 4-{6-[2-(5-Fluoro-4-methoxy-2-methyl-indol-1-yl)-ethylamino]-pyrimidin-4-yl}-2-isobutyl-benzoic acid (*1) | 1.00 (C) | 477.4 |
| 539 | 4-{6-[2-(4-Fluoro-7-methoxy-2-methyl-indol-1-yl)-ethylamino]-pyrimidin-4-yl}-2-isobutyl-benzoic acid (*1) | 1.06 (C) | 477.4 |
| 540 | 5-{6-[2-(7-Fluoro-4-methoxy-2-methyl-indol-1-yl)-ethylamino]-2-methyl-pyrimidin-4-yl}-3-trifluoromethyl-thiophene-2-carboxylic acid (*1) | 1.15 (C) | 509.3 |
| 541 | 5-{6-[2-(6-Fluoro-4-methoxy-2-methyl-indol-1-yl)-ethylamino]-2-methyl-pyrimidin-4-yl}-3-trifluoromethyl-thiophene-2-carboxylic acid (*1) | 1.16 (C) | 509.3 |
| 542 | 4-{6-[2-(7-Chloro-5-fluoro-4-methoxy-2-methyl-indol-1-yl)-ethylamino]-pyrimidin-4-yl}-2-ethylsulfanyl-benzoic acid (*1) | 1.1 (C) | 515.3 |
| 543 | 2-Ethoxy-4-{6-[2-(7-fluoro-2-methyl-4-trifluoromethyl-indol-1-yl)-ethylamino]-pyrimidin-4-yl}-benzoic acid | 1.08 (C) | 503.4 |
| 544 | 4-(4-{6-[2-(6-Fluoro-2,4-dimethyl-indol-1-yl)-ethylamino]-pyrimidin-4-yl}-phenyl)-thiazole-2-carboxylic acid (*1) | 0.91 (C) | 488.3 |
| 545 | 2-(4-{6-[2-(6-Fluoro-2,4-dimethyl-indol-1-yl)-ethylamino]-pyrimidin-4-yl}-phenyl)-thiazole-4-carboxylic acid (*1) | 0.96 (C) | 488.3 |
| 546 | 2-(4-{6-[2-(7-Fluoro-2,4-dimethyl-indol-1-yl)-ethylamino]-pyrimidin-4-yl}-phenyl)-thiazole-4-carboxylic acid (*1) | 0.97 (C) | 488.3 |
| 547 | [2-(6-Fluoro-2,4-dimethyl-indol-1-yl)-ethyl]-{6-[4-(3-methyl-3H-imidazol-4-yl)-phenyl]-pyrimidin-4-yl}-amine (*2) | 0.64 (C) | 441.4 |
| 548 | [2-(6-Fluoro-2,4-dimethyl-indol-1-yl)-ethyl]-{6-[4-(2-methyl-1H-imidazol-4-yl)-phenyl]-pyrimidin-4-yl}-amine (*2) | 0.63 (C) | 441.4 |
| 549 | N-(2-Dimethylamino-ethyl)-4-{6-[2-(7-fluoro-4-methoxy-2-methyl-indol-1-yl)-ethylamino]-pyrimidin-4-yl}-benzamide | 0.56 (C) | 491.4 |
| 550 | 4-(4-{6-[2-(4,6-Dichloro-2-methyl-indol-1-yl)-ethylamino]-pyrimidin-4-yl}-phenyl)-thiazole-2-carboxylic acid (*1) | 1.05 (C) | 524.3 |
| 551 | 2-(4-{6-[2-(4,6-Dichloro-2-methyl-indol-1-yl)-ethylamino]-pyrimidin-4-yl}-phenyl)-thiazole-4-carboxylic acid (*1) | 1.10 (C) | 524.3 |
| 552 | {6-[4-(2-Amino-oxazol-5-yl)-phenyl]-pyrimidin-4-yl}-[2-(6-fluoro-2,4-dimethyl-indol-1-yl)-ethyl]-amine (*2) | 0.77 (C) | 443.4 |
| 553 | [2-(7-Fluoro-2,4-dimethyl-indol-1-yl)-ethyl]-{6-[4-(5-methyl-[1,3,4]oxadiazol-2-yl)-phenyl]-pyrimidin-4-yl}-amine (*2) | 0.75 (A) | 443.17 |
| 554 | 1-(4-{6-[2-(7-Chloro-4-methoxy-2-methyl-indol-1-yl)-ethylamino]-pyrimidin-4-yl}-2-methoxy-phenyl)-3-ethyl-urea | 0.83 (C) | 509.4 |
| 555 | 1-Ethyl-3-(4-{6-[2-(7-fluoro-4-methoxy-2-methyl-indol-1-yl)-ethylamino]-pyrimidin-4-yl}-2-methoxy-phenyl)-urea | 0.78 (C) | 493.4 |

TABLE 8-continued

Examples 1-745

| Ex. | Compound | $t_R$ [min] (LC-MS) | MS Data m/z [M + H]+ |
|---|---|---|---|
| 556 | [2-(7-Fluoro-4-methoxy-2-methyl-indol-1-yl)-ethyl]-[6-(3-pyrazol-1-yl-phenyl)-pyrimidin-4-yl]-amine (*2) | 0.75 (A) | 443.25 |
| 557 | 2-(4-{6-[2-(4-Methoxy-2-methyl-indol-1-yl)-ethylamino]-pyrimidin-4-yl}-phenyl)-thiazole-4-carboxylic acid (*1) | 0.83 (C) | 486.3 |
| 558 | [2-(6-Fluoro-4-methoxy-2-methyl-indol-1-yl)-ethyl]-[6-(4-isoxazol-3-yl-phenyl)-pyrimidin-4-yl]-amine (*2) | 0.76 (A) | 444.09 |
| 559 | 4-{6-[2-(6-Fluoro-2,4-dimethyl-indol-1-yl)-ethylamino]-pyrimidin-4-yl}-2-(2,2,2-trifluoro-ethylamino)-benzoic acid | 1.06 (C) | 500.3 |
| 560 | 4-{6-[2-(7-Fluoro-2,4-dimethyl-indol-1-yl)-ethylamino]-pyrimidin-4-yl}-2-(2,2,2-trifluoro-ethylamino)-benzoic acid | 1.07 (C) | 502.4 |
| 561 | [2-(7-Fluoro-2,4-dimethyl-indol-1-yl)-ethyl]-[6-(4-pyridin-2-yl-phenyl)-pyrimidin-4-yl]-amine (*2) | 0.74 (A) | 438.31 |
| 562 | (6-{3-Ethoxy-4-[(methoxy-ethylamino)-methyl]-phenyl}-pyrimidin-4-yl)-[2-(7-fluoro-2,4-dimethyl-indol-1-yl)-ethyl]-amine | 0.71 (C) | 492.5 |
| 563 | 4-{6-[2-(7-Fluoro-2,4-dimethyl-indol-1-yl)-ethylamino]-pyrimidin-4-yl}-N-methyl-2-trifluoromethyl-benzenesulfonamide | 1.19 (C) | 522.3 |
| 564 | 1-(2-Fluoro-4-{6-[2-(7-fluoro-4-methoxy-2-methyl-indol-1-yl)-ethylamino]-pyrimidin-4-yl}-phenyl)-cyclopropanecarboxylic acid (*1) | 0.94 (C) | 479.4 |
| 565 | [2-(6-Fluoro-2,4-dimethyl-indol-1-yl)-ethyl]-{6-[4-(2-methyl-oxazol-4-yl)-(C)phenyl]-pyrimidin-4-yl}-amine (*2) | 0.77 (A) | 442.16 |
| 566 | [2-(4-Methoxy-2-methyl-indol-1-yl)-ethyl]-{6-[4-(2-methyl-thiazol-4-yl)-phenyl]-pyrimidin-4-yl}-amine (*2) | 0.92 (C) | 456.4 |
| 567 | 4-{6-[2-(7-Fluoro-4-methoxy-2-methyl-indol-1-yl)-ethylamino]-pyrimidin-4-yl}-2-trifluoromethyl-benzenesulfonamide | 1.03 (C) | 524.3 |
| 568 | 4-{6-[2-(4-Methoxy-2-methyl-indol-1-yl)-ethylamino]-pyrimidin-4-yl}-2-(2,2,2-trifluoro-ethylamino)-benzoic acid | 0.94 (C) | 500.4 |
| 569 | {6-[4-(5-Amino-[1,3,4]thiadiazol-2-yl)-phenyl]-pyrimidin-4-yl}-[2-(6-fluoro-2,4-dimethyl-indol-1-yl)-ethyl]-amine (*2) | 0.71 (A) | 460.24 |
| 570 | 4-{6-[2-(7-Fluoro-2-methyl-4-trifluoromethoxy-indol-1-yl)-ethylamino]-pyrimidin-4-yl}-2-propyl-benzoic acid | 1.15 (C) | 517.4 |
| 571 | rac-1-(2-Ethoxy-4-{6-[2-(7-fluoro-4-methoxy-2-methyl-indol-1-yl)-ethylamino]-pyrimidin-4-yl}-phenyl)-2,2,2-trifluoro-ethanol | 1.02 (C) | 519.4 |
| 572 | {6-[4-(2-Amino-oxazol-5-yl)-phenyl]-pyrimidin-4-yl}-[2-(6-fluoro-4-methoxy-2-methyl-indol-1-yl)-ethyl]-amine (*2) | 0.71 (C) | 459.4 |
| 573 | {6-[4-(2-Amino-oxazol-5-yl)-phenyl]-pyrimidin-4-yl}-[2-(7-fluoro-4-methoxy-2-methyl-indol-1-yl)-ethyl]-amine (*2) | 0.71 (C) | 459.4 |
| 574 | [2-(7-Fluoro-4-methoxy-2-methyl-indol-1-yl)-ethyl]-{6-[4-(5-methyl-[1,3,4]oxadiazol-2-yl)-phenyl]-pyrimidin-4-yl}-amine (*2) | 0.71 (A) | 459.14 |
| 575 | [2-(6,7-Difluoro-2,4-dimethyl-indol-1-yl)-ethyl]-{6-[4-(2-methyl-1H-imidazol-4-yl)-phenyl]-pyrimidin-4-yl}-amine (*2) | 0.66 (C) | 459.4 |
| 576 | [2-(6,7-Difluoro-2,4-dimethyl-indol-1-yl)-ethyl]-{6-[4-(3-methyl-3H-imidazol-4-yl)-phenyl]-pyrimidin-4-yl}-amine (*2) | 0.68 (C) | 459.4 |
| 577 | {6-[4-(2-Amino-oxazol-5-yl)-phenyl]-pyrimidin-4-yl}-[2-(6,7-difluoro-2,4-dimethyl-indol-1-yl)-ethyl]-amine (*2) | 0.81 (C) | 461.4 |
| 578 | 4-(4-{6-[2-(6-Fluoro-4-methoxy-2-methyl-indol-1-yl)-ethylamino]-pyrimidin-4-yl}-phenyl)-thiazole-2-carboxylic acid (*1) | 0.85 (C) | 504.3 |
| 579 | 2-(4-{6-[2-(6-Fluoro-4-methoxy-2-methyl-indol-1-yl)-ethylamino]-pyrimidin-4-yl}-phenyl)-thiazole-4-carboxylic acid (*1) | 0.89 (C) | 504.3 |
| 580 | 2-(4-{6-[2-(7-Fluoro-4-methoxy-2-methyl-indol-1-yl)-ethylamino]-pyrimidin-4-yl}-phenyl)-thiazole-4-carboxylic acid (*1) | 0.89 (C) | 504.4 |
| 581 | [2-(6-Fluoro-4-methoxy-2-methyl-indol-1-yl)-ethyl]-{6-[4-(2-methyl-1H-imidazol-4-yl)-phenyl]-pyrimidin-4-yl}-amine (*2) | 0.58 (C) | 457.4 |
| 582 | [2-(6-Fluoro-4-methoxy-2-methyl-indol-1-yl)-ethyl]-{6-[4-(3-methyl-3H-imidazol-4-yl)-phenyl]-pyrimidin-4-yl}-amine (*2) | 0.59 (C) | 457.4 |
| 583 | [2-(6-Fluoro-4-methoxy-2-methyl-indol-1-yl)-ethyl]-{6-[4-(5-methyl-1H-pyrazol-3-yl)-phenyl]-pyrimidin-4-yl}-amine (*2) | 0.72 (A) | 457.11 |
| 584 | [2-(7-Fluoro-4-methoxy-2-methyl-indol-1-yl)-ethyl]-{6-[4-(3-methyl-3H-imidazol-4-yl)-phenyl]-pyrimidin-4-yl}-amine (*2) | 0.59 (C) | 457.4 |
| 585 | [2-(6-Fluoro-4-methoxy-2-methyl-indol-1-yl)-ethyl]-{6-[4-(2-methyl-oxazol-4-yl)-phenyl]-pyrimidin-4-yl}-amine (*2) | 0.75 (A) | 458.16 |
| 586 | {6-[3-Ethoxy-4-(isobutylamino-methyl)-phenyl]-pyrimidin-4-yl}-[2-(7-fluoro-4-methoxy-2-methyl-indol-1-yl)-ethyl]-amine | 0.73 (C) | 506.5 |
| 587 | 4-{6-[2-(6-Fluoro-4-methoxy-2-methyl-indol-1-yl)-ethylamino]-pyrimidin-4-yl}-2-(2,2,2-trifluoro-ethylamino)-benzoic acid | 0.99 (C) | 518.4 |
| 588 | 4-{6-[2-(7-Fluoro-4-methoxy-2-methyl-indol-1-yl)-ethylamino]-pyrimidin-4-yl}-2-(2,2,2-trifluoro-ethylamino)-benzoic acid | 1.00 (C) | 518.4 |
| 589 | (6-{3-Ethoxy-4-[(methoxy-ethylamino)-methyl]-phenyl}-pyrimidin-4-yl)-[2-(7-fluoro-4-methoxy-2-methyl-indol-1-yl)-ethyl]-amine | 0.66 (C) | 508.4 |
| 590 | [2-(7-Fluoro-4-methoxy-2-methyl-indol-1-yl)-ethyl]-[6-(4-pyridin-2-yl-phenyl)-pyrimidin-4-yl]-amine (*2) | 0.71 (A) | 454.10 |
| 591 | 4-{6-[2-(7-Fluoro-4-methoxy-2-methyl-indol-1-yl)-ethylamino]-pyrimidin-4-yl}-N-methyl-2-trifluoromethyl-benzenesulfonamide | 1.12 (C) | 538.3 |
| 592 | [2-(6-Fluoro-2,4-dimethyl-indol-1-yl)-ethyl]-{6-[4-(5-methylamino-[1,3,4]thiadiazol-2-yl)-phenyl]-pyrimidin-4-yl}-amine (*2) | 0.74 (A) | 474.25 |

TABLE 8-continued

Examples 1-745

| Ex. | Compound | $t_R$ [min] (LC-MS) | MS Data m/z [M + H]+ |
|---|---|---|---|
| 593 | 3-(4-{6-[2-(7-Fluoro-4-methoxy-2-methyl-indol-1-yl)-ethylamino]-pyrimidin-4-yl}-phenyl)-1H-pyrazole-4-carboxylic acid (*1) | 0.71 (C) | 487.4 |
| 594 | 5-(4-{6-[2-(7-Fluoro-4-methoxy-2-methyl-indol-1-yl)-ethylamino]-pyrimidin-4-yl}-phenyl)-2H-pyrazole-3-carboxylic acid (*1) | 0.77 (C) | 487.4 |
| 595 | 2-Cyclopentyloxy-4-{6-[2-(7-fluoro-4-methoxy-2-methyl-indol-1-yl)-ethylamino]-pyrimidin-4-yl}-benzoic acid | 0.78 (A) | 505.1 |
| 596 | 5-(4-{6-[2-(7-Fluoro-4-methoxy-2-methyl-indol-1-yl)-ethylamino]-pyrimidin-4-yl}-phenyl)-3-methyl-isoxazole-4-carboxylic acid | 0.74 (A) | 501.88 |
| 597 | [6-(4-Cyclobutylaminomethyl-3-ethoxy-phenyl)-pyrimidin-4-yl]-[2-(7-fluoro-4-methoxy-2-methyl-indol-1-yl)-ethyl]-amine | 0.70 (C) | 504.4 |
| 598 | 2-Difluoromethoxy-4-{6-[2-(4-methoxy-2-methyl-indol-1-yl)-ethylamino]-pyrimidin-4-yl}-benzoic acid (*2) | 0.92 (C) | 469.4 |
| 599 | 2-Chloro-6-ethoxy-4-{6-[2-(4-methoxy-2-methyl-indol-1-yl)-ethylamino]-pyrimidin-4-yl}-benzoic acid (*2) | 0.90 (C) | 481.3 |
| 600 | 2-Difluoromethoxy-4-{6-[2-(6-fluoro-2,4-dimethyl-indol-1-yl)-ethylamino]-pyrimidin-4-yl}-benzoic acid (*2) | 1.05 (C) | 471.3 |
| 601 | 2-Difluoromethoxy-4-{6-[2-(7-fluoro-2,4-dimethyl-indol-1-yl)-ethylamino]-pyrimidin-4-yl}-benzoic acid (*2) | 1.06 (C) | 471.3 |
| 602 | 2-Ethanesulfonylamino-4-{6-[2-(7-fluoro-2,4-dimethyl-indol-1-yl)-ethylamino]-pyrimidin-4-yl}-benzoic acid (*1) | 0.76 (A) | 512.2 |
| 603 | 4-{6-[2-(2-Cyano-6-fluoro-4-methoxy-indol-1-yl)-ethylamino]-pyrimidin-4-yl}-2-isobutyl-benzoic acid (*1) | 0.78 (A) | 488.18 |
| 604 | 4-{6-[2-(6-Fluoro-4-methoxy-2-methyl-indol-1-yl)-ethylamino]-pyrimidin-4-yl}-2-trifluoromethoxy-benzoic acid (*1) | 1.09 (C) | 505.3 |
| 605 | 4-{6-[2-(7-Chloro-4-methoxy-2-methyl-indol-1-yl)-ethylamino]-pyrimidin-4-yl}-2-trifluoromethoxy-benzoic acid (*1) | 1.17 (C) | 521.3 |
| 606 | 4-{6-[2-(7-Fluoro-4-methoxy-2-methyl-indol-1-yl)-ethylamino]-pyrimidin-4-yl}-2-trifluoromethoxy-benzoic acid (*1) | 1.1 (C) | 505.3 |
| 607 | 2-Chloro-4-{6-[2-(6-fluoro-4-methoxy-2-methyl-indol-1-yl)-ethylamino]-pyrimidin-4-yl}-6-propoxy-benzoic acid (*1) | 1.04 (C) | 513.3 |
| 608 | 2-Fluoro-4-{6-[2-(6-fluoro-4-methoxy-2-methyl-indol-1-yl)-ethylamino]-pyrimidin-4-yl}-6-propoxy-benzoic acid (*1) | 1.01 (C) | 497.4 |
| 609 | 2-Chloro-4-{6-[2-(7-fluoro-4-methoxy-2-methyl-indol-1-yl)-ethylamino]-pyrimidin-4-yl}-6-propoxy-benzoic acid (*1) | 1.05 (C) | 513.4 |
| 610 | 2-Fluoro-4-{6-[2-(7-fluoro-4-methoxy-2-methyl-indol-1-yl)-ethylamino]-pyrimidin-4-yl}-6-propoxy-benzoic acid (*1) | 1.02 (C) | 497.4 |
| 611 | 2-Butoxy-4-{6-[2-(6-fluoro-4-methoxy-2-methyl-indol-1-yl)-ethylamino]-pyrimidin-4-yl}-benzoic acid (*1) | 1.06 (C) | 493.4 |
| 612 | 4-{6-[2-(6-Fluoro-4-methoxy-2-methyl-indol-1-yl)-ethylamino]-pyrimidin-4-yl}-2-isobutoxy-benzoic acid (*1) | 1.05 (C) | 493.4 |
| 613 | 2-Butoxy-4-{6-[2-(7-chloro-4-methoxy-2-methyl-indol-1-yl)-ethylamino]-pyrimidin-4-yl}-benzoic acid (*1) | 1.14 (C) | 509.4 |
| 614 | 4-{6-[2-(7-Chloro-4-methoxy-2-methyl-indol-1-yl)-ethylamino]-pyrimidin-4-yl}-2-isobutoxy-benzoic acid (*1) | 1.13 (C) | 509.4 |
| 615 | 2-Butoxy-4-{6-[2-(7-fluoro-4-methoxy-2-methyl-indol-1-yl)-ethylamino]-pyrimidin-4-yl}-benzoic acid (*1) | 1.07 (C) | 493.4 |
| 616 | 4-{6-[2-(7-Fluoro-4-methoxy-2-methyl-indol-1-yl)-ethylamino]-pyrimidin-4-yl}-2-isobutoxy-benzoic acid (*1) | 1.06 (C) | 493.4 |
| 617 | 4-{6-[2-(7-Chloro-4-methoxy-2-methyl-indol-1-yl)-ethylamino]-pyrimidin-4-yl}-2-ethoxy-6-ethyl-benzoic acid (*1) | 0.96 (C) | 509.4 |
| 618 | 2-Ethoxy-6-ethyl-4-{6-[2-(7-fluoro-4-methoxy-2-methyl-indol-1-yl)-ethylamino]-pyrimidin-4-yl}-benzoic acid (*1) | 0.90 (C) | 493.4 |
| 619 | 4-{6-[2-(7-Fluoro-4-methoxy-2-methyl-indol-1-yl)-ethylamino]-pyrimidin-4-yl}-2-methoxy-6-propyl-benzoic acid (*1) | 0.91 (C) | 493.4 |
| 620 | 2-Chloro-6-propoxy-4-{6-[2-(4,6,7-trifluoro-2-methyl-indol-1-yl)-ethylamino]-pyrimidin-4-yl}-benzoic acid (*1) | 0.81 (A) | 519.05 |
| 621 | 4-{6-[2-(6,7-Difluoro-4-methoxy-2-methyl-indol-1-yl)-ethylamino]-pyrimidin-4-yl}-2-isobutyl-benzoic acid (*1) | 1.08 (C) | 495.4 |
| 622 | 4-{6-[2-(5-Chloro-7-fluoro-4-methoxy-2-methyl-indol-1-yl)-ethylamino]-pyrimidin-4-yl}-2-isobutyl-benzoic acid (*1) | 1.12 (C) | 511.4 |
| 623 | 4-{6-[2-(6-Fluoro-4-methoxy-2-methyl-indol-1-yl)-ethylamino]-2-methyl-pyrimidin-4-yl}-2-isobutyl-benzoic acid (*1) | 0.88 (C) | 491.5 |
| 624 | 2-Ethoxy-4-{6-[2-(7-fluoro-2,4-dimethyl-indol-1-yl)-ethylamino]-pyrimidin-4-yl}-6-propyl-benzoic acid (*1) | 1.03 (C) | 491.4 |
| 625 | 4-{6-[2-(7-Fluoro-4-methoxy-2-methyl-indol-1-yl)-ethylamino]-2-methyl-pyrimidin-4-yl}-2-isobutyl-benzoic acid (*1) | 0.88 (C) | 491.4 |
| 626 | 3-Ethoxy-5-{6-[2-(6-fluoro-2,4-dimethyl-indol-1-yl)-ethylamino]-2-trifluoromethyl-pyrimidin-4-yl}-thiophene-2-carboxylic acid (*1) | 0.99 (A) | 523.16 |
| 627 | 4-{6-[2-(6,7-Difluoro-2,4-dimethyl-indol-1-yl)-ethylamino]-pyrimidin-4-yl}-2-fluoro-6-propoxy-benzoic acid (*1) | 1.14 (C) | 499.4 |
| 628 | 2-Chloro-4-{6-[2-(6,7-difluoro-2,4-dimethyl-indol-1-yl)-ethylamino]-pyrimidin-4-yl}-6-propoxy-benzoic acid (*1) | 1.16 (C) | 515.4 |
| 629 | 2-Chloro-4-{6-[2-(5,7-difluoro-2,4-dimethyl-indol-1-yl)-ethylamino]-pyrimidin-4-yl}-6-propoxy-benzoic acid (*1) | 0.80 (A) | 515.06 |

TABLE 8-continued

Examples 1-745

| Ex. | Compound | $t_R$ [min] (LC-MS) | MS Data m/z [M + H]+ |
|---|---|---|---|
| 630 | 2-Difluoromethoxy-4-{6-[2-(6-fluoro-4-methoxy-2-methyl-indol-1-yl)-ethylamino]-pyrimidin-4-yl}-benzoic acid (*2) | 0.98 (C) | 487.4 |
| 631 | 4-{6-[2-(7-Chloro-4-methoxy-2-methyl-indol-1-yl)-ethylamino]-pyrimidin-4-yl}-2-difluoromethoxy-benzoic acid (*2) | 1.06 (C) | 503.3 |
| 632 | 2-Difluoromethoxy-4-{6-[2-(7-fluoro-4-methoxy-2-methyl-indol-1-yl)-ethylamino]-pyrimidin-4-yl}-benzoic acid (*2) | 0.98 (C) | 487.3 |
| 633 | 4-{6-[2-(7-Chloro-4-methoxy-2-methyl-indol-1-yl)-ethylamino]-pyrimidin-4-yl}-2-ethoxy-6-propyl-benzoic acid (*1) | 1.02 (C) | 523.4 |
| 634 | 2-Ethoxy-4-{6-[2-(7-fluoro-4-methoxy-2-methyl-indol-1-yl)-ethylamino]-pyrimidin-4-yl}-6-propyl-benzoic acid (*1) | 0.96 (C) | 507.4 |
| 635 | 3-Ethoxy-5-{6-[2-(6-fluoro-4-methoxy-2-methyl-indol-1-yl)-ethylamino]-2-trifluoromethyl-pyrimidin-4-yl}-thiophene-2-carboxylic acid (*1) | 0.98 (A) | 539.03 |
| 636 | 4-{6-[2-(6,7-Difluoro-4-methoxy-2-methyl-indol-1-yl)-ethylamino]-pyrimidin-4-yl}-2-trifluoromethoxy-benzoic acid (*1) | 1.15 (C) | 523.3 |
| 637 | 4-{6-[2-(6,7-Difluoro-4-methoxy-2-methyl-indol-1-yl)-ethylamino]-pyrimidin-4-yl}-2-fluoro-6-propoxy-benzoic acid (*1) | 1.08 (C) | 515.4 |
| 638 | 2-Chloro-4-{6-[2-(6,7-difluoro-4-methoxy-2-methyl-indol-1-yl)-ethylamino]-pyrimidin-4-yl}-6-propoxy-benzoic acid (*1) | 1.10 (C) | 531.4 |
| 639 | {6-[4-(2-Amino-oxazol-5-yl)-phenyl]-pyrimidin-4-yl}-[2-(6,7-difluoro-4-methoxy-2-methyl-indol-1-yl)-ethyl]-amine (*2) | 0.76 (C) | 477.4 |
| 640 | [2-(6-Fluoro-4-methoxy-2-methyl-indol-1-yl)-ethyl]-[6-(2-trifluoromethyl-1H-benzoimidazol-5-yl)-pyrimidin-4-yl]-amine (*2) | 0.72 (A) | 484.82 |
| 641 | [2-(6,7-Difluoro-4-methoxy-2-methyl-indol-1-yl)-ethyl]-{6-[4-(3-methyl-3H-imidazol-4-yl)-phenyl]-pyrimidin-4-yl}-amine (*2) | 0.64 (C) | 475.4 |
| 642 | [2-(6,7-Difluoro-4-methoxy-2-methyl-indol-1-yl)-ethyl]-{6-[4-(2-methyl-1H-imidazol-4-yl)-phenyl]-pyrimidin-4-yl}-amine (*2) | 0.63 (C) | 475.4 |
| 643 | 3-[5-(4-{6-[2-(7-Fluoro-2,4-dimethyl-indol-1-yl)-ethylamino]-pyrimidin-4-yl}-phenyl)-oxazol-2-yl]-propionic acid (*1) | 0.9 (C) | 500.4 |
| 644 | 4-{6-[2-(6,7-Difluoro-4-methoxy-2-methyl-indol-1-yl)-ethylamino]-pyrimidin-4-yl}-2-(2,2,2-trifluoro-ethylamino)-benzoic acid | 1.04 (C) | 536.4 |
| 645 | [2-(6-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine (*2) | 0.72 (A) | 490.26 |
| 646 | 3-[5-(4-{6-[2-(7-Fluoro-4-methoxy-2-methyl-indol-1-yl)-ethylamino]-pyrimidin-4-yl}-phenyl)-oxazol-2-yl]-propionic acid (*1) | 0.83 (C) | 516.4 |
| 647 | 3-[5-(4-{6-[2-(6-Fluoro-2,4-dimethyl-indol-1-yl)-ethylamino]-pyrimidin-4-yl}-phenyl)-4-methyl-oxazol-2-yl]-propionic acid (*1) | 0.91 (C) | 514.4 |
| 648 | 3-[5-(4-{6-[2-(7-Fluoro-2,4-dimethyl-indol-1-yl)-ethylamino]-pyrimidin-4-yl}-phenyl)-4-methyl-oxazol-2-yl]-propionic acid (*1) | 0.92 (C) | 514.4 |
| 649 | 2-(4-Fluoro-phenoxy)-4-{6-[2-(4-methoxy-2-methyl-indol-1-yl)-ethylamino]-pyrimidin-4-yl}-benzoic acid (*1) | 1.01 (C) | 513.4 |
| 650 | 4-{6-[2-(7-Fluoro-2,4-dimethyl-indol-1-yl)-ethylamino]-pyrimidin-4-yl}-2-(4-fluoro-phenoxy)-benzoic acid (*1) | 1.14 (C) | 515.4 |
| 651 | 3-[5-(4-{6-[2-(6-Fluoro-4-methoxy-2-methyl-indol-1-yl)-ethylamino]-pyrimidin-4-yl}-phenyl)-4-methyl-oxazol-2-yl]-propionic acid (*1) | 0.85 (C) | 530.4 |
| 652 | 3-[5-(4-{6-[2-(7-Fluoro-4-methoxy-2-methyl-indol-1-yl)-ethylamino]-pyrimidin-4-yl}-phenyl)-4-methyl-oxazol-2-yl]-propionic acid (*1) | 0.86 (C) | 530.4 |
| 653 | 3-[5-(4-{6-[2-(6,7-Difluoro-2,4-dimethyl-indol-1-yl)-ethylamino]-pyrimidin-4-yl}-phenyl)-4-methyl-oxazol-2-yl]-propionic acid (*1) | 0.96 (C) | 532.4 |
| 654 | 4-{6-[2-(7-Fluoro-4-methoxy-2-methyl-indol-1-yl)-ethylamino]-pyrimidin-4-yl}-2-(4-fluoro-phenoxy)-benzoic acid (*1) | 1.07 (C) | 531.4 |
| 655 | 3-[5-(4-{6-[2-(6,7-Difluoro-4-methoxy-2-methyl-indol-1-yl)-ethylamino]-pyrimidin-4-yl}-phenyl)-4-methyl-oxazol-2-yl]-propionic acid (*1) | 0.90 (C) | 548.4 |
| 656 | [2-(6,7-Difluoro-4-methoxy-2-methyl-indol-1-yl)-ethyl]-{6-[3-ethoxy-5-fluoro-4-(1H-tetrazol-5-yl)-phenyl]-pyrimidin-4-yl}-amine (*1) | 0.77 (A) | 525.16 |
| 657 | [2-(6,7-Difluoro-2,4-dimethyl-indol-1-yl)-ethyl]-{6-[3-ethoxy-5-fluoro-4-(1H-tetrazol-5-yl)-phenyl]-pyrimidin-4-yl}-amine (*1) | 0.79 (A) | 509.12 |
| 658 | {6-[3-Ethoxy-5-fluoro-4-(1H-tetrazol-5-yl)-phenyl]-pyrimidin-4-yl}-[2-(6-fluoro-4-methoxy-2-methyl-indol-1-yl)-ethyl]-amine (*1) | 0.74 (A) | 507.07 |
| 659 | [2-(5-Chloro-7-methyl-[1,3]dioxolo[4,5-e]indol-6-yl)-ethyl]-{6-[3-ethylamino-4-(1H-tetrazol-5-yl)-phenyl]-pyrimidin-4-yl}-amine | 0.96 (C) | 518.4 |
| 660 | {6-[3-Ethoxy-5-fluoro-4-(1H-tetrazol-5-yl)-phenyl]-pyrimidin-4-yl}-[2-(6-fluoro-2,4-dimethyl-indol-1-yl)-ethyl]-amine (*1) | 0.76 (A) | 491.14 |
| 661 | {6-[3-Ethoxy-4-(1H-tetrazol-5-yl)-phenyl]-pyrimidin-4-yl}-[2-(7-fluoro-4-methoxy-2-methyl-indol-1-yl)-ethyl]-amine (*1) | 0.92 (C) | 489.4 |
| 662 | [2-(7-Chloro-4-methoxy-2-methyl-indol-1-yl)-ethyl]-{6-[3-ethoxy-4-(1H-tetrazol-5-yl)-phenyl]-pyrimidin-4-yl}-amine (*1) | 0.99 (C) | 505.4 |
| 663 | {6-[3-Ethoxy-4-(1H-tetrazol-5-yl)-phenyl]-pyrimidin-4-yl}-[2-(7-fluoro-2,4-dimethyl-indol-1-yl)-ethyl]-amine (*1) | 1.00 (C) | 473.4 |
| 664 | {6-[3-Ethoxy-4-(1H-tetrazol-5-yl)-phenyl]-pyrimidin-4-yl}-[2-(4-methoxy-2-methyl-indol-1-yl)-ethyl]-amine (*1) | 0.87 (C) | 471.4 |
| 665 | {6-[3-Ethylamino-4-(1H-tetrazol-5-yl)-phenyl]-pyrimidin-4-yl}-[2-(7-fluoro-4-methoxy-2-methyl-indol-1-yl)-ethyl]-amine | 0.91 (C) | 488.4 |
| 666 | [2-(7-Chloro-4-methoxy-2-methyl-indol-1-yl)-ethyl]-{6-[3-ethylamino-4-(1H-tetrazol-5-yl)-phenyl]-pyrimidin-4-yl}-amine | 0.97 (C) | 504.4 |

TABLE 8-continued

Examples 1-745

| Ex. | Compound | $t_R$ [min] (LC-MS) | MS Data m/z [M + H]$^+$ |
|---|---|---|---|
| 667 | {6-[3-Ethylamino-4-(1H-tetrazol-5-yl)-phenyl]-pyrimidin-4-yl}-[2-(4-methoxy-2-methyl-indol-1-yl)-ethyl]-amine | 0.86 (C) | 470.4 |
| 668 | {6-[3-Ethylamino-4-(1H-tetrazol-5-yl)-phenyl]-pyrimidin-4-yl}-[2-(7-fluoro-2,4-dimethyl-indol-1-yl)-ethyl]-amine | 0.98 (C) | 472.4 |
| 669 | {6-[3-Ethoxy-4-(1H-tetrazol-5-yl)-phenyl]-pyrimidin-4-yl}-[2-(2-methyl-indol-1-yl)-ethyl]-amine (*1) | 0.90 (C) | 441.4 |
| 670 | [2-(4-Methoxy-2-methyl-indol-1-yl)-ethyl]-{6-[3-methoxy-4-(1H-tetrazol-5-yl)-phenyl]-pyrimidin-4-yl}-amine | 0.81 (C) | 457.4 |
| 671 | {6-[3-Ethylamino-4-(1H-tetrazol-5-yl)-phenyl]-pyrimidin-4-yl}-[2-(2-methyl-indol-1-yl)-ethyl]-amine | 0.89 (C) | 440.4 |
| 672 | 3-Butoxy-5-{6-[2-(6-fluoro-4-methoxy-2-methyl-indol-1-yl)-ethylamino]-pyrimidin-4-yl}-thiophene-2-carboxylic acid (*1) | 0.85 (A) | 499.14 |
| 673 | 3-Butoxy-5-{6-[2-(7-fluoro-4-methoxy-2-methyl-indol-1-yl)-ethylamino]-pyrimidin-4-yl}-thiophene-2-carboxylic acid (*1) | 0.85 (A) | 499.15 |
| 674 | 5-{6-[2-(6-Fluoro-4-methoxy-2-methyl-indol-1-yl)-ethylamino]-pyrimidin-4-yl}-3-propoxy-thiophene-2-carboxylic acid (*1) | 0.81 (A) | 485.09 |
| 675 | 5-{6-[2-(7-Fluoro-4-methoxy-2-methyl-indol-1-yl)-ethylamino]-pyrimidin-4-yl}-3-isopropoxy-thiophene-2-carboxylic acid (*1) | 0.80 (A) | 485.16 |
| 676 | 5-{6-[2-(6-Fluoro-4-methoxy-2-methyl-indol-1-yl)-ethylamino]-pyrimidin-4-yl}-3-isopropoxy-thiophene-2-carboxylic acid (*1) | 0.81 (A) | 485.0 |
| 677 | 5-{6-[2-(7-Fluoro-4-methoxy-2-methyl-indol-1-yl)-ethylamino]-pyrimidin-4-yl}-3-propoxy-thiophene-2-carboxylic acid (*1) | 0.82 (A) | 485.0 |
| 678 | 3-(4-{6-[2-(6,7-Difluoro-4-methoxy-2-methyl-indol-1-yl)-ethylamino]-pyrimidin-4-yl}-phenyl)-4H-[1,2,4]oxadiazol-5-one | 0.73 (A) | 479.11 |
| 679 | 3-(4-{6-[2-(6-Chloro-4-methoxy-2-methyl-indol-1-yl)-ethylamino]-pyrimidin-4-yl}-phenyl)-4H-[1,2,4]oxadiazol-5-one | 0.73 (A) | 477.10 |
| 680 | 3-(4-{6-[2-(6,7-Difluoro-2,4-dimethyl-indol-1-yl)-ethylamino]-pyrimidin-4-yl}-phenyl)-4H-[1,2,4]oxadiazol-5-one | 0.75 (A) | 463.11 |
| 681 | 3-(4-{6-[2-(4,6-Dichloro-2-methyl-indol-1-yl)-ethylamino]-pyrimidin-4-yl}-phenyl)-4H-[1,2,4]oxadiazol-5-one | 0.77 (A) | 480.97 |
| 682 | 3-(4-{6-[2-(4,5,7-Trifluoro-2-methyl-indol-1-yl)-ethylamino]-pyrimidin-4-yl}-phenyl)-4H-[1,2,4]oxadiazol-5-one | 0.74 (A) | 466.90 |
| 683 | [2-(7-Fluoro-4-methoxy-2-methyl-indol-1-yl)-ethyl]-{6-[3-methoxy-4-(1H-tetrazol-5-yl)-phenyl]-pyrimidin-4-yl}-amine | 0.87 (C) | 475.4 |
| 684 | [2-(7-Chloro-4-methoxy-2-methyl-indol-1-yl)-ethyl]-{6-[3-methoxy-4-(1H-tetrazol-5-yl)-phenyl]-pyrimidin-4-yl}-amine | 0.93 (C) | 491.3 |
| 685 | [2-(6-Fluoro-2,4-dimethyl-indol-1-yl)-ethyl]-[6-(4-[1,2,4]oxadiazol-5-yl-phenyl)-pyrimidin-4-yl]-amine | 0.70 (A) | 429.28 |
| 686 | [2-(7-Fluoro-2,4-dimethyl-indol-1-yl)-ethyl]-[6-(2-methyl-benzooxazol-5-yl)-pyrimidin-4-yl]-amine | 0.74 (A) | 416.20 |
| 687 | [2-(6-Fluoro-4-methoxy-2-methyl-indol-1-yl)-ethyl]-[6-(2-methyl-benzooxazol-5-yl)-pyrimidin-4-yl]-amine | 0.72 (A) | 432.18 |
| 688 | [2-(7-Fluoro-4-methoxy-2-methyl-indol-1-yl)-ethyl]-[6-(2-methyl-benzooxazol-5-yl)-pyrimidin-4-yl]-amine | 0.71 (A) | 432.17 |
| 689 | [2-(6,7-Difluoro-4-methoxy-2-methyl-indol-1-yl)-ethyl]-[6-(2-methyl-benzooxazol-5-yl)-pyrimidin-4-yl]-amine | 0.74 (A) | 449.79 |
| 690 | 2-Chloro-4-{6-[2-(7-fluoro-4-methoxy-2-methyl-indol-1-yl)-ethylamino]-pyrimidin-4-yl}-6-isobutoxy-benzoic acid (*1) | 0.79 (A) | 527.0 |
| 691 | 2-Chloro-6-isobutoxy-4-{6-[2-(4-methoxy-2-methyl-indol-1-yl)-ethylamino]-pyrimidin-4-yl}-benzoic acid (*1) | 0.76 (A) | 509.0 |
| 692 | 2-Chloro-4-{6-[2-(6-fluoro-4-methoxy-2-methyl-indol-1-yl)-ethylamino]-pyrimidin-4-yl}-6-isobutoxy-benzoic acid (*1) | 0.79 (A) | 527.0 |
| 693 | 2-Chloro-4-{6-[2-(6-fluoro-2,4-dimethyl-indol-1-yl)-ethylamino]-pyrimidin-4-yl}-6-isobutoxy-benzoic acid (*1) | 0.81 (A) | 511.0 |
| 694 | 2-Chloro-4-{6-[2-(6,7-difluoro-2,4-dimethyl-indol-1-yl)-ethylamino]-pyrimidin-4-yl}-6-isobutoxy-benzoic acid (*1) | 0.84 (A) | 529.0 |
| 695 | [6-(1H-Indol-5-yl)-pyrimidin-4-yl]-[2-(2-methyl-indol-1-yl)-ethyl]-amine | 0.72 (A) | 368.20 |
| 696 | [2-(6,7-Difluoro-2,4-dimethyl-indol-1-yl)-ethyl]-[6-(1H-indol-5-yl)-pyrimidin-4-yl]-amine | 0.78 (A) | 417.98 |
| 697 | [2-(6-Fluoro-2,4-dimethyl-indol-1-yl)-ethyl]-[6-(1H-indol-5-yl)-pyrimidin-4-yl]-amine | 0.76 (A) | 400.28 |
| 698 | [2-(7-Fluoro-2,4-dimethyl-indol-1-yl)-ethyl]-[6-(1H-indol-5-yl)-pyrimidin-4-yl]-amine | 0.77 (A) | 400.25 |
| 699 | [2-(6-Fluoro-4-methoxy-2-methyl-indol-1-yl)-ethyl]-[6-(1H-indol-5-yl)-pyrimidin-4-yl]-amine | 0.73 (A) | 416.24 |
| 700 | [2-(7-Fluoro-4-methoxy-2-methyl-indol-1-yl)-ethyl]-[6-(1H-indol-5-yl)-pyrimidin-4-yl]-amine | 0.73 (A) | 416.19 |
| 701 | [2-(6,7-Difluoro-4-methoxy-2-methyl-indol-1-yl)-ethyl]-[6-(1H-indol-5-yl)-pyrimidin-4-yl]-amine | 0.75 (A) | 434.03 |
| 702 | [2-(6,7-Difluoro-2,4-dimethyl-indol-1-yl)-ethyl]-[6-(1-methyl-1H-indol-5-yl)-pyrimidin-4-yl]-amine | 0.82 (A) | 432.26 |
| 703 | [2-(6-Fluoro-2,4-dimethyl-indol-1-yl)-ethyl]-[6-(1-methyl-1H-indol-5-yl)-pyrimidin-4-yl]-amine | 0.80 (A) | 414.27 |
| 704 | [2-(7-Fluoro-2,4-dimethyl-indol-1-yl)-ethyl]-[6-(1-methyl-1H-indol-5-yl)-pyrimidin-4-yl]-amine | 0.80 (A) | 414.29 |
| 705 | [2-(6-Fluoro-4-methoxy-2-methyl-indol-1-yl)-ethyl]-[6-(1-methyl-1H-indol-5-yl)-pyrimidin-4-yl]-amine | 0.77 (A) | 430.27 |

TABLE 8-continued

Examples 1-745

| Ex. | Compound | $t_R$ [min] (LC-MS) | MS Data m/z [M + H]$^+$ |
|---|---|---|---|
| 706 | [2-(7-Fluoro-4-methoxy-2-methyl-indol-1-yl)-ethyl]-[6-(1-methyl-1H-indol-5-yl)-pyrimidin-4-yl]-amine | 0.76 (A) | 430.25 |
| 707 | [2-(6,7-Difluoro-4-methoxy-2-methyl-indol-1-yl)-ethyl]-[6-(1-methyl-1H-indol-5-yl)-pyrimidin-4-yl]-amine | 0.80 (A) | 448.24 |
| 708 | 3-(4-{6-[2-(7-Fluoro-2,4-dimethyl-indol-1-yl)-ethylamino]-pyrimidin-4-yl}-phenyl)-3-oxo-propionitrile | 0.76 (A) | 428.18 |
| 709 | 3-(4-{6-[2-(6-Fluoro-4-methoxy-2-methyl-indol-1-yl)-ethylamino]-pyrimidin-4-yl}-phenyl)-3-oxo-propionitrile | 0.74 (A) | 444.16 |
| 710 | 3-(4-{6-[2-(7-Fluoro-4-methoxy-2-methyl-indol-1-yl)-ethylamino]-pyrimidin-4-yl}-phenyl)-3-oxo-propionitrile | 0.73 (A) | 444.18 |
| 711 | 3-(4-{6-[2-(6,7-Difluoro-4-methoxy-2-methyl-indol-1-yl)-ethylamino]-pyrimidin-4-yl}-phenyl)-3-oxo-propionitrile | 0.76 (A) | 462.15 |
| 712 | [2-(2-Methyl-indol-1-yl)-ethyl]-{6-[4-(3-methyl-isoxazol-5-yl)-phenyl]-pyrimidin-4-yl}-amine | 0.76 (A) | 410.25 |
| 713 | [2-(6-Fluoro-2,4-dimethyl-indol-1-yl)-ethyl]-{6-[4-(3-methyl-isoxazol-5-yl)-phenyl]-pyrimidin-4-yl}-amine | 0.80 (A) | 442.16 |
| 714 | [2-(7-Fluoro-2,4-dimethyl-indol-1-yl)-ethyl]-{6-[4-(3-methyl-isoxazol-5-yl)-phenyl]-pyrimidin-4-yl}-amine | 0.81 (A) | 442.19 |
| 715 | [2-(6-Fluoro-4-methoxy-2-methyl-indol-1-yl)-ethyl]-{6-[4-(3-methyl-isoxazol-5-yl)-phenyl]-pyrimidin-4-yl}-amine | 0.78 (A) | 458.16 |
| 716 | [2-(7-Fluoro-4-methoxy-2-methyl-indol-1-yl)-ethyl]-{6-[4-(3-methyl-isoxazol-5-yl)-phenyl]-pyrimidin-4-yl}-amine | 0.78 (A) | 458.18 |
| 717 | [2-(6,7-Difluoro-4-methoxy-2-methyl-indol-1-yl)-ethyl]-{6-[4-(3-methyl-isoxazol-5-yl)-phenyl]-pyrimidin-4-yl}-amine | 0.80 (A) | 476.10 |
| 718 | 4-{6-[2-(7-Chloro-5-fluoro-2,4-dimethyl-indol-1-yl)-ethylamino]-pyrimidin-4-yl}-2-propoxy-benzoic acid | 0.81 (A) | 497.14 |
| 719 | [2-(6,7-Difluoro-2,4-dimethyl-indol-1-yl)-ethyl]-{6-[4-(4-methyl-isoxazol-5-yl)-phenyl]-pyrimidin-4-yl}-amine | 0.82 (A) | 460.14 |
| 720 | 2-Chloro-4-{6-[2-(4-methoxy-2-methyl-indol-1-yl)-ethylamino]-pyrimidin-4-yl}-6-(2,2,2-trifluoro-ethoxy)-benzoic acid (*1) | 0.75 (A) | 535.0 |
| 721 | 2-Chloro-4-{6-[2-(6-fluoro-4-methoxy-2-methyl-indol-1-yl)-ethylamino]-pyrimidin-4-yl}-6-(2,2,2-trifluoro-ethoxy)-benzoic acid (*1) | 0.77 (A) | 553.0 |
| 722 | 2-Chloro-4-{6-[2-(6,7-difluoro-4-methoxy-2-methyl-indol-1-yl)-ethylamino]-pyrimidin-4-yl}-6-(2,2,2-trifluoro-ethoxy)-benzoic acid (*1) | 0.82 (A) | 571.0 |
| 723 | 2-Chloro-4-{6-[2-(6-fluoro-2,4-dimethyl-indol-1-yl)-ethylamino]-pyrimidin-4-yl}-6-(2,2,2-trifluoro-ethoxy)-benzoic acid (*1) | 0.79 (A) | 537.0 |
| 724 | 2-Chloro-4-{6-[2-(6,7-difluoro-2,4-dimethyl-indol-1-yl)-ethylamino]-pyrimidin-4-yl}-6-(2,2,2-trifluoro-ethoxy)-benzoic acid (*1) | 0.82 (A) | 555.0 |
| 725 | 2-Chloro-4-{6-[2-(7-fluoro-4-methoxy-2-methyl-indol-1-yl)-ethylamino]-pyrimidin-4-yl}-6-(2,2,2-trifluoro-ethoxy)-benzoic acid (*1) | 0.78 (A) | 553.0 |
| 726 | [2-(6-Fluoro-4-methoxy-2-methyl-indol-1-yl)-ethyl]-[6-(3-pyrazol-1-yl-phenyl)-pyrimidin-4-yl]-amine (*2) | 0.75 (A) | 443.0 |
| 727 | [2-(6-Fluoro-4-methoxy-2-methyl-indol-1-yl)-ethyl]-[6-(4-pyridin-2-yl-phenyl)-pyrimidin-4-yl]-amine (*2) | 0.72 (A) | 454.0 |
| 728 | [2-(6-Fluoro-4-methoxy-2-methyl-indol-1-yl)-ethyl]-(6-isoquinolin-7-yl-pyrimidin-4-yl)-amine (*2) | 0.66 (A) | 428.0 |
| 729 | [2-(6-Fluoro-2,4-dimethyl-indol-1-yl)-ethyl]-[6-(3-pyrazol-1-yl-phenyl)-pyrimidin-4-yl]-amine (*2) | 0.79 (A) | 428.0 |
| 730 | [2-(6-Fluoro-2,4-dimethyl-indol-1-yl)-ethyl]-[6-(4-pyridin-2-yl-phenyl)-pyrimidin-4-yl]-amine (*2) | 0.73 (A) | 438.0 |
| 731 | [2-(6-Fluoro-2,4-dimethyl-indol-1-yl)-ethyl]-(6-isoquinolin-7-yl-pyrimidin-4-yl)-amine (*2) | 0.67 (A) | 412.0 |
| 732 | [2-(6-Fluoro-2,4-dimethyl-indol-1-yl)-ethyl]-(6-quinolin-6-yl-pyrimidin-4-yl)-amine (*2) | 0.71 (A) | 412.0 |
| 733 | [2-(6-Fluoro-2,4-dimethyl-indol-1-yl)-ethyl]-(6-quinoxalin-6-yl-pyrimidin-4-yl)-amine (*2) | 0.74 (A) | 413.30 |
| 734 | [2-(6-Fluoro-2,4-dimethyl-indol-1-yl)-ethyl]-{6-[4-(4-methyl-isoxazol-5-yl)-phenyl]-pyrimidin-4-yl}-amine | 0.80 (A) | 442.22 |
| 735 | [2-(7-Fluoro-2,4-dimethyl-indol-1-yl)-ethyl]-{6-[4-(4-methyl-isoxazol-5-yl)-phenyl]-pyrimidin-4-yl}-amine | 0.81 (A) | 442.19 |
| 736 | [2-(6-Fluoro-4-methoxy-2-methyl-indol-1-yl)-ethyl]-{6-[4-(4-methyl-isoxazol-5-yl)-phenyl]-pyrimidin-4-yl}-amine | 0.78 (A) | 458.20 |
| 737 | [2-(7-Fluoro-4-methoxy-2-methyl-indol-1-yl)-ethyl]-{6-[4-(4-methyl-isoxazol-5-yl)-phenyl]-pyrimidin-4-yl}-amine | 0.78 (A) | 458.11 |
| 738 | [2-(6,7-Difluoro-4-methoxy-2-methyl-indol-1-yl)-ethyl]-{6-[4-(4-methyl-isoxazol-5-yl)-phenyl]-pyrimidin-4-yl}-amine | 0.80 (A) | 476.13 |
| 739 | [6-(3H-Benzotriazol-5-yl)-pyrimidin-4-yl]-[2-(7-fluoro-2,4-dimethyl-indol-1-yl)-ethyl]-amine | 0.68 (A) | 402.05 |
| 740 | [6-(2,3-Dihydro-benzo[1,4]dioxin-6-yl)-pyrimidin-4-yl]-[2-(7-fluoro-2,4-dimethyl-indol-1-yl)-ethyl]-amine | 0.77 (A) | 419.17 |
| 741 | [2-(7-Fluoro-2,4-dimethyl-indol-1-yl)-ethyl]-[6-(4-[1,2,4]triazol-1-yl-phenyl)-pyrimidin-4-yl]-amine | 0.73 (A) | 428.18 |
| 742 | [2-(6,7-Difluoro-2,4-dimethyl-indol-1-yl)-ethyl]-[6-(4-isoxazol-5-yl-phenyl)-pyrimidin-4-yl]-amine | 0.79 (A) | 446.08 |

TABLE 8-continued

Examples 1-745

| Ex. | Compound | $t_R$ [min] (LC-MS) | MS Data m/z [M + H]+ |
|---|---|---|---|
| 743 | [2-(6-Fluoro-4-methoxy-2-methyl-indol-1-yl)-ethyl]-[6-(4-isoxazol-5-yl-phenyl)-pyrimidin-4-yl]-amine | 0.74 (A) | 444.17 |
| 744 | [2-(7-Fluoro-4-methoxy-2-methyl-indol-1-yl)-ethyl]-[6-(4-isoxazol-5-yl-phenyl)-pyrimidin-4-yl]-amine | 0.73 (A) | 444.09 |
| 745 | [2-(6,7-Difluoro-4-methoxy-2-methyl-indol-1-yl)-ethyl]-[6-(4-isoxazol-5-yl-phenyl)-pyrimidin-4-yl]-amine | 0.77 (A) | 462.06 |

Example 746: {6-[3-Methoxy-4-(1H-tetrazol-5-yl)-phenyl]-pyrimidin-4-yl}-[2-(2-methyl-indol-1-yl)-ethyl]-amine The title compound is prepared according to the procedure described for A.2.84., using 2-methoxy-4-(6-((2-(2-methyl-1H-indol-1-yl)ethyl)amino)pyrimidin-4-yl)benzonitrile. LC-MS A: $t_R$=0.69 min; [M+H]+=426.97.

a) 2-Methoxy-4-(6-((2-(2-methyl-1H-indol-1-yl)ethyl)amino)pyrimidin-4-yl)benzonitrile The title compound is prepared according to the general procedure A described above, using the building block A.1.1. and 4-cyano-3-methoxyphenylboronic acid. LC-MS A: $t_R$=0.97 min; [M+H]+=383.99.

Example 747: [2-(4,7-Difluoro-2-methyl-indol-1-yl)-ethyl]-{6-[3-methoxy-4-(1H-tetrazol-5-yl)-phenyl]-pyrimidin-4-yl}-amine The title compound is prepared according to the procedure described for A.2.84., using 4-(6-((2-(4,7-difluoro-2-methyl-1H-indol-1-yl)ethyl)amino)pyrimidin-4-yl)-2-methoxybenzonitrile. LC-MS A: $t_R$=0.73 min; [M+H]+=463.21.

a) 4-(6-((2-(4,7-Difluoro-2-methyl-1H-indol-1-yl)ethyl)amino)pyrimidin-4-yl)-2-methoxybenzonitrile The title compound is prepared according to the general procedure A described above, using the building block A.1.10. and 4-cyano-3-methoxyphenylboronic acid. LC-MS A: $t_R$=0.81 min; [M+H]+=420.03.

Example 748: [2-(7-Fluoro-2,4-dimethyl-indol-1-yl)-ethyl]-{6-[3-methoxy-4-(1H-tetrazol-5-yl)-phenyl]-pyrimidin-4-yl}-amine The title compound is prepared according to the procedure described for A.2.84., using 4-(6-((2-(7-fluoro-2,4-dimethyl-1H-indol-1-yl)ethyl)amino)pyrimidin-4-yl)-2-methoxybenzonitrile. LC-MS A: $t_R$=0.74 min; [M+H]+=459.12.

a) 4-(6-((2-(7-Fluoro-2,4-dimethyl-1H-indol-1-yl)ethyl)amino)pyrimidin-4-yl)-2-methoxybenzonitrile The title compound is prepared according to the general procedure A described above, using the building block A.1.8. and 4-cyano-3-methoxyphenylboronic acid. LC-MS A: $t_R$=0.82 min; [M+H]+=416.04.

Example 749: [2-(6-Fluoro-4-methoxy-2-methyl-indol-1-yl)-ethyl]-{6-[4-(6-methoxy-pyrimidin-4-yl)-phenyl]-pyrimidin-4-yl}-amine The title compound is prepared according to the general procedure A described above, using N-(2-(6-fluoro-4-methoxy-2-methyl-1H-indol-1-yl)ethyl)-6-(4-(4,4,5,5-tetramethyl-1,3,2-dioxaborolan-2-yl)phenyl)pyrimidin-4-amine and 4-chloro-6-methoxypyrimidine. LC-MS E: $t_R$=1.10 min; [M+H]+=484.88.

a) N-(2-(6-fluoro-4-methoxy-2-methyl-1H-indol-1-yl)ethyl)-6-(4-(4,4,5,5-tetramethyl-1,3,2-dioxaborolan-2-yl)phenyl)pyrimidin-4-amine The title compound is prepared according to the general procedure A described above, using the building block A.1.23. and 1,4-Phenylenediboronic acid, pinacol ester. LC-MS A: $t_R$=0.83 min; [M+H]+=503.22.

Following the procedure described for example 749, the coupling of N-(2-(6-fluoro-4-methoxy-2-methyl-1H-indol-1-yl)ethyl)-6-(4-(4,4,5,5-tetramethyl-1,3,2-dioxaborolan-2-yl)phenyl)pyrimidin-4-amine and the selected commercially available heteroaryl bromide, the following examples are synthesized:

TABLE 9

Examples 750-763

| Ex. | Compound | $t_R$ [min] (LC-MS) | MS Data m/z [M + H]+ |
|---|---|---|---|
| 750 | [2-(6-Fluoro-4-methoxy-2-methyl-indol-1-yl)-ethyl]-[6-(4-pyrazin-2-yl-phenyl)-pyrimidin-4-yl]-amine | 1.02 (E) | 454.89 |
| 751 | [2-(6-Fluoro-4-methoxy-2-methyl-indol-1-yl)-ethyl]-[6-(4-thiazol-2-yl-phenyl)-pyrimidin-4-yl]-amine | 1.10 (E) | 459.85 |
| 752 | {6-[4-(1,5-Dimethyl-1H-imidazol-2-yl)-phenyl]-pyrimidin-4-yl}-[2-(6-fluoro-4-methoxy-2-methyl-indol-1-yl)-ethyl]-amine | 0.69 (E) | 470.91 |
| 753 | [2-(6-Fluoro-4-methoxy-2-methyl-indol-1-yl)-ethyl]-{6-[4-(2-methyl-2H-[1,2,4]triazol-3-yl)-phenyl]-pyrimidin-4-yl}-amine | 0.75 (E) | 457.93 |

TABLE 9-continued

Examples 750-763

| Ex. | Compound | $t_R$ [min] (LC-MS) | MS Data m/z [M + H]$^+$ |
|---|---|---|---|
| 754 | [2-(6-Fluoro-4-methoxy-2-methyl-indol-1-yl)-ethyl]-{6-[4-(4-methoxy-pyrimidin-2-yl)-phenyl]-pyrimidin-4-yl}-amine | 0.91 (E) | 484.89 |
| 755 | [2-(6-Fluoro-4-methoxy-2-methyl-indol-1-yl)-ethyl]-[6-(4-pyrimidin-2-yl-phenyl)-pyrimidin-4-yl]-amine | 0.83 (E) | 454.9 |
| 756 | [2-(6-Fluoro-4-methoxy-2-methyl-indol-1-yl)-ethyl]-{6-[4-(6-methoxy-pyridazin-3-yl)-phenyl]-pyrimidin-4-yl}-amine | 0.85 (E) | 484.87 |
| 757 | [2-(6-Fluoro-4-methoxy-2-methyl-indol-1-yl)-ethyl]-{6-[4-(5-methoxy-pyrimidin-2-yl)-phenyl]-pyrimidin-4-yl}-amine | 0.89 (E) | 484.88 |
| 758 | [2-(6-Fluoro-4-methoxy-2-methyl-indol-1-yl)-ethyl]-{6-[4-(4-methyl-thiazol-2-yl)-phenyl]-pyrimidin-4-yl}-amine | 0.91 (E) | 473.88 |
| 759 | [2-(6-Fluoro-4-methoxy-2-methyl-indol-1-yl)-ethyl]-{6-[4-(4-fluoro-pyridin-2-yl)-phenyl]-pyrimidin-4-yl}-amine | 0.89 (E) | 471.86 |
| 760 | {6-[4-(4,5-Dimethyl-thiazol-2-yl)-phenyl]-pyrimidin-4-yl}-[2-(6-fluoro-4-methoxy-2-methyl-indol-1-yl)-ethyl]-amine | 0.96 (E) | 487.88 |
| 761 | [2-(6-Fluoro-4-methoxy-2-methyl-indol-1-yl)-ethyl]-{6-[4-(6-methoxy-pyrazin-2-yl)-phenyl]-pyrimidin-4-yl}-amine | 0.89 (E) | 484.88 |
| 762 | [2-(6-Fluoro-4-methoxy-2-methyl-indol-1-yl)-ethyl]-{6-[4-(5-fluoro-pyrimidin-2-yl)-phenyl]-pyrimidin-4-yl}-amine | 0.89 (E) | 472.87 |
| 763 | 6-(4-(6-((2-(6-Fluoro-4-methoxy-2-methyl-1H-indol-1-yl)ethyl)amino)pyrimidin-4-yl)phenyl)-N,N-dimethylpyrimidin-4-amine | 0.75 (E) | 497.95 |

Example 764: [2-(2-Methyl-indol-1-yl)-ethyl]-[6-(4-thiazol-2-yl-phenyl)-pyrimidin-4-yl]-amine The title compound is prepared according to the general procedure A described above, using N-(2-(2-methyl-1H-indol-1-yl)ethyl)-6-(4-(4,4,5,5-tetramethyl-1,3,2-dioxaborolan-2-yl)phenyl)pyrimidin-4-amine. LC-MS A: $t_R$=0.76 min; [M+H]+=412.15.

a) N-(2-(2-methyl-1H-indol-1-yl)ethyl)-6-(4-(4,4,5,5-tetramethyl-1,3,2-dioxaborolan-2-yl)phenyl)pyrimidin-4-amine The title compound is prepared according to the general procedure A described above, using the building block A.1.1. and 1,4-Phenylenediboronic acid, pinacol ester. LC-MSA: $t_R$=0.81 m; [M+H]+=455.36.

Example 765: 2-Ethoxy-4-{6-[2-(7-fluoro-4-methoxy-2-methyl-indol-1-yl)-ethylamino]-pyrimidin-4-yl}-N-methoxy-benzamide To a solution of 2-ethoxy-4-{6-[2-(7-fluoro-4-methoxy-2-methyl-indol-1-yl)-ethylamino]-pyrimidin-4-yl}-benzoic acid (example 326) (50 mg, 0.108 mmol) in DCM (2 mL) is added O-methylhydroxylamine hydrochloride (13.5 mg, 0.161 mmol) and DIPEA (0.0553 mL, 0.323 mmol) and the mixture is cooled to 0° C. Propylphosphonic anhydride (50% solution in DCM, 0.0705 mL, 0.118 mmol) is added and the solution allowed to warm up to RT and stirred overnight. The mixture is concentrated under reduced pressure. The residue is purified via preparative HPLC (large X Bridge prep C 18, basic), affording the title compound as a white powder. LC-MS A: $t_R$=0.70 min; [M+H]+=493.92.

Following the procedure described for example 765, the coupling of 2-ethoxy-4-{6-[2-(7-fluoro-4-methoxy-2-methyl-indol-1-yl)-ethylamino]-pyrimidin-4-yl}-benzoic acid (example 326) or 2-ethoxy-4-{6-[2-(7-fluoro-2,4-dimethyl-indol-1-yl)-ethylamino]-pyrimidin-4-yl}-benzoic acid (example 158) and the selected commercially available alkylhydroxylamine hydrochlorides, the following examples are synthesized:

TABLE 10

Examples 766-771

| Ex. | Compound | $t_R$ [min] (LC-MS) | MS Data m/z [M + H]$^+$ |
|---|---|---|---|
| 766 | N-Benzyloxy-2-ethoxy-4-{6-[2-(7-fluoro-4-methoxy-2-methyl-indol-1-yl)-ethylamino]-pyrimidin-4-yl}-benzamide | 0.81 (A) | 571.03 |
| 767 | 2,N-Diethoxy-4-{6-[2-(7-fluoro-4-methoxy-2-methyl-indol-1-yl)-ethylamino]-pyrimidin-4-yl}-benzamide | 0.95 (C) | 508.4 |
| 768 | N-Benzyloxy-2-ethoxy-4-{6-[2-(7-fluoro-2,4-dimethyl-indol-1-yl)-ethylamino]-pyrimidin-4-yl}-benzamide | 1.18 (C) | 554.5 |
| 769 | 2-Ethoxy-4-{6-[2-(7-fluoro-4-methoxy-2-methyl-indol-1-yl)-ethylamino]-pyrimidin-4-yl}-N-(2-hydroxy-ethoxy)-benzamide | 0.83 (C) | 522.4 |

TABLE 10-continued

Examples 766-771

| Ex. | Compound | $t_R$ [min] (LC-MS) | MS Data m/z [M + H]+ |
|---|---|---|---|
| 770 | 2-Ethoxy-4-{6-[2-(7-fluoro-4-methoxy-2-methyl-indol-1-yl)-ethylamino]-pyrimidin-4-yl}-N-isopropoxy-benzamide | 1.00 (C) | 522.4 |
| 771 | 2-Ethoxy-4-{6-[2-(7-fluoro-2,4-dimethyl-indol-1-yl)-ethylamino]-pyrimidin-4-yl}-N-(2-hydroxy-ethoxy)-benzamide | 0.69 (A) | 508.97 |

Example 772: 6-{6-[2-(2-Methyl-indol-1-yl)-ethyl-amino]-pyrimidin-4-yl}-1,2-dihydro-indazol-3-one A solution of methyl 2-fluoro-4-(6-((2-(2-methyl-1H-indol-1-yl)ethyl)amino)pyrimidin-4-yl)benzoate (100 mg, 0.247 mmol) in hydrazine hydrate (1.15 mL, 23.7 mmol) is refluxed for 5 h, then cooled to RT, and concentrated. The crude product is purified by prep LCMS under basic conditions, to afford the title compound as a yellow powder (76 mg, 80%). LC-MS A: $t_R$=0.61 min; [M+H]+=385.14.

a) Methyl 2-fluoro-4-(6-((2-(2-methyl-1H-indol-1-yl)ethyl)amino)pyrimidin-4-yl)benzoate To a solution of 2-fluoro-4-(6-((2-(2-methyl-1H-indol-1-yl)ethyl)amino)pyrimidin-4-yl)benzoic acid (300 mg, 0.768 mmol) in DMF (7.6 mL) is added K₂CO₃ (191 mg, 1.38 mmol) and iodomethane (218 mg, 1.54 mmol), and the RM is stirred at RT for 30 min. Water is added to the RM and it is extracted with Et₂O (3×). Organic layers are mixed and washed with water (2×), then dried over MgSO₄ and concentrated to dryness. The crude product is purified by FC, eluting with DCM/MeOH (50:1) to afford the product as a yellow solid (0.295 g, 95%). LC-MS A: $t_R$=0.78 min; [M+H]+= 405.15.

b) 2-Fluoro-4-(6-((2-(2-methyl-1H-indol-1-yl)ethyl)amino)pyrimidin-4-yl)benzoic acid Following general procedure A with A.1.1. and 3-fluoro-4-methoxycarbonylphenylboronic acid, the title compound is obtained as a white solid. LC-MS A: $t_R$=0.68 min; [M+H]+=391.16.

Example 773: 6-{6-[2-(7-Fluoro-4-methoxy-2-methyl-indol-1-yl)-ethylamino]-pyrimidin-4-yl}-1,2-dihydro-indazol-3-one Following the same method as described for example 772, using methyl 2-fluoro-4-(6-((2-(7-fluoro-4-methoxy-2-methyl-1H-indol-1-yl)ethyl)amino)pyrimidin-4-yl)benzoate, the title compound is obtained as a pale yellow solid. LC-MS A: $t_R$=0.63 min; [M+H]+=433.01.

a) Methyl 2-fluoro-4-(6-((2-(7-fluoro-4-methoxy-2-methyl-1H-indol-1-yl)ethyl)amino)pyrimidin-4-yl)benzoate Following the same method as described for example 772 a), using 2-fluoro-4-(6-((2-(7-fluoro-4-methoxy-2-methyl-1H-indol-1-yl)ethyl)amino)pyrimidin-4-yl) benzoic acid, the title compound is obtained as a yellow solid. LC-MS A: $t_R$=0.80 min; [M+H]+=453.05.

b) 2-Fluoro-4-(6-((2-(7-fluoro-4-methoxy-2-methyl-1H-indol-1-yl)ethyl)amino)pyrimidin-4-yl)benzoic acid Following general procedure A with A.1.25. and 3-fluoro-4-methoxycarbonylphenylboronic acid, the title compound is obtained as a pale yellow solid. LC-MS A: $t_R$=0.70 min; [M+H]+=439.03.

Example 774: 6-{6-[2-(2-Methyl-indol-1-yl)-ethyl-amino]-pyrimidin-4-yl}-benzo[d]isoxazol-3-one To a solution of N-hydroxyacetamide (83.1 mg, 1.11 mmol) in DMF (1.3 mL) is added potassium tert-butoxide (124 mg, 1.11 mmol) and the RM is stirred for 30 min before adding methyl 2-fluoro-4-(6-((2-(2-methyl-1H-indol-1-yl)ethyl)amino)pyrimidin-4-yl)benzoate (example 760 a) (179 mg, 0.443 mmol) in DMF (0.5 mL). The RM is stirred at 100° C. overnight. The RM is cooled and partitioned between EtOAc (10 mL) and 1N NaOH solution (10 mL). The aq. layer is washed with EtOAc, then acidified with 2N HCl solution (10 mL). The desired product is collected by filtration from the aq. layer as a pale yellow solid (109 mg, 64%). LC-MS A: $t_R$=0.68 min; [M+H]+=386.03.

Example 775: 4-{6-[2-(2,7-Dichloro-4-methoxy-indol-1-yl)-ethylamino]-pyrimidin-4-yl}-2-ethoxy-benzoic acid (*1)

To a suspension of ethyl 4-(6-((2-(2,7-dichloro-4-methoxy-1H-indol-1-yl)ethyl)amino)pyrimidin-4-yl)-2-ethoxybenzoate (80 mg, 0.151 mmol) in EtOH/H₂O (2:1, 1.2 mL) is added LiOH monohydrate (31.7 mg, 0.756 mmol), and the is stirred at 80° C. for 1 h 30, then cooled to RT, filtered through 0.45 um and 0.22 um filters and purified via HPLC prep. under basic condition, to afford the title compound as a pink powder (40 mg, 30%). LC-MS A: $t_R$=0.77 min; [M+H]+=500.86.

a) Ethyl 4-(6-((2-(2,7-dichloro-4-methoxy-1H-indol-1-yl)ethyl)amino)pyrimidin-4-yl)-2-ethoxybenzoate Ethyl 4-(6-((2-(7-chloro-4-methoxy-2-oxoindolin-1-yl)ethyl)amino)pyrimidin-4-yl)-2-ethoxybenzoate (157 mg, 0.307 mmol) is dissolved in POCl3 (1 mL) and stirred under reflux for 1 h. The RM is cooled to 0° C. and carefully quenched with NaOH 32% until basic pH then additional water is carefully added. The aqueous layer is extracted with DCM (×3). Organic layers are washed with brine, dried over MgSO₄. filtered. MeOH is added and the solvent is removed under reduced pressure to afford the crude title compound as a brown solid, quantitatively. LC-MS A: $t_R$=0.86 min; [M+H]+=528.79.

b) Ethyl 4-(6-((2-(7-chloro-4-methoxy-2-oxoindolin-1-yl)ethyl)amino)pyrimidin-4-yl)-2-ethoxybenzoate Following the general procedure A, 7-chloro-1-(2-((6-chloropyrimidin-4-yl)amino)ethyl)-4-methoxyindolin-2-one and ethyl 2-ethoxy-4-(4,4,5,5-tetramethyl-1,3,2-dioxaborolan-2-yl)benzoate are coupled, affording the title compound as a pale yellow solid. LC-MS A: $t_R$=0.78 min; [M+H]+=511.05.

c) 7-Chloro-1-(2-((6-chloropyrimidin-4-yl)amino) ethyl)-4-methoxyindolin-2-one

Following the procedure described for A.1.1. with 1-(2-aminoethyl)-7-chloro-4-methoxyindolin-2-one, the title compound is obtained as an orange solid. LC-MS A: $t_R$=0.81 min; [M+H]+=352.97.

d) 1-(2-Aminoethyl)-7-chloro-4-methoxyindolin-2-one

To a suspension of 7-chloro-1-(2-(1,3-dioxoisoindolin-2-yl)ethyl)-4-methoxyindoline-2,3-dione (2.694 g, 7 mmol) in Ethanol (60 mL) is added hydrazine monohydrate (4.08 mL, 84 mmol). The RM is stirred at 110° C. in a sealed tube for overnight, then cooled at RT and partitioned between DCM and NaOH 1M. The organic layer is dried over MgSO$_4$, filtrated and concentrated under vacuum to afford the crude product. It is triturated in Et$_2$O and filtered. This afforded the title compound as a beige solid (1.156 g, 69%). LC-MS A: $t_R$=0.52 min; [M+H]+=241.09.

e) 7-Chloro-1-(2-(1,3-dioxoisoindolin-2-yl)ethyl)-4-methoxyindoline-2,3-dione

To a suspension of NaH (926 mg, 23.2 mmol) in DMF (39 mL) is added at 0° C. 7-chloro-4-methoxyindoline-2,3-dione (2.45 g, 11.6 mmol) in DMF (15 mL). The RM is allowed to warm up to RT and stirred for 30 min. Then the mixture is heated up to 60° C. and N-(2-Bromoethyl)phthalimide (4.65 g, 17.4 mmol) in DMF (20 mL) is added dropwise to the mixture. The RM is then stirred at 60° C. overnight. It is cooled down to 0° C., quenched with water, the precipitate is filtered, washed with Et$_2$O, and dried, affording the title compound as a yellow solid (2.70 g, 61%). LC-MS A: $t_R$=0.83 min; [M+H]+=385.03.

f) 7-Chloro-4-methoxyindoline-2,3-dione

A flask is charged with concentrated H2SO4 (13.5 mL) and warm up to 60° C. (E)-N-(2-chloro-5-methoxyphenyl)-2-(hydroxyimino)acetamide (573 mg, 2.51 mmol) is added portionwise. The mixture is stirred at 60° C. for 20 min, then allowed to cooled to 0° C. and water is carefully added. The precipitate is filtered, well-washed with water, dissolved in acetone and dried with MgSO$_4$. The organic phase is filtered and the solvent is removed under reduced pressure to afford the title compound as a deep orange solid (3.00 g, 79%). LCMS A: $t_R$=0.60 min, no ionization.

g) (E)-N-(2-Chloro-5-methoxyphenyl)-2-(hydroxyimino)acetamide

To a solution of 2-Chloro-5-methoxyaniline (8.00 g, 50.8 mmol) in water (72 mL) is added concentrated HCl (35%) (4.32 mL), then a solution of chloral hydrate (8.43 g, 51 mmol) in water (176 mL) followed by sodium sulfate (24.6 g, 156 mmol). Hydroxylamine (50% in water, 7.68 mL, 254 mmol) is added, and the mixture is refluxed for 1.5 h. The RM is cooled to 0° C., the RM is filtered and the obtained precipitate is washed with water (×3). The solid is dissolved in acetone and dried with MgSO$_4$. The organic phase is filtered and the solvent is removed under reduced pressure to afford a dark brown solid. It is triturated in Et$_2$O, the solid is removed by filtration, well washed with Et$_2$O and discarded. The filtrate is concentrated to dryness. The resulting orange solid is triturated in DCM, the solid is filtered, and the filtrate is concentrated under vacuum, to be triturated again in DCM before being filtered (×3). This affords the pure product as a beige solid (4.08 g, 35%). LCMS A: $t_R$=0.73 min, [M+H]+=229.07.

Example 776: 4-{6-[2-(2-Chloro-7-fluoro-4-methoxy-indol-1-yl)-ethylamino]-pyrimidin-4-yl}-2-ethoxy-benzoic acid (*1)

Following the procedure described for example 775 using ethyl 4-(6-((2-(2-chloro-7-fluoro-4-methoxy-1H-indol-1-yl)ethyl)amino)pyrimidin-4-yl)-2-ethoxybenzoate, the title compound is obtained as a pink powder. LC-MS A: $t_R$=0.74 min; [M+H]+=484.89.

a) Ethyl 4-(6-((2-(2-chloro-7-fluoro-4-methoxy-1H-indol-1-yl)ethyl)amino)pyrimidin-4-yl)-2-ethoxybenzoate Following the procedure described for example 775 a) using ethyl 2-ethoxy-4-(6-((2-(7-fluoro-4-methoxy-2-oxoindolin-1-yl)ethyl)amino)pyrimidin-4-yl)benzoate, the title compound is obtained as an orange solid. LC-MS A: $t_R$=0.84 min; [M+H]+=512.97.

b) Ethyl 2-ethoxy-4-(6-((2-(7-fluoro-4-methoxy-2-oxoindolin-1-yl)ethyl)amino)pyrimidin-4-yl)benzoate Following the procedure described for example 775 b) using 1-(2-((6-chloropyrimidin-4-yl)amino)ethyl)-7-fluoro-4-methoxyindolin-2-one, the title compound is obtained as a pale yellow solid. LC-MS A: $t_R$=0.75 min; [M+H]+=495.07.

c) 1-(2-((6-Chloropyrimidin-4-yl)amino)ethyl)-7-fluoro-4-methoxyindolin-2-one

Following the procedure described for example 775 c) using 1-(2-aminoethyl)-7-fluoro-4-methoxyindolin-2-one, the title compound is obtained as an orange solid. LC-MS A: $t_R$=0.76 min; [M+H]+=336.96.

d) 1-(2-Aminoethyl)-7-fluoro-4-methoxyindolin-2-one

Following the procedure described for example 775 d) using 1-(2-(1,3-dioxoisoindolin-2-yl)ethyl)-7-fluoro-4- methoxyindoline-2,3-dione, the title compound is obtained as a beige solid. LC-MS A: $t_R$=0.46 min; [M+H]+=225.18.

e) 1-(2-(1,3-Dioxoisoindolin-2-yl)ethyl)-7-fluoro-4-methoxyindoline-2,3-dione

Following the procedure described for example 775 e) using 7-fluoro-4-methoxyindoline-2,3-dione, the title compound is obtained as an orange solid. LC-MS A: $t_R$=0.80 min; [M+H]+=369.043.

f) 7-Fluoro-4-methoxyindoline-2,3-dione

Following the procedure described for example 775 f) using (E)-N-(2-fluoro-5-methoxyphenyl)-2-(hydroxyimino)acetamide, the title compound is obtained as an orange solid. LC-MS A: $t_R$=0.54 min; no ionization.

g) (E)-N-(2-Fluoro-5-methoxyphenyl)-2-(hydroxyimino)acetamide

Following the procedure described for example 775 g) using 2-fluoro-5-methoxyaniline, the title compound is obtained as an off-white solid. LC-MS A: $t_R$=0.65 min; [M+H]+=213.06.

Example 777: 5-{6-[2-(2-Chloro-7-fluoro-4-methoxy-indol-1-yl)-ethylamino]-pyrimidin-4-yl}-3-ethoxy-thiophene-2-carboxylic acid (*1)

Following the procedure described for example 775 using methyl 5-(6-((2-(2-chloro-7-fluoro-4-methoxy-1H-indol-1-yl)ethyl)amino)pyrimidin-4-yl)-3-ethoxythiophene-2-carboxylate, the title compound is obtained as a beige powder. LC-MS A: $t_R$=0.79 min; [M+H]+=491.03.

a) Methyl 5-(6-((2-(2-chloro-7-fluoro-4-methoxy-1H-indol-1-yl)ethyl)amino)pyrimidin-4-yl)-3-ethoxythiophene-2-carboxylate Following the procedure described for example 775 a) using methyl 3-ethoxy-5-(6-((2-(7-fluoro-4-methoxy-2-oxoindolin-1-yl)ethyl)amino)pyrimidin-4-yl)thiophene-2-carboxylate, the title compound is obtained as an orange solid. LC-MS A: $t_R$=0.90 min; [M+H]+=505.00.

b) Methyl 3-ethoxy-5-(6-((2-(7-fluoro-4-methoxy-2-oxoindolin-1-yl)ethyl)amino)pyrimidin-4-yl)thiophene-2-carboxylate A suspension of 1-(2-((6-chloropyrimidin-4-yl)amino)ethyl)-7-fluoro-4-methoxyindolin-2-one (example 775 c)) (115 mg, 0.273 mmol), methyl 3-ethoxy-5-(4,4,5,5-tetramethyl-1,3,2-dioxaborolan-2-yl)thiophene-2-carboxylate (A.2.66.) (298 mg, 0.82 mmol), K3PO4 (203 mg, 0.956 mmol) and DMF (3.5 ml) is degassed by bubbling $N_2$ through. Tetrakis(triphenylphosphine)palladium (0) (31.9 mg, 0.0273 mmol) is added, and bubbling of $N_2$ is continued for 5 min. The RM is stirred at 85° C. for 1 h 30, cooled to RT and filtered over a 0.45 um Whatmann filter and purified by prep HPLC under basic conditions. This afforded the title compound as a yellow solid (40 mg, 30%). LC-MS A: $t_R$=0.79 min; [M+H]+=487.05.

Example 778: 4-{6-[2-(2,4-Dichloro-7-fluoro-indol-1-yl)-ethylamino]-pyrimidin-4-yl}-2-ethoxy-benzoic acid (*1)

Following the procedure described for example 775 using ethyl 4-(6-((2-(2,4-dichloro-7-fluoro-1H-indol-1-yl)ethyl)amino)pyrimidin-4-yl)-2-ethoxybenzoate, the title compound is obtained as a pink powder. LC-MS A: $t_R$=0.78 min; [M+H]+=488.82.

a) Ethyl 4-(6-((2-(2,4-dichloro-7-fluoro-1H-indol-1-yl)ethyl)amino)pyrimidin-4-yl)-2-ethoxybenzoate Following the procedure described for example 775 a) using ethyl 4-(6-((2-(4-chloro-7-fluoro-2-oxoindolin-1-yl)ethyl)amino)pyrimidin-4-yl)-2-ethoxybenzoate, the title compound is obtained as a yellow solid. LC-MS A: $t_R$=0.87 min; [M+H]+=517.03.

b) Ethyl 4-(6-((2-(4-chloro-7-fluoro-2-oxoindolin-1-yl)ethyl)amino)pyrimidin-4-yl)-2-ethoxybenzoate Following the procedure described for example 775 b) using 4-chloro-1-(2-((6-chloropyrimidin-4-yl)amino)ethyl)-7-fluoroindolin-2-one, the title compound is obtained as a pale yellow solid. LC-MS A: $t_R$=0.78 min; [M+H]+=499.02.

c) 4-Chloro-1-(2-((6-chloropyrimidin-4-yl)amino)ethyl)-7-fluoroindolin-2-one

Following the procedure described for example 775 c) using 1-(2-aminoethyl)-4-chloro-7-fluoroindolin-2-one, the title compound is obtained as an orange solid. LC-MS A: $t_R$=0.80 min; [M+H]+=341.02.

d) 1-(2-Aminoethyl)-4-chloro-7-fluoroindolin-2-one

Following the procedure described for example 775 d) using 4-chloro-1-(2-(1,3-dioxoisoindolin-2-yl)ethyl)-7-fluoroindoline-2,3-dione, the title compound is obtained as a purple solid. LC-MS A: $t_R$=0.50 min; [M+H]+=229.07.

e) 4-Chloro-1-(2-(1,3-dioxoisoindolin-2-yl)ethyl)-7-fluoroindoline-2,3-dione

Following the procedure described for example 775 e) using 4-chloro-7-fluoroindoline-2,3-dione, the title compound is obtained as an orange solid. LC-MS A: $t_R$=0.86 min; [M+H]+=373.05.

f) 4-Chloro-7-fluoroindoline-2,3-dione

Following the procedure described for example 775 f) using (E)-N-(5-chloro-2-fluorophenyl)-2-(hydroxyimino)acetamide, the title compound is obtained as an orange solid. LC-MS A: $t_R$=0.63 min; no ionization.

g) (E)-N-(5-Chloro-2-fluorophenyl)-2-(hydroxyimino)acetamide

Following the procedure described for example 775 g) using 5-chloro-2-fluoroaniline, the title compound is obtained as an off-white solid. LC-MS A: $t_R$=0.71 min; no ionization.

Example 779: 4-{6-[2-(2-Chloro-7-fluoro-4-methyl-indol-1-yl)-ethylamino]-pyrimidin-4-yl}-2-ethoxybenzoic acid Following the procedure described for example 775 using ethyl 4-(6-((2-(2-chloro-7-fluoro-4-methyl-1H-indol-1-yl)ethyl)amino)pyrimidin-4-yl)-2-ethoxybenzoate, the title compound is obtained as a white powder. LC-MS A: $t_R$=0.76 min; [M+H]+=468.93.

a) Ethyl 4-(6-((2-(2-chloro-7-fluoro-4-methyl-1H-indol-1-yl)ethyl)amino)pyrimidin-4-yl)-2-ethoxybenzoate Following the procedure described for example 775 a) using ethyl 2-ethoxy-4-(6-((2-(7-fluoro-4-methyl-2-oxoindolin-1-yl)ethyl)amino)pyrimidin-4-yl)benzoate, the title compound is obtained as a yellow solid. LC-MS A: $t_R$=0.86 min; [M+H]+=496.99.

b) Ethyl 2-ethoxy-4-(6-((2-(7-fluoro-4-methyl-2-oxoindolin-1-yl)ethyl)amino)pyrimidin-4-yl)benzoate Following the procedure described for example 775 b) using 1-(2-((6-chloropyrimidin-4-yl)amino)ethyl)-7-fluoro-4-methylindolin-2-one, the title compound is obtained as a pale yellow solid. LC-MS A: $t_R$=0.66 min; [M+H]+=451.03.

c) 1-(2-((6-Chloropyrimidin-4-yl)amino)ethyl)-7-fluoro-4-methylindolin-2-one Following the procedure described for example 775 c) using 1-(2-aminoethyl)-7-fluoro-4-methylindolin-2-one, the title compound is obtained as a brown solid. LC-MS A: $t_R$=0.78 min; [M+H]+=321.01.

d) 1-(2-Aminoethyl)-7-fluoro-4-methylindolin-2-one

Following the procedure described for example 775 d) using 1-(2-(1,3-dioxoisoindolin-2-yl)ethyl)-7-fluoro-4-methylindoline-2,3-dione, the title compound is obtained as a pale brown oil. LC-MS A: $t_R$=0.48 min; [M+H]+=209.20.

e) 1-(2-(1,3-Dioxoisoindolin-2-yl)ethyl)-7-fluoro-4-methylindoline-2,3-dione Following the procedure described for example 775 e) using 7-fluoro-4-methylindoline-2,3-dione, the title compound is obtained as an orange solid. LC-MS A: $t_R$=0.79 min; [M+H]+=353.82.

Example 780: 4-{6-[2-(4-Bromo-2-methyl-indol-1-yl)-ethylamino]-pyrimidin-4-yl}-2-ethoxy-benzoic acid 2-(4-Bromo-2-methyl-1H-indol-1-yl)ethan-1-amine (70 mg, 0.274 mmol) is dissolved in EtOH (2.5 mL) under $N_2$ at RT. TEA (0.0572 mL, 0.411 mmol) is added, followed by ethyl 4-(6-chloropyrimidin-4-yl)-2-ethoxybenzoate (84 mg, 0.274 mmol). The RM is heated at 110° C. overnight. NaOH 10% (1.88 mL, 4.69 mmol) is added and the mixture is stirred at 100° C. for 2 h, then cooled at RT, and purified by prep HPLC under basic conditions, then under acidic conditions. This afforded the title compound as a beige solid. LC-MS A: $t_R$=0.74 min; [M+H]+=495.24.

a) Ethyl 4-(6-chloropyrimidin-4-yl)-2-ethoxybenzoate

To a solution of ethyl 2-ethoxy-4-(4,4,5,5-tetramethyl-1,3,2-dioxaborolan-2-yl)benzoate (200 mg, 0.625 mmol), 4,6-dichloropyrimidine (144 mg, 0.937 mmol), $K_2CO_3$ 2M (0.935 mL, 1.87 mmol) in dioxane (3 mL) under argon is added tetrakis-(triphenylphosphine)-palladium (37.2 mg, 0.0312 mmol). The RM is heated at 120° C. for 2, then cooled to RT, filtered through a 0.45 nm Whatmann filter and purified by FC, eluting with Heptane/EtOAc 1:0 to 4:1. This afforded the title compound as a yellow solid (82 mg, 54%). LC-MS A: $t_R$-0.93 min; [M+H]+=306.98.

b) 2-(4-Bromo-2-methyl-1H-indol-1-yl)ethan-1-amine

Following the procedure described for A.1.1.1. using 4-bromo-2-methyl-1H-indole, the title compound is obtained as a white solid. LC-MS A: $t_R$=0.61 min; [M+H]+=253.07.

Example 781: 5-{6-[2-(4-Bromo-2-methyl-indol-1-yl)-ethylamino]-pyrimidin-4-yl}-3-ethoxy-thiophene-2-carboxylic acid (*1)

Following the procedure described for example 780, using methyl 5-(6-chloropyrimidin-4-yl)-3-ethoxythiophene-2-carboxylate, the title compound is obtained as a white solid. LC-MS A: $t_R$=0.81 min; [M+H]+=503.23.

a) Methyl 5-(6-chloropyrimidin-4-yl)-3-ethoxythiophene-2-carboxylate

Following the procedure described for example 780 a), using (4-ethoxy-5-(methoxycarbonyl)thiophen-2-yl)boronic acid (A.2.66.), the title compound is obtained as a yellow solid. LC-MS A: $t_R$=0.88 min; [M+H]+=299.02.

Example 782: 6-{6-[2-(7-Chloro-5-fluoro-4-methoxy-2-methyl-indol-1-yl)-ethylamino]-pyrimidin-4-yl}-1,2-dihydro-indazol-3-one Following the procedure described for example 772, using methyl 4-(6-((2-(7-chloro-5-fluoro-4-methoxy-2-methyl-1H-indol-1-yl)ethyl)amino)pyrimidin-4-yl)-2-fluorobenzoate, the title compound is obtained as a white solid. LC-MS A: $t_R$=0.68 min; [M+H]+=467.16.

a) Methyl 4-(6-((2-(7-chloro-5-fluoro-4-methoxy-2-methyl-1H-indol-1-yl)ethyl)amino)pyrimidin-4-yl)-2-fluorobenzoate Following the procedure described for example 772 a), using 4-(6-((2-(7-chloro-5-fluoro-4-methoxy-2-methyl-1H-indol-1-yl)ethyl)amino)pyrimidin-4-yl)-2-fluorobenzoic acid, the title compound is obtained as an orange solid. LC-MS A: $t_R$=0.86 min; [M+H]+=487.15.

b) 4-(6-((2-(7-Chloro-5-fluoro-4-methoxy-2-methyl-1H-indol-1-yl)ethyl)amino)pyrimidin-4-yl)-2-fluorobenzoic acid Following the procedure described for example 780 b), using 6-chloro-N-(2-(7-chloro-5-fluoro-4-methoxy-2- methyl-1H-indol-1-yl)ethyl)pyrimidin-4-amine (A.1.50.), the title compound is obtained as a yellow solid. LC-MS A: $t_R$=0.76 min; [M+H]+=473.15.

Example 783: 5-{6-[2-(7-Chloro-5-fluoro-4-methoxy-2-methyl-indol-1-yl)-ethylamino]-pyrimidin-4-yl}-1,2-dihydro-indazol-3-one Following the procedure described for example 772, using methyl 5-(6-((2-(7-chloro-5-fluoro-4-methoxy-2-methyl-1H-indol-1-yl)ethyl)amino)pyrimidin-4-yl)-2-fluorobenzoate, the title compound is obtained as an orange solid. LC-MS A: $t_R$=0.67 min; [M+H]+=467.18.

a) Methyl 5-(6-((2-(7-chloro-5-fluoro-4-methoxy-2-methyl-1H-indol-1-yl)ethyl)amino)pyrimidin-4-yl)-2-fluorobenzoate Following the procedure described for example 772 a), using 5-(6-((2-(7-chloro-5-fluoro-4-methoxy-2-methyl-1H-indol-1-yl)ethyl)amino)pyrimidin-4-yl)-2-fluorobenzoic acid, the title compound is obtained as a yellow oil. LC-MS A: $t_R$=0.82 min; [M+H]+=487.13.

b) 5-(6-((2-(7-Chloro-5-fluoro-4-methoxy-2-methyl-1H-indol-1-yl)ethyl)amino)pyrimidin-4-yl)-2-fluorobenzoic acid Following the procedure described for example 780 b), using 6-chloro-N-(2-(7-chloro-5-fluoro-4-methoxy-2-methyl-1H-indol-1-yl)ethyl)pyrimidin-4-amine (A.1.50.) and 3-ethoxycarbonyl-4-fluorophenylboronic acid, the title compound is obtained as a brown oil. LC-MS A: $t_R$=0.74 min; [M+H]+=473.15.

Example 784: 2-[4-(4-{6-[2-(7-Fluoro-2,4-dimethyl-indol-1-yl)-ethylamino]-pyrimidin-4-yl}-phenyl)-thiazol-2-yl]-acetamide Following the general procedure A with 6-chloro-N-(2-(7-fluoro-2,4-dimethyl-1H-indol-1-yl)ethyl)pyrimidin-4-amine (A.1.8.) and 2-(4-(4-(4,4,5,5-tetramethyl-1,3,2-dioxaborolan-2-yl)phenyl)thiazol-2-yl)acetonitrile, the title compound is obtained as a white powder. LC-MS A: $t_R$=0.68 min; [M+H]+=500.88.

a) 2-(4-(4-(4,4,5,5-Tetramethyl-1,3,2-dioxaborolan-2-yl)phenyl)thiazol-2-yl)acetonitrile Following the procedure described for example 772 a), using 2-(4-(4-bromophenyl)thiazol-2-yl)acetonitrile, the title compound is obtained as a beige powder. LC-MS A: $t_R$=0.94 min; [M+H]+=327.03.

Example 785: 2-[4-(4-{6-[2-(4-Methoxy-2-methyl-indol-1-yl)-ethylamino]-pyrimidin-4-yl}-phenyl)-thiazol-2-yl]-acetamide Following the synthesis described for example 784, with 6-chloro-N-(2-(4-methoxy-2-methyl-1H-indol-1-yl)ethyl)pyrimidin-4-amine (A.1.18.), the title compound is obtained as a white powder. LC-MS A: $t_R$=0.66 min; [M+H]+=498.88.

Example 786: 2-[4-(4-{6-[2-(7-Fluoro-4-methoxy-2-methyl-indol-1-yl)-ethylamino]-pyrimidin-4-yl}-phenyl)-thiazol-2-yl]-acetamide Following the synthesis described for example 784, with 6-chloro-N-(2-(7-fluoro-4-methoxy-2-methyl-1H-indol-1-yl)ethyl)pyrimidin-4-amine (A.1.25.), the title compound is obtained as a white powder. LC-MS A: $t_R$=0.68 min; [M+H]+=516.89.

Example 787: 4-{6-[2-(5,6-Difluoro-2,4-dimethyl-indol-1-yl)-ethylamino]-pyrimidin-4-yl}-2-ethoxybenzoic acid A solution of 4-(6-((2-(7-chloro-5,6-difluoro-2,4-dimethyl-1H-indol-1-yl)ethyl)amino)pyrimidin-4-yl)-2-ethoxybenzoic acid (62 mg, 0.12 mmol) in MeOH (5 mL) is purged with $N_2$, then palladium on activated charcoal (10% Pd; 62 mg) is added. The resulting black suspension is put under hydrogen atmosphere (1 atm) and energetically stirred at 40° C. overnight. The heterogeneous RM is filtered over a pad of celite, eluting with MeOH. The filtrate is concentrated to dryness under reduced pressure. The residue is purified by prep HPLC (basic conditions) to afford the title compound as a white solid. LC-MS A: $t_R$=0.75 min; [M+H]+=467.17.

a) 4-(6-((2-(7-Chloro-5,6-difluoro-2,4-dimethyl-1H-indol-1-yl)ethyl)amino)pyrimidin-4-yl)-2-ethoxybenzoic acid Following the general procedure A, using 6-chloro-N-(2-(7-chloro-5,6-difluoro-2,4-dimethyl-1H-indol-1-yl)ethyl)pyrimidin-4-amine and 4-borono-2-ethoxybenzoic acid, the title compound is obtained as a white powder. LC-MS A: $t_R$=0.80 min; [M+H]+=501.10.

b) 6-Chloro-N-(2-(7-chloro-5,6-difluoro-2,4-dimethyl-1H-indol-1-yl)ethyl)pyrimidin-4-amine Following the procedure described for A.1.1., using 2-(7-chloro-5,6-difluoro-2,4-dimethyl-1H-indol-1-yl)ethan-1-amine, the title compound is obtained as a yellow solid. LC-MS A: $t_R$=0.99 min; [M+H]+=371.04.

c) 2-(7-Chloro-5,6-difluoro-2,4-dimethyl-1H-indol-1-yl)ethan-1-amine

Following the procedure described for A.1.1.1., using 7-chloro-5,6-difluoro-2,4-dimethyl-1H-indole, the title compound is obtained as a brown oil. LC-MS A: $t_R$=0.66 min; [M+H]+=259.10.

d) 7-Chloro-5,6-difluoro-2,4-dimethyl-1H-indole

Following the procedure described for A.1.42.2., using 2-chloro-3,4-difluoro-5-methyl-1-nitrobenzene, the title compound is obtained as a brown solid. LC-MS A: $t_R$=0.94 min; [M+H]+=216.18.

e) 2-Chloro-3,4-difluoro-5-methyl-1-nitrobenzene

To a solution of 2,3-difluoro-4-methyl-6-nitrophenol (2.00 g, 10.60 mmol) in anhydrous DMF (24 mL) at −30/40° C. is added oxalyl chloride (1.81 mL, 21.20 mmol), dropwise. The resulting white heterogeneous mixture is heated up at reflux (80° C.) for 4 h 30, then cooled to RT. Ice and water (60 mL) are successively added, and the mixture is extracted with. $Et_2O$ (3×). The combined organic layers are washed with water/brine, dried over $MgSO_4$, filtered and concentrated under reduced pressure. The crude material is purified by FC, eluting with heptane/DCM 80/20. This afforded the title compound as a pale yellow oil (727 mg, 30%). LC-MS A: $t_R$=0.89 min; no ionization.

e) 2,3-Difluoro-4-methyl-6-nitrophenol

To a solution of 2,3-difluoro-4-methylphenol (3.95 g, 26.60 mmol) in acetic acid (40 mL) at 0° C. is added nitric acid 65% (3.60 mL, 79.80 mmol), dropwise. After 5 min of stirring at 0° C., the orange homogeneous mixture is warmed to RT and stirred further for 45 min. Water (80 mL) is added to the RM and it was cooled to 0° C. The yellow precipitate is filtered and dried under HV to give the title compound (4.57 g, 91%). LC-MS A: $t_R$=0.81 min; no ionization.

Example 788: 4-{6-[2-(7-Chloro-2,4-dimethyl-indol-1-yl)-ethylamino]-pyrimidin-4-yl}-2-((E)-2-fluoro-vinylsulfanyl)-benzoic acid Following the general procedure C, using 6-chloro-N-(2-(7-chloro-2,4-dimethyl-1H-indol-1-yl)ethyl)pyrimidin-4-amine (A.1.6.) and methyl 2-((2,2-difluoroethyl)thio)-4-(4,4,5,5-tetramethyl-1,3,2-dioxaborolan-2-yl)benzoate, the title compound is obtained as a beige solid. LC-MS A: $t_R$=0.80 min; [M+H]+=497.15.

a) Methyl 2-((2,2-difluoroethyl)thio)-4-(4,4,5,5-tetramethyl-1,3,2-dioxaborolan-2-yl)benzoate Following the method described for A.2.3., using methyl 4-bromo-2-((2,2-difluoroethyl)thio)benzoate, the title compound is obtained as a brown oil. LC-MS A: $t_R$=0.98 min; [M+H]+=359.17.

b) Methyl 4-bromo-2-((2,2-difluoroethyl)thio)benzoate

Following the method described for A.2.73.1., using 4-bromo-2-((2,2-difluoroethyl)thio)benzoic acid, the title compound is obtained as a white solid. LC-MS A: $t_R$=0.91 min; no ionization.

c) 4-Bromo-2-((2,2-difluoroethyl)thio)benzoic acid

Following the method described for A.2.73.2., using 4-bromo-2-sulfanylbenzoic acid and 1,1-Difluoro-2-iodoethane, the title compound is obtained as a pale yellow solid. LC-MS A: $t_R$=0.80 min; no ionization.

Example 789: 5-{6-[2-(2-Methyl-indol-1-yl)-ethyl-amino]-pyrimidin-4-yl}-2-(1H-tetrazol-5-yl)-phenol A MW vial is charged with 2-methoxy-4-(6-((2-(2-methyl-1H-indol-1-yl)ethyl)amino)pyrimidin-4-yl)benzonitrile (460 mg, 1.2 mmol), sodium azide (102 mg, 1.56 mmol), ammonium formate (113 mg, 1.8 mmol), and DMF (12 mL). The RM is irradiated at 130° C. for 1 h, then at 150° C. for 5 h. The mixture is filtered on a 0.45 um filter, rinsed with MeCN and purified by prep HPLC, affording the title compound as a yellow solid. LC-MS A: $t_R$=0.69 min; [M+H]+=426.97.

a) 2-Methoxy-4-(6-((2-(2-methyl-1H-indol-1-yl)ethyl)amino)pyrimidin-4-yl)benzonitrile Following the general procedure A, using 6-chloro-N-(2-(2-methyl-1H-indol-1-yl)ethyl)pyrimidin-4-amine (A.1.1.) and 4-cyano-3-methoxyphenylboronic acid, the title compound is obtained as a pale yellow solid. LC-MS A: $t_R$=0.77 min; [M+H]+=383.99.

Example 790: 3-Ethoxy-5-{6-[2-(7-fluoro-4-methoxy-2-methyl-indol-1-yl)-ethylamino]-pyrimidin-4-yl}-thiophene-2-carboxylic acid ethyl ester To a solution of 3-Ethoxy-5-{6-[2-(7-fluoro-4-methoxy-2-methyl-indol-1-yl)-ethylamino]-pyrimidin-4-yl}-thiophene-2-carboxylic acid (*1) (example 258) (90 mg, 0.191 mmol) in DMF (4 mL) is added $K_2CO_3$ (58.1 mg, 0.421 mmol) followed by Iodoethane (0.0308 mL, 0.383 mmol). The mixture is stirred at room temp for 1 h. The mixture is filtered over a 0.45 um filter and purified by prep HPLC under acidic conditions, affording the title compound as a white solid. LC-MS A: $t_R$=0.90 min; [M+H]+=499.08.

Example 791: 1-(4-{6-[2-(7-Fluoro-4-methoxy-2-methyl-indol-1-yl)-ethylamino]-pyrimidin-4-yl}-phenyl)-cyclopentanecarboxylic acid (*1)

To a solution of 1-(4-(6-((2-(7-fluoro-4-methoxy-2-methyl-1H-indol-1-yl)ethyl)amino)pyrimidin-4-yl)phenyl)cyclopentane-1-carbonitrile (37 mg, 0.076 mmol) in EtOH (1 mL) and water (1 mL) is added sodium hydroxide (16 mg, 0.38 mmol) and the mixture is stirred at reflux for 2.5 days. The mixture is filtered over a 0.45 uM filter, rinsed with DMF/water. The product is purified via HPLC prep. under basic conditions, affording the title compound as a white solid. LC-MS A: $t_R$=0.76 min; [M+H]+=488.97.

a) 1-(4-(6-((2-(7-Fluoro-4-methoxy-2-methyl-1H-indol-1-yl)ethyl)amino)pyrimidin-4-yl)phenyl)cyclopentane-1-carbonitrile Following the general procedure A, using building block A.1.25. and 1-(4-(4,4,5,5-tetramethyl-1,3,2-dioxaborolan-2-yl)phenyl)cyclopentane-1-carbonitrile, the title compound is obtained as a white solid. LC-MS A: $t_R$=0.80 min; [M+H]+=470.00.

b) 1-(4-(4,4,5,5-Tetramethyl-1,3,2-dioxaborolan-2-yl)phenyl)cyclopentane-1-carbonitrile Following the procedure described for A.2.3., using 1-(4-Bromophenyl)cyclopentanecarbonitrile, the title compound is obtained as a white solid. LC-MS A: $t_R$=1.00 min; [M+MeCN+H]+=339.06.

Example 792: [2-(2-Methyl-indol-1-yl)-ethyl]-{6-[5-(1H-tetrazol-5-yl)-thiophen-2-yl]-pyrimidin-4-yl}-amine A solution of 5-(6-((2-(2-methyl-1H-indol-1-yl)ethyl)amino)pyrimidin-4-yl)thiophene-2-carbonitrile (125 mg, 0.316 mmol) in dry DMF (5 mL) is treated with $NaN_3$ (103 mg, 1.58 mmol) and $ZnBr_2$ (143 mg, 0.633 mmol) and the mixture is heated at 150° C. for 3 hours. The mixture is cooled, filtered through 0.45 um and 0.22 um filters and well rinsed DMF/water. The product is purified via HPLC prep. under basic conditions, affording the title compound as a yellow solid. LC-MS A: $t_R$=0.73 min; [M+H]+=403.01.

a) 5-(6-((2-(2-Methyl-1H-indol-1-yl)ethyl)amino)pyrimidin-4-yl)thiophene-2-carbonitrile A MV vial is charged with A.1.1. (100 mg, 0.349 mmol), 5-Cyanothiophene-2-boronic acid (107 mg, 0.697 mmol), 2-Dicyclohexylphosphino-2',4',6'-triisopropyl-biphenyl (16.6 mg, 0.0349 mmol), Palladium(II)acetate (6.26 mg, 0.0279 mmol), Potassium fluoride (102 mg, 1.74 mmol) and ethylene glycol dimethyl ether (1.5 mL). The RM is purged three times with nitrogen/vacuum and subjected to MW radiation at 120° C. for 1 hour. The mixture is filtered through 0.45 um and 0.22 um filters and well rinsed DMF/water. The product is purified via HPLC prep. under basic conditions to obtain the title compound as a white solid (23 mg, 18%). LC-MS A: $t_R$=0.90 min; [M+H]+=360.00.

Example 793: [2-(7-Fluoro-4-methoxy-2-methyl-indol-1-yl)-ethyl]-{6-[5-(1H-tetrazol-5-yl)-thiophen-2-yl]-pyrimidin-4-yl}-amine Following the method described for example 792, using 5-(6-((2-(7-fluoro-4-methoxy-2-methyl-1H-indol-1-yl)ethyl)amino)pyrimidin-4-yl)thiophene-2-carbonitrile, the title compound is obtained as an orange solid. LC-MS A: $t_R$=0.74 min; [M+H]+=451.01.

a) 5-(6-((2-(7-Fluoro-4-methoxy-2-methyl-1H-indol-1-yl)ethyl)amino)pyrimidin-4-yl)thiophene-2-carbonitrile Following the method described for example 792 a), using building block A.1.25., the title compound is obtained as a yellow solid. LC-MS A: $t_R$=0.92 min; [M+H]+=408.04.

Example 794: rac-2-Ethoxy-4-{6-[2-(7-fluoro-4-methoxy-2-methyl-indol-1-yl)-propylamino]-pyrimidin-4-yl}-benzoic acid (*1)

Following the general procedure A, using rac-6-chloro-N-(2-(7-fluoro-4-methoxy-2-methyl-1H-indol-1-yl)propyl)pyrimidin-4-amine and 4-borono-2-ethoxybenzoic acid, the title compound is obtained as a white solid. LC-MS A: $t_R$=0.71 min; [M+H]+=479.17.

a) rac-6-Chloro-N-(2-(7-fluoro-4-methoxy-2-methyl-1H-indol-1-yl)propyl)pyrimidin-4-amine Following the method described for example A.1.1., using rac-2-(7-fluoro-4-methoxy-2-methyl-1H-indol-1-yl)propan-1-amine, the title compound is obtained as an orange oil. LC-MS A: $t_R$=0.89 min; [M+H]+=349.08.

b) rac-2-(7-Fluoro-4-methoxy-2-methyl-1H-indol-1-yl)propan-1-amine

To a solution of rac-tert-butyl (2-(7-fluoro-4-methoxy-2-methyl-1H-indol-1-yl)propyl)carbamate (1.00 g, 2.97 mmol) in DCM (20 mL) is added dropwise TFA (2.41 mL, 31.2 mmol) and the RM is stirred for 1 h at RT. It is then cooled at 0° C., and quenched by dropwise addition of NaOH 10% (15 mL, 37.5 mmol) and extracted twice with EtOAc. The combined organic extracts are dried (MgSO$_4$) and concentrated under reduced pressure, affording the title compound as a brown solid. LC-MS A: $t_R$=0.58 min; [M+H]+=237.16.

c) rac-Tert-butyl (2-(7-fluoro-4-methoxy-2-methyl-1H-indol-1-yl)propyl)carbamate To a suspension of NaH (60% in oil, 161 mg, 4.02 mmol) in DMF (5 mL) at 0° C. is added dropwise a solution of building block A.1.25. (600 mg, 3.35 mmol) in DMF (5 mL). The RM is then stirred at RT for 15 min and a solution of rac-N-boc-2-bromo-1-propanamine (837 mg, 3.52 mmol) in DMF (5 mL) is added dropwise. The RM is heated up to 85° C. overnight, then cooled to RT and partitioned between H$_2$O (30 mL) and DCM. The aqueous layer is re-extracted with DCM. The combined organic extracts are dried over MgSO$_4$ and concentrated under reduced pressure, affording the title compound as an orange solid. LC-MS A: $t_R$=0.93 min; [M+H]+=337.14.

Example 795: rac-4-{6-[2-(7-Fluoro-4-methoxy-2-methyl-indol-1-yl)-propylamino]-pyrimidin-4-yl}-2-isobutyl-benzoic acid (*1)

Following the general procedure A, using rac-6-chloro-N-(2-(7-fluoro-4-methoxy-2-methyl-1H-indol-1-yl)propyl)pyrimidin-4-amine (example 794 a) and 2-(2-methylpropyl)-4-(4,4,5,5-tetramethyl-1,3,2-dioxaborolan-2-yl)-benzoic acid, the title compound is obtained as a white solid. LC-MS A: $t_R$=0.77 min; [M+H]+=491.16.

Example 796: rac-3-Ethoxy-5-{6-[2-(7-fluoro-4-methoxy-2-methyl-indol-1-yl)-propylamino]-pyrimidin-4-yl}-thiophene-2-carboxylic acid (*1)

Following the general procedure A, using rac-6-chloro-N-(2-(7-fluoro-4-methoxy-2-methyl-1H-indol-1-yl)propyl)pyrimidin-4-amine (example 794 a) and building block A.2.66., the title compound is obtained as a white solid. LC-MS A: $t_R$=0.75 min; [M+H]+=485.11.

Example 797: rac-3-Ethoxy-5-{6-[2-(7-fluoro-4-methoxy-2-methyl-indol-1-yl)-1-methyl-ethyl-amino]-pyrimidin-4-yl}-thiophene-2-carboxylic acid (*1)

Following the general procedure A, using rac-6-chloro-N-(1-(7-fluoro-4-methoxy-2-methyl-1H-indol-1-yl)propan-2-yl)pyrimidin-4-amine and building block A.2.66., the title compound is obtained as a white solid. LC-MS A: $t_R$=0.77 min; [M+H]+=485.11.

a) rac-6-Chloro-N-(1-(7-fluoro-4-methoxy-2-methyl-1H-indol-1-yl)propyl)pyrimidin-4-amine Following the method described for example A.1.1., using rac-1-(7-fluoro-4-methoxy-2-methyl-1H-indol-1-yl)propan-1-amine, the title compound is obtained as a beige solid. LC-MS A: $t_R$ 0.89 min; [M+H]+=349.13.

b) rac-1-(7-Fluoro-4-methoxy-2-methyl-1H-indol-1-yl)propan-1-amine

Following the method described for example 794 b), using rac-tert-butyl (1-(7-fluoro-4-methoxy-2-methyl-1H-indol-1-yl)propan-2-yl)carbamate, the title compound is obtained as an orange oil. LC-MS A: $t_R$=0.59 min; [M+H]+=237.25.

c) rac-Tert-butyl (1-(7-fluoro-4-methoxy-2-methyl-1H-indol-1-yl)propan-2-yl)carbamate Following the method described for example 794 c), using rac-N-(1-bromopropan-2-yl)carbamate, the title compound is obtained as an orange oil. LC-MS A: $t_R$=0.94 min; [M+H]+=337.17.

Example 798: 4-(4-{6-[2-(7-Fluoro-4-methoxy-2-methyl-indol-1-yl)-ethylamino]-pyrimidin-4-yl}-phenyl)-thiazol-2-ol Following the general procedure A, using building block A.1.25. and 4-(4-(4,4,5,5-tetramethyl-1,3,2-dioxaborolan-2-yl)phenyl)thiazol-2-ol, the title compound is obtained as a beige solid. LC-MS A: $t_R$=0.73 min; [M+H]+=476.13.

a) 4-(4-(4,4,5,5-Tetramethyl-1,3,2-dioxaborolan-2-yl)phenyl)thiazol-2-ol

Following the method described for example A.2.3., using 4-(4-Bromophenyl)-2-hydroxythiazole, the title compound is obtained as a white solid. LC-MS A: $t_R$=0.86 min; [M+MeCN+H]+=345.04.

Example 799: 5-{6-[2-(7-Fluoro-4-methoxy-2-methyl-indol-1-yl)-ethylamino]-pyrimidin-4-yl}-3-hydroxy-thiophene-2-carboxylic acid (*2)

Following the general procedure B, using building block A.1.25. and methyl 3-hydroxy-5-(4,4,5,5-tetramethyl-1,3,2-dioxaborolan-2-yl)thiophene-2-carboxylate, the title compound is obtained as an ochre powder. LC-MS A: $t_R$=0.75 min; [M+H]+=443.10.

a) Methyl 3-hydroxy-5-(4,4,5,5-tetramethyl-1,3,2-dioxaborolan-2-yl)thiophene-2-carboxylate Following the method described for example A.2.66., using methyl 3-hydroxythiophene-2-carboxylate, the title compound is obtained as a brown solid. LC-MS A: $t_R$=0.56 min; no ionization.

Example 800: 5-{6-[2-(6-Fluoro-4-methoxy-2-methyl-indol-1-yl)-ethylamino]-pyrimidin-4-yl}-3-hydroxy-thiophene-2-carboxylic acid (*2)

Following the general procedure B, using building block A.1.23. and methyl 3-hydroxy-5-(4,4,5,5-tetramethyl-1,3,2-dioxaborolan-2-yl)thiophene-2-carboxylate (Example 799 a), the title compound is obtained as a beige powder. LC-MS A: $t_R$=0.75 min; [M+H]+=443.11.

Example 801: 5-{6-[2-(6-Fluoro-4-methoxy-2-methyl-indol-1-yl)-ethylamino]-pyrimidin-4-yl}-thiophen-3-ol (*1)

Following the general procedure B, using building block A.1.23. and methyl 3-hydroxy-5-(4,4,5,5-tetramethyl-1,3,2-dioxaborolan-2-yl)thiophene-2-carboxylate (Example 799 a), the title compound is obtained after decarboxylation after basic prep-HPLC. LC-MS C: $t_R$=0.83 min; [M+MeCN]+=443.05.

Example 802: 5-{6-[2-(2-Cyano-7-fluoro-4-methoxy-indol-1-yl)-ethylamino]-pyrimidin-4-yl}-3-isopropoxy-thiophene-2-carboxylic acid Following the general procedure A, using building blocks A.1.68. and A.2.89., the title compound is obtained as a light brown solid. LC-MS C: $t_R$=0.82 min; [M+H]+=496.12.

Example 803: 1-(2-{6-[3-Ethoxy-4-(1H-tetrazol-5-yl)-phenyl]-pyrimidin-4-ylamino}-ethyl)-7-fluoro-4-methoxy-1H-indole-2-carbonitrile Following the general procedure A, using building blocks A.1.68. and A.2.84., the title compound is obtained as a white solid. LC-MS C: $t_R$=0.75 min; [M+H]+=500.10.

Example 804: 5-{6-[2-(2-Cyano-7-fluoro-4-methoxy-indol-1-yl)-ethylamino]-pyrimidin-4-yl}-3-trifluoromethyl-thiophene-2-carboxylic acid Following the general procedure A, using building blocks A.1.68. and A.2.68., the title compound is obtained as an off-white solid. LC-MS C: $t_R$=0.89 min; [M+H]+=505.84.

Example 805: 5-{6-[2-(2-cyano-7-fluoro-4-methoxy-indol-1-yl)-ethylamino]-pyrimidin-4-yl}-3-ethoxy-thiophene-2-carboxylic acid Following the general procedure A, using building blocks A.1.68. and A.2.66., the title compound is obtained as a white solid. LC-MS C: $t_R$=0.78 min; [M+H]+=481.90.

Example 806: 5-{6-[2-(2-Cyano-7-fluoro-4-methoxy-indol-1-yl)-ethylamino]-pyrimidin-4-yl}-3-fluoro-thiophene-2-carboxylic acid Following the general procedure A, using building blocks A.1.68. and A.2.01., the title compound is obtained as a white solid. LC-MS C: $t_R$=0.83 min; [M+H]+=456.01.

Example 807: 4-{6-[2-(2-Cyano-7-fluoro-4-methoxy-indol-1-yl)-ethylamino]-pyrimidin-4-yl}-2-ethoxy-benzoic acid Following the general procedure A, using building blocks A.1.68. and 2-ethoxy-4-(4,4,5,5-tetramethyl-1,3,2-dioxaborolan-2-yl)benzoic acid, the title compound is obtained as a white solid. LC-MS C: $t_R$=0.72 min; [M+H]+=476.17.

Example 808: (4-{6-[2-(2-Cyano-7-fluoro-4-methoxy-indol-1-yl)-ethylamino]-pyrimidin-4-yl}-2-ethoxy-phenoxy)-acetic acid Following the general procedure A, using building blocks A.1.68. and A.2.99., the title compound is obtained as a beige solid. LC-MS C: $t_R$=0.71 min; [M+H]+=506.08.

Example 809: N-(5-{6-[2-(2-Cyano-7-fluoro-4-methoxy-indol-1-yl)-ethylamino]-pyrimidin-4-yl}-3-ethoxy-thiophene-2-carbonyl)-methanesulfonamide To a solution of 5-{6-[2-(2-cyano-7-fluoro-4-methoxy-indol-1-yl)-ethylamino]-pyrimidin-4-yl}-3-ethoxy-thiophene-2-carboxylic acid (210 mg, 0.436 mmol) in MeCN (6 mL) are added N-(3-dimethylaminopropyl)-N'-ethylcarbodiimide hydrochloride (127 mg, 0.654 mmol), 4-(dimethylamino)pyridine (113 mg, 0.916 mmol) and finally methanesulfonamide (131 mg, 1.31 mmol). The resulting mixture is stirred at RT for 3 h. Formic acid (0.5 mL) is added, and the resulting precipitate is filtered off, washed with cold MeCN, and dried under high vacuum. The filtrate is purified by prep HPLC (acidic conditions). The batches are combined, affording the title compound as a light yellow solid (0.14 g, 57%). LC-MS C: $t_R$=0.90 min; [M+H]+=558.98.

Example 810: (2-Ethoxy-4-{6-[2-(7-fluoro-4-methoxy-2-methyl-indol-1-yl)-ethylamino]-pyrimidin-4-yl}-phenoxy)-acetic acid Following the general procedure A, using building blocks A.1.25. and A.2.99., the title compound is obtained as a beige solid. LC-MS C: $t_R$=0.70 min; [M+H]+=495.11.

Example 811: (2-Ethoxy-4-{6-[2-(7-fluoro-4-methoxy-2-methyl-indol-1-yl)-ethylamino]-pyrimidin-4-yl}-phenylamino)-acetic acid Following the general procedure A, using building blocks A.1.25. and A.2.98., the title compound is obtained as a beige solid. LC-MS C: $t_R$=0.72 min; [M+H]+=494.18.

Example 812: 2-Ethoxy-4-{6-[2-(4-fluoro-2,7-dimethyl-indol-1-yl)-ethylamino]-pyrimidin-4-yl}-benzoic acid Following the general procedure A, using building blocks A.1.8. and 2-ethoxy-4-(4,4,5,5-tetramethyl-1,3,2-dioxaborolan-2-yl)benzoic acid, the title compound is obtained as an off-white solid. LC-MS C: $t_R$=0.74 min; [M+H]+= 449.19.

Example 813: 5-{6-[2-(2-Cyano-4-methoxy-indol-1-yl)-ethylamino]-pyrimidin-4-yl}-3-ethoxy-thiophene-2-carboxylic acid Following the general procedure A, using building blocks A.1.69. and A.2.66., the title compound is obtained as beige solid. LC-MS C: $t_R$=0.76 min; [M+H]+=464.04.

Example 814: N-(5-{6-[2-(2-Cyano-7-fluoro-4-methoxy-indol-1-yl)-ethylamino]-pyrimidin-4-yl}-3-ethoxy-thiophene-2-carbonyl)-benzenesulfonamide Following the method described for example 809, using benzene sulfonamide, the title compound is obtained as white solid. LC-MS C: $t_R$=0.98 min; [M+H]+=621.16.

Example 815: Propane-2-sulfonic acid (5-{6-[2-(2-cyano-7-fluoro-4-methoxy-indol-1-yl)-ethylamino]-pyrimidin-4-yl}-3-ethoxy-thiophene-2-carbonyl)-amide Following the method described for example 809, using propane-2-sulfonamide, the title compound is obtained as white solid. LC-MS C: $t_R$=0.95 min; [M+H]+ 587.13.

Example 816: Cyclopropanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide Following the method described for example 809, using cyclopropanesulfonamide, the title compound is obtained as white solid. LC-MS C: $t_R$=0.93 min; [M+H]+=585.10.

Example 817: Ethanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide Following the method described for example 809, using ethanesulfonamide, the title compound is obtained as a white solid. LC-MS C: $t_R$=0.93 min; [M+H]+=573.11

Compounds of Examples 818-1021 listed in Table 11 below are prepared by applying either one of the above-mentioned procedures A, B or C to the pyrimidine halide derivatives A.1.1.-A.1.82. coupled with commercially available boronic acid derivatives or with boronic acid derivatives A.2.1.-A.2.157.

TABLE 11

Examples 818-1021

| Ex. | Compound | $t_R$ [min] (LC-MS) | MS Data m/z [M + H]+ |
|---|---|---|---|
| 818 | 7-Fluoro-1-(2-{6-[4-(1H-imidazol-4-yl)-3-methoxy-phenyl]-pyrimidin-4-ylamino}-ethyl)-4-methoxy-1H-indole-2-carbonitrile | 0.62 (A) | 484.06 |
| 819 | 7-Fluoro-4-methoxy-1-(2-{6-[4-(5-methyl-1H-imidazol-4-yl)-phenyl]-pyrimidin-4-ylamino}-ethyl)-1H-indole-2-carbonitrile | 0.61 (A) | 468.03 |
| 820 | 1-(2-{6-[3-Ethoxy-4-((5-oxo-4,5-dihydro-[1,2,4]oxadiazol-3-yl)-phenyl]-pyrimidin-4-ylamino}-ethyl)-7-fluoro-4-methoxy-1H-indole-2-carbonitrile | 0.78 (A) | 516.03 |
| 821 | 1-(2-{6-[4-(2,5-Dimethyl-1H-imidazol-4-yl)-phenyl]-pyrimidin-4-ylamino}-ethyl)-7-fluoro-4-methoxy-1H-indole-2-carbonitrile | 0.62 (A) | 481.82 |
| 822 | 1-{2-[6-(3-Ethyl-4-hydroxy-phenyl)-pyrimidin-4-ylamino]-ethyl}-7-fluoro-4-methoxy-1H-indole-2-carbonitrile | 0.75 (A) | 432.11 |
| 823 | 1-(2-{6-[4-(1,5-Dimethyl-1H-imidazol-4-yl)-phenyl]-pyrimidin-4-ylamino}-ethyl)-7-fluoro-4-methoxy-1H-indole-2-carbonitrile | 0.62 (A) | 481.89 |
| 824 | 1-(2-{6-[4-(1,2-Dimethyl-1H-imidazol-4-yl)-phenyl]-pyrimidin-4-ylamino}-ethyl)-7-fluoro-4-methoxy-1H-indole-2-carbonitrile | 0.62 (A) | 481.83 |
| 825 | 7-Fluoro-1-(2-{6-[4-((5-oxo-4,5-dihydro-[1,2,4]oxadiazol-3-yl)-phenyl]-pyrimidin-4-ylamino}-ethyl)-4-methoxy-1H-indole-2-carbonitrile | 0.73 (A) | 471.99 |
| 826 | 7-Fluoro-1-(2-{6-[5-(3-hydroxy-oxetan-3-yl)-4-methoxy-thiophen-2-yl]-pyrimidin-4-ylamino}-ethyl)-4-methoxy-1H-indole-2-carbonitrile | 0.73 (A) | 496.34 |
| 827 | 1-(2-{6-[4-(2-Cyclopropyl-1-methyl-1H-imidazol-4-yl)-phenyl]-pyrimidin-4-ylamino}-ethyl)-7-fluoro-4-methoxy-1H-indole-2-carbonitrile | 0.64 (A) | 507.99 |
| 828 | (4-{6-[2-(2-Cyano-7-fluoro-4-methoxy-indol-1-yl)-ethylamino]-pyrimidin-4-yl}-2-trifluoromethoxy-phenoxy)-acetic acid | 0.77 (A) | 545.95 |
| 829 | 7-Fluoro-1-(2-{6-[4-(3H-imidazol-4-yl)-phenyl]-pyrimidin-4-ylamino}-ethyl)-4-methoxy-1H-indole-2-carbonitrile | 0.60 (A) | 454.1 |
| 830 | 3-(2-Ethoxy-4-{6-[2-(7-fluoro-4-methoxy-2-methyl-indol-1-yl)-ethylamino]-pyrimidin-4-yl}-phenyl)-[1,2,4]oxadiazol-5(4H)-one | 0.76 (A) | 504.98 |

TABLE 11-continued

Examples 818-1021

| Ex. | Compound | $t_R$ [min] (LC-MS) | MS Data m/z [M + H]$^+$ |
|---|---|---|---|
| 831 | 7-Fluoro-1-(2-{6-[4-(3-oxo-2,3-dihydro-[1,2,4]-oxadiazol-5-yl)-phenyl]-pyrimidin-4-ylamino}-ethyl)-4-methoxy-1H-indole-2-carbonitrile | 0.72 (A) | 472.06 |
| 832 | 5-{6-[2-(7-Fluoro-4-methoxy-2-methyl-indol-1-yl)-ethylamino]-pyrimidin-4-yl}-3-(2,2,2-trifluoro-ethoxy)-thiophene-2-carboxylic acid | 0.84 (A) | 525.09 |
| 833 | (4-{6-[2-(2-Cyano-7-fluoro-4-methoxy-indol-1-yl)-ethylamino]-pyrimidin-4-yl}-2-propoxy-phenyl)-acetic acid | 0.76 (A) | 504.11 |
| 834 | (4-{6-[2-(2-Cyano-7-fluoro-4-methoxy-indol-1-yl)-ethylamino]-pyrimidin-4-yl}-2-ethyl-phenoxy)-acetic acid | 0.74 (A) | 490.06 |
| 835 | 3-(2-Ethoxy-4-{6-[2-(6-fluoro-2,4-dimethyl-indol-1-yl)-ethylamino]-pyrimidin-4-yl}-phenyl)-[1,2,4]oxadiazol-5(4H)-one | 0.78 (A) | 489.05 |
| 836 | 2-butoxy-6-chloro-4-(6-((2-(7-fluoro-4-methoxy-2-methyl-1H-indol-1-yl)ethyl-1,1,2,2-d4)amino)pyrimidin-4-yl)benzoic acid | 0.79 (A) | 531.17 |
| 837 | 5-{6-[2-(7-Chloro-5-fluoro-2,4-dimethyl-indol-1-yl)-ethylamino]-pyrimidin-4-yl}-3-ethoxy-thiophene-2-carboxylic acid | 0.86 (A) | 489 |
| 838 | 5-{6-[2-(6-Fluoro-4-methoxy-2-methyl-indol-1-yl)-ethylamino]-pyrimidin-4-yl}-3-(2,2,2-trifluoro-ethoxy)-thiophene-2-carboxylic acid | 0.84 (A) | 525.12 |
| 839 | rac-2-(2-Ethoxy-4-{6-[2-(7-fluoro-4-methoxy-2-methyl-indol-1-yl)-ethylamino]-pyrimidin-4-yl}-phenylamino)-propionic acid | 0.75 (A) | 508.18 |
| 840 | 5-{6-[2-(2-Cyano-3-fluoro-indol-1-yl)-ethylamino]-pyrimidin-4-yl}-3-trifluoromethyl-thiophene-2-carboxylic acid | 0.89 (A) | 475.92 |
| 841 | (2-Chloro-4-{6-[2-(2-cyano-7-fluoro-4-methoxy-indol-1-yl)-ethylamino]-pyrimidin-4-yl}-phenoxy)-acetic acid | 0.72 (A) | 495.99 |
| 842 | [6-(3-Ethoxy-4-oxazol-2-yl-phenyl)-pyrimidin-4-yl]-[2-(7-fluoro-4-methoxy-2-methyl-indol-1-yl)-ethyl]-amine | 0.76 (A) | 488.18 |
| 843 | rac-2-(2-Ethoxy-4-{6-[2-(7-fluoro-4-methoxy-2-methyl-indol-1-yl)-ethylamino]-pyrimidin-4-yl}-phenoxy)-propionic acid | 0.72 (A) | 509.18 |
| 844 | 4-{6-[2-(7-Fluoro-4-methoxy-2-methyl-indol-1-yl)-ethylamino]-pyrimidin-4-yl}-2-(2,2,2-trifluoro-ethoxy)-benzoic acid | 0.74 (A) | 519.14 |
| 845 | 4-{6-[2-(6-Fluoro-4-methoxy-2-methyl-indol-1-yl)-ethylamino]-pyrimidin-4-yl}-2-(2,2,2-trifluoro-ethoxy)-benzoic acid | 0.74 (A) | 519.17 |
| 846 | 5-{6-[2-(2-Cyano-3-fluoro-indol-1-yl)-ethylamino]-pyrimidin-4-yl}-3-fluoro-thiophene-2-carboxylic acid | 0.83 (A) | 426.05 |
| 847 | (3-Ethoxy-5-{6-[2-(7-fluoro-4-methoxy-2-methyl-indol-1-yl)-ethylamino]-pyrimidin-4-yl}-thiophen-2-yl)-acetic acid | 0.72 (A) | 485.1 |
| 848 | {6-[4-(4,5-Dimethyl-oxazol-2-yl)-3-ethoxy-phenyl]-pyrimidin-4-yl}-[2-(7-fluoro-4-methoxy-2-methyl-indol-1-yl)-ethyl]-amine | 0.80 (A) | 516.23 |
| 849 | [6-(4-Benzooxazol-2-yl-3-ethoxy-phenyl)-pyrimidin-4-yl]-[2-(7-fluoro-4-methoxy-2-methyl-indol-1-yl)-ethyl]-amine | 0.85 (A) | 538.19 |
| 850 | 5-{6-[2-(4,6-Dichloro-2-cyano-indol-1-yl)-ethylamino]-pyrimidin-4-yl}-3-fluoro-thiophene-2-carboxylic acid | 0.89 (A) | 475.91 |
| 851 | 5-{6-[2-(2-Cyano-7-fluoro-4-methyl-indol-1-yl)-ethylamino]-pyrimidin-4-yl}-3-fluoro-thiophene-2-carboxylic acid | 0.83 (A) | 440.03 |
| 852 | 7-Fluoro-1-(2-{6-[4-(3-hydroxy-isoxazol-5-yl)-phenyl]-pyrimidin-4-ylamino}-ethyl)-4-methoxy-1H-indole-2-carbonitrile | 0.73 (A) | 471.03 |
| 853 | N-(4-{6-[2-(2-Cyano-7-fluoro-4-methoxy-indol-1-yl)-ethylamino]-pyrimidin-4-yl}-2-ethoxy-phenyl)-oxalamic acid | 0.72 (A) | 519.11 |
| 854 | (5-{6-[2-(2-Cyano-7-fluoro-4-methoxy-indol-1-yl)-ethylamino]-pyrimidin-4-yl}-3-ethoxy-thiophen-2-yl)-acetic acid | 0.74 (A) | 496.03 |
| 855 | 7-Fluoro-1-(2-{6-[4-(3-hydroxy-isoxazol-5-yl)-3-methoxy-phenyl]-pyrimidin-4-ylamino}-ethyl)-4-methoxy-1H-indole-2-carbonitrile | 0.75 (A) | 501.02 |
| 856 | 5-{6-[2-(4,6-Dichloro-2-cyano-indol-1-yl)-ethylamino]-pyrimidin-4-yl}-3-trifluoromethyl-thiophene-2-carboxylic acid | 0.94 (A) | 525.9 |
| 857 | 5-{6-[2-(2-Cyano-5,6-difluoro-4-methyl-indol-1-yl)-ethylamino]-pyrimidin-4-yl}-3-trifluoromethyl-thiophene-2-carboxylic acid | 0.91 (A) | 508.15 |
| 858 | 5-{6-[2-(2-Cyano-7-fluoro-4-methyl-indol-1-yl)-ethylamino]-pyrimidin-4-yl}-3-trifluoromethyl-thiophene-2-carboxylic acid | 0.90 (A) | 489.98 |
| 859 | 5-{6-[2-(2-Cyano-7-fluoro-indol-1-yl)-ethylamino]-pyrimidin-4-yl}-3-trifluoromethyl-thiophene-2-carboxylic acid | 0.88 (A) | 476.16 |
| 860 | 7-Fluoro-4-methoxy-1-(2-{6-[5-(3-methoxy-oxetan-3-yl)-thiophen-2-yl]-pyrimidin-4-ylamino}-ethyl)-1H-indole-2-carbonitrile | 0.80 (A) | 479.95 |
| 861 | (4-{6-[2-(2-Cyano-7-fluoro-4-methoxy-indol-1-yl)-ethylamino]-pyrimidin-4-yl}-2-ethoxy-phenylamino)-acetic acid | 0.74 (A) | 505.11 |
| 862 | rac-1-(2-{6-[4-(1,2-Dihydroxy-ethyl)-phenyl]-pyrimidin-4-ylamino}-ethyl)-7-fluoro-4-methoxy-1H-indole-2-carbonitrile | 0.63 (A) | 448.08 |
| 863 | 1-(2-{6-[4-(2-Cyclopropyl-1H-imidazol-4-yl)-phenyl]-pyrimidin-4-ylamino}-ethyl)-7-fluoro-4-methoxy-1H-indole-2-carbonitrile | 0.63 (A) | 493.94 |
| 864 | 5-{6-[2-(6-Chloro-7-fluoro-4-methoxy-2-methyl-indol-1-yl)-ethylamino]-pyrimidin-4-yl}-3-ethoxy-thiophene-2-carboxylic acid | 0.82 (A) | 505.09 |
| 865 | (4-{6-[2-(2-Cyano-4-methoxy-indol-1-yl)-ethylamino]-pyrimidin-4-yl}-2-ethoxy-phenylamino)-acetic acid | 0.72 (A) | 487.1 |
| 866 | 7-Fluoro-1-{2-[6-(4-hydroxy-3-trifluoromethoxy-phenyl)-pyrimidin-4-ylamino]-ethyl}-4-methoxy-1H-indole-2-carbonitrile | 0.77 (A) | 488.07 |
| 867 | 1-{2-[6-(3-Chloro-4-hydroxy-phenyl)-pyrimidin-4-ylamino]-ethyl}-7-fluoro-4-methoxy-1H-indole-2-carbonitrile | 0.73 (A) | 438.02 |

TABLE 11-continued

Examples 818-1021

| Ex. | Compound | $t_R$ [min] (LC-MS) | MS Data m/z [M + H]$^+$ |
|---|---|---|---|
| 868 | 5-{6-[2-(4,6-Dichloro-7-fluoro-2-methyl-indol-1-yl}-ethylamino]-pyrimidin-4-yl}-3-ethoxy-thiophene-2-carboxylic acid | 0.87 (A) | 509.05 |
| 869 | 5-{6-[2-(6-Chloro-4-methoxy-2-methyl-indol-1-yl)-ethylamino]-pyrimidin-4-yl}-3-isopropoxy-thiophene-2-carboxylic acid | 0.83 (A) | 501.11 |
| 870 | (4-{6-[2-(2-Cyano-4-methoxy-indol-1-yl)-ethylamino]-pyrimidin-4-yl}-2-ethoxy-phenoxy)-acetic acid | 0.69 (A) | 488.09 |
| 871 | 5-{6-[2-(6-Chloro-4-methoxy-2-methyl-indol-1-yl)-ethylamino]-pyrimidin-4-yl}-3-ethoxy-thiophene-2-carboxylic acid | 0.79 (A) | 487.11 |
| 872 | 2-Butoxy-4-{6-[2-(2-cyano-7-fluoro-4-methoxy-indol-1-yl)-ethylamino]-pyrimidin-4-yl}-benzoic acid | 0.79 (A) | 504.2 |
| 873 | (4-{6-[2-(2-Cyano-7-fluoro-4-methoxy-indol-1-yl)-ethylamino]-pyrimidin-4-yl}-2-ethoxy-phenyl)-acetic acid | 0.73 (A) | 490.08 |
| 874 | 4-{6-[2-(7-Fluoro-4-methoxy-2-methyl-indol-1-yl)-ethylamino]-pyrimidin-4-yl}-2-trifluoromethoxy-phenol | 0.76 (A) | 477.06 |
| 875 | 3-Ethoxy-5-{6-[2-(3-fluoro-2-methyl-indol-1-yl)-ethylamino]-pyrimidin-4-yl}-thiophene-2-carboxylic acid | 0.77 (A) | 441 |
| 876 | 5-{6-[2-(2-Cyano-3-fluoro-indol-1-yl)-ethylamino]-pyrimidin-4-yl}-3-ethoxy-thiophene-2-carboxylic acid | 0.81 (A) | 452.05 |
| 877 | (2-Ethoxy-4-{6-[2-(7-fluoro-2,4-dimethyl-indol-1-yl)-ethylamino]-pyrimidin-4-yl}-phenylamino)-acetic acid | 0.76 (A) | 478.22 |
| 878 | 2-Butoxy-4-{6-[2-(6,7-difluoro-4-methoxy-2-methyl-indol-1-yl)-ethylamino]-pyrimidin-4-yl}-benzoic acid | 0.80 (A) | 511.19 |
| 879 | 5-{6-[2-(2,4-Dimethyl-indol-1-yl)-ethylamino]-pyrimidin-4-yl}-3-isopropoxy-thiophene-2-carboxylic acid | 0.80 (A) | 451.17 |
| 880 | 5-{6-[2-(2,4-Dimethyl-indol-1-yl)-ethylamino]-pyrimidin-4-yl}-3-ethoxy-thiophene-2-carboxylic acid | 0.76 (A) | 437.18 |
| 881 | 3-(2-Ethoxy-4-{6-[2-(4-methoxy-2-methyl-indol-1-yl)-ethylamino]-pyrimidin-4-yl}-phenyl)-[1,2,4]oxadiazol-5(4H)-one | 0.73 (A) | 487.05 |
| 882 | (2-Ethoxy-4-{6-[2-(6-fluoro-4-methoxy-2-methyl-indol-1-yl)-ethylamino]-pyrimidin-4-yl}-phenylamino)-acetic acid | 0.73 (A) | 494.17 |
| 883 | 5-{6-[2-(4,7-Dichloro-5-fluoro-2-methyl-indol-1-yl)-ethylamino]-pyrimidin-4-yl}-3-ethoxy-thiophene-2-carboxylic acid | 0.86 (A) | 508.94 |
| 884 | 2-Butoxy-4-{6-[2-(6-chloro-7-fluoro-4-methoxy-2-methyl-indol-1-yl)-ethylamino]-pyrimidin-4-yl}benzoic acid | 0.82 (A) | 527.18 |
| 885 | 5-{6-[2-(7-Chloro-5-fluoro-4-methoxy-2-methyl-indol-1-yl)-ethylamino]-pyrimidin-4-yl}-3-ethoxy-thiophene-2-carboxylic acid | 0.83 (A) | 504.98 |
| 886 | (4-{6-[2-(7-Fluoro-4-methoxy-2-methyl-indol-1-yl)-ethylamino]-pyrimidin-4-yl}-2-methoxy-phenyl)-acetic acid | 0.69 (A) | 465.03 |
| 887 | (4-{6-[2-(2-Cyano-7-fluoro-4-methoxy-indol-1-yl)-ethylamino]-pyrimidin-4-yl}-phenyl)-difluoro-acetic acid | 0.66 (A) | 481.91 |
| 888 | 2-Cyano-4-{6-[2-(7-fluoro-4-methoxy-2-methyl-indol-1-yl)-ethylamino]-pyrimidin-4-yl}-benzoic acid | 0.71 (A) | 446.18 |
| 889 | 5-{6-[2-(4,6-Dichloro-2-cyano-indol-1-yl)-ethylamino]-pyrimidin-4-yl}-3-ethoxy-thiophene-2-carboxylic acid | 0.86 (A) | 501.94 |
| 890 | 5-{6-[2-(2-Cyano-5,6-difluoro-4-methyl-indol-1-yl)-ethylamino]-pyrimidin-4-yl}-3-ethoxy-thiophene-2-carboxylic acid | 0.82 (A) | 484.01 |
| 891 | 5-{6-[2-(2-Cyano-7-fluoro-4-methyl-indol-1-yl)-ethylamino]-pyrimidin-4-yl}-3-ethoxy-thiophene-2-carboxylic acid | 0.81 (A) | 465.92 |
| 892 | 5-{6-[2-(2-Cyano-7-fluoro-indol-1-yl)-ethylamino]-pyrimidin-4-yl}-3-ethoxy-thiophene-2-carboxylic acid | 0.78 (A) | 452.02 |
| 893 | (4-{6-[2-(2-Cyano-5,6-difluoro-4-methyl-indol-1-yl)-ethylamino]-pyrimidin-4-yl}-2-ethoxy-phenoxy)-acetic acid | 0.74 (A) | 508.04 |
| 894 | (4-{6-[2-(2-Cyano-7-fluoro-4-methyl-indol-1-yl)-ethylamino]-pyrimidin-4-yl}-2-ethoxy-phenoxy)-acetic acid | 0.72 (A) | 490.05 |
| 895 | (4-{6-[2-(2-Cyano-5,6-difluoro-4-methyl-indol-1-yl)-ethylamino]-pyrimidin-4-yl}-2-ethoxy-phenylamino)-acetic acid | 0.77 (A) | 507.28 |
| 896 | (4-{6-[2-(2-Cyano-7-fluoro-indol-1-yl)-ethylamino]-pyrimidin-4-yl}-2-ethoxy-phenylamino)-acetic acid | 0.74 (A) | 475.31 |
| 897 | (4-{6-[2-(7-Fluoro-4-methoxy-2-methyl-indol-1-yl)-ethylamino]-pyrimidin-4-yl}-phenyl)-acetic acid ethyl ester | 0.78 (A) | 463.12 |
| 898 | 7-Fluoro-4-methoxy-1-{2-[6-(2-methoxy-pyridin-4-yl)-pyrimidin-4-ylamino]-ethyl}-1H-indole-2-carbonitrile | 0.77 (A) | 419.15 |
| 899 | 1-{2-[6-(3-Ethoxy-4-hydroxy-phenyl)-pyrimidin-4-ylamino]-ethyl}-7-fluoro-4-methoxy-1H-indole-2-carbonitrile | 0.74 (A) | 448.1 |
| 900 | 5-{6-[2-(2-Cyano-7-fluoro-methoxy-indol-1-yl)-ethylamino]-pyrimidin-4-yl}-thiophene-2-carboxylic acid amide | 0.71 (A) | 437.11 |
| 901 | 5-{6-[2-(2-Cyano-7-fluoro-indol-1-yl)-ethylamino]-pyrimidin-4-yl}-3-fluoro-thiophene-2-carboxylic acid | 0.81 (A) | 426.07 |
| 902 | 5-{6-[2-(2-Cyano-4-methoxy-indol-1-yl)-ethylamino]-pyrimidin-4-yl}-3-fluoro-thiophene-2-carboxylic acid | 0.79 (A) | 438.08 |
| 903 | 5-{6-[2-(4-Chloro-2-cyano-indol-1-yl)-ethylamino]-pyrimidin-4-yl}-3-fluoro-thiophene-2-carboxylic acid | 0.83 (A) | 441.96 |
| 904 | 5-{6-[2-(4-Chloro-2-cyano-6,7-difluoro-indol-1-yl)-ethylamin0]-pyrimidin-4-yl}-3-fluoro-thiophene-2-carboxylic acid | 0.88 (A) | 478 |

TABLE 11-continued

Examples 818-1021

| Ex. | Compound | $t_R$ [min] (LC-MS) | MS Data m/z [M + H]+ |
|---|---|---|---|
| 905 | 2-Butoxy-4-{6-[2-(2-cyano-7-fluoro-4-methoxy-indol-1-yl)-ethylamino]-pyrimidin-4-yl}-6-fluoro-benzoic acid | 0.8 (A) | 522.13 |
| 906 | 2-Butoxy-6-chloro-4-{6-[2-(2-cyano-7-fluoro-4-methoxy-indol-1-yl)-ethylamino]-pyrimidin-4-yl}-benzoic acid | 0.81 (A) | 538.09 |
| 907 | 2-Chloro-4-{6-[2-(2-cyano-7-fluoro-4-methoxy-indol-1-yl)-ethylamino]-pyrimidin-4-yl}-6-propoxy-benzoic acid | 0.78 (A) | 524.08 |
| 908 | 4-{6-[2-(2-Cyano-7-fluoro-4-methoxy-indol-1-yl)-ethylamino]-pyrimidin-4-yl}-2-fluoro-6-propoxy-benzoic acid | 0.77 (A) | 508.11 |
| 909 | 5-{6-[2-(4-Chloro-2-cyano-indol-1-yl)-ethylamino]-pyrimidin-4-yl}-3-ethoxy-thiophene-2-carboxylic acid | 0.80 (A) | 468.05 |
| 910 | 5-{6-[2-(2-Cyano-4-methoxy-indol-1-yl)-ethylamino]-pyrimidin-4-yl}-3-trifluoromethyl-thiophene-2-carboxylic acid | 0.85 (A) | 488.07 |
| 911 | 5-{6-[2-(4-Chloro-2-cyano-indol-1-yl)-ethylamino]-pyrimidin-4-yl}-3-trifluoromethyl-thiophene-2-carboxylic acid | 0.89 (A) | 492.05 |
| 912 | 5-{6-[2-(4-Chloro-2-cyano-6,7-difluoro-indol-1-yl)-ethylamino]pyrimidin-4-yl}-3-trifluoromethyl-thiophene-2-carboxylic acid | 0.93 (A) | 527.97 |
| 913 | 2-Chloro-4-{6-[2-(2-cyano-7-fluoro-4-methoxy-indol-1-yl)-ethylamino]-pyrimidin-4-yl}-6-isobutoxy-benzoic acid | 0.81 (A) | 538.09 |
| 914 | (4-{6-[2-(4-Chloro-2-cyano-6,7-difluoro-indol-1-yl)-ethylamino]-pyrimidin-4-yl}-2-ethoxy-phenoxy)-acetic acid | 0.75 (A) | 528.03 |
| 915 | (4-{6-[2-(4-Chloro-2-cyano-indol-1-yl)-ethylamino]-pyrimidin-4-yl}-2-ethoxy-phenylamino)-acetic acid | 0.75 (A) | 491 |
| 916 | (4-{6-[2-(4-Chloro-2-cyano-6,7-difluoro-indol-1-yl)-ethylamino]-pyrimidin-4-yl}-2-ethoxy-phenylamino)-acetic acid | 0.78 (A) | 527.08 |
| 917 | 4-{6-[2-(2-Cyano-7-fluoro-4-methoxy-indol-1-yl)-ethylamino]-pyrimidin-4-yl}-2-difluoromethoxy-benzoic acid | 0.76 (A) | 497.97 |
| 918 | 7-Fluoro-4-methoxy-1-{2-[6-(3-methoxy-1H-indazol-6-yl)-pyrimidin-4-ylamino]-ethyl}-1H-indole-2-carbonitrile | 0.73 (A) | 458.1 |
| 919 | 7-Fluoro-4-methoxy-1-{2-[6-(1-methyl-2-oxo-1,2,3,4-tetrahydro-quinazolin-7-yl)-pyrimidin-4-ylamino]-ethyl}-1H-indole-2-carbonitrile | 0.69 (A) | 472.07 |
| 920 | 7-Fluoro-4-methoxy-1-{2-[6-(2-methyl-3-oxo-2,3-dihydro-1H-indazol-6-yl)-pyrimidin-4-ylamino]-ethyl}-1H-indole-2-carbonitrile | 0.65 (A) | 458.38 |
| 921 | 7-Fluoro-4-methoxy-1-{2-[6-(1-methyl-3-oxo-2,3-dihydro-1H-indazol-6-yl)-pyrimidin-4-ylamino]-ethyl}-1H-indole-2-carbonitrile | 0.69 (A) | 458.09 |
| 922 | 3-{6-[2-(2-Cyano-7-fluoro-4-methoxy-indol-1-yl)-ethylamino]-pyrimidin-4-yl}-5-ethylsulfanyl-benzoic acid | 0.77 (A) | 492.03 |
| 923 | 7-Fluoro-4-methoxy-1-(2-{6-[4-(3H-[1,2,3]triazol-4-yl)-phenyl]-pyrimidin-4-ylamino}-ethyl)-1H-indole-2-carbonitrile | 0.69 (A) | 455.15 |
| 924 | 3-(4-{6-[2-(2-Cyano-7-fluoro-4-methoxy-indol-1-yl)-ethylamino]-pyrimidin-4-yl}-2-ethoxy-phenyl)-propionic acid | 0.75 (A) | 504.19 |
| 925 | (6-{6-[2-(2-Cyano-7-fluoro-4-methoxy-indol-1-yl)-ethylamino]-pyrimidin-4-yl}-3-oxo-2,3-dihydro-indazol-1-yl)-acetic acid | 0.66 (A) | 501.83 |
| 926 | 3-(3-{6-[2-(2-Cyano-7-fluoro-4-methoxy-indol-1-yl)-ethylamino]-pyrimidin-4-yl}-5-ethoxy-phenoxy)-propionic acid | 0.79 (A) | 520.15 |
| 927 | 3-(4-{6-[2-(2-Cyano-7-fluoro-4-methoxy-indol-1-yl)-ethylamino]-pyrimidin-4-yl}-2-ethoxy-phenoxy)-propionic acid | 0.76 (A) | 520.14 |
| 928 | 4-{6-[2-(2-Cyano-7-fluoro-4-methoxy-indol-1-yl)-ethylamino]-pyrimidin-4-yl}-2-ethoxy-3-fluoro-benzoic acid | 0.78 (A) | 494.14 |
| 929 | 4-{6-[2-(2-Cyano-7-fluoro-4-methoxy-indol-1-yl)-ethylamino]-pyrimidin-4-yl}-2-ethoxy-benzenesulfonamide | 0.78 (A) | 511.13 |
| 930 | 1-(2-{6-[3-Ethoxy-4-(3H-[1,2,3]triazol-4-yl)-phenyl]-pyrimidin-4-ylamino}-ethyl)-7-fluoro-4-methoxy-1H-indole-2-carbonitrile | 0.77 (A) | 499.14 |
| 931 | (E)-3-(5-{6-[2-(2-Cyano-7-fluoro-4-methoxy-indol-1-yl)-ethylamino]-pyrimidin-4-yl}-3-ethoxy-thiophen-2-yl)-acrylic acid | 0.83 (A) | 508.14 |
| 932 | 3-(5-{6-[2-(2-Cyano-7-fluoro-4-methoxy-indol-1-yl)-ethylamino]-pyrimidin-4-yl}-3-ethoxy-thiophen-2-yl)-propionic acid | 0.83 (A) | 510.16 |
| 933 | 7-Fluoro-1-(2-{6-[4-(2-hydroxy-3,4-dioxo-cyclobut-1-enyl)-phenyl]-pyrimidin-4-ylamino}-ethyl)-4-methoxy-1H-indole-2-carbonitrile | 0.69 (A) | 484.03 |
| 934 | (4-{6-[2-(2-Cyano-7-fluoro-4-methoxy-indol-1-yl)-ethylamino]-pyrimidin-4-yl}-2-ethoxy-phenyl)-oxo-acetic acid | 0.70 (A) | 504.15 |
| 935 | 4-{6-[2-(2-Cyano-7-fluoro-4-methoxy-indol-1-yl)-ethylamino]-pyrimidin-4-yl}-2-propylsulfanyl-benzoic acid | 0.78 (A) | 506.15 |
| 936 | 4-{6-[2-(2-Cyano-6-fluoro-4-methoxy-indol-1-yl)-ethylamino]-pyrimidin-4-yl}-2-propylsulfanyl-benzoic acid | 0.87 (A) | 506.17 |
| 937 | 4-{6-[2-(2-Cyano-7-fluoro-4-methoxy-indol-1-yl)-ethylamino]-pyrimidin-4-yl}-2-isopropylsulfanyl-benzoic acid | 0.77 (A) | 506.11 |
| 938 | 4-{6-[2-(2-Cyano-6-fluoro-4-methoxy-indol-1-yl)-ethylamino]-pyrimidin-4-yl}-2-isopropylsulfanyl-benzoic acid | 0.86 (A) | 506.14 |
| 939 | 4-{6-[2-(2-Cyano-7-fluoro-4-methoxy-indol-1-yl)-ethylamino]-pyrimidin-4-yl}-2-fluoro-6-propyl-benzoic acid | 0.77(A) | 492.13 |
| 940 | 5-{6-[2-(2-Cyano-5,7-difluoro-4-methyl-indol-1-yl)-ethylamino]-pyrimidin-4-yl}-3-ethoxy-thiophene-2-carboxylic acid | 0.83 (A) | 484.1 |
| 941 | 5-{6-[2-(4-Chloro-2-cyano-6,7-difluoro-indol-1-yl)-ethylamino]-pyrimidin-4-yl}-3-ethoxy-thiophene-2-carboxylic acid | 0.84 (A) | 504.04 |

TABLE 11-continued

Examples 818-1021

| Ex. | Compound | $t_R$ [min] (LC-MS) | MS Data m/z [M + H]+ |
|---|---|---|---|
| 942 | 5-{6-[2-(2-Cyano-6,7-difluoro-4-methyl-indol-1-yl)-ethylamino]-pyrimidin-4-yl}-3-ethoxy-thiophene-2-carboxylic acid | 0.83 (A) | 484.1 |
| 943 | 5-{6-[2-(2-Cyano-6,7-difluoro-4-methoxy-indol-1-yl)-ethylamino]-pyrimidin-4-yl}-3-ethoxy-thiophene-2-carboxylic acid | 0.83 (A) | 500.09 |
| 944 | (4-{6-[2-(2-Cyano-6,7-difluoro-4-methoxy-indol-1-yl)-ethylamino]-pyrimidin-4-yl}-2-ethoxy-phenoxy)-acetic acid | 0.73 (A) | 524.13 |
| 945 | (4-{6-[2-(2-Cyano-6,7-difluoro-4-methoxy-indol-1-yl)-ethylamino]-pyrimidin-4-yl}-2-ethoxy-phenylamino)-acetic acid | 0.76 (A) | 523.13 |
| 946 | 4-{6-[2-(2-Cyano-7-fluoro-4-methoxy-indol-1-yl)-ethylamino]-pyrimidin-4-yl}-2-isobutyl-benzoic acid | 0.78 (A) | 488.16 |
| 947 | 4-{6-[2-(2-Cyano-7-fluoro-4-methoxy-indol-1-yl)-ethylamino]-pyrimidin-4-yl}-2-propyl-benzoic acid | 0.76 (A) | 474.16 |
| 948 | 4-{6-[2-(2-Cyano-7-fluoro-4-methoxy-indol-1-yl)-ethylamino]-pyrimidin-4-yl}-2-ethyl-benzoic acid | 0.73 (A) | 460.14 |
| 949 | 4-{6-[2-(2-Cyano-7-fluoro-4-methoxy-indol-1-yl)-ethylamino]-pyrimidin-4-yl}-2-isobutoxy-benzoic acid | 0.79 (A) | 504.12 |
| 950 | 4-{6-[2-(2-Cyano-7-fluoro-4-methoxy-indol-1-yl)-ethylamino]-pyrimidin-4-yl}-2-propoxy-benzoic acid | 0.76 (A) | 490.14 |
| 951 | 4-{6-[2-(2-Cyano-7-fluoro-4-methyl-indol-1-yl)-ethylamino]-pyrimidin-4-yl}-2-ethylsulfanyl-benzoic acid | 0.85 (A) | 476.16 |
| 952 | 4-{6-[2-(2-Cyano-4-methoxy-indol-1-yl)-ethylamino]-pyrimidin-4-yl}-2-ethylsulfanyl-benzoic acid | 0.73 (A) | 474.08 |
| 953 | 4-{6-[2-(2-Cyano-7-fluoro-4-methoxy-indol-1-yl)-ethylamino]-pyrimidin-4-yl}-2-ethylsulfanyl-benzoic acid | 0.75 (A) | 492.12 |
| 954 | 4-{6-[2-(2-Cyano-6-fluoro-4-methoxy-indol-1-yl)-ethylamino]-pyrimidin-4-yl}-2-ethylsulfanyl-benzoic acid | 0.83 (A) | 492.14 |
| 955 | 4-{6-[2-(2-Cyano-6,7-difluoro-4-methoxy-indol-1-yl)-ethylamino]-pyrimidin-4-yl}-2-ethylsulfanyl-benzoic acid | 0.78 (A) | 510.08 |
| 956 | 4-{6-[2-(2-Cyano-6,7-difluoro-4-methyl-indol-1-yl)-ethylamino]-pyrimidin-4-yl}-2-ethoxy-benzoic acid | 0.76 (A) | 478.11 |
| 957 | 4-{6-[2-(2-Cyano-6,7-difluoro-4-methoxy-indol-1-yl)-ethylamino]-pyrimidin-4-yl}-2-ethoxy-benzoic acid | 0.75 (A) | 494.13 |
| 958 | 4-{6-[2-(2-Cyano-4-methoxy-indol-1-yl)-ethylamino]-pyrimidin-4-yl}-2-methylamino-benzoic acid | 0.73 (A) | 443.21 |
| 959 | 2-{6-[2-(2-Cyano-7-fluoro-4-methoxy-indol-1-yl)-ethylamino]-pyrimidin-4-yl}-1H-indole-6-carboxylic acid methyl ester | 0.93 (A) | 485.06 |
| 960 | 2-{6-[2-(2-Cyano-7-fluoro-4-methoxy-indol-1-yl)-ethylamino]-pyrimidin-4-yl}-1H-indole-5-carboxylic acid | 0.77 (A) | 471.23 |
| 961 | 7-Fluoro-1-{2-[6-(1H-indol-2-yl)-pyrimidin-4-ylamino]-ethyl}-4-methoxy-1H-indole-2-carbonitrile | 0.83 (A) | 427.29 |
| 962 | 2-{6-[2-(2-Cyano-7-fluoro-4-methoxy-indol-1-yl)-ethylamino]-pyrimidin-4-yl}-1H-indole-5-carboxylic acid methyl ester | 0.87 (A) | 485.19 |
| 963 | 7-Fluoro-4-methoxy-1-(2-{6-[4-(2-methoxy-ethoxy)-phenyl]-pyrimidin-4-ylamino}-ethyl)-1H-indole-2-carbonitrile | 0.84 (A) | 462.04 |
| 964 | 7-Fluoro-1-(2-{6-[4-(2-hydroxy-ethoxy)-phenyl]-pyrimidin-4-ylamino}-ethyl)-4-methoxy-1H-indole-2-carbonitrile | 0.68 (A) | 448.1 |
| 965 | 4-{6-[2-(2-Cyano-7-fluoro-4-methoxy-indol-1-yl)-ethylamino]-pyrimidin-4-yl}-phthalic acid 2-ethyl ester | 0.75 (A) | 503.81 |
| 966 | 7-Fluoro-1-{2-[6-(1H-indol-6-yl)-pyrimidin-4-ylamino]-ethyl}-4-methoxy-1H-indole-2-carbonitrile | 0.75 (A) | 427.14 |
| 967 | 7-Fluoro-4-methoxy-1-{2-[6-(1H-pyrrolo[2,3-c]pyridin-3-yl)-pyrimidin-4-ylamino]-ethyl}-1H-indole-2-carbonitrile | 0.59 (A) | 428.14 |
| 968 | 7-Fluoro-1-{2-[6-(1H-indol-3-yl)-pyrimidin-4-ylamino]-ethyl}-4-methoxy-1H-indole-2-carbonitrile | 0.76 (A) | 427.16 |
| 969 | 7-Fluoro-1-{2-[6-(1H-indol-4-yl)-pyrimidin-4-ylamino]-ethyl}-4-methoxy-1H-indole-2-carbonitrile | 0.74 (A) | 427.17 |
| 970 | 7-Fluoro-4-methoxy-1-{2-[6-(2-oxo-1,2,3,4-tetrahydro-quinazolin-6-yl)-pyrimidin-4-ylamino]-ethyl}-1H-indole-2-carbonitrile | 0.65 (A) | 458.11 |
| 971 | N-(4-{6-[2-(2-Cyano-7-fluoro-4-methoxy-indol-1-yl)-ethylamino]-pyrimidin-4-yl}-phenyl)-formamide | 0.68 (A) | 431.14 |
| 972 | 7-Fluoro-4-methoxy-1-{2-[6-(2-oxo-2,3-dihydro-benzooxazol-6-yl)-pyrimidin-4-ylamino]-ethyl}-1H-indole-2-carbonitrile | 0.70 (A) | 445.08 |
| 973 | 7-Fluoro-4-methoxy-1-{2-[6-(3-methyl-2-oxo-2,3-dihydro-benzooxazol-5-yl)-pyrimidin-4-ylamino]-ethyl}-1H-indole-2-carbonitrile | 0.74 (A) | 459.06 |
| 974 | 4-{6-[2-(2-Cyano-7-fluoro-4-methoxy-indol-1-yl)-ethylamino]-pyrimidin-4-yl}-benzoic acid | 0.70 (A) | 432.13 |
| 975 | 1-{2-[6-(2-Azetidin-1-yl-pyridin-4-yl)-pyrimidin-4-ylamino]-ethyl}-7-fluoro-4-methoxy-1H-indole-2-carbonitrile | 0.70 (A) | 444.1 |
| 976 | 7-Fluoro-4-methoxy-1-{2-[6-(3,4,5,6-tetrahydro-2H-[1,2']bipyridinyl-4'-yl)-pyrimidin-4-ylamino]-ethyl}-1H-indole-2-carbonitrile | 0.75 (A) | 472.16 |
| 977 | 7-Fluoro-1-{2-[6-(1H-indazol-5-yl)-pyrimidin-4-ylamino]-ethyl}-4-methoxy-1H-indole-2-carbonitrile | 0.89 (E) | 428.08 |
| 978 | 7-Fluoro-4-methoxy-1-{2-[6-(1H-pyrrolo[2,3-b]pyridin-3-yl)-pyrimidin-4-ylamino]-ethyl}-1H-indole-2-carbonitrile | 0.89 (E) | 428.08 |

TABLE 11-continued

Examples 818-1021

| Ex. | Compound | t_R [min] (LC-MS) | MS Data m/z [M + H]+ |
|---|---|---|---|
| 979 | 7-Fluoro-4-methoxy-1-{2-[6-(1H-pyrrolo[2,3-b]pyridin-5-yl)-pyrimidin-4-ylamino]-ethyl}-1H-indole-2-carbonitrile | 0.90 (E) | 428.08 |
| 980 | 7-Fluoro-4-methoxy-1-{2-[6-(1-methyl-1H-pyrrolo[2,3-b]pyridin-5-yl)-pyrimidin-4-ylamino]-ethyl}-1H-indole-2-carbonitrile | 0.97 (E) | 442.08 |
| 981 | 7-Fluoro-4-methoxy-1-{2-[6-(6-methoxy-1H-indazol-5-yl)-pyrimidin-4-ylamino]-ethyl}-1H-indole-2-carbonitrile | 0.87 (E) | 458.09 |
| 982 | 1-(4-{6-[2-(2-Cyano-7-fluoro-4-methoxy-indol-1-yl)-ethylamino]-pyrimidin-4-yl}-2-methoxy-phenyl)-3-ethyl-urea | 0.95 (E) | 504.12 |
| 983 | N-(4-{6-[2-(2-Cyano-7-fluoro-4-methoxy-indol-1-yl)-ethylamino]-pyrimidin-4-yl}-benzyl)-methanesulfonamide | 0.91 (E) | 495.08 |
| 984 | 1-{2-[6-(1H-Benzoimidazol-5-yl)-pyrimidin-4-ylamino]-ethyl}-7-fluoro-4-methoxy-1H-indole-2-carbonitrile | 0.82 (E) | 428.05 |
| 985 | 1-{2-[6-(3H-Benzotriazol-5-yl)-pyrimidin-4-ylamino]-ethyl}-7-fluoro-4-methoxy-1H-indole-2-carbonitrile | 0.61 (E) | 429.05 |
| 986 | 1-{2-[6-(2-Cyclopropyl-pyridin-4-yl)-pyrimidin-4-ylamino]-ethyl}-7-fluoro-4-methoxy-1H-indole-2-carbonitrile | 1.02 (E) | 429.1 |
| 987 | 7-Fluoro-1-{2-[6-(2-oxo-2,3-dihydro-1H-benzo[d]imidazol-5-yl)-pyrimidin-4-ylamino]-ethyl}-4-methoxy-1H-indole-2-carbonitrile | 0.80 (E) | 444.07 |
| 988 | 1-{2-[6-(2-Amino-pyridin-4-yl)-pyrimidin-4-ylamino]-ethyl}-7-fluoro-4-methoxy-1H-indole-2-carbonitrile | 0.84 (E) | 404.02 |
| 989 | (4-(6-((2-(2-Cyano-7-fluoro-4-methoxy-1H-indol-1-yl)ethyl)amino)pyrimidin-4-yl)phenyl)boronic acid | 0.69 (A) | 432.17 |
| 990 | 7-Fluoro-4-methoxy-1-{2-[6-(1-oxo-1,2,3,4-tetrahydro-isoquinolin-6-yl)-pyrimidin-4-ylamino]-ethyl}-1H-indole-2-carbonitrile | 0.68 (A) | 457.09 |
| 991 | 7-Fluoro-4-methoxy-1-{2-(2'-methoxy-[4,5]bipyrimidinyl-6-ylamino)-ethyl]-1H-indole-2-carbonitrile | 0.74 (A) | 420.16 |
| 992 | 1-{2-[6-(3-Ethoxy-4-formyl-phenyl)-pyrimidin-4-ylamino]-ethyl}-7-fluoro-4-methoxy-1H-indole-2-carbonitrile | 0.91 (E) | 460.12 |
| 993 | 1-{2-[6-(3,5-Dimethyl-isoxazol-4-yl)-pyrimidin-4-ylamino]-ethyl}-7-fluoro-4-methoxy-1H-indole-2-carbonitrile | 0.81 (E) | 407.09 |
| 994 | 7-Fluoro-1-{2-[6-(1H-indol-5-yl)-pyrimidin-4-ylamino]-ethyl}-4-methoxy-1H-indole-2-carbonitrile | 0.82 (E) | 427.1 |
| 995 | 7-Fluoro-1-[2-(6-imidazo[1,2-a]pyridin-6-yl-pyrimidin-4-ylamino)-ethyl]-4-methoxy-1H-indole-2-carbonitrile | 0.72 (E) | 428.1 |
| 996 | 4-{6-[2-(2-Cyano-7-fluoro-4-methoxy-indol-1-yl)-ethylamino]-pyrimidin-4-yl}-N-(2-methoxy-ethyl)-benzamide | 0.77 (E) | 489.14 |
| 997 | 7-Fluoro-4-methoxy-1-{2-[6-(2-pyrrolidin-1-yl-pyridin-4-yl)-pyrimidin-4-ylamino]-ethyl}-1H-indole-2-carbonitrile | 0.79 (E) | 458.16 |
| 998 | 7-Fluoro-4-methoxy-1-{2-[6-(1,3,5-trimethyl-1H-pyrazol-4-yl)-pyrimidin-4-ylamino]-ethyl}-1H-indole-2-carbonitrile | 0.74 (E) | 420.14 |
| 999 | 4-{6-[2-(2-Cyano-7-fluoro-4-methoxy-indol-1-yl)-ethylamino]-pyrimidin-4-yl}-2-fluoro-benzoic acid methyl ester | 0.82 (A) | 464.09 |
| 1000 | 7-Fluoro-4-methoxy-1-{2-[6-(2-oxo-2,3-dihydro-1H-benzoimidazol-5-yl)-pyrimidin-4-ylamino]-ethyl}-1H-indole-2-carbonitrile | 0.65 (A) | 444.12 |
| 1001 | 7-Fluoro-1-{2-[6-(4-hydroxy-3-trifluoromethyl-phenyl)-pyrimidin-4-ylamino]-ethyl}-4-methoxy-1H-indole-2-carbonitrile | 0.77 (A) | 472.03 |
| 1002 | 3-{6-[2-(2-Cyano-7-fluoro-4-methoxy-indol-1-yl)-ethylamino]-pyrimidin-4-yl}-5-ethoxy-benzoic acid | 0.74 (A) | 476.12 |
| 1003 | 7-Fluoro-4-methoxy-1-{2-[6-(2-morpholin-4-yl-pyridin-4-yl)-pyrimidin-4-ylamino]-ethyl}-1H-indole-2-carbonitrile | 0.78 (E) | 474.15 |
| 1004 | (3-{6-[2-(2-Cyano-7-fluoro-4-methoxy-indol-1-yl)-ethylamino]-pyrimidin-4-yl}-phenyl)-acetic acid | 0.69 (A) | 446.15 |
| 1005 | 3-{6-[2-(2-Cyano-7-fluoro-4-methoxy-indol-1-yl)-ethylamino]-pyrimidin-4-yl}-5-methoxy-benzoic acid | 0.71 (A) | 462.14 |
| 1006 | 1-{2-[6-(2-Difluoromethoxy-pyridin-4-yl)-pyrimidin-4-ylamino]-ethyl}-7-fluoro-4-methoxy-1H-indole-2-carbonitrile | 0.87 (A) | 455.08 |
| 1007 | 7-Fluoro-4-methoxy-1-{2-[6-(2-trifluoromethyl-pyridin-4-yl)-pyrimidin-4-ylamino]-ethyl}-1H-indole-2-carbonitrile | 0.89 (A) | 457.07 |
| 1008 | 5-{6-[2-(2-Cyano-7-fluoro-4-methoxy-indol-1-yl)-ethylamino]-pyrimidin-4-yl}-thiophene-3-carboxylic acid | 0.74 (A) | 438.09 |
| 1009 | 5-{6-[2-(2-Cyano-7-fluoro-4-methoxy-indol-1-yl)-ethylamino]-pyrimidin-4-yl}-thiophene-3-carboxylic acid ethyl ester | 0.88 (A) | 465.94 |
| 1010 | 4-{6-[2-(2-Cyano-7-fluoro-4-methoxy-indol-1-yl)-ethylamino]-pyrimidin-4-yl}-2-methylamino-benzoic acid | 0.76 (A) | 461.19 |
| 1011 | 3-(3-{6-[2-(2-Cyano-7-fluoro-4-methoxy-indol-1-yl)-ethylamino]-pyrimidin-4-yl}-phenyl)-propionic acid | 0.70 (A) | 460.17 |
| 1012 | 4-{6-[2-(5,7-Difluoro-2,4-dimethyl-indol-1-yl)-ethylamino]-pyrimidin-4-yl}-2-methylamino-benzoic acid | 0.82 (A) | 452.2 |
| 1013 | 3-(5-{6-[2-(7-Fluoro-4-methoxy-2-methyl-indol-1-yl)-ethylamino]-pyrimidin-4-yl}-3-isopropoxy-thiophen-2-yl)-propionic acid | 0.81 (A) | 513.06 |
| 1014 | 3-Ethoxy-5-{6-[2-(7-fluoro-4-methoxy-2-methyl-indol-1-yl)-ethylamino]-pyrimidin-4-yl}-1H-pyrrole-2-carboxylic acid | 0.67 (A) | 454.16 |
| 1015 | 3-(3-Ethoxy-5-{6-[2-(7-fluoro-4-methoxy-2-methyl-indol-1-yl)-ethylamino]-pyrimidin-4-yl}-thiophen-2-yl)-propionic acid | 0.81 (A) | 499.18 |

TABLE 11-continued

Examples 818-1021

| Ex. | Compound | $t_R$ [min] (LC-MS) | MS Data m/z [M + H]$^+$ |
|---|---|---|---|
| 1016 | (E)-3-(3-Ethoxy-5-{6-[2-(7-fluoro-4-methoxy-2-methyl-indol-1-yl)-ethylamino]-pyrimidin-4-yl}-thiophen-2-yl)-acrylic acid | 0.81 (A) | 497.09 |
| 1017 | 4-{6-[2-(6-Fluoro-4-methoxy-2-methyl-indol-1-yl)-ethylamino]-pyrimidin-4-yl}-2-methylamino-benzoic acid | 0.74 (A) | 449.96 |
| 1018 | 7-Fluoro-4-methoxy-1-(2-{6-[4-(2,2,2-trifluoro-1,1-dihydroxy-ethyl)-phenyl]-pyrimidin-4-ylamino}-ethyl)-1H-indole-2-carbonitrile | 0.73 (A) | 502 |
| 1019 | 3-(4-{6-[2-(2-Cyano-7-fluoro-4-methoxy-indol-1-yl)-ethylamino]-pyrimidin-4-yl}-phenyl)-propionic acid | 0.7 (A) | 460.17 |
| 1020 | 3-Chloro-5-{6-[2-(4-chloro-2-cyano-indol-1-yl)-ethylamino]-pyrimidin-4-yl}-thiophene-2-carboxylic acid | 0.85 (A) | 457.96 |
| 1021 | 3-Chloro-5-{6-[2-(4-chloro-2-cyano-6,7-difluoro-indol-1-yl)-ethylamino]-pyrimidin-4-yl}-thiophene-2-carboxylic acid | 0.88 (A) | 493.99 |

Example 1022: N-(3-Ethoxy-5-{6-[2-(7-fluoro-4-methoxy-2-methyl-indol-1-yl)-ethylamino]-pyrimidin-4-yl}-thiophene-2-carbonyl)-methanesulfonamide Following the method described for example 809, using 3-Ethoxy-5-{6-[2-(7-fluoro-4-methoxy-2-methyl-indol-1-yl)-ethylamino]-pyrimidin-4-yl}-thiophene-2-carboxylic acid (example 258), the title compound is obtained as white solid. LC-MS A: $t_R$=0.88 min; [M+H]+=548.04.

Example 1023: 5-{6-[2-(2-Cyano-7-fluoro-4-methoxy-indol-1-yl)-ethylamino]-pyrimidin-4-yl}-3-ethoxy-thiophene-2-carboxylic acid methylamide To a solution of 5-{6-[2-(2-cyano-7-fluoro-4-methoxy-indol-1-yl)-ethylamino]-pyrimidin-4-yl}-3-ethoxy-thiophene-2-carboxylic acid (Example 805, 34 mg, 0.071 mmol) in DMF (2 ml) are added methylamine (0.056 mL, 0.092 mmol), TEA (0.030 mL, 0.212 mmol) and HATU (40.3 mg, 0.106 mmol). The resulting mixture is stirred at RT overnight. The RM is purified by prep HPLC (basic conditions), affording the title compound as a white solid (21 mg, 60%). LC-MS A: $t_R$=0.85 m; [M+H]+=495.16.

Following the method described for Example 1023, compounds of Examples 1024-1030 listed in Table 12 below are prepared, using the appropriate amine.

TABLE 12

Examples 1024-1030

| Ex. | Compound | $t_R$ [min] (LC-MS) | MS Data m/z [M + H]$^+$ |
|---|---|---|---|
| 1024 | 5-{6-[2-(2-Cyano-7-fluoro-4-methoxy-indol-1-yl)-ethylamino]-pyrimidin-4-yl}-3-ethoxy-thiophene-2-carboxylic acid ethylamide | 0.88 (A) | 509.16 |
| 1025 | 5-{6-[2-(2-Cyano-7-fluoro-4-methoxy-indol-1-yl)-ethylamino]-pyrimidin-4-yl}-3-ethoxy-thiophene-2-carboxylic acid dimethylamide | 0.84 (A) | 509.16 |
| 1026 | 5-{6-[2-(2-Cyano-7-fluoro-4-methoxy-indol-1-yl)-ethylamino]-pyrimidin-4-yl}-3-ethoxy-thiophene-2-carboxylic acid (2-hydroxy-ethyl)-amide | 0.78 (A) | 525.14 |
| 1027 | 5-{6-[2-(2-Cyano-7-fluoro-4-methoxy-indol-1-yl)-ethylamino]-pyrimidin-4-yl}-3-ethoxy-thiophene-2-carboxylic acid isopropylamide | 0.92 (A) | 523.17 |
| 1028 | 5-{6-[2-(2-Cyano-7-fluoro-4-methoxy-indol-1-yl)-ethylamino]-pyrimidin-4-yl}-3-ethoxy-thiophene-2-carboxylic acid (2-methoxy-ethyl)-amide | 0.87 (A) | 539.17 |
| 1029 | 5-(6-((2-(2-Cyano-7-fluoro-4-methoxy-1H-indol-1-yl)ethyl)amino)pyrimidin-4-yl)-3-ethoxy-N-sulfamoylthiophene-2-carboxamide | 0.83 (A) | 560.07 |
| 1030 | 5-{6-[2-(2-Cyano-7-fluoro-4-methoxy-indol-1-yl)-ethylamino]-pyrimidin-4-yl}-3-ethoxy-thiophene-2-carboxylic acid hydroxyamide | 0.83 (A) | 497.04 |

Example 1031: (3-Ethoxy-5-{6-[2-(7-fluoro-4-methoxy-2-methyl-indol-1-yl)-ethylamino]-pyrimidin-4-yl}-thiophen-2-yl)methanol Lithium aluminum hydride (2M in THF, 0.875 mL, 1.75 mmol) is added dropwise at RT to 3-ethoxy-5-{6-[2-(7-fluoro-4-methoxy-2-methyl-indol-1-yl)-ethylamino]-pyrimidin-4-yl}thiophene-2-carboxylic acid (Example 258, 285 mg, 0.585 mmol) in THF (20 mL). The RM is stirred at RT overnight. Lithium aluminum hydride (2M in THF, 0.875 mL, 1.75 mmol) is added dropwise, and the RM is stirred for 1.5 h. The RM is cooled at 0° C. and quenched with sat. aq. Rochelle's salt (ca 50 mL). The RM is extracted with EtOAc (3×). The combined organic extracts are dried (MgSO$_4$) and concentrated under reduced pressure. Purification by FC (DCM:MeOH 100:0 to 97:3) afforded the title compound as a pale yellow solid (86 mg, 32%). LC-MS A: $t_R$=0.73 min; [M+H]+=457.12.

Example 1032: 2-{6-[2-(7-Fluoro-4-methoxy-2-methyl-indol-1-yl)-ethylamino]-pyrimidin-4-yl}-4-isopropoxy-thiazole-5-carboxylic acid To a solution of ethyl 2-(6-((2-(7-fluoro-4-methoxy-2-methyl-1H-indol-1-yl)ethyl)amino)pyrimidin-4-yl)-4-isopropoxythiazole-5-carboxylate (45.8 mg, 0.0891 mmol) in MeOH (2 mL), THF (1 mL) and H2O (0.4 mL) at RT is added Lithium hydroxide monohydrate (11.2 mg, 0.267 mmol). The RM is stirred at RT for 40 h. Solvents are removed in vacuo. The remaining aqueous mixture is extracted with EtOAc (2×). The basic aqueous layer is acidified to pH=3-4 using HCl 1N and extracted with EtOAc (2×). The combined organic layers are washed with brine, dried over MgSO4, filtered and solvent is removed in vacuo yielding the title compound as a yellow powder (29 mg, 67%). LC-MS A: $t_R$=0.87 min; [M+H]+=486.08.

a) Ethyl 2-(6-((2-(7-fluoro-4-methoxy-2-methyl-1H-indol-1-yl)ethyl)amino)pyrimidin-4-yl)-4-isopropoxythiazole-5-carboxylate To a solution of ethyl 2-(6-((2-(7-fluoro-4-methoxy-2-methyl-1H-indol-1-yl)ethyl)amino)pyrimidin-4-yl)-4-hydroxythiazole-5-carboxylate (50 mg, 0.0891 mmol) in DMF (1 mL) at RT is added K2CO3 (25.8 mg, 0.183 mmol). The RM is stirred for 15 min at 60° C. then is added 2-iodopropane (0.0107 mL, 0.107 mmol) and the RM is stirred over night at the same temperature. The RM is allowed to cool to RT. The resulting solution is partitioned between EtOAc and water. The organic layer is washed once more with water, then brine, dried over MgSO4, filtered and evaporated to dryness yielding the title compound as a beige residue (50 mg, 99%). LC-MS A: $t_R$=1.03 min; [M+H]+=514.03.

b) Ethyl 2-(6-((2-(7-fluoro-4-methoxy-2-methyl-1H-indol-1-yl)ethyl)amino)pyrimidin-4-yl)-4-hydroxythiazole-5-carboxylate To a solution of 6-((2-(7-fluoro-4-methoxy-2-methyl-1H-indol-1-yl)ethyl)amino)pyrimidine-4-carbothioamide (625 mg, 1.74 mmol) in toluene (20 mL) at RT is added pyridine (0.564 mL, 6.96 mmol) and diethyl bromomalonate (0.322 mL, 1.74 mmol). The RM is heated at 110° C. for 3.5 h. Diethyl bromomalonate (80 microL) is added to the RM which is kept refluxing for 1 h 30. It is cooled to RT and concentrated in vacuo. The residue is partioned between EtOAc and water. The pH of the aqueous layer is adjusted to pH 7 using HCl 1N. The resulting aqueous layer is extracted twice with EtOAC. The combined organic layers are washed with water and brine, dried over MgSO4, filtered and evaporated to dryness. The residue is triturated in Et2O, filtered and dried, affording the title compound as a dark orange powder (500 mg, 61%). LC-MS A: $t_R$=0.95 min; [M+H]+=472.01.

c) 6-((2-(7-Fluoro-4-methoxy-2-methyl-1H-indol-1-yl)ethyl)amino)pyrimidine-4-carbothioamide To a suspension of 6-((2-(7-fluoro-4-methoxy-2-methyl-1H-indol-1-yl)ethyl)amino)pyrimidine-4-carbonitrile (1233 mg, 3.79 mmol) in EtOH (40 mL) is added sodium hydrosulfide hydrate (842 mg, 11.4 mmol) at RT. The RM is stirred at 90° C. for 2 h, cooled to RT, and concentrated under reduced pressure. The residue is partitioned between H2O and EtOAc. The aqueous layer is re-extracted 2× with EtOAc. The combined organic extracts are washed with brine, dried over MgSO4, filtered and concentrated under reduced pressure. The residue is purified by FC (Hept:EtOAc 100:0 to 70:30), affording the title compound as a bright yellow powder (730 mg, 54%). LC-MS A: $t_R$=0.77 min; [M+H]+=360.02.

d) 6-((2-(7-fluoro-4-methoxy-2-methyl-1H-indol-1-yl)ethyl)amino)pyrimidine-4-carbonitrile This reaction is done in two 20 mL-microwave vials. Each MW vial is charged with 6-chloro-N-(2-(7-fluoro-4-methoxy-2-methyl-1H-indol-1-yl)ethyl)pyrimidin-4-amine (A.1.25, 300 mg, 0.896 mmol), zinc cyanide (161 mg, 1.34 mmol) and DMF (10 mL). The RM is degassed then tetrakis(triphenylphosphine)palladium (0) (104 mg, 0.0896 mmol) is added. The microwave vial is sealed and RM is heated using the microwave Initiator at 180° C. for 20 min. To each microwave vial is added zinc cyanide (161 mg, 1.34 mmol) and tetrakis(triphenylphosphine)palladium(0) (104 mg, 0.0896 mmol). Each microwave vial is sealed and RM is heated using the microwave Initiator at 180° C. for 20 min. The 2 batches are combined, filtered through a Glass MicroFiber filter, washing with EtOAc. The filtrate is washed with water, the aqueous phase is re-extracted twice with EtOAc. The combined organic extracts are washed with brine, dried over MgSO4 and concentrated in vacuo. Purification by FC (Hept:EtOAc 100:0 to 70:30) afforded the title compound as a white powder (295 mg, 51%). LC-MS A: $t_R$=0.87 min; [M+H]+=326.26.

Following the method described for Example 1032, compounds of Examples 1033-1035 listed in Table 13 below are prepared, using the appropriate alkyl iodide.

TABLE 13

Examples 1033-1035

| Ex. | Compound | $t_R$ [min] (LC-MS) | MS Data m/z [M + H]+ |
|---|---|---|---|
| 1033 | 2-{6-[2-(7-Fluoro-4-methoxy-2-methyl-indol-1-yl)-ethylamino]-pyrimidin-4-yl}-4-methoxy-thiazole-5-carboxylic acid | 0.80 (A) | 458.07 |
| 1034 | 4-Ethoxy-2-{6-[2-(7-fluoro-4-methoxy-2-methyl-indol-1-yl)-ethylamino]-pyrimidin-4-yl}-thiazole-5-carboxylic acid | 0.84 (A) | 472.07 |

TABLE 13-continued

Examples 1033-1035

| Ex. | Compound | $t_R$ [min] (LC-MS) | MS Data m/z $[M + H]^+$ |
|---|---|---|---|
| 1035 | 2-{6-[2-(7-Fluoro-4-methoxy-2-methyl-indol-1-yl)-ethylamino]-pyrimidin-4-yl}-4-propoxy-thiazole-5-carboxylic acid | 0.89 (A) | 486.25 |

Example 1036: 2-{6-[2-(7-Fluoro-4-methoxy-2-methyl-indol-1-yl)-ethylamino]-pyrimidin-4-yl}-4-isobutyl-thiazole-5-carboxylic acid A MW vial is charged with 6-((2-(7-fluoro-4-methoxy-2-methyl-1H-indol-1-yl)ethyl)amino)pyrimidine-4-carbothioamide (Example 1032 c, 100 mg, 0.278 mmol) and EtOH (2 mL), it is purged with N2, and ethyl 2-chloro-5-methyl-3-oxohexanoate (90.8 mg, 0.417 mmol) is added. The vial is capped, and it is heated at 90° C. overnight. It is cooled to RT and the RM is partitioned between EtOAc and sat. aq. NaHCO$_3$. The aqueous phase is re-extracted with EtOAc (2×). The combined organic extracts are dried (MgSO$_4$), filtered and concentrated. The residue is purified by FC (Hept to Hept:EtOAc 80:20), affording the intermediate ester. It is dissolved in MeOH (5 mL) and treated with 2N NaOH (5 mL). The RM is stirred at RT o/n, concentrated under reduced pressure, and the residue is acidified with 1N HCl, and extracted with EtOAC (2×). The organic extracts are dried (MgSO$_4$), filtered and concentrated, affording the title compound as a yellow solid (48 mg, 36%). LC-MS A: $t_R$=0.91 min; [M+H]+=484.15.

Example 1037: 4-Ethyl-2-{6-[2-(7-fluoro-4-methoxy-2-methyl-indol-1-yl)-ethylamino]-pyrimidin-4-yl}-thiazole-5-carboxylic acid Following the method described for example 1036, using methyl 2-chloro-3-oxovalerate, the title compound is obtained as yellow solid. LC-MS A: $t_R$=0.6 min; [M+H]+=456.00.

Example 1038: 4-tert-Butyl-2-{6-[2-(7-fluoro-4-methoxy-2-methyl-indol-1-yl)-ethylamino]-pyrimidin-4-yl}-thiazole-5-carboxylic acid Following the method described for example 1036, using methyl 2-chloro-4,4-dimethyl-3-oxopentanoate, the title compound is obtained as an orange solid. LC-MS A: $t_R$=0.91 min; [M+H]+=484.14.

Example 1039: 4-{6-[2-(7-Fluoro-4-methoxy-2-methyl-indol-1-yl)-ethylamino]-pyrimidin-4-yl}-2-(2-oxaspiro[3.3]hept-6-yloxy)-benzoic acid To a solution of 4-{6-[2-(7-fluoro-4-methoxy-2-methyl-indol-1-yl)-ethylamino]-pyrimidin-4-yl}-2-hydroxy-benzoic acid (50 mg, 0.115 mmol) (60 mg, 0.137 mmol), TBAI (10.3 mg, 0.0275 mmol) and Cs2CO3 (134 mg, 0.412 mmol) in DMF (2 mL) is added 6-iodo-2-oxaspiro[3.3]heptane (97.3 mg, 0.412 mmol) and the RM is heated at 130° C. for 3 h in the microwave. NaOH 10% (0.275 mL, 0.687 mmol) is added and the RM is stirred at RT until full saponification (1 h). The mixture is filtered, rinsed with MeOH and purified by prep HPLC, to afford the title compound as a yellow solid (30 mg, 40%). LC-MS A: $t_R$=0.69 min; [M+H]+=533.19.

a) 4-{6-[2-(7-Fluoro-4-methoxy-2-methyl-indol-1-yl)-ethylamino]-pyrimidin-4-yl}-2-hydroxy-benzoic acid The title compound is prepared according to the synthesis of A.1.1.1. described above using 6-chloro-N-(2-(7-fluoro-4-methoxy-2-methyl-1H-indol-1-yl)ethyl)pyrimidin-4-amine (A.1.25.) and 2-hydroxy-4-(4,4,5,5-tetramethyl-1,3,2-dioxaborolan-2-yl)benzoic acid; LC-MS A: $t_R$=0.69 min; [M+H]+=437.16.

Example 1040: 1-(2-Ethoxy-4-{6-[2-(7-fluoro-4-methoxy-2-methyl-indol-1-yl)-ethylamino]-pyrimidin-4-yl}-phenyl)-2-hydroxy-ethanone To a solution of 1-(2-ethoxy-4-(6-((2-(7-fluoro-4-methoxy-2-methyl-1H-indol-1-yl)ethyl)amino)pyrimidin-4-yl)phenyl)ethan-1-one (57 mg, 0.123 mmol) in toluene (2 mL) is added TEA (0.0515 mL, 0.37 mmol). The mixture is cooled at 0° C. and trimethylsilyl trifluoromethanesulfonate (0.041 mL, 0.222 mmol) is added dropwise. The RM is stirred for 10 min at 0° C. then warmed up to rt and stirred for 4 h. The mixture is washed with saturated aqueous NaHCO$_3$ (3 mL), and extracted with DCM. The organic layer is dried (MgSO$_4$), filtered and concentrated in vacuo. The residue is dissolved in DCM (1.5 mL) and added dropwise to a cooled (−10° C.) suspension of 3-chloroperbenzoic acid (41.4 mg, 0.185 mmol) in DCM (1.5 mL). The RM is stirred at −10° C. for 45 min, then allowed to warm to rt over 1 h. It is diluted with DCM (5 mL) and poured into 10 mL of a 20% solution of Na$_2$S$_2$O$_3$. The mixture is vigorously stirred for 30 min. The organic layer is separated. The aqueous layer is extracted with DCM. The combined extracts are washed with saturated solution of Na2CO3 (20 mL) and concentrated in vacuo. The residue is purified by prep HPLC (basic conditions) affording the title compound as a green solid (3 mg, 5%). LC-MS A: $t_R$=0.72 min; [M+H]+=479.21.

a) 1-(2-Ethoxy-4-(6-((2-(7-fluoro-4-methoxy-2-methyl-1H-indol-1-yl)ethyl)amino)pyrimidin-4-yl)phenyl)ethan-1-one Following the general procedure A, using A.1.25 and 1-(2-ethoxy-4-(4,4,5,5-tetramethyl-1,3,2-dioxaborolan-2-yl)phenyl)ethan-1-one, the title compound is obtained as a beige solid (50 mg, 99%). LC-MS A: $t_R$=0.78 min; [M+H]+=463.23.

b) 1-(2-Ethoxy-4-(4,4,5,5-tetramethyl-1,3,2-dioxaborolan-2-yl)phenyl)ethan-1-one Following the procedure described for the synthesis of A.2.3. using 1-(4-bromo-2-ethoxyphenyl)ethan-1-one, the title compound is obtained as a white solid (50 mg, 99%). LC-MS A: $t_R$=0.95 min; [M+H]+=291.21.

Example 1041: (4-{6-[2-(7-Fluoro-4-methoxy-2-methyl-indol-1-yl)-ethylamino]-pyrimidin-4-yl}-phenyl)-carbamic acid methyl ester To a solution of [6-(4-amino-phenyl)-pyrimidin-4-yl]-[2-(7-fluoro-4-methoxy-2-methyl-indol-1-yl)-ethyl]-amine (Example 4, 50 mg, 0.117 mmol) in DCM (1 mL) are added DIPEA (0.06 mL, 0.351 mmol) and methyl chloroformate (0.0109 mL, 0.14 mmol). The RM is stirred at RT for 30 min, then partitioned between water (5 ml) and DCM (5 ml). The organic layer is dried ($MgSO_4$) and concentrated. The residue is purified by prep HPLC (basic conditions) affording the title compound as a white solid (18 mg, 34%). LC-MS A: $t_R$=0.72 min; [M+H]+=450.04.

Example 1042: (2-Ethoxy-4-{6-[2-(7-fluoro-4-methoxy-2-methyl-indol-1-yl)-ethylamino]-pyrimidin-4-yl}-phenylamino)-acetic acid methyl ester To a solution of (2-ethoxy-4-{6-[2-(7-fluoro-4-methoxy-2-methyl-indol-1-yl)-ethylamino]-pyrimidin-4-yl}-phenylamino)-acetic acid (Example 811, 20 mg, 0.0392 mmol) in MeOH (1 mL) is added dropwise HCl 4N in dioxane (0.07 mL, 0.274 mmol) and the mixture is stirred at RT for 48 h. The crude mixture is purified by prep HPLC (acidic conditions) affording the title compound as a ochre solid (14 mg, 70%). LC-MS A: $t_R$=0.80 min; [M+H]+=508.19.

Example 1043: 5-{6-[2-(2-Cyano-7-fluoro-4-methoxy-indol-1-yl)-ethylamino]-pyrimidin-4-yl}-3-ethoxy-thiophene-2-carboxylic acid carboxymethyl ester To a solution of 5-{6-[2-(2-cyano-7-fluoro-4-methoxy-indol-1-yl)-ethylamino]-pyrimidin-4-yl}-3-ethoxy-thiophene-2-carboxylic acid (Example 805, 50 mg, 0.104 mmol) in DMF (2 mL) is added K2CO3 (43 mg, 0.312 mmol) and methyl bromoacetate (0.0197 mL, 0.208 mmol). The mixture is stirred overnight at RT, then treated with NaOH 1N (0.104 mL, 0.104 mmol) and stirred at RT for 30 min. The crude mixture is filtered over a 0.45 m filter and purified by prep HPLC (basic conditions) affording the title compound as a white solid (16 mg, 28%). LC-MS A: $t_R$ 0.81 min; [M+H]+=540.07.

Example 1044: 5-{6-[2-(2-Cyano-7-fluoro-4-methoxy-indol-1-yl)-ethylamino]-pyrimidin-4-yl}-3-ethoxy-thiophene-2-carboxylic acid dimethylcarbamoylmethyl ester To a solution of 5-{6-[2-(2-cyano-7-fluoro-4-methoxy-indol-1-yl)-ethylamino]-pyrimidin-4-yl}-3-ethoxy-thiophene-2-carboxylic acid (Example 805, 50 mg, 0.104 mmol) in DMF dry (2 mL) is added K2CO3 (43 mg, 0.312 mmol) and a catalytic amount of KI, then 2-chloro-N,N-dimethyl-acetamide (0.0214 mL, 0.208 mmol) is added and the mixture is stirred overnight at 30° C. The crude mixture is filtered over a 0.45 µm filter and purified by prep HPLC (basic conditions) affording the title compound as a yellow solid (34 mg, 58%). LC-MS A: $t_R$=0.82 min; [M+H]+=567.11.

Following the method described for Example 1044, compounds of Examples 1045-1047 listed in Table 14 below are prepared, using the appropriate alkylating agent.

TABLE 14

Examples 1045-1047

| Ex. | Compound | $t_R$ [min] (LC-MS) | MS Data m/z [M + H]+ |
|---|---|---|---|
| 1045 | 5-{6-[2-(2-Cyano-7-fluoro-4-methoxy-indol-1-yl)-ethylamino]-pyrimidin-4-yl}-3-ethoxy-thiophene-2-carboxylic acid butyryloxymethyl ester | 0.97 (A) | 582.11 |
| 1046 | 5-{6-[2-(2-Cyano-7-fluoro-4-methoxy-indol-1-yl)-ethylamino]-pyrimidin-4-yl}-3-ethoxy-thiophene-2-carboxylic acid ethoxycarbonyloxymethyl ester | 0.94 (A) | 584.16 |
| 1047 | 5-{6-[2-(2-Cyano-7-fluoro-4-methoxy-indol-1-yl)-ethylamino]-pyrimidin-4-yl}-3-ethoxy-thiophene-2-carboxylic acid 5-methyl-2-oxo-[1,3]dioxol-4-ylmethyl ester | 0.92 (A) | 593.97 |

Example 1048: 5-{6-[2-(2-Cyano-7-fluoro-4-methoxy-indol-1-yl)-ethylamino]-pyrimidin-4-yl}-3-ethoxy-thiophene-2-carboxylic acid 2-dimethylamino-ethyl ester To a solution of 5-{6-[2-(2-cyano-7-fluoro-4-methoxy-indol-1-yl)-ethylamino]-pyrimidin-4-yl}-3-ethoxy-thiophene-2-carboxylic acid (Example 805, 50 mg, 0.104 mmol) in MeCN (2 mL) are added N-(3-dimethylaminopropyl)-N'-ethylcarbodiimide hydrochloride (30.2 mg, 0.156 mmol), 4-(dimethylamino)pyridine (25.6 mg, 0.208 mmol) and 2-dimethylaminoethanol (0.032 mL, 0.312 mmol). The RM is stirred at RT overnight. The crude mixture is filtered over a 0.45 m filter and purified by prep HPLC (basic conditions) affording the title compound as a beige solid (25 mg, 44%). LC-MS A: $t_R$=0.72 min; [M+H]+=553.18.

Example 1049: 5-{6-[2-(2-Cyano-7-fluoro-4-methoxy-indol-1-yl)-ethylamino]-pyrimidin-4-yl}-3-ethoxy-thiophene-2-carboxylic acid phenyl ester Following the method described for example 1048, using phenol, the title compound is obtained as a white solid. LC-MS A: $t_R$=0.99 min; [M+H]+=558.10.

Example 1050: (4-{6-[2-(2-Cyano-7-fluoro-4-methoxy-indol-1-yl)-ethylamino]-pyrimidin-4-yl}-2-methoxy-phenyl)-propynoic acid ethyl ester To a solution of 4-(6-((2-(2-cyano-7-fluoro-4-methoxy-1H-indol-1-yl)ethyl)amino)pyrimidin-4-yl)-2-methoxyphenyl trifluoromethanesulfonate (30 mg, 0.053 mmol) in DMSO (0.7 mL) at RT under argon is added ethyl propiolate (0.00814 mL, 0.0796 mmol) followed by TEA (0.0222 mL, 0.159 mmol), copper iodide (1.01 mg, 0.0053 mmol), tetrakis-(triphenylphosphine)-palladium (1.84 mg, 0.00159 mmol) and LiCl (0.5 M solution in THF, 0.318 mL, 0.159 mmol). The RM is stirred at 100° C. for 1 h by MW. Ethyl propiolate (0.00814 mL, 0.0796 mmol), TEA (0.0222 mL, 0.159 mmol), copper iodide (1.01 mg, 0.0053 mmol), tetrakis-(triphenylphosphine)-palladium (1.84 mg, 0.00159 mmol) and lithium chloride (0.5 M solution in THF, 0.318 mL, 0.159 mmol) are added and the RM is heated for 2 h at 100° C. under MW. It is filtered through a pad of celite and concentrated. The crude is diluted with EtOAc and extracted with water, purified by prep.HPLC basic conditions to afford the title compound as a pale-yellow solid (3 mg, 11%). LC-MS A: $t_R$=0.87 min; [M+H]+=513.6.

a) 4-(6-((2-(2-Cyano-7-fluoro-4-methoxy-1H-indol-1-yl)ethyl)amino)pyrimidin-4-yl)-2-methoxyphenyl trifluoromethanesulfonate 7-Fluoro-1-(2-((6-(4-hydroxy-3-methoxyphenyl)pyrimidin-4-yl)amino)ethyl)-4-methoxy-1H-indole-2-carbonitrile (110 mg, 0.254 mmol) and N-Phenyl-bis(trifluoromethanesulfonimide) (97 mg, 0.266 mmol) in DCM (1.75 mL) are cooled down to 0° C. and TEA (0.0392 mL, 0.279 mmol) is added. The mixture is stirred at 0° C. for 30 min then allowed to reach RT and stirred overnight. NaOH 1N is added and the RM is extracted with DCM then dried over MgSO$_4$ and concentrated under vacuum. Purification by FC (Hept:EtOAc) afforded the title compound as a white solid (100 mg, 70%). LC-MS A: $t_R$=0.89 min; [M+H]+=565.99.

b) 7-Fluoro-1-(2-((6-(4-hydroxy-3-methoxyphenyl)pyrimidin-4-yl)amino)ethyl)-4-methoxy-1H-indole-2-carbonitrile Following the general procedure A with A.1.68 and 4-hydroxy-3-methoxyphenyl boronic acid, the title compound is obtained as a white solid. LC-MS A: $t_R$=0.70 min; [M+H]+=434.03.

Example 1051: {6-[4-Ethoxy-5-(1H-tetrazol-5-yl)-thiophen-2-yl]-pyrimidin-4-yl}-[2-(7-fluoro-4-methoxy-2-methyl-indol-1-yl)-ethyl]-amine To a solution of 6-(4-ethoxy-5-(1H-tetrazol-5-yl)thiophen-2-yl)pyrimidin-4-ol (11.5 mg, 0.0396 mmol) in MeCN (0.4 mL), BOP (23.2 mg, 0.0515 mmol) and DBU (0.00906 mL, 0.0594 mmol) are sequentially added and the RM is stirred at RT for 20 min. 2-(7-Fluoro-4-methoxy-2-methyl-1H-indol-1-yl)ethan-1-amine (A.1.25.1; 10.5 mg, 0.047 mmol) was added and the RM is stirred at 60° C. for 60 h. Purification of the crude mixture by prep.-HPLC (basic conditions) afforded the title compound as a yellow solid (3 mg, 11%). LC-MS A: $t_R$=0.83 min; [M+H]+=495.02.

a) 6-(4-Ethoxy-5-(1H-tetrazol-5-yl)thiophen-2-yl)pyrimidin-4-ol 4-(4-Ethoxy-5-(1H-tetrazol-5-yl)thiophen-2-yl)-6-methoxypyrimidine (30 mg, 0.0986 mmol) is treated with HCl 4M in dioxane (0.5 mL) and the RM is stirred at 55-60° C. overnight. It is then concentrated under reduced pressure and purified by prep.-HPLC (acidic conditions) to afford the title compound as a white solid (12 mg, 42%). LC-MS A: $t_R$=0.59 min; [M+H]+=291.04.

b) 4-(4-Ethoxy-5-(1H-tetrazol-5-yl)thiophen-2-yl)-6-methoxypyrimidine

To a solution of 3-ethoxy-5-(6-methoxypyrimidin-4-yl)thiophene-2-carbonitrile (72 mg, 0.276 mmol) in toluene (2.1 mL), trimethylsilylazide (0.0544 mL, 0.413 mmol) and dibutyltin oxide (6.86 mg, 0.0276 mmol) are added. The RM is stirred at 110° C. overnight in a sealed tube. The solvent is evaporated, then the residue is dissolved in MeOH and adjusted to pH=10 with NaOH 2M. The solution is loaded onto a PE_AX cartridge for standard catch & release protocol, which afforded the title compound as a yellow solid (43 mg, 51%). LC-MS A: $t_R$=0.78 min; [M+H]+=305.06.

c) 3-Ethoxy-5-(6-methoxypyrimidin-4-yl)thiophene-2-carbonitrile

Following the procedure described for A.1.64.3, with 3-ethoxy-5-(6-methoxypyrimidin-4-yl)thiophene-2-carboxamide, the title compound is obtained as a white solid. LC-MS A: $t_R$=0.91 min; [M+H]+=262.14.

d) 3-Ethoxy-5-(6-methoxypyrimidin-4-yl)thiophene-2-carboxamide

Following the procedure described for A.1.64.4, with 3-ethoxy-5-(6-methoxypyrimidin-4-yl)thiophene-2-carboxylic acid, the title compound is obtained as a white solid. LC-MS A: $t_R$=0.73 min; [M+H]+=280.14.

e) 3-Ethoxy-5-(6-methoxypyrimidin-4-yl)thiophene-2-carboxylic acid

A mixture of 4-chloro-6-methoxypyrimidine (712 mg, 4.83 mmol), A.1.68. (300 mg, 1.01 mmol) and potassium phosphate tribasic monohydrate (695 mg, 3.02 mmol) in DMF (5 mL) and water (0.109 mL, 6.04 mmol) is degassed during 15 min. Then dichloro(1,1'-bis(diphenylphosphino) ferrocene) palladium (II) dichloromethane adduct) (82.2 mg, 0.101 mmol) is added and the solution is stirred overnight at rt. The RM is partitioned between sat. aq. NaHCO$_3$ and EtOAc. The aqueous layer is washed twice with EtOAc, then it is adjusted to pH=1 with HCl 2M and extracted once with AcOEt. This last organic layer is further washed (3×) with brine, dried (MgSO$_4$), filtered and concentrated. The residue is purified by FC (Hept to Hept/EtOAc 1:1) to give the title compound as a yellow solid (0.054 g, 19%). LC-MS A: $t_R$=0.71 min; [M+H]+=280.96.

Example 1052: 3-Ethoxy-5-{6-[2-(7-fluoro-4-methoxy-2-methyl-indol-1-yl)-ethylamino]-pyrimidin-4-yl}-N-hydroxy-thiophene-2-carboxamidine A suspension of 3-ethoxy-5-(6-((2-(7-fluoro-4-methoxy-2-methyl-1H-indol-1-yl)ethyl)amino)pyrimidin-4-yl)thiophene-2-carbonitrile (50 mg, 0.111 mmol), hydroxylamine hydrochloride (15.5 mg, 0.221 mmol) and NaHCO$_3$ (23.3 mg, 0.277 mmol) in water (0.025 mL) and EtOH (0.45 mL) is stirred in a sealed tube at 90° C. for 2 h. Once at rt, the RM is diluted with water and extracted with EtOAc. The organic layer is then washed twice with brine, dried over MgSO$_4$, filtered and concentrated. The residue is purified by FC (hept/EtOAc 2:8) to yield the title compound as a yellow solid (20 mg, 37%). LC-MS A: $t_R$=0.71 min; [M+H]+=485.04.

a) 3-Ethoxy-5-(6-((2-(7-fluoro-4-methoxy-2-methyl-1H-indol-1-yl)ethyl)amino)pyrimidin-4-yl)thiophene-2-carbonitrile A mixture of 5-(6-chloropyrimidin-4-yl)-3-ethoxythiophene-2-carbonitrile (78 mg, 0.294 mmol), 2-(7-fluoro-4-methoxy-2-methyl-1H-indol-1-yl)ethan-1-amine (A.1.25.1; 65.2 mg, 0.294 mmol) and TEA (0.123 mL, 0.881 mmol) in iPrOH (1 mL) is stirred at 90° C. overnight. The suspension is diluted with water and the solid is filtered off, washing with water, and then dried under high vacuum, affording the title compound as a yellow solid (106 mg, 80%). LC-MS A: $t_R$=0.97 min; [M+H]+=452.11.

b) 5-(6-Chloropyrimidin-4-yl)-3-ethoxythiophene-2-carbonitrile

Following the procedure described for A.1.64.3, with 5-(6-chloropyrimidin-4-yl)-3-ethoxythiophene-2-carboxamide, the title compound is obtained as a white solid. LC-MS A: $t_R$=0.92 min; [M+H]+=266.01.

c) 5-(6-Chloropyrimidin-4-yl)-3-ethoxythiophene-2-carboxamide

Following the procedure described for A.1.64.4, with 5-(6-chloropyrimidin-4-yl)-3-ethoxythiophene-2-carboxylic acid, the title compound is obtained as a yellow solid. LC-MS A: $t_R$=0.75 min; [M+H]+=284.06.

d) 5-(6-Chloropyrimidin-4-yl)-3-ethoxythiophene-2-carboxylic acid

Following the procedure described for example 1051 e), with 4,6-dichloropyrimidine, the title compound is obtained as a orange solid. LC-MS A: $t_R$=0.75 min; [M+H]+=285.05.

Example 1053: 1-(3-Ethoxy-5-{6-[2-(7-fluoro-4-methoxy-2-methyl-indol-1-yl)-ethylamino]-pyrimidin-4-yl}-thiophen-2-yl)-ethanol Sodium borohydride (4 mg, 0.106 mmol) is added at rt to a solution of 1-(3-ethoxy-5-(6-((2-(7-fluoro-4-methoxy-2-methyl-1H-indol-1-yl)ethyl)amino)pyrimidin-4-yl)thiophen-2-yl)ethan-1-one (8 mg, 0.0171 mmol) in EtOH (0.5 mL), and the RM is stirred at rt for 3 h, then quenched by dropwise addition of acetone and concentrated under reduced pressure. The residue is purified by FC (hept→hept/AcOEt 1:1) to yield the title compound as a white solid (4.5 mg, 56%). LC-MS A: $t_R$=0.76 min; [M+H]+=471.06.

a) 1-(3-Ethoxy-5-(6-((2-(7-fluoro-4-methoxy-2-methyl-1H-indol-1-yl)ethyl)amino)pyrimidin-4-yl)thiophen-2-yl)ethan-1-one Following the procedure described for Example 1051, using 1-(3-ethoxy-5-(6-hydroxypyrimidin-4-yl)thiophen-2-yl)ethan-1-one the title compound as a orange solid. LC-MS A: $t_R$=0.90 min; [M+H]+=469.09.

b) 1-(3-Ethoxy-5-(6-hydroxypyrimidin-4-yl)thiophen-2-yl)ethan-1-one

Following the procedure described for Example 1051a, with 1-(3-ethoxy-5-(6-methoxypyrimidin-4-yl)thiophen-2-yl)ethan-1-one, the title compound is obtained as a beige solid. LC-MS A: $t_R$=0.67 min; [M+H]+=275.15.

c) 1-(3-Ethoxy-5-(6-methoxypyrimidin-4-yl)thiophen-2-yl)ethan-1-one

To a solution of 3-ethoxy-5-(6-methoxypyrimidin-4-yl)thiophene-2-carbonitrile (Example 1051c; 317 mg, 1.21 mmol) in THF (7.0 mL), methylmagnesium bromide (3M in THF, 1.4 mL, 4.25 mmol) is added dropwise at 0° C., then the RM is stirred at rt overnight. The mixture is quenched at 0° C. with 2 N aqueous HCl and stirred at rt overnight. The biphasic mixture is adjusted to pH 10-11 with 5% aqueous NaOH and extracted with EtOAc. The organic phase is washed with brine (2×), dried over anhydrous MgSO$_4$, filtered and concentrated. The residue is purified by FC (hept→hept/AcOEt 1:1) to afford the expected product as a yellow solid (123 mg, 36%). LC-MS A: $t_R$=0.88 min; [M+H]+=279.15.

Example 1054: 3-(3-Ethoxy-5-{6-[2-(7-fluoro-4-methoxy-2-methyl-indol-1-yl)-ethylamino]-pyrimidin-4-yl}-thiophen-2-yl)-[1,2,4]oxadiazol-5(4H)-one A solution of 3-ethoxy-5-{6-[2-(7-fluoro-4-methoxy-2-methyl-indol-1-yl)-ethylamino]-pyrimidin-4-yl}-N-hydroxy-thiophene-2-carboxamidine (Example 1052; 18 mg, 0.0371 mmol), 1,1'-carbonyldiimidazole (9.04 mg, 0.0557 mmol) and DBU (0.01 mL, 0.0656 mmol) in dioxane (0.3 mL) is stirred at 90° C. for 3 h. Once at RT, the RM is diluted with DCM and washed with HCl 2M. The organic layer is separated through phase-separator cartridge and concentrated under reduced pressure. Purification by prep HPLC (basic conditions) afforded the title compound as a light yellow solid (7.6 mg, 40%). LC-MS A: $t_R$=0.87 min; [M+H]+=510.97.

Example 1055: 7-Fluoro-1-(2-{6-[5-(3-fluoro-oxetan-3-yl)-thiophen-2-yl]-pyrimidin-4-ylamino}-ethyl)-4-methoxy-1H-indole-2-carbonitrile Diethylaminosulfur trifluoride (0.01 mL, 0.0734 mmol) is added at −78° C. to a stirred suspension of 7-fluoro-1-(2-{6-[5-(3-hydroxy-oxetan-3-yl)-thiophen-2-yl]-pyrimidin-4-ylamino}-ethyl)-4-methoxy-1H-indole-2-carbonitrile (6 mg, 0.0129 mmol) in DCM (0.2 mL). The RM is stirred at −78° C. for 50 min, then allowed to warm to RT and quenched with MeOH. The RM is concentrated, and the residue is purified by FC (Hept→Hept/EtOAc 6:4) to yield the title compound as a white powder (5.5 mg, 91%). LC-MS A: $t_R$=0.82 min; [M+H]+=468.04.

a) 7-Fluoro-1-(2-{6-[5-(3-hydroxy-oxetan-3-yl)-thiophen-2-yl]-pyrimidin-4-ylamino}-ethyl)-4-methoxy-1H-indole-2-carbonitrile Following the general procedure A, using 1-(2-((6-chloropyrimidin-4-yl)amino)ethyl)-7-fluoro-4-methoxy- 1H-indole-2-carbonitrile (A.1.68.) and 3-(5-(4,4,5,5-tetramethyl-1,3,2-dioxaborolan-2-yl)thiophen-2-yl)oxetan-3-ol (A.2.135.), the title compound as a orange solid. LC-MS A: $t_R$=0.90 min; [M+H]+=469.09.

Example 1056: (4-{6-[2-(2-Cyano-7-fluoro-4-methoxy-indol-1-yl)-ethylamino]-pyrimidin-4-yl}-phenyl)-methyl-carbamic acid methyl ester A mixture of methyl (4-(6-((tert-butoxycarbonyl)(2-(2-cyano-7-fluoro-4-methoxy-1H-indol-1-yl)ethyl)amino)pyrimidin-4-yl)phenyl)(methyl)carbamate (36 mg, 0.0807 mmol) in HCl 4N in dioxane (0.75 mL, 2.6 mmol) is stirred at RT for 50 h. The solvent is evaporated under reduced pressure. The residue is partioned between DCM and sat.aq. NaHCO$_3$. The organic layer is separated and the aqueous layer is extracted with DCM. The combined organic layers are dried over MgSO$_4$ and concentrated under reduced pressure. The residue is purified by prep HPLC (basic conditions), affording the title compound as a white powder (17 mg, 45% yield). LC-MS A: $t_R$=0.74 min; [M+H]+=475.07.

a) Methyl (4-(6-((tert-butoxycarbonyl)(2-(2-cyano-7-fluoro-4-methoxy-1H-indol-1-yl)ethyl)amino)pyrimidin-4-yl)phenyl)(methyl)carbamate Following the procedure described for A.1.68.1, using methyl (4-(6-chloropyrimidin-4-yl)phenyl)(methyl)carbamate and tert-butyl (2-(2-cyano-7-fluoro-4-methoxy-1H-indol-1-yl)ethyl)carbamate (A.1.68.2), the title compound is obtained as a light yellow solid. LC-MS A: $t_R$=1.07 min; [M+H]+=575.09.

b) Methyl (4-(6-chloropyrimidin-4-yl)phenyl)(methyl)carbamate

To a solution of 4-(6-chloropyrimidin-4-yl)-N-methylaniline (86.1 mg, 0.361 mmol) in DCM (3.1 mL) are added DIPEA (0.189 mL, 1.08 mmol) and methyl chloroformate (0.0338 mL, 0.433 mmol). The RM is stirred at RT for 45 min, then partitioned between water (5 ml) and DCM (5 ml). The organic layer is separated, dried over MgSO$_4$, filtered, and concentrated to dryness. The residue is purified by FC (Heptane-EtOAc 7:3) to obtain the title product as a white solid (100 mg, quant.). LC-MS A: $t_R$=0.83 min; [M+H]+=278.13.

c) 4-(6-Chloropyrimidin-4-yl)-N-methylaniline

Following the general procedure A, using 4,6-dichloropyrimidine and 4-(methylamino)phenylboronic acid pinacol ester, the title compound is obtained as a yellow solid. LC-MS A: $t_R$=0.81 min; [M+H]+=220.15.

Example 1057: 5-{6-[2-(3,7-Difluoro-4-methoxy-2-methyl-indol-1-yl)-ethylamino]-pyrimidin-4-yl}-3-ethoxy-thiophene-2-carboxylic acid A mixture of 2-(3,7-difluoro-4-methoxy-2-methyl-1H-indol-1-yl)ethan-1-amine (48 mg, 0.169 mmol), 5-(6-chloropyrimidin-4-yl)-3-ethoxythiophene-2-carboxylic acid (Example 1052-d; 81 mg, 0.34 mmol) and TEA (0.117 mL, 0.843 mmol) in iPrOH (1.7 mL) is stirred at 90° C. for 2 days. The RM is concentrated and purified by prep-HPLC (basic conditions) to afford the title compound is obtained as a yellow solid (13.5 mg, LC-MS A: $t_R$=0.79 min; [M+H]+=488.80.

a) 2-(3,7-Difluoro-4-methoxy-2-methyl-1H-indol-1-yl)ethan-1-amine

Following the procedure described for A.1.1.1, using 3,7-difluoro-4-methoxy-2-methyl-1H-indole, the title compound is obtained as an orange oil. LC-MS A: $t_R$=0.58 min; [M+MeCN]$^+$=282.02.

b) 3,7-Difluoro-4-methoxy-2-methyl-1H-indole

To a solution of 3,7-difluoro-4-methoxy-2-methyl-1-(phenylsulfonyl)-1H-indole (112 mg, 0.332 mmol) in THF (3 mL) is added tetrabutylammonium fluoride (1N in THF, 0.5 mL, 0.498 mmol). The RM is refluxed for 6 h, then cooled to RT, diluted with EtOAc (10 mL), washed with saturated aqueous NaHCO$_3$ (10 mL) and brine, dried over MgSO$_4$, filtered and concentrated to dryness. The crude is purified by FC (EtOAc-Hept 0:1 to 1:9) to afford the title compound as a brown oil (49 mg, 75%). LC-MS A: $t_R$=0.82 min; no ionization.

c) 3,7-Difluoro-4-methoxy-2-methyl-1-(phenylsulfonyl)-1H-indole

Following the procedure described for A.1.66.3, using 3,7-difluoro-4-methoxy-1-(phenylsulfonyl)-1H-indole, the title compound is obtained as a brown solid. LC-MS A: $t_R$=0.96 min; [M+H]+=337.90.

d) 3,7-Difluoro-4-methoxy-1-(phenylsulfonyl)-1H-indole

To an ice-chilled solution of 7-fluoro-4-methoxyindoline-2,3-dione (Example 776-f; 476 mg, 2.19 mmol) in THF (20 mL) is added dropwise borane THF complex (solution 1N in THF, 8 mL, 8.11 mmol). The RM is stirred at 0° C. for 1 h and then at RT overnight. HCl 1N is added dropwise until pH 2. The RM is then neutralized with NaOH 2N. EtOAc is added and the two layers are decanted. The aqueous layer is extracted once more with EtOAc. The combined organic layers are washed twice with water, dried over MgSO$_4$, filtered and concentrated under reduced pressure. The crude mixture is purified by FC (EtOAc-Hept 0:1 to 1:4) to afford the title compound as a green oil (342 mg, 85%). LC-MS A: $t_R$=0.78 min; no ionization.

Example 1058: 5-{6-[2-(3,7-Difluoro-4-methoxy-2-methyl-indol-1-yl)-ethylamino]-pyrimidin-4-yl}-3-trifluoromethyl-thiophene-2-carboxylic acid Following the procedure described for Example 1057, using 5-(6-chloropyrimidin-4-yl)-3-(trifluoromethyl)thiophene-2-carboxylic acid, the title compound is obtained as a light orange solid. LC-MS A: $t_R$=0.89 min; [M+H]+=512.90.

a) 5-(6-Chloropyrimidin-4-yl)-3-(trifluoromethyl)thiophene-2-carboxylic acid

Following the general procedure A, using 4,6-dichloropyrimidine and 5-(4,4,5,5-Tetramethyl-1,3,2-dioxaborolan-2-yl)-3-(trifluoromethyl)thiophene-2-carboxylic acid (A.2.68.), the title compound is obtained as a beige solid. LC-MS A: $t_R$=0.83 min; [M+MeCN]$^+$= 349.91.

Example 1059: 5-{6-[2-(2-Cyano-3,7-difluoro-4-methoxy-indol-1-yl)-ethylamino]-pyrimidin-4-yl}-3-trifluoromethyl-thiophene-2-carboxylic acid Following the procedure described for Example 1056, using 5-(6-((tert-butoxycarbonyl)(2-(2-cyano-3,7-difluoro-4-methoxy-1H-indol-1-yl)ethyl)amino)pyrimidin-4-yl)-3-(trifluoromethyl)thiophene-2-carboxylic acid, the title compound is obtained as an off-white solid. LC-MS A: $t_R$=0.90 min; [M+H]+=523.93.

a) 5-(6-((Tert-butoxycarbonyl)(2-(2-cyano-3,7-difluoro-4-methoxy-1H-indol-1-yl)ethyl)amino)pyrimidin-4-yl)-3-(trifluoromethyl)thiophene-2-carboxylic acid Following the procedure described for Example 1056 a), using 5-(6-chloropyrimidin-4-yl)-3-(trifluoromethyl)thiophene-2-carboxylic acid (Example 1058 a) and tert-butyl (2-(2-cyano-3,7-difluoro-4-methoxy-1H-indol-1-yl)ethyl)carbamate, the title compound is obtained as a light yellow solid. LC-MS A: $t_R$-1.06 min; [M+H]+=623.97.

b) Tert-butyl (2-(2-cyano-3,7-difluoro-4-methoxy-1H-indol-1-yl)ethyl)carbamate

Following the procedure described for A.1.64.2, using 3,7-difluoro-4-methoxy-1H-indole-2-carbonitrile, the title compound is obtained as a beige solid. LC-MS A: $t_R$=0.93 min; [M+H]+=352.09.

c) 3,7-Difluoro-4-methoxy-1H-indole-2-carbonitrile

Following the procedure described for Example 1057 b), using 3,7-difluoro-4-methoxy-1-(phenylsulfonyl)-1H-indole-2-carbonitrile, the title compound is obtained as a white solid. LC-MS A: $t_R$=0.83 min; no ionization.

d) 3,7-Difluoro-4-methoxy-1-(phenylsulfonyl)-1H-indole-2-carbonitrile

Following the procedure described for A.1.64.3, using 3,7-difluoro-4-methoxy-1-(phenylsulfonyl)-1H-indole-2-carboxamide, the title compound is obtained as a yellow solid. LC-MS A: $t_R$=0.95 min; no ionization.

e) 3,7-Difluoro-4-methoxy-1-(phenylsulfonyl)-1H-indole-2-carboxamide

Following the procedure described for A.1.64.4, using 3,7-difluoro-4-methoxy-1-(phenylsulfonyl)-1H-indole-2-carboxylic acid, the title compound is obtained as a light pink solid. LC-MS A: $t_R$=0.80 min; [M+H]+= 367.02.

f) 3,7-Difluoro-4-methoxy-1-(phenylsulfonyl)-1H-indole-2-carboxylic acid n-Butyllithium (1.6 M in hexanes, 3.06 mL, 4.89 mmol) is added dropwise to a −78° C. solution of 3,7-difluoro-4-methoxy-1-(phenylsulfonyl)-1H-indole (Example 1057 d), 1357 mg, 4.07 mmol) in THF (39 mL) and the RM is stirred at this temperature for 30 min. Then an excess of dry CO2 gas is added. Bubbling is continued for 25 min at −78° C. Then the cooling bath is removed and the mixture is slowly warmed to rt over 30 min. The mixture is concentrated to dryness. The white solid obtained is dissolved in water (75 mL) and the aqueous solution washed with EtOAc (75 mL). The aqueous layer is acidified (to pH=1) with 2N HCl. It is then extracted twice with EtOAc (2×30 mL). The combined last organic layers are dried over MgSO$_4$, filtered and concentrated to dryness to obtain the title compound as a light green solid (1.5 g, quant.) LC-MS A: $t_R$=0.84 min; [M+H]+=368.01.

Example 1060: [2-(7-Fluoro-4-methoxy-2-methyl-indol-1-yl)-ethyl]-{6-[5-(2H-tetrazol-5-yl)-4-trifluoromethyl-thiophen-2-yl]-pyrimidin-4-yl}-amine Following the procedure described for Example 1051-b, using 5-(6-((2-(7-fluoro-4-methoxy-2-methyl-1H-indol-1-yl)ethyl)amino)pyrimidin-4-yl)-3-(trifluoromethyl)thiophene-2-carbonitrile, the title compound is obtained as a light brown solid. LC-MS A: $t_R$=0.86 min; [M+H]+=519.04.

a) 5-(6-((2-(7-Fluoro-4-methoxy-2-methyl-1H-indol-1-yl)ethyl)amino)pyrimidin-4-yl)-3-(trifluoromethyl) thiophene-2-carbonitrile A mixture of 5-(6-chloropyrimidin-4-yl)-3-(trifluoromethyl)thiophene-2-carbonitrile (205 mg, 0.708 mmol), 2-(7-fluoro-4-methoxy-2-methyl-1H-indol-1-yl)ethan-1-amine (A.1.25.1., 157 mg, 0.708 mmol) and TEA (0.296 mL, 2.12 mmol, 3 eq) in iPrOH (2.4 mL) is stirred at 90° C. overnight. It is then diluted with EtOAc, washed twice with HCl 1M (pH 1) and once with brine. The organic layer is dried over MgSO$_4$, filtered and concentrated. The residue is triturated in MeOH+Et2O to afford the desired product as a yellow solid (201 mg, 60%). LC-MS A: $t_R$=1.01 min; [M+H]+= 476.01.

b) 5-(6-Chloropyrimidin-4-yl)-3-(trifluoromethyl) thiophene-2-carbonitrile

Following the procedure described for A.1.64.3., using 5-(6-chloropyrimidin-4-yl)-3-(trifluoromethyl)thiophene-2-carboxamide, the title compound is obtained as a white solid. LC-MS A: $t_R$=0.94 min; no ionization.

c) 5-(6-Chloropyrimidin-4-yl)-3-(trifluoromethyl) thiophene-2-carboxamide

Following the procedure described for A.1.64.4., using 5-(6-chloropyrimidin-4-yl)-3-(trifluoromethyl)thiophene-2-carboxylic acid (Example 1058-a), the title compound is obtained as a white solid. LC-MS A: $t_R$=0.75 min; [M+H]+=307.97.

Example 1061: 5-{6-[2-(7-Fluoro-4-methoxy-2-methyl-indol-1-yl)-ethylamino]-pyrimidin-4-yl}-N-hydroxy-3-trifluoromethyl-thiophene-2-carboxamidine Following the procedure described for Example 1052, using 5-(6-((2-(7-fluoro-4-methoxy-2-methyl-1H-indol-1-yl)ethyl)amino)pyrimidin-4-yl)-3-(trifluoromethyl)thiophene-2-carbonitrile (Example 1060-a), the title compound is obtained as a white solid. LC-MS A: $t_R$=0.81 min; [M+H]+=509.03.

Example 1062: 3-(5-{6-[2-(7-Fluoro-4-methoxy-2-methyl-indol-1-yl)-ethylamino]-pyrimidin-4-yl}-3-trifluoromethyl-thiophen-2-yl)-[1,2,4]oxadiazol-5(4H)-one Following the procedure described for Example 1054, using 5-(6-((2-(7-fluoro-4-methoxy-2-methyl-1H-indol-1-yl)ethyl)amino)pyrimidin-4-yl)-3-(trifluoromethyl)thiophene-2-carbonitrile (Example 1060-a), the title compound is obtained as a light yellow solid. LC-MS A: $t_R$=0.91 min; [M+H]+=535.07.

Example 1063: 4-{6-[2-(2-Cyano-7-fluoro-4-methoxy-indol-1-yl)-ethylamino]-pyrimidin-4-yl}-2-ethoxy-N-hydroxy-benzamide Following the procedure described for Example 1023, using 4-(6-((2-(2-cyano-7-fluoro-4-methoxy-1H-indol-1-yl)ethyl)amino)pyrimidin-4-yl)-2-ethoxybenzoic acid (Example 807), the title compound is obtained as a white solid. LC-MS A: $t_R$=0.74 min; [M+H]+=491.18.

Example 1064: 1-{2-[6-(1,4-Dioxo-1,2,3,4-tetrahydro-phthalazin-6-yl)-pyrimidin-4-ylamino]-ethyl}-7-fluoro-4-methoxy-1H-indole-2-carbonitrile 4-{6-[2-(2-Cyano-7-fluoro-4-methoxy-indol-1-yl)-ethylamino]-pyrimidin-4-yl}-phthalic acid 2-ethyl ester (Example 965, 51.3 mg, 0.105 mmol) s suspended in DMF (0.6 mL) and hydrazine monohydrate (0.00814 mL, 0.21 mmol) is added. The RM is stirred at 100° C. for 2 h, then diluted with 0.4 mL DMF and purified by prep.HPLC (basic conditions), to obtain the title compound as a yellow solid (29 mg, 59%). LC-MS A: $t_R$=0.66 min; [M+H]+=472.06.

Example 1065: 5-(3-Ethoxy-5-{6-[2-(7-fluoro-4-methoxy-2-methyl-indol-1-yl)-ethylamino]-pyrimidin-4-yl}-thiophen-2-yl)-isoxazol-3-ol p-Toluenesulfonic acid monohydrate (3.29 mg, 0.0188 mmol) is added at RT to a solution of 3-(3-ethoxy-5-(6-((2-(7-fluoro-4-methoxy-2-methyl-1H-indol-1-yl)ethyl)amino)pyrimidin-4-yl)thiophen-2-yl)-3-oxo-N-((tetrahydro-2H-pyran-2-yl)oxy)propanamide (11.5 mg, 0.0188 mmol) in MeOH (0.3 mL). The RM is stirred at RT overnight, and at 55° C. for 1 d. It is purified by prep.-HPLC (acidic conditions) to obtain the product as a beige solid (1.4 mg, 15%). LC-MS A: $t_R$=0.79 min; [M+H]+=509.92.

a) 3-(3-Ethoxy-5-(6-((2-(7-fluoro-4-methoxy-2-methyl-1H-indol-1-yl)ethyl)amino)pyrimidin-4-yl)thiophen-2-yl)-3-oxo-N-((tetrahydro-2H-pyran-2-yl)oxy)propanamide To a solution of ethyl 3-(3-ethoxy-5-(6-((2-(7-fluoro-4-methoxy-2-methyl-1H-indol-1-yl)ethyl)amino)pyrimidin-4-yl)thiophen-2-yl)-3-oxopropanoate (100 mg, 0.185 mmol) in NMP (1.6 mL), O-(tetrahydro-2H-pyran-2-yl)hydroxylamine (45.1 mg, 0.37 mmol) and DMAP (22.6 mg, 0.185 mmol) are sequentially added at RT. The RM is then stirred at 85° C. in a sealed tube for 60 h. Once at RT, the RM is partitioned between HCl 0.5M and EtOAc. The organic layer is washed with brine, dried over MgSO$_4$, filtered and concentrated. The residue is purified by FC (Hept to Hept/EtOAc 1:9) yielding the title compound as a light yellow solid (32 mg, 38%). LC-MS A: $t_R$=0.84 min; [M+H]+=612.15.

b) Ethyl 3-(3-ethoxy-5-(6-((2-(7-fluoro-4-methoxy-2-methyl-1H-indol-1-yl)ethyl)amino)pyrimidin-4-yl)thiophen-2-yl)-3-oxopropanoate To a solution of 3-ethoxy-5-{6-[2-(7-fluoro-4-methoxy-2-methyl-indol-1-yl)-ethylamino]-pyrimidin-4-yl}-thiophene-2-carboxylic acid (Example 258, 100 mg, 0.213 mmol) in MeCN (2 mL) is added at RT CDI (35.5 mg, 0.213 mmol). The RM is stirred for 45 min. In parallel, a suspension of ethyl potassium malonate (76 mg, 0.446 mmol), magnesium chloride (50.6 mg, 0.531 mmol) and TEA (0.0949 mL, 0.68 mmol) in MeCN (1 mL) is stirred for 40 min at RT under N2. The imidazolide suspension is then added to the malonate suspension, and the RM is stirred for 1 h 30 min at 70° C. It is then partitioned between EtOAc and 1 M HCl. The organic layer is washed with brine, dried over MgSO$_4$, filtered and evaporated to afford the title compound as an orange solid (103 mg, 90%). LC-MS A: $t_R$=0.93 min; [M+H]+=541.10.

Example 1066: 5-{6-[2-(7-Fluoro-4-methoxy-2-methyl-indol-1-yl)-ethylamino]-pyrimidin-4-yl}-3-pyridin-2-yl-thiophene-2-carboxylic acid Tris(dibenzylideneacetone)dipalladium(0) (1.7 mg, 0.00185 mmol) and XPhos (3.64 mg, 0.00741 mmol) are suspended in THF (1 mL) under argon. The RM is stirred 10 min at 65° C. At RT, methyl 3-chloro-5-(6-((2-(7-fluoro-4-methoxy-2-methyl-1H-indol-1-yl)ethyl)amino)pyrimidin-4-yl)thiophene-2-carboxylate (44 mg, 0.0926 mmol) is added and the RM is stirred 15 min at 65° C. then cooled to RT. 2-Pyridylzinc bromide (solution 0.5 M in THF, 0.278 mL, 0.139 mmol) is added dropwise and the RM is stirred 5 h at 65° C. The RM is filtered through a glassmicrofiber filter, washed with THF. The filtrate is concentrated then dissolved in DMF and purified by prep HPLC (basic conditions), to afford the title compound as a white solid (3 mg, 6%). LC-MS A: $t_R$=0.76 min; [M+H]+=504.15.

a) Methyl 3-chloro-5-(6-((2-(7-fluoro-4-methoxy-2-methyl-1H-indol-1-yl)ethyl)amino)pyrimidin-4-yl)thiophene-2-carboxylate A MW-vial is charged with 6-chloro-N-(2-(7-fluoro-4-methoxy-2-methyl-1H-indol-1-yl)ethyl)pyrimidin-4-amine (A.1.25., 100 mg, 0.299 mmol), 4-chloro-5-(methoxycarbonyl)thiophene-2-boronic acid (132 mg, 0.597 mmol), 2M Na2CO3 (0.45 mL, 0.896 mmol), and DME (2 mL). The RM is degassed with N2. [1,1'-bis(diphenylphosphino)ferrocene]dichloropalladium(II) complex with CH2Cl2 (24.4 mg, 0.0299 mmol) is added, the vial is capped, and heated at 70° C. o/n. The RM is filtered through a Glass MicroFiber filter from Whatman, washing with EtOAc, then washed with sat. aq. NaHCO$_3$. The aq. layer is re-extracted 2× with EtOAc. The combined organics are dried (MgSO$_4$) and concentrated under reduced pressure. The residue is purified by FC (H:EE 100:0 to 50:50) yielding the title compound as a beige powder (30 mg, 30%). LC-MS A: $t_R$=0.95 min; [M+H]+= 475.10.

Example 1067: [6-(4-Ethylamino-thiophen-2-yl)-pyrimidin-4-yl]-[2-(7-fluoro-4-methoxy-2-methyl-indol-1-yl)-ethyl]-amine Following the general procedure B, using 6-chloro-N-(2-(7-fluoro-4-methoxy-2-methyl-1H-indol-1-yl)ethyl)pyrimidin-4-amine (A.1.25.) and methyl 3-(N-ethyl-2,2,2-trifluoroacetamido)-5-(4,4,5,5-tetramethyl-1,3,2-dioxaborolan-2-yl)thiophene-2-carboxylate (A.2.157.), the title compound is obtained after spontaneous decarboxylation. LC-MS A: $t_R$=0.74 min; [M+H]+=426.19.

Following the method described for Example 1067, compounds of Examples 1068-1070 listed in Table 15 below are prepared, using the appropriate alkylating agent.

TABLE 15

Examples 1068-1070

| Ex. | Compound | $t_R$ [min] (LC-MS) | MS Data m/z [M + H]+ |
| --- | --- | --- | --- |
| 1068 | [6-(4-Ethylamino-thiophen-2-yl)-pyrimidin-4-yl]-[2-(7-fluoro-2,4-dimethyl-indol-1-yl)-ethyl]-amine | 0.74 (A) | 410.12 |
| 1069 | [6-(4-Ethylamino-thiophen-2-yl)-pyrimidin-4-yl]-[2-(6-fluoro-2,4-dimethyl-indol-1-yl)-ethyl]-amine | 0.74 (A) | 410.17 |
| 1070 | [6-(4-Ethylamino-thiophen-2-yl)-pyrimidin-4-yl]-[2-(6-fluoro-4-methoxy-2-methyl-indol-1-yl)-ethyl]-amine | 0.71 (A) | 426.17 |

Example 1071: N-Ethyl-N-(5-{6-[2-(7-fluoro-4-methoxy-2-methyl-indol-1-yl)-ethylamino]-pyrimidin-4-yl}-thiophen-3-yl)-formamide Following the general procedure B, using 6-chloro-N-(2-(7-fluoro-4-methoxy-2-methyl-1H-indol-1-yl)ethyl)pyrimidin-4-amine (A.1.25.) and methyl 3-(N-ethyl-2,2,2-trifluoroacetamido)-5-(4,4,5,5-tetramethyl-1,3,2-dioxaborolan-2-yl)thiophene-2-carboxylate (A.2.157.), upon purification via acidic (formic acid/water and MeCN) prep LCMS and subsequent drying under high vacuum at 50° C., spontaneous decarboxylation and formylation occurs to afford the title compound. LC-MS A: $t_R$=0.77 min; [M+H]+=454.14.

Example 1072: N-(3-Ethoxy-5-{6-[2-(7-fluoro-4-methoxy-2-methyl-indol-1-yl)-ethylamino]-pyrimidin-4-yl}-thiophen-2-yl)-formamide A mixture of 6-(5-amino-4-ethoxythiophen-2-yl)-N-(2-(7-fluoro-4-methoxy-2-methyl-1H-indol-1-yl)ethyl)pyrimidin-4-amine (20 mg, 0.0453 mmol), ethyl formate (0.15 mL, 1.83 mmol) and TEA (0.0189 mL, 0.136 mmol) is stirred in a sealed tube at 85° C. overnight. It is then diluted with EtOAc and washed twice with brine. The organic layer is dried over MgSO$_4$, filtered and concentrated. The residue is purified by FC (Hept to Hept/EtOAc 3:7) to yield the title compound as a light orange solid (7.6 mg, 36%). LC-MS A: $t_R$=0.74 min; [M+H]+=470.08.

a) 6-(5-Amino-4-ethoxythiophen-2-yl)-N-(2-(7-fluoro-4-methoxy-2-methyl-1H-indol-1-yl)ethyl) pyrimidin-4-amine A solution of tert-butyl (3-ethoxy-5-(6-((2-(7-fluoro-4-methoxy-2-methyl-1H-indol-1-yl)ethyl)amino)pyrimidin-4-yl)thiophen-2-yl)carbamate (25 mg, 0.0462 mmol) in HCl 4M in dioxane (1 mL) is stirred at RT for 2 h 30 min, then solvents are evaporated under reduced pressure. The residue is diluted with EtOAc and washed twice with sat. NaHCO$_3$ and once with brine. The organic layer is dried over MgSO$_4$, filtered and concentrated to afford the title compound as a yellow solid (20 mg, 94%). LC-MS A: $t_R$=0.74 min; [M+H]+= 442.15.

b) Tert-butyl (3-ethoxy-5-(6-((2-(7-fluoro-4-methoxy-2-methyl-1H-indol-1-yl)ethyl)amino)pyrimidin-4-yl)thiophen-2-yl)carbamate 3-Ethoxy-5-(6-((2-(7-fluoro-4-methoxy-2-methyl-1H-indol-1-yl)ethyl)amino)pyrimidin-4-yl)thiophene-2-carboxylic acid (Example 258, 500 mg, 1.06 mmol) is suspended in tert-butanol (3.6 mL) and diphenyl phosphoryl azide (0.241 mL, 1.08 mmol) and TEA (0.15 mL, 1.07 mmol) are successively added under nitrogen at RT. The RM is stirred at 90° C. overnight. Diphenyl phosphoryl azide (0.241 mL, 1.08 mmol) and TEA (0.15 mL, 1.07 mmol) are added and stirring is continued at 90° C. for 4 h. It is then diluted with sat. aq. NaHCO$_3$ and extracted with EtOAc. The organic layer is washed twice with brine, dried over MgSO$_4$, filtered and concentrated. The residue is purified by FC (Hept to Hept/EtOAc 50:50) to afford the title compound as a yellow solid (325 mg, 25%). LC-MS A: $t_R$=0.86 min; [M+H]+=542.16.

Example 1073: N-(3-Ethoxy-5-{6-[2-(7-fluoro-4-methoxy-2-methyl-indol-1-yl)-ethylamino]-pyrimidin-4-yl}-thiophen-2-yl)-propionamide Following the procedure described for Example 1023, using 6-(5-amino-4-ethoxythiophen-2-yl)-N-(2-(7-fluoro-4-methoxy-2-methyl-1H-indol-1-yl)ethyl)pyrimidin-4-amine (Example 1072-a) and propionic acid, the title compound is obtained as a light yellow solid. LC-MS A: $t_R$=0.77 min; [M+H]+=498.00.

Example 1074: N-(3-Ethoxy-5-{6-[2-(7-fluoro-4-methoxy-2-methyl-indol-1-yl)-ethylamino]-pyrimidin-4-yl}-thiophen-2-yl)-3-hydroxy-propionamide Following the procedure described for Example 1023, using 6-(5-amino-4-ethoxythiophen-2-yl)-N-(2-(7-fluoro-4-methoxy-2-methyl-1H-indol-1-yl)ethyl)pyrimidin-4-amine (Example 1072-a) and 3-hydroxyproprionic acid, the title compound is obtained as a brown solid. LC-MS A: $t_R$=0.70 min; [M+H]+=513.84.

Example 1075: (3-Ethoxy-5-{6-[2-(7-fluoro-4-methoxy-2-methyl-indol-1-yl)-ethylamino]-pyrimidin-4-yl}-thiophen-2-yl)-urea Following the procedure described for Example 1072-b, using the ammonium salt of 3-ethoxy-5-(6-((2-(7-fluoro-4-methoxy-2-methyl-1H-indol-1-yl)ethyl)amino)pyrimidin-4-yl)thiophene-2-carboxylic acid, tert-butyl (3-ethoxy-5-(6-((2-(7-fluoro-4-methoxy-2-methyl-1H-indol-1-yl)ethyl)amino)pyrimidin-4-yl)thiophen-2-yl)carbamate (example 1072-b) is obtained, and then the title compound. LC-MS A: $t_R$=0.70 min; [M+H]+=485.10.

Example 1076: 2-(6-((2-(2-Cyano-7-fluoro-4-methoxy-1H-indol-1-yl)ethyl)amino)pyrimidin-4-yl)-1H-indole-6-carboxylic acid Following the general procedure B, using 1-(2-((6-chloropyrimidin-4-yl)amino)ethyl)-7-fluoro-4-methoxy-1H-indole-2-carbonitrile (A.1.68.) and 2-(tetramethyl-1,3,2-dioxaborolan-2-yl)-1H-indole-6-carboxylic acid, the title compound is obtained as a light yellow powder. LC-MS E: $t_R$=0.64 min; [M+H]+=471.03.

II. Biological Assays

Compounds of the present invention may be further characterized with regard to their general pharmacokinetic and pharmacological properties using conventional assays well known in the art such as angiogenesis assays or tumor growth inhibition assays, or for example relating to their bioavailability in different species (such as rat or dog); or for their properties with regard to drug safety and/or toxicological properties using conventional assays well known in the art, for example relating to cytochrome P450 enzyme inhibition and time dependent inhibition, pregnane X receptor (PXR) activation, glutathione binding, or phototoxic behavior.

Tumor Growth Inhibition Assay
EMT-6 Mouse Tumor Model

The EMT-6 cell line is established from a transplantable murine mammary carcinoma that arose in a BALB/cCRGL mouse after implantation of a hyperplastic mammary alveolar nodule (Volence F J, et al, J Surg Oncol. 1980, 13(1): 39-44), obtained from ATCC (American Type culture collection, Manassas, Virginia, USA).

EMT-6 tumour cells are grown as monolayer at 37° C. in a humidified atmosphere (5% CO2, 95% air) in RPMI 1640 containing 2 mM L glutamine supplemented with 10% fetal bovine serum. For experimental use, tumour cells are detached from the culture flask with trypsin. The cells are counted in a hemocytometer and their viability is assessed by trypan blue exclusion.

Tumours are induced in female BALB/c mice by either subcutaneous injection of 1×10⁶ EMT-6 cells in 200 μL of RPMI 1640 into the right flank or by injection of 2.5×10⁵ EMT-6 cells in 50 μL of RPM11640 into the mammary fat pad tissue. For the latter injection, female BALB/c mice are anaesthetized with Isoflurane and a 5 mm incision is made in the skin over the lateral thorax to expose the mammary fat pad tissue. After tumor cell injection the thoracic surface is gently dabbed with a 95% ethanol-dampened cotton-swab to kill tumor cells that may leak from the injection site. The skin of mice is closed with 4-0 crinerce sutures.

Animals are monitored daily for behavior and survival and twice weekly for body weight and tumor growth. Tumor size is measured with calipers and tumor volume is calculated according to the following formula: Tumor volume= (width$^2$×length)/2.

When tumors reach between 60 and 100 mm³ (depending on the experiment), treatment with EP2 and/or EP4 antagonists is started and compound is given daily for at least 3 weeks.

Tumor weight is measured at the end of the study.

Biological In Vitro Assays

The antagonistic activities of the compounds of formula (I) on the EP2 and EP4 receptors are determined in accordance with the following experimental method.

The assay is using the PathHunter™ HEK 293 PTGER2 and PTGER4 b-arrestin cell lines from DiscoverX. The system is based on the Enzyme Fragment Complementation Technology. Two complementing fragments of the b-galactosidase enzyme are expressed within stably transfected cells. The larger portion of b-gal, termed EA for Enzyme Acceptor, is fused to the C-terminus of b-arrestin 2. The smaller fragment, termed ProLink™ tag, is fused to PTGER2 (EP2) or PTRGER4 (EP4) at the C-terminus. Upon activation, b-arrestin is recruited which forces the interaction of ProLink and EA, allowing complementation of the two fragments of b-gal and the formation of a functional enzyme which is capable of hydrolysing the substrate and generating a chemiluminescent signal.

hEP2 b-Arrestin Assay:

The HEK 293 PTGER2 b-arrestin cells (DiscoverX 93-021-4C1) are detached from culture dishes with a cell dissociation buffer (Invitrogen, 13151-014), and collected in growing medium (GM: DMEM+Glutamax-I (Invitrogen 32430)/10% FCS, 1% Penicilin/streptomycin). 5000 cells per well of a 384 well plate (white with white bottom Greiner 781080) are seeded in 20 ul per well of GM. Plate is incubated at 37° C., 5% C02 for 24 hours. Stock solutions of test compounds are made at a concentration of 10 mM in DMSO, and serially diluted in DMSO to concentrations required for inhibition dose response curves (tested concentration range 10 M-2 nM or 1 μM-0.2 nM). PGE2 (Cayman 14010, stock solution: 10 mM in DMSO) is used as agonist at 5 μM final concentration, corresponding to EC80.

Five microliters of diluted compounds are transferred into the assay plate. Plate is pre-incubated 15 minutes at 37° C. Then five microliters of PGE2 (final conc. 5 μM) are transferred into the assay plate. Plate is incubated 120 minutes at 37° C.

PathHunter Glo Detection Kit components are thawed and mix according to manufacturer's instructions: 1 part Galacton Star Substrate with 5 parts Emerald II™ Solution, and 19 parts of PathHunter Cell Assay Buffer, respectively. Twelve μl of reagent are transferred to the assay plate and incubate for 1 hour at room temperature in the dark. Luminescence counts are read on a BMG Fluostar Optima reader according to manufacturer's instructions. For each compound concentration calculate of the percentage of activity compared to DMSO control value as average±STDEV. (each concentration is measured in duplicate)

IC50 values and curves are generated with XLfit software (IDBS) using Dose-Response One Site model 203. When compounds were measured multiple times, mean values are given.

hEP4 b-Arrestin Assay:

The HEK 293 PTGER4 b-arrestin cells (DiscoverX 93-030-4C1) are detached from culture dishes with a cell dissociation buffer (Invitrogen, 13151-014), and collected in growing medium (GM: DMEM+Glutamax-I (Invitrogen 32430)/10% FCS, 1% Penicilin/streptomycin). 5000 cells per well of a 384 well plate (white with white bottom Greiner 781080) are seeded in 20 ul per well of GM. Plate is incubated at 37° C., 5% C02 for 24 hours.

Stock solutions of test compounds are made at a concentration of 10 mM in DMSO, and serially diluted in DMSO to concentrations required for inhibition dose response curves (tested concentration range 10 µM-2 nM or 1 µM-0.2 nM). PGE2 (Cayman 14010, stock solution: 100 uM in DMSO) is used as agonist at 20 nM final concentration, corresponding to EC80.

Five microliters of diluted compounds are transferred into the assay plate. Plate is pre-incubated 15 minutes at 37° C. Then five microliters of PGE2 (final conc. 20 nM) are transferred into the assay plate. Plate is incubated 120 minutes at 37° C.

PathHunter Glo Detection Kit components are thawed and mix according to manufacturer's instructions: 1 part Galacton Star Substrate with 5 parts Emerald II™ Solution, and 19 parts of PathHunter Cell Assay Buffer, respectively. Twelve µl of reagent are transferred to the assay plate and incubate for 1 hour at room temperature in the dark. Luminescence counts are read on a BMG Fluostar Optima reader according to manufacturer's instructions. For each compound concentration calculate of the percentage of activity compared to DMSO control value as average±STDEV. (each concentration is measured in duplicate) IC50 values and curves are generated with XLfit software (IDBS) using Dose-Response One Site model 203. When compounds were measured multiple times, mean values are given.

The antagonistic activities of the compounds of formula (I) on the EP2 and EP4 receptors are also determined in accordance with the following experimental method.

Human tumor cell lines expressing endogenously either EP4 or EP2 are used and cAMP accumulation in cells upon $PGE_2$ stimulation is monitored. SF295 glioblastoma cells express high endogenous EP2 and no EP4, whereas BT549 breast cancer cells, express high endogenous EP4 levels and very low EP2 levels.

As a detection method for cAMP the HTRF (homogeneous time resolved fluorescence) Cisbio kit (HTRF cAMP dynamic 2 kit 20'000 tests Cisbio Cat. #62AM4PEC) was used, which is based on a competitive immunoassay using a Cryptate-labeled anti-cAMP antibody and d2-labeled cAMP. Native cAMP produced by cells or unlabeled cAMP (for the standard curve) compete with exogenously added d2-labeled cAMP (acceptor) for binding to monoclonal anti-cAMP-Eu3+Cryptate (donor). A FRET signal (Fluorescence Resonance Energy Transfer) is obtained only if the labeled anti-cAMP antibody binds the d2 labelled cAMP, thus the specific signal (i.e. energy transfer) is inversely proportional to the concentration of cAMP in the standard or sample.

hEP2 cAMP Assay:

The SF295 cells (NCI/No. 0503170) are detached from culture dishes with a cell dissociation buffer (Invitrogen, 13151-014), and collected in growing medium (GM: RPM11640 (Invitrogen 21875)/10% FCS, 1% Penicilin/streptomycin). Cells are counted washed and resuspended in assay buffer (AB; HBSS, 20 mM HEPES, 0.2% BSA; 2 mM IBMX). 4,000 cells in 5 µl of AB are seeded per well of a small volume 384 well plate (black with flat bottom, Greiner 784076).

Stock solutions of test compounds are made at a concentration of 10 mM in DMSO, and serially diluted in DMSO to concentrations required for inhibition dose response curves (tested concentration range 30 µM-0.4 nM; 30 µM-0.015 nM or 1 µM-0.01 nM).

$PGE_2$ (Cayman 14010, stock solution: 75 µM in DMSO) is used as agonist at 75 nM final concentration, corresponding to EC80.

Two point five microliters of diluted compounds are transferred into the assay plate. Plate is pre-incubated 45 minutes at room temperature. Subsequently, 2.5 microliters of $PGE_2$ (final conc. 75 nM) are transferred into the assay plate. Plate is incubated 30 minutes at room temperature. Five µl of each donor (anti-cAMP cryptate) and acceptor (cAMP-d2) are added and the plate is incubated another hour at room temperature in the dark and then read using a BMG LABTECH PHERAstar reader (Excitation: 337 nm, Emission: 620 and 665 nm).

The obtained Delta F (fluorescence) values (665 nm/620 nM) are converted into % cAMP values using the measurements of the cAMP calibrator provided in the kit. For each compound concentration the percentage of cAMP compared to DMSO control value as average±STDEV (each concentration is measured in duplicate) is calculated.

$IC_{50}$ values and curves are generated with XLfit software (IDBS) using Dose-Response One Site model 203. When compounds were measured multiple times, mean values are given.

hEP4 cAMP Assay:

The BT549 cells (NCI/No. 0507282) are detached from culture dishes with a cell dissociation buffer (Invitrogen, 13151-014), and collected in growing medium (GM: RPM11640 (Invitrogen 21875)/10% FCS, 1% Penicilin/streptomycin). Cells are counted washed and resuspended in assay buffer (AB; HBSS, 20 mM HEPES, 0.2% BSA; 2 mM IBMX). 4,000 cells in 5 µl of AB are seeded per well of a small volume 384 well plate (black with flat bottom, Greiner 784076).

Stock solutions of test compounds are made at a concentration of 10 mM in DMSO, and serially diluted in DMSO to concentrations required for inhibition dose response curves (tested concentration range 30 µM-0.4 nM; 30 µM-0.015 nM or 1 µM-0.01 nM).

$PGE_2$ (Cayman 14010, stock solution: 6 µM in DMSO) is used as agonist at 6 nM final concentration, corresponding to EC80.

Two point five microliters of diluted compounds are transferred into the assay plate. Plate is pre-incubated 45 minutes at room temperature. Subsequently, 2.5 microliters of $PGE_2$ (final conc. 6 nM) are transferred into the assay plate. Plate is incubated 30 minutes at room temperature. Five µl of each donor (anti-cAMP cryptate) and acceptor (cAMP-d2) are added and the plate is incubated another hour at room temperature in the dark and then read using a BMG LABTECH PHERAstar reader (Excitation: 337 nm, Emission: 620 and 665 nm).

The obtained Delta F (fluorescence) values (665 nm/620 nM) are converted into % cAMP values using the measurements of the cAMP calibrator provided in the kit. For each compound concentration the percentage of cAMP compared to DMSO control value as average±STDEV (each concentration is measured in duplicate) is calculated.

$IC_{50}$ values and curves are generated with XLfit software (IDBS) using Dose-Response One Site model 203. When compounds were measured multiple times, mean values are given.

Antagonistic activities of exemplified compounds are displayed in Table 16:

TABLE 16

| Ex. | $EP_2$ $IC_{50}$ [nM] | $EP_4$ $IC_{50}$ [nM] |
| --- | --- | --- |
| 1 | 50 | 616 |
| 2 | 267 | 251 |
| 3 | 100 | 769 |
| 4 | 22 | 412 |
| 5 | 5 | 629 |
| 6 | 3 | 911 |
| 7 | 98 | 556 |
| 8 | 9 | 333 |
| 9 | 6 | 108 |
| 10 | 69 | 691 |
| 11 | 20 | 124 |
| 12 | 11 | 144 |
| 13 | 14 | 428 |
| 14 | 4 | 82 |
| 15 | 62 | 542 |
| 16 | 9 | 202 |
| 17 | 12 | 174 |
| 18 | 27 | 123 |
| 19 | 17 | 99 |
| 20 | 94 | 328 |
| 21 | 42 | 287 |
| 22 | 78 | 369 |
| 23 | 3 | 143 |
| 24 | 94 | 895 |
| 25 | 27 | 616 |
| 26 | 9 | 975 |
| 27 | 10 | 90 |
| 28 | 17 | 249 |
| 29 | 18 | 575 |
| 30 | 34 | 243 |
| 31 | 24 | 543 |
| 32 | 26 | 162 |
| 33 | 3 | 678 |
| 34 | 16 | 123 |
| 35 | 15 | 952 |
| 36 | 5 | 219 |
| 37 | 34 | 436 |
| 38 | 5 | 39 |
| 39 | 19 | 515 |
| 40 | 86 | 392 |
| 41 | 101 | 91 |
| 42 | 21 | 494 |
| 43 | 11 | 44 |
| 44 | 5 | 240 |
| 45 | 14 | 75 |
| 46 | 29 | 970 |
| 47 | 18 | 136 |
| 48 | 24 | 351 |
| 49 | 4 | 235 |
| 50 | 1 | 161 |
| 51 | 3 | 143 |
| 52 | 221 | 583 |
| 53 | 98 | 350 |
| 54 | 125 | 305 |
| 55 | 63 | 570 |
| 56 | 151 | 698 |
| 57 | 16 | 113 |
| 58 | 22 | 477 |
| 59 | 213 | 485 |
| 60 | 85 | 290 |
| 61 | 98 | 518 |
| 62 | 11 | 32 |
| 63 | 26 | 227 |
| 64 | 47 | 231 |
| 65 | 41 | 697 |
| 66 | 21 | 189 |
| 67 | 10 | 59 |
| 68 | 24 | 388 |
| 69 | 29 | 94 |
| 70 | 33 | 145 |
| 71 | 86 | 758 |
| 72 | 45 | 28 |
| 73 | 214 | 970 |
| 74 | 45 | 916 |
| 75 | 7 | 95 |
| 76 | 21 | 651 |
| 77 | 8 | 89 |
| 78 | 20 | 557 |
| 79 | 11 | 197 |
| 80 | 238 | 713 |
| 81 | 44 | 86 |
| 82 | 193 | 968 |
| 83 | 48 | 158 |
| 84 | 89 | 310 |
| 85 | 74 | 392 |
| 86 | 12 | 873 |
| 87 | 121 | 885 |
| 88 | 54 | 185 |
| 89 | 115 | 132 |
| 90 | 7 | 461 |
| 91 | 32 | 144 |
| 92 | 48 | 358 |
| 93 | 183 | 475 |
| 94 | 30 | 299 |
| 95 | 59 | 167 |
| 96 | 17 | 572 |
| 97 | 177 | 527 |
| 98 | 7 | 230 |
| 99 | 113 | 123 |
| 100 | 11 | 202 |
| 101 | 37 | 548 |
| 102 | 142 | 597 |
| 103 | 13 | 58 |
| 104 | 24 | 44 |
| 105 | 34 | 934 |
| 106 | 44 | 698 |
| 107 | 5 | 46 |
| 108 | 1 | 15 |
| 109 | 49 | 955 |
| 110 | 3 | 46 |
| 111 | 31 | 166 |
| 112 | 4 | 69 |
| 113 | 8 | 57 |
| 114 | 4 | 27 |
| 115 | 56 | 742 |
| 116 | 19 | 382 |
| 117 | 1 | 114 |
| 118 | 612 | 933 |
| 119 | 18 | 941 |
| 120 | 6 | 495 |
| 121 | 5 | 765 |
| 122 | 9 | 974 |
| 123 | 30 | 158 |
| 124 | 7 | 151 |
| 125 | 8 | 932 |
| 126 | 128 | 928 |
| 127 | 4 | 192 |
| 128 | 16 | 417 |
| 129 | 48 | 622 |
| 130 | 4 | 78 |
| 131 | 23 | 402 |
| 132 | 43 | 277 |
| 133 | 29 | 990 |
| 134 | 1 | 174 |
| 135 | 96 | 288 |
| 136 | 5 | 48 |
| 137 | 2 | 897 |
| 138 | 7 | 567 |
| 139 | 28 | 939 |
| 140 | 11 | 476 |
| 141 | 20 | 992 |
| 142 | 16 | 588 |
| 143 | 5 | 658 |
| 144 | 3 | 658 |
| 145 | 8 | 302 |
| 146 | 8 | 334 |
| 147 | 16 | 109 |
| 148 | 7 | 943 |
| 149 | 10 | 605 |
| 150 | 54 | 458 |

TABLE 16-continued

| Ex. | EP$_2$ IC$_{50}$ [nM] | EP$_4$ IC$_{50}$ [nM] |
|---|---|---|
| 151 | 8 | 808 |
| 152 | 3 | 786 |
| 153 | 202 | 739 |
| 154 | 1 | 628 |
| 155 | 55 | 251 |
| 156 | 78 | 93 |
| 157 | 27 | 590 |
| 158 | 39 | 163 |
| 159 | 4 | 75 |
| 160 | 48 | 204 |
| 161 | 396 | 993 |
| 162 | 3 | 4 |
| 163 | 111 | 842 |
| 164 | 113 | 520 |
| 165 | 19 | 230 |
| 166 | 131 | 733 |
| 167 | 6 | 333 |
| 168 | 146 | 995 |
| 169 | 8 | 543 |
| 170 | 1 | 350 |
| 171 | 112 | 231 |
| 172 | 54 | 536 |
| 173 | 5 | 894 |
| 174 | 27 | 405 |
| 175 | 6 | 529 |
| 176 | 36 | 71 |
| 177 | 19 | 167 |
| 178 | 18 | 168 |
| 179 | 20 | 880 |
| 180 | 3 | 16 |
| 181 | 173 | 864 |
| 182 | 56 | 141 |
| 183 | 49 | 637 |
| 184 | 15 | 170 |
| 185 | 30 | 302 |
| 186 | 7 | 124 |
| 187 | 20 | 198 |
| 188 | 17 | 43 |
| 189 | 19 | 106 |
| 190 | 53 | 193 |
| 191 | 13 | 38 |
| 192 | 23 | 287 |
| 193 | 4 | 39 |
| 194 | 10 | 172 |
| 195 | 260 | 534 |
| 196 | 12 | 224 |
| 197 | 32 | 751 |
| 198 | 96 | 299 |
| 199 | 102 | 166 |
| 200 | 37 | 111 |
| 201 | 232 | 389 |
| 202 | 16 | 105 |
| 203 | 14 | 324 |
| 204 | 31 | 182 |
| 205 | 44 | 334 |
| 206 | 88 | 740 |
| 207 | 19 | 645 |
| 208 | 11 | 102 |
| 209 | 3 | 123 |
| 210 | 472 | 991 |
| 211 | 2 | 394 |
| 212 | 1 | 173 |
| 213 | 3 | 204 |
| 214 | 38 | 786 |
| 215 | 139 | 972 |
| 216 | 2 | 22 |
| 217 | 25 | 381 |
| 218 | 18 | 519 |
| 219 | 41 | 454 |
| 220 | 18 | 216 |
| 221 | 9 | 902 |
| 222 | 42 | 232 |
| 223 | 8 | 702 |
| 224 | 4 | 20 |
| 225 | 25 | 124 |
| 226 | 18 | 263 |
| 227 | 2 | 22 |
| 228 | 4 | 35 |
| 229 | 2 | 26 |
| 230 | 5 | 13 |
| 231 | 185 | 133 |
| 232 | 21 | 732 |
| 233 | 52 | 317 |
| 234 | 3 | 249 |
| 235 | 2 | 60 |
| 236 | 9 | 413 |
| 237 | 13 | 68 |
| 238 | 5 | 40 |
| 239 | 1 | 19 |
| 240 | 2 | 10 |
| 241 | 32 | 128 |
| 242 | 111 | 216 |
| 243 | 2 | 281 |
| 244 | 2 | 86 |
| 245 | 9 | 71 |
| 246 | 2 | 507 |
| 247 | 32 | 681 |
| 248 | 1 | 64 |
| 249 | 3 | 9 |
| 250 | 3 | 103 |
| 251 | 6 | 37 |
| 252 | 57 | 660 |
| 253 | 9 | 978 |
| 254 | 64 | 999 |
| 255 | 12 | 896 |
| 256 | 3 | 29 |
| 257 | 2 | 6 |
| 258 | 1 | 10 |
| 259 | 37 | 127 |
| 260 | 28 | 536 |
| 261 | 12 | 71 |
| 262 | 35 | 925 |
| 263 | 90 | 587 |
| 264 | 71 | 287 |
| 265 | 33 | 491 |
| 266 | 53 | 953 |
| 267 | 26 | 317 |
| 268 | 11 | 635 |
| 269 | 61 | 117 |
| 270 | 46 | 513 |
| 271 | 5 | 153 |
| 272 | 8 | 716 |
| 273 | 1 | 67 |
| 274 | 1 | 43 |
| 275 | 1 | 25 |
| 276 | 65 | 885 |
| 277 | 17 | 416 |
| 278 | 9 | 999 |
| 279 | 22 | 313 |
| 280 | 16 | 652 |
| 281 | 27 | 435 |
| 282 | 11 | 294 |
| 283 | 17 | 132 |
| 284 | 34 | 824 |
| 285 | 47 | 691 |
| 286 | 31 | 268 |
| 287 | 183 | 963 |
| 288 | 19 | 714 |
| 289 | 53 | 299 |
| 290 | 28 | 102 |
| 291 | 41 | 104 |
| 292 | 52 | 397 |
| 293 | 19 | 113 |
| 294 | 8 | 10 |
| 295 | 12 | 950 |
| 296 | 7 | 259 |
| 297 | 539 | 814 |
| 298 | 19 | 249 |
| 299 | 10 | 81 |
| 300 | 40 | 494 |
| 301 | 103 | 358 |
| 302 | 33 | 145 |
| 303 | 33 | 322 |
| 304 | 2 | 12 |

TABLE 16-continued

| Ex. | EP$_2$ IC$_{50}$ [nM] | EP$_4$ IC$_{50}$ [nM] |
|---|---|---|
| 305 | 297 | 566 |
| 306 | 408 | 207 |
| 307 | 25 | 47 |
| 308 | 383 | 429 |
| 309 | 11 | 86 |
| 310 | 39 | 415 |
| 311 | 4 | 232 |
| 312 | 44 | 85 |
| 313 | 7 | 110 |
| 314 | 15 | 303 |
| 315 | 46 | 268 |
| 316 | 245 | 906 |
| 317 | 320 | 873 |
| 318 | 338 | 894 |
| 319 | 10 | 296 |
| 320 | 68 | 345 |
| 321 | 72 | 439 |
| 322 | 55 | 295 |
| 323 | 18 | 708 |
| 324 | 4 | 23 |
| 325 | 159 | 968 |
| 326 | 18 | 224 |
| 327 | 482 | 629 |
| 328 | 62 | 570 |
| 329 | 27 | 653 |
| 330 | 102 | 667 |
| 331 | 98 | 829 |
| 332 | 5 | 588 |
| 333 | 15 | 483 |
| 334 | 28 | 603 |
| 335 | 56 | 468 |
| 336 | 46 | 199 |
| 337 | 89 | 308 |
| 338 | 858 | 357 |
| 339 | 5 | 989 |
| 340 | 5 | 645 |
| 341 | 42 | 396 |
| 342 | 5 | 621 |
| 343 | 15 | 728 |
| 344 | 34 | 319 |
| 345 | 89 | 164 |
| 346 | 56 | 50 |
| 347 | 11 | 239 |
| 348 | 5 | 76 |
| 349 | 26 | 301 |
| 350 | 6 | 993 |
| 351 | 52 | 688 |
| 352 | 49 | 481 |
| 353 | 13 | 213 |
| 354 | 32 | 772 |
| 355 | 48 | 134 |
| 356 | 15 | 165 |
| 357 | 54 | 272 |
| 358 | 369 | 731 |
| 359 | 34 | 500 |
| 360 | 75 | 372 |
| 361 | 67 | 678 |
| 362 | 3 | 281 |
| 363 | 1 | 474 |
| 364 | 84 | 543 |
| 365 | 25 | 409 |
| 366 | 22 | 262 |
| 367 | 14 | 961 |
| 368 | 63 | 360 |
| 369 | 87 | 238 |
| 370 | 35 | 992 |
| 371 | 70 | 875 |
| 372 | 260 | 381 |
| 373 | 79 | 183 |
| 374 | 53 | 67 |
| 375 | 20 | 57 |
| 376 | 50 | 184 |
| 377 | 51 | 697 |
| 378 | 340 | 449 |
| 379 | 63 | 354 |
| 380 | 58 | 677 |
| 381 | 3 | 84 |
| 382 | 27 | 359 |
| 383 | 17 | 147 |
| 384 | 13 | 60 |
| 385 | 183 | 468 |
| 386 | 40 | 559 |
| 387 | 2 | 556 |
| 388 | 34 | 963 |
| 389 | 26 | 734 |
| 390 | 38 | 146 |
| 391 | 2 | 3 |
| 392 | 7 | 97 |
| 393 | 9 | 745 |
| 394 | 15 | 296 |
| 395 | 24 | 137 |
| 396 | 1 | 65 |
| 397 | 1 | 20 |
| 398 | 3 | 178 |
| 399 | 17 | 483 |
| 400 | 6 | 418 |
| 401 | 19 | 182 |
| 402 | 10 | 159 |
| 403 | 20 | 128 |
| 404 | 96 | 448 |
| 405 | 18 | 356 |
| 406 | 47 | 266 |
| 407 | 15 | 636 |
| 408 | 4 | 3 |
| 409 | 345 | 146 |
| 410 | 51 | 390 |
| 411 | 20 | 443 |
| 412 | 36 | 79 |
| 413 | 29 | 55 |
| 414 | 35 | 199 |
| 415 | 53 | 153 |
| 416 | 14 | 99 |
| 417 | 28 | 396 |
| 418 | 74 | 691 |
| 419 | 90 | 403 |
| 420 | 95 | 93 |
| 421 | 60 | 342 |
| 422 | 34 | 148 |
| 423 | 44 | 35 |
| 424 | 31 | 257 |
| 425 | 73 | 521 |
| 426 | 17 | 759 |
| 427 | 85 | 240 |
| 428 | 11 | 164 |
| 429 | 25 | 775 |
| 430 | 9 | 88 |
| 431 | 51 | 191 |
| 432 | 21 | 117 |
| 433 | 61 | 108 |
| 434 | 49 | 318 |
| 435 | 13 | 159 |
| 436 | 46 | 787 |
| 437 | 15 | 201 |
| 438 | 64 | 106 |
| 439 | 19 | 272 |
| 440 | 57 | 905 |
| 441 | 11 | 113 |
| 442 | 12 | 234 |
| 443 | 175 | 487 |
| 444 | 7 | 94 |
| 445 | 5 | 235 |
| 446 | 16 | 8 |
| 447 | 28 | 27 |
| 448 | 46 | 508 |
| 449 | 4 | 242 |
| 450 | 9 | 117 |
| 451 | 2 | 240 |
| 452 | 34 | 468 |
| 453 | 31 | 904 |
| 454 | 14 | 445 |
| 455 | 74 | 154 |
| 456 | 233 | 944 |
| 457 | 888 | 480 |
| 458 | 25 | 74 |

TABLE 16-continued

| Ex. | EP$_2$ IC$_{50}$ [nM] | EP$_4$ IC$_{50}$ [nM] |
|---|---|---|
| 459 | 62 | 739 |
| 460 | 4 | 146 |
| 461 | 24 | 224 |
| 462 | 61 | 842 |
| 463 | 252 | 741 |
| 464 | 15 | 459 |
| 465 | 17 | 75 |
| 466 | 33 | 229 |
| 467 | 387 | 994 |
| 468 | 59 | 264 |
| 469 | 68 | 667 |
| 470 | 63 | 735 |
| 471 | 2 | 29 |
| 472 | 5 | 66 |
| 473 | 538 | 646 |
| 474 | 22 | 224 |
| 475 | 54 | 259 |
| 476 | 18 | 48 |
| 477 | 122 | 574 |
| 478 | 11 | 665 |
| 479 | 127 | 233 |
| 480 | 26 | 75 |
| 481 | 61 | 112 |
| 482 | 686 | 986 |
| 483 | 4 | 98 |
| 484 | 1 | 117 |
| 485 | 3 | 245 |
| 486 | 91 | 325 |
| 487 | 49 | 76 |
| 488 | 70 | 219 |
| 489 | 25 | 103 |
| 490 | 17 | 165 |
| 491 | 765 | 707 |
| 492 | 63 | 626 |
| 493 | 21 | 119 |
| 494 | 25 | 618 |
| 495 | 21 | 350 |
| 496 | 8 | 99 |
| 497 | 11 | 168 |
| 498 | 20 | 609 |
| 499 | 6 | 714 |
| 500 | 17 | 816 |
| 501 | 42 | 69 |
| 502 | 149 | 114 |
| 503 | 58 | 499 |
| 504 | 103 | 535 |
| 505 | 21 | 671 |
| 506 | 12 | 113 |
| 507 | 18 | 163 |
| 508 | 37 | 583 |
| 509 | 110 | 684 |
| 510 | 20 | 216 |
| 511 | 18 | 158 |
| 512 | 21 | 253 |
| 513 | 24 | 130 |
| 514 | 5 | 56 |
| 515 | 8 | 69 |
| 516 | 324 | 451 |
| 517 | 97 | 373 |
| 518 | 11 | 40 |
| 519 | 5 | 34 |
| 520 | 82 | 482 |
| 521 | 17 | 64 |
| 522 | 21 | 217 |
| 523 | 35 | 141 |
| 524 | 36 | 377 |
| 525 | 38 | 14 |
| 526 | 10 | 230 |
| 527 | 8 | 134 |
| 528 | 119 | 151 |
| 529 | 19 | 110 |
| 530 | 21 | 50 |
| 531 | 25 | 628 |
| 532 | 33 | 828 |
| 533 | 3 | 88 |
| 534 | 8 | 91 |
| 535 | 68 | 136 |
| 536 | 27 | 172 |
| 537 | 22 | 81 |
| 538 | 64 | 261 |
| 539 | 160 | 948 |
| 540 | 18 | 23 |
| 541 | 19 | 25 |
| 542 | 44 | 522 |
| 543 | 990 | 250 |
| 544 | 47 | 178 |
| 545 | 29 | 119 |
| 546 | 16 | 57 |
| 547 | 63 | 232 |
| 548 | 6 | 61 |
| 549 | 131 | 865 |
| 550 | 33 | 573 |
| 551 | 5 | 339 |
| 552 | 26 | 118 |
| 553 | 102 | 192 |
| 554 | 56 | 65 |
| 555 | 23 | 28 |
| 556 | 54 | 418 |
| 557 | 5 | 78 |
| 558 | 16 | 111 |
| 559 | 4 | 247 |
| 560 | 7 | 107 |
| 561 | 102 | 374 |
| 562 | 359 | 547 |
| 563 | 111 | 601 |
| 564 | 75 | 317 |
| 565 | 77 | 434 |
| 566 | 46 | 537 |
| 567 | 17 | 89 |
| 568 | 1 | 118 |
| 569 | 17 | 77 |
| 570 | 773 | 309 |
| 571 | 149 | 511 |
| 572 | 18 | 45 |
| 573 | 7 | 21 |
| 574 | 33 | 208 |
| 575 | 22 | 52 |
| 576 | 399 | 355 |
| 577 | 114 | 118 |
| 578 | 9 | 52 |
| 579 | 11 | 41 |
| 580 | 4 | 32 |
| 581 | 5 | 33 |
| 582 | 50 | 161 |
| 583 | 10 | 65 |
| 584 | 39 | 148 |
| 585 | 31 | 203 |
| 586 | 729 | 865 |
| 587 | 2 | 106 |
| 588 | 2 | 92 |
| 589 | 228 | 707 |
| 590 | 18 | 178 |
| 591 | 33 | 294 |
| 592 | 13 | 39 |
| 593 | 157 | 435 |
| 594 | 190 | 42 |
| 595 | 10 | 73 |
| 596 | 10 | 222 |
| 597 | 175 | 719 |
| 598 | 2 | 336 |
| 599 | 13 | 196 |
| 600 | 14 | 319 |
| 601 | 12 | 122 |
| 602 | 163 | 805 |
| 603 | 41 | 15 |
| 604 | 16 | 325 |
| 605 | 48 | 829 |
| 606 | 8 | 186 |
| 607 | 25 | 111 |
| 608 | 24 | 126 |
| 609 | 10 | 42 |
| 610 | 22 | 139 |
| 611 | 4 | 56 |
| 612 | 8 | 79 |

TABLE 16-continued

| Ex. | EP$_2$ IC$_{50}$ [nM] | EP$_4$ IC$_{50}$ [nM] |
| --- | --- | --- |
| 613 | 4 | 221 |
| 614 | 12 | 193 |
| 615 | 2 | 39 |
| 616 | 5 | 85 |
| 617 | 60 | 952 |
| 618 | 24 | 395 |
| 619 | 9 | 249 |
| 620 | 6 | 561 |
| 621 | 34 | 57 |
| 622 | 732 | 303 |
| 623 | 45 | 130 |
| 624 | 48 | 501 |
| 625 | 16 | 70 |
| 626 | 51 | 356 |
| 627 | 48 | 197 |
| 628 | 89 | 254 |
| 629 | 26 | 98 |
| 630 | 6 | 142 |
| 631 | 14 | 320 |
| 632 | 4 | 112 |
| 633 | 60 | 750 |
| 634 | 27 | 196 |
| 635 | 50 | 186 |
| 636 | 68 | 255 |
| 637 | 25 | 54 |
| 638 | 61 | 33 |
| 639 | 23 | 37 |
| 640 | 483 | 430 |
| 641 | 114 | 153 |
| 642 | 11 | 22 |
| 643 | 294 | 706 |
| 644 | 6 | 54 |
| 645 | 9 | 16 |
| 646 | 48 | 312 |
| 647 | 146 | 302 |
| 648 | 195 | 893 |
| 649 | 13 | 768 |
| 650 | 93 | 443 |
| 651 | 166 | 257 |
| 652 | 60 | 136 |
| 653 | 428 | 527 |
| 654 | 26 | 313 |
| 655 | 152 | 191 |
| 656 | 52 | 89 |
| 657 | 71 | 189 |
| 658 | 24 | 287 |
| 659 | 6 | 54 |
| 660 | 16 | 303 |
| 661 | 4 | 39 |
| 662 | 8 | 136 |
| 663 | 13 | 53 |
| 664 | 4 | 95 |
| 665 | 2 | 13 |
| 666 | 7 | 40 |
| 667 | 2 | 17 |
| 668 | 8 | 22 |
| 669 | 2 | 644 |
| 670 | 8 | 406 |
| 671 | 2 | 136 |
| 672 | 1 | 3 |
| 673 | 2 | 3 |
| 674 | 2 | 6 |
| 675 | 4 | 7 |
| 676 | 3 | 9 |
| 677 | 2 | 12 |
| 678 | 33 | 40 |
| 679 | 20 | 95 |
| 680 | 56 | 113 |
| 681 | 14 | 247 |
| 682 | 12 | 251 |
| 683 | 6 | 162 |
| 684 | 36 | 471 |
| 685 | 6 | 109 |
| 686 | 239 | 842 |
| 687 | 91 | 778 |
| 688 | 80 | 680 |
| 689 | 211 | 558 |
| 690 | 5 | 35 |
| 691 | 4 | 177 |
| 692 | 7 | 64 |
| 693 | 20 | 234 |
| 694 | 49 | 120 |
| 695 | 4 | 999 |
| 696 | 42 | 131 |
| 697 | 15 | 77 |
| 698 | 21 | 79 |
| 699 | 9 | 63 |
| 700 | 7 | 44 |
| 701 | 15 | 24 |
| 702 | 165 | 225 |
| 703 | 34 | 140 |
| 704 | 47 | 177 |
| 705 | 21 | 80 |
| 706 | 10 | 55 |
| 707 | 38 | 57 |
| 708 | 36 | 704 |
| 709 | 14 | 535 |
| 710 | 15 | 373 |
| 711 | 16 | 429 |
| 712 | 11 | 703 |
| 713 | 73 | 267 |
| 714 | 72 | 958 |
| 715 | 16 | 240 |
| 716 | 12 | 510 |
| 717 | 242 | 527 |
| 718 | 45 | 593 |
| 719 | 223 | 389 |
| 720 | 10 | 150 |
| 721 | 18 | 60 |
| 722 | 32 | 80 |
| 723 | 37 | 287 |
| 724 | 57 | 206 |
| 725 | 6 | 58 |
| 726 | 41 | 388 |
| 727 | 34 | 238 |
| 728 | 36 | 109 |
| 729 | 45 | 783 |
| 730 | 30 | 489 |
| 731 | 36 | 276 |
| 732 | 41 | 341 |
| 733 | 88 | 809 |
| 734 | 95 | 465 |
| 735 | 93 | 620 |
| 736 | 39 | 399 |
| 737 | 25 | 156 |
| 738 | 63 | 177 |
| 739 | 43 | 450 |
| 740 | 183 | 655 |
| 741 | 37 | 505 |
| 742 | 130 | 753 |
| 743 | 10 | 315 |
| 744 | 8 | 251 |
| 745 | 25 | 840 |
| 746 | 10 | 869 |
| 747 | 3 | 318 |
| 748 | 70 | 170 |
| 749 | 81 | 425 |
| 750 | 16 | 91 |
| 751 | 8 | 105 |
| 752 | 85 | 633 |
| 753 | 101 | 548 |
| 754 | 32 | 234 |
| 755 | 41 | 452 |
| 756 | 85 | 194 |
| 757 | 44 | 345 |
| 758 | 32 | 113 |
| 759 | 55 | 760 |
| 760 | 90 | 795 |
| 761 | 40 | 161 |
| 762 | 98 | 304 |
| 763 | 25 | 139 |
| 764 | 8 | 815 |
| 765 | 13 | 403 |
| 766 | 57 | 80 |

TABLE 16-continued

| Ex. | EP$_2$ IC$_{50}$ [nM] | EP$_4$ IC$_{50}$ [nM] |
|---|---|---|
| 767 | 20 | 251 |
| 768 | 35 | 928 |
| 769 | 11 | 259 |
| 770 | 16 | 374 |
| 771 | 19 | 310 |
| 772 | 15 | 317 |
| 773 | 32 | 49 |
| 774 | 4 | 637 |
| 775 | 10 | 206 |
| 776 | 6 | 44 |
| 777 | 2 | 3 |
| 778 | 15 | 175 |
| 779 | 28 | 242 |
| 780 | 6 | 826 |
| 781 | 1 | 18 |
| 782 | 39 | 91 |
| 783 | 271 | 912 |
| 784 | 63 | 512 |
| 785 | 13 | 906 |
| 786 | 16 | 319 |
| 787 | 21 | 729 |
| 788 | 49 | 925 |
| 789 | 6 | 923 |
| 790 | 42 | 101 |
| 791 | 325 | 639 |
| 792 | 2 | 227 |
| 793 | 3 | 18 |
| 794 | 309 | 798 |
| 795 | 85 | 306 |
| 796 | 48 | 131 |
| 797 | 33 | 64 |
| 798 | 28 | 123 |
| 799 | 21 | 59 |
| 800 | 12 | 44 |
| 801 | 20 | 139 |
| 802 | 7 | 1 |
| 803 | 10 | 4 |
| 804 | 3 | 2 |
| 805 | 4 | 5 |
| 806 | 7 | 10 |
| 807 | 32 | 55 |
| 808 | 7 | 4 |
| 809 | 3 | 6 |
| 810 | 9 | 28 |
| 811 | 3 | 20 |
| 812 | 2 | 976 |
| 813 | 2 | 3 |
| 814 | 7 | 2 |
| 815 | 8 | 7 |
| 816 | 24 (*) | 15 (*) |
| 817 | 4 | 5 |
| 818 | 2 | 1 |
| 819 | 7 | 2 |
| 820 | 6 | 2 |
| 821 | 4 | 2 |
| 822 | 6 | 5 |
| 823 | 5 | 5 |
| 824 | 8 | 7 |
| 825 | 14 | 8 |
| 826 | 13 | 8 |
| 827 | 16 | 7 |
| 828 | 10 | 11 |
| 829 | 15 | 12 |
| 830 | 3 | 12 |
| 831 | 19 | 17 |
| 832 | 5 | 25 |
| 833 | 62 | 27 |
| 834 | 15 | 28 |
| 835 | 19 | 31 |
| 836 | 7 | 32 |
| 837 | 28 | 39 |
| 838 | 4 | 41 |
| 839 | 3 | 44 |
| 840 | 48 | 47 |
| 841 | 25 | 61 |
| 842 | 13 | 94 |
| 843 | 11 | 111 |
| 844 | 5 | 142 |
| 845 | 7 | 215 |
| 846 | 24 | 221 |
| 847 | 35 | 309 |
| 848 | 20 | 321 |
| 849 | 39 | 589 |
| 850 | 2 | 79 |
| 851 | 18 | 28 |
| 852 | 12 | 22 |
| 853 | 5 | 1 |
| 854 | 232 | 193 |
| 855 | 6 | 3 |
| 856 | 8 | 52 |
| 857 | 58 | 212 |
| 858 | 22 | 4 |
| 859 | 6 | 60 |
| 860 | 421 | 121 |
| 861 | 5 | 2 |
| 862 | 90 | 194 |
| 863 | 5 | 3 |
| 864 | 3 | 5 |
| 865 | 7 | 5 |
| 866 | 8 | 5 |
| 867 | 8 | 6 |
| 868 | 1 | 7 |
| 869 | 2 | 8 |
| 870 | 8 | 12 |
| 871 | 2 | 16 |
| 872 | 12 | 18 |
| 873 | 77 | 18 |
| 874 | 4 | 19 |
| 875 | 4 | 26 |
| 876 | 4 | 32 |
| 877 | 5 | 34 |
| 878 | 1 | 22 |
| 879 | 4 | 36 |
| 880 | 2 | 42 |
| 881 | 5 | 41 |
| 882 | 11 | 55 |
| 883 | 7 | 63 |
| 884 | 10 | 84 |
| 885 | 40 | 89 |
| 886 | 42 | 125 |
| 887 | 89 | 177 |
| 888 | 41 | 472 |
| 889 | 1 | 35 |
| 890 | 2 | 23 |
| 891 | 6 | 3 |
| 892 | 1 | 24 |
| 893 | 42 | 118 |
| 894 | 23 | 10 |
| 895 | 20 | 66 |
| 896 | 2 | 34 |
| 897 | 380 | 453 |
| 898 | 41 | 123 |
| 899 | 5 | 16 |
| 900 | 26 | 22 |
| 901 | 7 | 76 |
| 902 | 3 | 8 |
| 903 | 4 | 69 |
| 904 | 1 | 49 |
| 905 | 22 | 5 |
| 906 | 30 | 3 |
| 907 | 24 | 12 |
| 908 | 17 | 33 |
| 909 | 3 | 14 |
| 910 | 23 | 10 |
| 911 | 7 | 27 |
| 912 | 4 | 29 |
| 913 | 13 | 5 |
| 914 | 32 | 68 |
| 915 | 12 | 27 |
| 916 | 20 | 18 |
| 917 | 24 | 35 |
| 918 | 26 | 73 |
| 919 | 10 | 3 |
| 920 | 39 | 68 |

TABLE 16-continued

| Ex. | EP$_2$ IC$_{50}$ [nM] | EP$_4$ IC$_{50}$ [nM] |
|---|---|---|
| 921 | 6 | 9 |
| 922 | 19 | 19 |
| 923 | 20 | 42 |
| 924 | 224 | 308 |
| 925 | 83 | 155 |
| 926 | 4 | 20 |
| 927 | 31 | 3 |
| 928 | 37 | 45 |
| 929 | 20 | 33 |
| 930 | 4 | 2 |
| 931 | 35 (*) | 14 (*) |
| 932 | 14 | 3 |
| 933 | 12 | 4 |
| 934 | 16 | 31 |
| 935 | 7 | 4 |
| 936 | 18 | 8 |
| 937 | 21 | 13 |
| 938 | 38 | 29 |
| 939 | 15 | 17 |
| 940 | 10 | 3 |
| 941 | 11 (*) | 29 (*) |
| 942 | 3 | 6 |
| 943 | 4 | 2 |
| 944 | 16 | 7 |
| 945 | 9 | 2 |
| 946 | 54 | 10 |
| 947 | 30 | 16 |
| 948 | 50 | 45 |
| 949 | 7 | 14 |
| 950 | 18 | 42 |
| 951 | 15 | 27 |
| 952 | 5 | 21 |
| 953 | 5 | 21 |
| 954 | 15 | 41 |
| 955 | 13 | 19 |
| 956 | 21 | 37 |
| 957 | 56 | 54 |
| 958 | 13 | 18 |
| 959 | 3 | 137 |
| 960 | 9 | 4 |
| 961 | 12 | 34 |
| 962 | 3 | 11 |
| 963 | 194 | 126 |
| 964 | 41 | 22 |
| 965 | 53 | 43 |
| 966 | 14 | 31 |
| 967 | 6 | 17 |
| 968 | 4 | 15 |
| 969 | 56 | 25 |
| 970 | 31 | 27 |
| 971 | 39 | 24 |
| 972 | 6 | 18 |
| 973 | 15 | 49 |
| 974 | 36 | 84 |
| 975 | 44 | 55 |
| 976 | 194 | 317 |
| 977 | 5 | 6 |
| 978 | 1 | 16 |
| 979 | 4 | 15 |
| 980 | 21 | 12 |
| 981 | 59 | 58 |
| 982 | 18 | 3 |
| 983 | 248 | 244 |
| 984 | 8 | 28 |
| 985 | 25 | 14 |
| 986 | 9 | 66 |
| 987 | 44 | 67 |
| 988 | 51 | 197 |
| 989 | 67 | 62 |
| 990 | 3 | 19 |
| 991 | 142 | 540 |
| 992 | 27 | 35 |
| 993 | 80 | 344 |
| 994 | 7 | 6 |
| 995 | 13 | 52 |
| 996 | 39 | 99 |
| 997 | 58 | 143 |
| 998 | 48 | 686 |
| 999 | 30 | 23 |
| 1000 | 35 | 79 |
| 1001 | 6 | 7 |
| 1002 | 20 | 31 |
| 1003 | 55 | 131 |
| 1004 | 117 | 144 |
| 1005 | 18 | 55 |
| 1006 | 131 | 450 |
| 1007 | 24 | 67 |
| 1008 | 234 | 507 |
| 1009 | 20 | 11 |
| 1010 | 3 | 7 |
| 1011 | 120 | 228 |
| 1012 | 5 | 37 |
| 1013 | 14 | 17 |
| 1014 | 7 | 351 |
| 1015 | 15 | 18 |
| 1016 | 5 | 5 |
| 1017 | 7 | 31 |
| 1018 | 94 | 69 |
| 1019 | 485 | 167 |
| 1020 | 2 | 29 |
| 1021 | 2 | 39 |
| 1022 | 4 | 18 |
| 1023 | 8 | 1 |
| 1024 | 14 | 2 |
| 1025 | 33 | 6 |
| 1026 | 21 | 1 |
| 1027 | 39 | 3 |
| 1028 | 9 | 2 |
| 1029 | 4 | 6 |
| 1030 | 15 | 3 |
| 1031 | 3 | 19 |
| 1032 | 10 | 14 |
| 1033 | 7 | 37 |
| 1034 | 5 | 17 |
| 1035 | 2 | 29 |
| 1036 | 24 | 20 |
| 1037 | 60 | 100 |
| 1038 | 64 | 20 |
| 1039 | 104 | 224 |
| 1040 | 91 | 407 |
| 1041 | 26 | 246 |
| 1042 | 11 | 57 |
| 1043 | 5 | 1 |
| 1044 | 9 | 3 |
| 1045 | 16 | 4 |
| 1046 | 27 | 5 |
| 1047 | 5 | 3 |
| 1048 | 10 | 4 |
| 1049 | 21 | 10 |
| 1050 | 34 | 19 |
| 1051 | 2 | 4 |
| 1052 | 3 | 7 |
| 1053 | 10 | 100 |
| 1054 | 1 | 1 |
| 1055 | 249 | 60 |
| 1056 | 120 | 119 |
| 1057 | 6 | 9 |
| 1058 | 51 | 19 |
| 1059 | 54 | 3 |
| 1060 | 17 | 36 |
| 1061 | 19 | 36 |
| 1062 | 33 | 13 |
| 1063 | 1 | 21 |
| 1064 | 25 | 151 |
| 1065 | 21 | 22 |
| 1066 | 3 | 48 |
| 1067 | 88 | 67 |
| 1068 | 10 | 15 |
| 1069 | 9 | 41 |
| 1070 | 10 | 18 |
| 1071 | 23 | 40 |
| 1072 | 3 | 17 |
| 1073 | 7 | 14 |
| 1074 | 9 | 34 |

TABLE 16-continued

| Ex. | EP$_2$ IC$_{50}$ [nM] | EP$_4$ IC$_{50}$ [nM] |
|---|---|---|
| 1075 | 7 | 49 |
| 1076 | 6 | 39 |

(*): IC$_{50}$ values measured using the cAMP assay

The invention claimed is:

1. A method of treatment by antagonizing prostaglandin 2 receptors EP2 and/or EP4 of pain; endometriosis; autosomal dominant polycystic kidney disease; or pneumonia; or for the control of female fertility; comprising administering to a subject in need thereof a compound of formula (I), or a pharmaceutically acceptable salt thereof,

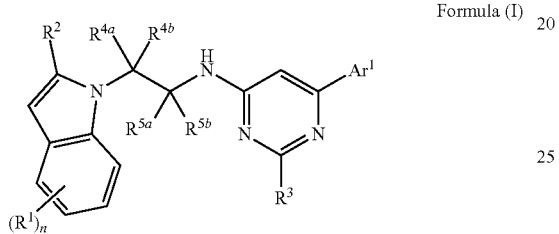

Formula (I)

$(R^1)_n$ represents one, two or three optional substituents on the indole ring, wherein said substituents are independently selected from $(C_{1-3})$alkyl, $(C_{1-3})$alkoxy, halogen, $(C_{1-3})$fluoroalkyl, $(C_{1-3})$fluoroalkoxy, or cyano; or two $R^1$ together form a group —O—CH$_2$—O—, and the remaining $R^1$, if present, represent halogen;

$R^2$ represents $(C_{1-4})$alkyl, halogen, or cyano;

$R^3$ represents hydrogen, methyl or trifluoromethyl;

$R^{4a}$ and $R^{4b}$ independently represent hydrogen, methyl, or $R^{4a}$ and $R^{4b}$ together with the carbon atom to which they are attached represent a cycloprop-1,1-diyl group;

$R^{5a}$ and $R^{5b}$ independently represent hydrogen, methyl, or $R^{5a}$ and $R^{5b}$ together with the carbon atom to which they are attached represent a cycloprop-1,1-diyl group;

$Ar^1$ represents phenyl, or 5- or 6-membered heteroaryl; wherein said phenyl or 5- or 6-membered heteroaryl independently is mono-, di- or tri-substituted, wherein the substituents are independently selected from $(C_{1-6})$alkyl;

$(C_{1-4})$alkoxy;

$(C_{1-3})$fluoroalkyl, wherein said $(C_{1-3})$fluoroalkyl is optionally substituted with hydroxy;

$(C_{1-3})$fluoroalkoxy;

halogen;

cyano;

$(C_{3-6})$cycloalkyl, wherein said $(C_{3-6})$cycloalkyl is unsubstituted or mono-substituted with amino;

$(C_{4-6})$cycloalkyl containing a ring oxygen atom, wherein said $(C_{4-6})$cycloalkyl containing a ring oxygen atom is unsubstituted or mono-substituted with fluoro, hydroxy, or methoxy;

$(C_{3-6})$cycloalkyl-oxy;

hydroxy;

nitro;

B(OH)$_2$;

2,2,2-trifluoro-1,1-dihydroxy-ethyl;

$X^1$—CO—$R^{O1}$, wherein $X^1$ represents a direct bond, $(C_{1-3})$alkylene, —O—$(C_{1-3})$alkylene-*, —NH—$(C_{1-3})$alkylene-*, —S—CH$_2$—*, —CF$_2$—, —CH=CH—, —C≡C—, —NH—CO—*, —CO—, or $(C_{3-5})$cycloalkylene; wherein the asterisks indicate the bond that is linked to the —CO—$R^{O1}$ group; and $R^{O1}$ represents

—OH;

—O—$(C_{1-4})$alkyl;

—NH—SO$_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —NH$_2$;

O-phenyl;

O—CH$_2$—CO—$R^{O4}$, wherein $R^{O4}$ represents hydroxy, or $(C_{1-4})$alkoxy, or —N[$(C_{1-4})$alkyl]$_2$;

O—CH$_2$—O—CO—$R^{O5}$, wherein $R^{O5}$ represents $(C_{1-4})$alkyl or $(C_{1-4})$alkoxy;

O—CH$_2$—CH$_2$—N[$(C_{1-4})$alkyl]$_2$; or (5-methyl-2-oxo-[1,3]dioxol-4-yl)-methyloxy-;

—CO—CH$_2$—CN;

—CO—CH$_2$—OH;

—CO—H;

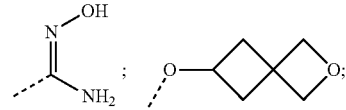

2-hydroxy-3,4-dioxo-cyclobut-1-enyl;

hydroxy-$(C_{1-4})$alkyl;

dihydroxy-$(C_{2-4})$alkyl;

hydroxy-$(C_{2-4})$alkoxy;

$(C_{1-4})$alkoxy-$(C_{2-4})$alkoxy;

$(CH_2)_m$—NR$^{N1}$R$^{N2}$, wherein m represents the integer 0 or 1; and wherein $R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl, -or —SO$_2$—$(C_{1-4})$alkyl;

or $R^{N1}$ independently represents hydrogen or $(C_{1-4})$alkyl, and $R^{N2}$ independently represents —CO—H, —CO—$(C_{1-3})$alkyl, —CO—$(C_{1-3})$alkylene-OH, or —CO—O—$(C_{1-3})$alkyl;

or $R^{N1}$ and $R^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;

—CO—NR$^{N3}$R$^{N4}$ wherein $R^{N3}$ and $R^{N4}$ independently represent hydrogen, $(C_{1-4})$alkyl, hydroxy-$(C_{2-4})$alkyl, $(C_{1-3})$alkoxy-$(C_{2-4})$alkyl, dimethylamino-$(C_{2-4})$alkyl, $(C_{1-4})$alkoxy, hydroxy-$(C_{2-4})$alkoxy, benzyloxy, or hydroxy;

—NH—CO—NR$^{N5}$R$^{N6}$ wherein $R^{N5}$ and $R^{N6}$ independently represent hydrogen or $(C_{1-4})$alkyl;

SO$_2$—$R^{S1}$ wherein $R^{S1}$ represents hydroxy, $(C_{1-4})$alkyl, or —NR$^{N7}$R$^{N8}$ wherein $R^{N7}$ and $R^{N8}$ independently represent hydrogen or $(C_{1-3})$alkyl;

S—$R^{S2}$ wherein $R^{S2}$ represents $(C_{1-4})$alkyl, $(C_{3-6})$cycloalkyl, or 2-fluoro-vinyl;

5-oxo-4,5-dihydro-[1,2,4]oxadiazol-3-yl, or 3-oxo-2,3-dihydro-[1,2,4]oxadiazol-5-yl;

phenyl-oxy, wherein the phenyl is optionally mono-substituted with halogen;

benzooxazol-2-yl; or $(CH_2)_p$-HET, wherein p represents the integer 0 or 1; and wherein HET represents a 5- or 6-membered heteroaryl, wherein said 5- or 6-membered heteroaryl is unsubstituted, or mono- or di-substituted, wherein the substituents are independently selected from $(C_{1-4})$alkyl, $(C_{1-4})$alkoxy, —COOH, hydroxy, fluoro, 2-amino-2-oxo-ethyl, 2-carboxy-ethyl, $(C_{3-5})$cycloalkyl, or —$NR^{N9}R^{N10}$ wherein $R^{N9}$ and $R^{N10}$ independently represent hydrogen or $(C_{1-3})$alkyl;

or $Ar^1$ represents 8- to 10-membered bicyclic heteroaryl; wherein said 8- to 10-membered bicyclic heteroaryl independently is unsubstituted, mono-, di- or tri-substituted, wherein the substituents are independently selected from $(C_{1-4})$alkyl; $(C_{1-4})$alkoxy; $(C_{1-3})$fluoroalkyl; $(C_{1-3})$fluoroalkoxy; halogen; cyano; hydroxy, or —$(C_{0-3})$alkylene-$COOR^{O2}$ wherein $R^{O2}$ represents hydrogen or $(C_{1-4})$alkyl;

or $Ar^1$ represents 8- to 10-membered partially aromatic fused bicyclic heterocyclyl comprising one to four heteroatoms independently selected from nitrogen, oxygen and sulfur; wherein said 8- to 10-membered heterocyclyl is linked to the rest of the molecule at the aromatic ring moiety; wherein said 8- to 10-membered heterocyclyl independently is unsubstituted, mono-, or di-substituted, wherein the substituents are independently selected from oxo, $(C_{1-6})$alkyl, and —$(C_{0-3})$alkylene-$COOR^{O3}$ wherein $R^{O3}$ represents hydrogen or $(C_{1-3})$alkyl.

2. A method according to claim 1; wherein $R^3$ represents hydrogen.

3. A method according to claim 1; wherein
$R^{4a}$ and $R^{4b}$ both represent hydrogen; and
$R^{5a}$ and $R^{5b}$ both represent hydrogen.

4. A method according to claim 1; wherein $Ar^1$ represents phenyl, or 5- or 6-membered heteroaryl; wherein said phenyl or 5- or 6-membered heteroaryl independently is mono-, di- or tri-substituted;

wherein one of said substituents is selected from
$(C_{1-4})$alkoxy;
$(C_{1-3})$fluoroalkyl, wherein said $(C_{1-3})$fluoroalkyl is unsubstituted or mono-substituted with hydroxy;
$(C_{3-6})$cycloalkyl, wherein said $(C_{3-6})$cycloalkyl is unsubstituted or mono-substituted with amino;
$(C_{4-6})$cycloalkyl containing a ring oxygen atom, wherein said $(C_{4-6})$cycloalkyl containing a ring oxygen atom is unsubstituted or mono-substituted with fluoro, hydroxy, or methoxy;
hydroxy;
—$B(OH)_2$;
2,2,2-trifluoro-1,1-dihydroxy-ethyl;
$X^1$—CO—$R^{O1}$, wherein
$X^1$ represents a direct bond, $(C_{1-3})$alkylene, —O—$(C_{1-3})$alkylene-*, —NH—$(C_{1-3})$alkylene-*, —S—$CH_2$—*, —$CF_2$—, —CH=CH—, —C≡C—, —NH—CO—*, —CO—, or $(C_{3-5})$cycloalkylene; wherein the asterisks indicate the bond that is linked to the —CO—$R^{O1}$ group; and $R^{O1}$ represents
—OH;
—O—$(C_{1-4})$alkyl;
—NH—$SO_2$—$R^{S3}$ wherein $R^{S3}$ represents $(C_{1-4})$alkyl, $(C_{3-6})$cycloalkyl wherein the $(C_{3-6})$cycloalkyl optionally contains a ring oxygen atom, $(C_{3-6})$cycloalkyl-$(C_{1-3})$alkylene wherein the $(C_{3-6})$cycloalkyl optionally contains a ring oxygen atom, $(C_{1-3})$fluoroalkyl, phenyl, or —$NH_2$;
—O-phenyl;
—O—$CH_2$—CO—$R^{O4}$, wherein $R^{O4}$ represents hydroxy, or $(C_{1-4})$alkoxy, or —$N[(C_{1-4})$alkyl]2;
—O—$CH_2$—O—CO—$R^{O5}$, wherein $R^{O5}$ represents $(C_{1-4})$alkyl or $(C_{1-4})$alkoxy;
—O—$CH_2$—$CH_2$—$N[(C_{1-4})$alkyl]$_2$; or
(5-methyl-2-oxo-[1,3]dioxol-4-yl)-methyloxy-;
—CO—$CH_2$—CN;
—CO—$CH_2$—OH;
—CO—H;

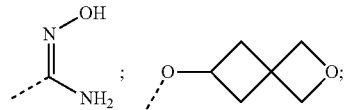

2-hydroxy-3,4-dioxo-cyclobut-1-enyl;
hydroxy-$(C_{1-4})$alkyl;
dihydroxy-$(C_{2-4})$alkyl;
hydroxy-$(C_{2-4})$alkoxy;
$(C_{1-4})$alkoxy-$(C_{2-4})$alkoxy;
—$(CH_2)_m$—$NR^{N1}R^{N2}$, wherein m represents the integer 0 or 1; and wherein
$R^{N1}$ and $R^{N2}$ independently represent hydrogen, $(C_{1-4})$alkyl, $(C_{1-4})$alkoxy-$(C_{2-4})$alkyl, $(C_{3-6})$cycloalkyl, $(C_{2-3})$fluoroalkyl, -or —$SO_2$—$(C_{1-4})$alkyl;
or $R^{N1}$ independently represents hydrogen or $(C_{1-4})$alkyl, and $R^{N2}$ independently represents —CO—H, —CO—$(C_{1-3})$alkyl, —CO—$(C_{1-3})$alkylene-OH, or —CO—O—$(C_{1-3})$alkyl;
or $R^{N1}$ and $R^{N2}$ together with the nitrogen to which they are attached form a 4-, 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;
—CO—$NR^{N3}R^{N4}$ wherein $R^{N3}$ and $R^{N4}$ independently represent hydrogen, $(C_{1-4})$alkyl, hydroxy-$(C_{2-4})$alkyl, $(C_{1-3})$alkoxy-$(C_{2-4})$alkyl, dimethylamino-$(C_{2-4})$alkyl, $(C_{1-4})$alkoxy, hydroxy-$(C_{2-4})$alkoxy, benzyloxy, or hydroxy;
—NH—CO—$NR^{N5}R^{N6}$ wherein $R^{N5}$ and $R^{N6}$ independently represent hydrogen or $(C_{1-4})$alkyl;
—$SO_2$—$R^{S1}$ wherein $R^{S1}$ represents hydroxy, $(C_{1-4})$alkyl, or —$NR^{N7}R^{N8}$ wherein $R^{N7}$ and $R^{N8}$ independently represent hydrogen or $(C_{1-3})$alkyl;
5-oxo-4,5-dihydro-[1,2,4]oxadiazol-3-yl or 3-oxo-2,3-dihydro-[1,2,4]oxadiazol-5-yl;
benzooxazol-2-yl; or
—$(CH_2)_p$-HET, wherein p represents the integer 0 or 1; and wherein HET represents a 5- or 6-membered heteroaryl, wherein said 5- or 6-membered heteroaryl is unsubstituted, or mono- or di-substituted, wherein the substituents are independently selected from $(C_{1-4})$alkyl, $(C_{1-4})$alkoxy, —COOH, hydroxy, fluoro, 2-amino-2-oxo-ethyl, 2-carboxy-ethyl, $(C_{3-5})$ cycloalkyl, or —NR$^{N9}$R$^{N10}$ wherein R$^{N9}$ and R$^{N10}$ independently represent hydrogen or (C$_{1-3}$)alkyl;

and the remaining one or two of said substituents, if present, is/are independently selected from (C$_{1-6}$)alkyl;
(C$_{1-4}$)alkoxy;
(C$_{1-3}$)fluoroalkyl;
(C$_{1-3}$)fluoroalkoxy;
halogen;
(C$_{3-6}$)cycloalkyl;
(C$_{3-6}$)cycloalkyl-oxy;
hydroxy;
nitro;
(CH$_2$)$_m$—NR$^{N1}$R$^{N2}$, wherein m represents the integer 0 or 1; and wherein R$^{N1}$ and R$^{N2}$ independently represent hydrogen, (C$_{1-4}$)alkyl, (C$_{1-4}$)alkoxy-(C$_{2-4}$)alkyl, (C$_{3-6}$)cycloalkyl, (C$_{2-3}$)fluoroalkyl, -or —SO$_2$—(C$_{1-4}$)alkyl; or R$^{N1}$ and R$^{N2}$ together with the nitrogen to which they are attached form a 5- or 6-membered saturated ring optionally containing one ring oxygen or ring sulfur atom, wherein said ring is unsubstituted, or mono-substituted with oxo on a ring carbon atom, or disubstituted with oxo on a ring sulfur atom;
—S—R$^{S2}$ wherein R$^{S2}$ represents (C$_{1-4}$)alkyl, (C$_{3-6}$)cycloalkyl, or 2-fluoro-vinyl; or
phenyl-oxy, wherein the phenyl is optionally mono-substituted with halogen;

or Ar$^1$ represents 8- to 10-membered bicyclic heteroaryl; wherein said 8- to 10-membered bicyclic heteroaryl independently is unsubstituted, mono-, di- or tri-substituted, wherein the substituents are independently selected from (C$_{1-4}$)alkyl; (C$_{1-4}$)alkoxy; (C$_{1-3}$)fluoroalkyl; halogen; and —(C$_{0-3}$)alkylene-COOR$^{O2}$ wherein R$^{O2}$ represents hydrogen or (C$_{1-4}$)alkyl;

or Ar$^1$ represents 8- to 10-membered partially aromatic fused bicyclic heterocyclyl comprising one to four heteroatoms independently selected from nitrogen, oxygen and sulfur; wherein said 8- to 10-membered heterocyclyl is linked to the rest of the molecule at the aromatic ring moiety; wherein said 8- to 10-membered heterocyclyl independently is unsubstituted, mono-, or di-substituted, wherein the substituents are independently selected from oxo, (C$_{1-6}$)alkyl, and —(C$_{0-3}$)alkylene-COOR$^{O3}$ wherein R$^{O3}$ represents hydrogen or (C$_{1-3}$)alkyl.

5. A method according to claim 1; wherein Ar$^1$ represents a phenyl group of the structure (Ar-IV):

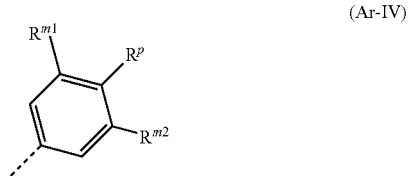

(Ar-IV)

wherein
R$^p$ represents:
(C$_{4-6}$)cycloalkyl containing a ring oxygen atom, wherein said (C$_{4-6}$)cycloalkyl containing a ring oxygen atom is unsubstituted or mono-substituted with fluoro, hydroxy, or methoxy;
hydroxy;

—X$^1$—CO—R$^{O1}$, wherein
X$^1$ represents a direct bond, (C$_{1-3}$)alkylene, —O—(C$_{1-3}$)alkylene-*, —NH—(C$_{1-3}$)alkylene-*, —S—CH$_2$—*, —CF$_2$—, —CH=CH—, —C≡C—, —NH—CO—*, —CO—, or (C$_{3-5}$)cycloalkylene; wherein the asterisks indicate the bond that is linked to the —CO—R$^{O1}$ group; and R$^{O1}$ represents
—OH;
—O—(C$_{1-4}$)alkyl;
—NH—SO$_2$—R$^{S3}$ wherein R$^{S3}$ represents (C$_{1-4}$)alkyl, (C$_{3-6}$)cycloalkyl wherein the (C$_{3-6}$)cycloalkyl optionally contains a ring oxygen atom, (C$_{3-6}$)cycloalkyl-(C$_{1-3}$)alkylene wherein the (C$_{3-6}$)cycloalkyl optionally contains a ring oxygen atom, (C$_{1-3}$)fluoroalkyl, phenyl, or —NH$_2$;
—O—CH$_2$—CO—R$^{O4}$, wherein R$^{O4}$ represents hydroxy, or (C$_{1-4}$)alkoxy, or —N[(C$_{1-4}$)alkyl]$_2$;
—O—CH$_2$—O—CO—R$^{O5}$, wherein R$^{O5}$ represents (C$_{1-4}$)alkyl or (C$_{1-4}$)alkoxy;
—O—CH$_2$—CH$_2$—N[(C$_{1-4}$)alkyl]$_2$; or
(5-methyl-2-oxo-[1,3]dioxol-4-yl)-methyloxy-;
—CO—H;

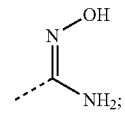

2-hydroxy-3,4-dioxo-cyclobut-1-enyl;
NR$^{N1}$R$^{N2}$, wherein
R$^{N1}$ independently represents hydrogen or (C$_{1-4}$)alkyl, and R$^{N2}$ independently represents
—CO—H, —CO—(C$_{1-3}$)alkyl, or —CO—(C$_{1-3}$)alkylene-OH;
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, or hydroxy;
—NH—CO—NR$^{N5}$R$^{N6}$ wherein R$^{N5}$ and R$^{N6}$ independently represent hydrogen or (C$_{1-4}$)alkyl;
5-oxo-4,5-dihydro-[1,2,4]oxadiazol-3-yl or 3-oxo-2,3-dihydro-[1,2,4]oxadiazol-5-yl;
HET, wherein HET represents a 5- or 6-membered heteroaryl, wherein said 5- or 6-membered heteroaryl is unsubstituted, or mono- or di-substituted, wherein the substituents are independently selected from (C$_{1-4}$)alkyl, (C$_{1-4}$)alkoxy, —COOH, hydroxy, fluoro, 2-amino-2-oxo-ethyl, 2-carboxy-ethyl, (C$_{3-5}$)cycloalkyl, or —NR$^{N9}$R$^{N10}$ wherein R$^{N9}$ and R$^{N10}$ independently represent hydrogen or (C$_{1-3}$)alkyl;

R$^{m1}$ represents
(C$_{1-6}$)alkyl;
(C$_{1-4}$)alkoxy;
(C$_{1-3}$)fluoroalkyl;
(C$_{1-3}$)fluoroalkoxy;
halogen;
(C$_{3-6}$)cycloalkyl;
(C$_{3-6}$)cycloalkyl-oxy;
—NR$^{N1}$R$^{N2}$, wherein R$^{N1}$ and R$^{N2}$ independently represent hydrogen, (C$_{1-4}$)alkyl, or (C$_{3-6}$)cycloalkyl; or —S—R$^{S2}$ wherein R$^{S2}$ represents (C$_{1-4}$)alkyl, (C$_{3-6}$)cycloalkyl, or 2-fluoro-vinyl; and R$^{m2}$ represents hydrogen, fluoro, or chloro;

or R$^p$ represents hydrogen;

R$^{m1}$ represents 1H-pyrazol-1-yl; or —X$^1$—COOH, wherein X$^1$ represents a direct bond, (C$_{1-3}$)alkylene, or —O—(C$_{1-3}$)alkylene-*, wherein the asterisks indicate the bond that is linked to the —COOH group;

and R$^{m}$2 represents hydrogen, (C$_{1-4}$)alkoxy; or —S—(C$_{1-4}$)alkyl;

or Ar$^1$ represents a 5-membered heteroaryl group of the structure (Ar-II):

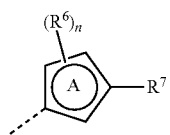

wherein in (Ar-II) the ring A represents a thiophenyl or a thiazolyl ring;

wherein

R$^7$ represents
3-hydroxy-oxetan-3-yl;
hydroxy;
2,2,2-trifluoro-1,1-dihydroxy-ethyl;
—X$^1$—CO—R$^{O1}$, wherein
X$^1$ represents a direct bond, (C$_{1-3}$)alkylene, —O—(C$_{1-3}$)alkylene-*, —NH—(C$_{1-3}$)alkylene-*, —S—CH$_2$—*, —CF$_2$—, —CH=CH—, —C≡C—, —NH—CO—*, —CO—, or (C$_{3-5}$)cycloalkylene; wherein the asterisks indicate the bond that is linked to the —CO—R$^{O1}$ group; and
R$^{O1}$ represents
—OH;
—O—(C$_{1-4}$)alkyl;
—NH—SO$_2$—R$^{S3}$ wherein R$^{S3}$ represents (C$_{1-4}$)alkyl, (C$_{3-6}$)cycloalkyl wherein the (C$_{3-6}$)cycloalkyl optionally contains a ring oxygen atom, (C$_{3-6}$)cycloalkyl-(C$_{1-3}$)alkylene wherein the (C$_{3-6}$)cycloalkyl optionally contains a ring oxygen atom, (C$_{1-3}$)fluoroalkyl, phenyl, or —NH$_2$;
—O-phenyl;
—O—CH$_2$—CO—R$^{O4}$, wherein R$^{O4}$ represents hydroxy, or (C$_{1-4}$)alkoxy, or —N[(C$_{1-4}$)alkyl]$_2$;
—O—CH$_2$—O—CO—R$^{O5}$, wherein R$^{O5}$ represents (C$_{1-4}$)alkyl or (C$_{1-4}$)alkoxy;
—O—CH$_2$—CH$_2$—N[(C$_{1-4}$)alkyl]$_2$; or
(5-methyl-2-oxo-[1,3]dioxol-4-yl)-methyloxy-;
—CO—CH$_2$—OH;
—CO—H;

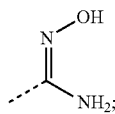

hydroxy-(C$_{1-4}$)alkyl;

—NR$^{N1}$R$^{N2}$, wherein
R$^{N1}$ and R$^{N2}$ independently represent hydrogen, (C$_{1-4}$)alkyl, or (C$_{3-6}$)cycloalkyl;
or R$^{N1}$ independently represents hydrogen or (C$_{1-4}$)alkyl, and R$^{N2}$ independently represents —CO—H, —CO—(C$_{1-3}$)alkyl, or —CO—(C$_{1-3}$)alkylene-OH;
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, hydroxy-(C$_{2-4}$)alkoxy, benzyloxy, or hydroxy;
—NH—CO—NR$^{N5}$R$^{N6}$ wherein R$^{N5}$ and R$^{N6}$ independently represent hydrogen or (C$_{1-4}$)alkyl;
5-oxo-4,5-dihydro-[1,2,4]oxadiazol-3-yl or 3-oxo-2,3-dihydro-[1,2,4]oxadiazol-5-yl; or
HET, wherein HET represents a 5- or 6-membered heteroaryl, wherein said 5- or 6-membered heteroaryl is unsubstituted, or mono- or di-substituted, wherein the substituents are independently selected from (C$_{1-4}$)alkyl, (C$_{1-4}$)alkoxy, —COOH, hydroxy, fluoro, 2-amino-2-oxo-ethyl, 2-carboxy-ethyl, (C$_{3-5}$)cycloalkyl, or —NR$^{N9}$R$^{N10}$ wherein R$^{N9}$ and R$^{N10}$ independently represent hydrogen or (C$_{1-3}$)alkyl;

and (R$^6$)$_n$ represents one optional substituent independently selected from
(C$_{1-6}$)alkyl;
(C$_{1-4}$)alkoxy;
(C$_{1-3}$)fluoroalkyl;
(C$_{1-3}$)fluoroalkoxy;
halogen;
(C$_{3-6}$)cycloalkyl;
(C$_{3-6}$)cycloalkyl-oxy;
hydroxy;
pyridinyl; and
—NR$^{N1}$R$^{N2}$, wherein R$^{N1}$ and R$^{N2}$ independently represent hydrogen, (C$_{1-4}$)alkyl, or (C$_{3-6}$)cycloalkyl;

or Ar$^1$ represents 9- or 10-membered bicyclic heteroaryl; wherein said 9- or 10-membered bicyclic heteroaryl independently is unsubstituted, mono-, or di-substituted, wherein the substituents are independently selected from (C$_{1-4}$)alkyl; (C$_{1-4}$)alkoxy; (C$_{1-3}$)fluoroalkyl; (C$_{1-3}$)fluoroalkoxy; halogen; cyano; hydroxy, or —(C$_{0-3}$)alkylene-COOR$^{O2}$ wherein R$^{O2}$ represents hydrogen or (C$_{1-4}$)alkyl;

or Ar$^1$ represents a group of the structure (Ar-III):

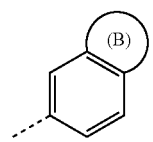

wherein ring (B) represents a non-aromatic 5- or 6-membered ring fused to the phenyl group, wherein ring (B) comprises one or two heteroatoms independently selected from nitrogen and oxygen; wherein said ring (B) independently is unsubstituted, mono-, or di-substituted, wherein the substituents are independently selected from oxo, (C$_{1-6}$)alkyl, and —(C$_{0-3}$)alkylene-COOR$^{O3}$ wherein R$^{O3}$ represents hydrogen or (C$_{1-3}$)alkyl.

6. A method according to claim 1; wherein Ar¹ represents a phenyl group selected from:
a)
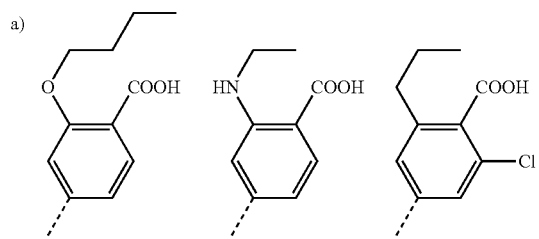
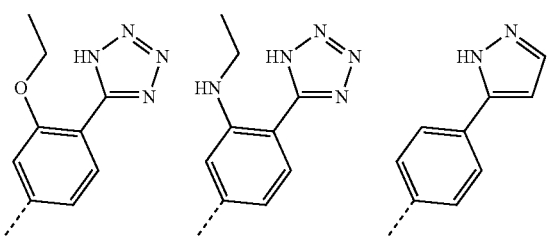
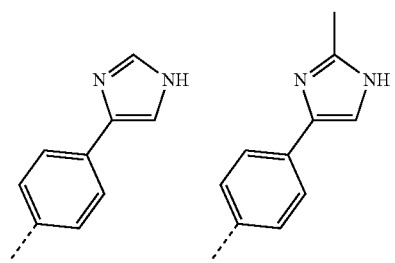
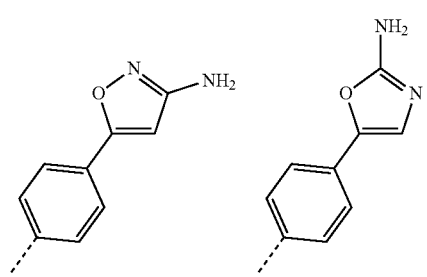
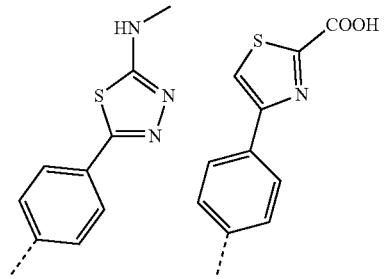
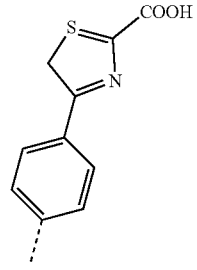
; or
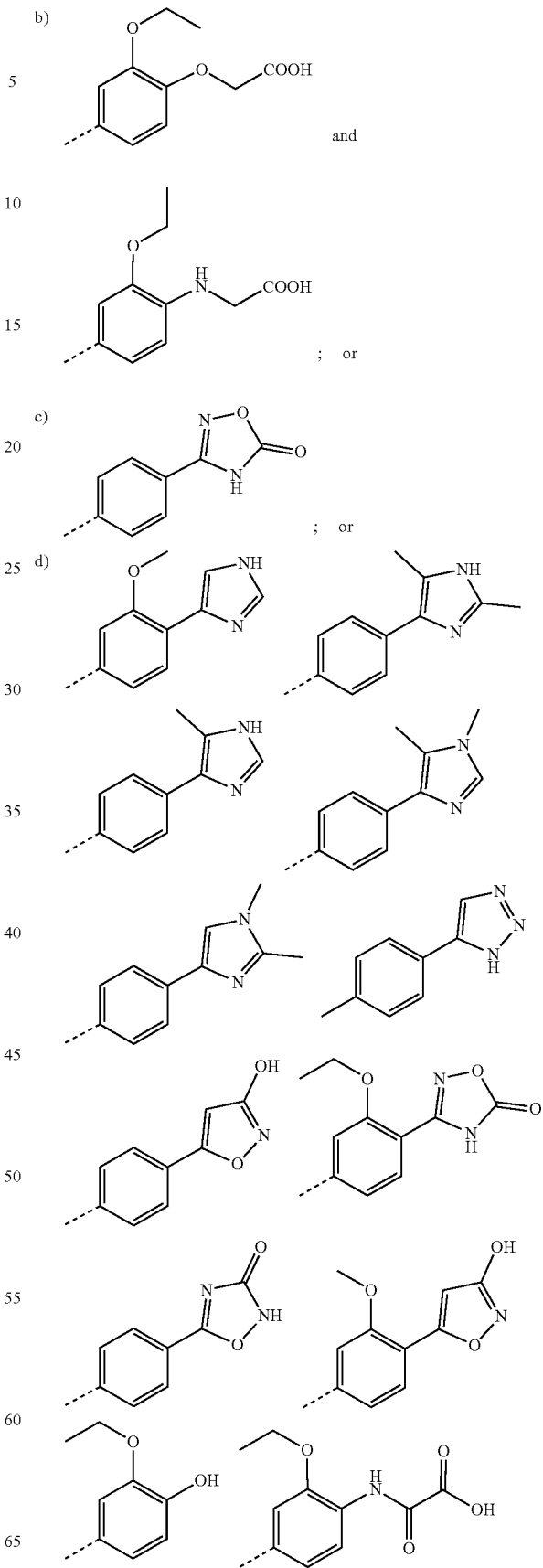

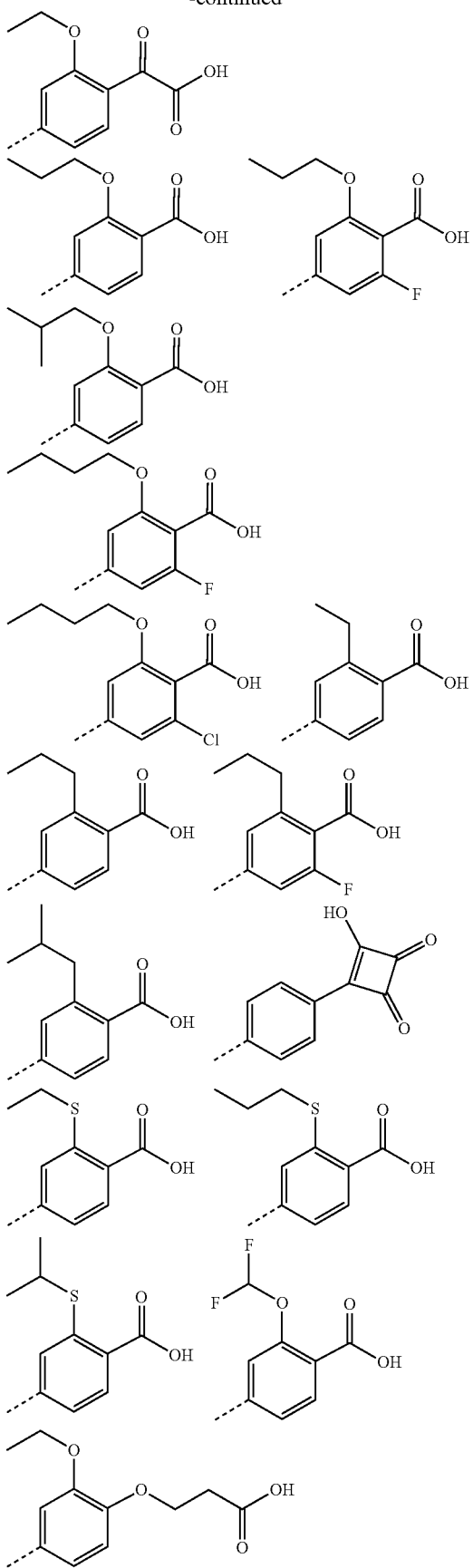
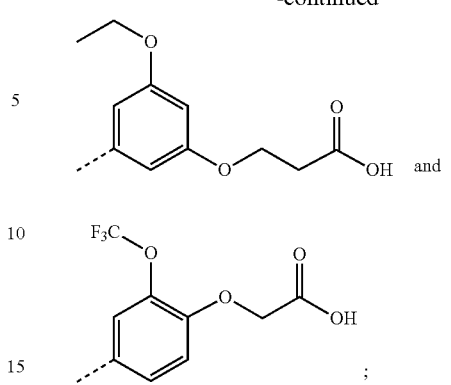
or Ar¹ represents a thiophenyl group selected from:
a)
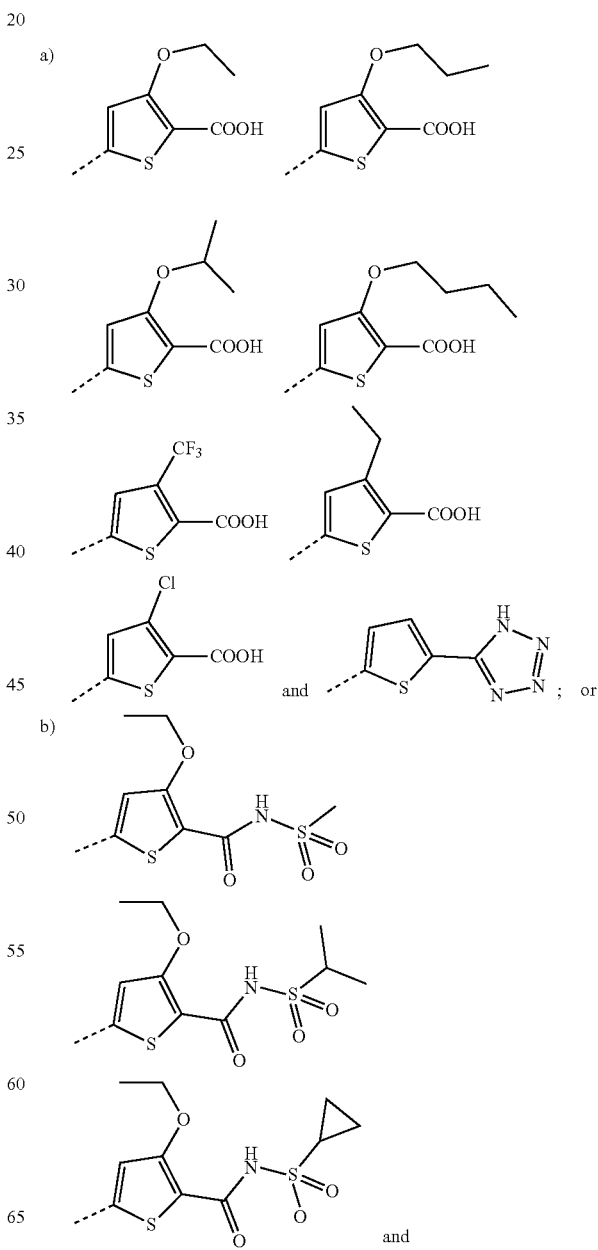
and

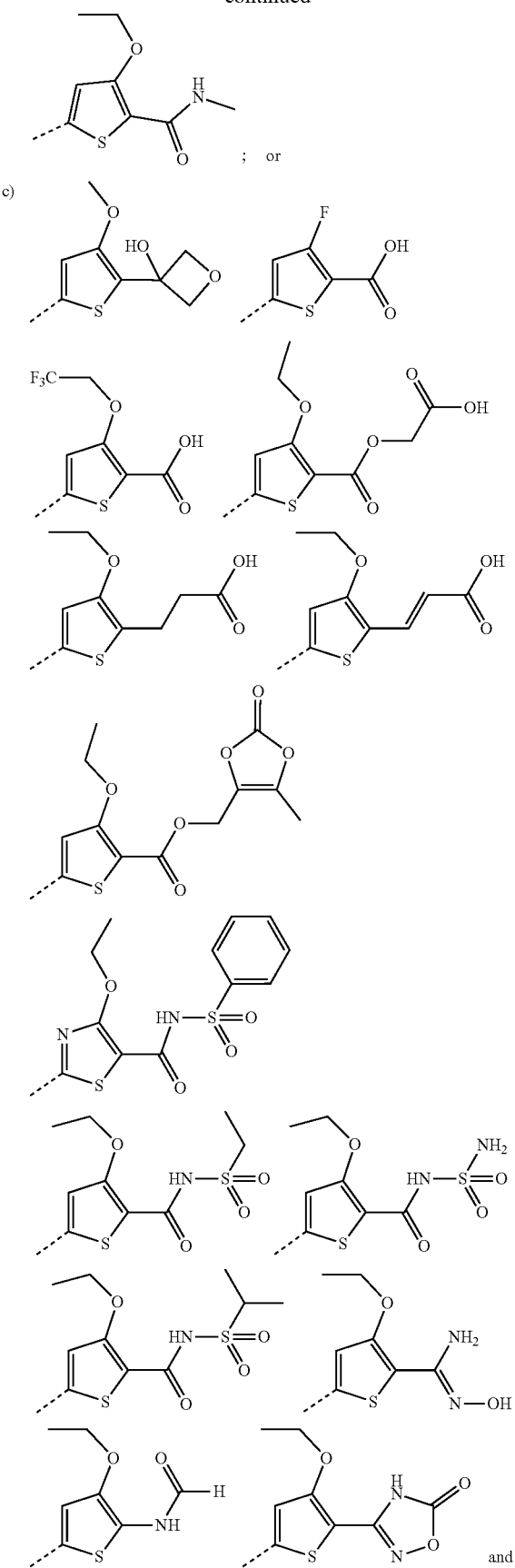
c)
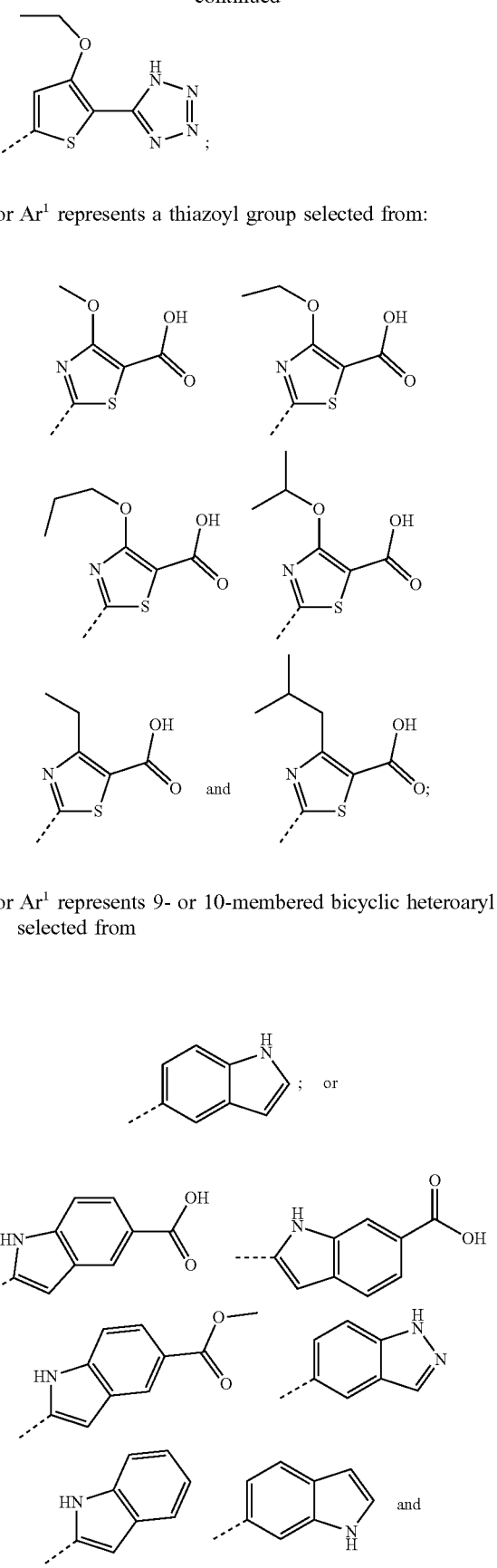
or Ar¹ represents a thiazoyl group selected from:
or Ar¹ represents 9- or 10-membered bicyclic heteroaryl selected from
a)
b)

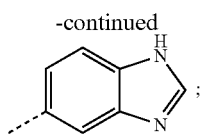

or Ar¹ represents a group selected from:

a)

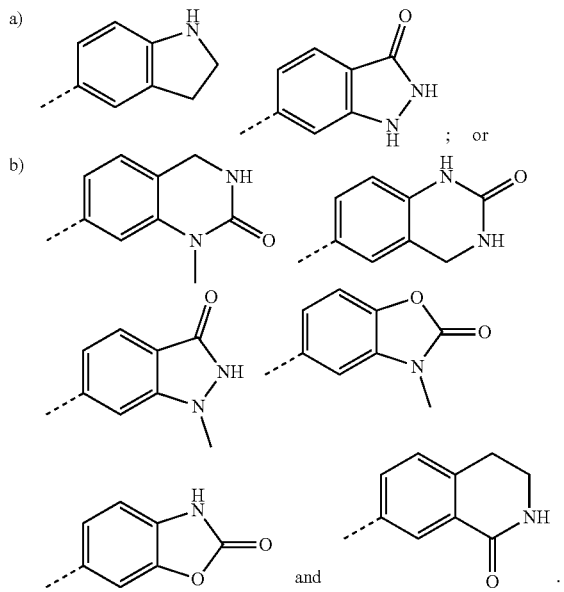

b)

and

7. A method according to claim 1; wherein the group

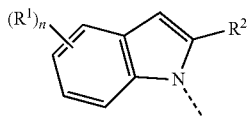

represents

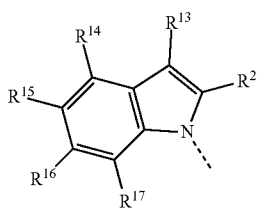

wherein
R² represents methyl, chloro, or cyano; and
R¹³ represents hydrogen; and
R¹⁴, R¹⁵, R¹⁶, and R¹⁷ independently represent the following:
R⁴ represents hydrogen, methyl, ethyl, methoxy, bromo, chloro, fluoro, trifluoromethyl, trifluoromethoxy, or cyano;
R¹⁵ represents hydrogen, methyl, methoxy, chloro, or fluoro;
R¹⁶ represents hydrogen, methoxy, or fluoro; and
R¹⁷ represents hydrogen, methyl, methoxy, chloro, fluoro, or cyano;

wherein at least one of R¹⁴, R¹⁵, R¹⁶, and R¹⁷ represents hydrogen;
or R¹⁴ and R¹⁵ together form a group —O—CH₂—O—, R¹⁶ represents hydrogen and R¹⁷ represents hydrogen or halogen;
or
R² represents (C₁₋₃)alkyl, halogen, or cyano; and
R¹³ represents fluoro; and
R¹⁴, R¹⁵, R¹⁶, and R¹⁷ independently represent the following:
R⁴ represents hydrogen, methyl, ethyl, methoxy, bromo, chloro, fluoro, trifluoromethyl, trifluoromethoxy, or cyano;
R¹⁵ represents hydrogen, methyl, methoxy, chloro, or fluoro;
R¹⁶ represents hydrogen, methoxy, or fluoro; and
R¹⁷ represents hydrogen, methyl, methoxy, chloro, fluoro, or cyano;
wherein at least two of R¹⁴, R¹⁵, R¹⁶, and R¹⁷ represent hydrogen.

8. A method according to claim 1; wherein the group

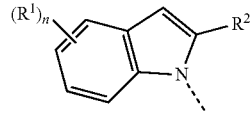

represents a group selected from the following groups A), B), C), D) and E):

A)
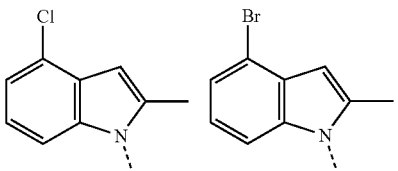
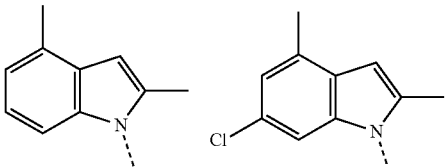
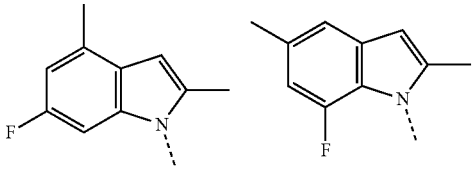
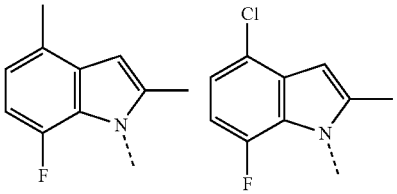
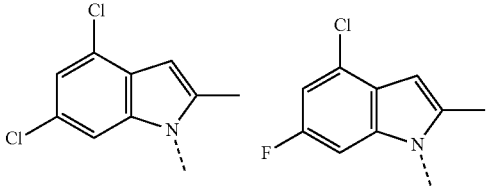

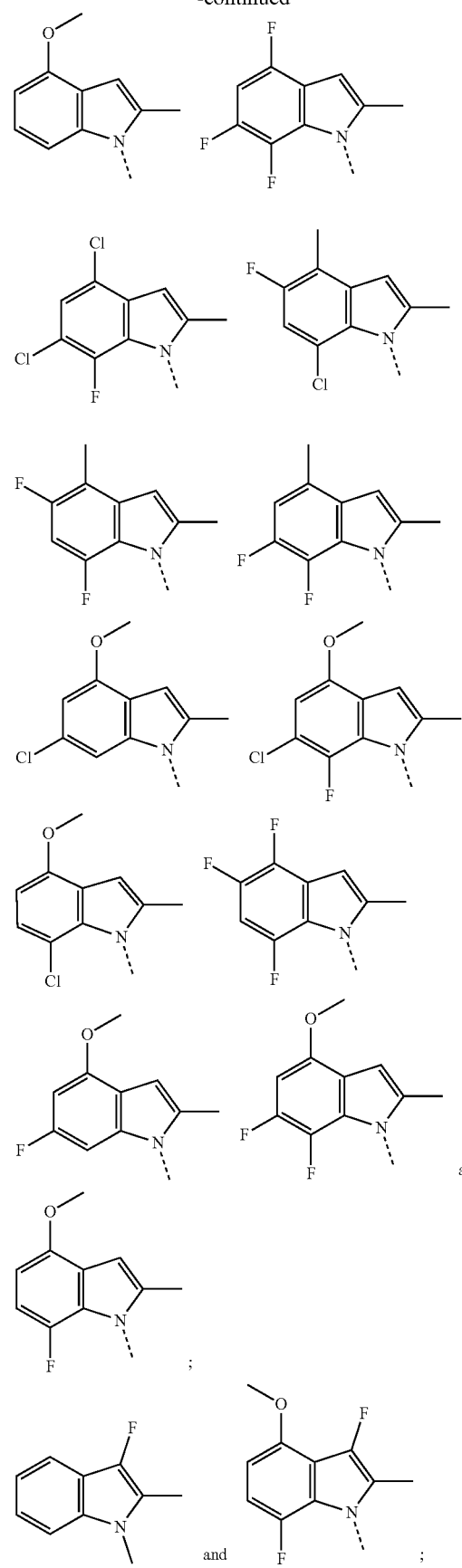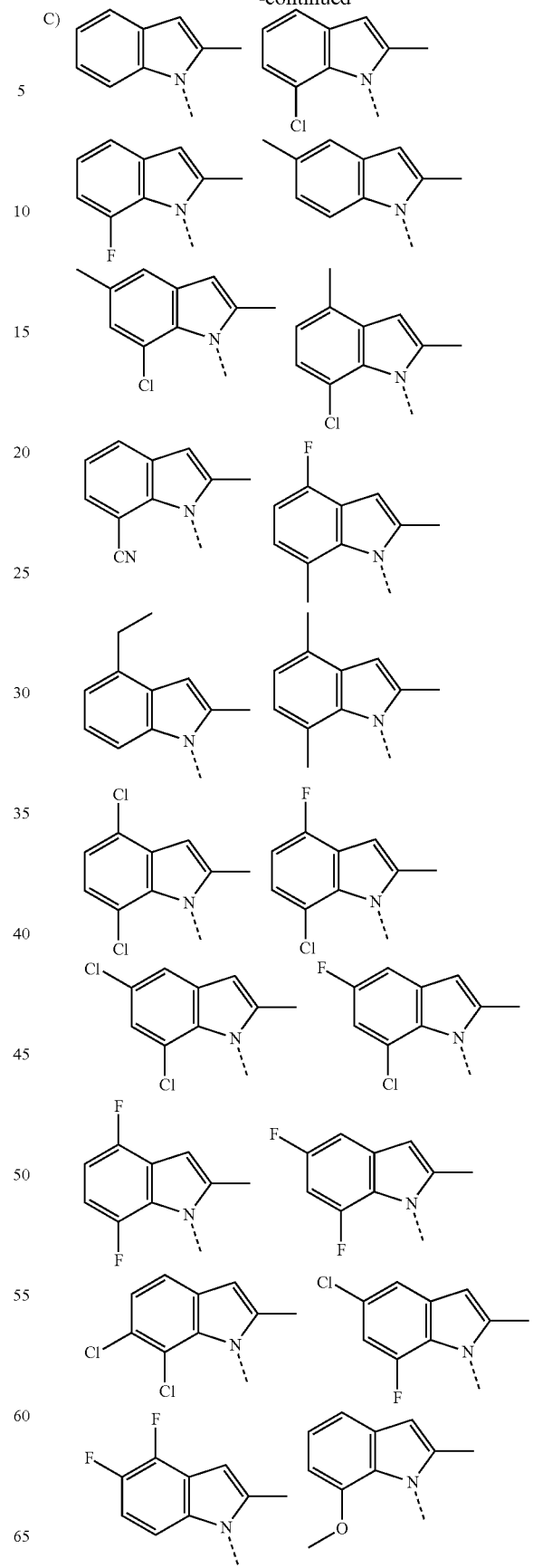

-continued
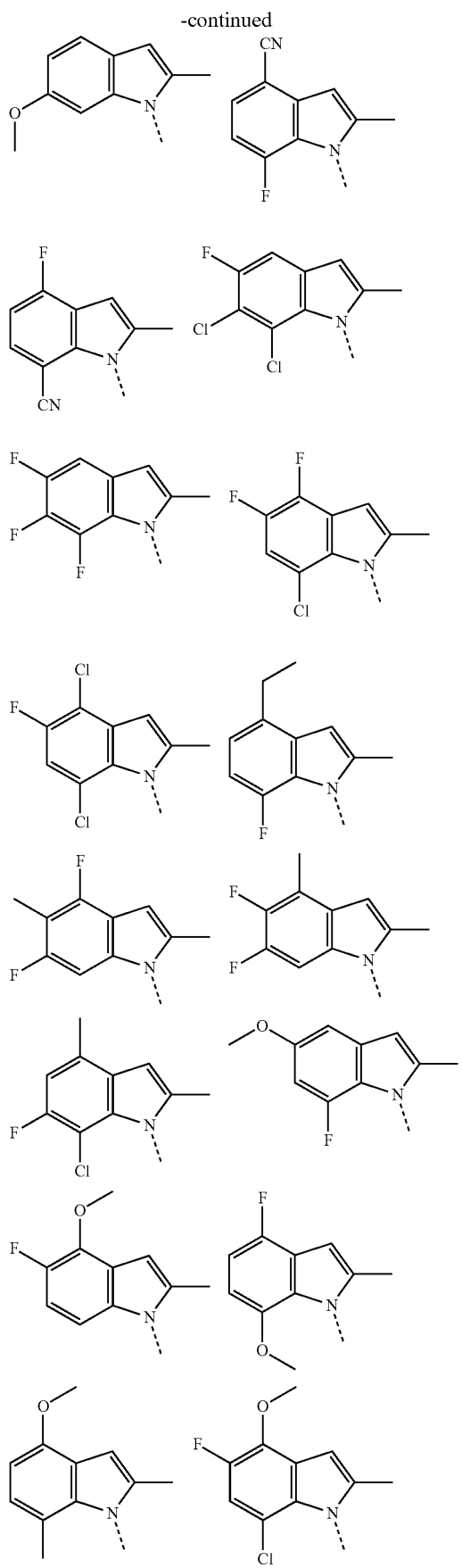
-continued
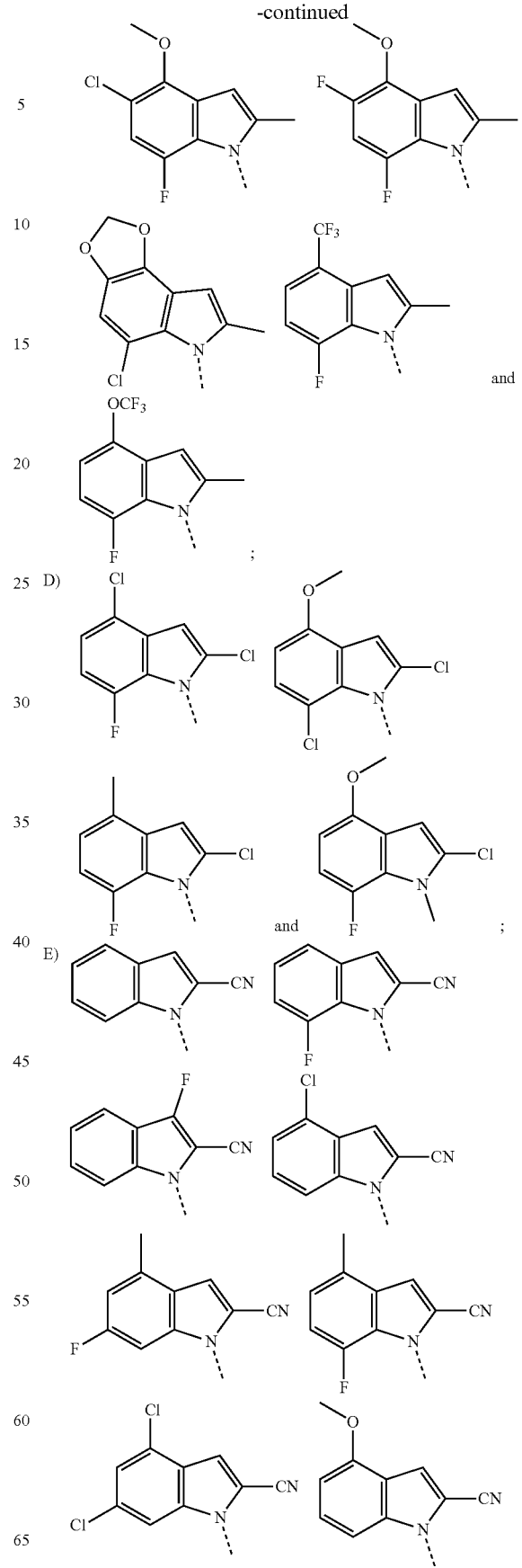
D)
E)

-continued
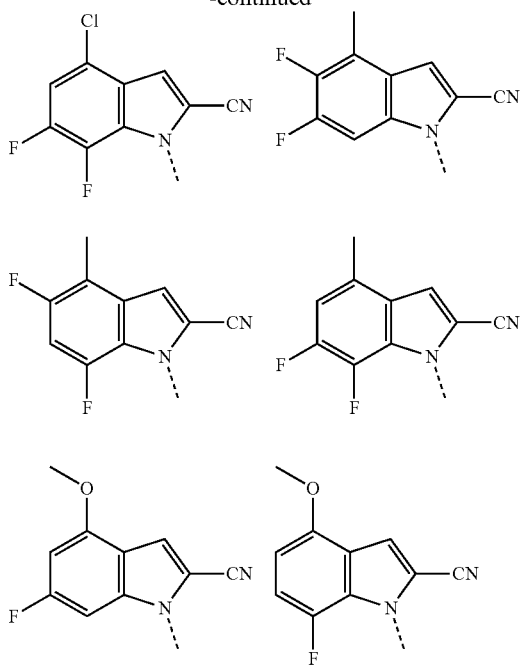
9. A method according to claim 1; wherein the compound is a compound of Formula (III):
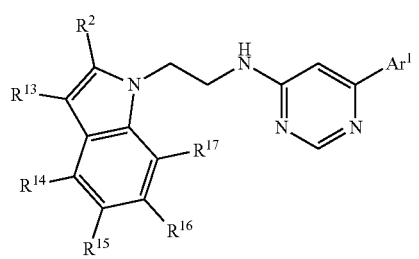
Formula (III)
wherein the group:
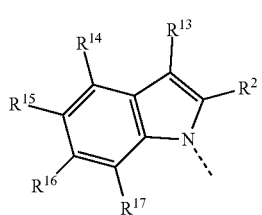
represents a group selected from the following groups A), B), C), D) and E):
A)
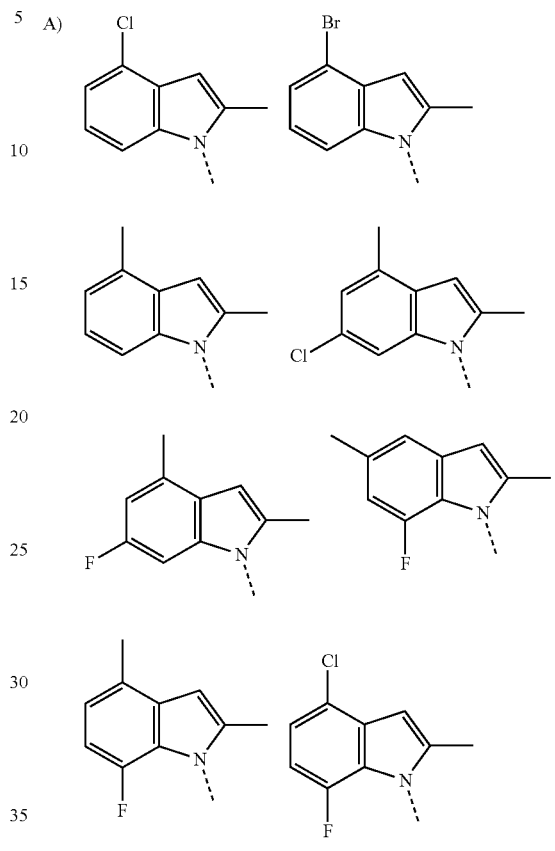
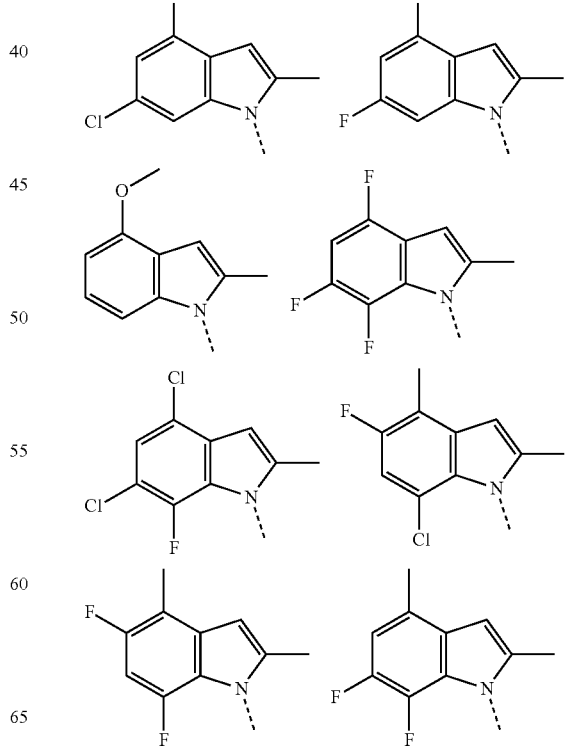

-continued

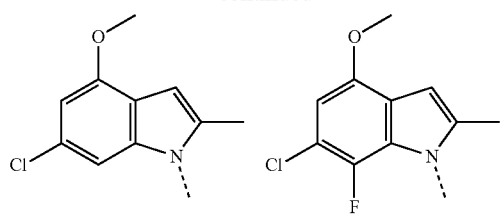

B)

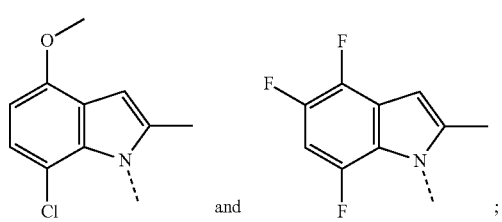

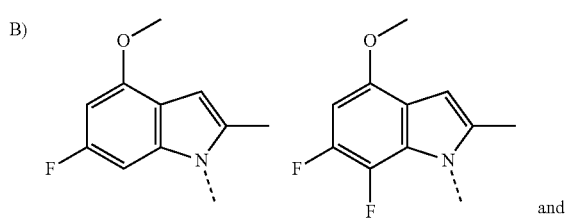

C)

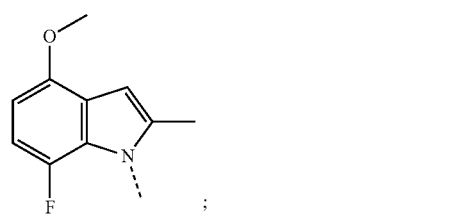

D)

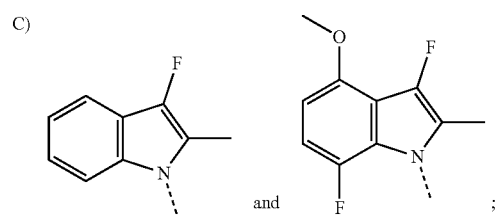

E)

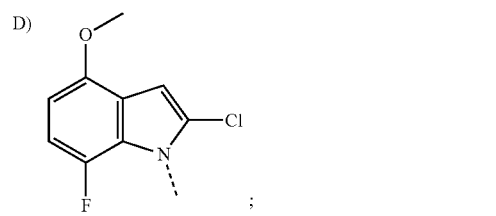

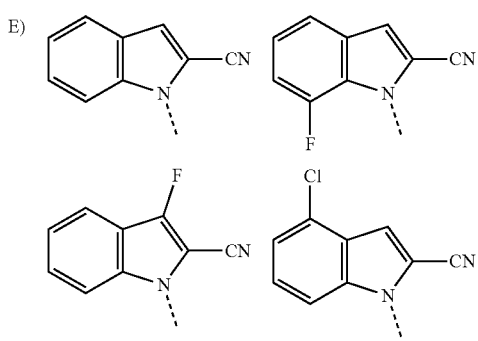

-continued

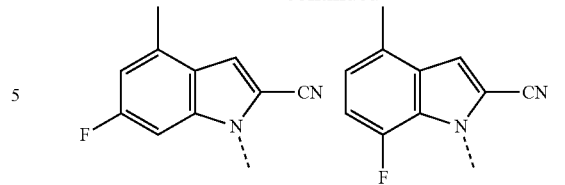

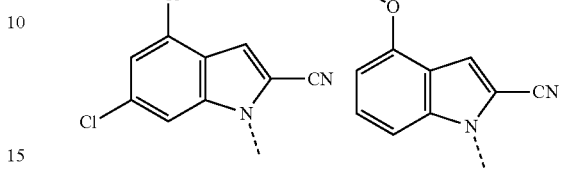

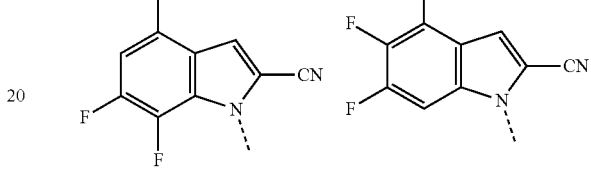

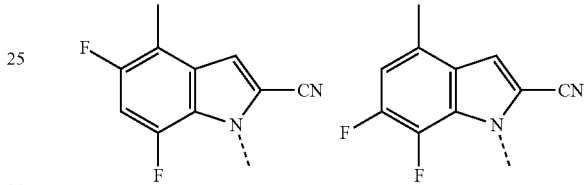

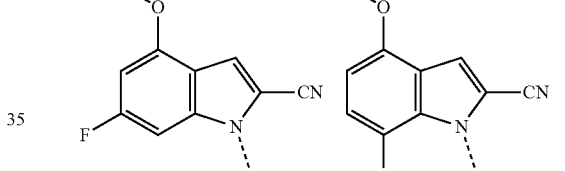

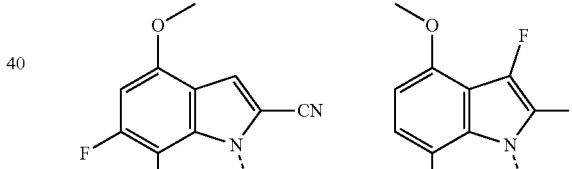

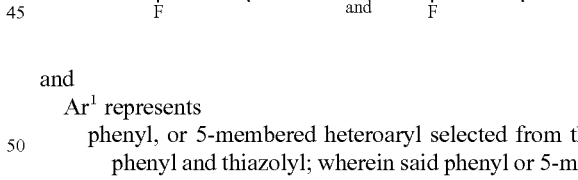

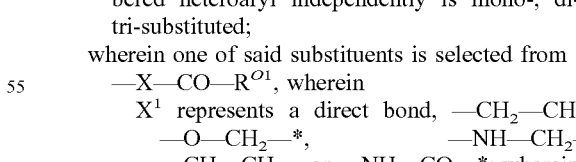

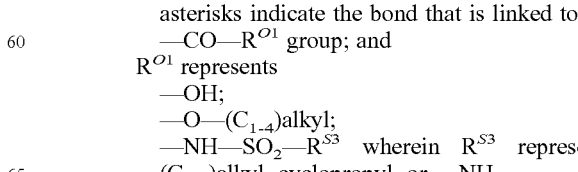

and

Ar¹ represents
phenyl, or 5-membered heteroaryl selected from thiophenyl and thiazolyl; wherein said phenyl or 5-membered heteroaryl independently is mono-, di- or tri-substituted;
wherein one of said substituents is selected from
—X—CO—$R^{O1}$, wherein
$X^1$ represents a direct bond, —CH$_2$—CH$_2$—, —O—CH$_2$—*, —NH—CH$_2$—*, —CH=CH—, or —NH—CO—*; wherein the asterisks indicate the bond that is linked to the —CO—$R^{O1}$ group; and
$R^{O1}$ represents
—OH;
—O—(C$_{1-4}$)alkyl;
—NH—SO$_2$—$R^{S3}$ wherein $R^{S3}$ represents (C$_{1-3}$)alkyl, cyclopropyl, or —NH$_2$,
—O—CH$_2$—CO—$R^{O4}$, wherein $R^{O4}$ represents hydroxy or (C$_{1-4}$)alkoxy; or —O—CH₂—O—CO—R^O5, wherein R^O5 represents (C_{1-4})alkyl or (C_{1-4})alkoxy;
—NR^N1R^N2, wherein R^N1 independently represents hydrogen or (C_{1-3})alkyl, and R^N2 represents —CO—H;
5-oxo-4,5-dihydro-[1,2,4]oxadiazol-3-yl, or 3-oxo-2,3-dihydro-[1,2,4]oxadiazol-5-yl;
1H-tetrazol-5-yl;
3-hydroxy-isoxazol-5-yl;
imidazolyl, which is unsubstituted, or mono- or di-substituted with methyl;
pyrazolyl;
isoxazolyl, oxazolyl, or thiadiazolyl; wherein said isoxazolyl, oxazolyl, or thiadiazolyl is mono-substituted with —NR^N9R^N10, wherein R^N9 represents hydrogen, and R^N10 represents hydrogen or methyl;

and the remaining one or two of said substituents (if present) is/are independently selected from
(C_{1-4})alkyl;
(C_{1-4})alkoxy;
2,2,2-trifluoroethoxy;
halogen;
—NR^N1R^N2, wherein R^N1 represents hydrogen, and R^N2 represents (C_{1-3})alkyl;
—S—R^S2 wherein R^S2 represents (C_{1-4})alkyl;
or Ar¹ represents 8- to 10-membered bicyclic heteroaryl selected from unsubstituted benzimidazol; unsubstituted indazolyl, and indolyl which is unsubstituted or mono-substituted with —COOR^O2 wherein R^O2 represents hydrogen or (C_{1-4})alkyl;
or Ar¹ represents oxo-substituted 8- to 10-membered partially aromatic fused bicyclic heterocyclyl selected from 2-oxo-2,3-dihydro-benzooxazolyl, 3-oxo-2,3-dihydro-1H-indazolyl, 2-oxo-1,2,3,4-tetrahydro-quinazolinyl, and 1-oxo-1,2,3,4-tetrahydro-isoquinolinyl; wherein said oxo-substituted heterocyclyl is unsubstituted or mono-substituted on a ring nitrogen atom with (C_{1-3})alkyl.

10. A method according to claim 1; wherein the compound is selected from the group consisting of:
3-Chloro-5-{6-[2-(6-fluoro-4-methoxy-2-methyl-indol-1-yl)-ethylamino]-pyrimidin-4-yl}-thiophene-2-carboxylic acid;
5-{6-[2-(2-Cyano-indol-1-yl)-ethylamino]-pyrimidin-4-yl}-3-ethoxy-thiophene-2-carboxylic acid;
[6-(2,3-Dihydro-1H-indol-5-yl)-pyrimidin-4-yl]-[2-(6-fluoro-4-methoxy-2-methyl-indol-1-yl)-ethyl]-amine;
[2-(7-Fluoro-2,4-dimethyl-indol-1-yl)-ethyl]-{6-[4-(1H-imidazol-4-yl)-phenyl]-pyrimidin-4-yl}-amine;
3-Ethyl-5-{6-[2-(6-fluoro-2,4-dimethyl-indol-1-yl)-ethylamino]-pyrimidin-4-yl}-thiophene-2-carboxylic acid;
5-{6-[2-(7-Fluoro-4-methoxy-2-methyl-indol-1-yl)-ethylamino]-pyrimidin-4-yl}-3-methyl-thiophene-2-carboxylic acid;
5-{6-[2-(4-Chloro-2-methyl-indol-1-yl)-ethylamino]-pyrimidin-4-yl}-3-ethoxy-thiophene-2-carboxylic acid;
3-Ethyl-5-{6-[2-(4-methoxy-2-methyl-indol-1-yl)-ethylamino]-pyrimidin-4-yl}-thiophene-2-carboxylic acid;
3-Chloro-5-{6-[2-(7-fluoro-4-methoxy-2-methyl-indol-1-yl)-ethylamino]-pyrimidin-4-yl}-thiophene-2-carboxylic acid;
4-{6-[2-(7-Fluoro-2,4-dimethyl-indol-1-yl)-ethylamino]-pyrimidin-4-yl}-2-methylamino-benzoic acid;
5-{6-[2-(5,7-Difluoro-2,4-dimethyl-indol-1-yl)-ethylamino]-pyrimidin-4-yl}-3-ethoxy-thiophene-2-carboxylic acid;
{6-[4-(3-Amino-isoxazol-5-yl)-phenyl]-pyrimidin-4-yl}-[2-(4-methoxy-2-methyl-indol-1-yl)-ethyl]-amine;
[2-(6-Fluoro-4-methoxy-2-methyl-indol-1-yl)-ethyl]-{6-[4-(1H-imidazol-4-yl)-phenyl]-pyrimidin-4-yl}-amine;
[2-(7-Fluoro-4-methoxy-2-methyl-indol-1-yl)-ethyl]-{6-[4-(1H-imidazol-4-yl)-phenyl]-pyrimidin-4-yl}-amine;
[2-(7-Fluoro-4-methoxy-2-methyl-indol-1-yl)-ethyl]-{6-[4-(2H-pyrazol-3-yl)-phenyl]-pyrimidin-4-yl}-amine;
3-Ethoxy-5-{6-[2-(4-methoxy-2-methyl-indol-1-yl)-ethylamino]-pyrimidin-4-yl}-thiophene-2-carboxylic acid;
5-{6-[2-(6-Chloro-2,4-dimethyl-indol-1-yl)-ethylamino]-pyrimidin-4-yl}-3-ethoxy-thiophene-2-carboxylic acid;
3-Ethoxy-5-{6-[2-(7-fluoro-2,4-dimethyl-indol-1-yl)-ethylamino]-pyrimidin-4-yl}-thiophene-2-carboxylic acid;
3-Ethoxy-5-{6-[2-(7-fluoro-2,5-dimethyl-indol-1-yl)-ethylamino]-pyrimidin-4-yl}-thiophene-2-carboxylic acid;
3-Ethoxy-5-{6-[2-(6-fluoro-2,4-dimethyl-indol-1-yl)-ethylamino]-pyrimidin-4-yl}-thiophene-2-carboxylic acid;
3-Ethyl-5-{6-[2-(7-fluoro-4-methoxy-2-methyl-indol-1-yl)-ethylamino]-pyrimidin-4-yl}-thiophene-2-carboxylic acid;
5-{6-[2-(4,6-Dichloro-2-methyl-indol-1-yl)-ethylamino]-pyrimidin-4-yl}-3-ethoxy-thiophene-2-carboxylic acid;
5-{6-[2-(4-Chloro-6-fluoro-2-methyl-indol-1-yl)-ethylamino]-pyrimidin-4-yl}-3-ethoxy-thiophene-2-carboxylic acid;
5-{6-[2-(4-Chloro-7-fluoro-2-methyl-indol-1-yl)-ethylamino]-pyrimidin-4-yl}-3-ethoxy-thiophene-2-carboxylic acid;
5-{6-[2-(2-Cyano-6-fluoro-4-methyl-indol-1-yl)-ethylamino]-pyrimidin-4-yl}-3-ethoxy-thiophene-2-carboxylic acid;
4-{6-[2-(7-Fluoro-4-methoxy-2-methyl-indol-1-yl)-ethylamino]-pyrimidin-4-yl}-2-methylamino-benzoic acid;
5-{6-[2-(7-Chloro-4-methoxy-2-methyl-indol-1-yl)-ethylamino]-pyrimidin-4-yl}-3-ethoxy-thiophene-2-carboxylic acid;
3-Ethoxy-5-{6-[2-(6-fluoro-4-methoxy-2-methyl-indol-1-yl)-ethylamino]-pyrimidin-4-yl}-thiophene-2-carboxylic acid;
3-Ethoxy-5-{6-[2-(7-fluoro-4-methoxy-2-methyl-indol-1-yl)-ethylamino]-pyrimidin-4-yl}-thiophene-2-carboxylic acid;
3-Ethoxy-5-{6-[2-(4,6,7-trifluoro-2-methyl-indol-1-yl)-ethylamino]-pyrimidin-4-yl}-thiophene-2-carboxylic acid;
3-Ethoxy-5-{6-[2-(4,5,7-trifluoro-2-methyl-indol-1-yl)-ethylamino]-pyrimidin-4-yl}-thiophene-2-carboxylic acid;
5-{6-[2-(6,7-Difluoro-2,4-dimethyl-indol-1-yl)-ethylamino]-pyrimidin-4-yl}-3-ethoxy-thiophene-2-carboxylic acid;
{6-[4-(3-Amino-isoxazol-5-yl)-phenyl]-pyrimidin-4-yl}-[2-(7-fluoro-4-methoxy-2-methyl-indol-1-yl)-ethyl]-amine;

[2-(6,7-Difluoro-4-methoxy-2-methyl-indol-1-yl)-ethyl]-{6-[4-(1H-imidazol-4-yl)-phenyl]-pyrimidin-4-yl}-amine;

[2-(7-Fluoro-2,4-dimethyl-indol-1-yl)-ethyl]-{6-[4-(5-methylamino-[1,3,4]thiadiazol-2-yl)-phenyl]-pyrimidin-4-yl}-amine;

5-{6-[2-(2-Cyano-6-fluoro-4-methoxy-indol-1-yl)-ethylamino]-pyrimidin-4-yl}-3-ethoxy-thiophene-2-carboxylic acid;

2-Ethylamino-4-{6-[2-(7-fluoro-4-methoxy-2-methyl-indol-1-yl)-ethylamino]-pyrimidin-4-yl}-benzoic acid;

5-{6-[2-(6,7-Difluoro-4-methoxy-2-methyl-indol-1-yl)-ethylamino]-pyrimidin-4-yl}-3-ethoxy-thiophene-2-carboxylic acid;

5-{6-[2-(6-Fluoro-2,4-dimethyl-indol-1-yl)-ethylamino]-2-methyl-pyrimidin-4-yl}-3-trifluoromethyl-thiophene-2-carboxylic acid;

5-{6-[2-(7-Fluoro-4-methoxy-2-methyl-indol-1-yl)-ethylamino]-pyrimidin-4-yl}-3-trifluoromethyl-thiophene-2-carboxylic acid;

5-{6-[2-(6-Fluoro-4-methoxy-2-methyl-indol-1-yl)-ethylamino]-pyrimidin-4-yl}-3-trifluoromethyl-thiophene-2-carboxylic acid;

[2-(7-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine;

4-(4-{6-[2-(7-Fluoro-4-methoxy-2-methyl-indol-1-yl)-ethylamino]-pyrimidin-4-yl}-phenyl)-thiazole-2-carboxylic acid;

2-Chloro-4-{6-[2-(6-chloro-4-methoxy-2-methyl-indol-1-yl)-ethylamino]-pyrimidin-4-yl}-6-propyl-benzoic acid;

2-Chloro-4-{6-[2-(6-fluoro-4-methoxy-2-methyl-indol-1-yl)-ethylamino]-pyrimidin-4-yl}-6-propyl-benzoic acid;

5-{6-[2-(6,7-Difluoro-4-methoxy-2-methyl-indol-1-yl)-ethylamino]-pyrimidin-4-yl}-3-trifluoromethyl-thiophene-2-carboxylic acid;

4-{6-[2-(6-Fluoro-4-methoxy-2-methyl-indol-1-yl)-ethylamino]-pyrimidin-4-yl}-2-isobutyl-benzoic acid;

5-{6-[2-(7-Fluoro-4-methoxy-2-methyl-indol-1-yl)-ethylamino]-2-methyl-pyrimidin-4-yl}-3-trifluoromethyl-thiophene-2-carboxylic acid;

5-{6-[2-(6-Fluoro-4-methoxy-2-methyl-indol-1-yl)-ethylamino]-2-methyl-pyrimidin-4-yl}-3-trifluoromethyl-thiophene-2-carboxylic acid;

1-Ethyl-3-(4-{6-[2-(7-fluoro-4-methoxy-2-methyl-indol-1-yl)-ethylamino]-pyrimidin-4-yl}-2-methoxy-phenyl)-urea;

{6-[4-(2-Amino-oxazol-5-yl)-phenyl]-pyrimidin-4-yl}-[2-(6-fluoro-4-methoxy-2-methyl-indol-1-yl)-ethyl]-amine;

{6-[4-(2-Amino-oxazol-5-yl)-phenyl]-pyrimidin-4-yl}-[2-(7-fluoro-4-methoxy-2-methyl-indol-1-yl)-ethyl]-amine;

2-(4-{6-[2-(6-Fluoro-4-methoxy-2-methyl-indol-1-yl)-ethylamino]-pyrimidin-4-yl}-phenyl)-thiazole-4-carboxylic acid;

2-(4-{6-[2-(7-Fluoro-4-methoxy-2-methyl-indol-1-yl)-ethylamino]-pyrimidin-4-yl}-phenyl)-thiazole-4-carboxylic acid;

[2-(6-Fluoro-4-methoxy-2-methyl-indol-1-yl)-ethyl]-{6-[4-(2-methyl-1H-imidazol-4-yl)-phenyl]-pyrimidin-4-yl}-amine;

[2-(6-Fluoro-2,4-dimethyl-indol-1-yl)-ethyl]-{6-[4-(5-methylamino-[1,3,4]thiadiazol-2-yl)-phenyl]-pyrimidin-4-yl}-amine;

4-{6-[2-(2-Cyano-6-fluoro-4-methoxy-indol-1-yl)-ethylamino]-pyrimidin-4-yl}-2-isobutyl-benzoic acid;

2-Chloro-4-{6-[2-(7-fluoro-4-methoxy-2-methyl-indol-1-yl)-ethylamino]-pyrimidin-4-yl}-6-propoxy-benzoic acid;

2-Butoxy-4-{6-[2-(7-fluoro-4-methoxy-2-methyl-indol-1-yl)-ethylamino]-pyrimidin-4-yl}-benzoic acid;

{6-[4-(2-Amino-oxazol-5-yl)-phenyl]-pyrimidin-4-yl}-[2-(6,7-difluoro-4-methoxy-2-methyl-indol-1-yl)-ethyl]-amine;

[2-(6,7-Difluoro-4-methoxy-2-methyl-indol-1-yl)-ethyl]-{6-[4-(2-methyl-1H-imidazol-4-yl)-phenyl]-pyrimidin-4-yl}-amine;

[2-(6-Fluoro-4-methoxy-2-methyl-indol-1-yl)-ethyl]-{6-[4-(5-methylamino-[1,3,4]thiadiazol-2-yl)-phenyl]-pyrimidin-4-yl}-amine;

{6-[3-Ethoxy-4-(1H-tetrazol-5-yl)-phenyl]-pyrimidin-4-yl}-[2-(7-fluoro-4-methoxy-2-methyl-indol-1-yl)-ethyl]-amine;

{6-[3-Ethylamino-4-(1H-tetrazol-5-yl)-phenyl]-pyrimidin-4-yl}-[2-(7-fluoro-4-methoxy-2-methyl-indol-1-yl)-ethyl]-amine;

[2-(7-Chloro-4-methoxy-2-methyl-indol-1-yl)-ethyl]-{6-[3-ethylamino-4-(1H-tetrazol-5-yl)-phenyl]-pyrimidin-4-yl}-amine;

{6-[3-Ethylamino-4-(1H-tetrazol-5-yl)-phenyl]-pyrimidin-4-yl}-[2-(4-methoxy-2-methyl-indol-1-yl)-ethyl]-amine;

{6-[3-Ethylamino-4-(1H-tetrazol-5-yl)-phenyl]-pyrimidin-4-yl}-[2-(7-fluoro-2,4-dimethyl-indol-1-yl)-ethyl]-amine;

3-Butoxy-5-{6-[2-(6-fluoro-4-methoxy-2-methyl-indol-1-yl)-ethylamino]-pyrimidin-4-yl}-thiophene-2-carboxylic acid;

3-Butoxy-5-{6-[2-(7-fluoro-4-methoxy-2-methyl-indol-1-yl)-ethylamino]-pyrimidin-4-yl}-thiophene-2-carboxylic acid;

5-{6-[2-(6-Fluoro-4-methoxy-2-methyl-indol-1-yl)-ethylamino]-pyrimidin-4-yl}-3-propoxy-thiophene-2-carboxylic acid;

5-{6-[2-(7-Fluoro-4-methoxy-2-methyl-indol-1-yl)-ethylamino]-pyrimidin-4-yl}-3-isopropoxy-thiophene-2-carboxylic acid;

5-{6-[2-(6-Fluoro-4-methoxy-2-methyl-indol-1-yl)-ethylamino]-pyrimidin-4-yl}-3-isopropoxy-thiophene-2-carboxylic acid;

5-{6-[2-(7-Fluoro-4-methoxy-2-methyl-indol-1-yl)-ethylamino]-pyrimidin-4-yl}-3-propoxy-thiophene-2-carboxylic acid;

3-(4-{6-[2-(6,7-Difluoro-4-methoxy-2-methyl-indol-1-yl)-ethylamino]-pyrimidin-4-yl}-phenyl)-4H-[1,2,4]oxadiazol-5-one;

2-Chloro-4-{6-[2-(7-fluoro-4-methoxy-2-methyl-indol-1-yl)-ethylamino]-pyrimidin-4-yl}-6-isobutoxy-benzoic acid;

[2-(7-Fluoro-4-methoxy-2-methyl-indol-1-yl)-ethyl]-[6-(1H-indol-5-yl)-pyrimidin-4-yl]-amine;

[2-(6,7-Difluoro-4-methoxy-2-methyl-indol-1-yl)-ethyl]-[6-(1H-indol-5-yl)-pyrimidin-4-yl]-amine;

6-{6-[2-(7-Fluoro-4-methoxy-2-methyl-indol-1-yl)-ethylamino]-pyrimidin-4-yl}-1,2-dihydro-indazol-3-one;

4-{6-[2-(2-Chloro-7-fluoro-4-methoxy-indol-1-yl)-ethylamino]-pyrimidin-4-yl}-2-ethoxy-benzoic acid;

5-{6-[2-(2-Chloro-7-fluoro-4-methoxy-indol-1-yl)-ethylamino]-pyrimidin-4-yl}-3-ethoxy-thiophene-2-carboxylic acid;

5-{6-[2-(4-Bromo-2-methyl-indol-1-yl)-ethylamino]-pyrimidin-4-yl}-3-ethoxy-thiophene-2-carboxylic acid;
[2-(7-Fluoro-4-methoxy-2-methyl-indol-1-yl)-ethyl]-{6-[5-(1H-tetrazol-5-yl)-thiophen-2-yl]-pyrimidin-4-yl}-amine;
5-{6-[2-(6-Fluoro-4-methoxy-2-methyl-indol-1-yl)-ethylamino]-pyrimidin-4-yl}-3-hydroxy-thiophene-2-carboxylic acid;
5-{6-[2-(2-Cyano-7-fluoro-4-methoxy-indol-1-yl)-ethylamino]-pyrimidin-4-yl}-3-isopropoxy-thiophene-2-carboxylic acid;
1-(2-{6-[3-Ethoxy-4-(1H-tetrazol-5-yl)-phenyl]-pyrimidin-4-ylamino}-ethyl)-7-fluoro-4-methoxy-1H-indole-2-carbonitrile;
5-{6-[2-(2-Cyano-7-fluoro-4-methoxy-indol-1-yl)-ethylamino]-pyrimidin-4-yl}-3-trifluoromethyl-thiophene-2-carboxylic acid;
5-{6-[2-(2-cyano-7-fluoro-4-methoxy-indol-1-yl)-ethylamino]-pyrimidin-4-yl}-3-ethoxy-thiophene-2-carboxylic acid;
5-{6-[2-(2-Cyano-7-fluoro-4-methoxy-indol-1-yl)-ethylamino]-pyrimidin-4-yl}-3-fluoro-thiophene-2-carboxylic acid;
4-{6-[2-(2-Cyano-7-fluoro-4-methoxy-indol-1-yl)-ethylamino]-pyrimidin-4-yl}-2-ethoxy-benzoic acid;
(4-{6-[2-(2-Cyano-7-fluoro-4-methoxy-indol-1-yl)-ethylamino]-pyrimidin-4-yl}-2-ethoxy-phenoxy)-acetic acid;
N-(5-{6-[2-(2-Cyano-7-fluoro-4-methoxy-indol-1-yl)-ethylamino]-pyrimidin-4-yl}-3-ethoxy-thiophene-2-carbonyl)-methanesulfonamide;
(2-Ethoxy-4-{6-[2-(7-fluoro-4-methoxy-2-methyl-indol-1-yl)-ethylamino]-pyrimidin-4-yl}-phenoxy)-acetic acid;
(2-Ethoxy-4-{6-[2-(7-fluoro-4-methoxy-2-methyl-indol-1-yl)-ethylamino]-pyrimidin-4-yl}-phenylamino)-acetic acid;
5-{6-[2-(2-Cyano-4-methoxy-indol-1-yl)-ethylamino]-pyrimidin-4-yl}-3-ethoxy-thiophene-2-carboxylic acid;
N-(5-{6-[2-(2-Cyano-7-fluoro-4-methoxy-indol-1-yl)-ethylamino]-pyrimidin-4-yl}-3-ethoxy-thiophene-2-carbonyl)-benzenesulfonamide;
Propane-2-sulfonic acid (5-{6-[2-(2-cyano-7-fluoro-4-methoxy-indol-1-yl)-ethylamino]-pyrimidin-4-yl}-3-ethoxy-thiophene-2-carbonyl)-amide;
Cyclopropanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide;
5-{6-[2-(2-Cyano-7-fluoro-4-methoxy-indol-1-yl)-ethylamino]-pyrimidin-4-yl}-3-ethoxy-thiophene-2-carboxylic acid methylamide;
Ethanesulfonic acid (5-{6-[2-(2-cyano-7-fluoro-4-methoxy-indol-1-yl)-ethylamino]-pyrimidin-4-yl}-3-ethoxy-thiophene-2-carbonyl)-amide;
7-Fluoro-1-(2-{6-[4-(1H-imidazol-4-yl)-3-methoxy-phenyl]-pyrimidin-4-ylamino}-ethyl)-4-methoxy-1H-indole-2-carbonitrile;
7-Fluoro-4-methoxy-1-(2-{6-[4-(5-methyl-1H-imidazol-4-yl)-phenyl]-pyrimidin-4-ylamino}-ethyl)-1H-indole-2-carbonitrile;
1-(2-{6-[3-Ethoxy-4-(5-oxo-4,5-dihydro-[1,2,4]oxadiazol-3-yl)-phenyl]-pyrimidin-4-ylamino}-ethyl)-7-fluoro-4-methoxy-1H-indole-2-carbonitrile;
1-(2-{6-[4-(2,5-Dimethyl-1H-imidazol-4-yl)-phenyl]-pyrimidin-4-ylamino}-ethyl)-7-fluoro-4-methoxy-1H-indole-2-carbonitrile;
1-{2-[6-(3-Ethyl-4-hydroxy-phenyl)-pyrimidin-4-ylamino]-ethyl}-7-fluoro-4-methoxy-1H-indole-2-carbonitrile;
1-(2-{6-[4-(1,5-Dimethyl-1H-imidazol-4-yl)-phenyl]-pyrimidin-4-ylamino}-ethyl)-7-fluoro-4-methoxy-1H-indole-2-carbonitrile;
1-(2-{6-[4-(1,2-Dimethyl-1H-imidazol-4-yl)-phenyl]-pyrimidin-4-ylamino}-ethyl)-7-fluoro-4-methoxy-1H-indole-2-carbonitrile;
7-Fluoro-1-(2-{6-[4-(5-oxo-4,5-dihydro-[1,2,4]oxadiazol-3-yl)-phenyl]-pyrimidin-4-ylamino}-ethyl)-4-methoxy-1H-indole-2-carbonitrile;
7-Fluoro-1-(2-{6-[5-(3-hydroxy-oxetan-3-yl)-4-methoxy-thiophen-2-yl]-pyrimidin-4-ylamino}-ethyl)-4-methoxy-1H-indole-2-carbonitrile;
1-(2-{6-[4-(2-Cyclopropyl-1-methyl-1H-imidazol-4-yl)-phenyl]-pyrimidin-4-ylamino}-ethyl)-7-fluoro-4-methoxy-1H-indole-2-carbonitrile;
(4-{6-[2-(2-Cyano-7-fluoro-4-methoxy-indol-1-yl)-ethylamino]-pyrimidin-4-yl}-2-trifluoromethoxy-phenoxy)-acetic acid;
7-Fluoro-1-(2-{6-[4-(3H-imidazol-4-yl)-phenyl]-pyrimidin-4-ylamino}-ethyl)-4-methoxy-1H-indole-2-carbonitrile;
3-(2-Ethoxy-4-{6-[2-(7-fluoro-4-methoxy-2-methyl-indol-1-yl)-ethylamino]-pyrimidin-4-yl}-phenyl)-[1,2,4]oxadiazol-5(4H)-one;
7-Fluoro-1-(2-{6-[4-(3-oxo-2,3-dihydro-1,2,4-oxadiazol-5-yl)-phenyl]-pyrimidin-4-ylamino}-ethyl)-4-methoxy-1H-indole-2-carbonitrile;
5-{6-[2-(7-Fluoro-4-methoxy-2-methyl-indol-1-yl)-ethylamino]-pyrimidin-4-yl}-3-(2,2,2-trifluoro-ethoxy)-thiophene-2-carboxylic acid;
(4-{6-[2-(2-Cyano-7-fluoro-4-methoxy-indol-1-yl)-ethylamino]-pyrimidin-4-yl}-2-ethyl-phenoxy)-acetic acid;
3-(2-Ethoxy-4-{6-[2-(6-fluoro-2,4-dimethyl-indol-1-yl)-ethylamino]-pyrimidin-4-yl}-phenyl)-[1,2,4]oxadiazol-5(4H)-one;
2-butoxy-6-chloro-4-(6-((2-(7-fluoro-4-methoxy-2-methyl-1H-indol-1-yl)ethyl-1,1,2,2-d4)amino)pyrimidin-4-yl)benzoic acid;
5-{6-[2-(7-Chloro-5-fluoro-2,4-dimethyl-indol-1-yl)-ethylamino]-pyrimidin-4-yl}-3-ethoxy-thiophene-2-carboxylic acid;
5-{6-[2-(6-Fluoro-4-methoxy-2-methyl-indol-1-yl)-ethylamino]-pyrimidin-4-yl}-3-(2,2,2-trifluoro-ethoxy)-thiophene-2-carboxylic acid;
2-(2-Ethoxy-4-{6-[2-(7-fluoro-4-methoxy-2-methyl-indol-1-yl)-ethylamino]-pyrimidin-4-yl}-phenylamino)-propionic acid;
5-{6-[2-(2-Cyano-3-fluoro-indol-1-yl)-ethylamino]-pyrimidin-4-yl}-3-trifluoromethyl-thiophene-2-carboxylic acid;
5-{6-[2-(2-Cyano-7-fluoro-4-methyl-indol-1-yl)-ethylamino]-pyrimidin-4-yl}-3-fluoro-thiophene-2-carboxylic acid;
7-Fluoro-1-(2-{6-[4-(3-hydroxy-isoxazol-5-yl)-phenyl]-pyrimidin-4-ylamino}-ethyl)-4-methoxy-1H-indole-2-carbonitrile;
N-(4-{6-[2-(2-Cyano-7-fluoro-4-methoxy-indol-1-yl)-ethylamino]-pyrimidin-4-yl}-2-ethoxy-phenyl)-oxalamic acid;
7-Fluoro-1-(2-{6-[4-(3-hydroxy-isoxazol-5-yl)-3-methoxy-phenyl]-pyrimidin-4-ylamino}-ethyl)-4-methoxy-1H-indole-2-carbonitrile;

5-{6-[2-(2-Cyano-7-fluoro-4-methyl-indol-1-yl)-ethylamino]-pyrimidin-4-yl}-3-trifluoromethyl-thiophene-2-carboxylic acid;
(4-{6-[2-(2-Cyano-7-fluoro-4-methoxy-indol-1-yl)-ethylamino]-pyrimidin-4-yl}-2-ethoxy-phenylamino)-acetic acid;
1-(2-{6-[4-(2-Cyclopropyl-1H-imidazol-4-yl)-phenyl]-pyrimidin-4-ylamino}-ethyl)-7-fluoro-4-methoxy-1H-indole-2-carbonitrile;
5-{6-[2-(6-Chloro-7-fluoro-4-methoxy-2-methyl-indol-1-yl)-ethylamino-pyrimidin-4-yl}-3-ethoxy-thiophene-2-carboxylic acid;
(4-{6-[2-(2-Cyano-4-methoxy-indol-1-yl)-ethylamino]-pyrimidin-4-yl}-2-ethoxy-phenylamino)-acetic acid;
7-Fluoro-1-{2-[6-(4-hydroxy-3-trifluoromethoxy-phenyl)-pyrimidin-4-ylamino]-ethyl}-4-methoxy-1H-indole-2-carbonitrile;
1-{2-[6-(3-Chloro-4-hydroxy-phenyl)-pyrimidin-4-ylamino]-ethyl}-7-fluoro-4-methoxy-1H-indole-2-carbonitrile;
5-{6-[2-(4,6-Dichloro-7-fluoro-2-methyl-indol-1-yl)-ethylamino]-pyrimidin-4-yl}-3-ethoxy-thiophene-2-carboxylic acid;
5-{6-[2-(6-Chloro-4-methoxy-2-methyl-indol-1-yl)-ethylamino]-pyrimidin-4-yl}-3-isopropoxy-thiophene-2-carboxylic acid;
(4-{6-[2-(2-Cyano-4-methoxy-indol-1-yl)-ethylamino]-pyrimidin-4-yl}-2-ethoxy-phenoxy)-acetic acid;
5-{6-[2-(6-Chloro-4-methoxy-2-methyl-indol-1-yl)-ethylamino]-pyrimidin-4-yl}-3-ethoxy-thiophene-2-carboxylic acid;
2-Butoxy-4-{6-[2-(2-cyano-7-fluoro-4-methoxy-indol-1-yl)-ethylamino]-pyrimidin-4-yl}-benzoic acid;
4-{6-[2-(7-Fluoro-4-methoxy-2-methyl-indol-1-yl)-ethylamino]-pyrimidin-4-yl}-2-trifluoromethoxy-phenol;
3-Ethoxy-5-{6-[2-(3-fluoro-2-methyl-indol-1-yl)-ethylamino]-pyrimidin-4-yl}-thiophene-2-carboxylic acid;
5-{6-[2-(2-Cyano-3-fluoro-indol-1-yl)-ethylamino]-pyrimidin-4-yl}-3-ethoxy-thiophene-2-carboxylic acid;
(2-Ethoxy-4-{6-[2-(7-fluoro-2,4-dimethyl-indol-1-yl)-ethylamino]-pyrimidin-4-yl}-phenylamino)-acetic acid;
2-Butoxy-4-{6-[2-(6,7-difluoro-4-methoxy-2-methyl-indol-1-yl)-ethylamino]-pyrimidin-4-yl}-benzoic acid;
5-{6-[2-(2,4-Dimethyl-indol-1-yl)-ethylamino]-pyrimidin-4-yl}-3-isopropoxy-thiophene-2-carboxylic acid;
5-{6-[2-(2,4-Dimethyl-indol-1-yl)-ethylamino]-pyrimidin-4-yl}-3-ethoxy-thiophene-2-carboxylic acid;
3-(2-Ethoxy-4-{6-[2-(4-methoxy-2-methyl-indol-1-yl)-ethylamino]-pyrimidin-4-yl}-phenyl)-[1,2,4]oxadiazol-5(4H)-one;
5-{6-[2-(4,6-Dichloro-2-cyano-indol-1-yl)-ethylamino]-pyrimidin-4-yl}-3-ethoxy-thiophene-2-carboxylic acid;
5-{6-[2-(2-Cyano-5,6-difluoro-4-methyl-indol-1-yl)-ethylamino]-pyrimidin-4-yl}-3-ethoxy-thiophene-2-carboxylic acid;
5-{6-[2-(2-Cyano-7-fluoro-4-methyl-indol-1-yl)-ethylamino]-pyrimidin-4-yl}-3-ethoxy-thiophene-2-carboxylic acid;
5-{6-[2-(2-Cyano-7-fluoro-indol-1-yl)-ethylamino]-pyrimidin-4-yl}-3-ethoxy-thiophene-2-carboxylic acid;
(4-{6-[2-(2-Cyano-7-fluoro-4-methyl-indol-1-yl)-ethylamino]-pyrimidin-4-yl}-2-ethoxy-phenoxy)-acetic acid;
(4-{6-[2-(2-Cyano-7-fluoro-indol-1-yl)-ethylamino]-pyrimidin-4-yl}-2-ethoxy-phenylamino)-acetic acid;
1-{2-[6-(3-Ethoxy-4-hydroxy-phenyl)-pyrimidin-4-ylamino]-ethyl}-7-fluoro-4-methoxy-1H-indole-2-carbonitrile;
5-{6-[2-(2-Cyano-7-fluoro-4-methoxy-indol-1-yl)-ethylamino]-pyrimidin-4-yl}-thiophene-2-carboxylic acid amide;
5-{6-[2-(2-Cyano-4-methoxy-indol-1-yl)-ethylamino]-pyrimidin-4-yl}-3-fluoro-thiophene-2-carboxylic acid;
5-{6-[2-(4-Chloro-2-cyano-6,7-difluoro-indol-1-yl)-ethylamino]-pyrimidin-4-yl}-3-fluoro-thiophene-2-carboxylic acid;
2-Butoxy-4-{6-[2-(2-cyano-7-fluoro-4-methoxy-indol-1-yl)-ethylamino]-pyrimidin-4-yl}-6-fluoro-benzoic acid;
2-Butoxy-6-chloro-4-{6-[2-(2-cyano-7-fluoro-4-methoxy-indol-1-yl)-ethylamino]-pyrimidin-4-yl}-benzoic acid;
2-Chloro-4-{6-[2-(2-cyano-7-fluoro-4-methoxy-indol-1-yl)-ethylamino]-pyrimidin-4-yl}-6-propoxy-benzoic acid;
4-{6-[2-(2-Cyano-7-fluoro-4-methoxy-indol-1-yl)-ethylamino]-pyrimidin-4-yl}-2-fluoro-6-propoxy-benzoic acid;
5-{6-[2-(4-Chloro-2-cyano-indol-1-yl)-ethylamino]-pyrimidin-4-yl}-3-ethoxy-thiophene-2-carboxylic acid;
5-{6-[2-(2-Cyano-4-methoxy-indol-1-yl)-ethylamino]-pyrimidin-4-yl}-3-trifluoromethyl-thiophene-2-carboxylic acid;
5-{6-[2-(4-Chloro-2-cyano-indol-1-yl)-ethylamino]-pyrimidin-4-yl}-3-trifluoromethyl-thiophene-2-carboxylic acid;
5-{6-[2-(4-Chloro-2-cyano-6,7-difluoro-indol-1-yl)-ethylamino]-pyrimidin-4-yl}-3-trifluoromethyl-thiophene-2-carboxylic acid;
2-Chloro-4-{6-[2-(2-cyano-7-fluoro-4-methoxy-indol-1-yl)-ethylamino]-pyrimidin-4-yl}-6-isobutoxy-benzoic acid;
(4-{6-[2-(4-Chloro-2-cyano-indol-1-yl)-ethylamino]-pyrimidin-4-yl}-2-ethoxy-phenylamino)-acetic acid;
(4-{6-[2-(4-Chloro-2-cyano-6,7-difluoro-indol-1-yl)-ethylamino]-pyrimidin-4-yl}-2-ethoxy-phenylamino)-acetic acid;
4-{6-[2-(2-Cyano-7-fluoro-4-methoxy-indol-1-yl)-ethylamino]-pyrimidin-4-yl}-2-difluoromethoxy-benzoic acid;
7-Fluoro-4-methoxy-1-{2-[6-(1-methyl-2-oxo-1,2,3,4-tetrahydro-quinazolin-7-yl)-pyrimidin-4-ylamino]-ethyl}-1H-indole-2-carbonitrile;
7-Fluoro-4-methoxy-1-{2-[6-(1-methyl-3-oxo-2,3-dihydro-1H-indazol-6-yl)-pyrimidin-4-ylamino]-ethyl}-1H-indole-2-carbonitrile;
3-{6-[2-(2-Cyano-7-fluoro-4-methoxy-indol-1-yl)-ethylamino]-pyrimidin-4-yl}-5-ethylsulfanyl-benzoic acid;
7-Fluoro-4-methoxy-1-(2-{6-[4-(3H-[1,2,3]triazol-4-yl)-phenyl]-pyrimidin-4-ylamino}-ethyl)-1H-indole-2-carbonitrile;
3-(3-{6-[2-(2-Cyano-7-fluoro-4-methoxy-indol-1-yl)-ethylamino]-pyrimidin-4-yl}-5-ethoxy-phenoxy)-propionic acid;
3-(4-{6-[2-(2-Cyano-7-fluoro-4-methoxy-indol-1-yl)-ethylamino]-pyrimidin-4-yl}-2-ethoxy-phenoxy)-propionic acid;
4-{6-[2-(2-Cyano-7-fluoro-4-methoxy-indol-1-yl)-ethylamino]-pyrimidin-4-yl}-2-ethoxy-3-fluoro-benzoic acid;

4-{6-[2-(2-Cyano-7-fluoro-4-methoxy-indol-1-yl)-ethyl-amino]-pyrimidin-4-yl}-2-ethoxy-benzenesulfonamide;
1-(2-{6-[3-Ethoxy-4-(3H-[1,2,3]triazol-4-yl)-phenyl]-pyrimidin-4-ylamino}-ethyl)-7-fluoro-4-methoxy-1H-indole-2-carbonitrile;
3-(5-{6-[2-(2-Cyano-7-fluoro-4-methoxy-indol-1-yl)-ethylamino]-pyrimidin-4-yl}-3-ethoxy-thiophen-2-yl)-propionic acid;
7-Fluoro-1-(2-{6-[4-(2-hydroxy-3,4-dioxo-cyclobut-1-enyl)-phenyl]-pyrimidin-4-ylamino}-ethyl)-4-methoxy-1H-indole-2-carbonitrile;
(4-{6-[2-(2-Cyano-7-fluoro-4-methoxy-indol-1-yl)-ethylamino]-pyrimidin-4-yl}-2-ethoxy-phenyl)-oxo-acetic acid;
4-{6-[2-(2-Cyano-7-fluoro-4-methoxy-indol-1-yl)-ethylamino]-pyrimidin-4-yl}-2-propylsulfanyl-benzoic acid;
4-{6-[2-(2-Cyano-6-fluoro-4-methoxy-indol-1-yl)-ethylamino]-pyrimidin-4-yl}-2-propylsulfanyl-benzoic acid;
4-{6-[2-(2-Cyano-7-fluoro-4-methoxy-indol-1-yl)-ethylamino]-pyrimidin-4-yl}-2-isopropylsulfanyl-benzoic acid;
4-{6-[2-(2-Cyano-6-fluoro-4-methoxy-indol-1-yl)-ethylamino]-pyrimidin-4-yl}-2-isopropylsulfanyl-benzoic acid;
4-{6-[2-(2-Cyano-7-fluoro-4-methoxy-indol-1-yl)-ethylamino]-pyrimidin-4-yl}-2-fluoro-6-propyl-benzoic acid;
5-{6-[2-(2-Cyano-5,7-difluoro-4-methyl-indol-1-yl)-ethylamino]-pyrimidin-4-yl}-3-ethoxy-thiophene-2-carboxylic acid;
5-{6-[2-(2-Cyano-6,7-difluoro-4-methyl-indol-1-yl)-ethylamino]-pyrimidin-4-yl}-3-ethoxy-thiophene-2-carboxylic acid;
5-{6-[2-(2-Cyano-6,7-difluoro-4-methoxy-indol-1-yl)-ethylamino]-pyrimidin-4-yl}-3-ethoxy-thiophene-2-carboxylic acid;
(4-{6-[2-(2-Cyano-6,7-difluoro-4-methoxy-indol-1-yl)-ethylamino]-pyrimidin-4-yl}-2-ethoxy-phenoxy)-acetic acid;
(4-{6-[2-(2-Cyano-6,7-difluoro-4-methoxy-indol-1-yl)-ethylamino]-pyrimidin-4-yl}-2-ethoxy-phenylamino)-acetic acid;
4-{6-[2-(2-Cyano-7-fluoro-4-methoxy-indol-1-yl)-ethylamino]-pyrimidin-4-yl}-2-propyl-benzoic acid;
4-{6-[2-(2-Cyano-7-fluoro-4-methoxy-indol-1-yl)-ethylamino]-pyrimidin-4-yl}-2-ethyl-benzoic acid;
4-{6-[2-(2-Cyano-7-fluoro-4-methoxy-indol-1-yl)-ethylamino]-pyrimidin-4-yl}-2-isobutoxy-benzoic acid;
4-{6-[2-(2-Cyano-7-fluoro-4-methoxy-indol-1-yl)-ethylamino]-pyrimidin-4-yl}-2-propoxy-benzoic acid;
4-{6-[2-(2-Cyano-7-fluoro-4-methyl-indol-1-yl)-ethylamino]-pyrimidin-4-yl}-2-ethylsulfanyl-benzoic acid;
4-{6-[2-(2-Cyano-4-methoxy-indol-1-yl)-ethylamino]-pyrimidin-4-yl}-2-ethylsulfanyl-benzoic acid;
4-{6-[2-(2-Cyano-7-fluoro-4-methoxy-indol-1-yl)-ethylamino]-pyrimidin-4-yl}-2-ethylsulfanyl-benzoic acid;
4-{6-[2-(2-Cyano-6-fluoro-4-methoxy-indol-1-yl)-ethylamino]-pyrimidin-4-yl}-2-ethylsulfanyl-benzoic acid;
4-{6-[2-(2-Cyano-6,7-difluoro-4-methoxy-indol-1-yl)-ethylamino]-pyrimidin-4-yl}-2-ethylsulfanyl-benzoic acid;
4-{6-[2-(2-Cyano-6,7-difluoro-4-methyl-indol-1-yl)-ethylamino]-pyrimidin-4-yl}-2-ethoxy-benzoic acid;
4-{6-[2-(2-Cyano-4-methoxy-indol-1-yl)-ethylamino]-pyrimidin-4-yl}-2-methylamino-benzoic acid;
2-{6-[2-(2-Cyano-7-fluoro-4-methoxy-indol-1-yl)-ethylamino]-pyrimidin-4-yl}-1H-indole-5-carboxylic acid;
7-Fluoro-1-{2-[6-(1H-indol-2-yl)-pyrimidin-4-ylamino]-ethyl}-4-methoxy-1H-indole-2-carbonitrile;
2-{6-[2-(2-Cyano-7-fluoro-4-methoxy-indol-1-yl)-ethylamino]-pyrimidin-4-yl}-1H-indole-5-carboxylic acid methyl ester;
7-Fluoro-1-(2-{6-[4-(2-hydroxy-ethoxy)-phenyl]-pyrimidin-4-ylamino}-ethyl)-4-methoxy-1H-indole-2-carbonitrile;
7-Fluoro-1-{2-[6-(1H-indol-6-yl)-pyrimidin-4-ylamino]-ethyl}-4-methoxy-1H-indole-2-carbonitrile;
7-Fluoro-4-methoxy-1-{2-[6-(1H-pyrrolo[2,3-c]pyridin-3-yl)-pyrimidin-4-ylamino]-ethyl}-1H-indole-2-carbonitrile;
7-Fluoro-1-{2-[6-(1H-indol-3-yl)-pyrimidin-4-ylamino]-ethyl}-4-methoxy-1H-indole-2-carbonitrile;
7-Fluoro-4-methoxy-1-{2-[6-(2-oxo-1,2,3,4-tetrahydroquinazolin-6-yl)-pyrimidin-4-ylamino]-ethyl}-1H-indole-2-carbonitrile;
N-(4-{6-[2-(2-Cyano-7-fluoro-4-methoxy-indol-1-yl)-ethylamino]-pyrimidin-4-yl}-phenyl)-formamide;
7-Fluoro-4-methoxy-1-{2-[6-(2-oxo-2,3-dihydro-benzooxazol-6-yl)-pyrimidin-4-ylamino]-ethyl}-1H-indole-2-carbonitrile;
7-Fluoro-4-methoxy-1-{2-[6-(3-methyl-2-oxo-2,3-dihydro-benzooxazol-5-yl)-pyrimidin-4-ylamino]-ethyl}-1H-indole-2-carbonitrile;
7-Fluoro-1-{2-[6-(1H-indazol-5-yl)-pyrimidin-4-ylamino]-ethyl}-4-methoxy-1H-indole-2-carbonitrile;
7-Fluoro-4-methoxy-1-{2-[6-(1H-pyrrolo[2,3-b]pyridin-3-yl)-pyrimidin-4-ylamino]-ethyl}-1H-indole-2-carbonitrile;
7-Fluoro-4-methoxy-1-{2-[6-(1H-pyrrolo[2,3-b]pyridin-5-yl)-pyrimidin-4-ylamino]-ethyl}-1H-indole-2-carbonitrile;
7-Fluoro-4-methoxy-1-{2-[6-(1-methyl-1H-pyrrolo[2,3-b]pyridin-5-yl)-pyrimidin-4-ylamino]-ethyl}-1H-indole-2-carbonitrile;
1-(4-{6-[2-(2-Cyano-7-fluoro-4-methoxy-indol-1-yl)-ethylamino]-pyrimidin-4-yl}-2-methoxy-phenyl)-3-ethyl-urea;
1-{2-[6-(1H-Benzoimidazol-5-yl)-pyrimidin-4-ylamino]-ethyl}-7-fluoro-4-methoxy-1H-indole-2-carbonitrile;
1-{2-[6-(3H-Benzotriazol-5-yl)-pyrimidin-4-ylamino]-ethyl}-7-fluoro-4-methoxy-1H-indole-2-carbonitrile;
7-Fluoro-4-methoxy-1-{2-[6-(1-oxo-1,2,3,4-tetrahydro-isoquinolin-6-yl)-pyrimidin-4-ylamino]-ethyl}-1H-indole-2-carbonitrile;
1-{2-[6-(3-Ethoxy-4-formyl-phenyl)-pyrimidin-4-ylamino]-ethyl}-7-fluoro-4-methoxy-1H-indole-2-carbonitrile;
7-Fluoro-1-{2-[6-(1H-indol-5-yl)-pyrimidin-4-ylamino]-ethyl}-4-methoxy-1H-indole-2-carbonitrile;
4-{6-[2-(2-Cyano-7-fluoro-4-methoxy-indol-1-yl)-ethylamino]-pyrimidin-4-yl}-2-fluoro-benzoic acid methyl ester;
7-Fluoro-1-{2-[6-(4-hydroxy-3-trifluoromethyl-phenyl)-pyrimidin-4-ylamino]-ethyl}-4-methoxy-1H-indole-2-carbonitrile;
3-{6-[2-(2-Cyano-7-fluoro-4-methoxy-indol-1-yl)-ethylamino]-pyrimidin-4-yl}-5-ethoxy-benzoic acid;
5-{6-[2-(2-Cyano-7-fluoro-4-methoxy-indol-1-yl)-ethylamino]-pyrimidin-4-yl}-thiophene-3-carboxylic acid ethyl ester;

4-{6-[2-(2-Cyano-7-fluoro-4-methoxy-indol-1-yl)-ethylamino]-pyrimidin-4-yl}-2-methylamino-benzoic acid;
4-{6-[2-(5,7-Difluoro-2,4-dimethyl-indol-1-yl)-ethylamino]-pyrimidin-4-yl}-2-methylamino-benzoic acid;
3-(5-{6-[2-(7-Fluoro-4-methoxy-2-methyl-indol-1-yl)-ethylamino]-pyrimidin-4-yl}-3-isopropoxy-thiophen-2-yl)-propionic acid;
3-(3-Ethoxy-5-{6-[2-(7-fluoro-4-methoxy-2-methyl-indol-1-yl)-ethylamino]-pyrimidin-4-yl}-thiophen-2-yl)-propionic acid;
(E)-3-(3-Ethoxy-5-{6-[2-(7-fluoro-4-methoxy-2-methyl-indol-1-yl)-ethylamino]-pyrimidin-4-yl}-thiophen-2-yl)-acrylic acid;
4-{6-[2-(6-Fluoro-4-methoxy-2-methyl-indol-1-yl)-ethylamino]-pyrimidin-4-yl}-2-methylamino-benzoic acid;
3-Chloro-5-{6-[2-(4-chloro-2-cyano-indol-1-yl)-ethylamino]-pyrimidin-4-yl}-thiophene-2-carboxylic acid;
3-Chloro-5-{6-[2-(4-chloro-2-cyano-6,7-difluoro-indol-1-yl)-ethylamino]-pyrimidin-4-yl}-thiophene-2-carboxylic acid;
N-(3-Ethoxy-5-{6-[2-(7-fluoro-4-methoxy-2-methyl-indol-1-yl)-ethylamino]-pyrimidin-4-yl}-thiophene-2-carbonyl)-methanesulfonamide;
5-{6-[2-(2-Cyano-7-fluoro-4-methoxy-indol-1-yl)-ethylamino]-pyrimidin-4-yl}-3-ethoxy-thiophene-2-carboxylic acid ethylamide;
5-{6-[2-(2-Cyano-7-fluoro-4-methoxy-indol-1-yl)-ethylamino]-pyrimidin-4-yl}-3-ethoxy-thiophene-2-carboxylic acid dimethylamide;
5-{6-[2-(2-Cyano-7-fluoro-4-methoxy-indol-1-yl)-ethylamino]-pyrimidin-4-yl}-3-ethoxy-thiophene-2-carboxylic acid (2-hydroxy-ethyl)-amide;
5-{6-[2-(2-Cyano-7-fluoro-4-methoxy-indol-1-yl)-ethylamino]-pyrimidin-4-yl}-3-ethoxy-thiophene-2-carboxylic acid isopropylamide;
5-{6-[2-(2-Cyano-7-fluoro-4-methoxy-indol-1-yl)-ethylamino]-pyrimidin-4-yl}-3-ethoxy-thiophene-2-carboxylic acid (2-methoxy-ethyl)-amide;
5-(6-((2-(2-cyano-7-fluoro-4-methoxy-1H-indol-1-yl)ethyl)amino)pyrimidin-4-yl)-3-ethoxy-N-sulfamoyl-thiophene-2-carboxamide;
5-{6-[2-(2-Cyano-7-fluoro-4-methoxy-indol-1-yl)-ethylamino]-pyrimidin-4-yl}-3-ethoxy-thiophene-2-carboxylic acid hydroxyamide;
(3-Ethoxy-5-{6-[2-(7-fluoro-4-methoxy-2-methyl-indol-1-yl)-ethylamino]-pyrimidin-4-yl}-thiophen-2-yl)-methanol;
2-{6-[2-(7-Fluoro-4-methoxy-2-methyl-indol-1-yl)-ethylamino]-pyrimidin-4-yl}-4-isopropoxy-thiazole-5-carboxylic acid;
2-{6-[2-(7-Fluoro-4-methoxy-2-methyl-indol-1-yl)-ethylamino]-pyrimidin-4-yl}-4-methoxy-thiazole-5-carboxylic acid;
4-Ethoxy-2-{6-[2-(7-fluoro-4-methoxy-2-methyl-indol-1-yl)-ethylamino]-pyrimidin-4-yl}-thiazole-5-carboxylic acid;
2-{6-[2-(7-Fluoro-4-methoxy-2-methyl-indol-1-yl)-ethylamino]-pyrimidin-4-yl}-4-propoxy-thiazole-5-carboxylic acid;
2-{6-[2-(7-Fluoro-4-methoxy-2-methyl-indol-1-yl)-ethylamino]-pyrimidin-4-yl}-4-isobutyl-thiazole-5-carboxylic acid;
5-{6-[2-(2-Cyano-7-fluoro-4-methoxy-indol-1-yl)-ethylamino]-pyrimidin-4-yl}-3-ethoxy-thiophene-2-carboxylic acid carboxymethyl ester;
5-{6-[2-(2-Cyano-7-fluoro-4-methoxy-indol-1-yl)-ethylamino]-pyrimidin-4-yl}-3-ethoxy-thiophene-2-carboxylic acid dimethylcarbamoylmethyl ester;
5-{6-[2-(2-Cyano-7-fluoro-4-methoxy-indol-1-yl)-ethylamino]-pyrimidin-4-yl}-3-ethoxy-thiophene-2-carboxylic acid butyryloxymethyl ester;
5-{6-[2-(2-Cyano-7-fluoro-4-methoxy-indol-1-yl)-ethylamino]-pyrimidin-4-yl}-3-ethoxy-thiophene-2-carboxylic acid ethoxycarbonyloxymethyl ester;
5-{6-[2-(2-Cyano-7-fluoro-4-methoxy-indol-1-yl)-ethylamino]-pyrimidin-4-yl}-3-ethoxy-thiophene-2-carboxylic acid 5-methyl-2-oxo-[1,3]dioxol-4-ylmethyl ester;
5-{6-[2-(2-Cyano-7-fluoro-4-methoxy-indol-1-yl)-ethylamino]-pyrimidin-4-yl}-3-ethoxy-thiophene-2-carboxylic acid 2-dimethylamino-ethyl ester;
5-{6-[2-(2-Cyano-7-fluoro-4-methoxy-indol-1-yl)-ethylamino]-pyrimidin-4-yl}-3-ethoxy-thiophene-2-carboxylic acid phenyl ester;
(4-{6-[2-(2-Cyano-7-fluoro-4-methoxy-indol-1-yl)-ethylamino]-pyrimidin-4-yl}-2-methoxy-phenyl)-propynoic acid ethyl ester;
{6-[4-Ethoxy-5-(1H-tetrazol-5-yl)-thiophen-2-yl]-pyrimidin-4-yl}-[2-(7-fluoro-4-methoxy-2-methyl-indol-1-yl)-ethyl]-amine;
3-Ethoxy-5-{6-[2-(7-fluoro-4-methoxy-2-methyl-indol-1-yl)-ethylamino]-pyrimidin-4-yl}-N-hydroxy-thiophene-2-carboxamidine;
3-(3-Ethoxy-5-{6-[2-(7-fluoro-4-methoxy-2-methyl-indol-1-yl)-ethylamino]-pyrimidin-4-yl}-thiophen-2-yl)-[1,2,4]oxadiazol-5(4H)-one;
5-{6-[2-(3,7-Difluoro-4-methoxy-2-methyl-indol-1-yl)-ethylamino]-pyrimidin-4-yl}-3-ethoxy-thiophene-2-carboxylic acid;
[2-(7-Fluoro-4-methoxy-2-methyl-indol-1-yl)-ethyl]-{6-[5-(2H-tetrazol-5-yl)-4-trifluoromethyl-thiophen-2-yl]-pyrimidin-4-yl}-amine;
5-{6-[2-(7-Fluoro-4-methoxy-2-methyl-indol-1-yl)-ethylamino]-pyrimidin-4-yl}-N-hydroxy-3-trifluoromethyl-thiophene-2-carboxamidine;
3-(5-{6-[2-(7-Fluoro-4-methoxy-2-methyl-indol-1-yl)-ethylamino]-pyrimidin-4-yl}-3-trifluoromethyl-thiophen-2-yl)-[1,2,4]oxadiazol-5(4H)-one;
4-{6-[2-(2-Cyano-7-fluoro-4-methoxy-indol-1-yl)-ethylamino]-pyrimidin-4-yl}-2-ethoxy-N-hydroxy-benzamide;
5-(3-Ethoxy-5-{6-[2-(7-fluoro-4-methoxy-2-methyl-indol-1-yl)-ethylamino]-pyrimidin-4-yl}-thiophen-2-yl)-isoxazol-3-ol;
5-{6-[2-(7-Fluoro-4-methoxy-2-methyl-indol-1-yl)-ethylamino]-pyrimidin-4-yl}-3-pyridin-2-yl-thiophene-2-carboxylic acid;
[6-(4-Ethylamino-thiophen-2-yl)-pyrimidin-4-yl]-[2-(7-fluoro-2,4-dimethyl-indol-1-yl)-ethyl]-amine;
[6-(4-Ethylamino-thiophen-2-yl)-pyrimidin-4-yl]-[2-(6-fluoro-2,4-dimethyl-indol-1-yl)-ethyl]-amine;
[6-(4-Ethylamino-thiophen-2-yl)-pyrimidin-4-yl]-[2-(6-fluoro-4-methoxy-2-methyl-indol-1-yl)-ethyl]-amine;
N-Ethyl-N-(5-{6-[2-(7-fluoro-4-methoxy-2-methyl-indol-1-yl)-ethylamino]-pyrimidin-4-yl}-thiophen-3-yl)-formamide;
N-(3-Ethoxy-5-{6-[2-(7-fluoro-4-methoxy-2-methyl-indol-1-yl)-ethylamino]-pyrimidin-4-yl}-thiophen-2-yl)-formamide;
N-(3-Ethoxy-5-{6-[2-(7-fluoro-4-methoxy-2-methyl-indol-1-yl)-ethylamino]-pyrimidin-4-yl}-thiophen-2-yl)-propionamide;

N-(3-Ethoxy-5-{6-[2-(7-fluoro-4-methoxy-2-methyl-indol-1-yl)-ethylamino]-pyrimidin-4-yl}-thiophen-2-yl)-3-hydroxy-propionamide;
(3-Ethoxy-5-{6-[2-(7-fluoro-4-methoxy-2-methyl-indol-1-yl)-ethylamino]-pyrimidin-4-yl}-thiophen-2-yl)-urea; and
5-{6-[2-(2-Cyano-3,7-difluoro-4-methoxy-indol-1-yl)-ethylamino]-pyrimidin-4-yl}-3-trifluoromethyl-thiophene-2-carboxylic acid;
or a pharmaceutically acceptable salt thereof.

11. A method according to claim 1; wherein the compound is selected from the group consisting of:

3-Chloro-5-{6-[2-(4-chloro-7-fluoro-2-methyl-indol-1-yl)-ethylamino]-pyrimidin-4-yl}-thiophene-2-carboxylic acid;
3-Chloro-5-{6-[2-(6-fluoro-2,4-dimethyl-indol-1-yl)-ethylamino]-pyrimidin-4-yl}-thiophene-2-carboxylic acid;
(2-Chloro-4-{6-[2-(7-fluoro-4-methoxy-2-methyl-indol-1-yl)-ethylamino]-pyrimidin-4-yl}-phenyl)-methanol;
5-{6-[2-(7-Fluoro-2,4-dimethyl-indol-1-yl)-ethylamino]-pyrimidin-4-yl}-3-methyl-thiophene-2-carboxylic acid;
[6-(2,3-Dihydro-1H-indol-5-yl)-pyrimidin-4-yl]-[2-(7-fluoro-4-methoxy-2-methyl-indol-1-yl)-ethyl]-amine;
[2-(6-Fluoro-2,4-dimethyl-indol-1-yl)-ethyl]-{6-[4-(1H-imidazol-4-yl)-phenyl]-pyrimidin-4-yl}-amine;
[2-(4-Methoxy-2-methyl-indol-1-yl)-ethyl]-{6-[4-(2H-pyrazol-3-yl)-phenyl]-pyrimidin-4-yl}-amine;
{6-[4-(1H-Imidazol-4-yl)-phenyl]-pyrimidin-4-yl}-[2-(4-methoxy-2-methyl-indol-1-yl)-ethyl]-amine;
[2-(7-Fluoro-4-methoxy-2-methyl-indol-1-yl)-ethyl]-[6-(2-methyl-1H-benzoimidazol-5-yl)-pyrimidin-4-yl]-amine;
3-Ethyl-5-{6-[2-(7-fluoro-2,4-dimethyl-indol-1-yl)-ethylamino]-pyrimidin-4-yl}-thiophene-2-carboxylic acid;
3-Fluoro-5-{6-[2-(7-fluoro-4-methoxy-2-methyl-indol-1-yl)-ethylamino]-pyrimidin-4-yl}-thiophene-2-carboxylic acid;
3-Fluoro-5-{6-[2-(6-fluoro-4-methoxy-2-methyl-indol-1-yl)-ethylamino]-pyrimidin-4-yl}-thiophene-2-carboxylic acid;
(4-{6-[2-(7-Fluoro-4-methoxy-2-methyl-indol-1-yl)-ethylamino]-pyrimidin-4-yl}-2-methoxy-phenyl)-methanol;
(2-Ethoxy-4-{6-[2-(7-fluoro-4-methoxy-2-methyl-indol-1-yl)-ethylamino]-pyrimidin-4-yl}-phenyl)-methanol;
[2-(6,7-Difluoro-2,4-dimethyl-indol-1-yl)-ethyl]-{6-[4-(1H-imidazol-4-yl)-phenyl]-pyrimidin-4-yl}-amine;
5-{6-[2-(4,5-Difluoro-2-methyl-indol-1-yl)-ethylamino]-pyrimidin-4-yl}-3-ethoxy-thiophene-2-carboxylic acid;
5-{6-[2-(5-Chloro-7-fluoro-2-methyl-indol-1-yl)-ethylamino]-pyrimidin-4-yl}-3-ethoxy-thiophene-2-carboxylic acid;
2-Ethylamino-4-{6-[2-(6-fluoro-2,4-dimethyl-indol-1-yl)-ethylamino]-pyrimidin-4-yl}-benzoic acid;
2-Ethylamino-4-{6-[2-(7-fluoro-2,4-dimethyl-indol-1-yl)-ethylamino]-pyrimidin-4-yl}-benzoic acid;
2-Ethylamino-4-{6-[2-(4-methoxy-2-methyl-indol-1-yl)-ethylamino]-pyrimidin-4-yl}-benzoic acid;
3-Ethoxy-5-{6-[2-(4-methoxy-2,7-dimethyl-indol-1-yl)-ethylamino]-pyrimidin-4-yl}-thiophene-2-carboxylic acid;
3-Ethoxy-5-{6-[2-(5,6,7-trifluoro-2-methyl-indol-1-yl)-ethylamino]-pyrimidin-4-yl}-thiophene-2-carboxylic acid;
[2-(6,7-Difluoro-4-methoxy-2-methyl-indol-1-yl)-ethyl]-[6-(4-[1,2,4]oxadiazol-5-yl-phenyl)-pyrimidin-4-yl]-amine;
[2-(6-Fluoro-4-methoxy-2-methyl-indol-1-yl)-ethyl]-{6-[4-(1-methyl-1H-pyrazol-3-yl)-phenyl]-pyrimidin-4-yl}-amine;
3-(4-{6-[2-(6-Fluoro-4-methoxy-2-methyl-indol-1-yl)-ethylamino]-pyrimidin-4-yl}-phenyl)-4H-[1,2,4]oxadiazol-5-one;
4-{6-[2-(7-Fluoro-4-methoxy-2-methyl-indol-1-yl)-ethylamino]-pyrimidin-4-yl}-2-propyl-benzoic acid;
1-Ethyl-3-(2-methoxy-4-{6-[2-(4-methoxy-2-methyl-indol-1-yl)-ethylamino]-pyrimidin-4-yl}-phenyl)-urea;
2-Chloro-6-ethylamino-4-{6-[2-(7-fluoro-4-methoxy-2-methyl-indol-1-yl)-ethylamino]-pyrimidin-4-yl}-benzoic acid;
[2-(7-Fluoro-4-methoxy-2-methyl-indol-1-yl)-ethyl]-(6-quinolin-6-yl-pyrimidin-4-yl)-amine;
2-Ethylamino-6-fluoro-4-{6-[2-(7-fluoro-2,4-dimethyl-indol-1-yl)-ethylamino]-pyrimidin-4-yl}-benzoic acid;
4-{6-[2-(4-Chloro-4-methoxy-2-methyl-indol-1-yl)-ethylamino]-pyrimidin-4-yl}-2-ethylamino-benzoic acid;
2-Chloro-4-{6-[2-(6-fluoro-2,4-dimethyl-indol-1-yl)-ethylamino]-pyrimidin-4-yl}-6-propyl-benzoic acid;
2-Chloro-4-{6-[2-(7-fluoro-2,4-dimethyl-indol-1-yl)-ethylamino]-pyrimidin-4-yl}-6-propyl-benzoic acid;
2-Fluoro-4-{6-[2-(7-fluoro-2,4-dimethyl-indol-1-yl)-ethylamino]-pyrimidin-4-yl}-6-propyl-benzoic acid;
4-{6-[2-(5,7-Difluoro-2,4-dimethyl-indol-1-yl)-ethylamino]-pyrimidin-4-yl}-2-ethoxy-benzoic acid;
2-Chloro-4-{6-[2-(4-methoxy-2-methyl-indol-1-yl)-ethylamino]-pyrimidin-4-yl}-6-propyl-benzoic acid;
{6-[4-(2-Amino-5-methyl-thiazol-4-yl)-phenyl]-pyrimidin-4-yl}-[2-(7-fluoro-4-methoxy-2-methyl-indol-1-yl)-ethyl]-amine;
5-{6-[2-(7-Fluoro-4-methoxy-2-methyl-indol-1-yl)-ethylamino]-pyrimidin-4-yl}-3-propyl-2,3-dihydro-isoindol-1-one;
2-Cyclobutoxy-4-{6-[2-(7-fluoro-4-methoxy-2-methyl-indol-1-yl)-ethylamino]-pyrimidin-4-yl}-benzoic acid;
4-{6-[2-(2-Cyano-6-fluoro-4-methoxy-indol-1-yl)-ethylamino]-pyrimidin-4-yl}-2-ethoxy-benzoic acid;
2-Ethylamino-6-fluoro-4-{6-[2-(7-fluoro-4-methoxy-2-methyl-indol-1-yl)-ethylamino]-pyrimidin-4-yl}-benzoic acid;
4-{6-[2-(6,7-Difluoro-4-methoxy-2-methyl-indol-1-yl)-ethylamino]-pyrimidin-4-yl}-2-ethoxy-benzoic acid;
4-{6-[2-(7-Fluoro-4-methoxy-2-methyl-indol-1-yl)-ethylamino]-pyrimidin-4-yl}-2-propoxy-benzoic acid;
4-{6-[2-(5,7-Difluoro-2,4-dimethyl-indol-1-yl)-ethylamino]-pyrimidin-4-yl}-2-isobutyl-benzoic acid;
2-Chloro-4-{6-[2-(7-fluoro-4-methoxy-2-methyl-indol-1-yl)-ethylamino]-pyrimidin-4-yl}-6-propyl-benzoic acid;
2-Fluoro-4-{6-[2-(7-fluoro-4-methoxy-2-methyl-indol-1-yl)-ethylamino]-pyrimidin-4-yl}-6-propyl-benzoic acid;
2-Fluoro-4-{6-[2-(6-fluoro-4-methoxy-2-methyl-indol-1-yl)-ethylamino]-pyrimidin-4-yl}-6-propyl-benzoic acid;
2-Butoxy-4-{6-[2-(7-fluoro-2,4-dimethyl-indol-1-yl)-ethylamino]-pyrimidin-4-yl}-benzoic acid;
4-{6-[2-(7-Fluoro-2,4-dimethyl-indol-1-yl)-ethylamino]-pyrimidin-4-yl}-2-isobutoxy-benzoic acid;

4-{6-[2-(7-Fluoro-4-methoxy-2-methyl-indol-1-yl)-ethylamino]-pyrimidin-4-yl}-2-isobutyl-benzoic acid;
2-(4-{6-[2-(7-Fluoro-2,4-dimethyl-indol-1-yl)-ethylamino]-pyrimidin-4-yl}-phenyl)-thiazole-4-carboxylic acid;
[2-(6-Fluoro-2,4-dimethyl-indol-1-yl)-ethyl]-{6-[4-(2-methyl-1H-imidazol-4-yl)-phenyl]-pyrimidin-4-yl}-amine;
2-(4-{6-[2-(4-Methoxy-2-methyl-indol-1-yl)-ethylamino]-pyrimidin-4-yl}-phenyl)-thiazole-4-carboxylic acid;
4-{6-[2-(7-Fluoro-4-methoxy-2-methyl-indol-1-yl)-ethylamino]-pyrimidin-4-yl}-2-trifluoromethyl-benzenesulfonamide;
{6-[4-(5-Amino-[1,3,4]thiadiazol-2-yl)-phenyl]-pyrimidin-4-yl}-[2-(6-fluoro-2,4-dimethyl-indol-1-yl)-ethyl]-amine;
[2-(6,7-Difluoro-2,4-dimethyl-indol-1-yl)-ethyl]-{6-[4-(2-methyl-1H-imidazol-4-yl)-phenyl]-pyrimidin-4-yl}-amine;
4-(4-{6-[2-(6-Fluoro-4-methoxy-2-methyl-indol-1-yl)-ethylamino]-pyrimidin-4-yl}-phenyl)-thiazole-2-carboxylic acid;
[2-(6-Fluoro-4-methoxy-2-methyl-indol-1-yl)-ethyl]-{6-[4-(5-methyl-1H-pyrazol-3-yl)-phenyl]-pyrimidin-4-yl}-amine;
4-{6-[2-(7-Fluoro-4-methoxy-2-methyl-indol-1-yl)-ethylamino]-pyrimidin-4-yl}-2-(2,2,2-trifluoro-ethylamino)-benzoic acid;
2-Cyclopentyloxy-4-{6-[2-(7-fluoro-4-methoxy-2-methyl-indol-1-yl)-ethylamino]-pyrimidin-4-yl}-benzoic acid;
2-Butoxy-4-{6-[2-(6-fluoro-4-methoxy-2-methyl-indol-1-yl)-ethylamino]-pyrimidin-4-yl}-benzoic acid;
4-{6-[2-(6-Fluoro-4-methoxy-2-methyl-indol-1-yl)-ethylamino]-pyrimidin-4-yl}-2-isobutoxy-benzoic acid;
4-{6-[2-(7-Fluoro-4-methoxy-2-methyl-indol-1-yl)-ethylamino]-pyrimidin-4-yl}-2-isobutoxy-benzoic acid;
4-{6-[2-(6,7-Difluoro-4-methoxy-2-methyl-indol-1-yl)-ethylamino]-pyrimidin-4-yl}-2-isobutyl-benzoic acid;
4-{6-[2-(7-Fluoro-4-methoxy-2-methyl-indol-1-yl)-ethylamino]-2-methyl-pyrimidin-4-yl}-2-isobutyl-benzoic acid;
2-Chloro-4-{6-[2-(5,7-difluoro-2,4-dimethyl-indol-1-yl)-ethylamino]-pyrimidin-4-yl}-6-propoxy-benzoic acid;
4-{6-[2-(6,7-Difluoro-4-methoxy-2-methyl-indol-1-yl)-ethylamino]-pyrimidin-4-yl}-2-fluoro-6-propoxy-benzoic acid;
4-{6-[2-(6,7-Difluoro-4-methoxy-2-methyl-indol-1-yl)-ethylamino]-pyrimidin-4-yl}-2-(2,2,2-trifluoro-ethylamino)-benzoic acid;
[2-(5-Chloro-7-methyl-[1,3]dioxolo[4,5-e]indol-6-yl)-ethyl]-{6-[3-ethylamino-4-(1H-tetrazol-5-yl)-phenyl]-pyrimidin-4-yl}-amine;
{6-[3-Ethoxy-4-(1H-tetrazol-5-yl)-phenyl]-pyrimidin-4-yl}-[2-(7-fluoro-2,4-dimethyl-indol-1-yl)-ethyl]-amine;
{6-[3-Ethoxy-4-(1H-tetrazol-5-yl)-phenyl]-pyrimidin-4-yl}-[2-(4-methoxy-2-methyl-indol-1-yl)-ethyl]-amine;
3-(4-{6-[2-(6-Chloro-4-methoxy-2-methyl-indol-1-yl)-ethylamino]-pyrimidin-4-yl}-phenyl)-4H-[1,2,4]oxadiazol-5-one;
2-Chloro-4-{6-[2-(6-fluoro-4-methoxy-2-methyl-indol-1-yl)-ethylamino]-pyrimidin-4-yl}-6-isobutoxy-benzoic acid;
[2-(6-Fluoro-2,4-dimethyl-indol-1-yl)-ethyl]-[6-(1H-indol-5-yl)-pyrimidin-4-yl]-amine;
[2-(7-Fluoro-2,4-dimethyl-indol-1-yl)-ethyl]-[6-(1H-indol-5-yl)-pyrimidin-4-yl]-amine;
[2-(6-Fluoro-4-methoxy-2-methyl-indol-1-yl)-ethyl]-[6-(1H-indol-5-yl)-pyrimidin-4-yl]-amine;
[2-(6-Fluoro-4-methoxy-2-methyl-indol-1-yl)-ethyl]-[6-(1-methyl-1H-indol-5-yl)-pyrimidin-4-yl]-amine;
[2-(7-Fluoro-4-methoxy-2-methyl-indol-1-yl)-ethyl]-[6-(1-methyl-1H-indol-5-yl)-pyrimidin-4-yl]-amine;
[2-(6,7-Difluoro-4-methoxy-2-methyl-indol-1-yl)-ethyl]-[6-(1-methyl-1H-indol-5-yl)-pyrimidin-4-yl]-amine;
2-Chloro-4-{6-[2-(6-fluoro-4-methoxy-2-methyl-indol-1-yl)-ethylamino]-pyrimidin-4-yl}-6-(2,2,2-trifluoro-ethoxy)-benzoic acid;
2-Chloro-4-{6-[2-(6,7-difluoro-4-methoxy-2-methyl-indol-1-yl)-ethylamino]-pyrimidin-4-yl}-6-(2,2,2-trifluoro-ethoxy)-benzoic acid;
2-Chloro-4-{6-[2-(7-fluoro-4-methoxy-2-methyl-indol-1-yl)-ethylamino]-pyrimidin-4-yl}-6-(2,2,2-trifluoro-ethoxy)-benzoic acid;
[2-(6-Fluoro-4-methoxy-2-methyl-indol-1-yl)-ethyl]-[6-(4-pyrazin-2-yl-phenyl)-pyrimidin-4-yl]-amine;
6-{6-[2-(7-Chloro-5-fluoro-4-methoxy-2-methyl-indol-1-yl)-ethylamino]-pyrimidin-4-yl}-1,2-dihydro-indazol-3-one;
3-Ethoxy-5-{6-[2-(7-fluoro-4-methoxy-2-methyl-indol-1-yl)-1-methyl-ethylamino]-pyrimidin-4-yl}-thiophene-2-carboxylic acid;
5-{6-[2-(7-Fluoro-4-methoxy-2-methyl-indol-1-yl)-ethylamino]-pyrimidin-4-yl}-3-hydroxy-thiophene-2-carboxylic acid;
1-(3-Ethoxy-5-{6-[2-(7-fluoro-4-methoxy-2-methyl-indol-1-yl)-ethylamino]-pyrimidin-4-yl}-thiophen-2-yl)-ethanol;
(2-Ethoxy-4-{6-[2-(7-fluoro-4-methoxy-2-methyl-indol-1-yl)-ethylamino]-pyrimidin-4-yl}-phenylamino)-acetic acid methyl ester;
7-Fluoro-4-methoxy-1-{2-[6-(2-trifluoromethyl-pyridin-4-yl)-pyrimidin-4-ylamino]-ethyl}-1H-indole-2-carbonitrile;
3-{6-[2-(2-Cyano-7-fluoro-4-methoxy-indol-1-yl)-ethylamino]-pyrimidin-4-yl}-5-methoxy-benzoic acid;
7-Fluoro-4-methoxy-1-{2-[6-(2-oxo-2,3-dihydro-1H-benzoimidazol-5-yl)-pyrimidin-4-ylamino]-ethyl}-1H-indole-2-carbonitrile;
4-{6-[2-(2-Cyano-7-fluoro-4-methoxy-indol-1-yl)-ethylamino]-pyrimidin-4-yl}-N-(2-methoxy-ethyl)-benzamide;
7-Fluoro-1-[2-(6-imidazo[1,2-a]pyridin-6-yl-pyrimidin-4-ylamino)-ethyl]-4-methoxy-1H-indole-2-carbonitrile;
7-Fluoro-1-{2-[6-(2-oxo-2,3-dihydro-1H-benzo[d]imidazol-5-yl)-pyrimidin-4-ylamino]-ethyl}-4-methoxy-1H-indole-2-carbonitrile;
1-{2-[6-(2-Cyclopropyl-pyridin-4-yl)-pyrimidin-4-ylamino]-ethyl}-7-fluoro-4-methoxy-1H-indole-2-carbonitrile;
1-{2-[6-(2-Azetidin-1-yl-pyridin-4-yl)-pyrimidin-4-ylamino]-ethyl}-7-fluoro-4-methoxy-1H-indole-2-carbonitrile;
4-{6-[2-(2-Cyano-7-fluoro-4-methoxy-indol-1-yl)-ethylamino]-pyrimidin-4-yl}-benzoic acid;
7-Fluoro-4-methoxy-1-{2-[6-(2-methyl-3-oxo-2,3-dihydro-1H-indazol-6-yl)-pyrimidin-4-ylamino]-ethyl}-1H-indole-2-carbonitrile;
7-Fluoro-4-methoxy-1-{2-[6-(3-methoxy-1H-indazol-6-yl)-pyrimidin-4-ylamino]-ethyl}-1H-indole-2-carbonitrile;

(4-{6-[2-(4-Chloro-2-cyano-6,7-difluoro-indol-1-yl)-ethylamino]-pyrimidin-4-yl}-2-ethoxy-phenoxy)-acetic acid;

5-{6-[2-(4-Chloro-2-cyano-indol-1-yl)-ethylamino]-pyrimidin-4-yl}-3-fluoro-thiophene-2-carboxylic acid;

5-{6-[2-(2-Cyano-7-fluoro-indol-1-yl)-ethylamino]-pyrimidin-4-yl}-3-fluoro-thiophene-2-carboxylic acid;

(4-{6-[2-(2-Cyano-5,6-difluoro-4-methyl-indol-1-yl)-ethylamino]-pyrimidin-4-yl}-2-ethoxy-phenylamino)-acetic acid;

5-{6-[2-(7-Chloro-5-fluoro-4-methoxy-2-methyl-indol-1-yl)-ethylamino]-pyrimidin-4-yl}-3-ethoxy-thiophene-2-carboxylic acid;

2-Butoxy-4-{6-[2-(6-chloro-7-fluoro-4-methoxy-2-methyl-indol-1-yl)-ethylamino]-pyrimidin-4-yl}-benzoic acid;

5-{6-[2-(4,7-Dichloro-5-fluoro-2-methyl-indol-1-yl)-ethylamino]-pyrimidin-4-yl}-3-ethoxy-thiophene-2-carboxylic acid;

(2-Ethoxy-4-{6-[2-(6-fluoro-4-methoxy-2-methyl-indol-1-yl)-ethylamino]-pyrimidin-4-yl}-phenylamino)-acetic acid;

5-{6-[2-(2-Cyano-7-fluoro-indol-1-yl)-ethylamino]-pyrimidin-4-yl}-3-trifluoromethyl-thiophene-2-carboxylic acid;

5-{6-[2-(4,6-Dichloro-2-cyano-indol-1-yl)-ethylamino]-pyrimidin-4-yl}-3-trifluoromethyl-thiophene-2-carboxylic acid;

5-{6-[2-(4,6-Dichloro-2-cyano-indol-1-yl)-ethylamino]-pyrimidin-4-yl}-3-fluoro-thiophene-2-carboxylic acid;

[6-(3-Ethoxy-4-oxazol-2-yl-phenyl)-pyrimidin-4-yl]-[2-(7-fluoro-4-methoxy-2-methyl-indol-1-yl)-ethyl]-amine; and (2-Chloro-4-{6-[2-(2-cyano-7-fluoro-4-methoxy-indol-1-yl)-ethylamino]-pyrimidin-4-yl}-phenoxy)-acetic acid;

or a pharmaceutically acceptable salt thereof.

12. A method according to claim 1; wherein the compound is a compound of Formula (II)

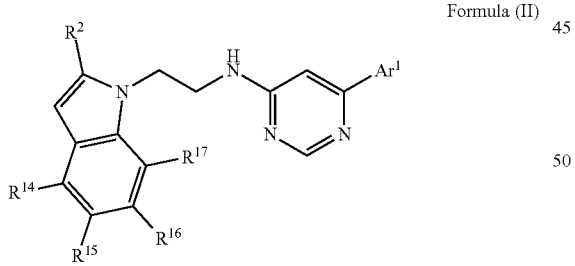

Formula (II)

wherein $R^2$ represents methyl, chloro, or cyano; and $R^{14}$, $R^{15}$, $R^{16}$, and $R^{17}$ independently represent the following:

$R^{14}$ represents methyl, methoxy, halogen, or cyano;

$R^{15}$ represents hydrogen, methyl, chloro, or fluoro;

$R^{16}$ represents hydrogen or fluoro; and $R^{17}$ represents hydrogen, chloro, or fluoro;

wherein at least one of $R^{15}$, $R^{16}$, and $R^{17}$ represents hydrogen;

and $Ar^1$ represents a phenyl group of the structure (Ar-IV):

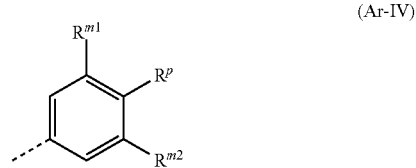

(Ar-IV)

wherein $R^p$ represents:

hydroxy;

—COOH;

—CO—CH$_2$—CN;

—CO—(C$_{1-4}$)alkoxy;

—CO—NH—SO$_2$—$R^{S3}$ wherein $R^{S3}$ represents (C$_{1-4}$)alkyl, (C$_{3-6}$)cycloalkyl; (C$_{3-6}$)cycloalkyl-(C$_{1-3}$)alkylene; (C$_{1-3}$)fluoroalkyl, phenyl, or —NH$_2$;

—X$^1$—CH$_2$—COOH, wherein X$^1$ represents O, or NH;

—CO—NR$^{N3}$R$^{N4}$ wherein $R^{N3}$ and $R^{N4}$ independently represent hydrogen, (C$_{1-4}$)alkyl, hydroxy-(C$_{2-4}$)alkyl, (C$_{1-3}$)alkoxy-(C$_{2-4}$)alkyl, dimethylamino-(C$_{2-4}$)alkyl, (C$_{1-4}$)alkoxy, or hydroxy-(C$_{2-4}$)alkoxy;

—NH—CO—NR$^{N5}$R$^{N6}$ wherein $R^{N5}$ and $R^{N6}$ independently represent hydrogen or (C$_{1-4}$)alkyl;

—SO$_2$—R$^{S1}$ wherein $R^{S1}$ represents hydroxy, (C$_{1-4}$)alkyl, or —NR$^{N7}$R$^{N8}$ wherein $R^{N7}$ and $R^{N8}$ independently represent hydrogen or (C$_{1-3}$)alkyl;

5-oxo-4,5-dihydro-[1,2,4]oxadiazol-3-yl;

tetrazolyl; or 5- or 6-membered heteroaryl selected from oxazolyl, isoxazolyl, oxadiazolyl, thiazolyl, isothiazolyl, thiadiazolyl, imidazolyl, pyrazolyl, triazolyl, pyridinyl, pyrimidinyl, pyridazinyl, or pyrazinyl; wherein said 5- or 6-membered heteroaryl is unsubstituted, or mono- or di-substituted, wherein the substituents are independently selected from (C$_{1-3}$)alkyl, (C$_{1-3}$)alkoxy, —COOH, hydroxy, fluoro, 2-amino-2-oxo-ethyl, 2-carboxy-ethyl, or —NR$^{N9}$R$^{N10}$ wherein $R^{N9}$ and $R^{N10}$ independently represent hydrogen or (C$_{1-3}$)alkyl;

$R^{m1}$ represents hydrogen;

(C$_{1-6}$)alkyl;

(C$_{1-4}$)alkoxy;

(C$_{1-3}$)fluoroalkyl;

(C$_{1-3}$)fluoroalkoxy;

halogen;

(C$_{3-6}$)cycloalkyl;

(C$_{3-6}$)cycloalkyl-oxy;

hydroxy;

—(CH$_2$)$_m$—NR$^{N1}$R$^{N2}$, wherein m represents the integer 0 or 1; and wherein $R^{N1}$ and $R^{N2}$ independently represent hydrogen, (C$_{1-3}$)alkyl, or (C$_{2-3}$)fluoroalkyl; or $R^{N1}$ and $R^{N2}$ together with the nitrogen to which they are attached form a pyrrolidinyl ring; or —S—R$^{S2}$ wherein R$^{S2}$ represents (C$_{1-4}$)alkyl, or (C$_{3-6}$)cycloalkyl;
and R$^{m2}$ represents
hydrogen; or
(C$_{1-6}$)alkyl;
(C$_{1-3}$)alkoxy; or
halogen;
or Ar$^1$ represents a 5-membered heteroaryl group of the structure (Ar-V):

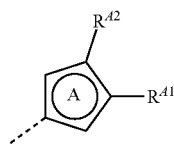

(Ar-V)

wherein in (Ar-V) the ring A represents a thiophenyl or a thiazolyl ring;
wherein R$^{A1}$ represents
—COOH;
tetrazolyl;
—CO—(C$_{1-4}$)alkoxy;
—CO—NH—SO$_2$—R$^{S3}$ wherein R$^{S3}$ represents R$^{S3}$ represents (C$_{1-4}$)alkyl, (C$_{3-6}$)cycloalkyl; (C$_{3-6}$)cycloalkyl-(C$_{1-3}$)alkylene; (C$_{1-3}$)fluoroalkyl, phenyl, or —NH$_2$;
—X$^1$—CH$_2$—COOH, wherein X$^1$ represents O, or NH; or
—CO—NR$^{N3}$R$^{N4}$ wherein R$^{N3}$ and R$^{N4}$ independently represent hydrogen, (C$_{1-4}$)alkyl, hydroxy-(C$_{2-4}$)alkyl, or (C$_{1-3}$)alkoxy-(C$_{2-4}$)alkyl;
and R$^{A2}$ represents
hydrogen;
(C$_{1-6}$)alkyl;
(C$_{1-4}$)alkoxy;
(C$_{1-3}$)fluoroalkyl;
halogen; or
hydroxy;
or Ar$^1$ represents 9- or 10-membered bicyclic heteroaryl selected from 1H-indol-5-yl, 1H-indol-4-yl, 1H-indol-6-yl, indazol-6-yl, 1H-benzoimidazol-5-yl, 1H-benzotriazol-5-yl, quinoxalin-6-yl, isoquinolin-7-yl, and quinolin-6-yl; wherein said 9- or 10-membered bicyclic heteroaryl independently is unsubstituted, mono-, or di-substituted, wherein the substituents are independently selected from (C$_{1-4}$)alkyl or —COOH;

or Ar$^1$ represents a group of the structure (Ar-III):

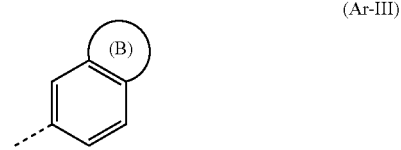

(Ar-III)

wherein ring (B) represents a non-aromatic 5-membered ring fused to the phenyl group, wherein ring (B) comprises one or two nitrogen ring atoms; wherein said ring (B) independently is unsubstituted, mono-, or di-substituted, wherein the substituents are independently selected from oxo and (C$_{1-6}$)alkyl;
or a pharmaceutically acceptable salt thereof.

13. A method according to claim 1; wherein the compound is 4-{6-[2-(2-Chloro-7-fluoro-4-methoxy-indol-1-yl)-ethylamino]-pyrimidin-4-yl}-2-ethoxy-benzoic acid, or a pharmaceutically acceptable salt thereof.

14. A method according to claim 1; wherein the compound is 4-{6-[2-(2-Cyano-7-fluoro-4-methoxy-indol-1-yl)-ethylamino]-pyrimidin-4-yl}-2-ethoxy-benzoic acid, or a pharmaceutically acceptable salt thereof.

15. A method according to claim 1; wherein the compound is 4-{6-[2-(2-Cyano-7-fluoro-4-methoxy-indol-1-yl)-ethylamino]-pyrimidin-4-yl}-2-ethoxy-benzoic acid in pharmaceutically acceptable salt form.

16. A method according to claim 1 for treatment of endometriosis; autosomal dominant polycystic kidney disease; or pneumonia; or for the control of female fertility.

17. A method according to claim 10 for treatment of endometriosis; autosomal dominant polycystic kidney disease; or pneumonia; or for the control of female fertility.

18. A method according to claim 11 for treatment of endometriosis; autosomal dominant polycystic kidney disease; or pneumonia; or for the control of female fertility.

19. A method according to claim 14 for treatment of autosomal dominant polycystic kidney disease; or pneumonia; or for the control of female fertility.

20. A method according to claim 1 for treatment of pain selected from inflammatory pain and painful menstruation.

21. A method according to claim 10 for treatment of pain selected from inflammatory pain and painful menstruation.

22. A method according to claim 11 for treatment of pain selected from inflammatory pain and painful menstruation.

23. A method according to claim 14 for treatment of pain selected from inflammatory pain and painful menstruation.

* * * * *